US009440970B2

(12) United States Patent
Okano et al.

(10) Patent No.: US 9,440,970 B2
(45) Date of Patent: Sep. 13, 2016

(54) PYRAZOLE DERIVATIVE

(71) Applicant: MOCHIDA PHARMACEUTICAL CO., LTD., Tokyo (JP)

(72) Inventors: Akihiro Okano, Tokyo (JP); Muneyoshi Makabe, Tokyo (JP)

(73) Assignee: MOCHIDA PHARMACEUTICAL CO., LTD., Tokyo (JP)

(*) Notice: Subject to any disclaimer, the term of this patent is extended or adjusted under 35 U.S.C. 154(b) by 0 days.

(21) Appl. No.: 14/601,775

(22) Filed: Jan. 21, 2015

(65) Prior Publication Data

US 2015/0133448 A1    May 14, 2015

Related U.S. Application Data

(63) Continuation of application No. 14/477,683, filed on Sep. 4, 2014, now Pat. No. 8,980,889, which is a continuation of application No. PCT/JP2014/054773, filed on Feb. 26, 2014.

(30) Foreign Application Priority Data

Feb. 27, 2013  (JP) ................................ 2013-038030

(51) Int. Cl.

| | | |
|---|---|---|
| A61K 31/535 | (2006.01) |
| C07D 471/04 | (2006.01) |
| C07D 401/04 | (2006.01) |
| C07D 417/04 | (2006.01) |
| A61K 31/437 | (2006.01) |
| A61K 31/444 | (2006.01) |
| A61K 31/497 | (2006.01) |
| A61K 31/501 | (2006.01) |
| A61K 31/506 | (2006.01) |
| A61K 31/5377 | (2006.01) |
| A61K 45/06 | (2006.01) |
| C07D 403/04 | (2006.01) |

(52) U.S. Cl.
CPC ........... *C07D 471/04* (2013.01); *A61K 31/437* (2013.01); *A61K 31/444* (2013.01); *A61K 31/497* (2013.01); *A61K 31/501* (2013.01); *A61K 31/506* (2013.01); *A61K 31/5377* (2013.01); *A61K 45/06* (2013.01); *C07D 401/04* (2013.01); *C07D 403/04* (2013.01); *C07D 417/04* (2013.01)

(58) Field of Classification Search
None
See application file for complete search history.

(56) References Cited

U.S. PATENT DOCUMENTS

| | | | |
|---|---|---|---|
| 8,263,584 B2 | 9/2012 | Alberati et al. | |
| 2003/0032579 A1 | 2/2003 | Lebel et al. | |
| 2004/0249148 A1 | 12/2004 | Erguden et al. | |
| 2015/0166536 A1* | 6/2015 | Okano ................. | C07D 401/04 514/233.2 |

FOREIGN PATENT DOCUMENTS

| | | |
|---|---|---|
| EP | 1250923 A2 | 10/2002 |
| WO | WO 03/000693 A1 | 1/2003 |
| WO | WO 2005/082883 A2 | 9/2005 |
| WO | WO 2006/072828 A2 | 7/2006 |
| WO | WO 2011/036127 A1 | 3/2011 |
| WO | WO 2011/117264 A1 | 9/2011 |
| WO | WO 2011/154327 A1 | 12/2011 |
| WO | WO 2012/009009 A2 | 1/2012 |
| WO | WO 2012/076430 A1 | 6/2012 |
| WO | WO 2012/133607 A1 | 10/2012 |

OTHER PUBLICATIONS

Castner et al., "Reversal of Antipsychotic-Induced Working Memory Deficits by Short-Term Dopamine D1 Receptor Stimulation," Science, vol. 287, Mar. 17, 2000, pp. 2020-2022.
Chappie et al., "Current Landscape of Phosphodiesterase 10A (PDE10A) Inhibition," Journal of Medicinal Chemistry, vol. 55, Jul. 26, 2012, pp. 7299-7331.

(Continued)

*Primary Examiner* — Heidi Reese
(74) *Attorney, Agent, or Firm* — Birch, Stewart, Kolasch & Birch, LLP

(57) ABSTRACT

It has been desired to develop a pharmaceutical composition, which is used in agents for preventing and/or treating various diseases related to PDE10 (e.g. mental disorder and neurodegenerative disorder). The present invention provides: compounds having PDE10 inhibitory effect, in particular, compounds having a 4-heteroarylpyrazole-5-carboxylic acid amide structure represented by the following formula (I), or their pharmaceutically acceptable salts, or their solvates; pharmaceutical compositions comprising, as active ingredients, the compounds, or their pharmaceutically acceptable salts, or their solvates; and medical use of the compounds, or their pharmaceutically acceptable salts, or their solvates.

7 Claims, No Drawings

(56) References Cited

OTHER PUBLICATIONS

Essayan, "Cyclic nucleotide phosphodiesterases," Journal of Allergy and Clinical Immunology, vol. 108 (Series: Molecular mechanisms in allergy and clinical immunology), 2001, pp. 671-680.

Francis et al., "Cyclic Nucleotide Phosphodiesterases: Relating Structure and Function," Progress in Nucleic Acid Research and Molecular Biology, vol. 65, 2001, pp. 1-52.

Fujishige et al., "Cloning and Characterization of a Novel Human Phosphodiesterase That Hydrolyzes Both cAMP and cGMP (PDE10A)," The Journal of Biological Chemistry, vol. 274, No. 26, Jun. 25, 1999, pp. 18438-18445.

Fujishige et al., "Striatum- and testis-specific phosphodiesterase PDE10A Isolation and Characterization of a rat PDE10A," European Journal of Biochemistry, vol. 266, 1999, pp. 1118-1127.

Houslay et al., "cAMP-Specific Phosphodiesterase-4 Enzymes in the Cardiovascular System a Molecular Toolbox for Generating Compartmentalized cAMP Signaling," Circulation Research, vol. 100, 2007, pp. 950-966.

International Search Report (Form PCT/ISA/210) for International Application No. PCT/JP2014/054773, dated Apr. 8, 2014, with an English translation.

Japan Office Action for Appl. No. 2014-530451 dated Sep. 9, 2014 (w/ English translation).

Kostowski et al., "Papaverine, Drug-Induced Stereotypy and Catalepsy and Biogenic Amines in the Brain of the Rat," Pharmacology Biochemistry and Behavior, vol. 5, 1976, pp. 15-17.

Lapiz et al., "Influence of Postweaning Social Isolation in the Rat on Brain Development, Conditioned Behavior, and Neurotransmission," Neuroscience and Behavioral Physiology, vol. 33, No. 1, 2003, pp. 13-29 (First Published in Rossiiskii Fiziologicheskii Zhurnal . . . , vol. 87, No. 6, Jun. 2001, pp. 730-751).

Loughney et al., "Isolation and characterization of PDE10A, a novel human 3', 5'-cyclic nucleotide phosphodiesterase," Gene, vol. 234, 1999, pp. 109-117.

Menniti et al., "Phosphodiesterase 10A inhibitors: A novel approach to the treatment of the symptoms of schizophrenia," Current Opinion in Investigational Drugs, vol. 8, No. 1, 2007, pp. 54-59.

Menniti et al., "Phosphodiesterases in the CNS: targets for drug development," Nature, vol. 5, Aug. 2006, pp. 660-670.

Mutschler et al., "Mutschler Drug Reactions," Textbook of Pharmacology and Toxicology, 8th Ed., 2001, pp. 147-153, 158, 311-313, with an English translation.

Registry File [STN online], Apr. 15, 2012, RN 1368131-71-8.

Sawaguchi, "The role of D1-dopamine receptors in working memory-guided movements mediated by frontal cortical areas," Parkinsonism and Related Disorders, vol. 7, 2001, pp. 9-19.

Seeger et al., "Immunohistochemical localization of PDE10A in the rat brain," Brain Research, vol. 985, 2003, pp. 113-126.

Soderling et al., "Isolation and characterization of a dual-substrate phosphodiesterase gene family: PDE10A," Proceedings of the National Academy of Sciences of the United States of America, vol. 96, Jun. 1999, pp. 7071-7076.

Xie et al., "Cellular and Subcellular Localization of PDE10A, A Striatum-Enriched Phosphodiesterase," Neuroscience, vol. 139, 2006, pp. 597-607.

\* cited by examiner

PYRAZOLE DERIVATIVE

CROSS REFERENCE TO RELATED APPLICATIONS

This application is a Continuation of U.S. application Ser. No. 14/477,683, filed Sep. 4, 2014, which is a Continuation of PCT International Application No. PCT/JP2014/054773, filed on Feb. 26, 2014, which claims priority under 35 U.S.C. 119(a) to Patent Application No. 2013-038030, filed in Japan on Feb. 27, 2013, all of which are hereby expressly incorporated by reference into the present application.

TECHNICAL FIELD

The present invention relates to a compound having phosphodiesterase 10 (hereinafter referred to as "PDE10") inhibitory effect, in particular, a compound having a 4-heteroarylpyrazole-5-carboxylic acid amide structure represented by the following formula (I), or a pharmaceutically acceptable thereof, or a solvate thereof; and a pharmaceutical composition comprising, as an active ingredient, the compound, or a pharmaceutically acceptable salt thereof, or a solvate thereof; or an agent for preventing and/or treating various diseases related to PDE10 (e.g. mental disorders and neurodegenerative disorders).

BACKGROUND ART

Phosphodiesterase (PDE, cyclic nucleotide phosphodiesterase) is a superfamily of enzymes encoded by 21 different genes. To date, eleven phosphodiesterases have been identified in mammals, based on structural/functional characteristics such as amino acid sequence homology, biochemical properties, and characterization using inhibitors (Non Patent Literatures 1 and 2).

The role of the PDE in cell signaling cascade is to hydrolyze the phosphodiester bond of cyclic nucleotides, adenosine 3',5'-cyclic monophosphate (cAMP) and/or guanosine 3',5'-cyclic monophosphate (cGMP), that is to say, to selectively catalyze the hydrolysis of a 3'-ester bond so as to form inactive 5'-monophosphoric acid so as to metabolically inactivate the cyclic nucleotides.

The eleven PDE families are classified into three groups, namely, cAMP-specific PDEs (PDE 4, 7, and 8), cGMP-specific PDEs (PDE 5, 6, and 9), and double substrate PDEs (PDE 1, 2, 3, 10, and 11) (Non Patent Literatures 3 and 4) based on substrate specificity.

Since cAMP and cGMP are important second messengers in intracellular signaling via G protein coupled receptors (GPCR), PDEs are involved in a wide range of physiological mechanisms and play an important role in the homeostasis of organisms. Specifically, PDEs are related to various physiological processes such as generation of proinflammatory mediators and the action thereof, ion channel function, muscle relaxation, learning and memory formation, differentiation, apoptosis, lipogenesis, glycogenolysis, and gluconeogenesis. Particularly, in nerve cells, PDEs play an important role in the differentiation and survival of nerve cells and the regulation of neurotransmission (Non Patent Literature 5).

Regulation of these processes by cAMP and cGMP is related to activation of protein kinase A (PKA) and protein kinase G (PKG), and thus, various substrates that regulate various physiological processes, such as transcriptional factors, ion channels, and receptors, are phosphorylated. The intracellular levels of cAMP and cGMP are fluctuated in response to extracellular signals, and are regulated based on the balance between enzymes involved in the synthesis of cAMP and cGMP (adenyl cyclase (AC) and guanyl cyclase (GC)), and PDEs involved in the hydrolysis of these enzymes (Non Patent Literature 6).

The presence of PDE10 in humans, mice, and rats was reported in 1999 (Non Patent Literatures 7 and 8). PDE10 is mainly expressed in the brain, testis, thyroid gland, and the like in humans. In particular, PDE10 is highly expressed in medium-sized spiny neurons (MSNs) in the corpus striatum of the brain, and is moderately expressed in the thalamus, hippocampus, frontal cortex, and olfactory tubercle (Non Patent Literatures 9 and 10). In addition, PDE10 is highly expressed in the brain and testis also in mice and rats (Non Patent Literature 11). Since the brain sites where PDE10 is expressed play an important role in the pathological mechanism of mental diseases, it has been suggested that PDE10 is involved in the pathological mechanism of mental disorders, neurodegenerative disorders, and the like (Non Patent Literature 12).

There are two types of MSN, namely, MSN that mainly expresses D1 dopamine receptors and forms a nigrostriatal pathway (direct pathway) and MSN that mainly expresses D2 dopamine receptors and forms a striatum-globus pallidus pathway (indirect pathway). The direct pathway is involved in the functions of motor execution and reward learning, and the indirect pathway is involved in the suppression of movement. For example, deterioration of movements in Parkinson's disease is caused by excessive action of the indirect pathway, and excessive movements observed in disorders such as Huntington's disease are caused by excessive action of the direct pathway. The activity of the output nucleus of the basal ganglia is regulated by the balance between antagonistic inputs from these two types of pathways. Since PDE10 is expressed in MSNs in both pathways, both pathways are considered to be activated by inhibition of PDE10 (Non Patent Literature 13).

The existing antipsychotic agents are mainly $D_2$ receptor blocking agents, and are mainly mediated by activation of the indirect pathway. On the other hand, PDE10 is expressed in both MSNs in the direct pathway and the indirect pathway, and thus, a PDE10 inhibitor is expected to have the same antipsychotic action as that of the existing agents. Since the direct pathway is involved in motor execution, the direct pathway is considered to antagonistically act against extrapyramidal disorder caused by excessive activation of the indirect pathway. Moreover, it can also be expected that the direct pathway has action to reinforce the output from the corpus striatum-thalamus circuit and to promote cognitive function such as reward learning or problem solving.

As a result of an increase in the intracellular cAMP level by activation of the $D_1$ receptor, a series of neurites involved in working memory in the prefrontal cortex are likely to be regulated (Non Patent Literature 14). Furthermore, it has been reported that working memory deficits of schizophrenia patients may be improved by activation of the $D_1$ receptor (Non Patent Literature 15). Accordingly, it can be anticipated that the cognitive symptoms of schizophrenia will be improved by activation of the $D_1$ receptor.

Potential antipsychotic action of a PDE10 inhibitor has been attested by the study of Kostowski et al. (Non Patent Literature 16). According to U.S. Patent Application No. 2003/0032579, papaverine a PDE10 inhibitor having a moderate selectivity decreases apomorphine-induced stereotypy in rats which is an animal model of psychosis, and increases haloperidol-induced catalepsy in rat, and at the same time, papaverine also decreases the dopamine level in the rat brain and has conventional action as an antipsychotic agent. Further, the antipsychotic action of papaverine has been also proved by the application thereof to patients, and papaverine has been established as a PDE10 inhibitor for the treatment of psychosis (Patent Literature 1).

With regard to compounds having PDE10 inhibitory effect (PDE10 inhibitors), there are the following reports. For instance, International Publication No. WO2005/082883 (Patent Literature 2) and European Patent Application No. 1250923 (Patent Literature 3) disclose, as PDE10 inhibitors, papaverine (isoquinoline alkaloid contained in *Papaver* plants) and various types of aromatic heterocyclic compounds (quinazoline and isoquinazoline compounds, etc.). In addition, it has also been disclosed that the PDE10 inhibitor is useful for treating or preventing diseases or symptoms, such as mental disorder (e.g. schizophrenia, schizophreniform disorder, paranoid disorder, substance-induced psychosis, paranoic personality disorder, and schizophrenic personality disorder), anxiety disorder (e.g. panic disorder, agoraphobia, specific phobias, anthropophobia, obsessive-compulsive disorder, posttraumatic stress disorder, acute stress disorder, and generalized anxiety disorder), motor disorder (e.g. Huntington's disease, dyskinesia associated with dopamine agonist therapy, Parkinson's disease, and restless legs syndrome), drug dependence (e.g. alcohol, amphetamine, cocaine or opiate addiction), diseases attended with the symptoms of cognitive disorder (e.g. dementia (Alzheimer's disease, multi-infarct dementia, etc.), delirium, amnestic defect, posttraumatic stress disorder, mental retardation, learning disorder, attention-deficit hyperactivity disorder (ADHD), and age-related cognitive function reduction), and mood disorder (e.g. major depressive disorder, dysthymic disorder, minor depressive disorder, and bipolar disorder (bipolar disorder type I and bipolar disorder type II), and cyclothymic disorder), or mood symptoms (e.g. major depressive episode, manic or mixed affective episode, and hypomanic episode). Moreover, it has also been disclosed that the PDE10 inhibitor is useful for treating or preventing neurodegenerative disease (e.g. Parkinson's disease and Huntington's disease).

The publication of Menniti et al. reports that the PDE10 inhibitor has a potential as an antipsychotic agent and also has a potential for improving cognitive function disorder in schizophrenia (Non Patent Literature 17).

International Publication No. WO2003/000693 discloses an imidazotriazine compound as a PDE10 inhibitor, and that the PDE10 inhibitor is useful for treating or preventing neurodegenerative diseases (in particular, Parkinson's disease) (Patent Literature 4).

As described above, it is anticipated that the PDE10 inhibitor can be a therapeutic agent with reduced adverse drug reactions, which is useful for treating and/or preventing mental disorders related to PDE10 (e.g. (1) paranoid, disorganized, catatonic, undifferentiated, or residual schizophrenia, (2) schizophreniform disorder, (3) paranoid or depressive schizoaffective disorder, (4) paranoid disorder, (5) substance-induced mental disorder, for example, psychosis induced by alcohol, amphetamine, *cannabis*, cocaine, a hallucinatory drug, an inhalant, opioid, or phencyclidine, (6) paranoic personality disorder, and (7) schizotypal personality disorder); neurodegenerative disorders related to PDE10 (e.g. (1) Parkinson's disease, (2) Huntington's disease, (3) dementia, such as Alzheimer's disease, multi-infarct dementia, AIDS-related dementia, and frontotemporal dementia, (4) neurodegeneration associated with brain damage, (5) neurodegeneration associated with stroke and neurodegeneration associated with cerebral infarction, (6) hypoglycemia-induced neurodegeneration, (7) neurodegeneration associated with epileptic seizure, (8) neurodegeneration associated with neurotoxic addiction, (9) multiple system atrophy, and (10) neurodegeneration of striatal medium-sized spiny neurons); and the like.

International Publication No. WO2006/0072828 (Patent Literature 5) discloses, as a PDE10 inhibitors, compounds having a 1-methyl-4-heteroarylpyrazole structure as a partial structure thereof. However, this structure is different from the structure of the compound in the present invention.

International Publication No. WO2011/036127 (Patent Literature 6), International Publication No. WO2011/154327 (Patent Literature 7), and International Publication No. WO2012/076430 (Patent Literature 8) disclose compounds having a pyrazole-5-carboxylic acid amide structure as a PDE10 inhibitors. However, the structures of the compounds of Patent Literatures 6, 7, and 8 are all different from the structure of the compound in the present invention in that the compounds of Patent Literatures 6 and 8 have a dicarboxylic acid amide structure and in that the compound of Patent Literature 7 is a carboxylic acid amide of 7-aminoimidazo[1,2-a]pyrimidine.

PRIOR ART DOCUMENTS

Patent Documents

Patent Literature 1: U.S. Patent Application No. 2003/0032579
Patent Literature 2: International Publication No. WO2005/082883
Patent Literature 3: European Patent Application No. 1250923
Patent Literature 4: International Publication No. WO2003/000693
Patent Literature 5: International Publication No. WO2006/072828
Patent Literature 6: International Publication No. WO2011/036127
Patent Literature 7: International Publication No. WO2011/154327
Patent Literature 8: International Publication No. WO2012/076430

Non-Patent Documents

Non Patent Literature 1: Essayan D M., J Allergy Clin Immunol, 108, p 671-680, 2001.
Non Patent Literature 2: Francis S H., Prog Nucleic Acid Res Mol Biol., 65, p 1-52, 2001.
Non Patent Literature 3: Soderling S H., Proc Natl Acad USA, 96(12), p 7071-7076, 1999.
Non Patent Literature 4: Chappie T A., Journal of Medicinal Chemistry, 55, p 7299-7331, 2012.
Non Patent Literature 5: Menniti F S., Nat Rev Drug Discov, 5(8), p 660-670, 2006.
Non Patent Literature 6: Houslay M D., Cir Res, 100(7), p 950-966, 2007.
Non Patent Literature 7: Omori K., J Biol Chem, 274(26), p 18438-18445, 1999.
Non Patent Literature 8: Loughney K., Gene, 234(1), p 109-117, 1999.
Non Patent Literature 9: Omori K., Eur J Biochem, 266(3), p 1118-1127, 1999.
Non Patent Literature 10: Menniti F S., Brain Res, 985(2), p 113-126, 2003.

Non Patent Literature 11: Xie Z., Neuroscience., 139(2), p 597-607, 2006.
Non Patent Literature 12: Lapiz et al., Neurosci Behav Physiol, 33(1), p 13-29, 2003.
Non Patent Literature 13: Mutschler., Arzneimittelwirkungen. 8$^{th}$ ed. Stuttgart: Wissenschaftliche Verlagsgesellschaft mbH, 2001.
Non Patent Literature 14: Sawaguchi., Parkinsonism Relat Disord., 7(1), p 9-19, 2000.
Non Patent Literature 15: Castner S A., Science., 287(5460), p 2020-2022, 2000.
Non Patent Literature 16: Kostowski W., Pharmacol Biochem Behav., 5(1), p 15-17, 1976.
Non Patent Literature 17: Menniti F S., Curr Opin Investig Drugs., 8(1), p 54-59, 2007.

SUMMARY OF THE INVENTION

Problems to be Solved by the Invention

At present, various antipsychotic agents can be used in drug therapy for schizophrenia. However, such antipsychotic agents have a low level of satisfaction in treatment. Conventional antipsychotic agents having high affinity for dopamine $D_2$ receptors, such as haloperidol, exhibit strong adverse effects including extra pyramidal symptom (EPS) and do not improve the negative symptoms of schizophrenia, thus the agents cannot get patients back to daily life. Clozapine, which had been developed as standard therapy for improving the positive, negative, and cognitive symptoms of schizophrenia and which has not exhibited EPS, has been placed on the market as a benchmark for treating and recovering the positive, negative, and cognitive symptoms of schizophrenia. However, this clozapine causes granulocytopenia as a severe potentially lethal adverse drug reaction (Capuano B., Curr Med Chem, 9 (5), pp. 521-548, 2002). Moreover, many therapy-resistant cases are still present (Lindenmayer J P., J Clin Psychiatry, 63 (10), pp. 931-935, 2002). In conclusion, it has been desired to develop a novel antipsychotic agent for improving the positive, negative, and cognitive symptoms of psychosis and having a better adverse effect profile.

Moreover, in the development of pharmaceutical products, it is required to satisfy strict criteria, not only in terms of pharmacological activities of interest, but also in terms of various aspects such as absorption, distribution, metabolism, and excretion. For example, pharmaceutical products are required to overcome various problems regarding drug interaction, desensitization or tolerance, gastrointestinal absorption upon oral administration, rate of transferring into the small intestine, absorption rate and first pass effect, organ barriers, protein binding, induction or inhibition of drug metabolizing enzymes, excretion pathway and inner clearance, application methods (application site, method, and purpose), and the like. It is difficult to discover a pharmaceutical product that satisfies these requirements.

There have been several reports regarding a compound having inhibitory effect on the PDE10 receptor. However, the above-mentioned general problems have always remained unsolved during the development of pharmaceutical products, and thus, such a compound has not yet been placed on the market. More specifically, regarding usefulness and safety, there are problems such as poor solubility, low metabolic stability and difficult systemic exposure by oral administration, poor drug pharmacokinetics such as absorbability and persistence, that a compound exhibits inhibitory activity on human ether-a-go-go related gene (hERG) channel, which may have a risk of causing arrhythmia, that a compound exhibits an activity of inducing or inhibiting drug metabolizing enzyme (e.g. cytochrome P450), and that a compound exhibits a high protein-binding rate. It has been desired to discover a compound that solves as many of these problems as possible and has high effectiveness.

Means for Solving the Problems

The present inventors have conducted intensive studies directed towards solving the aforementioned problems and obtaining a PDE10 inhibitor that is highly safe and/or is excellent in effectiveness. As a result, the inventors have discovered that a compound having a 4-heteroarylpyrazole-5-carboxylic acid amide structure represented by a formula (I), or a pharmaceutically acceptable salt thereof, or a solvate thereof has PDE10 inhibitory effect. The compounds in the present invention have PDE10 inhibitory effect and also have effect to improve various diseases related to PDE10 (e.g. mental disorder and neurodegenerative disorder).

Effects of the Invention

[Formula 1]

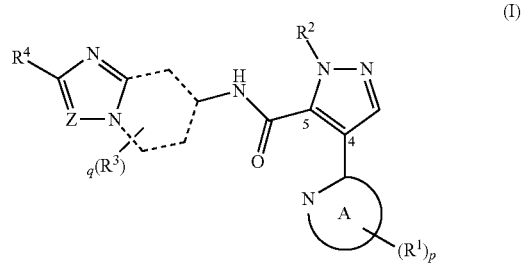

The present invention is a compound having a 4-heteroarylpyrazole-5-carboxylic acid amide structure represented by the formula (I), or a pharmaceutically acceptable salt thereof, or a solvate thereof; and a pharmaceutical composition comprising, as an active ingredient, the compound, or a pharmaceutically acceptable salt thereof, or a solvate thereof.

The compound in the present invention is a compound having PDE10 inhibitory effect. This compound has action to inhibit the hydrolysis of a phosphodiester bond of cAMP in striatal GABA neurons and increase nerve ignition by inhibiting PDE10, and to improve various diseases related to PDE10 (e.g. mental disorders and neurodegenerative disorders) by promoting the activation of the corpus striatum.

A pharmaceutical composition comprising, as an active ingredient, the compound in the present invention can be preferably administered by oral administration, and it is expected to be an agent for preventing and/or treating diseases related to PDE10.

Moreover, a group of the compounds of the present invention is highly useful because these compounds have at least one characteristic of good solubility, high metabolic stability, excellent oral absorbability, and having only small action to inhibit the hERG channel.

EMBODIMENTS FOR CARRYING OUT THE INVENTION

The present invention is a compound having a 4-heteroarylpyrazole-5-carboxylic acid amide structure represented by the following formula (I), or a pharmaceutically acceptable salt thereof, or a solvate thereof; a pharmaceutical composition comprising, as an active ingredient, the compound, a pharmaceutically acceptable salt thereof, or a solvate thereof; and a PDE10 inhibitor as medicinal use of the compounds, a pharmaceutically acceptable salt thereof, or a solvate thereof, which are described in the following embodiments.

The present invention includes the following embodiments [1] to [17].

A first embodiment of the present invention is

[1] a compound represented by the following formula (I), or a pharmaceutically acceptable salt thereof, or a solvate thereof:

[Formula 2]

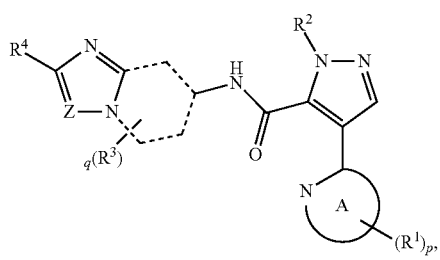

(I)

wherein p represents an integer of 0 to 4; q represents an integer of 0 to 4; Z represents N or $CR^5$; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxycarbonyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfinyl group, a $C_{1-6}$ alkylsulfonyl group, an —$NR^7R^8$ group, or a —$CONR^7R^8$ group wherein $R^7$ and $R^8$ in the —$NR^7R^8$ group and the —$CONR^7R^8$ group each independently represent a substituent selected from among a hydrogen atom, a $C_{1-6}$ alkyl group, a halogenated $C_{1-6}$ alkyl group, a hydroxy $C_{1-6}$ alkyl group, a cyanated $C_{1-6}$ alkyl group, a $C_{2-6}$ alkenyl group, a $C_{2-6}$ alkynyl group, a $C_{3-8}$ cycloalkyl group, a $C_{6-14}$ aryl group, a $C_{7-20}$ aralkyl group, a heterocyclic group, a $C_{2-7}$ alkanoyl group, a hydroxy $C_{2-7}$ alkanoyl group, a halogenated $C_{2-7}$ alkanoyl group, a $C_{3-8}$ cycloalkylcarbonyl group, a $C_{6-14}$ arylcarbonyl group, a $C_{7-20}$ aralkylcarbonyl group, a heterocyclic carbonyl group, a mono-/di-$C_{1-6}$ alkylcarbamoyl group, a mono-/di-halogenated $C_{1-6}$ alkylcarbamoyl group, a mono-/di-$C_{3-8}$ cycloalkylcarbamoyl group, a mono-/di-$C_{6-14}$ arylcarbamoyl group, a mono-/di-$C_{7-20}$ aralkylcarbamoyl group, a mono-/di-heterocyclic carbamoyl group, a $C_{1-6}$ alkylsulfonyl group, a halogenated $C_{1-6}$ alkylsulfonyl group, a $C_{3-8}$ cycloalkylsulfonyl group, a $C_{6-14}$ arylsulfonyl group, a $C_{7-20}$ aralkylsulfonyl group, a heterocyclic sulfonyl group, a mono-/di-$C_{1-6}$ alkylsulfamoyl group, a mono-/di-halogenated $C_{1-6}$ alkylsulfamoyl group, a mono-/di-$C_{3-8}$ cycloalkylsulfamoyl group, a mono-/di-$C_{6-14}$ arylsulfamoyl group, a mono-/di-$C_{7-20}$ aralkylsulfamoyl group, and a mono-/di-heterocyclic sulfamoyl group; $R^2$ represents a hydrogen atom, a $C_{1-6}$ alkyl group, a halogenated $C_{1-6}$ alkyl group, a hydroxy $C_{1-6}$ alkyl group, or a $C_{1-6}$ alkoxyl $C_{1-6}$ alkyl group; $R^3$ each independently represents a halogen atom, a cyano group, a $C_{1-6}$ alkyl group, a halogenated $C_{1-6}$ alkyl group, a hydroxy $C_{1-6}$ alkyl group, a $C_{1-6}$ alkoxyl group, a halogenated $C_{1-6}$ alkoxyl group, or a $C_{1-6}$ alkoxyl $C_{1-6}$ alkyl group; $R^4$ represents a halogen atom, a $C_{1-6}$ alkyl group, a halogenated $C_{1-6}$ alkyl group, a $C_{3-8}$ cycloalkyl group, a hydroxy $C_{1-6}$ alkyl group, a $C_{1-6}$ alkoxyl group, a halogenated $C_{1-6}$ alkoxyl group, a $C_{1-6}$ alkoxyl $C_{1-6}$ alkyl group, a $C_{1-6}$ alkylthio group, a $C_{1-6}$ alkylsulfonyl group, a —$CONR^7R^8$ group, an —$NR^7R^8$ group wherein $R^7$ and $R^8$ in the —$NR^7R^8$ group and the —$CONR^7R^8$ group have the same definitions as those of $R^7$ and $R^8$ in the above $R^1$, a $C_{6-14}$ aryl group, a 3- to 14-membered non-aromatic heterocyclic group, or a 5- to 7-membered monocyclic heteroaryl group, wherein the $C_{3-8}$ cycloalkyl group, the $C_{6-14}$ aryl group, the 3- to 14-membered non-aromatic heterocyclic group, and the 5- to 7-membered monocyclic heteroaryl group, which are represented by $R^4$, are optionally substituted with one to three groups selected from among a hydroxyl group, a nitro group, a cyano group, a halogen atom, a $C_{1-6}$ alkyl group, a halogenated $C_{1-6}$ alkyl group, a hydroxy $C_{1-6}$ alkyl group, a $C_{1-6}$ alkoxyl group, a halogenated $C_{1-6}$ alkoxyl group, a $C_{1-6}$ alkoxyl $C_{1-6}$ alkyl group, a $C_{1-6}$ alkylthio group, a $C_{1-6}$ alkylsulfonyl group, a —$CONR^7R^8$ group, an —$NR^7R^8$ group wherein $R^7$ and $R^8$ in the —$NR^7R^8$ group and the —$CONR^7R^8$ group have the same definitions as those of $R^7$ and $R^8$ in the above $R^1$, a $C_{6-14}$ aryl group, a 3- to 14-membered non-aromatic heterocyclic group, and a 5- to 7-membered monocyclic heteroaryl group; $R^5$ represents a hydrogen atom, a halogen atom, a $C_{1-6}$ alkyl group, a halogenated $C_{1-6}$ alkyl group, a $C_{1-6}$ alkoxyl group, a halogenated $C_{1-6}$ alkoxyl group, or a $C_{1-6}$ alkoxyl $C_{1-6}$ alkyl group;

ring A represented by the following partial structural formula (II):

[Formula 3]

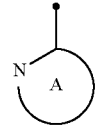

(II)

represents a 5- to 7-membered monocyclic heteroaryl group which has a structure in which position 4 of a pyrazole ring directly binds to position a to a nitrogen atom of the 5- to 7-membered monocyclic heteroaryl group, and is selected from the group of the heteroaryls consisting of the following:

[Formula 4]

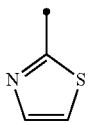

(II-1)

(II-2)

-continued
(II-3)
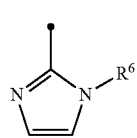
(II-4)
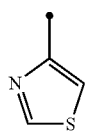
(II-5)
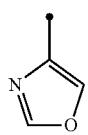
(II-6)
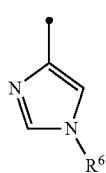
(II-7)
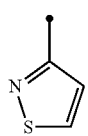
(II-8)
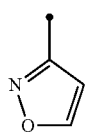
(II-9)
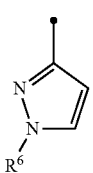
(II-10)
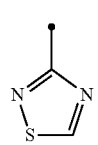
(II-11)
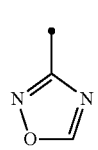
(II-12)
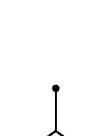
-continued
(II-13)
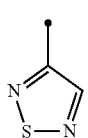
(II-14)
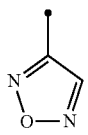
(II-15)
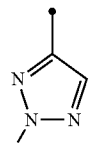
(II-16)
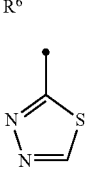
(II-17)
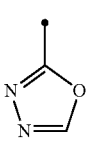
(II-18)
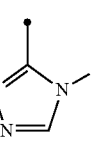
(II-19)
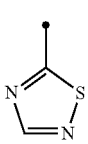
(II-20)
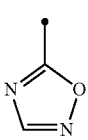
(II-21)
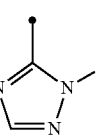
(II-22)
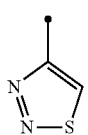
(II-23)
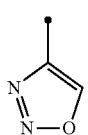

(II-24) 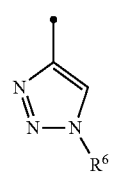
(II-25) 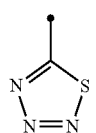
(II-26) 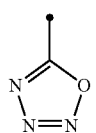
(II-27) 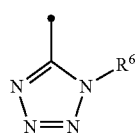
(II-28) 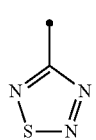
(II-29) 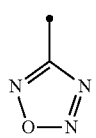
(II-30) 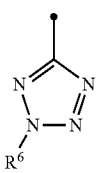
(II-31) 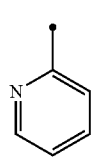
(II-32) 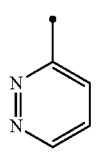
(II-33) 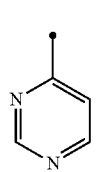
(II-34) 
(II-35) 
(II-36) 
(II-37) 
(II-38) 
(II-39) 
(II-40) 
(II-41) 
(II-42) 
(II-43) 
$R^6$ represents a hydrogen atom, a $C_{1-6}$ alkyl group, a halogenated $C_{1-6}$ alkyl group, or a hydroxy $C_{1-6}$ alkyl group; and fused ring B represented by the following partial structural formula (III):

[Formula 5]

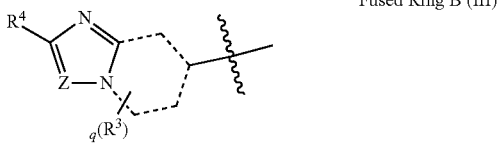

Fused Ring B (III)

is selected from the group consisting of the following:

[Formula 6]

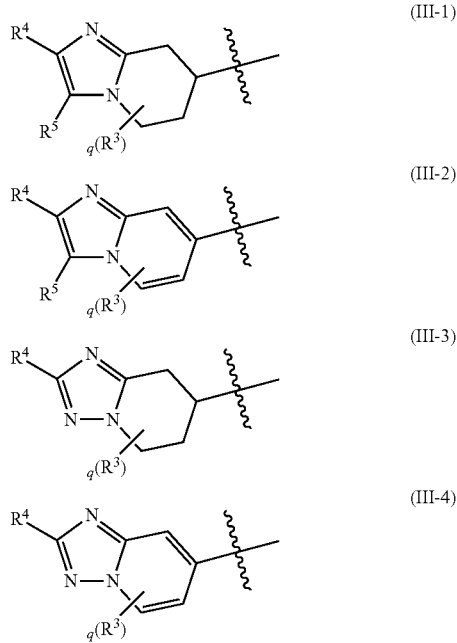

Hereinafter, individual groups in the above formula (I) of the embodiment [1] will be specifically described.

In explanation regarding the compound in the present invention, for example, the term "$C_{1-6}$" indicates that the number of constituent carbon atoms is 1 to 6, and it indicates the number of carbon atoms in a straight-chain, branched-chain, or cyclic group, unless otherwise specified. The number of constituent carbon atoms includes the total number of carbon atoms of groups including straight-chain or branched-chain groups substituted with cyclic groups, or cyclic groups substituted with straight-chain or branched-chain groups. Accordingly, the chain group means a "straight chain or branched chain, the number of constituent carbon atoms of which is 1 to 6." On the other hand, the cyclic group means a "cyclic group in which the number of carbon atoms that constitute a ring is 1 to 6." A group comprising a chain group and a cyclic group means a "group, the total number of carbon atoms of which is 1 to 6."

In the present specification, unless otherwise specified, examples of the "halogen atom" include a fluorine atom, a chlorine atom, a bromine atom, and an iodine atom.

In the present specification, unless otherwise specified, the term "halogenated" means that a group optionally has one to five of the above described "halogen atoms" as substituents. In addition, the term "halogenated" can be restated as "optionally halogenated" or "halogeno."

In the present specification, unless otherwise specified, the term "cyanated" means that a group optionally has one to five of the above described "cyano groups" as substituents. In addition, the term "cyanated" can be restated as "optionally cyanated."

In the present specification, unless otherwise specified, examples of the "alkyl group" include a "$C_{1-6}$ alkyl group."

In the present specification, unless otherwise specified, examples of the "$C_{1-6}$ alkyl group" include methylethyl, propyl, isopropyl, butyl, isobutyl, sec-butyl, tert-butyl, pentyl, isopentyl, neopentyl, tert-pentyl 3-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclobutylmethyl, cyclopentylmethyl, 1-cyclopropylethyl, 2-cyclopropylethyl, 2-cyclobutylethyl, and 2-methylcyclopropyl.

In the present specification, unless otherwise specified, the term "halogenated $C_{1-6}$ alkyl group" means a group in which the above described "$C_{1-6}$ alkyl group" is optionally substituted with one to five halogen atoms. Examples of the halogenated $C_{1-6}$ alkyl group include fluoromethyl, difluoromethyl, trifluoromethyl, 2,2,2-trifluoroethyl, 1,1,2,2-tetrafluoroethyl, and pentafluoroethyl.

In the present specification, unless otherwise specified, the term "hydroxy $C_{1-6}$ alkyl group" means a group in which the above described "$C_{1-6}$ alkyl group" is optionally substituted with one to five hydroxyl groups. Examples of the hydroxy $C_{1-6}$ alkyl group include hydroxymethyl, hydroxyethyl (specifically, 1-hydroxyethyl and 2-hydroxyethyl), hydroxypropyl (specifically, 1-hydroxypropyl, 2-hydroxypropyl, 3-hydroxypropyl, etc.), and 2-hydroxy-2-methylethyl.

In the present specification, unless otherwise specified, the term "cyanated $C_{1-6}$ alkyl group" means a group in which the above described "$C_{1-6}$ alkyl group" is optionally substituted with one to five cyano groups. Examples of the cyanated $C_{1-6}$ alkyl group include cyanomethyl, 1-cyanoethyl, and 2-cyanoethyl.

In the present specification, unless otherwise specified, examples of the "alkenyl group" include a "$C_{2-6}$ alkenyl group."

In the present specification, unless otherwise specified, examples of the "$C_{2-6}$ alkenyl group" include vinyl, allyl, isopropenyl, 1-propen-1-yl, 2-methylallyl, butenyl, pentenyl, isopentenyl, hexenyl, 1-cyclopropen-1-yl, 2-cyclopropen-1-yl, 1-cyclobuten-1-yl, 1-cyclopenten-1-yl, 2-cyclopenten-1-yl, 3-cyclopenten-1-yl, 1-cyclohexen-1-yl, 2-cyclohexen-1-yl, 3-cyclohexen-1-yl, 2,4-cyclopentadien-1-yl, and 2,5-cyclohexadien-1-yl.

In the present specification, unless otherwise specified, examples of the "alkynyl group" include a "$C_{2-6}$ alkynyl group."

In the present specification, unless otherwise specified, examples of the "$C_{2-6}$ alkynyl group" include ethynyl, 1-propynyl, 2-propynyl, butynyl, pentynyl, and hexynyl.

In the present specification, unless otherwise specified, examples of the "aryl group" include a "$C_{6-14}$ aryl group."

In the present specification, unless otherwise specified, the "$C_{6-14}$ aryl group" includes a "monocyclic aryl group,"

a "fused-ring aryl group (including bicyclic or tricyclic groups)," and a "partially hydrogenated fused-ring aryl group (including bicyclic or tricyclic groups)."

In the present specification, unless otherwise specified, examples of the "$C_{6-14}$ aryl group" include phenyl, 1-naphthyl, 2-naphthyl, 2-, 3-, or 4-biphenylanthryl, phenanthryl, and acenaphthyl.

In the present specification, unless otherwise specified, the term "partially hydrogenated fused-ring aryl group" means a monovalent group formed by removing any given hydrogen atom from a partially hydrogenated fused ring in the above described "fused-ring aryl group." Either a hydrogen atom in the aromatic ring portion of the fused ring or a hydrogen atom in the hydrogenated portion thereof may be removed.

In the present specification, unless otherwise specified, examples of the "partially hydrogenated fused-ring aryl group" include indanyl, indenyl, and 1,2,3,4-tetrahydronaphthyl.

The "aryl group" may be restated as an "aromatic hydrocarbon group." That is to say, the "$C_{6-14}$ aryl group" means the same group as a "$C_{6-14}$ aromatic hydrocarbon group."

In the present specification, unless otherwise specified, the term "aralkyl group" means a group in which the above described "aryl group" is substituted with the above described "alkyl group."

In the present specification, unless otherwise specified, examples of the "aralkyl group" include a "$C_{7-20}$ aralkyl group."

In the present specification, unless otherwise specified, examples of the "$C_{7-20}$ aralkyl group" include benzyl, phenethyl, diphenylmethyl, 2,2-diphenylethyl, 3-phenylpropyl, 4-phenylbutyl, 5-phenylpentyl, 2-biphenylmethyl, 3-biphenylmethyl, 4-biphenylmethyl, 1-naphthylmethyl, 2-naphthylmethyl, 2-(1-naphthyl)ethyl, 2-(2-naphthyl)ethyl, 1-indanylmethyl, 2-indanylmethyl, 1,2,3,4-tetrahydronaphthalen-1-ylmethyl, and 1,2,3,4-tetrahydronaphthalen-2-ylmethyl.

In the present specification, unless otherwise specified, examples of the "non-aromatic hydrocarbon group" include a non-aromatic hydrocarbon ring containing three to eight carbon atoms, such as a "$C_{3-8}$ cycloalkyl group."

In the present specification, unless otherwise specified, examples of the "$C_{3-8}$ cycloalkyl group" include cyclopropyl, cyclobutyl, cyclopentyl, cyclohexyl, cycloheptyl and cyclooctyl.

In the present specification, unless otherwise specified, the term "heterocyclic group" means a monovalent group formed by removing any given hydrogen atom from a 3- to 14-membered monocyclic or fused ring containing one to five heteroatoms that are of at least one optionally selected from among a nitrogen atom, a sulfur atom, and an oxygen atom.

In the present specification, unless otherwise specified, examples of the "heterocyclic group" include a "heteroaryl group," a "partially hydrogenated fused-ring heteroaryl group," and a "non-aromatic heterocyclic group."

In the present specification, unless otherwise specified, the term "heterocyclic group" can be restated as a "hetero ring group," the term "heteroaryl group" can be restated as an "aromatic heterocyclic group," and the term "non-aromatic heterocyclic group" can be restated as a "non-aromatic hetero ring group."

In the present specification, unless otherwise specified, the above described "heteroaryl group" means a 5- to 14-membered heteroaryl ring group having one to five heteroatoms selected from among a nitrogen atom, a sulfur atom, and an oxygen atom.

In the present specification, unless otherwise specified, examples of the above described "heteroaryl group" include a "monocyclic heteroaryl group" and a "fused-ring heteroaryl group."

In the present specification, unless otherwise specified, the above described "monocyclic heteroaryl group" is preferably a group having five to seven ring members. That is to say, examples of the "5- to 7-membered monocyclic heteroaryl group" include pyrrolyl, furyl, thienyl, thiazolyl, oxazolyl, 1H-imidazolyl, isothiazolyl, isoxazolyl, 1H-pyrazolyl, 1,2,4-thiadiazolyl, 1,2,4-oxadiazolyl, 1H-1,2,4-triazolyl, 1,2,5-thiadiazolyl, 1,2,5-oxadiazolyl(furazanyl), 2H-1,2,3-triazolyl, 1,3,4-thiadiazolyl, 1,3,4-oxadiazolyl, 4H-1,2,4-triazolyl, 1,2,4-thiadiazolyl, 1,2,4-oxadiazolyl, 1H-1,2,4-triazolyl, 1,2,3-thiadiazolyl, 1,2,3-oxadiazolyl, 1H-1,2,3-triazolyl, 1,2,3,4-thiatriazolyl, 1,2,3,4-oxatriazolyl, 1,2,3,5-thiatriazolyl, 1,2,3,5-oxatriazolyl, 1H-tetrazolyl, 2H-tetrazolyl, pyridinyl, pyridazinyl, pyrimidinyl, pyrazinyl, 1,2,3-triazinyl, 1,2,4-triazinyl, 1,3,5-triazinyl, 1,2,4,5-tetrazinyl, 1,2,3,4-tetrazinyl, 1,2,3,5-tetrazinyl, 2H-1,2,3-thiadiazinyl, 4H-1,2,4-thiadiazinyl, 6H-1,3,4-thiadiazinyl, 1,4-diazepinyl, and 1,4-oxazepinyl.

In the present specification, unless otherwise specified, the above described "fused-ring heteroaryl group" means a monovalent group formed by removing any given hydrogen atom from a fused ring that is formed by condensation of a "heterocyclic group" and an "aryl group," or of a "heterocyclic group" and a "monocyclic heteroaryl group." The any given hydrogen atom may be removed from any of the fused rings.

In the present specification, unless otherwise specified, the above described "fused-ring heteroaryl group" is preferably a group having 8 to 12 ring members. That is to say, examples of the "8- to 12-membered fused-ring heteroaryl group" include indolyl, isoindolyl, benzofuranyl, isobenzofuranyl, benzothienyl, isobenzothienyl, benzoxazolyl, 1,2-benzoisoxazolyl, benzothiazolyl, 1,2-benzisothiazolyl, 1H-benzimidazolyl, 1H-indazolyl, 1H-benzotriazolyl, 2,1,3-benzothiadiazinyl, chromenyl, isochromenyl, 4H-1,4-benzoxazinyl, 4H-1,4-benzothiazinyl, quinolyl, isoquinolyl, cinnolinyl, quinazolinyl, quinoxalinyl, phthalazinyl, benzoxazepinyl, benzazepinyl, benzodiazepinyl, naphthyridinyl, purinyl, pteridinyl, carbazolyl, carbolinyl, acridinyl, phenoxazinyl, phenothiazinyl, phenazinyl, phenoxathiinyl, thianthrenyl, thianthrenyl, phenanthridinyl, phenanthrolinyl, indolizinyl, thieno[3,2-c]pyridyl, thiazolo[5,4-c]pyridyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,5-a]pyrimidinyl, 1,2,4-triazolo[4,3-a]pyridyl, 1,2,4-triazolo[4,3-b]pyridazinyl, 1H-pyrazolo[3,4-b]pyridyl, and 1,2,4-triazolo[1,5-a]pyrimidinyl.

In the present specification, unless otherwise specified, the term "partially hydrogenated fused-ring heteroaryl group" means a monovalent group formed by removing any given hydrogen atom from a partially hydrogenated fused ring in a fused ring that is formed by condensation of a "heterocyclic group" and an "aryl group," or of a "heterocyclic group" and a "heteroaryl group." As the any given hydrogen atom, either a hydrogen atom in any ring portions of the "heterocyclic group," the "aryl group," and the "heteroaryl group" in the fused ring, or a hydrogen atom in the hydrogenated ring portion, may be removed. For example, if quinoline is partially hydrogenated tetrahydroquinolyl, examples of the partially hydrogenated fused-ring heteroaryl group include 5,6,7,8-tetrahydroquinolyl and 1,2,3,4-tetrahydroquinolyl. Depending on the position from which any given hydrogen atom is removed, examples of the 5,6,7,8-tetrahydroquinolyl include groups with suffixes -2-yl, -3-yl, -4-yl, -5-yl, -6-yl, -7-yl, and -8-yl, and examples of the 1,2,3,4-tetrahydroquinolyl include groups with suffixes -1-yl, -2-yl, -3-yl, -4-yl, -5-yl, -6-yl, -7-yl, and -8-yl.

In the present specification, unless otherwise specified, the "partially hydrogenated fused-ring heteroaryl group" is preferably a group having 8 to 12 ring members. That is to say, examples of the "partially hydrogenated 8- to 12-membered fused-ring heteroaryl group" include indolinyl, 4,5,6,7-tetrahydro-1H-indonyl, 2,3-dihydrobenzofuranyl, 4,5,6,7-tetrahydro-benzofuranyl, 2,3-dihydrobenzo[d]oxazolyl, 2,3-dihydrobenzo[d]thiazolyl, chromanyl, 2H-chromenyl, 4H-chromenyl, isochromanyl, 1H-isochromenyl, 3,4-dihydro-2H-1,4-benzoxazinyl, 3,4-dihydro-2H-1,4-benzothiazinyl, 5,6,7,8-tetrahydroquinolyl, 1,2,3,4-tetrahydroquinolyl, 1,2-dihydroquinolyl, 1,2,3,4-tetrahydroquinazolyl, 1,2-dihydroquinazolyl, 2,4-dihydro-1H-benzo[d][1,3]oxazinyl, 2,4-dihydro-1H-benzo[d][1,3]thiazinyl, 5,6,7,8-tetrahydroisoquinolyl, 1,2-dihydroisoquinolyl, 1,2,3,4-tetrahydroisoquinolyl, 1,2-dihydroquinoxalinyl, 1,4-dihydroquinoxalinyl, 1,2,3,4-tetrahydroquinoxalinyl, 4H-benzo[d][1,3]dioxanyl, 2,3-dihydrobenzo[b][1,4]dioxanyl, 1,3-benzodioxolyl, 2,3,4,5-tetrahydrobenzo[b][1,4]oxazepinyl, 2,3,4,5-tetrahydro-1H-benzo[b]azepinyl, 2,3,4,5-tetrahydro-1H-benzo[b]oxepinyl, 2,3,4,5-tetrahydro-1H-benzo[b]thiepinyl, and 6,7,8,9-tetrahydro-5H-cyclohept[b]pyridyl.

In the present specification, unless otherwise specified, the term "non-aromatic heterocyclic group" means a "3- to 14-membered saturated or unsaturated non-aromatic heterocyclic group."

In the present specification, unless otherwise specified, the term "3- to 14-membered saturated or unsaturated non-aromatic heterocyclic group" means a monovalent group formed by removing any given hydrogen atom from a 3- to 14-membered saturated or unsaturated heterocyclic ring containing one to four heteroatoms selected from among an oxygen atom, a sulfur atom, and a nitrogen atom.

In the present specification, unless otherwise specified, examples of the "3- to 14-membered non-aromatic heterocyclic group" include aziridinyl, azetidinyl, oxiranyl, thiiranyl, oxetanyl, thietanyl, pyrrolidinyl, tetrahydrofuryl, dihydrofuryl, thiolanyl, pyrazolinyl, pyrazolidinyl, imidazolidinyl, piperidinyl, dihydropyranyl, tetrahydropyranyl(oxanyl), tetrahydrothiopyranyl, piperazinyl, dioxanyl, oxazolidinyl, isoxazolynyl, 1,3-oxazolidinyl, isoxazolidinyl, thiazolinyl, isothiazolinyl, 1,3-thiazolidinyl, isothiazolidinyl, oxadiazolinyl, 1,3,4-oxadiazolidinyl, morpholinyl, thiomorpholinyl, quinuclidinyl, azepanyl, diazepinyl, and oxepanyl.

In the present specification, unless otherwise specified, the term "alkoxyl group" means a group in which the above described "alkyl group" is substituted with an oxygen atom, and examples of the alkoxyl group include a "$C_{1-6}$ alkoxyl group." The alkoxyl group is generally represented by RO— (R=alkyl group).

In the present specification, unless otherwise specified, examples of the "$C_{1-6}$ alkoxyl group" include methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethylpropoxy, 1-ethylpropoxy, hexyloxy, isohexyloxy, 1-methylpentyloxy, 2-methylpentyloxy, 3-methylpentyloxy, 1,1-dimethylbutyloxy, 1,2-dimethylbutyloxy, 2,2-dimethylbutyloxy, 1,3-dimethylbutyloxy, 2,3-dimethylbutyloxy, 3,3-dimethylbutoxy, 1-ethylbutyloxy, 2-ethylbutyloxy, 1,1,2-trimethylpropyloxy, 1,2,2-trimethylpropyloxy, 1-ethyl-1-methylpropyloxy, 1-ethyl-2-methylpropyloxy, cyclopropyloxy, cyclobutyloxy, cyclopentyloxy, cyclohexyloxy, cyclopropylmethoxy, cyclobutylmethoxy, cyclopentylmethoxy, 1-cyclopropylethoxy, 2-cyclopropylethoxy, 2-cyclobutylethoxy, and 2-methylcyclopropyloxy.

In the present specification, unless otherwise specified, the term "aryloxy group" means a group in which the above described "aryl group" is substituted with an oxygen atom, and examples of the aryloxy group include a "$C_{6-14}$ aryloxy group."

In the present specification, unless otherwise specified, examples of the "$C_{6-14}$ aryloxy group" include phenoxy, 1-naphthyloxy, 2-naphthyloxy, 2-anthryloxy, and phenanthryloxy.

In the present specification, unless otherwise specified, the term "aralkyloxy group" means a group in which the above described "aralkyl group" is substituted with an oxygen atom, and examples of the aralkyloxy group include a "$C_{2-20}$ aralkyloxy group."

In the present specification, unless otherwise specified, examples of the "$C_{2-20}$ aralkyloxy group" include benzyloxy, phenethyloxy, 3-phenylpropoxy, 1-naphthylmethoxy, 2-naphthylmethoxy, 2-(1-naphthyl)ethoxy, 2-(2-naphthyl)ethoxy, 1-indanylmethoxy, 2-indanylmethoxy, 1,2,3,4-tetrahydronaphthalen-1-ylmethoxy, and 1,2,3,4-tetrahydronaphthalen-2-ylmethoxy.

In the present specification, unless otherwise specified, the term "$C_{1-6}$ alkoxyl $C_{1-6}$ alkyl group" means a group in which the above described "$C_{1-6}$ alkoxyl group" is substituted with the above described "$C_{1-6}$ alkyl group." In the present specification, unless otherwise specified, examples of the "$C_{1-6}$ alkoxyl $C_{1-6}$ alkyl group" include methoxymethyl, methoxyethyl, ethoxymethyl, ethoxyethyl, 1,1-dimethoxymethyl, and 1,1-diethoxyethyl.

In the present specification, unless otherwise specified, the term "$C_{1-6}$ alkoxyl $C_{2-6}$ alkenyl group" means a group in which the above described "$C_{1-6}$ alkoxyl group" is substituted with the above described "$C_{2-6}$ alkenyl group." In the present specification, unless otherwise specified, examples of the "$C_{1-6}$ alkoxyl $C_{2-6}$ alkenyl group" include 2-methoxyvinyl, 2-ethoxyvinyl, 2-propoxyvinyl, 3-methoxyallyl, 3-ethoxyallyl, and 3-ethoxyallyl.

In the present specification, unless otherwise specified, the term "halogenated $C_{1-6}$ alkoxyl group" means a group in which a "$C_{1-6}$ alkyl group" portion of the above described "$C_{1-6}$ alkoxyl group" is optionally substituted with one to five halogen atoms. Examples of the halogenated $C_{1-6}$ alkoxyl group include fluoromethoxy, difluoromethoxy, trifluoromethoxy, 2,2,2-trifluoroethoxy, 1,1,2,2-tetrafluoroethoxy, and pentafluoroethoxy.

In the present specification, unless otherwise specified, the term "alkanoyl group" means an "alkylcarbonyl group" in which a carbonyl group binds to the above described "alkyl group." Examples of the alkanoyl group include a "$C_{2-7}$ alkanoyl group." The alkanoyl group is generally represented by R—CO— (R=alkyl group).

In the present specification, unless otherwise specified, examples of the "$C_{2-7}$ alkanoyl group" include acetyl, propionyl, butyryl, isobutyryl, valeryl, isovaleryl, pivaloyl, hexanoyl, heptanoyl, cyclopropylcarbonyl, cyclobutylcarbonyl, cyclopentylcarbonyl, cyclohexylcarbonyl, cyclopropylmethylcarbonyl, and 2-methylcyclopropylcarbonyl.

In the present specification, unless otherwise specified, the term "halogenated $C_{2-7}$ alkanoyl group" means a group in which a "$C_{1-6}$ alkyl group" portion of the above described "$C_{2-7}$ alkanoyl group" is optionally substituted with one to five halogen atoms. Examples of the halogenated $C_{2-7}$ alkanoyl group include trifluoroacetyl and 3,3,3-trifluoropropionyl.

In the present specification, unless otherwise specified, the term "hydroxy $C_{2-7}$ alkanoyl group" means a group in which the above described "$C_{2-7}$ alkanoyl group" is optionally substituted with one to five hydroxyl groups. Examples of the hydroxy $C_{2-7}$ alkanoyl group include hydroxyacetyl and 3-hydroxypropionyl.

In the present specification, unless otherwise specified, the term "$C_{3-8}$ cycloalkylcarbonyl group" means a group in which a carbonyl group binds to the above described "$C_{3-8}$ cycloalkyl group." Examples of the $C_{3-8}$ cycloalkylcarbonyl group include cyclopropylcarbonyl, cyclobutylcarbonyl, cyclopentylcarbonyl, cyclohexylcarbonyl, cycloheptylcarbonyl, and cyclooctylcarbonyl.

In the present specification, unless otherwise specified, the term "alkylthio group" means a group in which a hydrogen atom of a "thiol group (—SH)" is substituted with the above described "alkyl group." Examples of the alkylthio group include a "$C_{1-6}$ alkylthio group." The alkylthio group is generally represented by —SR (R=alkyl group).

In the present specification, unless otherwise specified, examples of the "$C_{1-6}$ alkylthio group" include methylthio, ethylthio, propylthio, isopropylthio, butylthio, isobutylthio, sec-butylthio, tert-butylthio, pentylthio, isopentylthio, neopentylthio, tert-pentylthio, 1-methylbutylthio, 2-methylbutylthio, 1,2-dimethylpropylthio, 1-ethylpropylthio, hexylthio, isohexylthio, 1-methylpentylthio, 2-methylpentylthio, 3-methylpentylthio, 1,1-dimethylbutylthio, 1,2-dimethylbutylthio, 2,2-dimethylbutylthio, 1,3-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, and 1-ethyl-2-methylpropylthio. In addition, the "alkylthio group" can be restated as an "alkylsulfanyl group." That is to say, the "$C_{1-6}$ alkylthio group" means the same group as a "$C_{1-6}$ alkylsulfanyl group."

In the present specification, unless otherwise specified, examples of the "$C_{3-8}$ cycloalkylthio group" include cyclopropylthio, cyclobutylthio, cyclopentylthio, and cyclohexylthio.

In the present specification, unless otherwise specified, the term "alkylsulfinyl group" means a group in which a "sulfinyl group (—S(O)—)" is substituted with the above described "alkyl group." Examples of the alkylsulfinyl group include a "$C_{1-6}$ alkylsulfinyl group." The alkylsulfinyl group is generally represented by —S(O)R (R=alkyl group).

In the present specification, unless otherwise specified, examples of the "$C_{1-6}$ alkylsulfinyl group" include methylsulfinyl, ethylsulfinyl, propylsulfinyl, and isopropylsulfinyl.

In the present specification, unless otherwise specified, the term "alkylsulfonyl group" means a group in which a "sulfonyl group (—SO$_2$—)" is substituted with the above described "alkyl group." Examples of the alkylsulfonyl group include a "$C_{1-6}$ alkylsulfonyl group." The alkylsulfonyl group is generally represented by —SO$_2$R (R=alkyl group).

In the present specification, unless otherwise specified, examples of the "$C_{1-6}$ alkylsulfonyl group" include methylsulfonyl, ethylsulfonyl, propylsulfonyl, and isopropylsulfonyl.

In the present specification, unless otherwise specified, the term "$C_{3-8}$ cycloalkylsulfonyl group" means a group in which a "sulfonyl group (—SO$_2$—)" is substituted with the above described "$C_{3-8}$ cycloalkyl group." Examples of the $C_{3-8}$ cycloalkylsulfonyl group include cyclopropylsulfonyl, cyclobutylsulfonyl, cyclopentylsulfonyl, cyclohexylsulfonyl, cycloheptylsulfonyl, and cyclooctylsulfonyl.

In the present specification, unless otherwise specified, the term "halogenated $C_{1-6}$ alkylsulfonyl group" means a group in which an "alkyl group" portion of the above described "$C_{1-6}$ alkylsulfonyl group" is optionally substituted with one to five halogen atoms. Examples of the halogenated $C_{1-6}$ alkylsulfonyl group include trifluoromethanesulfonyl.

In the present specification, unless otherwise specified, the term "arylsulfonyl group" means a group in which a "sulfonyl group (—SO$_2$—)" is substituted with the above described "aryl group." Examples of the arylsulfonyl group include a "$C_{6-14}$ arylsulfonyl group."

In the present specification, unless otherwise specified, examples of the "$C_{6-14}$ arylsulfonyl group" include phenylsulfonyl, 1-naphthylsulfonyl, 2-naphthylsulfonyl, indan-4-sulfonyl, indene-4-sulfonyl, and 5,6,7,8-tetrahydronaphthyl-1-sulfonyl.

In the present specification, unless otherwise specified, the term "aralkylsulfonyl group" means a group in which a "sulfonyl group (—SO$_2$—)" is substituted with the above described "aralkyl group." Examples of the aralkylsulfonyl group include a "$C_{7-20}$ aralkylsulfonyl group."

In the present specification, unless otherwise specified, examples of the "$C_{7-20}$ aralkylsulfonyl group" include benzylsulfonyl and phenethylsulfonyl.

In the present specification, unless otherwise specified, the term "heterocyclic sulfonyl group" means a group in which the above described "heterocyclic group" is substituted with a "sulfonyl group (—SO$_2$—)." Examples of a "heterocyclic ring" portion of the "heterocyclic sulfonyl group" include a "heteroaryl group," a "partially hydrogenated fused-ring heteroaryl group," and a "non-aromatic heterocyclic group," which are exemplified in the above described "heterocyclic group."

In the present specification, unless otherwise specified, examples of the "heterocyclic sulfonyl group" include a "heteroarylsulfonyl group," a "partially hydrogenated fused-ring heteroarylsulfonyl group," and a "non-aromatic heterocyclic sulfonyl group."

In the present specification, unless otherwise specified, examples of the "heteroarylsulfonyl group" include pyridylsulfonyl, furanylsulfonyl, and indonylsulfonyl.

In the present specification, unless otherwise specified, examples of the "partially hydrogenated fused-ring heteroarylsulfonyl group" include indolinylsulfonyl, chromanylsulfonyl, 5,6,7,8-tetrahydroquinolylsulfonyl, 1,2,3,4-tetrahydroquinolyloxycarbonyloxy, 1,2,3,4-tetrahydroisoquinolylsulfonyl, and 2,3-dihydrobenzo[b][1,4]dioxanylsulfonyl.

In the present specification, unless otherwise specified, examples of the "non-aromatic heterocyclic sulfonyl group" include pyrrolidinylsulfonyl, piperidinylsulfonyl, piperazinylsulfonyl, and morpholinylsulfonyl.

In the present specification, unless otherwise specified, the term "$C_{1-6}$ alkoxylcarbonyl group" means a group in which a hydrogen atom of a "carboxy group (—COOH)" is substituted with the above described "$C_{1-6}$ alkyl group," namely, it means an "ester group." The $C_{1-6}$ alkoxylcarbonyl group is generally represented by "the group: —COOC$_{1-6}$ alkyl."

In the present specification, unless otherwise specified, examples of the "$C_{1-6}$ alkoxylcarbonyl group" include methyl ester (methoxycarbonyl), ethyl ester (ethoxycarbonyl), and tert-butyl ester (tert-butoxycarbonyl).

In the present specification, unless otherwise specified, the term "arylcarbonyl group" means a group in which a carbonyl group binds to the above described "aryl group." Examples of the arylcarbonyl group include a "$C_{6-14}$ arylcarbonyl group."

In the present specification, unless otherwise specified, examples of the "$C_{6-14}$ arylcarbonyl group" include benzoyl, 1-naphthoyl (1-naphthylcarbonyl), 2-naphthoyl (2-naphthylcarbonyl), indan-4-carbonyl, indene-4-carbonyl, and 5,6,7,8-tetrahydronaphthyl-1-carbonyl.

In the present specification, unless otherwise specified, the term "aralkylcarbonyl group" means a group in which a carbonyl group binds to the above described "aralkyl group." Examples of the aralkylcarbonyl group include a "$C_{7-20}$ aralkylcarbonyl group."

In the present specification, unless otherwise specified, examples of the "$C_{7-20}$ aralkylcarbonyl group" include phenylacetyl and 3-phenylpropionyl.

In the present specification, unless otherwise specified, the term "heterocyclic carbonyl group" means a group in which a carbonyl group binds to the above described "heterocyclic group." Examples of a "heterocyclic ring" portion of the "heterocyclic carbonyl group" include a "heteroaryl group," a "partially hydrogenated fused-ring heteroaryl group," and a "non-aromatic heterocyclic group," which are exemplified in the above described "heterocyclic group."

In the present specification, unless otherwise specified, examples of the "heterocyclic carbonyl group" include a "heteroarylcarbonyl group," a "partially hydrogenated fused-ring heteroarylcarbonyl group," and a "non-aromatic heterocyclic carbonyl group."

In the present specification, unless otherwise specified, examples of the "heteroarylcarbonyl group," in which the "heteroaryl group" portion is a "monocyclic heteroaryl group," include pyrrolylcarbonyl, furylcarbonyl, thienylcarbonyl, imidazolylcarbonyl, pyrazolylcarbonyl, oxazolylcarbonyl, isoxazolylcarbonyl, thiazolylcarbonyl, isothiazolylcarbonyl, 1,2,3-triazolylcarbonyl, 1,2,4-triazolylcarbonyl, 1,2,3-oxadiazolylcarbonyl, 1,2,4-oxadiazolylcarbonyl, 1,3,4-oxadiazolylcarbonyl, furazanylcarbonyl, 1,2,3-thiadiazolylcarbonyl, 1,2,4-thiadiazolylcarbonyl, 1,3,4-thiadiazolylcarbonyl, tetrazolylcarbonyl, pyridylcarbonyl, pyridazinylcarbonyl, pyrimidinylcarbonyl, pyrazinylcarbonyl, 1,2,3-triazinylcarbonyl, 1,2,4-triazinylcarbonyl, 1,3,5-triazinylcarbonyl, 2H-1,2,3-thiadiazinylcarbonyl, 4H-1,2,4-thiadiazinylcarbonyl, 6H-1,3,4-thiadiazinylcarbonyl, 1,4-diazepinylcarbonyl, and 1,4-oxazepinylcarbonyl.

Moreover, examples of the "heteroarylcarbonyl group," in which the "heteroaryl group" portion is a "fused-ring heteroaryl group," include indolylcarbonyl, isoindolylcarbonyl, benzofuranylcarbonyl, isobenzofuranylcarbonyl, benzothienylcarbonyl, isobenzothienylcarbonyl, benzoxazolylcarbonyl, 1,2-benzisoxazolylcarbonyl, benzothiazolylcarbonyl, 1,2-benzisothiazolylcarbonyl, 1H-benzimidazolylcarbonyl, 1H-indazolylcarbonyl, 1H-benzotriazolylcarbonyl, 2,1,3-benzothiadiazinylcarbonyl, quinolylcarbonyl, isoquinolylcarbonyl, cinnolinylcarbonyl, quinazolinylcarbonyl, quinoxalinylcarbonyl, phthalazinylcarbonyl, benzoxazepinylcarbonyl, benzazepinylcarbonyl, benzodiazepinylcarbonyl, naphthyridinylcarbonyl, purinylcarbonyl, pteridinylcarbonyl, carbazolylcarbonyl, carbolinylcarbonyl, acridinylcarbonyl, phenoxazinylcarbonyl, phenothiazinylcarbonyl, phenazinylcarbonyl, phenoxathiinylcarbonyl, thianthrenylcarbonyl, phenanthridinyl carbonyl, phenanthrolinyl carbonyl, indolizinylcarbonyl, thieno[3,2-c]pyridylcarbonyl, thiazolo[5,4-c]pyridylcarbonyl, pyrrolo[1,2-b]pyridazinylcarbonyl, pyrazolo[1,5-a]pyridylcarbonyl, imidazo[1,2-a]pyridylcarbonyl, imidazo[1,5-a]pyridylcarbonyl, imidazo[1,2-b]pyridazinylcarbonyl, imidazo[1,5-a]pyrimidinylcarbonyl, 1,2,4-triazolo[4,3-a]pyridylcarbonyl, 1,2,4-triazolo[4,3-b]pyridazinylcarbonyl, 1H-pyrazolo[3,4-b]pyridylcarbonyl, and 1,2,4-triazolo[1,5-a]pyrimidinylcarbonyl.

In the present specification, unless otherwise specified, examples of the "partially hydrogenated fused-ring heteroarylcarbonyl group" include indolinylcarbonyl, 4,5,6,7-tetrahydro-1H-indonylcarbonyl, 2,3-dihydrobenzofuranylcarbonyl, 4,5,6,7-tetrahydro-benzofuranylcarbonyl, 2,3-dihydrobenzo[d]oxazolylcarbonyl, 2,3-dihydrobenzo[d]thiazolylcarbonyl, chromanylcarbonyl, 2H-chromenylcarbonyl, 4H-chromenylcarbonyl, isochromanylcarbonyl, 1H-isochromenylcarbonyl, 3,4-dihydro-2H-1,4-benzoxazinylcarbonyl, 3,4-dihydro-2H-1,4-benzothiazinylcarbonyl, 5,6,7,8-tetrahydroquinolylcarbonyl, 1,2,3,4-tetrahydroquinolylcarbonyl, 1,2-dihydroquinolylcarbonyl, 1,2,3,4-tetrahydroquinazolylcarbonyl, 1,2-dihydroquinazolylcarbonyl, 2,4-dihydro-1H-benzo[d][1,3]oxazinylcarbonyl, 2,4-dihydro-1H-benzo[d][1,3]thiazinylcarbonyl, 5,6,7,8-tetrahydroisoquinolylcarbonyl, 1,2-dihydroisoquinolylcarbonyl, 1,2,3,4-tetrahydroisoquinolylcarbonyl, 1,2-dihydroquinoxalinylcarbonyl, 1,4-dihydroquinoxalinylcarbonyl, 1,2,3,4-tetrahydroquinoxalinylcarbonyl, 4H-benzo[d][1,3]dioxanylcarbonyl, 2,3-dihydrobenzo[b][1,4]dioxanylcarbonyl, 1,3-benzodioxolylcarbonyl, 2,3,4,5-tetrahydrobenzo[b][1,4]oxazepinylcarbonyl, 2,3,4,5-tetrahydro-1H-benzo[b]azepinylcarbonyl, 2,3,4,5-tetrahydro-1H-benzo[b]oxepinylcarbonyl, 2,3,4,5-tetrahydro-1H-benzo[b]thiepinylcarbonyl, and 6,7,8,9-tetrahydro-5H-cyclohept[b]pyridylcarbonyl.

In the present specification, unless otherwise specified, examples of the "non-aromatic heterocyclic carbonyl group" include aziridinylcarbonyl, azetidinylcarbonyl, pyrrolidinylcarbonyl, tetrahydrofurylcarbonyl, piperidinylcarbonyl, tetrahydropyranylcarbonyl, piperazinylcarbonyl, and morpholinylcarbonyl.

In the present specification, unless otherwise specified, the term "amino group" means a substituent wherein, in the "—$NR^7R^8$ group," $R^7$ and $R^8$ are each a hydrogen atom.

In the present specification, unless otherwise specified, the term "mono-/di-alkylcarbamoyl group" means a carbamoyl group in which one or two hydrogen atoms on a nitrogen atom of the above described "carbamoyl group" (or $R^7$ and $R^8$ in "the group: —$CONR^7R^8$") are substituted with the above described "alkyl groups." Examples of the mono-/di-alkylcarbamoyl group include a "mono-/di-$C_{1-6}$ alkylcarbamoyl group."

In the present specification, unless otherwise specified, examples of the "mono-/di-$C_{1-6}$ alkylcarbamoyl group" include methylcarbamoyl, ethylcarbamoyl, propylcarbamoyl, isopropylcarbamoyl, butylcarbamoyl, isobutylcarbamoyl, pentylcarbamoyl, isopentylcarbamoyl, hexylcarbamoyl, isohexylcarbamoyl, dimethylcarbamoyl, diethylcarbamoyl, dipropylcarbamoyl, diisopropylcarbamoyl, dibutylcarbamoyl, dipentylcarbamoyl, ethylmethylcarbamoyl, methylpropylcarbamoyl, ethylpropylcarbamoyl, butylmethylcarbamoyl, butylethylcarbamoyl, and butylpropylcarbamoyl.

In the present specification, unless otherwise specified, the term "mono-/di-cycloalkylcarbamoyl group" means a carbamoyl group in which one or two hydrogen atoms on a nitrogen atom of the above described "carbamoyl group" (or $R^7$ and $R^8$ in "the group: —$CONR^7R^8$") are substituted with the above described "cycloalkyl groups." Examples of the mono-/di-cycloalkylcarbamoyl group include a "mono-/di-$C_{3-8}$ cycloalkylcarbamoyl group."

In the present specification, unless otherwise specified, examples of the "mono-/di-$C_{3-8}$ cycloalkylcarbamoyl group" include cyclopropylcarbamoyl, cyclobutylcarbamoyl, cyclopentylcarbamoyl, and cyclohexylcarbamoyl.

In the present specification, unless otherwise specified, the term "mono-/di-halogenated $C_{1-6}$ alkylcarbamoyl group" means a substituent in which a "$C_{1-6}$ alkyl group" portion of the above described "mono-/di-$C_{1-6}$ alkylcarbamoyl group" is optionally substituted with one to five halogen atoms. Examples of the mono-/di-halogenated $C_{1-6}$ alkylcarbamoyl group include trifluoromethylcarbamoyl, 1,1,1-trifluoroethylcarbamoyl, and ditrifluoromethylcarbamoyl.

In the present specification, unless otherwise specified, the term "mono-/di-arylcarbamoyl group" means a carbamoyl group in which one or two hydrogen atoms on a nitrogen atom of the above described "carbamoyl group" (or $R^7$ and $R^8$ in "the group: —CONR$^7$R$^8$") are substituted with the above described "aryl groups." Examples of the mono-/di-arylcarbamoyl group include a "mono-/di-$C_{6-14}$ arylcarbamoyl group."

In the present specification, unless otherwise specified, specific examples of the "mono-/di-$C_{6-14}$ arylcarbamoyl group" include phenylcarbamoyl, 2-naphthylcarbamoyl, diphenylcarbamoyl, and 2-naphthylphenylcarbamoyl.

In the present specification, unless otherwise specified, the term "mono-/di-aralkylcarbamoyl group" means a carbamoyl group in which one or two hydrogen atoms on a nitrogen atom of the above described "carbamoyl group" (or $R^7$ and $R^8$ in "the group: —CONR$^7$R$^8$") are substituted with the above described "aralkyl groups." Examples of the mono-/di-aralkylcarbamoyl group include a "mono-/di-$C_{7-20}$ aralkylcarbamoyl group."

In the present specification, unless otherwise specified, specific examples of the "mono-/di-$C_{7-20}$ aralkylcarbamoyl group" include benzylcarbamoyl and dibenzylcarbamoyl.

In the present specification, unless otherwise specified, the term "mono-/di-heterocyclic carbamoyl group" means a carbamoyl group in which one or two hydrogen atoms on a nitrogen atom of the above described "carbamoyl group" (or $R^7$ and $R^8$ in "the group: —CONR$^7$R$^8$") are substituted with the above described "heterocyclic groups." Examples of a "heterocyclic ring" portion of the "mono-/di-heterocyclic carbamoyl group" include a "heteroaryl group," a "partially hydrogenated fused-ring heteroaryl group," and a "non-aromatic heterocyclic group," which are exemplified in the above described "heterocyclic group."

In the present specification, unless otherwise specified, examples of the "mono-/di-heterocyclic carbamoyl group" include a "mono-/di-heteroarylcarbamoyl group," a "mono-/di-partially hydrogenated fused-ring heteroarylcarbamoyl group," and a "mono-/di-non-aromatic heterocyclic carbamoyl group."

In the present specification, unless otherwise specified, examples of the "mono-/di-heteroarylcarbamoyl group," the "mono-/di-partially hydrogenated fused-ring heteroarylcarbamoyl group," and the "mono-/di-non-aromatic heterocyclic carbamoyl group" include pyridylcarbamoyl, indolylcarbamoyl, tetrahydropyranylcarbamoyl, dipyridylcarbamoyl, benzofuranylpyridylcarbamoyl, furanylpiperidinylcarbamoyl, 3,4-dihydro-2H-benzo[b][1,4]oxazinylcarbamoyl, and ditetrahydroquinolylcarbamoyl.

In the present specification, unless otherwise specified, the term "mono-/di-alkylsulfamoyl group" means a sulfamoyl group in which one or two hydrogen atoms of the above described "sulfamoyl group" (or $R^7$ and $R^8$ in "the group: —SO$_2$NR$^7$R$^8$") are substituted with the above described "alkyl groups." Examples of the mono-/di-alkylsulfamoyl group include a "mono-/di-$C_{1-6}$ alkylsulfamoyl group."

In the present specification, unless otherwise specified, examples of the "mono-/di-$C_{1-6}$ alkylsulfamoyl group" include methylsulfamoyl, ethylsulfamoyl, propylsulfamoyl, isopropylsulfamoyl, butylsulfamoyl, isobutylsulfamoyl, pentylsulfamoyl, isopentylsulfamoyl, hexylsulfamoyl, isohexylsulfamoyl, dimethylsulfamoyl, diethylsulfamoyl, dipropylsulfamoyl, diisopropylsulfamoyl, dibutylsulfamoyl, dipentylsulfamoyl, ethylmethylsulfamoyl, methylpropylsulfamoyl, ethylpropylsulfamoyl, butylmethylsulfamoyl, butylethylsulfamoyl, and butylpropylsulfamoyl.

In the present specification, unless otherwise specified, the term "mono-/di-cycloalkylsulfamoyl group" means a sulfamoyl group in which one or two hydrogen atoms of the above described "sulfamoyl group" (or $R^7$ and $R^8$ in "the group: —SO$_2$NR$^7$R$^8$") are substituted with the above described "cycloalkyl groups." Examples of the mono-/di-cycloalkylsulfamoyl group include a "mono-/di-$C_{3-8}$ cycloalkylsulfamoyl group."

In the present specification, unless otherwise specified, examples of the "mono-/di-$C_{3-8}$ cycloalkylsulfamoyl group" include cyclopropylsulfamoyl, cyclobutylsulfamoyl, cyclopentylsulfamoyl, and cyclohexylsulfamoyl.

In the present specification, unless otherwise specified, the term "mono-/di-halogenated $C_{1-6}$ alkylsulfamoyl group" means a substituent in which a "$C_{1-6}$ alkyl group" portion of the above described "mono-/di-$C_{1-6}$ alkylsulfamoyl group" is optionally substituted with one to five halogen atoms. Examples of the mono-/di-halogenated $C_{1-6}$ alkylsulfamoyl group include trifluoromethylsulfamoyl, 1,1,1-trifluoroethylsulfamoyl, and ditrifluoromethylsulfamoyl.

In the present specification, unless otherwise specified, the term "mono-/di-arylsulfamoyl group" means a sulfamoyl group in which one or two hydrogen atoms of the above described "sulfamoyl group" (or $R^7$ and $R^8$ in "the group: —SO$_2$NR$^7$R$^8$") are substituted with the above described "aryl groups." Examples of the mono-/di-arylsulfamoyl group include a "mono-/di-$C_{6-14}$ arylsulfamoyl group."

In the present specification, unless otherwise specified, examples of the "mono-/di-$C_{6-14}$ arylsulfamoyl group" include phenylsulfamoyl, 2-naphthylsulfamoyl, diphenylsulfamoyl, and 2-naphthylphenylsulfamoyl.

In the present specification, unless otherwise specified, the term "mono-/di-aralkylsulfamoyl group" means a sulfamoyl group in which one or two hydrogen atoms of the above described "sulfamoyl group" (or $R^7$ and $R^8$ in "the group: —SO$_2$NR$^7$R$^8$") are substituted with the above described "aralkyl groups." Examples of the mono-/di-aralkylsulfamoyl group include a "mono-/di-$C_{7-20}$ aralkylsulfamoyl group."

In the present specification, unless otherwise specified, examples of the "mono-/di-$C_{7-20}$ aralkylsulfamoyl group" include benzylsulfamoyl and dibenzylsulfamoyl.

In the present specification, unless otherwise specified, the term "mono-/di-heterocyclic sulfamoyl group" means a sulfamoyl group in which one or two hydrogen atoms of the above described "sulfamoyl group" (or $R^7$ and $R^8$ in "the group: —SO$_2$NR$^7$R$^8$") are substituted with the above described "heterocyclic groups." Examples of a "heterocyclic ring" portion of the "mono-/di-heterocyclic sulfamoyl group" include a "heteroaryl group," a "partially hydrogenated fused-ring heteroaryl group," and a "non-aromatic heterocyclic group," which are exemplified in the above described "heterocyclic group."

In the present specification, unless otherwise specified, examples of the "mono-/di-heterocyclic sulfamoyl group" include a "mono-/di-heteroarylsulfamoyl group," a "mono-/di-partially hydrogenated fused-ring heteroarylsulfamoyl group," and a "mono-/di-non-aromatic heterocyclic sulfamoyl group."

In the present specification, unless otherwise specified, examples of the "mono-/di-heteroarylsulfamoyl group," the "mono-/di-partially hydrogenated fused-ring heteroarylsulfamoyl group," and the "mono-/di-non-aromatic heterocyclic sulfamoyl group" include pyridylsulfamoyl, indolylsulfamoyl, tetrahydropyranylsulfamoyl, dipyridylsulfamoyl, benzofuranylpyridylsulfamoyl, furanylpiperidinylsulfamoyl, 3,4-dihydro-2H-benzo[b][1,4]oxazinylsulfamoyl, and ditetrahydroquinolylsulfamoyl.

[1-1]

A preferred compound of the above embodiment [1] is a compound represented by the formula (I) wherein the definition of p, q, Z, $R^2$, $R^3$, $R^4$, $R^5$, $R^6$, $R^7$, $R^8$, ring A, and fused ring B in the formula (I) have the same definitions as those described in the above embodiment [1]; and $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfonyl group, an —$NR^7R^8$ group, or a —$CONR^7R^8$ group wherein $R^7$ and $R^8$ in the —$NR^7R^8$ group and the —$CONR^7R^8$ group have the same definitions as those described in the above embodiment [1], or a pharmaceutically acceptable salt thereof, or a solvate thereof.

[1-1-2]

More preferably, the compound of the above embodiment [1] is a compound represented by the above formula (I) wherein the definition of q, Z, $R^2$, $R^3$, $R^4$, $R^5$, $R^6$, $R^7$, $R^8$, ring A, and fused ring B in the formula (I) have the same definitions as those described in the above embodiment [1]; p is an integer of 0 to 3; and $R^1$ each independently represents a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a hydroxy $C_{1-6}$ alkyl group, a $C_{1-6}$ alkoxyl $C_{1-6}$ alkyl group, a $C_{1-6}$ alkylthio group, a $C_{1-6}$ alkylsulfonyl group, an —$NR^{7A}R^{8A}$ group, or a —$CONR^{7A}R^{8A}$ group wherein $R^{7A}$ and $R^{8A}$ in the —$NR^{7A}R^{8A}$ group and the —$CONR^{7A}R^{8A}$ group each independently represent a substituent selected from among a hydrogen atom, a $C_{1-6}$ alkyl group, a halogenated $C_{1-6}$ alkyl group, a hydroxy $C_{1-6}$ alkyl group, a $C_{2-7}$ alkanoyl group, a hydroxy $C_{2-7}$ alkanoyl group, a halogenated $C_{2-7}$ alkanoyl group, a $C_{1-6}$ alkylsulfonyl group, and a halogenated $C_{1-6}$ alkylsulfonyl group, or a pharmaceutically acceptable salt thereof, or a solvate thereof.

[1-1-2-2]

Even more preferably, the compound of the above embodiment [1] is a compound represented by the above formula (I) wherein the definition of p, q, Z, $R^2$, $R^3$, $R^4$, $R^5$, $R^6$, $R^7$, $R^8$, ring A, and fused ring B in the formula (I) have the same definitions as those described in the above embodiment [1-1-2]; and $R^1$ each independently represents a $C_{2-7}$ alkanoyl group, and has the same definitions as those described in the above embodiment [1-1-2], or a pharmaceutically acceptable salt thereof, or a solvate thereof.

[1-1-3]

Further preferably, the compound of the above embodiment [1] is a compound represented by the above formula (I) wherein the definition of p, q, Z, $R^2$, $R^3$, $R^4$, $R^5$, $R^6$, $R^7$, $R^8$, ring A, and fused ring B in the formula (I) have the same definitions as those described in the above embodiment [1]; p is an integer of 1 to 3; and $R^1$ each independently represents a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a hydroxy $C_{1-6}$ alkyl group, a $C_{1-6}$ alkoxyl $C_{1-6}$ alkyl group, a $C_{1-6}$ alkylthio group, or a $C_{1-6}$ alkylsulfonyl group, or a pharmaceutically acceptable salt thereof, or a solvate thereof.

[1-1-3-2]

Still further preferably, the compound of the above embodiment [1] is a compound represented by the above formula (I) wherein the definition of p, q, Z, $R^2$, $R^3$, $R^4$, $R^5$, $R^6$, $R^7$, $R^8$, ring A, and fused ring B in the formula (I) have the same definitions as those described in the above embodiment [1-1-3]; p is an integer of 0 to 3; and $R^1$ each independently represents a $C_{2-7}$ alkanoyl group, and has the same definitions as those described in the above embodiment [1-1-3], or a pharmaceutically acceptable salt thereof, or a solvate thereof.

[1-1-4]

Particularly preferably, the compound of the above embodiment [1] is a compound represented by the above formula (I) wherein the definition of p, q, Z, $R^2$, $R^3$, $R^4$, $R^5$, $R^6$, $R^7$, $R^8$, ring A, and fused ring B in the formula (I) have the same definitions as those described in the above embodiment [1]; p is an integer of 1 or 2; and $R^1$ each independently represents a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, or a $C_{1-6}$ alkoxyl $C_{1-6}$ alkyl group, and more specifically, $R^1$ represents fluorine, chlorine, bromine, a cyano group, a methyl group, an ethyl group, an isopropyl group, a cyclopropyl group, a difluoromethyl group, a trifluoromethyl group, a vinyl group, a methoxy group, an ethoxyethyl group, or the like, or a pharmaceutically acceptable salt thereof, or a solvate thereof.

[1-1-4-2]

More particularly preferably, the compound of the above embodiment [1] is a compound represented by the above formula (I) wherein the definition of p, q, Z, $R^2$, $R^3$, $R^4$, $R^5$, $R^6$, $R^7$, $R^8$, ring A, and fused ring B in the formula (I) have the same definitions as those described in the above embodiment [1-1-4]; p is an integer of 0 to 3; and $R^1$ each independently represents a hydroxy $C_{1-6}$ alkyl group or a $C_{2-7}$ alkanoyl group, and has the same definitions as those described in the above embodiment [1-1-4], and more specifically, $R^1$ represents fluorine, chlorine, bromine, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group, an ethoxyethyl group, or the like, or a pharmaceutically acceptable salt thereof, or a solvate thereof.

[1-2]

Preferably, the compound of the above embodiment [1] is a compound represented by the formula (I) wherein the definition of p, q, Z, $R^1$, $R^3$, $R^4$, $R^5$, $R^6$, $R^7$, $R^8$, ring A, and fused ring B in the formula (I) have the same definitions as those described in the above embodiment [1]; and $R^2$ represents a hydrogen atom, a $C_{1-6}$ alkyl group, a halogenated $C_{1-6}$ alkyl group, or a $C_{1-6}$ alkoxyl $C_{1-6}$ alkyl group, or a pharmaceutically acceptable salt thereof, or a solvate thereof.

[1-2-2]

More preferably, the compound of the above embodiment [1] is a compound represented by the above formula (I) wherein the definition of p, q, Z, $R^1$, $R^3$, $R^4$, $R^5$, $R^6$, $R^7$, $R^8$, ring A, and fused ring B in the formula (I) have the same definitions as those described in the above embodiment [1]; and $R^2$ represents a hydrogen atom, a $C_{1-6}$ alkyl group, or a halogenated $C_{1-6}$ alkyl group, or a pharmaceutically acceptable salt thereof, or a solvate thereof.

[1-2-3]

Even more preferably, the compound of the above embodiment [1] is a compound represented by the above formula (I) wherein the definition of p, q, Z, $R^1$, $R^3$, $R^4$, $R^5$, $R^6$, $R^7$, $R^8$, ring A, and fused ring B in the formula (I) have the same definitions as those described in the above embodiment [1]; and $R^2$ represents a hydrogen atom or a $C_{1-6}$ alkyl group, and more specifically, $R^2$ represents a hydrogen atom, a methyl group, or the like, or a pharmaceutically acceptable salt thereof, or a solvate thereof.

[1-2-4]

Particularly preferably, the compound of the above embodiment [1] is a compound represented by the above formula (I) wherein the definition of p, q, Z, $R^1$, $R^3$, $R^4$, $R^5$, $R^6$, $R^7$, $R^8$, ring A, and fused ring B in the formula (I) have the same definitions as those described in the above embodiment [1]; and $R^2$ represents a $C_{1-6}$ alkyl group, and more specifically, $R^2$ represents a methyl group, or a pharmaceutically acceptable salt thereof, or a solvate thereof.

[1-3]

Preferably, the compound of the above embodiment [1] is a compound represented by the formula (I) wherein the definition of p, q, Z, $R^1$, $R^2$, $R^4$, $R^5$, $R^6$, $R^7$, $R^8$, ring A, and fused ring B in the formula (I) have the same definitions as those described in the above embodiment [1]; and $R^3$ each independently represents a halogen atom, a cyano group, a $C_{1-6}$ alkyl group, a halogenated $C_{1-6}$ alkyl group, a $C_{1-6}$ alkoxyl group, or a halogenated $C_{1-6}$ alkoxyl group, or a pharmaceutically acceptable salt thereof, or a solvate thereof.

[1-3-2]

More preferably, the compound of the above embodiment [1] is a compound represented by the above formula (I) wherein the definition of p, q, Z, $R^1$, $R^2$, $R^4$, $R^5$, $R^6$, $R^7$, $R^8$, ring A, and fused ring B in the formula (I) have the same definitions as those described in the above embodiment [1]; q represents an integer of 0 to 3; and $R^3$ each independently represents a halogen atom, a cyano group, a $C_{1-6}$ alkyl group, or a $C_{1-6}$ alkoxyl group, or a pharmaceutically acceptable salt thereof, or a solvate thereof.

[1-3-3]

Even more preferably, the compound of the above embodiment [1] is a compound represented by the above formula (I) wherein the definition of p, q, Z, $R^1$, $R^2$, $R^4$, $R^5$, $R^6$, $R^7$, $R^8$, ring A, and fused ring B in the formula (I) have the same definitions as those described in the above embodiment [1]; q represents an integer of 0 to 2; and $R^3$ each independently represents a halogen atom, a cyano group, a $C_{1-6}$ alkyl group, or a $C_{1-6}$ alkoxyl group, or a pharmaceutically acceptable salt thereof, or a solvate thereof.

[1-3-4]

Particularly preferably, the compound of the above embodiment [1] is a compound represented by the above formula (I) wherein the definition of p, q, Z, $R^1$, $R^2$, $R^4$, $R^5$, $R^6$, $R^7$, $R^8$, ring A, and fused ring B in the formula (I) have the same definitions as those described in the above embodiment [1]; q represents an integer of 0 or 1; and $R^3$ each independently represents a hydrogen atom, a halogen atom, or a cyano group, and more specifically, $R^3$ represents fluorine, chlorine, a cyano group, or the like, or a pharmaceutically acceptable salt thereof, or a solvate thereof.

[1-3-5]

More particularly preferably, the compound of the above embodiment [1] is a compound represented by the above formula (I) wherein the definition of p, q, Z, $R^1$, $R^2$, $R^4$, $R^5$, $R^6$, $R^7$, $R^8$, ring A, and fused ring B in the formula (I) have the same definitions as those described in the above embodiment [1]; q represents an integer of 0 or 1; and $R^3$ represents a halogen atom, and more specifically, $R^3$ represents fluorine, chlorine, or the like, or a pharmaceutically acceptable salt thereof, or a solvate thereof.

[1-4]

Preferably, the compound of the above embodiment [1] is a compound represented by the formula (I) wherein the definition of p, q, Z, $R^1$, $R^2$, $R^3$, $R^5$, $R^6$, $R^7$, $R^8$, ring A, and fused ring B in the formula (I) have the same definitions as those described in the above embodiment [1]; and $R^4$ represents a halogen atom, a $C_{1-6}$ alkyl group, a halogenated $C_{1-6}$ alkyl group, a $C_{3-8}$ cycloalkyl group, a $C_{1-6}$ alkoxyl group, a halogenated $C_{1-6}$ alkoxyl group, a $C_{1-6}$ alkylthio group, a $C_{1-6}$ alkylsulfonyl group, a —$CONR^7R^8$ group, an —$NR^7R^8$ group wherein $R^7$ and $R^8$ in the —$NR^7R^8$ group and the —$CONR^7R^8$ group have the same definitions as those described in the above embodiment [1], a $C_{6-14}$ aryl group, a 3- to 14-membered non-aromatic heterocyclic group, or a 5- to 7-membered monocyclic heteroaryl group wherein the $C_{3-8}$ cycloalkyl group, the $C_{6-14}$ aryl group, the 3- to 14-membered non-aromatic heterocyclic group, and the 5- to 7-membered monocyclic heteroaryl group, which are represented by $R^4$, are optionally substituted with one to three groups selected from among a hydroxyl group, a nitro group, a cyano group, a halogen atom, a $C_{1-6}$ alkyl group, a halogenated $C_{1-6}$ alkyl group, a hydroxy $C_{1-6}$ alkyl group, a $C_{1-6}$ alkoxyl group, a halogenated $C_{1-6}$ alkoxyl group, a $C_{1-6}$ alkoxyl $C_{1-6}$ alkyl group, a $C_{1-6}$ alkylthio group, a $C_{1-6}$ alkylsulfonyl group, a —$CONR^7R^8$ group, an —$NR^7R^8$ group wherein $R^7$ and $R^8$ in the —$NR^7R^8$ group and the —$CONR^7R^8$ group have the same definitions as those described in the above embodiment [1], a $C_{6-14}$ aryl group, a 3- to 14-membered non-aromatic heterocyclic group, and a 5- to 7-membered monocyclic heteroaryl group, or a pharmaceutically acceptable salt thereof, or a solvate thereof.

[1-4-2]

More preferably, the compound of the above embodiment [1] is a compound represented by the above formula (I) wherein the definition of p, q, Z, $R^1$, $R^2$, $R^3$, $R^5$, $R^6$, $R^7$, $R^8$, ring A, and fused ring B in the formula (I) have the same definitions as those described in the above embodiment [1]; and $R^4$ represents a halogen atom, a $C_{1-6}$ alkyl group, a $C_{3-8}$ cycloalkyl group, a $C_{1-6}$ alkoxyl group, a $C_{1-6}$ alkylthio group, a $C_{1-6}$ alkylsulfonyl group, an —$NR^{7A}R^{8A}$ group wherein $R^{8A}$ and $R^{8A}$ in the —$NR^{7A}R^{8A}$ group have the same definitions as those of $R^{7A}$ and $R^{8A}$ in the above embodiment [1-1-2], a $C_{6-14}$ aryl group, a 3- to 14-membered non-aromatic heterocyclic group, or a 5- to 7-membered monocyclic heteroaryl group wherein the $C_{3-8}$ cycloalkyl group, the $C_{6-14}$ aryl group, the 3- to 14-membered non-aromatic heterocyclic group, and the 5- to 7-membered monocyclic heteroaryl group, which are represented by $R^4$, are optionally substituted with one to three groups selected from among a hydroxyl group, a nitro group, a cyano group, a halogen atom, a $C_{1-6}$ alkyl group, a halogenated $C_{1-6}$ alkyl group, a hydroxy $C_{1-6}$ alkyl group, a $C_{1-6}$ alkoxyl group, a halogenated $C_{1-6}$ alkoxyl group, a $C_{1-6}$ alkoxyl $C_{1-6}$ alkyl group, a $C_{1-6}$ alkylthio group, a $C_{1-6}$ alkylsulfonyl group, a —CONR$^{7A}$R$^{8A}$ group, an —NR$^{7A}$R$^{8A}$ group wherein R$^{7A}$ and R$^{8A}$ in the —NR$^{7A}$R$^{8A}$ group and the —CONR$^{7A}$R$^{8A}$ group have the same definitions as those of R$^{7A}$ and R$^{8A}$ in the above embodiment [1-1-2], a $C_{6-14}$ aryl group, a 3- to 14-membered non-aromatic heterocyclic group, and a 5- to 7-membered monocyclic heteroaryl group, or a pharmaceutically acceptable salt thereof, or a solvate thereof.

[1-4-3]

Even more preferably, the compound of the above embodiment [1] is a compound represented by the above formula (I) wherein the definition of p, q, Z, R$^1$, R$^2$, R$^3$, R$^5$, R$^6$, R$^7$, R$^8$, ring A, and fused ring B in the formula (I) have the same definitions as those described in the above embodiment [1]; and R$^4$ represents a halogen atom, a $C_{1-6}$ alkyl group, a $C_{3-8}$ cycloalkyl group, a $C_{1-6}$ alkoxyl group, a $C_{1-6}$ alkylsulfonyl group, a $C_{6-14}$ aryl group, a 3- to 14-membered non-aromatic heterocyclic group, or a 5- to 7-membered monocyclic heteroaryl group wherein the $C_{3-8}$ cycloalkyl group, the $C_{6-14}$ aryl group, the 3- to 14-membered non-aromatic heterocyclic group, and the 5- to 7-membered monocyclic heteroaryl group, which are represented by R$^4$, are optionally substituted with one to three groups selected from among a hydroxyl group, a nitro group, a cyano group, a halogen atom, a $C_{1-6}$ alkyl group, a halogenated $C_{1-6}$ alkyl group, a hydroxy $C_{1-6}$ alkyl group, a $C_{1-6}$ alkoxyl group, a halogenated $C_{1-6}$ alkoxyl group, a $C_{1-6}$ alkoxyl $C_{1-6}$ alkyl group, a $C_{1-6}$ alkylthio group, a $C_{1-6}$ alkylsulfonyl group, a —CONR$^{7A}$R$^{8A}$ group, an —NR$^{7A}$R$^{8A}$ group wherein R$^{7A}$ and R$^{8A}$ in the —NR$^{7A}$R$^{8A}$ group and the —CONR$^{7A}$R$^{8A}$ group have the same definitions as those of R$^{7A}$ and R$^{8A}$ in the above embodiment [1-1-2], a $C_{6-14}$ aryl group, a 3- to 14-membered non-aromatic heterocyclic group, and a 5- to 7-membered monocyclic heteroaryl group, or a pharmaceutically acceptable salt thereof, or a solvate thereof.

[1-4-4]

Particularly preferably, the compound of the above embodiment [1] is a compound represented by the above formula (I) wherein the definition of p, q, Z, R$^1$, R$^2$, R$^3$, R$^5$, R$^6$, R$^7$, R$^8$, ring A, and fused ring B in the formula (I) have the same definitions as those described in the above embodiment [1]; and R$^4$ represents a halogen atom, a $C_{6-14}$ aryl group, or a 3- to 14-membered non-aromatic heterocyclic group wherein the $C_{6-14}$ aryl group and the 3- to 14-membered non-aromatic heterocyclic group, which are represented by R$^4$, are optionally substituted with one or two groups selected from among a halogen atom, a $C_{1-6}$ alkyl group, a halogenated $C_{1-6}$ alkyl group, a $C_{1-6}$ alkoxyl group, and a $C_{1-6}$ alkoxyl $C_{1-6}$ alkyl group, and specifically, R$^4$ represents chlorine, bromine, a phenyl group, a pyrrolidinyl group, or a morpholinyl group wherein the phenyl group, the pyrrolidinyl group, and the morpholinyl group are each optionally substituted with one or two groups selected from among fluorine, a methyl group, a methoxy group, and a methoxymethyl group, and more specifically, R$^4$ represents chlorine, bromine, phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 2-methylphenyl, 3-methylphenyl, 4-methylphenyl, 2-methoxyphenyl, 3-methoxyphenyl, 4-methoxyphenyl, 2-methoxymethylphenyl, 3-methoxymethylphenyl, 4-methoxymethylphenyl, pyrrolidinyl, 2-fluoropyrrolidinyl, 3-fluoropyrrolidinyl, 2-methylpyrrolidinyl, 3-methylpyrrolidinyl, 2-trifluoromethylpyrrolidinyl, 3-trifluoromethylpyrrolidinyl, 2-methoxypyrrolidinyl, 3-methoxypyrrolidinyl, 2-methoxymethylpyrrolidinyl, 3-methoxymethylpyrrolidinyl, 2-fluoromorpholinyl, 3-fluoromorpholinyl, 3,5-difluoromorpholinyl, 2,6-difluoromorpholinyl, 2-methylmorpholinyl, 3-methylmorpholinyl, 3,5-dimethylmorpholinyl, 2,6-dimethylmorpholinyl, 2-methoxymethylmorpholinyl, 3-methoxymethylmorpholinyl, 3,5-di(methoxymethyl)morpholinyl, 2,6-di(methoxymethyl)morpholinyl, or the like, or a pharmaceutically acceptable salt thereof, or a solvate thereof.

[1-4-4-2]

More particularly preferably, the compound of the above embodiment [1] is a compound represented by the above formula (I) wherein the definition of p, q, Z, R$^1$, R$^2$, R$^3$, R$^5$, R$^6$, R$^7$, R$^8$, ring A, and fused ring B in the formula (I) have the same definitions as those described in the above embodiment [1-4-4]; and R$^4$ represents a halogen atom, a $C_{6-14}$ aryl group, a 3- to 14-membered non-aromatic heterocyclic group, or a 5- to 7-membered monocyclic heteroaryl group wherein the $C_{6-14}$ aryl group, the 3- to 14-membered non-aromatic heterocyclic group, and the 5- to 7-membered monocyclic heteroaryl group, which are represented by R$^4$, are optionally substituted with one or two groups selected from among a halogen atom, a $C_{1-6}$ alkyl group, a halogenated $C_{1-6}$ alkyl group, a $C_{1-6}$ alkoxyl group, and a $C_{1-6}$ alkoxyl $C_{1-6}$ alkyl group, and specifically, R$^4$ represents chlorine, bromine, a phenyl group, a pyridinyl group, a pyrrolidinyl group, or a morpholinyl group wherein the phenyl group, the pyridinyl group, the pyrrolidinyl group, and the morpholinyl group are each optionally substituted with one or two groups selected from among fluorine, a methyl group, a methoxy group, and a methoxymethyl group, and more specifically, R$^4$ represents chlorine, bromine, phenyl, 2-pyridinyl, 3-pyridinyl, 4-pyridinyl, 2-fluorophenyl, 3-fluorophenyl, 4-fluorophenyl, 2,3-difluorophenyl, 2,4-difluorophenyl, 2,5-difluorophenyl, 2,6-difluorophenyl, 2-methylphenyl, 3-methylphenyl, 4-methylphenyl, 2-methoxyphenyl, 3-methoxyphenyl, 4-methoxyphenyl, 2-methoxymethylphenyl, 3-methoxymethylphenyl, 4-methoxymethylphenyl, pyrrolidinyl, 2-fluoropyrrolidinyl, 3-fluoropyrrolidinyl, 2-methylpyrrolidinyl, 3-methylpyrrolidinyl, 2-trifluoromethylpyrrolidinyl, 3-trifluoromethylpyrrolidinyl, 2-methoxypyrrolidinyl, 3-methoxypyrrolidinyl, 2-methoxymethylpyrrolidinyl, 3-methoxymethylpyrrolidinyl, 2-fluoromorpholinyl, 3-fluoromorpholinyl, 3,5-difluoromorpholinyl, 2,6-difluoromorpholinyl, 2-methylmorpholinyl, 3-methylmorpholinyl, 3,5-dimethylmorpholinyl, 2,6-dimethylmorpholinyl, 2-methoxymethylmorpholinyl, 3-methoxymethylmorpholinyl, 3,5-di(methoxymethyl)morpholinyl, 2,6-di(methoxymethyl)morpholinyl, or the like, or a pharmaceutically acceptable salt thereof, or a solvate thereof.

[1-4-5]

Even more particularly preferably, the compound of the above embodiment [1] is a compound represented by the above formula (I) wherein the definition of p, q, Z, R$^1$, R$^2$, R$^3$, R$^5$, R$^6$, R$^7$, R$^8$, ring A, and fused ring B in the formula (I) have the same definitions as those described in the above embodiment [1]; and R$^4$ represents a $C_{6-14}$ aryl group, a 3- to 14-membered non-aromatic heterocyclic group, or a 5- to 7-membered monocyclic heteroaryl group wherein the $C_{6-14}$ aryl group, the 3- to 14-membered non-aromatic heterocyclic group, and the 5- to 7-membered monocyclic heteroaryl group, which are represented by R$^4$, are optionally substituted with one or two groups selected from among a halogen atom, a $C_{1-6}$ alkyl group, a halogenated $C_{1-6}$ alkyl group, a $C_{1-6}$ alkoxyl group, and a $C_{1-6}$ alkoxyl $C_{1-6}$ alkyl group, and specifically, $R^4$ represents phenyl, 2-pyridinyl, 2-fluorophenyl, 3-fluorophenyl, 4-fluorophenyl, 2,5-difluorophenyl, 2-methylphenyl, 2-methoxyphenyl, pyrrolidinyl, 3-fluoropyrrolidinyl, 2-methylpyrrolidinyl, 2-trifluoromethylpyrrolidinyl, 2-methoxymethylpyrrolidinyl, or 2,6-dimethylmorpholinyl, or a pharmaceutically acceptable salt thereof, or a solvate thereof.

[1-5]

Preferably, the compound of the above embodiment [1] is a compound represented by the formula (I) wherein the definition of p, q, Z, $R^1$, $R^2$, $R^3$, $R^4$, $R^6$, $R^7$, $R^8$, ring A, and fused ring B in the formula (I) have the same definitions as those described in the above embodiment [1]; and $R^5$ represents a hydrogen atom, a halogen atom, a $C_{1-6}$ alkyl group, a halogenated $C_{1-6}$ alkyl group, a $C_{1-6}$ alkoxyl group, or a halogenated $C_{1-6}$ alkoxyl group, or a pharmaceutically acceptable salt thereof, or a solvate thereof.

[1-5-2]

More preferably, the compound of the above embodiment [1] is a compound represented by the above formula (I) wherein the definition of p, q, Z, $R^1$, $R^2$, $R^3$, $R^4$, $R^6$, $R^7$, $R^8$, ring A, and fused ring B in the formula (I) have the same definitions as those described in the above embodiment [1]; and $R^5$ represents a hydrogen atom, a halogen atom, a $C_{1-6}$ alkyl group, or a $C_{1-6}$ alkoxyl group, or a pharmaceutically acceptable salt thereof, or a solvate thereof.

[1-5-3]

Even more preferably, the compound of the above embodiment [1] is a compound represented by above the formula (I) wherein the definition of p, q, Z, $R^1$, $R^2$, $R^3$, $R^4$, $R^6$, $R^7$, $R^8$, ring A, and fused ring B in the formula (I) have the same definitions as those described in the above embodiment [1]; and $R^5$ represents a hydrogen atom, a halogen atom, or a $C_{1-6}$ alkyl group, and more specifically, $R^5$ represents a hydrogen atom, fluorine, a methyl group, or the like, or a pharmaceutically acceptable salt thereof, or a solvate thereof.

[1-5-4]

Particularly preferably, the compound of the above embodiment [1] is a compound represented by the above formula (I) wherein the definition of p, q, Z, $R^1$, $R^2$, $R^3$, $R^4$, $R^6$, $R^7$, $R^8$, ring A, and fused ring B in the formula (I) have the same definitions as those described in the above embodiment [1]; and $R^5$ represents a hydrogen atom or a halogen atom, and more specifically, $R^5$ represents a hydrogen atom, fluorine, or the like, or a pharmaceutically acceptable salt thereof, or a solvate thereof.

[1-6]

Preferably, the compound of the above embodiment [1] is a compound represented by the formula (I) wherein the definition of p, q, Z, $R^1$, $R^2$, $R^3$, $R^4$, $R^5$, $R^7$, $R^8$, and fused ring B in the formula (I) have the same definitions as those described in the above embodiment [1];

ring A represented by the following partial structural formula (II):

[Formula 7]

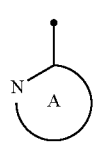

(II)

is selected from the group of the heteroaryls consisting of the following:

[Formula 8]

(II-1)

(II-3)

(II-4)

(II-6)

(II-7)

(II-9)

(II-10)

(II-12)

(II-13)

(II-15)

(II-16), (II-18), (II-19), (II-21), (II-22), (II-24), (II-25), (II-27), (II-29), (II-30), (II-31), (II-32), (II-33), (II-34), (II-35), (II-36), (II-37), (II-38), (II-39), (II-40), (II-41)

(II-42)

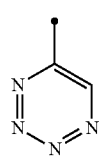

(II-43)

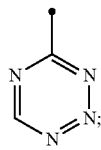

and R⁶ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[1-6-2]
More preferably, the compound of the above embodiment [1] is a compound represented by the above formula (I) wherein the definition of p, q, Z, $R^1$, $R^2$, $R^3$, $R^4$, $R^5$, $R^7$, $R^8$, and fused ring B in the formula (I) have the same definitions as those described in the above embodiment [1];

ring A represented by the following partial structural formula (II):

[Formula 9]

(II)

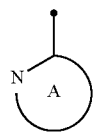

is selected from the group of the heteroaryls consisting of the following:

[Formula 10]

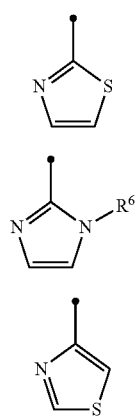

(II-7)

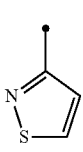

(II-9)

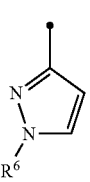

(II-10)

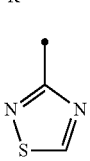

(II-12)

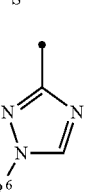

(II-13)

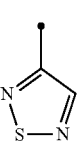

(II-15)

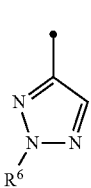

(II-16)

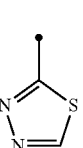

(II-18)

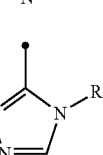

(II-19)

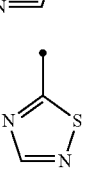

(II-21)

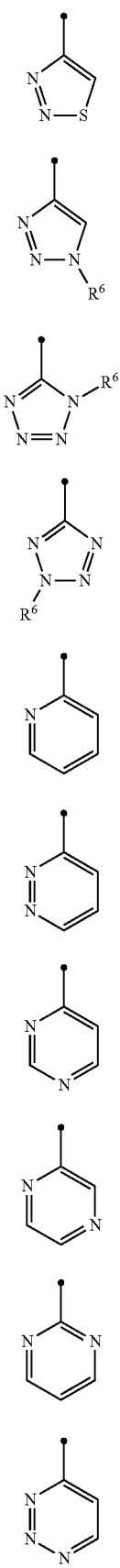
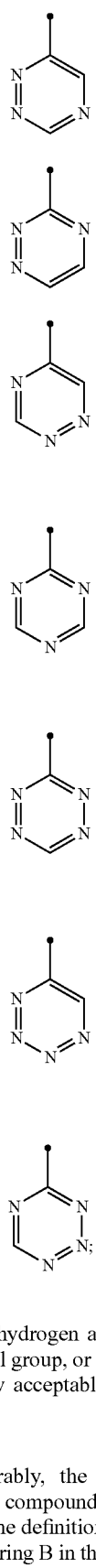

and R⁶ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[1-6-3]

Even more preferably, the compound of the above embodiment [1] is a compound represented by the above formula (I) wherein the definition of p, q, Z, $R^1$, $R^2$, $R^3$, $R^4$, $R^5$, $R^7$, $R^8$, and fused ring B in the formula (I) have the same definitions as those described in the above embodiment [1];

ring A represented by the following partial structural formula (II):
[Formula 11]
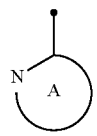
(II)
is selected from the group of the heteroaryls consisting of the following:
[Formula 12]
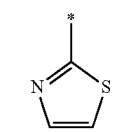
(II-1)
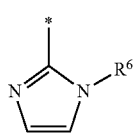
(II-3)
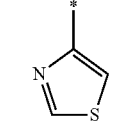
(II-4)
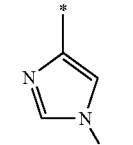
(II-6)
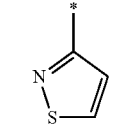
(II-7)
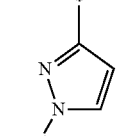
(II-9)
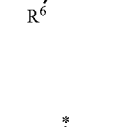
(II-10)
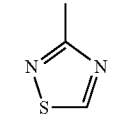
-continued
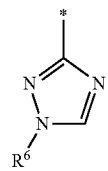
(II-12)
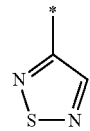
(II-13)
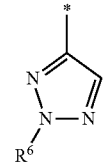
(II-15)
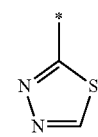
(II-16)
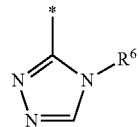
(II-18)
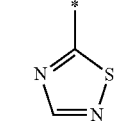
(II-19)
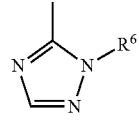
(II-21)
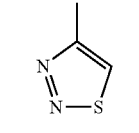
(II-22)
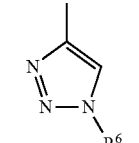
(II-24)
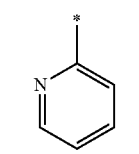
(II-31)

-continued

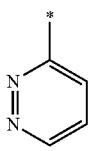 (II-32)

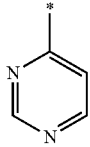 (II-33)

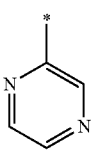 (II-34)

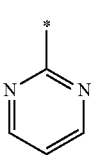 (II-35)

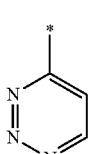 (II-36)

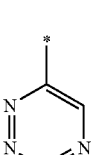 (II-37)

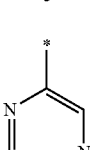 (II-39)

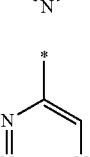 (II-42)

;

and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[1-6-4]

Particularly preferably, the compound of the above embodiment [1] is a compound represented by the above formula (I) wherein the definition of p, q, Z, $R^1$, $R^2$, $R^3$, $R^4$, $R^5$, $R^7$, $R^8$, and fused ring B in the formula (I) have the same definitions as those described in the above embodiment [1];

ring A represented by the following partial structural formula (II):

[Formula 13]

 (II)

is selected from the group of the heteroaryls consisting of the following:

[Formula 14]

 (II-1)

 (II-4)

 (II-6)

 (II-16)

 (II-19)

 (II-31)

 (II-32)

 (II-33)

-continued

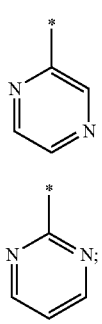
(II-34)

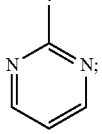
(II-35)

and R⁶ represents a hydrogen atom or a $C_{1-6}$ alkyl group, and more specifically, R⁶ represents a hydrogen atom, a methyl group, or the like, or a pharmaceutically acceptable salt thereof, or a solvate thereof.

[1-6-5]

More particularly preferably, the compound of the above embodiment [1] is a compound represented by the above formula (I) wherein the definition of p, q, Z, $R^1$, $R^2$, $R^3$, $R^4$, $R^5$, $R^7$, $R^8$, and fused ring B in the formula (I) have the same definitions as those described in the above embodiment [1]; ring A and $R^6$ have the same definitions as those described in the above embodiment [1-6-4]; and a specific ring A group, in which the definitions of the above described p, $R^1$, and ring A are combined, represents a 1-methyl-1H-imidazol-4-yl group, a 4-(difluoromethyl)-5-ethylthiazol-2-yl group, a 4-(difluoromethyl)-5-vinylthiazol-2-yl group, a 4-(difluoromethyl)-5-methylthiazol-2-yl group, a 4-(difluoromethyl)-5-methylthiazol-2-yl group, a 4-(difluoromethyl)thiazol-2-yl group, a 4-(difluoromethyl)thiazol-2-yl group, a 4-(trifluoromethyl)thiazol-2-yl group, a 4-(trifluoromethyl)thiazol-2-yl group, a 4,5-dimethylthiazol-2-yl group, a 4-tert-butylthiazol-2-yl group, a 4-ethylthiazol-2-yl group, a 4-cyanothiazol-2-yl group, a 4-methylthiazol-2-yl group, a 4-methylthiazol-2-yl group, a 5-(2-ethoxyethyl)-4-methylthiazol-2-yl group, a 5-chloro-4-(difluoromethyl)thiazol-2-yl group, a 5-chloro-4-(difluoromethyl)thiazol-2-yl group, a 5-cyclopropyl-4-(difluoromethyl)thiazol-2-yl group, a 5-cyclopropyl-4-methylthiazol-2-yl group, a 5-bromo-4-methylthiazol-2-yl group, a 5-methylthiazol-2-yl group, a thiazol-2-yl group, a 2,5-dimethyl-thiazol-4-yl group, a 2-methylthiazol-4-yl group, a 5-(1-hydroxyethyl)-2-methylthiazol-4-yl group, a 5-acetyl-2-methylthiazol-4-yl group, a 5-bromo-2-methylthiazol-4-yl group, a thiazol-4-yl group, a 3-isopropyl-1,2,4-thiadiazol-5-yl group, a 3-methyl-1,2,4-thiadiazol-5-yl group, a 5-ethyl-1,3,4-thiadiazol-2-yl group, a 5-methyl-1,3,4-thiadiazol-2-yl group, a 4-methylpyrimidin-2-yl group, a 4,6-dimethylpyrimidin-2-yl group, a 4-methylpyrimidin-2-yl group, a 2,5,6-trimethylpyrimidin-4-yl group, a 2,5-dimethylpyrimidin-4-yl group, a 2,6-dimethylpyrimidin-4-yl group, a 2,6-dimethoxypyrimidin-4-yl group, a 2-methylpyrimidin-4-yl group, a 2-methoxypyrimidin-4-yl group, a 5,6-dimethylpyrimidin-4-yl group, a 5-chloro-2-methylpyrimidin-4-yl group, a 5-chloropyrimidin-4-yl group, a 5-fluoro-2-methylpyrimidin-4-yl group, a 5-fluoro-2-methoxypyrimidin-4-yl group, a 5-fluoro-6-methylpyrimidin-4-yl group, a 5-methylpyrimidin-4-yl group, a 5-methoxypyrimidin-4-yl group, a 6-methylpyrimidin-4-yl group, a 6-methoxy-5-methylpyrimidin-4-yl group, a 4-methylpyridazin-3-yl group, a 5-methylpyridazin-3-yl group, a 6-methylpyridazin-3-yl group, a pyridazin-3-yl group, a 3-cyanopyridin-2-yl group, a 3-cyano-pyridin-2-yl group, a 3-methylpyridin-2-yl group, a 3-methoxypyridin-2-yl group, a 4,6-dimethylpyridin-2-yl group, a 4-fluoropyridin-2-yl group, a 4-methylpyridin-2-yl group, a 4-methylpyridin-2-yl group, a 4-methoxypyridin-2-yl group, a 4-methoxy-pyridin-2-yl group, a 5-cyanopyridin-2-yl group, a 5-fluoropyridin-2-yl group, a 5-methylpyridin-2-yl group, a 5-methylpyridin-2-yl group, a 6-(trifluoromethyl)pyridin-2-yl group, a 6-cyano-pyridin-2-yl group, a 6-methylpyridin-2-yl group, a 6-methoxypyridin-2-yl group, a 3,6-dimethylpyrazin-2-yl group, a 3,6-dimethyl-pyrazin-2-yl group, a 3-methylpyrazin-2-yl group, a 3-methoxypyrazin-2-yl group, a 5-methylpyrazin-2-yl group, a 6-methylpyrazin-2-yl group, or a 6-methoxypyrazin-2-yl group, or a pharmaceutically acceptable salt thereof, or a solvate thereof.

[1-7]

Preferably, the compound of the above embodiment [1] is a compound represented by the formula (I) wherein the definition of p, Z, $R^1$, $R^2$, $R^3$, $R^4$, $R^5$, $R^6$, $R^7$, $R^8$, and ring A in the formula (I) have the same definitions as those described in the above embodiment [1]; q is an integer represented by 0 to 3; and fused ring B represented by the following partial structural formula (III):

[Formula 15]

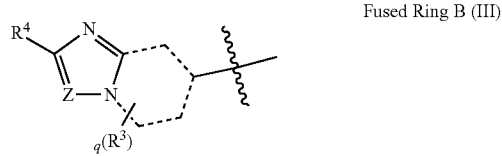
Fused Ring B (III)

is selected from the group consisting of the following:

[Formula 16]

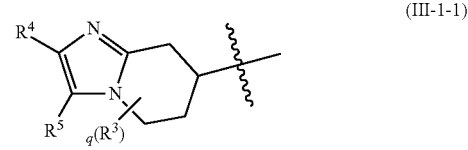
(III-1-1)

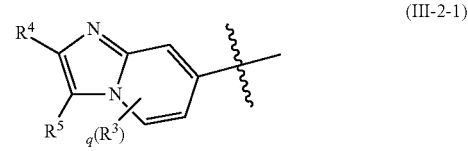
(III-2-1)

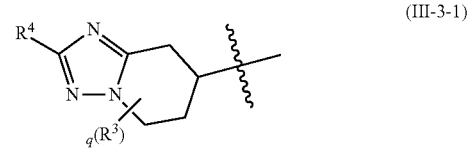
(III-3-1)

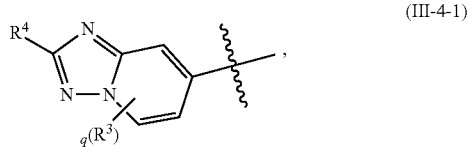
(III-4-1)

or a pharmaceutically acceptable salt thereof, or a solvate thereof.

[1-7-2]

More preferably, the compound of the above embodiment [1] is a compound represented by the above formula (I)

wherein the definition of p, Z, $R^1$, $R^2$, $R^3$, $R^4$, $R^5$, $R^6$, $R^7$, $R^8$, and ring A in the formula (I) have the same definitions as those described in the above embodiment [1]; q is an integer represented by 0 to 2; and fused ring B represented by the following partial structural formula (III):

[Formula 17]

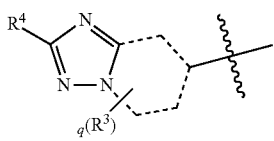

Fused Ring B (III)

is selected from the group consisting of the following:

[Formula 18]

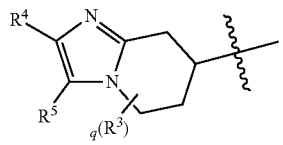

(III-1-1)

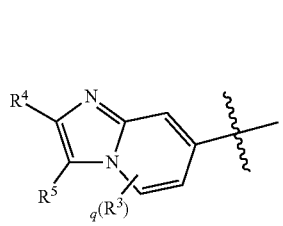

(III-2-1)

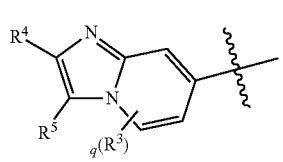

(III-3-1)

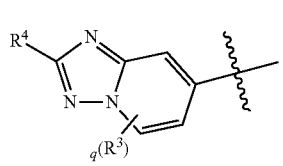

(III-4-1)

or a pharmaceutically acceptable salt thereof, or a solvate thereof.

[1-7-3]

Even more preferably, the compound of the above embodiment [1] is a compound represented by the above formula (I) wherein the definition of p, Z, $R^1$, $R^2$, $R^3$, $R^4$, $R^5$, $R^6$, $R^7$, $R^8$, and ring A in the formula (I) have the same definitions as those described in the above embodiment [1]; q is an integer represented by 0 or 1; and fused ring B represented by the following partial structural formula (III):

[Formula 19]

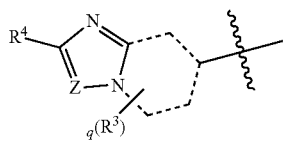

(III)

Fused Ring B is selected from the group consisting of the following:

[Formula 20]

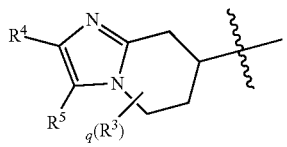

(III-1-1)

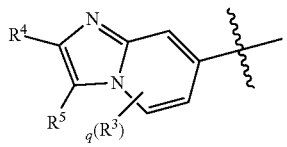

(III-2-1)

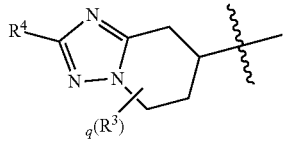

(III-3-1)

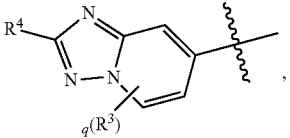

(III-4-1)

or a pharmaceutically acceptable salt thereof, or a solvate thereof.

[1-7-4]

Particularly preferably, the compound of the above embodiment [1] is a compound represented by the above formula (I) wherein the definition of p, Z, $R^1$, $R^2$, $R^3$, $R^4$, $R^5$, $R^6$, $R^7$, $R^8$, and ring A in the formula (I) have the same definitions as those described in the above embodiment [1]; q is an integer represented by 0 or 1; and fused ring B represented by the following partial structural formula (III):

[Formula 21]

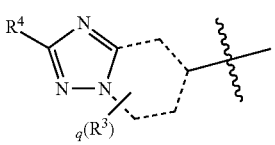

Fused Ring B (III)

is selected from the group consisting of the following:

[Formula 22]

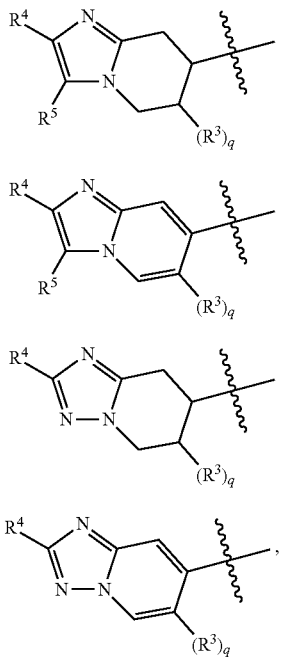

or a pharmaceutically acceptable salt thereof, or a solvate thereof.

[1a]

The compound of the above embodiment [1] is a compound represented by the following formula (I):

[Formula 23]

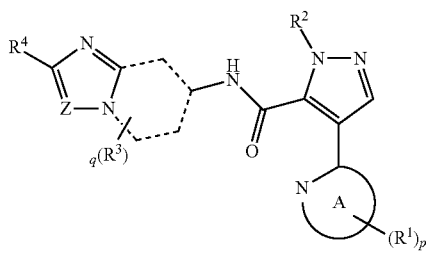

wherein the definition of p, q, Z, $R^1$, $R^3$, $R^4$, $R^5$, $R^6$, ring A represented by the partial structural formula (II), and fused ring B represented by the partial structural formula (III) in the formula (I) have the same definitions as those described in the above embodiment [1]; and $R^2$ represents a $C_{1-6}$ alkyl group, a halogenated $C_{1-6}$ alkyl group, a hydroxy $C_{1-6}$ alkyl group, or a $C_{1-6}$ alkoxyl $C_{1-6}$ alkyl group, or a pharmaceutically acceptable salt thereof, or a solvate thereof.

[1a-1]

Preferably, the compound of the above embodiment [1] is a compound represented by the above formula (I) wherein p represents an integer of 0 to 4; q represents an integer of 0 to 3; Z represents N or $CR^5$; $R^1$ has the same definitions as those described in the above embodiment [1-1]; $R^2$ represents a $C_{1-6}$ alkyl group, a halogenated $C_{1-6}$ alkyl group, or a $C_{1-6}$ alkoxyl $C_{1-6}$ alkyl group; $R^3$ has the same definitions as those described in the above embodiment [1-3]; $R^4$ has the same definitions as those described in the above embodiment [1-4]; $R^5$ has the same definitions as those described in the above embodiment [1-5]; ring A represented by the partial structural formula (II) and $R^6$ have the same definitions as those described in the above embodiment [1-6]; and fused ring B represented by the partial structural formula (III) has the same definitions as those described in the above embodiment [1-7], or a pharmaceutically acceptable salt thereof, or a solvate thereof.

[1a-1-2]

More preferably, the compound of the above embodiment [1] is a compound represented by the above formula (I) wherein p represents an integer of 0 to 3; q represents an integer of 0 to 2; Z represents N or $CR^5$; $R^1$ has the same definitions as those described in the above embodiment [1-1-2-2]; $R^2$ represents a $C_{1-6}$ alkyl group or a halogenated $C_{1-6}$ alkyl group; $R^3$ has the same definitions as those described in the above embodiment [1-3-2]; $R^4$ has the same definitions as those described in the above embodiment [1-4-2]; $R^5$ has the same definitions as those described in the above embodiment [1-5-2]; ring A represented by the partial structural formula (II) and $R^6$ have the same definitions as those described in the above embodiment [1-6-2]; and fused ring B represented by the partial structural formula (III) has the same definitions as those described in the above embodiment [1-7-2], or a pharmaceutically acceptable salt thereof, or a solvate thereof.

[1a-1-3]

Even more preferably, the compound of the above embodiment [1] is a compound represented by the above formula (I) wherein p represents an integer of 0 to 3; q represents an integer of 0 or 1; Z represents N or $CR^5$; $R^1$ has the same definitions as those described in the above embodiment [1-1-3-2]; $R^2$ represents a $C_{1-6}$ alkyl group; $R^3$ has the same definitions as those described in the above embodiment [1-3-3]; $R^4$ has the same definitions as those described in the above embodiment [1-4-3]; $R^5$ has the same definitions as those described in the above embodiment [1-5-3]; ring A represented by the partial structural formula (II) and $R^6$ have the same definitions as those described in the above embodiment [1-6-3]; and fused ring B represented by the partial structural formula (III) has the same definitions as those described in the above embodiment [1-7-3], or a pharmaceutically acceptable salt thereof, or a solvate thereof.

[1a-1-4]

Particularly preferably, the compound of the above embodiment [1] is a compound represented by the above formula (I) wherein p represents an integer of 0 to 3; q represents an integer of 0 or 1; Z represents N or $CR^5$; $R^1$ has the same definitions as those described in the above embodiment [1-1-4-2]; $R^2$ represents a $C_{1-6}$ alkyl group; $R^3$ has the same definitions as those described in the above embodiment [1-3-4]; $R^4$ has the same definitions as those described in the above embodiment [1-4-4-2]; $R^5$ has the same definitions as those described in the above embodiment [1-5-4]; ring A represented by the partial structural formula (II) and $R^6$ have the same definitions as those described in the above embodiment [1-6-4]; and fused ring B represented by the partial structural formula (III) has the same definitions as those described in the above embodiment [1-7-4], or a pharmaceutically acceptable salt thereof, or a solvate thereof.

[1a-1-5]

More particularly preferably, the compound of the above embodiment [1] is a compound represented by the above formula (I) wherein the definition of p, q, Z, $R^1$, $R^2$, $R^3$, $R^4$, $R^5$, $R^6$, ring A represented by the partial structural formula (II), and fused ring B represented by the partial structural formula (III) in the formula (I) have the same definitions as those described in the above embodiment [1a-1-4]; and a specific ring A group, in which the definitions of the above described p, $R^1$, and ring A are combined, represents a 1-methyl-1H-imidazol-4-yl group, a 4-(difluoromethyl)-5-ethylthiazol-2-yl group, a 4-(difluoromethyl)-5-vinylthiazol-2-yl group, a 4-(difluoromethyl)-5-methylthiazol-2-yl group, a 4-(difluoromethyl)-5-methylthiazol-2-yl group, a 4-(difluoromethyl)thiazol-2-yl group, a 4-(difluoromethyl) thiazol-2-yl group, a 4-(trifluoromethyl)thiazol-2-yl group, a 4-(trifluoromethyl)thiazol-2-yl group, a 4,5-dimethylthiazol-2-yl group, a 4-tert-butylthiazol-2-yl group, a 4-ethylthiazol-2-yl group, a 4-cyanothiazol-2-yl group, a 4-methylthiazol-2-yl group, a 4-methylthiazol-2-yl group, a 5-(2-ethoxyethyl)-4-methylthiazol-2-yl group, a 5-chloro-4-(difluoromethyl)thiazol-2-yl group, a 5-chloro-4-(difluoromethyl)thiazol-2-yl group, a 5-cyclopropyl-4-(difluoromethyl)thiazol-2-yl group, a 5-cyclopropyl-4-methylthiazol-2-yl group, a 5-bromo-4-methylthiazol-2-yl group, a 5-methylthiazol-2-yl group, a thiazol-2-yl group, a 2,5-dimethyl-thiazol-4-yl group, a 2-methylthiazol-4-yl group, a 5-(1-hydroxyethyl)-2-methylthiazol-4-yl group, a 5-acetyl-2-methylthiazol-4-yl group, a 5-bromo-2-methylthiazol-4-yl group, a thiazol-4-yl group, a 3-isopropyl-1,2,4-thiadiazol-5-yl group, a 3-methyl-1,2,4-thiadiazol-5-yl group, a 5-ethyl-1,3,4-thiadiazol-2-yl group, a 5-methyl-1,3,4-thiadiazol-2-yl group, a 4-methylpyrimidin-2-yl group, a 4,6-dimethylpyrimidin-2-yl group, a 4-methylpyrimidin-2-yl group, a 2,5,6-trimethylpyrimidin-4-yl group, a 2,5-dimethylpyrimidin-4-yl group, a 2,6-dimethylpyrimidin-4-yl group, a 2,6-dimethoxypyrimidin-4-yl group, a 2-methylpyrimidin-4-yl group, a 2-methoxypyrimidin-4-yl group, a 5,6-dimethylpyrimidin-4-yl group, a 5-chloro-2-methylpyrimidin-4-yl group, a 5-chloropyrimidin-4-yl group, a 5-fluoro-2-methylpyrimidin-4-yl group, a 5-fluoro-2-methoxypyrimidin-4-yl group, a 5-fluoro-6-methylpyrimidin-4-yl group, a 5-methylpyrimidin-4-yl group, a 5-methoxypyrimidin-4-yl group, a 6-methylpyrimidin-4-yl group, a 6-methoxy-5-methylpyrimidin-4-yl group, a 4-methylpyridazin-3-yl group, a 5-methylpyridazin-3-yl group, a 6-methylpyridazin-3-yl group, a pyridazin-3-yl group, a 3-cyanopyridin-2-yl group, a 3-cyano-pyridin-2-yl group, a 3-methylpyridin-2-yl group, a 3-methoxypyridin-2-yl group, a 4,6-dimethylpyridin-2-yl group, a 4-fluoropyridin-2-yl group, a 4-methylpyridin-2-yl group, a 4-methylpyridin-2-yl group, a 4-methoxypyridin-2-yl group, a 4-methoxy-pyridin-2-yl group, a 5-cyanopyridin-2-yl group, a 5-fluoropyridin-2-yl group, a 5-methylpyridin-2-yl group, a 5-methylpyridin-2-yl group, a 6-(trifluoromethyl)pyridin-2-yl group, a 6-cyano-pyridin-2-yl group, a 6-methylpyridin-2-yl group, a 6-methoxypyridin-2-yl group, a 3,6-dimethylpyrazin-2-yl group, a 3,6-dimethyl-pyrazin-2-yl group, a 3-methylpyrazin-2-yl group, a 3-methoxypyrazin-2-yl group, a 5-methylpyrazin-2-yl group, a 6-methylpyrazin-2-yl group, or a 6-methoxypyrazin-2-yl group, or a pharmaceutically acceptable salt thereof, or a solvate thereof.

[1-8]

The compound of the above embodiment [1] represented by the above formula (I) is preferably a compound represented by the following formula (I-a):

[Formula 24]

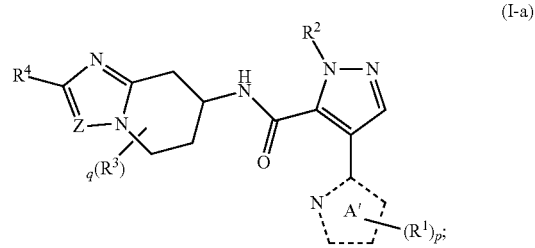

(I-a)

wherein the definition of q, Z, $R^2$, $R^3$, $R^4$, and $R^5$ in the formula (I-a) have the same definitions as those described in the above embodiment [1]; p represents an integer of 0 to 2; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfinyl group, a $C_{1-6}$ alkylsulfonyl group, an —$NR^7R^8$ group, or a —$CONR^7R^8$ group wherein $R^7$ and $R^8$ in the —$NR^7R^8$ group and the —$CONR^7R^8$ group have the same definitions as those described in the above embodiment [1];

ring A' represented by the following partial structural formula (II'):

[Formula 25]

(II')

is selected from the group of the heteroaryls consisting of the following:

[Formula 26]

(II-1)

(II-2)

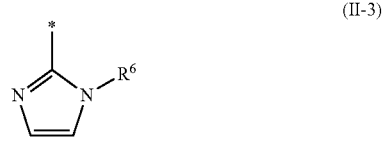

(II-3)

(II-4) 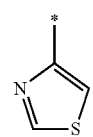
(II-5) 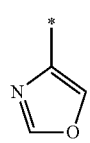
(II-6) 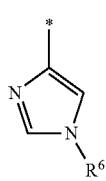
(II-7) 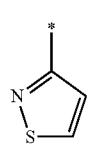
(II-8) 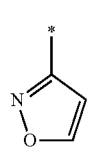
(II-9) 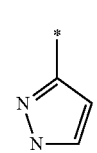
(II-10) 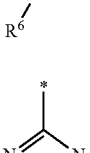
(II-11) 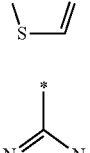
(II-12) 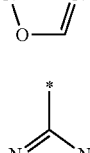
(II-13) 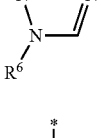
(II-14) 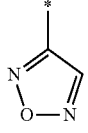
(II-15) 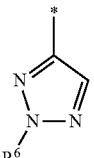
(II-16) 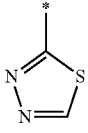
(II-17) 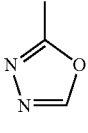
(II-18) 
(II-19) 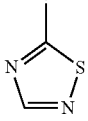
(II-20) 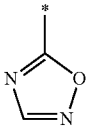
(II-21) 
(II-22) 
(II-23) 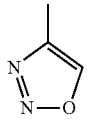
(II-24) 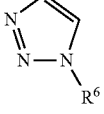

-continued (II-25) 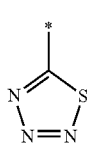

(II-26) 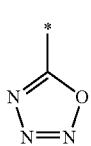

(II-27) 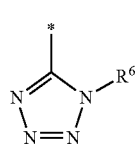

(II-28) 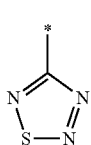

(II-29) 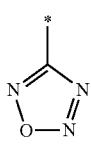

(II-30) 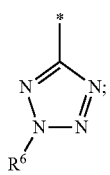

and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[1-8-2]

Preferably, the compound of the above embodiment [1-8] is a compound represented by the above formula (I-a) wherein the definition of q, Z, $R^2$, $R^3$, $R^4$, and $R^5$ in the formula (I-a) have the same definitions as those described in the above embodiment [1]; p represents an integer of 0 to 2; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfonyl group, an —$NR^7R^8$ group, or a —$CONR^7R^8$ group wherein $R^7$ and $R^8$ in the —$NR^7R^8$ group and the —$CONR^7R^8$ group have the same definitions as those described in the above embodiment [1];

ring A' represented by the following partial structural formula (II'):

[Formula 27]

is selected from the group of the heteroaryls consisting of the following:

[Formula 28]

(II-1) 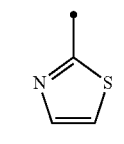

(II-3) 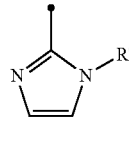

(II-4) 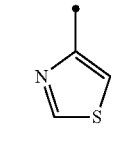

(II-6) 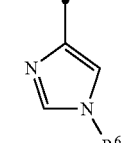

(II-7) 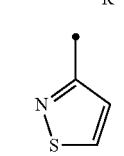

(II-9) 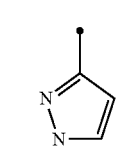

(II-10) 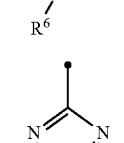

(II-12) 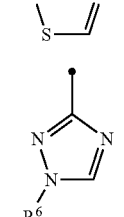

(II-13) 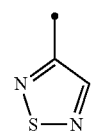

(II-15) 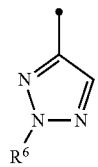

(II-16) 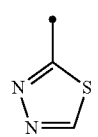

(II-18) 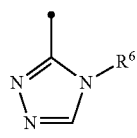

(II-19) 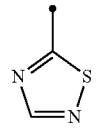

(II-21) 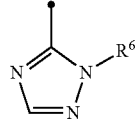

(II-22) 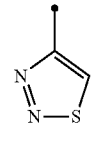

(II-24) 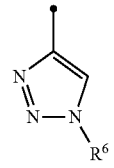

(II-25) 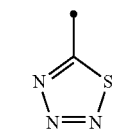

(II-27) 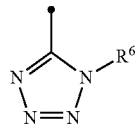

(II-29) 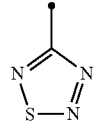

(II-30) 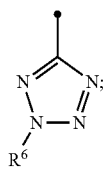

and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[1-8-3]

More preferably, the compound of the above embodiment [1-8] is a compound represented by the above formula (I-a) wherein the definition of q, Z, $R^2$, $R^3$, $R^4$, and $R^5$ in the formula (I-a) have the same definitions as those described in the above embodiment [1]; p represents an integer of 0 to 2; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfonyl group, a —$CONR^{7A}R^{8A}$ group, or an —$NR^{7A}R^{8A}$ group wherein $R^{7A}$ and $R^{8A}$ in the —$NR^{7A}R^{8A}$ group and the —$CONR^{7A}R^{BA}$ group have the same definitions as those of $R^{7A}$ and $R^{8A}$ in the above embodiment [1-1-2];

ring A' represented by the following partial structural formula (II'):

[Formula 29]

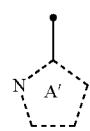

(II')

is selected from the group of the heteroaryls consisting of the following:

[Formula 30]

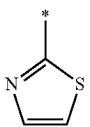

(II-1)

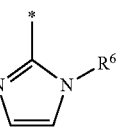

(II-3)

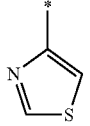

(II-4)

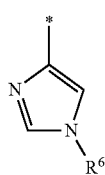 (II-6)

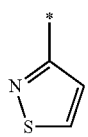 (II-7)

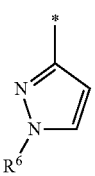 (II-9)

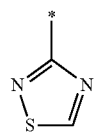 (II-10)

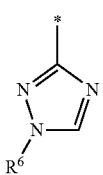 (II-12)

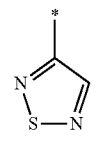 (II-13)

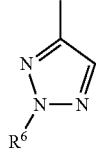 (II-15)

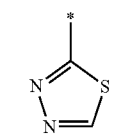 (II-16)

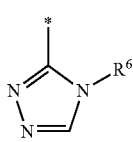 (II-18)

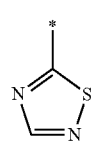 (II-19)

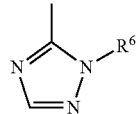 (II-21)

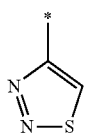 (II-22)

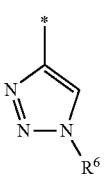 (II-24)

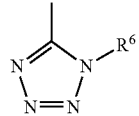 (II-27)

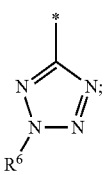 (II-30)

and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[1-8-3-2]

Even more preferably, the compound of the above embodiment [1-8] is a compound represented by the above formula (I-a) wherein the definition of p, q, Z, $R^2$, $R^3$, $R^4$, $R^5$, $R^6$, and ring A' represented by the partial structural formula (II') in the formula (I-a) have the same definitions as those described in the above embodiment [1-8-3]; and $R^1$ each independently represents a hydroxy $C_{1-6}$ alkyl group, and has the same definitions as those described in the above embodiment [1-8-3], or a pharmaceutically acceptable salt thereof, or a solvate thereof.

[1-8-4]

Further preferably, the compound of the above embodiment [1-8] is a compound represented by the above formula (I-a) wherein the definition of q, Z, $R^2$, $R^3$, $R^4$, and $R^5$ in the formula (I-a) have the same definitions as those described in the above embodiment [1]; p represents an integer of 1 or 2; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxyl $C_{1-6}$ alkyl group, a $C_{2-7}$ alkanoyl group, a $C_{1-6}$ alkylthio group, or a $C_{1-6}$ alkylsulfonyl group;

ring A' represented by the following partial structural formula (II'):

[Formula 31]

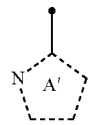
(II')

is selected from the group of the heteroaryls consisting of the following:

[Formula 32]

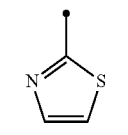
(II-1)

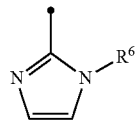
(II-3)

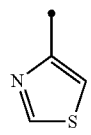
(II-4)

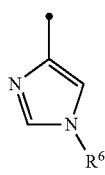
(II-6)

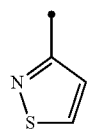
(II-7)

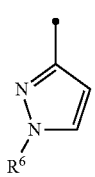
(II-9)

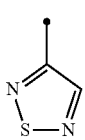
(II-13)

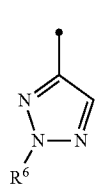
(II-15)

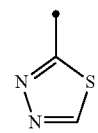
(II-16)

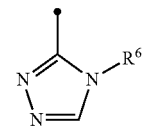
(II-18)

(II-19)

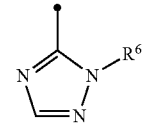
(II-21)

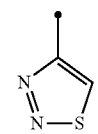
(II-22)

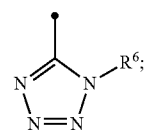
(II-24)

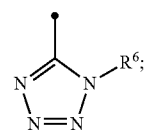
(II-27)

and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[1-8-4-2]

Still further preferably, the compound of the above embodiment [1-8] is a compound represented by the above formula (I-a) wherein the definition of q, Z, $R^2$, $R^3$, $R^4$, $R^5$, $R^6$, and ring A' represented by the partial structural formula (II') in the formula (I-a) have the same definitions as those described in the above embodiment [1-8-4]; p represents an integer of 0 to 2; and $R^1$ each independently represents a hydroxy $C_{1-6}$ alkyl group, and has the same definitions as those described in the above embodiment [1-8-4], or a pharmaceutically acceptable salt thereof, or a solvate thereof.

[1-8-5]

Particularly preferably, the compound of the above embodiment [1-8] is a compound represented by the above formula (I-a) wherein the definition of q, Z, $R^2$, $R^3$, $R^4$, and $R^5$ in the formula (I-a) have the same definitions as those described in the above embodiment [1]; p represents an integer of 1 or 2; and $R^1$ each independently represents a halogen atom, a cyano group, a $C_{1-6}$ alkyl group, a $C_{3-8}$ cycloalkyl group, a halogenated $C_{1-6}$ alkyl group, a $C_{2-6}$ alkenyl group, or a $C_{1-6}$ alkoxyl $C_{1-6}$ alkyl group, and more specifically, $R^1$ represents chlorine, bromine, a cyano group, a methyl group, an ethyl group, an isopropyl group, a cyclopropyl group, a vinyl group, a difluoromethyl group, a trifluoromethyl group, an ethoxyethyl group, or the like;

ring A' represented by the following partial structural formula (II'):

[Formula 33]

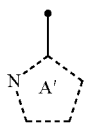

(II')

is selected from the group of the heteroaryls consisting of the following:

[Formula 34]

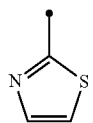

(II-1)

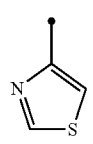

(II-4)

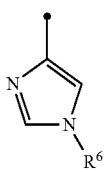

(II-6)

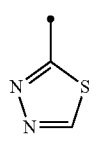

(II-16)

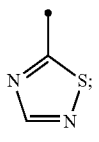

(II-19)

and $R^6$ represents a hydrogen atom or a $C_{1-6}$ alkyl group, and more specifically, $R^6$ represents a hydrogen atom, a methyl group, or the like, or a pharmaceutically acceptable salt thereof, or a solvate thereof.

[1-8-5-2]

More particularly preferably, the compound of the above embodiment [1-8] is a compound represented by the above formula (I-a) wherein the definition of q, Z, $R^2$, $R^3$, $R^4$, $R^5$, $R^6$, and ring A' represented by the partial structural formula (II') in the formula (I-a) have the same definitions as those described in the above embodiment [1-8-5]; p represents an integer of 0 to 2; and $R^1$ each independently represents a hydroxy $C_{1-6}$ alkyl group or a $C_{2-7}$ alkanoyl group, and has the same definitions as those described in the above embodiment [1-8-5], and more specifically, $R^1$ represents chlorine, bromine, a cyano group, a methyl group, an ethyl group, an isopropyl group, a tert-butyl group, a cyclopropyl group, a vinyl group, a difluoromethyl group, a trifluoromethyl group, a 1-hydroxyethyl group, an ethoxyethyl group, an acetyl group, or the like, or a pharmaceutically acceptable salt thereof, or a solvate thereof.

[1-8-6]

Even more particularly preferably, the compound of the above embodiment [1-8] is a compound represented by the above formula (I-a) wherein the definition of p, q, Z, $R^1$, $R^2$, $R^3$, $R^4$, $R^5$, $R^6$, and ring A' in the formula (I-a) have the same definitions as those described in the above embodiment [1-8-5-2]; and a specific ring A' group, in which the definitions of the above described p, $R^1$, and ring A' are combined, represents a 1-methyl-1H-imidazol-4-yl group, a 4-(difluoromethyl)-5-ethylthiazol-2-yl group, a 4-(difluoromethyl)-5-vinylthiazol-2-yl group, a 4-(difluoromethyl)-5-methylthiazol-2-yl group, a 4-(difluoromethyl)thiazol-2-yl group, a 4-(trifluoromethyl)thiazol-2-yl group, a 4,5-dimethylthiazol-2-yl group, a 4-tert-butylthiazol-2-yl group, a 4-cyanothiazol-2-yl group, a 4-methylthiazol-2-yl group, a 5-(2-ethoxyethyl)-4-methylthiazol-2-yl group, a 5-chloro-4-(difluoromethyl)thiazol-2-yl group, a 5-cyclopropyl-4-(difluoromethyl)thiazol-2-yl group, a 5-cyclopropyl-4-methylthiazol-2-yl group, a 5-bromo-4-methylthiazol-2-yl group, a 5-methylthiazol-2-yl group, a thiazol-2-yl group, a 2,5-dimethyl-thiazol-4-yl group, a 2-methylthiazol-4-yl group, a 5-(1-hydroxyethyl)-2-methylthiazol-4-yl group, a 5-acetyl-2-methylthiazol-4-yl group, a 5-bromo-2-methyl-thiazol-4-yl group, a thiazol-4-yl group, a 3-isopropyl-1,2,4-thiadiazol-5-yl group, a 3-methyl-1,2,4-thiadiazol-5-yl group, a 5-ethyl-1,3,4-thiadiazol-2-yl group, or a 5-methyl-1,3,4-thiadiazol-2-yl group, or a pharmaceutically acceptable salt thereof, or a solvate thereof.

[1-8a]

The compound of the above embodiment [1] represented by the above formula (I) is preferably a compound represented by the following formula (I-a):

[Formula 35]

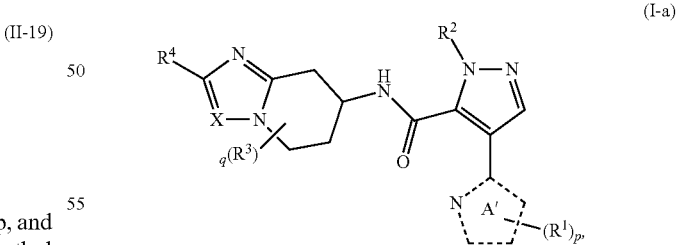

(I-a)

wherein the definition of q, Z, $R^3$, $R^4$, $R^5$, and $R^6$ in the formula (I-a) have the same definitions as those described in the above embodiment [1]; p, $R^1$, $R^6$, and ring A' represented by the partial structural formula (II') have the same definitions as those described in the above embodiment [1-8]; and $R^2$ represents a $C_{1-6}$ alkyl group, a halogenated $C_{1-6}$ alkyl group, a hydroxy $C_{1-6}$ alkyl group, or a $C_{1-6}$ alkoxyl $C_{1-6}$ alkyl group, or a pharmaceutically acceptable salt thereof, or a solvate thereof.

[1-8a-2]

Preferably, the compound of the above embodiment [1-8a] is a compound represented by the above formula (I-a) wherein $R^3$ has the same definitions as those described in the above embodiment [1-3]; $R^4$ has the same definitions as those described in the above embodiment [1-4]; Z and $R^5$ have the same definitions as those described in the above embodiment [1-5]; q has the same definitions as those described in the above embodiment [1-7]; p, $R^1$, $R^6$, and ring A' represented by the partial structural formula (II') have the same definitions as those described in the above embodiment [1-8-2]; and $R^2$ represents a $C_{1-6}$ alkyl group, a halogenated $C_{1-6}$ alkyl group, or a $C_{1-6}$ alkoxyl $C_{1-6}$ alkyl group, or a pharmaceutically acceptable salt thereof, or a solvate thereof.

[1-8a-3]

More preferably, the compound of the above embodiment [1-8a] is a compound represented by the above formula (I-a) wherein $R^3$ has the same definitions as those described in the above embodiment [1-3-2]; $R^4$ has the same definitions as those described in the above embodiment [1-4-2]; Z and $R^5$ have the same definitions as those described in the above embodiment [1-5-2]; q has the same definitions as those described in the above embodiment [1-7-2]; p, $R^1$, $R^6$, and ring A' represented by the partial structural formula (II') have the same definitions as those described in the above embodiment [1-8-3-2]; and $R^2$ represents a $C_{1-6}$ alkyl group or a halogenated $C_{1-6}$ alkyl group, or a pharmaceutically acceptable salt thereof, or a solvate thereof.

[1-8a-4]

Even more preferably, the compound of the above embodiment [1-8a] is a compound represented by the above formula (I-a) wherein $R^3$ has the same definitions as those described in the above embodiment [1-3-3]; $R^4$ has the same definitions as those described in the above embodiment [1-4-3]; Z and $R^5$ have the same definitions as those described in the above embodiment [1-5-3]; q has the same definitions as those described in the above embodiment [1-7-3]; p, $R^1$, $R^6$, and ring A' represented by the partial structural formula (II') have the same definitions as those described in the above embodiment [1-8-4-2]; and $R^2$ represents a $C_{1-6}$ alkyl group, or a pharmaceutically acceptable salt thereof, or a solvate thereof.

[1-8a-5]

Particularly preferably, the compound of the above embodiment [1-8a] is a compound represented by the above formula (I-a) wherein $R^3$ has the same definitions as those described in the above embodiment [1-3-4]; Z and $R^5$ have the same definitions as those described in the above embodiment [1-5-4]; q has the same definitions as those described in the above embodiment [1-7-4]; p, $R^1$, $R^6$, and ring A' represented by the partial structural formula (II') have the same definitions as those described in the above embodiment [1-8-5-2]; $R^2$ represents a $C_{1-6}$ alkyl group, and more specifically, $R^2$ represents a methyl group or the like; and $R^4$ represents a $C_{6-14}$ aryl group or a 3- to 14-membered non-aromatic heterocyclic group wherein the $C_{6-14}$ aryl group and the 3- to 14-membered non-aromatic heterocyclic group, which are represented by $R^4$, are optionally substituted with one or two groups selected from among a halogen atom, a $C_{1-6}$ alkoxyl group, and a $C_{1-6}$ alkoxyl $C_{1-6}$ alkyl group, and specifically, $R^4$ represents phenyl, 2-fluorophenyl, 3-fluorophenyl, 4-fluorophenyl, 2,5-difluorophenyl, 2-methoxyphenyl, 3-methoxyphenyl, 4-methoxyphenyl, pyrrolidinyl, 2-fluoropyrrolidinyl, 3-fluoropyrrolidinyl, 2-methoxypyrrolidinyl, 3-methoxypyrrolidinyl, 2-methoxymethylpyrrolidinyl, 3-methoxymethylpyrrolidinyl, or the like, and preferably represents phenyl, 2-fluorophenyl, 3-fluorophenyl, 4-fluorophenyl, 2,5-difluorophenyl, 2-methoxyphenyl, pyrrolidinyl, or 2-methoxymethylpyrrolidinyl, or a pharmaceutically acceptable salt thereof, or a solvate thereof.

[1-8a-6]

More particularly preferably, the compound of the above embodiment [1-8a] is a compound represented by the above formula (I-a) wherein p, q, Z, $R^1$, $R^2$, $R^3$, $R^4$, $R^5$, $R^6$, and ring A' have the same definitions as those described in the above embodiment [1-8a-5]; and a specific ring A' group, in which the definitions of the above described p, $R^1$, and ring A' are combined, represents a 1-methyl-1H-imidazol-4-yl group, a 4-(difluoromethyl)-5-ethylthiazol-2-yl group, a 4-(difluoromethyl)-5-vinylthiazol-2-yl group, a 4-(difluoromethyl)-5-methylthiazol-2-yl group, a 4-(difluoromethyl)thiazol-2-yl group, a 4-(trifluoromethyl)thiazol-2-yl group, a 4,5-dimethylthiazol-2-yl group, a 4-tert-butylthiazol-2-yl group, a 4-cyanothiazol-2-yl group, a 4-methylthiazol-2-yl group, a 5-(2-ethoxyethyl)-4-methylthiazol-2-yl group, a 5-chloro-4-(difluoromethyl)thiazol-2-yl group, a 5-cyclopropyl-4-(difluoromethyl)thiazol-2-yl group, a 5-cyclopropyl-4-methylthiazol-2-yl group, a 5-bromo-4-methylthiazol-2-yl group, a 5-methylthiazol-2-yl group, a thiazol-2-yl group, a 2,5-dimethyl-thiazol-4-yl group, a 2-methylthiazol-4-yl group, a 5-(1-hydroxyethyl)-2-methylthiazol-4-yl group, a 5-acetyl-2-methylthiazol-4-yl group, a 5-bromo-2-methylthiazol-4-yl group, a thiazol-4-yl group, a 3-isopropyl-1,2,4-thiadiazol-5-yl group, a 3-methyl-1,2,4-thiadiazol-5-yl group, a 5-ethyl-1,3,4-thiadiazol-2-yl group, or a 5-methyl-1,3,4-thiadiazol-2-yl group, or a pharmaceutically acceptable salt thereof, or a solvate thereof.

[1-9]

The compound of the above embodiment [1] represented by the above formula (I) is preferably a compound represented by the following formula (I-b):

[Formula 36]

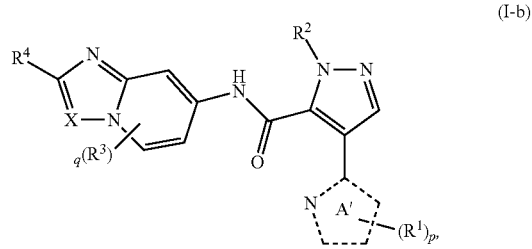

wherein the definition of Z, $R^2$, $R^3$, $R^4$, and $R^5$ in the formula (I-b) have the same definitions as those described in the above embodiment [1]; p represents an integer of 0 to 2; q represents an integer of 0 to 3; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfinyl group, a $C_{1-6}$ alkylsulfonyl group, an —$NR^7R^8$ group, or a —$CONR^7R^8$ group wherein $R^7$ and $R^8$ in the —$NR^7R^8$ group and the —$CONR^7R^8$ group have the same definitions as those described in the above embodiment [1];

ring A' represented by the following partial structural formula (II'):
[Formula 37]
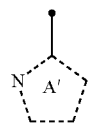 (II')
is selected from the group of the heteroaryls consisting of the following:
[Formula 38]
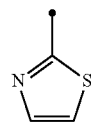 (II-1)
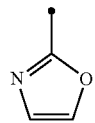 (II-2)
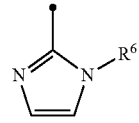 (II-3)
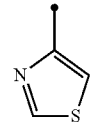 (II-4)
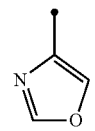 (II-5)
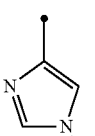 (II-6)
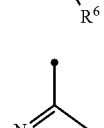 (II-7)
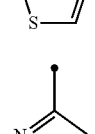 (II-8)
-continued
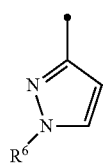 (II-9)
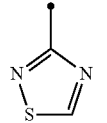 (II-10)
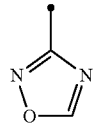 (II-11)
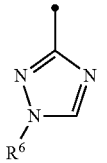 (II-12)
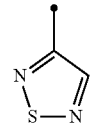 (II-13)
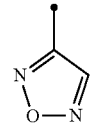 (II-14)
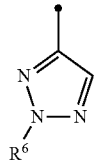 (II-15)
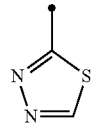 (II-16)
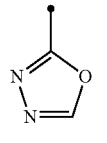 (II-17)
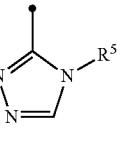 (II-18)
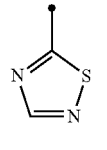 (II-19)

(II-20) 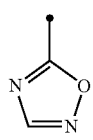

(II-21) 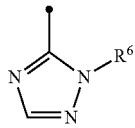

(II-22) 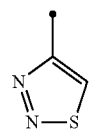

(II-23) 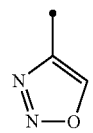

(II-24) 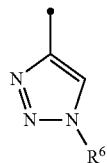

(II-25) 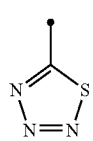

(II-26) 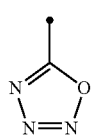

(II-27) 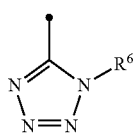

(II-28) 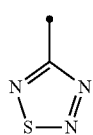

(II-29) 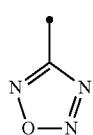

(II-30) 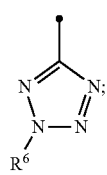

and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[1-9-2]

Preferably, the compound of the above embodiment [1-9] is a compound represented by the above formula (I-b) wherein the definition of Z, $R^2$, $R^3$, $R^4$, and $R^5$ in the formula (I-b) have the same definitions as those described in the above embodiment [1]; p represents an integer of 0 to 2; q represents an integer of 0 to 3; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfonyl group, an —$NR^7R^8$ group, or a —$CONR^7R^8$ group wherein $R^7$ and $R^8$ in the —$NR^7R^8$ group and the —$CONR^7R^8$ group have the same definitions as those described in the above embodiment [1];

ring A' represented by the following partial structural formula (II'):

[Formula 39]

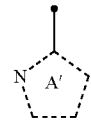 (II')

is selected from the group of the heteroaryls consisting of the following:

[Formula 40]

(II-1) 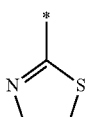

(II-3) 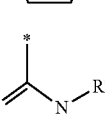

(II-4) 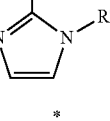

(II-6) 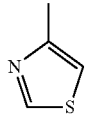

(II-7) 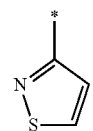

(II-9) 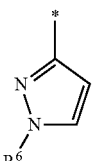

(II-10) 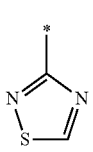

(II-12) 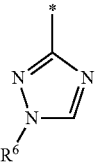

(II-13) 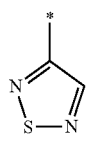

(II-15) 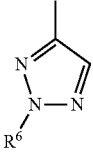

(II-16) 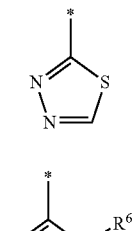

(II-18) 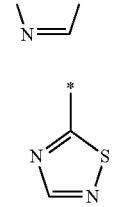

(II-19) 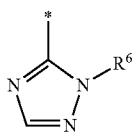

(II-21)

(II-22) 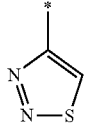

(II-24) 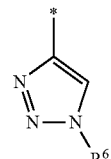

(II-25) 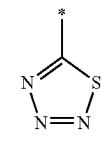

(II-27) 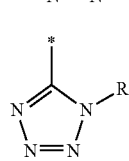

(II-29) 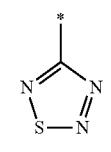

(II-30) 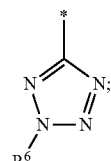

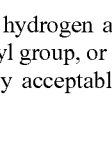

and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[1-9-3]

More preferably, the compound of the above embodiment [1-9] is a compound represented by the above formula (I-b) wherein the definition of Z, $R^2$, $R^3$, $R^4$, and $R^5$ in the formula (I-b) have the same definitions as those described in the above embodiment [1]; p represents an integer of 0 to 2; q represents an integer of 0 to 2; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfonyl group, a —CONR$^{2A}$R$^{8A}$ group, or an —NR$^{7A}$R$^{8A}$ group wherein R$^{7A}$ and R$^{8A}$ in the —NR$^{7A}$R$^{8A}$ group and the —CONR$^{7A}$R$^{8A}$ group have the same definitions as those of R$^{7A}$ and R$^{8A}$ in the above embodiment [1-1-2]);

ring A' represented by the following partial structural formula (II'):

[Formula 41]

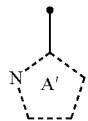
(II')

is selected from the group of the heteroaryls consisting of the following:

[Formula 42]

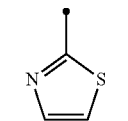
(II-1)

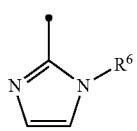
(II-3)

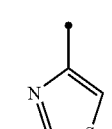
(II-4)

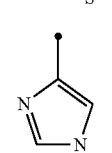
(II-6)

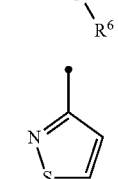
(II-7)

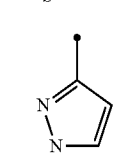
(II-9)

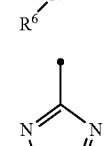
(II-10)

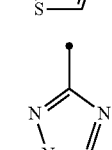
(II-12)

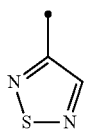
(II-13)

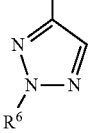
(II-15)

(II-16)

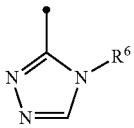
(II-18)

(II-19)

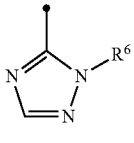
(II-21)

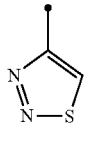
(II-22)

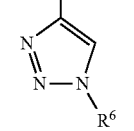
(II-24)

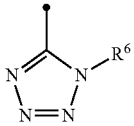
(II-27)

and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[1-9-4]

Even more preferably, the compound of the above embodiment [1-9] is a compound represented by the above formula (I-b) wherein the definition of Z, $R^2$, $R^3$, $R^4$, and $R^5$ in the formula (I-b) have the same definitions as those described in the above embodiment [1]; p represents an integer of 1 or 2; q represents an integer of 0 to 2; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxyl $C_{1-6}$ alkyl group, a $C_{2-7}$ alkanoyl group, a $C_{1-6}$ alkylthio group, or a $C_{1-6}$ alkylsulfonyl group;

ring A' represented by the following partial structural formula (II'):

[Formula 43]

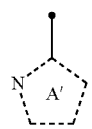

(II')

is selected from the group of the heteroaryls consisting of the following:

[Formula 44]

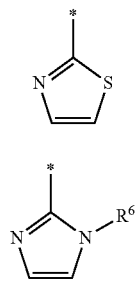

(II-1)

(II-3)

(II-4)

(II-6)

(II-7)

-continued

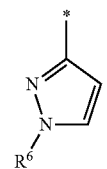

(II-9)

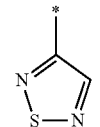

(II-13)

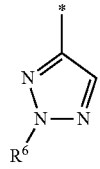

(II-15)

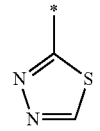

(II-16)

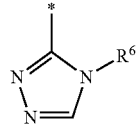

(II-18)

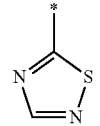

(II-19)

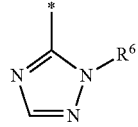

(II-21)

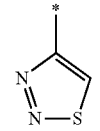

(II-22)

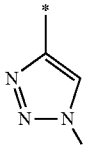

(II-24)

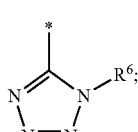

(II-27)

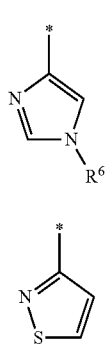

and R⁶ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[1-9-4-2]

Further preferably, the compound of the above embodiment [1-9] is a compound represented by the above formula (I-b) wherein the definition of q, Z, $R^1$, $R^2$, $R^3$, $R^4$, $R^5$, $R^6$, and ring A' represented by the partial structural formula (II') in the formula (I-b) have the same definitions as those described in the above embodiment [1-9-4]; and p represents an integer of 0 to 2, or a pharmaceutically acceptable salt thereof, or a solvate thereof.

[1-9-5]

Particularly preferably, the compound of the above embodiment [1-9] is a compound represented by above the formula (I-b) wherein the definition of Z, $R^2$, $R^3$, $R^4$, and $R^5$ in the formula (I-b) have the same definitions as those described in the above embodiment [1]; p represents an integer of 1 or 2; q represents an integer of 0 or 1; $R^1$ each independently represents a halogen atom, a $C_{1-6}$ alkyl group, or a halogenated $C_{1-6}$ alkyl group, and more specifically, $R^1$ represents chlorine, a methyl group, an ethyl group, a difluoromethyl group, a trifluoromethyl group, or the like;

ring A' represented by the following partial structural formula (II'):

[Formula 45]

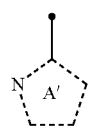

(II')

is selected from the group of the heteroaryls consisting of the following:

[Formula 46]

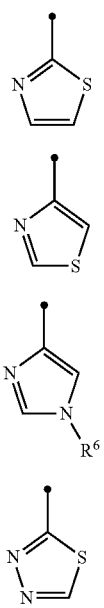

and R⁶ represents a hydrogen atom or a $C_{1-6}$ alkyl group, and more specifically, $R^6$ represents a hydrogen atom, a methyl group, or the like, or a pharmaceutically acceptable salt thereof, or a solvate thereof.

[1-9-5-2]

More particularly preferably, the compound of the above embodiment [1-9] is a compound represented by the above formula (I-b) wherein the definition of q, Z, $R^1$, $R^2$, $R^3$, $R^4$, and $R^5$ in the formula (I-b) have the same definitions as those described in the above embodiment [1-9-5]; p represents an integer of 0 to 2; ring A' represented by the following partial structural formula (II'):

[Formula 47]

is selected from the group of the heteroaryls consisting of the following:

[Formula 48]

and R⁶ represents a hydrogen atom or a $C_{1-6}$ alkyl group, and more specifically, $R^6$ represents a hydrogen atom, a methyl group, or the like, or a pharmaceutically acceptable salt thereof, or a solvate thereof.

[1-9-6]

Even more particularly preferably, the compound of the above embodiment [1-9] is a compound represented by the above formula (I-b) wherein the definition of p, q, Z, $R^1$, $R^2$, $R^3$, $R^4$, $R^5$, $R^6$, and ring A' in the formula (I-b) have the same definitions as those described in the above embodiment [1-9-5-2]; and a specific ring A' group, in which the definitions of the above described p, $R^1$, and ring A' are combined, represents a 1-methyl-1H-imidazol-4-yl group, a 4-(difluoromethyl)-5-methylthiazol-2-yl group, a 4-(difluoromethyl)thiazol-2-yl group, a 4-(trifluoromethyl)thiazol-2-yl group, a 4-ethylthiazol-2-yl group, a 4-methylthiazol-2-yl group, a 5-chloro-4-(difluoromethyl)thiazol-2-yl group, or a pharmaceutically acceptable salt thereof, or a solvate thereof.

[1-9a]

The compound of the above embodiment [1] represented by the above formula (I) is preferably a compound represented by the following formula (I-b):

[Formula 49]

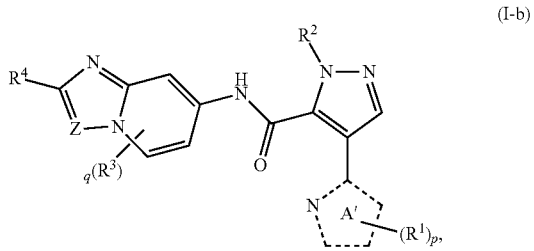

(I-b)

wherein the definition of q, Z, $R^3$, $R^4$, $R^5$, and $R^6$ in the formula (I-b) have the same definitions as those described in the above embodiment [1]; p, $R^1$, $R^6$, and ring A' represented by the partial structural formula (II') have the same definitions as those described in the above embodiment [1-9]; and $R^2$ represents a $C_{1-6}$ alkyl group, a halogenated $C_{1-6}$ alkyl group, a hydroxy $C_{1-6}$ alkyl group, or a $C_{1-6}$ alkoxyl $C_{1-6}$ alkyl group, or a pharmaceutically acceptable salt thereof, or a solvate thereof.

[1-9a-2]

Preferably, the compound of the above embodiment [1-9a] is a compound represented by the above formula (I-b) wherein $R^3$ has the same definitions as those described in the above embodiment [1-3]; $R^4$ has the same definitions as those described in the above embodiment [1-4]; Z and $R^5$ have the same definitions as those described in the above embodiment [1-5]; q has the same definitions as those described in the above embodiment [1-7]; p, $R^1$, $R^6$, and ring A' represented by the partial structural formula (II') have the same definitions as those described in the above embodiment [1-9-2]; and $R^2$ represents a $C_{1-6}$ alkyl group, a halogenated $C_{1-6}$ alkyl group, or a $C_{1-6}$ alkoxyl $C_{1-6}$ alkyl group, or a pharmaceutically acceptable salt thereof, or a solvate thereof.

[1-9a-3]

More preferably, the compound of the above embodiment [1-9a] is a compound represented by the above formula (I-b) wherein $R^3$ has the same definitions as those described in the above embodiment [1-3-2]; $R^4$ has the same definitions as those described in the above embodiment [1-4-2]; Z and $R^5$ have the same definitions as those described in the above embodiment [1-5-2]; q has the same definitions as those described in the above embodiment [1-7-2]; p, $R^1$, $R^6$, and ring A' represented by the partial structural formula (II') have the same definitions as those described in the above embodiment [1-9-3]; and $R^2$ represents a $C_{1-6}$ alkyl group or a halogenated $C_{1-6}$ alkyl group, or a pharmaceutically acceptable salt thereof, or a solvate thereof.

[1-9a-4]

Even more preferably, the compound of the above embodiment [1-9a] is a compound represented by the above formula (I-b) wherein $R^3$ has the same definitions as those described in the above embodiment [1-3-3]; $R^4$ has the same definitions as those described in the above embodiment [1-4-3]; Z and $R^5$ have the same definitions as those described in the above embodiment [1-5-3]; q has the same definitions as those described in the above embodiment [1-7-3]; p, $R^1$, $R^6$, and ring A' represented by the partial structural formula (II') have the same definitions as those described in the above embodiment [1-9-4-2]; and $R^2$ represents a $C_{1-6}$ alkyl group, or a pharmaceutically acceptable salt thereof, or a solvate thereof.

[1-9a-5]

Particularly preferably, the compound of the above embodiment [1-9a] is a compound represented by the above formula (I-b) wherein $R^3$ has the same definitions as those described in the above embodiment [1-3-4]; Z and $R^5$ have the same definitions as those described in the above embodiment [1-5-4]; q has the same definitions as those described in the above embodiment [1-7-4]; p, $R^1$, $R^6$, and ring A' represented by the partial structural formula (II') have the same definitions as those described in the above embodiment [1-9-5-2]; $R^2$ represents a $C_{1-6}$ alkyl group, and more specifically, $R^2$ represents a methyl group or the like; and $R^4$ represents a $C_{6-14}$ aryl group, or a 3- to 14-membered non-aromatic heterocyclic group wherein the $C_{6-14}$ aryl group and the 3- to 14-membered non-aromatic heterocyclic group, which are represented by $R^4$, are each optionally substituted with one or two groups selected from among a halogen atom, a $C_{1-6}$ alkyl group, and a $C_{1-6}$ alkoxyl group, and specifically, $R^4$ represents phenyl, 2-fluorophenyl, 3-fluorophenyl, 4-fluorophenyl, 2,5-difluorophenyl, 2-methylphenyl, 3-methylphenyl, 4-methylphenyl, 2,5-dimethylphenyl, 2,6-dimethylphenyl, 3,5-dimethylphenyl, 2-methoxyphenyl, 3-methoxyphenyl, 4-methoxyphenyl, pyrrolidinyl, 2-fluoropyrrolidinyl, 3-fluoropyrrolidinyl, 2-methoxypyrrolidinyl, 3-methoxypyrrolidinyl, 2-methylpyrrolidinyl, 3-methylpyrrolidinyl, morpholinyl, 2-methylmorpholinyl, 3-methylmorpholinyl, 2,6-dimethylmorpholinyl, 3,5-dimethylmorpholinyl, or the like, and $R^4$ preferably represents phenyl, 3-fluorophenyl, 2-methoxyphenyl, pyrrolidinyl, 3-fluoropyrrolidinyl, 2-methylpyrrolidinyl, or 2,6-dimethylmorpholinyl, or a pharmaceutically acceptable salt thereof, or a solvate thereof.

[1-9a-6]

More particularly preferably, the compound of the above embodiment [1-9a] is a compound represented by the above formula (I-b) wherein p, q, Z, $R^1$, $R^2$, $R^3$, $R^4$, $R^5$, $R^6$, and ring A' have the same definitions as those described in the above embodiment [1-9a-5]; and a specific ring A' group, in which the definitions of the above described p, $R^1$, and ring A' are combined, represents a 1-methyl-1H-imidazol-4-yl group, a 4-(difluoromethyl)-5-methylthiazol-2-yl group, a 4-(difluoromethyl)thiazol-2-yl group, a 4-(trifluoromethyl)thiazol-2-yl group, a 4-ethylthiazol-2-yl group, a 4-methylthiazol-2-yl group, or a 5-chloro-4-(difluoromethyl)thiazol-2-yl group, or a pharmaceutically acceptable salt thereof, or a solvate thereof.

[1-10]

The compound of the above embodiment [1] represented by the above formula (I) is preferably a compound represented by the following formula (I-c):

[Formula 50]

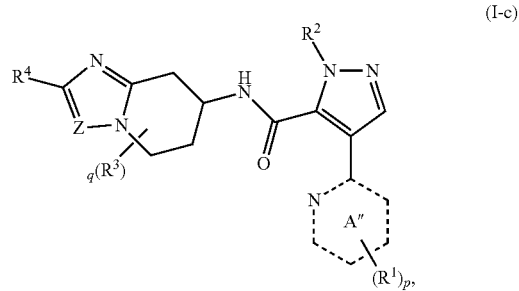

(I-c)

wherein the definition of q, Z, $R^2$, $R^3$, $R^4$, and $R^5$ in the formula (I-c) have the same definitions as those described in the above embodiment [1]; p represents an integer of 0 to 4; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfinyl group, a $C_{1-6}$ alkylsulfonyl group, an —$NR^7R^8$ group, or a —$CONR^7R^8$ group wherein $R^7$ and $R^8$ in the —$NR^7R^8$ group and the —$CONR^7R^8$ group have the same definitions as those described in the above embodiment [1]; and ring A″ represented by the following partial structural formula (II″):

[Formula 51]

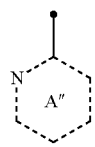

(II″)

is selected from the group of the heteroaryls consisting of the following:

[Formula 52]

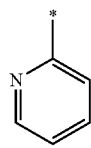

(II-31)

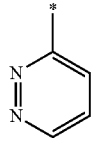

(II-32)

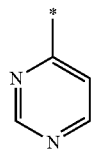

(II-33)

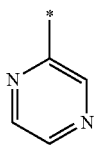

(II-34)

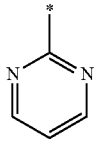

(II-35)

-continued

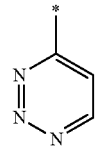

(II-36)

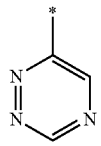

(II-37)

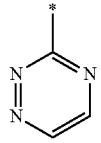

(II-38)

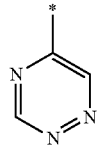

(II-39)

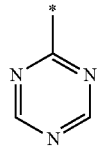

(II-40)

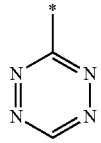

(II-41)

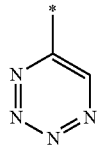

(II-42)

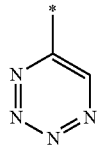

(II-43)

or a pharmaceutically acceptable salt thereof, or a solvate thereof.

[1-10-2]

Preferably, the compound of the above embodiment [1-10] is a compound represented by the above formula (I-c) wherein the definition of q, Z, $R^2$, $R^3$, $R^4$, and $R^5$ in the formula (I-c) have the same definitions as those described in the above embodiment [1]; p represents an integer of 0 to 4; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfonyl group, an —$NR^7R^8$ group, or a —$CONR^7R^8$ group wherein $R^7$ and $R^8$ in the —$NR^7R^8$ group and the —$CONR^7R^8$ group have the same definitions as those described in the above embodiment [1]; and ring A" represented by the following partial structural formula (II"):

[Formula 53]

(II")

is selected from the group of the heteroaryls consisting of the following:

[Formula 54]

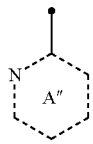
(II-31)

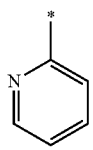
(II-32)

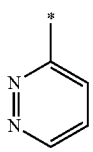
(II-33)

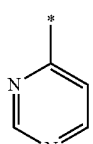
(II-34)

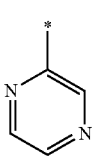
(II-35)

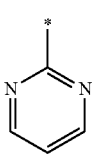
(II-36)

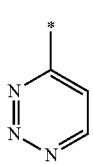

-continued

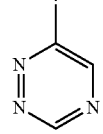
(II-37)

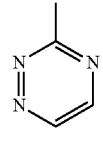
(II-38)

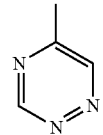
(II-39)

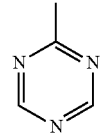
(II-40)

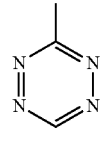
(II-41)

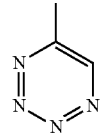
(II-42)

(II-43)

or a pharmaceutically acceptable salt thereof, or a solvate thereof.

[1-10-2-2]

More preferably, the compound of the above embodiment [1-10] is a compound represented by the above formula (I-c) wherein the definition of p, Z, $R^1$, $R^2$, $R^3$, $R^4$, $R^5$, and ring A" represented by the partial structural formula (II") in the formula (I-c) have the same definitions as those described in the above embodiment [1-10-2]; and q represents an integer of 0 to 3, or a pharmaceutically acceptable salt thereof, or a solvate thereof.

[1-10-3]

Even more preferably, the compound of the above embodiment [1-10] is a compound represented by the above formula (I-c) wherein the definition of q, Z, $R^2$, $R^3$, $R^4$, and $R^5$ in the formula (I-c) have the same definitions as those described in the above embodiment [1]; p represents an integer of 0 to 3; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfonyl group, a —$CONR^{7A}R^{BA}$ group, or an —$NR^{7A}R^{BA}$ group wherein $R^{7A}$ and $R^{8A}$ in the —$NR^{7A}R^{8A}$ group and the —$CONR^{7A}R^{BA}$ group have the same definitions as those of $R^{7A}$ and $R^{8A}$ in the above embodiment [1-1-2]; and ring A" represented by the following partial structural formula (II"):

[Formula 55]

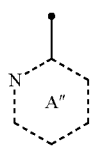

(II")

is selected from the group of the heteroaryls consisting of the following:

[Formula 56]

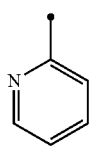

(II-31)

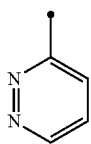

(II-32)

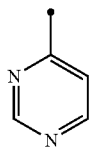

(II-33)

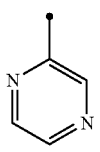

(II-34)

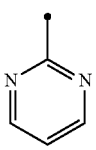

(II-35)

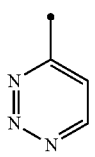

(II-36)

-continued

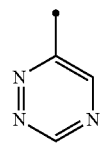

(II-37)

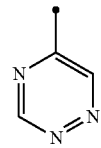

(II-39)

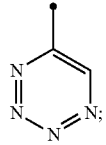

(II-42)

or a pharmaceutically acceptable salt thereof, or a solvate thereof.

[1-10-3-2]

Further preferably, the compound of the above embodiment [1-10] is a compound represented by the above formula (I-c) wherein the definition of p, Z, $R^1$, $R^2$, $R^3$, $R^4$, $R^5$, and ring A" represented by the partial structural formula (II") in the formula (I-c) have the same definitions as those described in the above embodiment [1-10-3]; and q represents an integer of 0 to 2, or a pharmaceutically acceptable salt thereof, or a solvate thereof.

[1-10-4]

Still further preferably, the compound of the above embodiment [1-10] is a compound represented by the above formula (I-c) wherein the definition of q, Z, $R^2$, $R^3$, $R^4$, and $R^5$ in the formula (I-c) have the same definitions as those described in the above embodiment [1]; p represents an integer of 1 to 3; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxyl $C_{1-6}$ alkyl group, a $C_{2-7}$ alkanoyl group, a $C_{1-6}$ alkylthio group, or a $C_{1-6}$ alkylsulfonyl group; and ring A" represented by the following partial structural formula (II"):

[Formula 57]

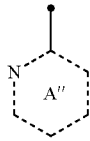

(II")

is selected from the group of the heteroaryls consisting of the following:

[Formula 58]

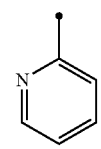

(II-31)

(II-32)

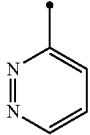

(II-33)

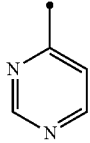

(II-34)

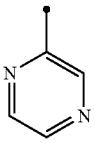

(II-35)

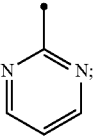

or a pharmaceutically acceptable salt thereof, or a solvate thereof.

[1-10-4-2]

Still further preferably, the compound of the above embodiment [1-10] is a compound represented by the above formula (I-c) wherein the definition of Z, $R^1$, $R^2$, $R^3$, $R^4$, $R^5$, and ring A" represented by the partial structural formula (II") in the formula (I-c) have the same definitions as those described in the above embodiment [1-10-4]; p represents an integer of 0 to 3; and q represents an integer of 0 or 1, or a pharmaceutically acceptable salt thereof, or a solvate thereof.

[1-10-5]

Particularly preferably, the compound of the above embodiment [1-10] is a compound represented by the above formula (I-c) wherein q, Z, $R^2$, $R^3$, $R^4$, and $R^5$ have the same definitions as those described in the above embodiment [1]; p represents an integer of 1 or 2; $R^1$ each independently represents a $C_{1-6}$ alkyl group or a $C_{1-6}$ alkoxyl group, and more specifically, $R^1$ represents a methyl group, a methoxy group, or the like; and ring A" represented by the following partial structural formula (II"):

[Formula 59]

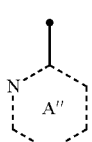

(II")

is selected from the group of the heteroaryls consisting of the following:

[Formula 60]

(II-31)

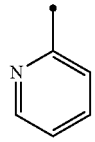

(II-34)

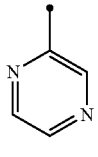

(II-35)

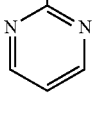

or a pharmaceutically acceptable salt thereof, or a solvate thereof.

[1-10-5-2]

More particularly preferably, the compound of the above embodiment [1-10] is a compound represented by the above formula (I-c) wherein the definition of Z, $R^2$, $R^3$, $R^4$, $R^5$, $R^5$, and ring A" represented by the partial structural formula (II") in the formula (I-c) have the same definitions as those described in the above embodiment [1-10-5]; p represents an integer of 0 to 3; q represents an integer of 0 or 1; $R^1$ each independently represents a halogen atom, a $C_{1-6}$ alkyl group, a cyano group, a halogenated $C_{1-6}$ alkyl group, or a $C_{1-6}$ alkoxyl group, and more specifically, $R^1$ represents fluorine, a cyano group, a methyl group, a trifluoromethyl group, a methoxy group, or the like, or a pharmaceutically acceptable salt thereof, or a solvate thereof.

[1-10-6]

Even more particularly preferably, the compound of the above embodiment [1-10] is a compound represented by the above formula (I-c) wherein the definition of p, q, Z, $R^1$, $R^2$, $R^3$, $R^4$, $R^5$, and ring A" in the formula (I-c) have the same definitions as those described in the above embodiment [1-10-5-2]; and a specific ring A" group, in which the definitions of the above described p, $R^1$, and ring A" are combined, represents a 4-methylpyrimidin-2-yl group, a 3-cyano-pyridin-2-yl group, a 3-methylpyridin-2-yl group, a 4-fluoropyridin-2-yl group, a 4-methylpyridin-2-yl group, a 4-methoxy-pyridin-2-yl group, a 5-fluoropyridin-2-yl group, a 5-methylpyridin-2-yl group, a 6-cyano-pyridin-2-yl group, a 6-methylpyridin-2-yl group, a 6-methoxypyridin-2-yl group, a 3,6-dimethylpyrazin-2-yl group, or a 6-methylpyrazin-2-yl group, or a pharmaceutically acceptable salt thereof, or a solvate thereof.

[1-10a]

The compound of the above embodiment [1] represented by the above formula (I) is preferably a compound represented by the following formula (I-c):

[Formula 61]

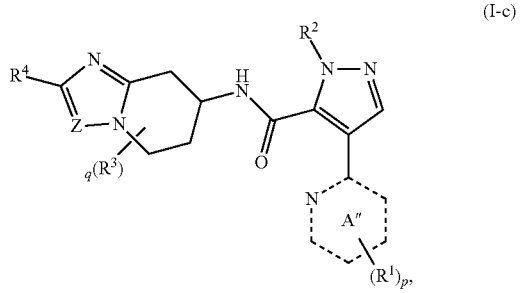

wherein the definition of q, Z, $R^3$, $R^4$, and $R^5$ in the formula (I-c) have the same definitions as those described in the above embodiment [1]; p, $R^1$, $R^6$, and ring A" represented by the partial structural formula (II") have the same definitions as those described in the above embodiment [1-10]; and $R^2$ represents a $C_{1-6}$ alkyl group, a halogenated $C_{1-6}$ alkyl group, a hydroxy $C_{1-6}$ alkyl group, or a $C_{1-6}$ alkoxyl $C_{1-6}$ alkyl group, or a pharmaceutically acceptable salt thereof, or a solvate thereof.

[1-10a-2]

Preferably, the compound of the above embodiment [1-10a] is a compound represented by the above formula (I-c) wherein $R^3$ has the same definitions as those described in the above embodiment [1-3]; $R^4$ has the same definitions as those described in the above embodiment [1-4]; Z and $R^5$ have the same definitions as those described in the above embodiment [1-5]; q has the same definitions as those described in the above embodiment [1-7]; p, $R^1$, and ring A" represented by the partial structural formula (II") have the same definitions as those described in the above embodiment [1-10-2-2]; and $R^2$ represents a $C_{1-6}$ alkyl group, a halogenated $C_{1-6}$ alkyl group, or a $C_{1-6}$ alkoxyl $C_{1-6}$ alkyl group, or a pharmaceutically acceptable salt thereof, or a solvate thereof.

[1-10a-3]

More preferably, the compound of the above embodiment [1-10a] is a compound represented by the above formula (I-c) wherein $R^3$ has the same definitions as those described in the above embodiment [1-3-2]; $R^4$ has the same definitions as those described in the above embodiment [1-4-2]; Z and $R^5$ have the same definitions as those described in the above embodiment [1-5-2]; q has the same definitions as those described in the above embodiment [1-7-2]; p, $R^1$, and ring A" represented by the partial structural formula (II") have the same definitions as those described in the above embodiment [1-10-3-2]; and $R^2$ represents a $C_{1-6}$ alkyl group or a halogenated $C_{1-6}$ alkyl group, or a pharmaceutically acceptable salt thereof, or a solvate thereof.

[1-10a-4]

Even more preferably, the compound of the above embodiment [1-10a] is a compound represented by the above formula (I-c) wherein $R^3$ has the same definitions as those described in the above embodiment [1-3-3]; $R^4$ has the same definitions as those described in the above embodiment [1-4-3]; Z and $R^5$ have the same definitions as those described in the above embodiment [1-5-3]; q has the same definitions as those described in the above embodiment [1-7-3]; p, $R^1$, and ring A" represented by the partial structural formula (II") have the same definitions as those described in the above embodiment [1-10-4-2]; and $R^2$ represents a $C_{1-6}$ alkyl group, or a pharmaceutically acceptable salt thereof, or a solvate thereof.

[1-10a-5]

Particularly preferably, the compound of the above embodiment [1-10a] is a compound represented by the above formula (I-c) wherein $R^3$ has the same definitions as those described in the above embodiment [1-3-4]; Z and $R^5$ have the same definitions as those described in the above embodiment [1-5-4]; q has the same definitions as those described in the above embodiment [1-7-4]; p, $R^1$, and ring A" represented by the partial structural formula (II") have the same definitions as those described in the above embodiment [1-10-5-2]; $R^2$ represents a $C_{1-6}$ alkyl group, and more specifically, $R^2$ represents a methyl group or the like; and $R^4$ represents a $C_{6-14}$ aryl group or a 3- to 14-membered non-aromatic heterocyclic group wherein the $C_{6-14}$ aryl group and the 3- to 14-membered non-aromatic heterocyclic group, which are represented by $R^4$, are each optionally substituted with one or two halogen atoms, and specifically, $R^4$ represents phenyl, 2-fluorophenyl, 3-fluorophenyl, 4-fluorophenyl, 2,5-difluorophenyl, pyrrolidinyl, 2-fluoropyrrolidinyl, 3-fluoropyrrolidinyl, or the like, and $R^4$ preferably represents phenyl, 3-fluorophenyl, or pyrrolidinyl, or a pharmaceutically acceptable salt thereof, or a solvate thereof.

[1-10a-6]

More particularly preferably, the compound of the above embodiment [1-10a] is a compound represented by the above formula (I-c) wherein p, q, Z, $R^1$, $R^2$, $R^3$, $R^4$, $R^5$, and ring A" have the same definitions as those described in the above embodiment [1-10a-5]; and a specific ring A" group, in which the definitions of the above described p, $R^1$, and ring A" are combined, represents a 4-methylpyrimidin-2-yl group, a 3-cyano-pyridin-2-yl group, a 3-methylpyridin-2-yl group, a 4-fluoropyridin-2-yl group, a 4-methylpyridin-2-yl group, a 4-methoxy-pyridin-2-yl group, a 5-fluoropyridin-2-yl group, a 5-methylpyridin-2-yl group, a 6-cyano-pyridin-2-yl group, a 6-methylpyridin-2-yl group, a 6-methoxy-pyridin-2-yl group, a 3,6-dimethylpyrazin-2-yl group, or a 6-methylpyrazin-2-yl group, or a pharmaceutically acceptable salt thereof, or a solvate thereof.

[1-11]

The compound of the above embodiment [1] represented by the above formula (I) is preferably a compound represented by the following formula (I-d):

[Formula 62]

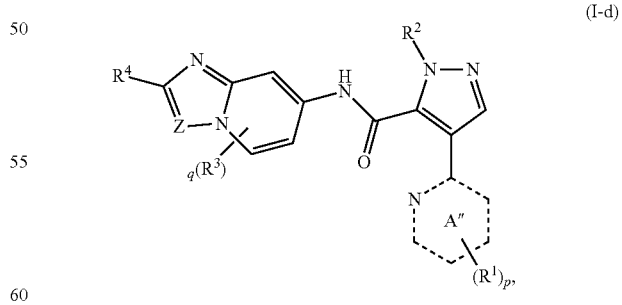

wherein the definition of Z, $R^2$, $R^3$, $R^4$, and $R^5$ in the formula (I-d) have the same definitions as those described in the above embodiment [1]; p represents an integer of 0 to 4; q represents an integer of 0 to 3; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfinyl group, a $C_{1-6}$ alkylsulfonyl group, an —$NR^7R^8$ group, or a —$CONR^7R^8$ group wherein $R^7$ and $R^8$ in the —$NR^7R^8$ group and the —$CONR^7R^8$ group have the same definitions as those described in the above embodiment [1]; and ring A" represented by the following partial structural formula (II"):

[Formula 63]

(II")

is selected from the group of the heteroaryls consisting of the following:

[Formula 64]

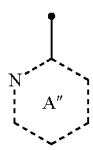
(II-31)

(II-32)

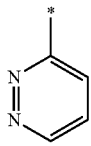
(II-33)

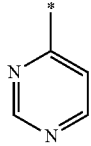
(II-34)

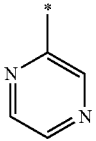
(II-35)

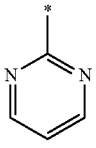
(II-36)

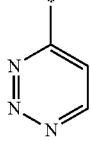

-continued

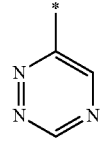
(II-37)

(II-38)

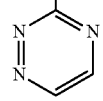
(II-39)

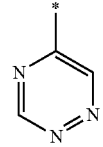
(II-40)

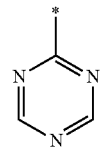
(II-41)

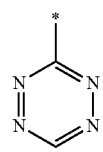
(II-42)

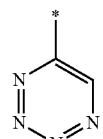
(II-43)

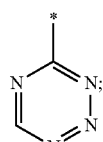

or a pharmaceutically acceptable salt thereof, or a solvate thereof.

[1-11-2]

Preferably, the compound of the above embodiment [1-11] is a compound represented by the above formula (I-d) wherein the definition of Z, $R^2$, $R^3$, $R^4$, and $R^5$ in the formula (I-d) have the same definitions as those described in the above embodiment [1]; p represents an integer of 0 to 4; q represents an integer of 0 to 3; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfonyl group, an —$NR^7R^8$ group, or a —$CONR^7R^8$ group wherein $R^7$ and $R^8$ in the —$NR^7R^8$ group and the —$CONR^7R^8$ group have the same definitions as those described in the above embodiment [1]; and ring A" represented by the following partial structural formula (II"):

[Formula 65]

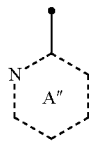

(II")

is selected from the group of the heteroaryls consisting of the following:

[Formula 66]

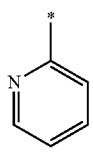

(II-31)

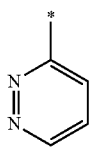

(II-32)

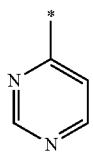

(II-33)

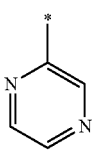

(II-34)

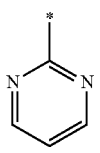

(II-35)

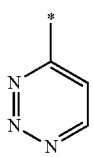

(II-36)

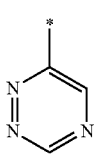

(II-37)

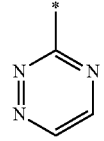

(II-38)

(II-39)

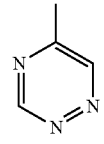

(II-40)

(II-41)

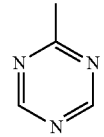

(II-42)

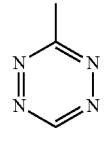

(II-43)

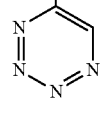

or a pharmaceutically acceptable salt thereof, or a solvate thereof.

[1-11-3]

More preferably, the compound of the above embodiment [1-11] is a compound represented by the above formula (I-d) wherein the definition of Z, $R^2$, $R^3$, $R^4$, and $R^5$ in the formula (I-d) have the same definitions as those described in the above embodiment [1]; p represents an integer of 0 to 3; q represents an integer of 0 to 2; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfonyl group, a —$CONR^{7A}R^{8A}$ group, or an —$NR^{7A}R^{8A}$ group wherein $R^{7A}$ and $R^{8A}$ in the —$NR^{7A}R^{8A}$ group and the —$CONR^{7A}R^{8A}$ group have the same definitions as those of $R^{7A}$ and $R^{8A}$ in the above embodiment [1-1-2];

ring A" represented by the following partial structural formula (II"):

[Formula 67]

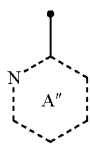
(II")

is selected from the group of the heteroaryls consisting of the following:

[Formula 68]

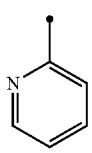
(II-31)

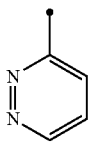
(II-32)

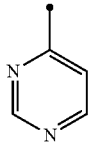
(II-33)

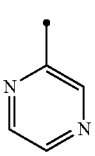
(II-34)

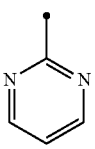
(II-35)

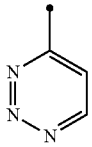
(II-36)

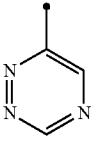
(II-37)

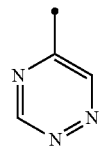
(II-39)

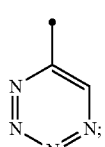
(II-42)

or a pharmaceutically acceptable salt thereof, or a solvate thereof.

[1-11-4]

Even more preferably, the compound of the above embodiment [1-11] is a compound represented by the above formula (I-d) wherein the definition of Z, $R^2$, $R^3$, $R^4$, and $R^5$ in the formula (I-d) have the same definitions as those described in the above embodiment [1]; p represents an integer of 1 to 3; q represents an integer of 0 to 2; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxyl $C_{1-6}$ alkyl group, a $C_{2-7}$ alkanoyl group, a $C_{1-6}$ alkylthio group, or a $C_{1-6}$ alkylsulfonyl group; and ring A" represented by the following partial structural formula (II"):

[Formula 69]

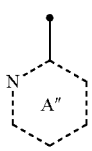
(II")

is selected from the group of the heteroaryls consisting of the following:

[Formula 70]

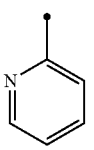
(II-31)

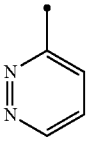
(II-32)

(II-33)

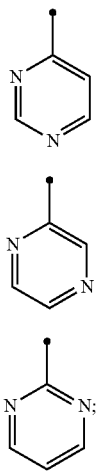

(II-34)

(II-35)

or a pharmaceutically acceptable salt thereof, or a solvate thereof.

[1-11-4-2]

Further preferably, the compound of the above embodiment [1-11] is a compound represented by the above formula (I-d) wherein the definition of Z, $R^1$, $R^2$, $R^3$, $R^4$, $R^5$, and ring A" represented by the partial structural formula (II") in the formula (I-d) have the same definitions as those described in the above embodiment [1-11-4]; p represents an integer of 0 to 3; and q represents an integer of 0 or 1, or a pharmaceutically acceptable salt thereof, or a solvate thereof.

[1-11-5]

Particularly preferably, the compound of the above embodiment [1-11] is a compound represented by the above formula (I-d) wherein the definition of Z, $R^2$, $R^3$, $R^4$, and $R^5$ in the formula (I-d) have the same definitions as those described in the above embodiment [1]; p represents an integer of 1 to 3; q represents an integer of 0 or 1; $R^1$ each independently represents a halogen atom, a cyano group, a $C_{1-6}$ alkyl group, a halogenated $C_{1-6}$ alkyl group, or a $C_{1-6}$ alkoxyl group, and more specifically, $R^1$ represents fluorine, chlorine, a cyano group, a methyl group, a trifluoromethyl group, a methoxy group, or the like;

ring A" represented by the following partial structural formula (II"):

[Formula 71]

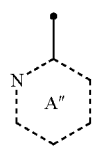

(II")

is selected from the group of the heteroaryls consisting of the following:

[Formula 72]

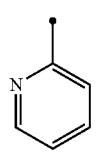

(II-31)

(II-32)

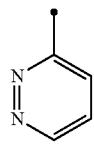

(II-33)

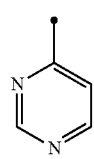

(II-34)

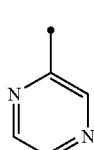

(II-35)

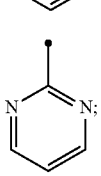

or a pharmaceutically acceptable salt thereof, or a solvate thereof.

[1-11-5-2]

More particularly preferably, the compound of the above embodiment [1-11] is a compound represented by the above formula (I-d) wherein the definition of Z, $R^1$, $R^2$, $R^3$, $R^4$, $R^5$, and ring A" represented by the partial structural formula (II") in the formula (I-d) have the same definitions as those described in the above embodiment [1-11-4]; p represents an integer of 0 to 3; and q represents an integer of 0 or 1, or a pharmaceutically acceptable salt thereof, or a solvate thereof.

[1-11-6]

Even more particularly preferably, the compound of the above embodiment [1-11] is a compound represented by the above formula (I-d) wherein the definition of p, q, Z, $R^1$, $R^2$, $R^3$, $R^4$, $R^5$, and ring A" in the formula (I-d) have the same definitions as those described in the above embodiment [1-11-5-2]; and a specific ring A" group, in which the definitions of the above described p, $R^1$, and ring A" are combined, represents a 4,6-dimethylpyrimidin-2-yl group, a 4-methylpyrimidin-2-yl group, a 2,5,6-trimethylpyrimidin-4-yl group, a 2,5-dimethylpyrimidin-4-yl group, a 2,6-dimethylpyrimidin-4-yl group, a 2,6-dimethoxypyrimidin-4-yl group, a 2-methylpyrimidin-4-yl group, a 2-methoxypyrimidin-4-yl group, a 5,6-dimethylpyrimidin-4-yl group, a 5-chloro-2-methylpyrimidin-4-yl group, a 5-chloropyrimidin-4-yl group, a 5-fluoro-2-methylpyrimidin-4-yl group, a 5-fluoro-2-methoxypyrimidin-4-yl group, a 5-fluoro-6-methylpyrimidin-4-yl group, a 5-methylpyrimidin-4-yl group, a 5-methoxypyrimidin-4-yl group, a 6-methylpyrimidin-4-yl group, a 6-methoxy-5-methylpyrimidin-4-yl group, a 4-methylpyridazin-3-yl group, a 5-methylpyridazin-3-yl group, a 6-methylpyridazin-3-yl group, a pyridazin-3-yl group, a 3-cyanopyridin-2-yl group, a 3-methoxypyridin-2-yl group, a 4,6-dimethylpyridin-2-yl group, a 4-fluoropyridin-2-yl group, a 4-methylpyridin-2-yl group, a 4-methoxypyridin-2-yl group, a 5-cyanopyridin-2-yl group, a 5-fluoropyridin-2-yl group, a 5-methylpyridin-2-yl group, a 6-(trifluoromethyl)pyridin-2-yl group, a 6-methylpyridin-2- yl group, a 3,6-dimethyl-pyrazin-2-yl group, a 3-methylpyrazin-2-yl group, a 3-methoxypyrazin-2-yl group, a 5-methylpyrazin-2-yl group, a 6-methylpyrazin-2-yl group, or a 6-methoxypyrazin-2-yl group, or a pharmaceutically acceptable salt thereof, or a solvate thereof.

[1-11a]

The compound of the above embodiment [1] represented by the above formula (I) is preferably a compound represented by the following formula (I-d):

[Formula 73]

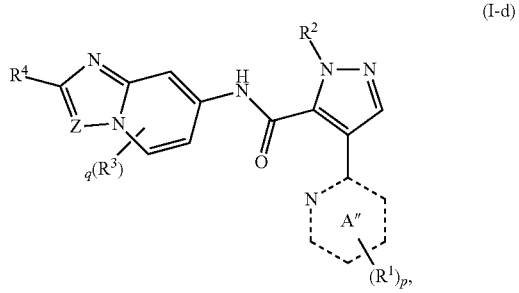

(I-d)

wherein the definition of q, Z, $R^3$, $R^4$, and $R^5$ in the formula (I-d) have the same definitions as those described in the above embodiment [1]; p, $R^1$, $R^6$, and ring A" represented by the partial structural formula (II") have the same definitions as those described in the above embodiment [1-11]; and $R^2$ represents a $C_{1-6}$ alkyl group, a halogenated $C_{1-6}$ alkyl group, a hydroxy $C_{1-6}$ alkyl group, or a $C_{1-6}$ alkoxyl $C_{1-6}$ alkyl group, or a pharmaceutically acceptable salt thereof, or a solvate thereof.

[1-11a-2]

Preferably, the compound of the above embodiment [1-11a] is a compound represented by the above formula (I-d) wherein $R^3$ has the same definitions as those described in the above embodiment [1-3]; $R^4$ has the same definitions as those described in the above embodiment [1-4]; Z and $R^5$ have the same definitions as those described in the above embodiment [1-5]; q has the same definitions as those described in the above embodiment [1-7]; p, $R^1$, and ring A" represented by the partial structural formula (II") have the same definitions as those described in the above embodiment [1-11-2]; and $R^2$ represents a $C_{1-6}$ alkyl group, a halogenated $C_{1-6}$ alkyl group, or a $C_{1-6}$ alkoxyl $C_{1-6}$ alkyl group, or a pharmaceutically acceptable salt thereof, or a solvate thereof.

[1-11a-3]

More preferably, the compound of the above embodiment [1-11a] is a compound represented by the above formula (I-d) wherein $R^3$ has the same definitions as those described in the above embodiment [1-3-2]; $R^4$ has the same definitions as those described in the above embodiment [1-4-2]; Z and $R^5$ have the same definitions as those described in the above embodiment [1-5-2]; q has the same definitions as those described in the above embodiment [1-7-2]; p, $R^1$, and ring A" represented by the partial structural formula (II") have the same definitions as those described in the above embodiment [1-11-3]; and $R^2$ represents a $C_{1-6}$ alkyl group or a halogenated $C_{1-6}$ alkyl group, or a pharmaceutically acceptable salt thereof, or a solvate thereof.

[1-11a-4]

Even more preferably, the compound of the above embodiment [1-11a] is a compound represented by the above formula (I-d) wherein $R^3$ has the same definitions as those described in the above embodiment [1-3-3]; $R^4$ has the same definitions as those described in the above embodiment [1-4-3]; Z and $R^5$ have the same definitions as those described in the above embodiment [1-5-3]; q has the same definitions as those described in the above embodiment [1-7-3]; p, $R^1$, and ring A" represented by the partial structural formula (II") have the same definitions as those described in the above embodiment [1-11-4-2]; and $R^2$ represents a $C_{1-6}$ alkyl group, or a pharmaceutically acceptable salt thereof, or a solvate thereof.

[1-11a-5]

Particularly preferably, the compound of the above embodiment [1-11a] is a compound represented by the above formula (I-d) wherein $R^3$ has the same definitions as those described in the above embodiment [1-3-4]; Z and $R^5$ have the same definitions as those described in the above embodiment [1-5-4]; q has the same definitions as those described in the above embodiment [1-7-4]; p, $R^1$, and ring A" represented by the partial structural formula (II") have the same definitions as those described in the above embodiment [1-11-5-2]; $R^2$ represents a $C_{1-6}$ alkyl group, and more specifically, $R^2$ represents a methyl group or the like; and $R^4$ represents a $C_{6-14}$ aryl group, a 3- to 14-membered non-aromatic heterocyclic group, or a 5- to 7-membered monocyclic heteroaryl group wherein the $C_{6-14}$ aryl group, the 3- to 14-membered non-aromatic heterocyclic group, and the 5- to 7-membered monocyclic heteroaryl group, which are represented by $R^4$, are each optionally substituted with one or two halogen atoms, $C_{1-6}$ alkyl groups, or halogenated $C_{1-6}$ alkyl groups, and specifically, $R^4$ represents phenyl, 2-methylphenyl, 3-methylphenyl, 4-methylphenyl, 2,5-dimethylphenyl, 2-fluorophenyl, 3-fluorophenyl, 4-fluorophenyl, 2,5-difluorophenyl, pyrrolidinyl, 2-fluoropyrrolidinyl, 3-fluoropyrrolidinyl, 2-methylpyrrolidinyl, 3-methylpyrrolidinyl, 2-trifluoromethylpyrrolidinyl, 3-trifluoromethylpyrrolidinyl, 2-pyridinyl, 3-pyridinyl, 2-pyridinyl, or the like, and $R^4$ preferably represents phenyl, 2-methylphenyl, 4-fluorophenyl, pyrrolidinyl, 2-methylpyrrolidinyl, 3-fluoropyrrolidinyl, 2-trifluoromethylpyrrolidinyl, or 3-pyridinyl, or a pharmaceutically acceptable salt thereof, or a solvate thereof.

[1-11a-6]

More particularly preferably, the compound of the above embodiment [1-11a] is a compound represented by the above formula (I-d) wherein the definition of p, q, Z, $R^1$, $R^2$, $R^3$, $R^4$, $R^5$, and ring A" in the formula (I-d) have the same definitions as those described in the above embodiment [1-11a-5]; and a specific ring A" group, in which the definitions of the above described p, $R^1$, and ring A" are combined, represents a 4,6-dimethylpyrimidin-2-yl group, a 4-methylpyrimidin-2-yl group, a 2,5,6-trimethylpyrimidin-4-yl group, a 2,5-dimethylpyrimidin-4-yl group, a 2,6-dimethylpyrimidin-4-yl group, a 2,6-dimethoxypyrimidin-4-yl group, a 2-methylpyrimidin-4-yl group, a 2-methoxypyrimidin-4-yl group, a 5,6-dimethylpyrimidin-4-yl group, a 5-chloro-2-methylpyrimidin-4-yl group, a 5-chloropyrimidin-4-yl group, a 5-fluoro-2-methylpyrimidin-4-yl group, a 5-fluoro-2-methoxypyrimidin-4-yl group, a 5-fluoro-6-methylpyrimidin-4-yl group, a 5-methylpyrimidin-4-yl group, a 5-methoxypyrimidin-4-yl group, a 6-methylpyrimidin-4-yl group, a 6-methoxy-5-methylpyrimidin-4-yl group, a 4-methylpyridazin-3-yl group, a 5-methylpyridazin-3-yl group, a 6-methylpyridazin-3-yl group, a pyridazin-3-yl group, a 3-cyanopyridin-2-yl group, a 3-methoxypyridin-2-yl group, a 4,6-dimethylpyridin-2-yl group, a 4-fluoropyridin-2-yl group, a 4-methylpyridin-2-yl group, a 4-methoxypyridin-2-yl group, a 5-cyanopyridin-2-yl group, a 5-fluoropyridin-2-yl group, a 5-methylpyridin-2-yl group, a 6-(trifluoromethyl)pyridin-2-yl group, a 6-methylpyridin-2-yl group, a 3,6-dimethyl-pyrazin-2-yl group, a 3-methyl-pyrazin-2-yl group, a 3-methoxypyrazin-2-yl group, a 5-methylpyrazin-2-yl group, a 6-methylpyrazin-2-yl group, or a 6-methoxypyrazin-2-yl group, or a pharmaceutically acceptable salt thereof, or a solvate thereof.

[1-12]

As described above, the embodiments [1-1] to [1-11a-6] of the present invention, the preferred embodiments thereof, and further, definitions of substituents are appropriately combined, so that preferred embodiments of the compound of the above embodiment [1] represented by the above formula (I) can be arbitrarily formed.

[2]

A second embodiment of the present invention is illustrated, by way of example, with the below-listed compounds that are preferable as the compounds of the above embodiment [1] represented by the above formula (I), or pharmaceutically acceptable salts thereof, or their solvates, or their optical isomers. It is to be noted that the following compound names are based on English names obtained in accordance with the chemical nomenclature program of Cambridge Soft Chem BioDraw Ultra 12.0.2.1076.

TABLE 1-1

| Compound name | Example No. |
|---|---|
| 1-methyl-4-(5-methylpyridin-2-yl)-N-(2-phenylimidazo[1,2-a]pyridin-7-yl)-1H-pyrazole-5-carboxamide | 1.1 |
| 1-methyl-4-(4-methylthiazol-2-yl)-N-(2-phenylimidazo[1,2-a]pyridin-7-yl)-1H-pyrazole-5-carboxamide | 1.2 |
| 4-(4-(difluoromethyl)thiazol-2-yl)-1-methyl-N-(2-phenylimidazo[1,2-a]pyridin-7-yl)-1H-pyrazole-5-carboxamide | 1.3 |
| 4-(4-(difluoromethyl)-5-methylthiazol-2-yl)-1-methyl-N-(2-phenylimidazo[1,2-a]pyridin-7-yl)-1H-pyrazole-5-carboxamide | 1.4 |

TABLE 1-1-continued

| Compound name | Example No. |
|---|---|
| 1-methyl-N-(2-phenylimidazo[1,2-a]pyridin-7-yl)-4-(4-(trifluoromethyl)thiazol-2-yl)-1H-pyrazole-5-carboxamide | 1.5 |
| 1-methyl-N-(2-phenylimidazo[1,2-a]pyridin-7-yl)-4-(6-(trifluoromethyl)pyridin-2-yl)-1H-pyrazole-5-carboxamide | 1.6 |
| 4-(5-chloro-4-(difluoromethyl)thiazol-2-yl)-1-methyl-N-(2-phenylimidazo[1,2-a]pyridin-7-yl)-1H-pyrazole-5-carboxamide | 1.7 |
| 1-methyl-4-(4-methylthiazol-2-yl)-N-(2-phenyl-5,6,7,8-tetrahydroimidazo[1,2-a]pyridin-7-yl)-1H-pyrazole-5-carboxamide | 2.1 |

TABLE 1-2

| Compound name | Example No. |
|---|---|
| 4-(4,5-dimethylthiazol-2-yl)-1-methyl-N-(2-phenyl-5,6,7,8-tetrahydroimidazo[1,2-a]pyridin-7-yl)-1H-pyrazole-5-carboxamide | 2.2 |
| 1-methyl-N-(2-phenyl-5,6,7,8-tetrahydroimidazo[1,2-a]pyridin-7-yl)-4-(4-(trifluoromethyl)thiazol-2-yl)-1H-pyrazole-5-carboxamide | 2.3 |
| 4-(4-(difluoromethyl)thiazol-2-yl)-1-methyl-N-(2-phenyl-5,6,7,8-tetrahydroimidazo[1,2-a]pyridin-7-yl)-1H-pyrazole-5-carboxamide | 2.4 |
| 4-(5-chloro-4-(difluoromethyl)thiazol-2-yl)-1-methyl-N-(2-phenyl-5,6,7,8-tetrahydroimidazo[1,2-a]pyridin-7-yl)-1H-pyrazole-5-carboxamide | 2.5 |
| 4-(4-(difluoromethyl)-5-methylthiazol-2-yl)-1-methyl-N-(2-phenyl-5,6,7,8-tetrahydroimidazo[1,2-a]pyridin-7-yl)-1H-pyrazole-5-carboxamide | 2.6 |
| 4-(4-(difluoromethyl)-5-methylthiazol-2-yl)-N-(2-(3-fluorophenyl)-5,6,7,8-tetrahydroimidazo[1,2-a]pyridin-7-yl)-1-methyl-1H-pyrazole-5-carboxamide | 2.7 |
| N-(2-(3-fluorophenyl)-5,6,7,8-tetrahydroimidazo[1,2-a]pyridin-7-yl)-1-methyl-4-(4-(trifluoromethyl)thiazol-2-yl)-1H-pyrazole-5-carboxamide | 2.8 |

TABLE 1-3

| Compound name | Example No. |
|---|---|
| 1-methyl-4-(6-methylpyridin-2-yl)-N-(2-phenyl-5,6,7,8-tetrahydroimidazo[1,2-a]pyridin-7-yl)-1H-pyrazole-5-carboxamide | 2.9 |
| 1-methyl-4-(5-methyl-1,3,4-thiadiazol-2-yl)-N-(2-phenyl-5,6,7,8-tetrahydroimidazo[1,2-a]pyridin-7-yl)-1H-pyrazole-5-carboxamide | 2.10 |
| 4-(6-methoxypyridin-2-yl)-1-methyl-N-(2-phenyl-5,6,7,8-tetrahydroimidazo[1,2-a]pyridin-7-yl)-1H-pyrazole-5-carboxamide | 2.11 |
| 1-methyl-4-(2-methylthiazol-4-yl)-N-(2-phenyl-5,6,7,8-tetrahydroimidazo[1,2-a]pyridin-7-yl)-1H-pyrazole-5-carboxamide | 2.12 |
| 1-methyl-4-(6-methylpyrazin-2-yl)-N-(2-phenyl-5,6,7,8-tetrahydroimidazo[1,2-a]pyridin-7-yl)-1H-pyrazole-5-carboxamide | 2.13 |
| 4-(3-isopropy1-1,2,4-thiadiazol-5-yl)-1-methyl-N-(2-phenyl-5,6,7,8-tetrahydroimidazo[1,2-a]pyridin-7-yl)-1H-pyrazole-5-carboxamide | 2.14 |
| 1-methyl-4-(5-methylthiazol-2-yl)-N-(2-phenyl-5,6,7,8-tetrahydroimidazo[1,2-a]pyridin-7-yl)-1H-pyrazole-5-carboxamide | 2.15 |

TABLE 1-4

| Compound name | Example No. |
|---|---|
| 1-methyl-4-(4-methylpyrimidin-2-yl)-N-(2-phenyl-5,6,7,8-tetrahydroimidazo[1,2-a]pyridin-7-yl)-1H-pyrazole-5-carboxamide | 2.16 |
| 1-methyl-4-(1-methyl-1H-imidazol-4-yl)-N-(2-phenyl-5,6,7,8-tetrahydroimidazo[1,2-a]pyridin-7-yl)-1H-pyrazole-5-carboxamide | 2.17 |
| N-(2-(2,5-difluorophenyl)-5,6,7,8-tetrahydroimidazo[1,2-a]pyridin-7-yl)-1-methyl-4-(5-methyl-1,3,4-thiadiazol-2-yl)-1H-pyrazole-5-carboxamide | 2.18 |
| N-(3-fluoro-2-phenyl-5,6,7,8-tetrahydroimidazo[1,2-a]pyridin-7-yl)-1-methyl-4-(4-(trifluoromethyl)thiazol-2-yl)-1H-pyrazole-5-carboxamide | 2.19 |

TABLE 1-4-continued

| Compound name | Example No. |
|---|---|
| 4-(4-(difluoromethyl)thiazol-2-yl)-N-(2-(3-fluorophenyl)-5,6,7,8-tetrahydroimidazo[1,2-a]pyridin-7-yl)-1-methyl-1H-pyrazole-5-carboxamide | 2.20 |
| 1-methyl-4-(5-methylpyridin-2-yl)-N-(2-phenyl-5,6,7,8-tetrahydroimidazo[1,2-a]pyridin-7-yl)-1H-pyrazole-5-carboxamide | 2.21 |
| 1-methyl-4-(4-methylpyridin-2-yl)-N-(2-phenyl-5,6,7,8-tetrahydroimidazo[1,2-a]pyridin-7-yl)-1H-pyrazole-5-carboxamide | 2.22 |

TABLE 1-5

| Compound name | Example No. |
|---|---|
| N-(2-(3-fluorophenyl)-5,6,7,8-tetrahydroimidazo[1,2-a]pyridin-7-yl)-1-methyl-4-(4-methylpyrimidin-2-yl)-1H-pyrazole-5-carboxamide | 2.23 |
| N-(2-(3-fluorophenyl)-5,6,7,8-tetrahydroimidazo[1,2-a]pyridin-7-yl)-1-methyl-4-(6-methylpyrazin-2-yl)-1H-pyrazole-5-carboxamide | 2.24 |
| 1-methyl-N-(2-phenyl-5,6,7,8-tetrahydroimidazo[1,2-a]pyridin-7-yl)-4-(thiazol-4-yl)-1H-pyrazole-5-carboxamide | 2.25 |
| 1-methyl-N-(2-phenyl-5,6,7,8-tetrahydroimidazo[1,2-a]pyridin-7-yl)-4-(thiazol-2-yl)-1H-pyrazole-5-carboxamide | 2.26 |
| 4-(4-(tert-butyl)thiazol-2-yl)-1-methyl-N-(2-phenyl-5,6,7,8-tetrahydroimidazo[1,2-a]pyridin-7-yl)-1H-pyrazole-5-carboxamide | 2.27 |
| 4-(4-(difluoromethyl)thiazol-2-yl)-N-(2-(4-fluorophenyl)-5,6,7,8-tetrahydroimidazo[1,2-a]pyridin-7-yl)-1-methyl-1H-pyrazole-5-carboxamide | 2.28 |
| N-(2-(4-fluorophenyl)-5,6,7,8-tetrahydroimidazo[1,2-a]pyridin-7-yl)-1-methyl-4-(4-(trifluoromethyl)thiazol-2-yl)-1H-pyrazole-5-carboxamide | 2.29 |

TABLE 1-6

| Compound name | Example No. |
|---|---|
| N-(6-fluoro-2-phenyl-[1,2,4]triazolo[1,5-a]pyridin-7-yl)-1-methyl-4-(3-methylpyridin-2-yl)-1H-pyrazole-5-carboxamide | 3.1 |
| N-(6-fluoro-2-phenyl-[1,2,4]triazolo[1,5-a]pyridin-7-yl)-1-methyl-4-(5-methylpyrazin-2-yl)-1H-pyrazole-5-carboxamide | 3.2 |
| N-(6-fluoro-2-phenyl-[1,2,4]triazolo[1,5-a]pyridin-7-yl)-1-methyl-4-(6-methylpyridin-2-yl)-1H-pyrazole-5-carboxamide | 3.3 |
| N-(6-fluoro-2-phenyl-[1,2,4]triazolo[1,5-a]pyridin-7-yl)-4-(4-fluoropyridin-2-yl)-1-methyl-1H-pyrazole-5-carboxamide | 3.4 |
| N-(6-fluoro-2-phenyl-[1,2,4]triazolo[1,5-a]pyridin-7-yl)-1-methyl-4-(4-methylpyridin-2-yl)-1H-pyrazole-5-carboxamide | 3.5 |
| N-(6-fluoro-2-phenyl-[1,2,4]triazolo[1,5-a]pyridin-7-yl)-1-methyl-4-(4-(trifluoromethyl)thiazol-2-yl)-1H-pyrazole-5-carboxamide | 3.6 |
| N-(6-fluoro-2-phenyl-[1,2,4]triazolo[1,5-a]pyridin-7-yl)-4-(3-methoxypyridin-2-yl)-1-methyl-1H-pyrazole-5-carboxamide | 3.7 |

TABLE 1-7

| Compound name | Example No. |
|---|---|
| N-(6-fluoro-2-phenyl-[1,2,4]triazolo[1,5-a]pyridin-7-yl)-4-(5-fluoropyridin-2-yl)-1-methyl-1H-pyrazole-5-carboxamide | 3.8 |
| N-(6-fluoro-2-phenyl-[1,2,4]triazolo[1,5-a]pyridin-7-yl)-1-methyl-4-(6-methylpyrazin-2-yl)-1H-pyrazole-5-carboxamide | 3.9 |
| N-(6-fluoro-2-phenyl-[1,2,4]triazolo[1,5-a]pyridin-7-yl)-1-methyl-4-(6-(trifluoromethyl)pyridin-2-yl)-1H-pyrazole-5-carboxamide | 3.10 |
| 4-(4,6-dimethylpyridin-2-yl)-N-(6-fluoro-2-phenyl-[1,2,4]-[1,5-a]pyridin-7-yl)-1-methyl-1H-pyrazole-5-carboxamide | 3.11 |
| 4-(4-(difluoromethyl)thiazol-2-yl)-N-(6-fluoro-2-phenyl-[1,2,4]triazolo[1,5-a]pyridin-7-yl)-1-methyl-1H-pyrazole-5-carboxamide | 3.12 |
| 4-(3-cyanopyridin-2-yl)-N-(6-fluoro-2-phenyl-[1,2,4]triazolo[1,5-a]pyridin-7-yl)-1-methyl-1H-pyrazole-5-carboxamide | 3.13 |
| 4-(3,6-dimethyl-pyrazin-2-yl)-N-(6-fluoro-2-phenyl-[1,2,4]triazolo[1,5-a]pyridin-7-yl)-1-methyl-1H-pyrazole-5-carboxamide | 3.14 |

TABLE 1-8

| Compound name | Example No. |
|---|---|
| 4-(4-(difluoromethyl)thiazol-2-yl)-1-methyl-N-(2-phenyl-[1,2,4]triazolo[1,5-a]pyridin-7-yl)-1H-pyrazole-5-carboxamide | 3.15 |
| 4-(4-(difluoromethyl)thiazol-2-yl)-N-(2-(2-methoxyphenyl)-[1,2,4]triazolo[1,5-a]pyridin-7-yl)-1-methyl-1H-pyrazole-5-carboxamide | 3.16 |
| 4-(4-(difluoromethyl)thiazol-2-yl)-N-(2-(3-fluorophenyl)-[1,2,4]triazolo[1,5-a]pyridin-7-yl)-1-methyl-1H-pyrazole-5-carboxamide | 3.17 |

TABLE 1-8-continued

| Compound name | Example No. |
| --- | --- |
| 4-(4-ethylthiazol-2-yl)-1-methyl-N-(2-phenyl-[1,2,4]triazolo[1,5-a]pyridin-7-yl)-1H-pyrazole-5-carboxamide | 3.18 |
| 4-(4-(difluoromethyl)thiazol-2-yl)-N-(2-((2S,6R)-2,6-dimethylmorpholino)-[1,2,4]triazolo[1,5-a]pyridin-7-yl)-1-methy1-1H-pyrazole-5-carboxamide | 3.19 |
| 4-(5-chloro-4-(difluoromethyl)thiazol-2-yl)-1-methyl-N-(2-phenyl-[1,2,4]triazolo[1,5-a]pyridin-7-yl)-1H-pyrazole-5-carboxamide | 3.20 |
| N-(5-chloro-2-(2-methoxyphenyl)-[1,2,4]triazolo[1,5-a]pyridin-7-yl)-4-(5-chloro-4-(difluoromethyl)thiazol-2-yl)-1-methyl-1H-pyrazole-5-carboxamide | 3.21 |

TABLE 1-9

| Compound name | Example No. |
| --- | --- |
| 4-(2,5-dimethylpyrimidin-4-yl)-N-(6-fluoro-2-phenyl-[1,2,4]triazolo[1,5-a]pyridin-7-yl)-1-methyl-1H-pyrazole-5-carboxamide | 3.22 |
| 4-(5-cyanopyridin-2-yl)-N-(6-fluoro-2-phenyl-[1,2,4]triazolo[1,5-a]pyridin-7-yl)-1-methyl-1H-pyrazole-5-carboxamide | 3.23 |
| N-(6-fluoro-2-phenyl-[1,2,4]triazolo[1,5-a]pyridin-7-yl)-1-methyl-4-(4-methylpyridazin-3-yl)-1H-pyrazole-5-carboxamide | 3.24 |
| N-(6-fluoro-2-phenyl-[1,2,4]triazolo[1,5-a]pyridin-7-yl)-1-methyl-4-(2-methylpyrimidin-4-yl)-1H-pyrazole-5-carboxamide | 3.25 |
| N-(6-fluoro-2-phenyl-[1,2,4]triazolo[1,5-a]pyridin-7-yl)-4-(2-methoxypyrimidin-4-yl)-1-methyl-1H-pyrazole-5-carboxamide | 3.26 |
| 4-(5-fluoro-2-methoxypyrimidin-4-yl)-N-(6-fluoro-2-phenyl-[1,2,4]triazolo[1,5-a]pyridin-7-yl)-1-methyl-1H-pyrazole-5-carboxamide | 3.27 |
| N-(6-fluoro-2-phenyl-[1,2,4]triazolo[1,5-a]pyridin-7-yl)-4-(3-methoxypyrazin-2-yl)-1-methyl-1H-pyrazole-5-carboxamide | 3.28 |

TABLE 1-10

| Compound name | Example No. |
| --- | --- |
| 4-(5-chloropyrimidin-4-yl)-N-(6-fluoro-2-phenyl-[1,2,4]triazolo[1,5-a]pyridin-7-yl)-1-methyl-1H-pyrazole-5-carboxamide | 3.29 |
| 4-(2,6-dimethylpyrimidin-4-yl)-N-(6-fluoro-2-phenyl-[1,2,4]triazolo[1,5-a]pyridin-7-yl)-1-methyl-1H-pyrazole-5-carboxamide | 3.30 |
| N-(6-fluoro-2-phenyl-[1,2,4]triazolo[1,5-a]pyridin-7-yl)-4-(6-methoxy-5-methylpyrimidin-4-yl)-1-methyl-1H-pyrazole-5-carboxamide | 3.31 |
| N-(6-fluoro-2-phenyl-[1,2,4]triazolo[1,5-a]pyridin-7-yl)-1-methyl-4-(3-methylpyrazin-2-yl)-1H-pyrazole-5-carboxamide | 3.32 |
| N-(6-fluoro-2-phenyl-[1,2,4]triazolo[1,5-a]pyridin-7-yl)-1-methyl-4-(5-methylpyrimidin-4-yl)-1H-pyrazole-5-carboxamide | 3.33 |
| N-(6-fluoro-2-phenyl-[1,2,4]triazolo[1,5-a]pyridin-7-yl)-4-(5-methoxypyrimidin-4-yl)-1-methyl-1H-pyrazole-5-carboxamide | 3.34 |
| 4-(5,6-dimethylpyrimidin-4-yl)-N-(6-fluoro-2-phenyl-[1,2,4]triazolo[1,5-a]pyridin-7-yl)-1-methyl-1H-pyrazole-5-carboxamide | 3.35 |

TABLE 1-11

| Compound name | Example No. |
| --- | --- |
| 4-(5-fluoro-2-methylpyrimidin-4-yl)-N-(6-fluoro-2-phenyl-[1,2,4]triazolo[1,5-a]pyridin-7-yl)-1-methyl-1H-pyrazole-5-carboxamide | 3.36 |
| N-(6-fluoro-2-phenyl-[1,2,4]triazolo[1,5-a]pyridin-7-yl)-1-methyl-4-(2,5,6-trimethylpyrimidin-4-yl)-1H-pyrazole-5-carboxamide | 3.37 |
| N-(6-fluoro-2-phenyl-[1,2,4]triazolo[1,5-a]pyridin-7-yl)-4-(5-fluoro-6-methylpyrimidin-4-yl)-1-methyl-1H-pyrazole-5-carboxamide | 3.38 |
| N-(6-fluoro-2-phenyl-[1,2,4]triazolo[1,5-a]pyridin-7-yl)-1-methyl-4-(6-methylpyrimidin-4-yl)-1H-pyrazole-5-carboxamide | 3.39 |
| 4-(2,6-dimethoxypyrimidin-4-yl)-N-(6-fluoro-2-phenyl-[1,2,4]triazolo[1,5-a]pyridin-7-yl)-1-methyl-1H-pyrazole-5-carboxamide | 3.40 |
| 4-(5-chloro-2-methylpyrimidin-4-yl)-N-(6-fluoro-2-phenyl-[1,2,4]triazolo[1,5-a]pyridin-7-yl)-1-methyl-1H-pyrazole-5-carboxamide | 3.41 |
| N-(6-fluoro-2-phenyl-[1,2,4]triazolo[1,5-a]pyridin-7-yl)-4-(6-methoxypyrazin-2-yl)-1-methyl-1H-pyrazole-5-carboxamide | 3.42 |

TABLE 1-12

| Compound name | Example No. |
|---|---|
| N-(6-fluoro-2-phenyl-[1,2,4]triazolo[1,5-a]pyridin-7-yl)-1-methyl-4-(4-methylpyrimidin-2-yl)-1H-pyrazole-5-carboxamide | 3.43 |
| 4-(4,6-dimethylpyrimidin-2-yl)-N-(6-fluoro-2-phenyl-[1,2,4]triazolo[1,5-a]pyridin-7-yl)-1-methyl-1H-pyrazole-5-carboxamide | 3.44 |
| N-(6-fluoro-2-phenyl-[1,2,4]triazolo[1,5-a]pyridin-7-yl)-1-methyl-4-(6-methylpyridazin-3-yl)-1H-pyrazole-5-carboxamide | 3.45 |
| N-(6-fluoro-2-phenyl-[1,2,4]triazolo[1,5-a]pyridin-7-yl)-1-methyl-4-(5-methylpyridazin-3-yl)-1H-pyrazole-5-carboxamide | 3.46 |
| N-(6-fluoro-2-phenyl-[1,2,4]triazolo[1,5-a]pyridin-7-yl)-1-methyl-4-(pyridazin-3-yl)-1H-pyrazole-5-carboxamide | 3.47 |
| N-(6-fluoro-2-phenyl-[1,2,4]triazolo[1,5-a]pyridin-7-yl)-1-methyl-4-(1-methyl-1H-imidazol-4-yl)-1H-pyrazole-5-carboxamide | 3.48 |
| 4-(2,5-dimethylpyrimidin-4-yl)-N-(6-fluoro-2-(pyridin-3-yl)-[1,2,4]triazolo[1,5-a]pyridin-7-yl)-1-methyl-1H-pyrazole-5-carboxamide | 3.49 |

TABLE 1-13

| Compound name | Example No. |
|---|---|
| 4-(2,5-dimethylpyrimidin-4-yl)-N-(6-fluoro-2-(o-tolyl)-[1,2,4]triazolo[1,5-a]pyridin-7-yl)-1-methyl-1H-pyrazole-5-carboxamide | 3.50 |
| N-(6-fluoro-2-phenyl-[1,2,4]triazolo[1,5-a]pyridin-7-yl)-1-methyl-4-(5-methylpyridin-2-yl)-1H-pyrazole-5-carboxamide | 3.51 |
| N-(6-fluoro-2-phenyl-[1,2,4]triazolo[1,5-a]pyridin-7-yl)-4-(4-methoxypyridin-2-yl)-1-methyl-1H-pyrazole-5-carboxamide | 3.52 |
| 4-(4,6-dimethylpyridin-2-yl)-N-(6-fluoro-2-phenyl-[1,2,4]triazolo[1,5-a]pyridin-7-yl)-1-methyl-1H-pyrazole-5-carboxamide | 3.53 |
| 4-(4,6-dimethylpyridin-2-yl)-N-(6-fluoro-2-(4-fluorophenyl)-[1,2,4]triazolo[1,5-a]pyridin-7-yl)-1-methyl-1H-pyrazole-5-carboxamide | 3.54 |
| (S)-4-(4-(difluoromethyl)thiazol-2-yl)-1-methyl-N-(2-(2-methylpyrrolidin-1-yl)-[1,2,4]triazolo[1,5-a]pyridin-7-yl)-1H-pyrazole-5-carboxamide | 4.1 |
| (S)-4-(5-chloro-4-(difluoromethyl)thiazol-2-yl)-1-methyl-N-(2-(2-methylpyrrolidin-1-yl)-[1,2,4]triazolo[1,5-a]pyridin-7-yl)-1H-pyrazole-5-carboxamide | 4.2 |

TABLE 1-14

| Compound name | Example No. |
|---|---|
| (S)-1-methyl-N-(2-(2-methylpyrrolidin-1-yl)-[1,2,4]triazolo[1,5-a]pyridin-7-yl)-4-(6-(trifluoromethyl)pyridin-2-yl)-1H-pyrazole-5-carboxamide | 4.3 |
| (S)-1-methyl-4-(4-methylpyridin-2-yl)-N-(2-(2-methylpyrrolidin-1-yl)-[1,2,4]triazolo[1,5-a]pyridin-7-yl)-1H-pyrazole-5-carboxamide | 4.4 |
| (S)-4-(4-methoxypyridin-2-yl)-1-methyl-N-(2-(2-methylpyrrolidin-1-yl)-[1,2,4]triazolo[1,5-a]pyridin-7-yl)-1H-pyrazole-5-carboxamide | 4.5 |
| (S)-1-methyl-4-(6-methylpyrazin-2-yl)-N-(2-(2-methylpyrrolidin-1-yl)-[1,2,4]triazolo[1,5-a]pyridin-7-yl)-1H-pyrazole-5-carboxamide | 4.6 |
| (S)-1-methyl-4-(6-methylpyridin-2-yl)-N-(2-(2-methylpyrrolidin-1-yl)-[1,2,4]triazolo[1,5-a]pyridin-7-yl)-1H-pyrazole-5-carboxamide | 4.7 |
| (S)-4-(4,6-dimethylpyridin-2-yl)-1-methyl-N-(2-(2-methylpyrrolidin-1-yl)-[1,2,4]triazolo[1,5-a]pyridin-7-yl)-1H-pyrazole-5-carboxamide | 4.8 |
| (S)-4-(4-(difluoromethyl)-5-methylthiazol-2-yl)-1-methyl-N-(2-(2-methylpyrrolidin-1-yl)-[1,2,4]triazolo[1,5-a]pyridin-7-yl)-1H-pyrazole-5-carboxamide | 4.9 |

TABLE 1-15

| Compound name | Example No. |
|---|---|
| (S)-1-methyl-N-(2-(2-methylpyrrolidin-1-yl)-[1,2,4]triazolo[1,5-a]pyridin-7-yl)-4-(4-(trifluoromethyl)thiazol-2-yl)-1H-pyrazole-5-carboxamide | 4.10 |
| (R)-N-(6-fluoro-2-(2trifluoromethyl)pyrrolidin-1-yl)-[1,2,4]triazolo[1,5-a]pyridin-7-yl)-1-methyl-4-(6-methylpyridin-2-yl)-1H-pyrazole-5-carboxamide | 4.11 |
| (R)-4-(4-(difluoromethyl)thiazol-2-yl)-N-(2-(3-fluoropyrrolidin-1-yl)-[1,2,4]triazolo[1,5-a]pyridin-7-yl)-1-methyl-1H-pyrazole-5-carboxamide | 4.12 |
| (R)-N-(2-(3-fluoropyrrolidin-1-yl)-[1,2,4]triazolo[1,5-a]pyridin-7-yl)-1-methyl-4-(4-(trifluoromethyl)thiazol-2-yl)-1H-pyrazole-5-carboxamide | 4.13 |
| (R)-4-(4-(difluoromethyl)-5-methylthiazol-2-yl)-N-(2-(3-fluoropyrrolidin-1-yl)-[1,2,4]triazolo[1,5-a]pyridin-7-yl)-1-methyl-1H-pyrazole-5-carboxamide | 4.14 |
| (S)-4-(4-(difluoromethyl)thiazol-2-yl)-N-(2-(3-fluoropyrrolidin-1-yl)-[1,2,4]triazolo[1,5-a]pyridin-7-yl)-1-methyl-1H-pyrazole-5-carboxamide | 4.15 |

TABLE 1-15-continued

| Compound name | Example No. |
| --- | --- |
| (S)-N-(2-(3-fluoropyrrolidin-1-yl)-[1,2,4]triazolo[1,5-a]pyridin-7-yl)-1-methyl-4-(6-(trifluoromethyl)pyridin-2-yl)-1H-pyrazole-5-carboxamide | 4.16 |

TABLE 1-16

| Compound name | Example No. |
| --- | --- |
| (S)-N-(2-(3-fluoropyrrolidin-1-yl)-[1,2,4]triazolo[1,5-a]pyridin-7-yl)-1-methyl-4-(4-methylpyridin-2-yl)-1H-pyrazole-5-carboxamide | 4.17 |
| (S)-N-(2-(3-fluoropyrrolidin-1-yl)-[1,2,4]triazolo[1,5-a]pyridin-7-yl)-4-(4-methoxypyridin-2-yl)-1-methyl-1H-pyrazole-5-carboxamide | 4.18 |
| (S)-N-(2-(3-fluoropyrrolidin-1-yl)-[1,2,4]triazolo[1,5-a]pyridin-7-yl)-1-methyl-4-(6-methylpyrazin-2-yl)-1H-pyrazole-5-carboxamide | 4.19 |
| (S)-4-(4,6-dimethylpyridin-2-yl)-N-(2-(3-fluoropyrrolidin-1-yl)-[1,2,4]triazolo[1,5-a]pyridin-7-yl)-1-methyl-1H-pyrazole-5-carboxamide | 4.20 |
| (S)-N-(2-(3-fluoropyrrolidin-1-yl)-[1,2,4]triazolo[1,5-a]pyridin-7-yl)-1-methyl-4-(6-methylpyridin-2-yl)-1H-pyrazole-5-carboxamide | 4.21 |
| (S)-N-(2-(3-fluoropyrrolidin-1-yl)-[1,2,4]triazolo[1,5-a]pyridin-7-yl)-1-methyl-4-(4-(trifluoromethyl)thiazol-2-yl)-1H-pyrazole-5-carboxamide | 4.22 |
| (S)-4-(4-(difluoromethyl)-5-methylthiazol-2-yl)-N-(2-(3-fluoropyrrolidin-1-yl)-[1,2,4]triazolo[1,5-a]pyridin-7-yl)-1-methyl-1H-pyrazole-5-carboxamide | 4.23 |

TABLE 1-17

| Compound name | Example No. |
| --- | --- |
| (S)-4-(4,6dimethylpyridin-2-yl)-N-(6-fluoro-2-(3-fluoropyrrolidin-1-yl)-[1,2,4]triazolo[1,5-a]pyridin-7-yl)-1-methyl-1H-pyrazole-5-carboxamide | 4.24 |
| 4-(4-(difluoromethyl)thiazol-2-yl)-1-methyl-N-(2-(pyrrolidin-1-yl)-[1,2,4]triazolo[1,5-a]pyridin-7-yl)-1H-pyrazole-5-carboxamide | 4.25 |
| 4-(5-chloro-4-(difluoromethyl)thiazol-2-yl)-1-methyl-N-(2-(pyrrolidin-1-yl)-[1,2,4]triazolo[1,5-a]pyridin-7-yl)-1H-pyrazole-5-carboxamide | 4.26 |
| 1-methyl-N-(2-(pyrrolidin-1-yl)-[1,2,4]triazolo[1,5-a]pyridin-7-yl)-4-(6-(trifluoromethyl)pyridin-2-yl)-1H-pyrazole-5-carboxamide | 4.27 |
| 4-(4-methoxypyridin-2-yl)-1-methyl-N-(2-(pyrrolidin-1-yl)-[1,2,4]triazolo[1,5-a]pyridin-7-yl)-1H-pyrazole-5-carboxamide | 4.28 |
| 1-methyl-4-(6-methylpyrazin-2-yl)-N-(2-(pyrrolidin-1-yl)-[1,2,4]triazolo[1,5-a]pyridin-7-yl)-1H-pyrazole-5-carboxamide | 4.29 |
| 1-methyl-4-(4-methylpyridin-2-yl)-N-(2-(pyrrolidin-1-yl)-[1,2,4]triazolo[1,5-a]pyridin-7-yl)-1H-pyrazole-5-carboxamide | 4.30 |

TABLE 1-18

| Compound name | Example No. |
| --- | --- |
| 1-methyl-4-(6-methylpyridin-2-yl)-N-(2-(pyrrolidin-1-yl)-[1,2,4]triazolo[1,5-a]pyridin-7-yl)-1H-pyrazole-5-carboxamide | 4.31 |
| 4-(4,6-dimethylpyridin-2-yl)-1-methyl-N-(2-(pyrrolidin-1-yl)-[1,2,4]triazolo[1,5-a]pyridin-7-yl)-1H-pyrazole-5-carboxamide | 4.32 |
| 4-(4-(difluoromethyl)-5-methylthiazol-2-yl)-1-methyl-N-(2-(pyrrolidin-1-yl)-[1,2,4]triazolo[1,5-a]pyridin-7-yl)-1H-pyrazole-5-carboxamide | 4.33 |
| 1-methyl-N-(2-(pyrrolindin-1-yl)-[1,2,4]triazolo[1,5-a]pyridin-7-yl)-4-(4-(trifluoromethyl)thiazol-2-yl)-1H-pyrazole-5-carboxamide | 4.34 |
| 4-(2,5-dimethylpyrimidin-4-yl)-N-(6-fluoro-2-(pyrrolidin-1-yl)-[1,2,4]triazolo[1,5-a]pyridin-7-yl)-1-methyl-1H-pyrazole-5-carboxamide | 4.35 |
| 4-(5-chloro-4-(difluoromethyl)thiazol-2-yl)-N-(2-((2S,6R)-2,6-dimethylmorpholino)-[1,2,4]triazolo[1,5-a]pyridin-7-yl)-1-methyl-1H-pyrazole-5-carboxamide | 4.36 |
| 4-(4-(difluoromethyl)-5-methylthiazol-2-yl)-1-methyl-N-(2-phenyl-5,6,7,8-tetrahydro-[1,2,4]triazolo[1,5-a]pyridin-7-yl)-1H-pyrazole-5-carboxamide | 5.1 |

TABLE 1-19

| Compound name | Example No. |
| --- | --- |
| 4-(4-(difluoromethyl)thiazol-2-yl)-N-(2-(4-fluorophenyl)-5,6,7,8-tetrahydro-[1,2,4]triazolo[1,5-a]pyridin-7-yl)-1-methyl-1H-pyrazole-5-carboxamide | 5.2 |
| 4-(5-chloro-4-(difluoromethyl)thiazol-2-yl)-N-(2-(4-fluorophenyl)-5,6,7,8-tetrahydro-[1,2,4]triazolo[1,5-a]pyridin-7-yl)-1-methyl-1H-pyrazole-5-carboxamide | 5.3 |
| 4-(4,5-dimethylthiazol-2-yl)-1-methyl-N-(2-phenyl-5,6,7,8-tetrahydro-[1,2,4]triazolo[1,5-a]pyridin-7-yl)-1H-pyrazole-5-carboxamide | 5.4 |
| 4-(4-(difluoromethyl)-5-vinylthiazol-2-yl)-1-methyl-N-(2-phenyl-5,6,7,8-tetrahydro-[1,2,4]triazolo[1,5-a]pyridin-7-yl)-1H-pyrazole-5-carboxamide | 5.5 |
| 4-(4-(difluoromethyl)-5-ethylthiazol-2-yl)-1-methyl-N-(2-phenyl-5,6,7,8-tetrahydro-[1,2,4]triazolo[1,5-a]pyridin-7-yl)-1H-pyrazole-5-carboxamide | 5.6 |
| 4-(5-bromo-4-methylthiazol-2-yl)-1-methyl-N-(2-phenyl-5,6,7,8-tetrahydro-[1,2,4]triazolo[1,5-a]pyridin-7-yl)-1H-pyrazole-5-carboxamide | 5.7 |

TABLE 1-19-continued

| Compound name | Example No. |
|---|---|
| 4-(5-cyclopropyl-4-(diflyoromethyl)thiazol-2-y1)-1-methyl-N-(2-phenyl-5,6,7,8-tetrahydro-[1,2,4]triazolo[1,5-a]pyridin-7-y1)-1H-pyrazole-5-carboxamide | 5.8 |

TABLE 1-20

| Compound name | Example No. |
|---|---|
| 1-methyl-N-(2-phenyl-5,6,7,8-tetrahydro-[1,2,4]triazolo[1,5-a]pyridin-7-y1)-4-(4trifluoromethyl)thiazol-2-y1)-1H-pyrazole-5-carboxamide | 5.9 |
| 4-(4-cyanothiazol-2-y1)-1-methyl-N-(2-phenyl-5,6,7,8-tetrahydro-[1,2,4]triazolo[1,5-a]pyridin-7-y1)-1H-pyrazole-5-carboxamide | 5.10 |
| 4-(5-(2-ethoxyethyl)-4-methylthiazol-2-y1)-1-methyl-N-(2-phenyl-5,6,7,8-thtrahydro-[1,2,4]triazolo[1,5-a]pyridin-7-y1)-1H-pyrazole-5-carboxamide | 5.11 |
| 4-(5-ethyl-1,3,4-thiadiazol-2-y1)-1-methyl-N-(2-phenyl-5,6,7,8-tetrahydro-[1,2,4]triazolo[1,5-a]pyridin-7-y1)-1H-pyrazole-5-carboxamine | 5.12 |
| 4-(5-bromo-2-methylthiazol-4-y1)-1-methyl-N-(2-phenyl-5,6,7,8-tetrahydro-[1,2,4]triazolo[1,5-a]pyridin-7-y1)-1H-pyrazole-5-carboxamide | 5.13 |
| 4-(3,6-dimethylpyrazin-2-y1)-1-methyl-N-(2-phenyl-5,6,7,8-tetrahydro-[1,2,4]triazolo[1,5-a]pyridin-7-y1)-1H-pyrazole-5-carboxamide | 5.14 |
| 1-methyl-4-(3-methyl-1,2,4-thiadiazol-5-y1)-N-(2-phenyl-5,6,7,8-tetrahydro-[1,2,4]triazolo[1,5-a]pyridin-7-y1)-1H-pyrazole-5-carboxamide | 5.15 |

TABLE 1-21

| Compound name | Example No. |
|---|---|
| 4-(4-(difluoromethyl)thiazol-2-yl)-N-(2-((R)-2-(methoxymethyl)pyrrolidin-l-y1)-5,6,7,8-tetrahydro-[1,2,4[triazolo[1,5-a]pyridin-7-y1)-1-methyl-1H-pyrazole-5-carboxamide | 5.16 |
| 4-(4-(difluoromethyl)thiazol-2-y1)-1-methyl-N-(2-pheny1-5,6,7,8-tetrahydro-[1,2,4[triazolo[1,5-a]pyridin-7-y1)-1H-pyrazole-5-carboxamide | 5.17 |
| 1-methyl-4-(4-methylthiazol-2-y1)-N-(2-phenyl-5,6,7,8-tetrahydro-[1,2,4]triazolo[1,5-a]pyridin-7-y1)-1H-pyrazole-5-carboxamide | 5.18 |
| 1-methyl-4-(6-methylpyridin-2-y1)-N-(2-phenyl-5,6,7,8-tetrahydro-[1,2,4]triazolo[1,5-a]pyridin-7-y1)-1H-pyrazole-5-carboxamide | 5.19 |
| 1-methyl-4-(4-methylpyridin-2-y1)-N-(2-phenyl-5,6,7,8-tetrahydro-[1,2,4]triazolo[1,5-a]pyridin-7-y1)-1H-pyrazole-5-carboxamide | 5.20 |
| 1-methyl-N-(2-pheny1-5,6,7,8-tetrahydro-[1,2,4]triazolo[1,5-a]pyridin-7-y1)-4-(6-(trifluoromethyl)pyridin-2-y1)-1H-pyrazole-5-carboxamide | 5.21 |
| 1-methyl-4-(3-methylpyridin-2-y1)-N-(2-phenyl-5,6,7,8-tetrahydro-[1,2,4]triazolo[1,5-a]pyridin-7-y1)-1H-pyrazole-5-carboxamide | 5.22 |

TABLE 1-22

| Compound name | Example No. |
|---|---|
| 4-(4-fluoropyridin-2-y1)-1-methyl-N-(2-phenyl-5,6,7,8-tetrahydro-[1,2,4]triazolo[1,5-a]pyridin-7-y1)-1H-pyrazole-5-carboxamide | 5.23 |

TABLE 1-22-continued

| Compound name | Example No. |
|---|---|
| 4-(5-fluoropyridin-2-y1)-1-methyl-N-(2-phenyl-5,6,7,8-tetrahydro-[1,2,4]triazolo[1,5-a]pyridin-7-y1)-1H-pyrazole-5-carboxamide | 5.24 |
| 4-(4-methoxypyridin-2-y1)-1-methyl-N-(2-phenyl-5,6,7,8-tetrahydro-[1,2,4]triazolo[1,5-a]pyridin-7-y1)-1H-pyrazole-5-carboxamide | 5.25 |
| 1-methyl-4-(5-methylpyridin-2-y1)-N-(2-phenyl-5,6,7,8-tetrahydro-[1,2,4]triazolo[1,5-a]pyridin-7-y1)-1H-pyrazole-5-carboxamide | 5.26 |
| 4-(3-cyanopyridin-2-y1)-1-methyl-N-(2-phenyl-5,6,7,8-tetrahydro-[1,2,4]triazolo[1,5-a]pyridin-7-y1)-1H-pyrazole-5-carboxamide | 5.27 |
| 4-(2,5-dimethylthiazol-4-y1)-N-(2-(4-fluorophenyl)-5,6,7,8-tetrahydro-[1,2,4]triazolo[1,5-a]pyridin-7-y1)-1-methyl-1H-pyrazole-5-carboxamide | 5.28 |
| 4-(5-chloro-4-(difluoromethyl)thiazol-2-y1)-1-methyl-N-(2-phenyl-5,6,7,8-tetrahydro-[1,2,4]triazolo[1,5-a]pyridin-7-y1)-1H-pyrazole-5-carboxamide | 5.29 |

TABLE 1-23

| Compound name | Example No. |
|---|---|
| 4-(5-acetyl-2-methylthiazol-4-y1)-1-methyl-N-(2-phenyl-5,6,7,8-tetrahydro-[1,2,4]triazole[1,5-a]pyridin-7-y1)-1H-pyrazole-5-carboxamide | 5.30 |
| 4-(5-(1-hydroxyethyl)-2-methylthiazol-4-y1)-1-methyl-N-(2-phenyl-5,6,7,8-tetrahydro-[1,2,4]triazolo[1,5-a]pyridin-7-y1)-1H-pyrazole-5-carboxamide | 5.31 |
| 4-(4-(difluoromethyl)thiazol-2-y1)-N-(2-(2-fluorophenyl)-5,6,7,8-tetrahydro-[1,2,4]triazolo[1,5-a]pyridin-7-y1)-1-methyl-1H-pyrazole-5-carboxamide | 5.32 |
| 4-(4-(difluoromethyl)thiazol-2-y1)-N-(2-(3-fluorophenyl)-5,6,7,8-tetrahydro-[1,2,4]triazolo[1,5-a]pyridin-7-y1)-1-methyl-1H-pyrazole-5-carboxamide | 5.33 |
| 4-(4-(difluoromethyl)thiazol-2-y1)-N-(2-(2-methoxyphenyl)-5,6,7,8-tetrahydro-[1,2,4]trizolo[1,5-a]pyridin-7-y1)-1-methyl-1H-pyrazole-5-carboxamide | 5.34 |
| 4-(5-cyclopropyl-4-(difluoromethyl)thiazol-2-y1)-N-(2-(4-fluorophenyl)-5,6,7,8-tetrahydro-[1,2,4]triazole[1,5-a]pyridin-7-y1)-1-methyl-1H-pyrazole-5-carboxamide | 5.35 |
| 4-(4-(difluoromethyl)-5-methylthiazol-2-y1)-N-(2-(4-fluorophenyl)-5,6,7,8-tetrahydro-[1,2,4]trizolo[1,5-a]pyridin-7-y1)-1-methyl-1H-pyrazole-5-carboxamide | 5.36 |

TABLE 1-24

| Compound name | Example No. |
|---|---|
| 4-(5-chloro-4-(difluoromethyl)thiazol-2-y1)-N-(2-(3-fluorophenyl)-5,6,7,8-tetrahydro-[1,2,4]triazolo[1,5-a]pyridin-7-y1)-1-methyl-1H-pyrazole-5-carboxamide | 5.37 |
| 4-(5-cyclopropyl-4-methylthiazol-2-y1)-1-methyl-N-(2-phenyl-5,6,7,8-tetrahydro-[1,2,4]triazolo[1,5-a]pyridin-7-y1)-1H-pyrazole-5-carboxamide | 5.38 |
| 4-(2,5-dimethylthiazol-4-y1)-1-methyl-N-(2-phenyl-5,6,7,8-tetrahydro-[1,2,4]triazolo[1,5-a]pyridin-7-y1)-1H-pyrazole-5-carboxamide | 5.39 |
| 4-(6-cyanopyridin-2-y1)-1-methyl-N-(2-phenyl-5,6,7,8-tetrahydro-[1,2,4]triazolo[1,5-a]pyridin-7-y1)-1H-pyrazole-5-carboxamide | 5.40 |
| 4-(4-cyanothiazol-2-y1)-N-(2-(4-fluorophenyl)-5,6,7,8-tetrahydro-[1,2,4]triazolo[1,5-a]pyridin-7-y1)-1-methyl-1H-pyrazole-5-carboxamide | 5.41 |
| 4-(5-cyclopropyl-4-(difluoromethyl)thiazol-2-y1)-N-(2-(3-fluorophenyl)-5,6,7,8-tetrahydro-[1,2,4]triazolo[1,5-a]pyridin-7-y1)-1-methyl-1H-pyrazole-5-carboxamide | 5.42 |

TABLE 1-24-continued

| Compound name | Example No. |
|---|---|
| 4-(5-cyclopropyl-4-methylthiazol-2-yl)-N-(2-(4-fluorophenyl)-5,6,7,8-tetrahydro-[1,2,4]triazolo[1,5-a]pyridin-7-yl)-1-methyl-1H-pyrazole-5-carboxamide | 5.43 |

TABLE 1-25

| Compound name | Example No. |
|---|---|
| 4-(5-acetyl-2-methylthiazol-4-yl)-N-(2-(3-fluorophenyl)-5,6,7,8-tetrahydro-[1,2,4]triazolo[1,5-a]pyridin-7-yl)-1-methyl-1H-pyrazole-5-carboxamide | 5.44 |
| 4-(4,5-dimethylthiazol-2-yl)-1-methyl-N-(2-(pyrrolidin-1-yl)-5,6,7,8-tetrahydro-[1,2,4]triazolo[1,5-a]pyridin-7-yl)-1H-pyrazole-5-carboxamide | 5.45 |
| 1-methyl-N-(2-(pyrrolidin-l-yl)-5,6,7,8-tetrahydro-[1,2,4]triazolo[1,5-a]pyridin-7-yl)-4-(4trifluoromethyl)thiazol-2-yl)-1H-pyrazole-5-carboxamide | 5.46 |
| 1-methyl-4-(6-methylpyridin-2-yl)-N-(2-(pyrrolidin-l-yl)-5,6,7,8-tetrahydro-[1,2,4]triazolo[1,5-a]pyridin-7-yl)-1H-pyrazole-5-carboxamide | 5.47 |

In the compound of the above formula (I), the amide bond is a bond that may be converted to an imide acid bond by proton tautomeric isomerism, and the generated tautomeric isomer is included in the above formula (I). The abundance ratio of these structures may change, depending on the state of the compound represented by the formula (I), namely, a solid state, or a state in which the compound is dissolved in a liquid.

[Formula 74]

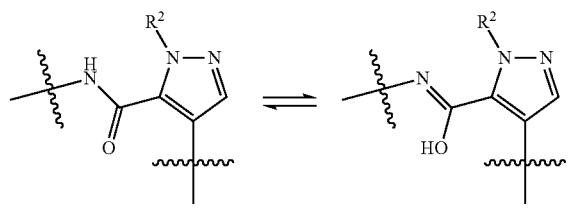

The description regarding any given specific tautomeric isomer in any given structural formula in the present specification is not intended to limit a tautomeric isomer to the any given specific tautomeric isomer, but it is intended to mean that the any given specific tautomeric isomer is a representative of the entire set of tautomeric isomers.

Specifically, if the compound of Example 1.1, for example, has a compound name "1-methyl-4-(5-methylpyridin-2-yl)-N-(2-phenylimidazo[1,2-a]pyridin-7-yl)-1H-pyrazole-5-carboxamide," its tautomeric isomer, 1-methyl-4-(5-methylpyridin-2-yl)-N-(2-phenylimidazo[1,2-a]pyridin-7-yl)-1H-pyrazole-5-carbimidic acid (which is not distinguished in terms of E form and Z form) is also included in the compound of Example 1.1.

In the present specification, unless otherwise specified, when a cyclic group is substituted with a variable substituent, it means that the variable substituent does not bind to a specific carbon atom of the cyclic group or to a specific NH group in the cyclic group. For example, it means that the variable substituent $R^x$ in the following formula A can be substituted with any of carbon atoms i, ii, iii and iv in the formula A; the variable substituent $R^y$ in the following formula B can be substituted on any of carbon atoms v and vi in the formula B; and the variable substituent $R^z$ in the following formula C can be substituted on any of carbon atoms vii, viii, ix, and x in the formula C.

[Formula 75]

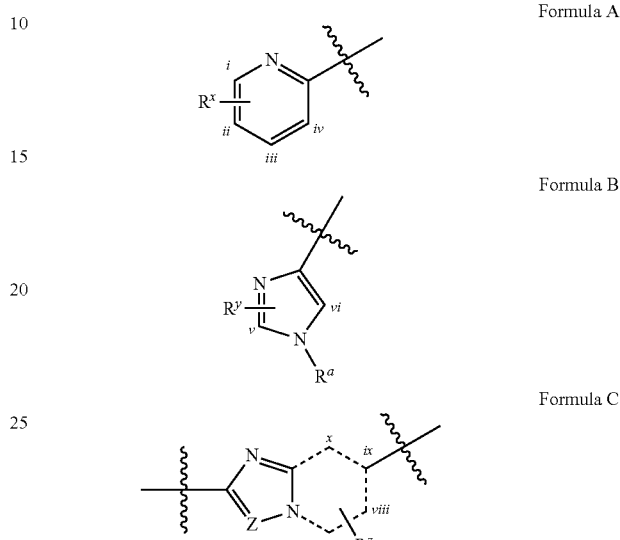

[3] A third embodiment of the present invention is a pharmaceutical composition comprising, as an active ingredient, at least one of the compound represented by the above formula (I), a pharmaceutically acceptable salt thereof, and a solvate thereof.

[4] A fourth embodiment of the present invention is a pharmaceutical composition for treating at least one disease or condition selected from the group consisting of certain types of mental disorders and conditions, such as mental disorder, paranoid disorder, and drug-induced psychosis, anxiety disorders such as panic disorder and obsessive-compulsive disorder, motor disorders including Parkinson's disease and Huntington's disease, mood disorder, neurodegenerative disorder, disorder involving deficits in attention and/or cognition, obesity, and drug addiction, wherein the pharmaceutical composition comprises, as an active ingredient, at least one of the compound represented by the above formula (I), a pharmaceutically acceptable salt thereof, and a solvate thereof, in an effective amount for treating the disease or condition.

Examples of the "mental disorders and conditions" that can be treated according to the present invention include (1) paranoid, disorganized, catatonic, undifferentiated, or residual schizophrenia, (2) schizophreniform disorder, (3) paranoid or depressive schizoaffective disorder, (4) paranoid disorder, (5) substance-induced mental disorder, for example, psychosis induced by alcohol, amphetamine, *cannabis*, cocaine, a hallucinatory drug, an inhalant, opioid, or phencyclidine, (6) paranoic personality disorder, and (7) schizotypal personality disorder. However, the mental disorders and conditions are not limited thereto.

In the present specification, unless otherwise specified, examples of the symptoms of "schizophrenia and schizophreniform disorder" include (1) positive symptom, negative symptom, and delusional and/or hallucinogenic symptom associated therewith, (2) disorganized speech (frequent off-topic or incoherent speech), (3) flattening of emotion (a significant reduction in the width and strength of emotional expression), (4) alogia (a reduction in content and amount of speech), (5) anhedonia (the disappearance/diminution of ability to experience pleasure), (6) inappropriate affect, (7) dysphoria (e.g. depression, anxiety, and anger), (8) loss of motivation, (9) unsocial personality (loss of capacity of obtaining pleasure from social interaction), and (10) a part of cognitive function disorder. However, the schizophrenia and schizophreniform disorder are not limited thereto.

Examples of the "motor disorders" that can be treated according to the present invention include (1) Huntington's disease and dyskinesia associated with dopamine agonist therapy, (2) Parkinson's disease, (3) restless legs syndrome (RLS), and (4) essential tremor. However, the motor disorders are not limited thereto.

Examples of the "other disorders" that can be treated according to the present invention include (1) obsessive-compulsive disorder, (2) Tourette's syndrome, and (3) tic disorder. However, the other disorders are not limited thereto.

Examples of the "anxiety disorders" that can be treated according to the present invention include (1) panic disorder, (2) agoraphobia, (3) specific phobias, (4) social phobias, (5) obsessive-compulsive disorder, (6) posttraumatic stress disorder, (7) acute stress disorder, and (8) generalized anxiety disorder. However, the anxiety disorders are not limited thereto.

In the present specification, unless otherwise specified, the term "drug addiction" means abnormal desire for drugs. In general, the drug addiction has characteristics including motivational disorder such as compulsion to take a desired drug, and an episode of strong desire for drugs. Examples of the drug addiction include alcohol, amphetamine, cocaine, and opium addiction.

In the present specification, unless otherwise specified, the term "deficits in attention and/or cognition" in the context of "disorder involving deficits in attention and/or cognition" means that one or more cognitive functions in a specific individual, such as memory, intellectual, learning, and logical capacity, are below normal level in comparison with other individuals of the same age. Moreover, the term "deficits in attention and/or cognition" means a reduction in the functions of any given specific individual, in terms of one or more cognitive aspects, for example, caused by age-related cognitive decline.

Examples of the "disorder involving deficits in attention and/or cognition" that can be treated according to the present invention include (1) dementia, such as Alzheimer's disease, multiple cerebral infarction, alcoholic dementia or other drug-related dementia, dementia associated with intracranial tumor or brain damage, dementia associated with Huntington's disease or Parkinson's disease, or AIDS-related dementia, (2) delirium, (3) amnestic disorder, (4) posttraumatic stress disorder (PTSD), (5) mental retardation, (6) learning disorder, such as dyslexia, mathematics disorder, or disorder of written expression, (7) attention-deficit hyperactivity disorder (ADHA), and (8) age-related cognitive decline. However, the disorder involving deficits in attention and/or cognition are not limited thereto.

Examples of the "mood disorder" and the "mood episode" that can be treated according to the present invention include (1) major depressive episode (mild level, middle level, or severe level type), manic episode, mixed affective episode, and hypomanic episode, (2) atypical depression, (3) melancholic depression, (4) catatonic depression, (5) postpartum mood episode, (6) postapoplectic depression, (7) major depressive disorder, (8) dysthymic disorder/dysthymia, (9) minor depressive disorder, (10) premenstrual dysphoric disorder, (12) postschizophrenic depressive disorder, (13) major depressive disorder occurring with paranoid disorder or mental disorder such as schizophrenia, (14) bipolar disorder, such as bipolar disorder type I and bipolar disorder type II, and (15) cyclothymic disorder. However, the mood disorder and the mood episode are not limited thereto.

In the present specification, unless otherwise specified, the term "neurodegenerative disorder or condition" means nervous function disorder or condition, which is caused by neuronal dysfunction and/or neuronal death in the central nerve system. Examples of the treatment for the aforementioned disorder and condition include administration of a drug for enhancing the function of damaged or normally working neurons, so as to prevent neuronal dysfunction and/or neuronal death that are under critical conditions, and/or to compensate the loss of function caused by such neuronal dysfunction or neuronal death that is under critical conditions, in the aforementioned disorder or condition.

Examples of the "neurodegenerative disorder and condition" that can be treated according to the present invention include (1) Parkinson's disease, (2) Huntington's disease, (3) dementia, such as Alzheimer's disease, multi-infarct dementia, AIDS-related dementia, and frontotemporal dementia, (4) neurodegeneration associated with brain damage, (5) neurodegeneration associated with stroke, and neurodegeneration associated with cerebral infarction, (6) hypoglycemia-induced neurodegeneration, (7) neurodegeneration associated with epileptic seizure, (8) neurodegeneration associated with neurotoxic addiction, (9) multiple system atrophy, and (10) neurodegeneration of striatal medium-sized spiny neurons. However, the neurodegenerative disorder and condition are not limited thereto.

In the present specification, unless otherwise specified, the term "neurotoxic addiction" indicates intoxication by neurotoxin. Neurotoxin is any given chemical substance or substance that may cause neural death, namely, neurological damage. Examples of the neurotoxin include alcohol. When a pregnant woman abuses alcohol, her newborn child would suffer from alcoholic intoxication and neurological damage, which are considered to be fetal alcohol syndrome. Other examples of the neurotoxin include kainic acid, domoic acid, acromelic acid, certain types of agricultural chemicals (e.g. dichloro diphenyl trichloroethane (DDT)), certain types of insecticides (e.g. organophosphorus acids), volatile organic solvents (e.g. toluene), metals (e.g. lead, mercury, arsenic, phosphorus, and aluminum), certain types of chemical substances used as weapons (e.g. Agent Orange that is a defoliant, and nerve gas), and neurotoxic anti-tumor agents. However, the neurotoxin is not limited thereto.

In the present specification, unless otherwise specified, the term "treat" used in the context of the phrase "treat the disease or condition" means to recover, alleviate, or suppress progression of the "disease or condition" or one or more "diseases or conditions." In addition, in the present specification, the term "treat" also includes, depending on conditions of patients, prevention of "disease or condition" which includes prevention of the onset of the "disease or condition" or the onset of any given symptoms associated therewith, and reduction of the severity of "disease or condition" or the any given symptoms associated therewith before the onset. In the present specification, the term "treat" includes to prevent and improve the recurrence of a certain "disease or condition."

[5] A fifth embodiment of the present invention is a pharmaceutical composition for treating at least one disease or condition selected from the group consisting of certain types of mental disorders and conditions, such as mental disorder, paranoid disorder, and drug-induced psychosis, anxiety disorders such as panic disorder and obsessive-compulsive disorder, motor disorders including Parkinson's disease and Huntington's disease, mood disorder, neurodegenerative disorder, disorder involving deficits in attention and/or cognition, obesity, and drug addiction, wherein the pharmaceutical composition comprises, as an active ingredient, at least one of the compound represented by the above formula (I), a pharmaceutically acceptable salt thereof, and a solvate thereof, in an effective amount for inhibiting PDE10.

[6] A sixth embodiment of the present invention is an agent for preventing and/or treating at least one disease or condition selected from the group consisting of certain types of mental disorders and conditions such as mental disorder, paranoid disorder, and drug-induced psychosis, anxiety disorders such as panic disorder and obsessive-compulsive disorder, motor disorders including Parkinson's disease and Huntington's disease, mood disorder, neurodegenerative disorder, disorder involving deficits in attention and/or cognition, obesity, and drug addiction, wherein the agent comprises, as an active ingredient, at least one of the compound represented by the above formula (I), a pharmaceutically acceptable salt thereof, and a solvate thereof.

[7] A seventh embodiment of the present invention is an agent for treating at least one disease or condition selected from the group consisting of certain types of mental disorders and conditions such as mental disorder, paranoid disorder and drug-induced mental psychosis, anxiety disorders such as panic disorder and obsessive-compulsive disorder, motor disorders including Parkinson's disease and Huntington's disease, mood disorder, neurodegenerative disorder, disorder involving deficits in attention and/or cognition, obesity, and drug addiction, wherein the agent comprises, as an active ingredient, at least one of the compound represented by the above formula (I), a pharmaceutically acceptable salt thereof, and a solvate thereof.

[8] An eighth embodiment of the present invention is an agent for preventing and/or treating diseases related to a PDE10 receptor, wherein the agent comprises, as an active ingredient, at least one of the compound represented by the above formula (I), a pharmaceutically acceptable salt thereof, and a solvate thereof.

[9] A ninth embodiment of the present invention is an agent for treating diseases related to a PDE10 receptor, wherein the agent comprises, as an active ingredient, at least one of the compound represented by the above formula (I), a pharmaceutically acceptable salt thereof, and a solvate thereof.

[10] A tenth embodiment of the present invention is a PDE10 inhibitor consisting of one or more of the compound represented by the above formula (I), a pharmaceutically acceptable salt thereof, and a solvate thereof.

[11] An eleventh embodiment of the present invention is use of at least one of the compound represented by the above formula (I), a pharmaceutically acceptable salt thereof, and a solvate thereof, as a pharmaceutical composition.

[11a] An 11a-th embodiment of the present invention is use of at least one of the compound represented by the above formula (I), a pharmaceutically acceptable salt thereof, and a solvate thereof, in the production of a pharmaceutical composition.

[12] A twelfth embodiment of the present invention is use of at least one of the compound represented by the above formula (I), a pharmaceutically acceptable salt thereof, and a solvate thereof, as a PDE10 inhibitor.

[13] A thirteenth embodiment of the present invention is a method for treating at least one disease or condition selected from the group consisting of certain types of mental disorders and conditions such as mental disorder, paranoid disorder and drug-induced psychosis, anxiety disorders such as panic disorder and obsessive-compulsive disorder, motor disorders including Parkinson's disease and Huntington's disease, mood disorder, neurodegenerative disorder, disorder involving deficits in attention and/or cognition, obesity, and drug addiction, wherein the method comprises administering at least one of the compound represented by the above formula (I), a pharmaceutically acceptable salt thereof, and a solvate thereof, in an effective amount for treating the disease or condition, to a subject in need of treatment for the disease or condition.

[14] A fourteenth embodiment of the present invention is a method for treating at least one disease or condition selected from the group consisting of certain types of mental disorders and conditions such as mental disorder, paranoid disorder and drug-induced psychosis, anxiety disorders such as panic disorder and obsessive-compulsive disorder, motor disorders including Parkinson's disease and Huntington's disease, mood disorder, neurodegenerative disorder, disorder involving deficits in attention and/or cognition, obesity, and drug addiction, wherein the method comprises administering at least one of the compound represented by the above formula (I), a pharmaceutically acceptable salt thereof, and a solvate thereof, in an effective amount for inhibiting PDE10, to a subject in need of treatment for the disease or condition.

[15] A fifteenth embodiment of the present invention is the pharmaceutical composition according to the embodiment [3] or the method according to the embodiment [13], wherein the disease or condition is at least one disease or condition selected from the group consisting of (1) paranoid, disorganized, catatonic, undifferentiated, or residual schizophrenia, (2) schizophreniform disorder, (3) paranoid or depressive schizoaffective disorder, (4) paranoid disorder, (5) substance-induced mental disorder, (6) psychosis induced by alcohol, amphetamine, *cannabis*, cocaine, a hallucinatory drug, an inhalant, opioid, or phencyclidine, (7) paranoic personality disorder, (8) schizotypal personality disorder, (9) Huntington's disease, (10) dyskinesia associated with dopamine agonist therapy, (11) Parkinson's disease, (12) restless legs syndrome, (13) essential tremor, (14) obsessive-compulsive disorder, (15) Tourette's syndrome, (16) tic disorder, (17) panic disorder, (18) agoraphobia, (19) specific phobias, (20) social phobias, (21) posttraumatic stress disorder, (22) acute stress disorder, (23) generalized anxiety disorder, (24) dementia; Alzheimer's disease, multiple cerebral infarction, alcoholic dementia or other drug-related dementia, dementia associated with intracranial tumor or brain damage, dementia associated with Huntington's disease or Parkinson's disease, AIDS-related dementia, or frontotemporal dementia, (25) delirium, (26) amnestic disorder, (27) mental retardation, (28) learning disorder; dyslexia, mathematics disorder, or disorder of written expression, (29) attention-deficit hyperactivity disorder, (30) age-related cognitive decline, (31) major depressive episode (mild level, middle level, or severe level type), manic episode, mixed affective episode, or hypomanic episode, (32) atypical depression, (33) melancholic depression, (34) catatonic depression, (35) postpartum mood episode, (36) postapoplectic depression, (37) major depressive disorder, (38) dysthymic disorder/dysthymia, (39) minor depressive disorder, (40) premenstrual dysphoric disorder, (41) post-schizophrenic depressive disorder, (42) major depressive disorder occurring with paranoid disorder or mental disorder such as schizophrenia, (43) bipolar disorder; bipolar disorder type I and bipolar disorder type II, (44) cyclothymic disorder, (45) neurodegeneration associated with brain damage, (46) neurodegeneration associated with stroke, or neurodegeneration associated with cerebral infarction, (47) hypoglycemia-induced neurodegeneration, (48) neurodegeneration associated with epileptic seizure, (49) neurodegeneration associated with neurotoxic addiction, (50) multiple system atrophy, and (51) neurodegeneration of striatal medium-sized spiny neurons.

In each of the aforementioned embodiments [1] to [15] of the present invention, when PDE10 inhibitory effect is measured by an appropriately selected method, for example, when it is measured in the after-mentioned Pharmacological Experiment Example 1 (human-derived PDE10 inhibitory effect), it is preferable to use a compound having an $IC_{50}$ value of preferably 100 nM or less, more preferably 50 nM or less, even more preferably 10 nM or less, further preferably 5.0 nM or less, and particularly preferably 1.0 nM or less.

In Pharmacological Experiment Example 1 (human PDE10 inhibitory effect), the compound represented by the formula (I) of the present invention, or a pharmaceutically acceptable salt thereof, or a solvate thereof has an excellent PDE10 inhibitory activity. Moreover, the compound represented by the formula (I) of the present invention, or a pharmaceutically acceptable salt thereof, or a solvate thereof is extremely selective to PDE10, and thus, is a selective PDE10 inhibitor.

In the present specification, unless otherwise specified, the term "selective PDE10 inhibitor" means a compound having a significant inhibitory activity on PDE10, rather than on PDEs 1 to 9 or PDE11.

In one embodiment, the "selective PDE10 inhibitor" is preferably a compound having an inhibitory activity on PDE10, which is approximately ¹⁄₁₀₀₀ or less of the $IC_{50}$ values of the compound to inhibit any other PDE enzymes (e.g. PDE 1A, 2A, 3A, 4A, 4B, 5A, 6, 7A, 7B, 8A, 9A, and 11A). (In other word, this compound inhibits the activity of PDE10 at an $IC_{50}$ value that is approximately ¹⁄₁₀₀₀ or less of its $IC_{50}$ values necessary for inhibition of any other PDE enzymes.)

In the present specification, unless otherwise specified, when the term "the compound of the formula (I)," "the compound represented by the formula (I)," or the like is used, it also refers to "the compound of the formula (I-a)," "the compound of the formula (I-b)," "the compound of the formula (I-c)," "the compound of the formula (I-d)," and the like, which are the subordinate concepts of "the compound of the formula (I)."

[16]

A sixteenth embodiment of the present invention is an intermediate compound represented by the following formula (I'), or a pharmaceutically acceptable salt thereof, or a solvate thereof:

[Formula 76]

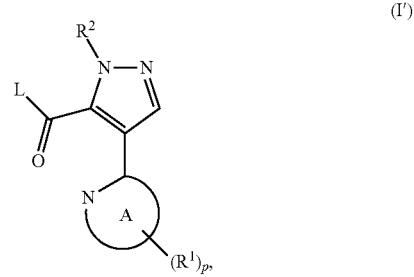

(I')

wherein p represents an integer of 0 to 3; L represents a hydroxyl group, a halogen atom, a $C_{1-6}$ alkoxyl group, a $C_{6-14}$ aryloxy group, or a $C_{7-20}$ aralkyloxy group; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a $C_{1-6}$ alkoxyl $C_{2-6}$ alkenyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfinyl group, a $C_{1-6}$ alkylsulfonyl group, a 3- to 14-membered non-aromatic heterocyclic group, a 5- to 7-membered monocyclic heteroaryl group, an —$NR^7R^8$ group, or a —$CONR^7R^8$ group wherein $R^7$ and $R^8$ in the —$NR^7R^8$ group and the —$CONR^7R^8$ group each independently represent a substituent selected from among a hydrogen atom, a $C_{1-6}$ alkyl group, a halogenated $C_{1-6}$ alkyl group, a hydroxy $C_{1-6}$ alkyl group, a cyanated $C_{1-6}$ alkyl group, a $C_{2-6}$ alkenyl group, a $C_{2-6}$ alkynyl group, a $C_{3-8}$ cycloalkyl group, a $C_{6-14}$ aryl group, a $C_{7-20}$ aralkyl group, a heterocyclic group, a $C_{2-7}$ alkanoyl group, a hydroxy $C_{2-7}$ alkanoyl group, a halogenated $C_{2-7}$ alkanoyl group, a $C_{3-8}$ cycloalkylcarbonyl group, a $C_{6-14}$ arylcarbonyl group, a $C_{7-20}$ aralkylcarbonyl group, a heterocyclic carbonyl group, a mono-/di-$C_{1-6}$ alkylcarbamoyl group, a mono-/di-halogenated $C_{1-6}$ alkylcarbamoyl group, a mono-/di-$C_{3-8}$ cycloalkylcarbamoyl group, a mono-/di-$C_{6-14}$ arylcarbamoyl group, a mono-/di-$C_{7-20}$ aralkylcarbamoyl group, a mono-/di-heterocyclic carbamoyl group, a $C_{1-6}$ alkylsulfonyl group, a halogenated $C_{1-6}$ alkylsulfonyl group, a $C_{3-8}$ cycloalkylsulfonyl group, a $C_{6-14}$ arylsulfonyl group, a $C_{7-20}$ aralkylsulfonyl group, a heterocyclic sulfonyl group, a mono-/di-$C_{1-6}$ alkylsulfamoyl group, a mono-/di-halogenated $C_{1-6}$ alkylsulfamoyl group, a mono-/di-$C_{3-8}$ cycloalkylsulfamoyl group, a mono-/di-$C_{6-14}$ arylsulfamoyl group, a mono-/di-$C_{7-20}$ aralkylsulfamoyl group, and a mono-/di-heterocyclic sulfamoyl group; $R^2$ represents a hydrogen atom, a $C_{1-6}$ alkyl group, a halogenated $C_{1-6}$ alkyl group, a hydroxy $C_{1-6}$ alkyl group, or a $C_{1-6}$ alkoxyl $C_{1-6}$ alkyl group;

ring A represented by the following partial structural formula (II):

[Formula 77]

(II)

is selected from the group of the heteroaryls consisting of the following:
[Formula 78]
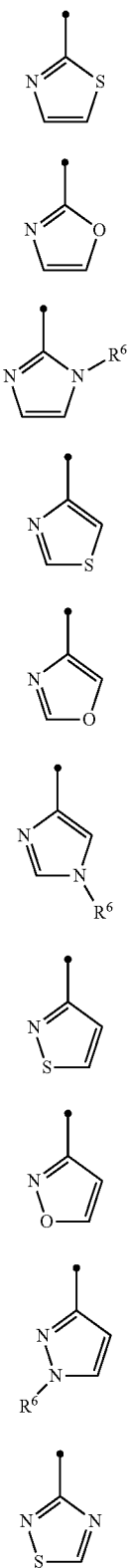
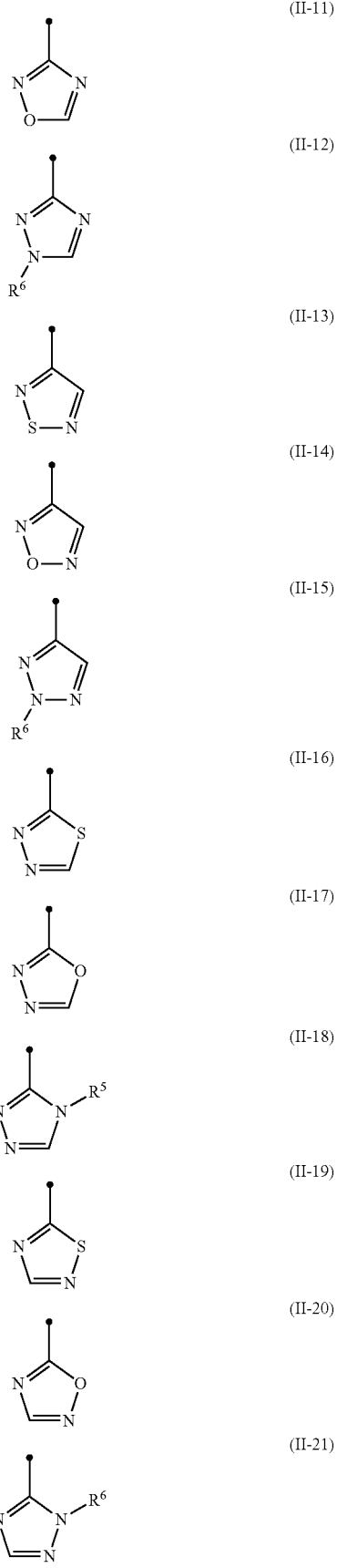

121
-continued
(II-22) 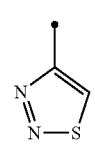
(II-23) 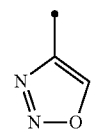
(II-24) 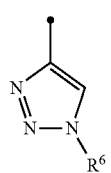
(II-25) 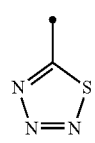
(II-26) 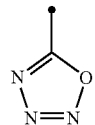
(II-27) 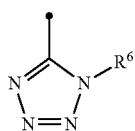
(II-28) 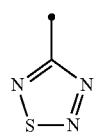
(II-29) 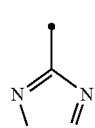
(II-30) 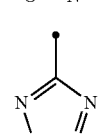
(II-31) 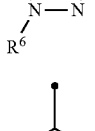
(II-32) 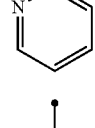
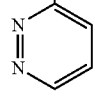
122
-continued
(II-33) 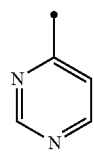
(II-34) 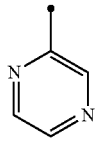
(II-35) 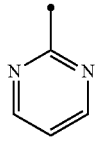
(II-36) 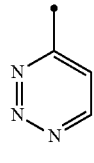
(II-37) 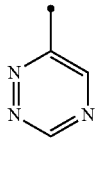
(II-38) 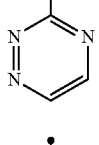
(II-39) 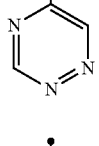
(II-40) 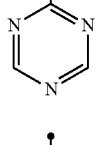
(II-41) 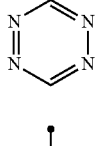
(II-42) 

-continued

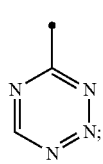
(II-43)

provided that when the ring A is represented by the formula (II-31), p represents an integer of 1 to 3; and $R^6$ represents a hydrogen atom, a $C_{1-6}$ alkyl group, a halogenated $C_{1-6}$ alkyl group, or a hydroxy $C_{1-6}$ alkyl group.

[16-1]

Preferably, the intermediate compound of the above embodiment [16] is an intermediate compound represented by the above formula (I') wherein p and L have the same definitions as those described in the embodiment [16]; $R^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a hydroxy $C_{1-6}$ alkyl group, a $C_{1-6}$ alkoxyl $C_{1-6}$ alkyl group, a $C_{1-6}$ alkoxyl $C_{2-6}$ alkenyl group, a $C_{2-7}$ alkanoyl group, a $C_{1-6}$ alkylthio group, a $C_{1-6}$ alkylsulfonyl group, an —$NR^7R^8$ group, or a —$CONR^7R^8$ group wherein $R^7$ and $R^8$ in the —$NR^7R^8$ group and the —$CONR^7R^8$ group have the same definitions as those described in the above embodiment [16]; $R^2$ represents a hydrogen atom, a $C_{1-6}$ alkyl group, or a halogenated $C_{1-6}$ alkyl group;

ring A represented by the following partial structural formula (II):

[Formula 79]

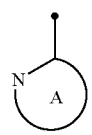
(II)

is selected from the group of the heteroaryls consisting of the following:

[Formula 80]

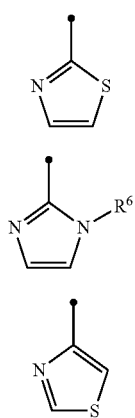

(II-1)

(II-3)

(II-4)

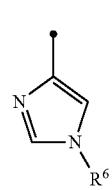
(II-6)

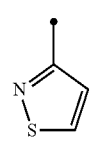
(II-7)

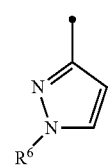
(II-9)

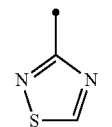
(II-10)

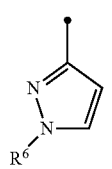
(II-12)

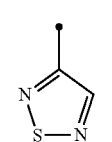
(II-13)

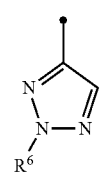
(II-15)

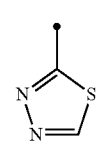
(II-16)

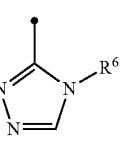
(II-18)

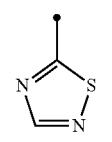
(II-19)

(II-21) 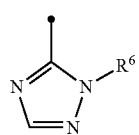
(II-22) 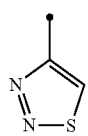
(II-24) 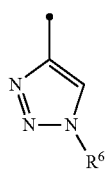
(II-25) 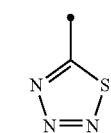
(II-27) 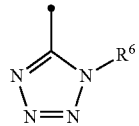
(II-29) 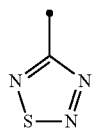
(II-30) 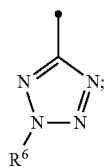
(II-31) 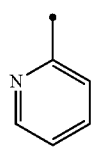
(II-32) 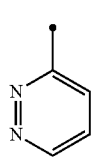
(II-33) 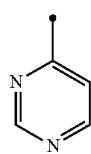
(II-34) 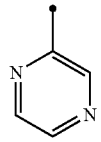
(II-35) 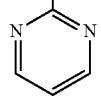
(II-36) 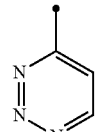
(II-37) 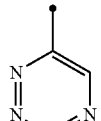
(II-38) 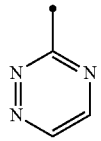
(II-39) 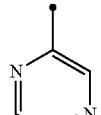
(II-40) 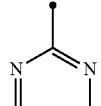
(II-41) 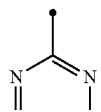
(II-42) 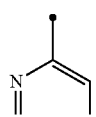
(II-43) 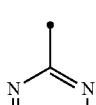
provided that when the ring A is represented by the formula (II-31), p represents an integer of 1 to 3; and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[16-1-2]

More preferably, the intermediate compound of the above embodiment [16] is an intermediate compound represented by the above formula (I') wherein p and L have the same definitions as those described in the embodiment [16]; $R^1$ each independently represents a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a hydroxy $C_{1-6}$ alkyl group, a $C_{1-6}$ alkoxyl $C_{1-6}$ alkyl group, a $C_{1-6}$ alkoxyl $C_{2-6}$ alkenyl group, a $C_{1-6}$ alkylthio group, a $C_{1-6}$ alkylsulfonyl group, an $-NR^{7A}R^{8A}$ group, or a $-CONR^{7A}R^{8A}$ group wherein $R^{7A}$ and $R^{8A}$ in the $-NR^{7A}R^{8A}$ group and the $-CONR^{7A}R^{8A}$ group each independently represent a substituent selected from among a hydrogen atom, a $C_{1-6}$ alkyl group, a halogenated $C_{1-6}$ alkyl group, a hydroxy $C_{1-6}$ alkyl group, a $C_{2-7}$ alkanoyl group, a hydroxy $C_{2-7}$ alkanoyl group, a halogenated $C_{2-7}$ alkanoyl group, a $C_{1-6}$ alkylsulfonyl group, and a halogenated $C_{1-6}$ alkylsulfonyl group; $R^2$ represents a hydrogen atom, a $C_{1-6}$ alkyl group, or a halogenated $C_{1-6}$ alkyl group;

ring A represented by the following partial structural formula (II):

[Formula 81]

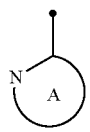
(II)

is selected from the group of the heteroaryls consisting of the following:

[Formula 82]

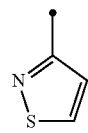
(II-1)

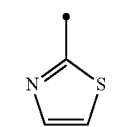
(II-3)

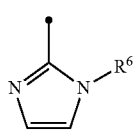
(II-4)

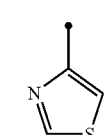
(II-6)

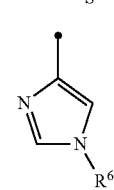

-continued

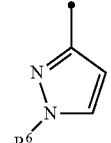
(II-7)

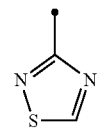
(II-9)

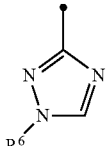
(II-10)

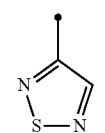
(II-12)

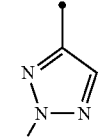
(II-13)

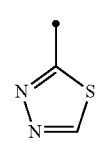
(II-15)

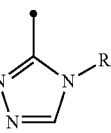
(II-16)

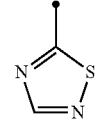
(II-18)

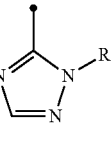
(II-19)

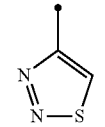
(II-21)

(II-22)

-continued (II-24) 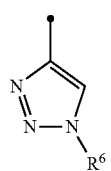

(II-27) 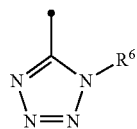

(II-30) 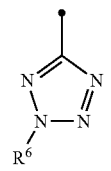

(II-31) 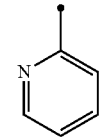

(II-32) 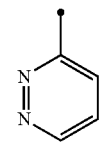

(II-33) 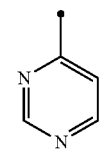

(II-34) 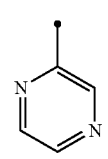

(II-35) 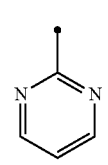

(II-36) 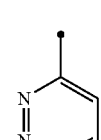

(II-37) 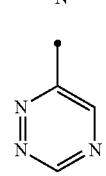

(II-38) 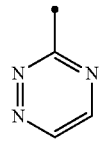

(II-39) 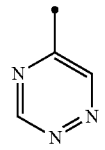

(II-40) 

(II-41) 

(II-42) 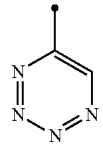

(II-43) 

provided that when the ring A is represented by the formula (II-31), p represents an integer of 1 to 3; and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[16-1-2-2]

Even more preferably, the intermediate compound of the above embodiment [16] is an intermediate compound represented by the above formula (I') wherein p, L, $R^2$, $R^6$, and ring A represented by the partial structural formula (II) have the same definitions as those described in the embodiment [16-1-2] provided that when the ring A is represented by the formula (II-31), p represents an integer of 1 to 3; and $R^1$ each independently represents a $C_{2-7}$ alkanoyl group, and has the same definitions as those described in the embodiment [16-1-2], or a pharmaceutically acceptable salt thereof, or a solvate thereof.

[16-1-3]

Further preferably, the intermediate compound of the above embodiment [16] is an intermediate compound represented by the above formula (I') wherein p and L have the same definitions as those described in the embodiment [16]; $R^1$ each independently represents a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a hydroxy $C_{1-6}$ alkyl group, a $C_{1-6}$ alkoxyl $C_{1-6}$ alkyl group, a $C_{1-6}$ alkoxyl C$_{2-6}$ alkenyl group, a C$_{1-6}$ alkylthio group, a C$_{1-6}$ alkylsulfonyl group, an —NR$^A$R$^{8A}$ group, or a —CONR$^{7A}$R$^{8A}$ group wherein R$^{7A}$ and R$^{8A}$ in the —NR$^{7A}$R$^{8A}$ group and the —CONR$^{7A}$R$^{8A}$ group have the same definitions as those described in the above embodiment [16-1-2]; R$^2$ represents a hydrogen atom, a C$_{1-6}$ alkyl group, or a halogenated C$_{1-6}$ alkyl group;

ring A represented by the following partial structural formula (II):

[Formula 83]

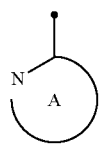
(II)

is selected from the group of the heteroaryls consisting of the following:

[Formula 84]

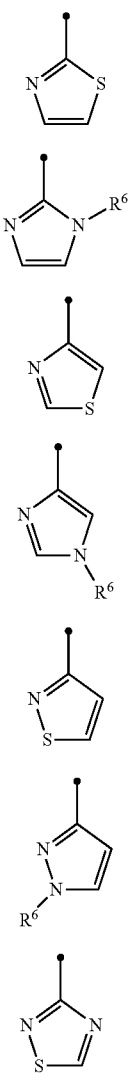

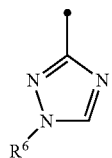
(II-12)

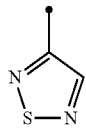
(II-13)

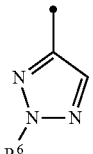
(II-15)

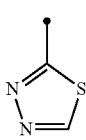
(II-16)

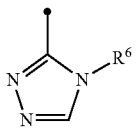
(II-18)

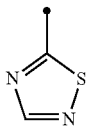
(II-19)

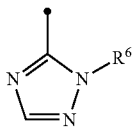
(II-21)

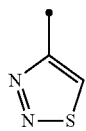
(II-22)

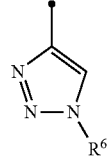
(II-24)

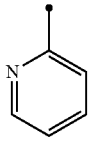
(II-31)

-continued

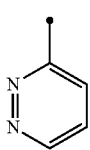
(II-32)

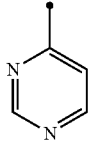
(II-33)

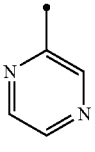
(II-34)

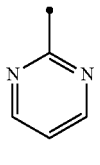
(II-35)

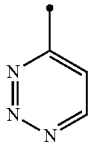
(II-36)

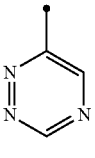
(II-37)

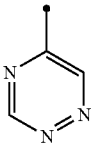
(II-39)

(II-42)

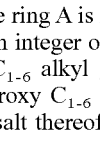

provided that when the ring A is represented by the formula (II-31), p represents an integer of 1 to 3; and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[16-1-3-2]

Still further preferably, the intermediate compound of the above embodiment [16] is an intermediate compound represented by the above formula (I') wherein p, L, $R^2$, $R^6$, and ring A represented by the partial structural formula (II) have the same definitions as those described in the embodiment [16-1-3] provided that when the ring A is represented by the formula (II-31), p represents an integer of 1 to 3; and $R^1$ each independently represents a $C_{2-7}$ alkanoyl group, and has the same definitions as those described in the embodiment [16-1-3], or a pharmaceutically acceptable salt thereof, or a solvate thereof.

[16-1-4]

Particularly preferably, the intermediate compound of the above embodiment [16] is an intermediate compound represented by the above formula (I') wherein p and L have the same definitions as those described in the embodiment [16]; $R^1$ each independently represents a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a $C_{1-6}$ alkoxyl $C_{1-6}$ alkyl group, or a $C_{1-6}$ alkoxyl $C_{2-6}$ alkenyl group, and more specifically, $R^1$ represents fluorine, chlorine, a cyano group, a methyl group, an ethyl group, an isopropyl group, a cyclopropyl group, a difluoromethyl group, a trifluoromethyl group, a vinyl group, a methoxy group, an ethoxyethyl group, a 2-ethoxyvinyl group, or the like; $R^2$ represents a hydrogen atom or a $C_{1-6}$ alkyl group, and more specifically, $R^2$ represents a hydrogen atom, a methyl group, or the like;

ring A represented by the following partial structural formula (II):

[Formula 85]

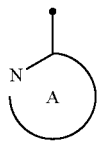
(II)

is selected from the group of the heteroaryls consisting of the following:

[Formula 86]

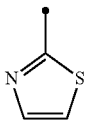
(II-1)

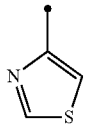
(II-4)

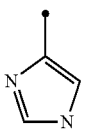
(II-6)

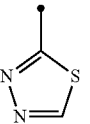
(II-16)

-continued

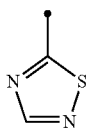
(II-19)

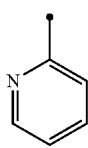
(II-31)

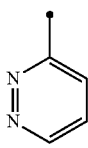
(II-32)

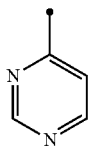
(II-33)

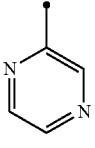
(II-34)

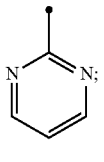
(II-35)

provided that when the ring A is represented by the formula (II-31), p represents an integer of 1 to 3; and $R^6$ represents a hydrogen atom or a $C_{1-6}$ alkyl group, and more specifically, $R^6$ represents a hydrogen atom, a methyl group, or the like, or a pharmaceutically acceptable salt thereof, or a solvate thereof.

[16-1-4-2]

More particularly preferably, the intermediate compound of the above embodiment [16] is an intermediate compound represented by the above formula (I') wherein p, L, $R^2$, $R^6$, and ring A represented by the partial structural formula (II) have the same definitions as those described in the embodiment [16-1-4] provided that when the ring A is represented by the formula (II-31), p represents an integer of 1 to 3; and $R^1$ each independently represents a $C_{2-7}$ alkanoyl group, and has the same definitions as those described in the embodiment [16-1-4], and more specifically, $R^1$ represents fluorine, chlorine, a cyano group, a methyl group, an ethyl group, an isopropyl group, a tert-butyl group, a cyclopropyl group, a difluoromethyl group, a trifluoromethyl group, a vinyl group, a methoxy group, an ethoxyethyl group, a 2-ethoxyvinyl group, an acetyl group, or the like, or a pharmaceutically acceptable salt thereof, or a solvate thereof.

[16-1-5]

Even more particularly preferably, the intermediate compound of the above embodiment [16] is an intermediate compound represented by the above formula (I') wherein p, L, $R^1$, $R^2$, $R^6$, and ring A have the same definitions as those described in the above embodiment [16-1-4-2], and a specific ring A group, in which the definitions of the above described p, $R^1$, and ring A are combined, represents a 1-methyl-1H-imidazol-4-yl group, a 4-(difluoromethyl)-5-ethylthiazol-2-yl group, a 4-(difluoromethyl)-5-vinylthiazol-2-yl group, a 4-(difluoromethyl)-5-methylthiazol-2-yl group, a 4-(difluoromethyl)-5-methylthiazol-2-yl group, a 4-(difluoromethyl)thiazol-2-yl group, a 4-(difluoromethyl)thiazol-2-yl group, a 4-(trifluoromethyl)thiazol-2-yl group, a 4-(trifluoromethyl)thiazol-2-yl group, a 4,5-dimethylthiazol-2-yl group, a 4-tert-butylthiazol-2-yl group, a 4-ethylthiazol-2-yl group, a 4-cyanothiazol-2-yl group, a 4-methylthiazol-2-yl group, a 4-methylthiazol-2-yl group, a 5-(2-ethoxyethyl)-4-methylthiazol-2-yl group, a 5-chloro-4-(difluoromethyl)thiazol-2-yl group, a 5-chloro-4-(difluoromethyl)thiazol-2-yl group, a 5-cyclopropyl-4-(difluoromethyl)thiazol-2-yl group, a 5-cyclopropyl-4-methylthiazol-2-yl group, a 5-bromo-4-methylthiazol-2-yl group, a 5-methylthiazol-2-yl group, a thiazol-2-yl group, a 2,5-dimethyl-thiazol-4-yl group, a 2-methylthiazol-4-yl group, a 5-acetyl-2-methylthiazol-4-yl group, a 5-bromo-2-methylthiazol-4-yl group, a thiazol-4-yl group, a 3-isopropyl-1,2,4-thiadiazol-5-yl group, a 3-methyl-1,2,4-thiadiazol-5-yl group, a 5-ethyl-1,3,4-thiadiazol-2-yl group, a 5-methyl-1,3,4-thiadiazol-2-yl group, a 5-(2-ethoxyvinyl)4-methylthiazol-2-yl group, a 4-methylpyrimidin-2-yl group, a 4,6-dimethylpyrimidin-2-yl group, a 4-methylpyrimidin-2-yl group, a 2,5,6-trimethylpyrimidin-4-yl group, a 2,5-dimethylpyrimidin-4-yl group, a 2,6-dimethylpyrimidin-4-yl group, a 2,6-dimethoxypyrimidin-4-yl group, a 2-methylpyrimidin-4-yl group, a 2-methoxypyrimidin-4-yl group, a 5,6-dimethylpyrimidin-4-yl group, a 5-chloro-2-methylpyrimidin-4-yl group, a 5-chloropyrimidin-4-yl group, a 5-fluoro-2-methylpyrimidin-4-yl group, a 5-fluoro-2-methoxypyrimidin-4-yl group, a 5-fluoro-6-methylpyrimidin-4-yl group, a 5-methylpyrimidin-4-yl group, a 5-methoxypyrimidin-4-yl group, a 6-methylpyrimidin-4-yl group, a 6-methoxy-5-methylpyrimidin-4-yl group, a 4-methylpyridazin-3-yl group, a 5-methylpyridazin-3-yl group, a 6-methylpyridazin-3-yl group, a pyridazin-3-yl group, a 3-cyanopyridin-2-yl group, a 3-cyano-pyridin-2-yl group, a 3-methylpyridin-2-yl group, a 3-methoxypyridin-2-yl group, a 4,6-dimethylpyridin-2-yl group, a 4-fluoropyridin-2-yl group, a 4-methylpyridin-2-yl group, a 4-methylpyridin-2-yl group, a 4-methoxypyridin-2-yl group, a 4-methoxy-pyridin-2-yl group, a 5-cyanopyridin-2-yl group, a 5-fluoropyridin-2-yl group, a 5-methylpyridin-2-yl group, a 5-methylpyridin-2-yl group, a 6-(trifluoromethyl)pyridin-2-yl group, a 6-cyano-pyridin-2-yl group, a 6-methylpyridin-2-yl group, a 6-methoxypyridin-2-yl group, a 3,6-dimethylpyrazin-2-yl group, a 3,6-dimethyl-pyrazin-2-yl group, a 3-methylpyrazin-2-yl group, a 3-methoxypyrazin-2-yl group, a 5-methylpyrazin-2-yl group, a 6-methylpyrazin-2-yl group, or a 6-methoxypyrazin-2-yl group, or a pharmaceutically acceptable salt thereof, or a solvate thereof.

[16-2]

An intermediate compound represented by the following formula (I'-a), or a pharmaceutically acceptable salt thereof, or a solvate thereof:

[Formula 87]
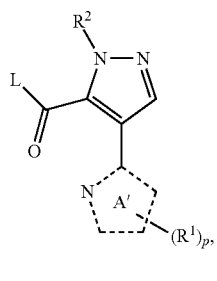
(I'-a)
wherein p, L, R¹, and R² have the same definitions as those described in the above embodiment [16];
ring A' represented by the following partial structural formula (II'):
[Formula 88]
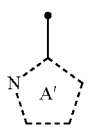
(II')
is selected from the group of the heteroaryls consisting of the following:
[Formula 89]
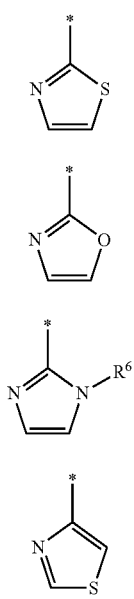
(II-1)
(II-2)
(II-3)
(II-4)
(II-5)
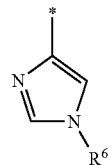
(II-6)
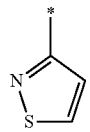
(II-7)
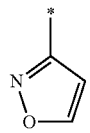
(II-8)
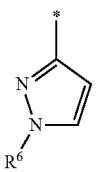
(II-9)
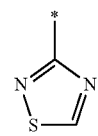
(II-10)
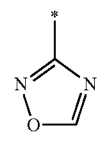
(II-11)
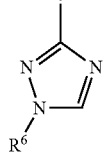
(II-12)
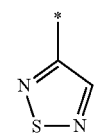
(II-13)
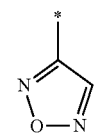
(II-14)
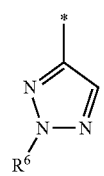
(II-15)

(II-16) 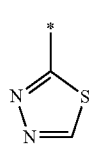

(II-17) 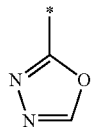

(II-18) 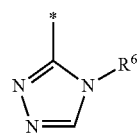

(II-19) 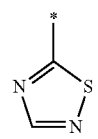

(II-20) 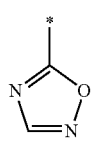

(II-21) 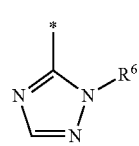

(II-22) 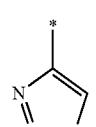

(II-23) 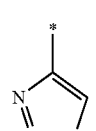

(II-24) 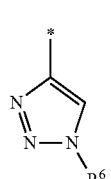

(II-25) 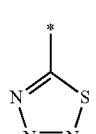

(II-26) 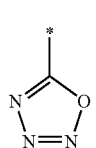

(II-27) 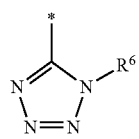

(II-28) 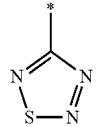

(II-29) 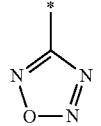

(II-30) 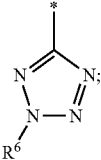

and $R^6$ represents a hydrogen atom, a $C_{1-6}$ alkyl group, a halogenated $C_{1-6}$ alkyl group, or a hydroxy $C_{1-6}$ alkyl group.

[16-2-2]

Preferably, the intermediate compound of the above embodiment [16-2] is an intermediate compound represented by the above formula (I'-a) wherein p, L, $R^1$, and $R^2$ have the same definitions as those described in the above embodiment [16-1];

ring A' represented by the following partial structural formula (II'):

[Formula 90]

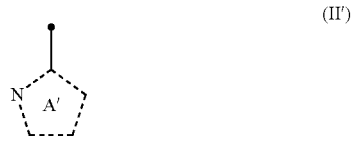

is selected from the group of the heteroaryls consisting of the following:

[Formula 91]

  (II-1)

(II-3) 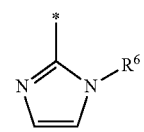

-continued (II-4) 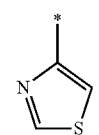

(II-6) 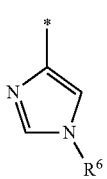

(II-7) 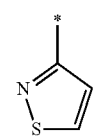

(II-9) 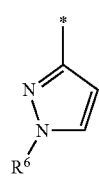

(II-10) 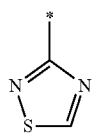

(II-12) 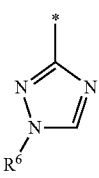

(II-13) 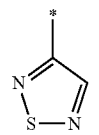

(II-15) 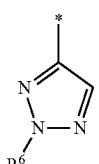

(II-16) 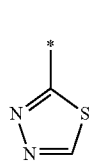

(II-18) 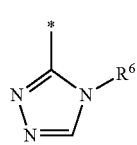

-continued (II-19) 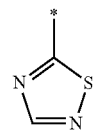

(II-21) 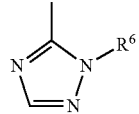

(II-22) 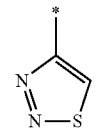

(II-24) 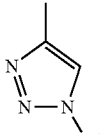

(II-25) 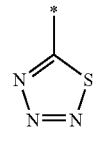

(II-27) 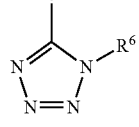

(II-29) 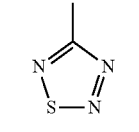

(II-30) 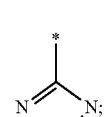

and $R^6$ represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[16-2-3]

More preferably, the intermediate compound of the above embodiment [16-2] is an intermediate compound represented by the above formula (I'-a) wherein p, L, $R^1$, and $R^2$ have the same definitions as those described in the above embodiment [16-1-2-2];

ring A' represented by the following partial structural formula (II'):
[Formula 92]
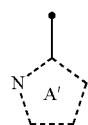
(II')
is selected from the group of the heteroaryls consisting of the following:
[Formula 93]
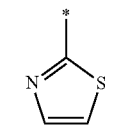
(II-1)
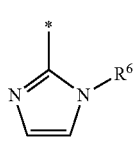
(II-3)
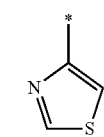
(II-4)
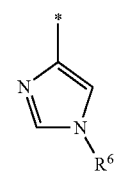
(II-6)
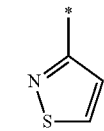
(II-7)
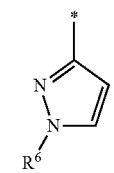
(II-9)
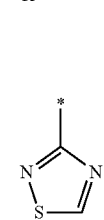
(II-10)
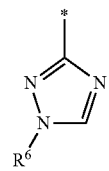
(II-12)
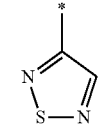
(II-13)
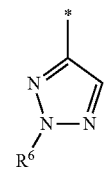
(II-15)
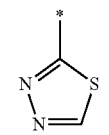
(II-16)
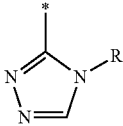
(II-18)
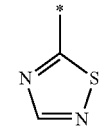
(II-19)
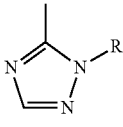
(II-21)
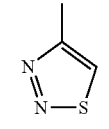
(II-22)
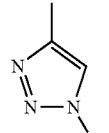
(II-24)
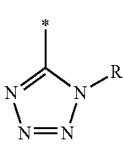
(II-27)

-continued (II-30)
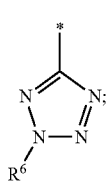

and R[6] represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[16-2-4]

Further preferably, the intermediate compound of the above embodiment [16-2] is an intermediate compound represented by the above formula (I'-a) wherein p, L, R[1], and R[2] have the same definitions as those described in the above embodiment [16-1-3-2];

ring A' represented by the following partial structural formula (II'):

[Formula 94]

(II')
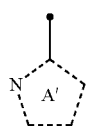

is selected from the group of the heteroaryls consisting of the following:

[Formula 95]

(II-1)
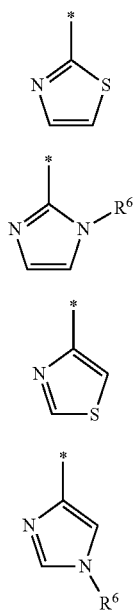

(II-3)

(II-4)

(II-6)

(II-7)

-continued (II-9)
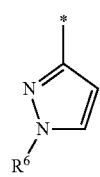

(II-10)
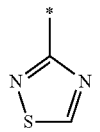

(II-12)
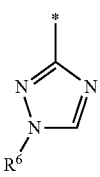

(II-13)
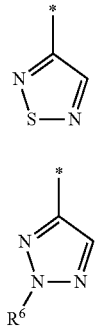

(II-15)

(II-16)
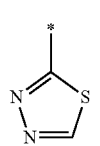

(II-18)
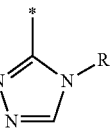

(II-19)
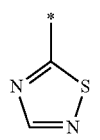

(II-21)
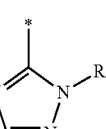

(II-22)
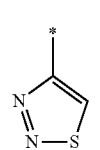

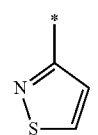

(II-24)

and R[6] represents a hydrogen atom, a $C_{1-6}$ alkyl group, a halogenated $C_{1-6}$ alkyl group, or a hydroxy $C_{1-6}$ alkyl group, or a pharmaceutically acceptable salt thereof, or a solvate thereof.

[16-2-5]

Particularly preferably, the intermediate compound of the above embodiment [16-2] is an intermediate compound represented by the above formula (I'-a) wherein p, L, R[1], and R[2] have the same definitions as those described in the above embodiment [16-1-4-2];

ring A' represented by the following partial structural formula (II'):

[Formula 96]

(II')

is selected from the group of the heteroaryls consisting of the following:

[Formula 97]

(II-1)

(II-4)

(II-6)

(II-16)

(II-19)

and R[6] represents a hydrogen atom or a $C_{1-6}$ alkyl group, and more specifically, R[6] represents a hydrogen atom, a methyl group, or the like, or a pharmaceutically acceptable salt thereof, or a solvate thereof.

[16-2-6]

More particularly preferably, the intermediate compound of the above embodiment [16-2] is an intermediate compound represented by the above formula (I'-a) wherein p, L, R[1], R[2], R[6], and ring A' have the same definitions as those described in the above embodiment [16-2-5], and a specific ring A' group, in which the definitions of the above described p, R[1], and ring A' are combined, represents a 1-methyl-1H-imidazol-4-yl group, a 4-(difluoromethyl)-5-ethylthiazol-2-yl group, a 4-(difluoromethyl)-5-vinylthiazol-2-yl group, a 4-(difluoromethyl)-5-methylthiazol-2-yl group, a 4-(difluoromethyl)thiazol-2-yl group, a 4-(trifluoromethyl)thiazol-2-yl group, a 4,5-dimethylthiazol-2-yl group, a 4-tert-butylthiazol-2-yl group, a 4-ethylthiazol-2-yl group, a 4-cyanothiazol-2-yl group, a 4-methylthiazol-2-yl group, a 4-methylthiazol-2-yl group, a 5-(2-ethoxyethyl)-4-methylthiazol-2-yl group, a 5-chloro-4-(difluoromethyl)thiazol-2-yl group, a 5-cyclopropyl-4-(difluoromethyl)thiazol-2-yl group, a 5-cyclopropyl-4-methylthiazol-2-yl group, a 5-bromo-4-methylthiazol-2-yl group, a 5-methylthiazol-2-yl group, a thiazol-2-yl group, a 2,5-dimethyl-thiazol-4-yl group, a 2-methylthiazol-4-yl group, a 5-acetyl-2-methyl-thiazol-4-yl group, a 5-bromo-2-methylthiazol-4-yl group, a thiazol-4-yl group, a 3-isopropyl-1,2,4-thiadiazol-5-yl group, a 3-methyl-1,2,4-thiadiazol-5-yl group, a 5-ethyl-1,3,4-thiadiazol-2-yl group, a 5-methyl-1,3,4-thiadiazol-2-yl group, or a 5-(2-ethoxyvinyl)4-methylthiazol-2-yl group, or a pharmaceutically acceptable salt thereof, or a solvate thereof.

[16-3]

An intermediate compound represented by the following formula (I'-b), or a pharmaceutically acceptable salt thereof, or a solvate thereof:

[Formula 98]

(I'-b)

wherein p, L, R[1], and R[2] have the same definitions as those described in the above embodiment [16];

ring A" represented by the following partial structural formula (II"):

[Formula 99]

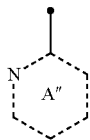
(II")

is selected from the group of the heteroaryls consisting of the following:

[Formula 100]

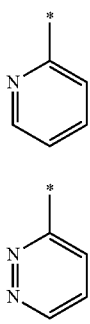
(II-31)

(II-32)

(II-33)

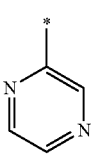
(II-34)

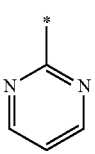
(II-35)

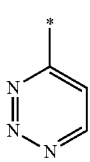
(II-36)

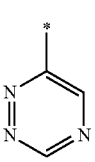
(II-37)

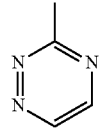
(II-38)

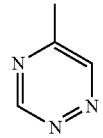
(II-39)

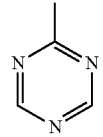
(II-40)

(II-41)

(II-42)

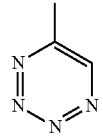
(II-43)

provided that when the ring A" is represented by the formula (II-31), p represents an integer of 1 to 3.

[16-3-2]

Preferably, the intermediate compound of the above embodiment [16-3] is an intermediate compound represented by the above formula (I'-b) wherein p, L, R¹, and R² have the same definitions as those described in the above embodiment [16-1]; and ring A" represented by the partial structural formula (II") has the same definitions as those described in the above embodiment [16-3] provided that when the ring A" is represented by the formula (II-31), p represents an integer of 1 to 3, or a pharmaceutically acceptable salt thereof, or a solvate thereof.

[16-3-3]

More preferably, the intermediate compound of the above embodiment [16-3] is an intermediate compound represented by the above formula (I'-b) wherein p, L, R¹, and R² have the same definitions as those described in the above embodiment [16-1-2-2]; and ring A" represented by the partial structural formula (II") has the same definitions as those described in the above embodiment [16-3] provided that when the ring A" is represented by the formula (II-31), p represents an integer of 1 to 3, or a pharmaceutically acceptable salt thereof, or a solvate thereof.

[16-3-4]

Further preferably, the intermediate compound of the above embodiment [16-3] is an intermediate compound represented by the above formula (I'-b) wherein p, L, R¹, and R² have the same definitions as those described in the above embodiment [16-1-3-2]; and ring A" represented by the following partial structural formula (II"):

[Formula 101]

(II")

is selected from the group of the heteroaryls consisting of the following:

[Formula 102]

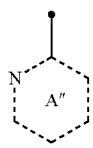
(II-31)

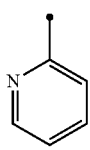
(II-32)

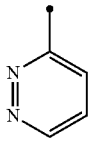
(II-33)

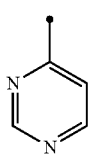
(II-34)

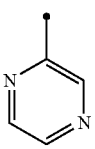
(II-35)

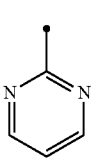
(II-36)

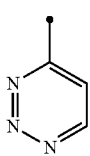
(II-37)

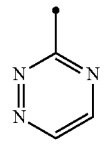
(II-38)

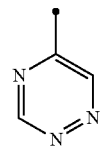
(II-39)

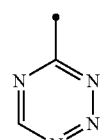
(II-43)

provided that when the ring A" is represented by the formula (II-31), p represents an integer of 1 to 3, or a pharmaceutically acceptable salt thereof, or a solvate thereof.

[16-3-5]

Particularly preferably, the intermediate compound of the above embodiment [16-3] is an intermediate compound represented by the above formula (I'-b) wherein p, L, R¹, and R² have the same definitions as those described in the above embodiment [16-1-4-2]; and ring A" represented by the following partial structural formula (II"):

[Formula 103]

(II")

is selected from the group of the heteroaryls consisting of the following:

[Formula 104]

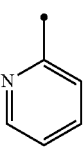
(II-31)

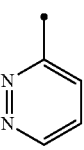
(II-32)

(II-33)

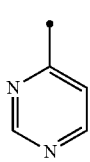

(II-34)

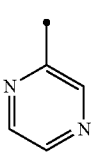

(II-35)

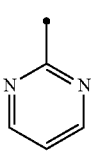

provided that when the ring A" is represented by the formula (II-31), p represents an integer of 1 to 3, or a pharmaceutically acceptable salt thereof, or a solvate thereof.

[16-3-6]

More particularly preferably, the intermediate compound of the above embodiment [16-3] is an intermediate compound represented by the above formula (I'-b) wherein p, L, $R^1$, $R^2$, and ring A" have the same definitions as those described in the above embodiment [16-3-5], and a specific ring A" group, in which the definitions of the above described p, $R^1$, and ring A" are combined, represents a 4,6-dimethylpyrimidin-2-yl group, a 4-methylpyrimidin-2-yl group, a 2,5,6-trimethylpyrimidin-4-yl group, a 2,5-dimethylpyrimidin-4-yl group, a 2,6-dimethylpyrimidin-4-yl group, a 2,6-dimethoxypyrimidin-4-yl group, a 2-methylpyrimidin-4-yl group, a 2-methoxypyrimidin-4-yl group, a 5,6-dimethylpyrimidin-4-yl group, a 5-chloro-2-methylpyrimidin-4-yl group, a 5-chloropyrimidin-4-yl group, a 5-fluoro-2-methylpyrimidin-4-yl group, a 5-fluoro-2-methoxypyrimidin-4-yl group, a 5-fluoro-6-methylpyrimidin-4-yl group, a 5-methylpyrimidin-4-yl group, a 5-methoxypyrimidin-4-yl group, a 6-methylpyrimidin-4-yl group, a 6-methoxy-5-methylpyrimidin-4-yl group, a 4-methylpyridazin-3-yl group, a 5-methylpyridazin-3-yl group, a 6-methylpyridazin-3-yl group, a pyridazin-3-yl group, a 3-cyano-pyridin-2-yl group, a 3-methylpyridin-2-yl group, a 3-methoxypyridin-2-yl group, a 4,6-dimethylpyridin-2-yl group, a 4-fluoropyridin-2-yl group, a 4-methylpyridin-2-yl group, a 4-methoxypyridin-2-yl group, a 5-cyanopyridin-2-yl group, a 5-fluoropyridin-2-yl group, a 5-methylpyridin-2-yl group, a 6-(trifluoromethyl)pyridin-2-yl group, a 6-cyano-pyridin-2-yl group, a 6-methylpyridin-2-yl group, a 6-methoxypyridin-2-yl group, a 3,6-dimethylpyrazin-2-yl group, a 3-methylpyrazin-2-yl group, a 3-methoxypyrazin-2-yl group, a 5-methylpyrazin-2-yl group, a 6-methylpyrazin-2-yl group, a 6-methylpyrazin-2-yl group, or a 6-methoxypyrazin-2-yl group, or a pharmaceutically acceptable salt thereof, or a solvate thereof.

[17]

A seventeenth embodiment of the present invention is illustrated, by way of example, with the below-listed intermediate compounds that are preferable as the compounds of the above embodiment [16] represented by the above formula (I'), the compounds of the above embodiment [16-2] represented by the above formula (I'-a), and the compounds of the above embodiment [16-3] represented by the above formula (I'-b), or pharmaceutically acceptable salts thereof, or their solvates. The shown intermediate compounds are obtained from individual steps with Example numbers corresponding to compound names. For example, in the case of Example number 1.1-2, it means that an intermediate compound corresponding to (Example 1.1) <Step 2> is obtained. It is to be noted that the following compound names are based on English names obtained in accordance with the chemical nomenclature program of Cambridge Soft Chem BioDraw Ultra 12.0.2.1076.

TABLE 2-1

| Compound name | Example No. |
|---|---|
| methyl 1-methyl-4-(5-methylpyridin-2-yl)-1H-pyrazole-5-carboxylate | 1.1-2 |
| 1-methyl-4-(5-methylpyridin-2-yl)-1H-pyrazole-5-carboxylic acid | 1.1-3 |
| methyl 1-methyl-4-(4-methylthiazol-2-yl)-1H-pyrazole-5-carboxylate | 1.2-1 |
| 1-methyl-4-(4-methylthiazol-2-yl)-1H-pyrazole-5-carboxylic acid | 1.2-2 |
| methyl 4-(4-(difluoromethyl)thiazol-2-yl)-1-methyl-1H-pyrazole-5-carboxylate | 1.3-1 |
| methyl 4-(5-bromo-4-(difluoromethyl)thiazol-2-yl)-1-methyl-1H-pyrazole-5-carboxylate | 1.4-1 |
| methyl 4-(4-(difluoromethyl)-5-methylthiazol-2-yl)-1-methyl-1H-pyrazole-5-carboxylate | 1.4-2 |
| methyl 1-methyl-4-(4-(trifluoromethyl)thiazol-2-yl)-1H-pyrazole-5-carboxylate | 1.5-1 |
| methyl 1-methyl-4-(6-(trifluoromethyl)pyridin-2-yl)-1H-pyrazole-5-carboxylate | 1.6-1 |

TABLE 2-2

| Compound name | Example No. |
|---|---|
| methyl 4-(5-chloro-4-(difluoromethyl)thiazol-2-y1)-1-methyl-1H-pyrazole-5-carboxylate | 1.7-1 |
| 4-(5-chloro-4-(difluoromethyl)thiazol-2-y1)-1-methyl-1H-pyrazole-5-carboxylic acid | 1.7-2 |
| methyl 4-(4,5-dimethylthiazol-2-y1)-1-methyl-1H-pyrazole-5-carboxylate | 2.2-1 |
| 4-(4,5-dimethylthiazol-2-y1)-1-methyl-1H-pyrazole-5-carboxylic acid | 2.2-2 |
| 1-methyl-4-(4-(trifluoromethyl)thiazol-2-y1)-1H-pyrazole-5-carboxylicacid | 2.8-1 |
| methyl 1-methyl-4-(6-methylpyridin-2-y1)-1H-pyrazole-5-carboxylate | 2.9-1 |
| methyl 1-methyl-4-(5-methyl-1,3,4-thiadiazol-2-y1)-1H-pyrazole-5-carboxylate | 2.10-1 |
| 1-methyl-4-(5-methyl-1,3,4-thiadiazol-2-y1)-1H-pyrazole-5-carboxylic acid | 2.10-2 |
| methyl 4-(6-methoxypyridin-2-y1)-1-methyl-1H-pyrazole-5-carboxylate | 2.11-1 |
| 4-(6-methoxypyridin-2-y1)-1-methyl-1H-pyrazole-5-carboxylic acid | 2.11-2 |
| methyl 1-methyl-4-(2-methylthiazol-4-y1)-1H-pyrazole-5-carboxylate | 2.12-1 |

TABLE 2-3

| Compound name | Example No. |
|---|---|
| methyl 1-methyl-4-(6-methylpyrazin-2-y1)-1H-pyrazole-5-carboxylate | 2.13-1 |
| 1-methyl-4-(6-methylpyrazin-2-y1)-1H-pyrazole-5-carboxylic acid | 2.13-2 |
| methyl 4-(3-isopropy1-1,2,4-thiadiazol-5-y1)-1-methyl-1H-pyrazole-5-carboxylate | 2.14-1 |
| methyl 1-methy1-4-(5-methylthiazol-2-y1)-1H-pyrazole-5-carboxylate | 2.15-1 |

TABLE 2-3-continued

| Compound name | Example No. |
|---|---|
| methyl 1-methyl-4-(4-methylpyrimidin-2-yl)-1H-pyrazole-5-carboxylate | 2.16-1 |
| 1-methyl-4-(4-methylpyrimidin-2-yl)-1H-pyrazole-5-carboxylic acid | 2.16-2 |
| methyl 1-methyl-4-(1-methyl-1H-imidazol-4-yl)-1H-pyrazole-5-carboxylate | 2.17-1 |
| 1-methyl-4-(trifluoromethyl)thiazol-2-yl)-1H-pyrazole-5-carboxylic acid | 2.19-7 |
| methyl 1-methyl-4-(thiazol-4-yl)-1H-pyrazole-5-carboxylate | 2.25-1 |
| methyl 1-methyl-4-(thiazol-2-yl)-1H-pyrazole-5-carboxylate | 2.26-1 |
| methyl 4-(4-(tert-butyl)thiazol-2-yl)-1-methyl-1H-pyrazole-5-carboxylate | 2.27-1 |
| methyl 1-methyl-4-(3-methylpyridin-2-yl)-1H-pyrazole-5-carboxylate | 3.1-2 |
| 1-methyl-4-(3-methylpyridin-2-yl)-1H-pyrazole-5-carboxylic acid | 3.1-3 |

TABLE 2-4

| Compound name | Example No. |
|---|---|
| 1-methyl-4-(5-methylpyrazin-2-yl)-1H-pyrazole-5-carboxylic acid | 3.2-1 |
| 1-methyl-4-(6-methylpyridin-2-yl)-1H-pyrazole-5-carboxylic acid | 3.3-1 |
| 4-(4-fluoropyridin-2-yl)-1-methyl-1H-pyrazole-5-carboxylic acid | 3.4-1 |
| 1-methyl-4-(4-methylpyridin-2-yl)-1H-pyrazole-5-carboxylic acid | 3.5-1 |
| 1-methyl-4-(4-(trifluoromethyl)thiazol-2-yl)-1H-pyrazole-5-carboxylic acid | 3.6-1 |
| 4-(3-methoxypyridin-2-yl)-1-methyl-1H-pyrazole-5-carboxylic acid | 3.7-1 |
| 4-(5-fluoropyridin-2-yl)-1-methyl-1H-pyrazole-5-carboxylic acid | 3.8-1 |
| methyl 1-methyl-4-(6-methylpyrazin-2-yl)-1H-pyrazole-5-carboxylate | 3.9-1 |
| 1-methyl-4-(6-methylpyrazin-2-yl)-1H-pyrazole-5-carboxylic acid | 3.9-2 |
| 1-methyl-4-(6-(trifluoromethyl)pyridin-2-yl)-1H-pyrazole-5-carboxylic acid | 3.10-1 |
| 4-(4,6-dimethylpyridin-2-yl)-1-methyl-1H-pyrazole-5-carboxylic acid | 3.11-1 |
| 4-(4-difluoromethyl)thiazol-2-yl)-1-methyl-1H-pyrazole-5-carboxylic acid | 3.12-1 |
| methyl 4-(3-cyanopyridin-2-yl)-1-methyl-1H-pyrazole-5-carboxylate | 3.13-1 |
| 4-(3-cyanopyridin-2-yl)-1-methyl-1H-pyrazole-5-carboxylic acid | 3.13-2 |

TABLE 2-5

| Compound name | Example No. |
|---|---|
| methyl 4-(3,6-dimethylpyrazin-2-yl)-1-methyl-1H-pyrazole-5-carboxylate | 3.14-1 |
| 4-(3,6-dimethylpyrazin-2-yl)-1-methyl-1H-pyrazole-5-carboxylic acid | 3.14-2 |
| methyl 4-(4-ethylthiazol-2-yl)-1-methyl-1H-pyrazole-5-carboxylate | 3.18-1 |
| 4-(4-ethylthiazol-2-yl)-1-methyl-1H-pyrazole-5-carboxylic acid | 3.18-2 |
| methyl 4-(2,5-dimethylpyrimidin-4-yl)-1-methyl-1H-pyrazole-5-carboxylate | 3.22-1 |
| 4-(2,5-dimethylpyrimidin-4-yl)-1-methyl-1H-pyrazole-5-carboxylic acid | 3.22-2 |
| 4-(5-cyanopyridin-2-yl)-1-methyl-1H-pyrazole-5-carboxylic acid | 3.23-1 |
| methyl 1-methyl-4-(4-methylpyridazin-3-yl)-1H-pyrazole-5-carboxylate | 3.24-1 |
| 1-methyl-4-(4-methylpyridazin-3-yl)-1H-pyrazole-5-carboxylic acid | 3.24-2 |
| methyl 1-methyl-4-(2-methylpyrimidin-4-yl)-1H-pyrazole-5-carboxylate | 3.25-1 |
| 1-methyl-4-(2-methylpyrimidin-4-yl)-1H-pyrazole-5-carboxylic acid | 3.25-2 |
| methyl 4-(2-methoxypyrimidin-4-yl)-1-methyl-1H-pyrazole-5-carboxylate | 3.26-1 |
| 4-(2-methoxypyrimidin-4-yl)-1-methyl-1H-pyrazole-5-carboxylic acid | 3.26-2 |

TABLE 2-5-continued

| Compound name | Example No. |
|---|---|
| methyl 4-(5-fluoro-2-methoxypyrimidin-4-yl)-1-methyl-1H-pyrazole-5-carboxylate | 3.27-1 |

TABLE 2-6

| Compound name | Example No. |
|---|---|
| 4-(5-fluoro-2-methoxypyrimidin-4-yl)-1-methyl-1H-pyrazole-5-carboxylic acid | 3.27-2 |
| methyl 4-(3-methoxypyrazin-2-yl)-1-methyl-1H-pyrazole-5-carboxylate | 3.28-1 |
| 4-(3-methoxypyrazin-2-yl)-1-methyl-1H-pyrazole-5-carboxylic acid | 3.28-2 |
| methyl 4-(5-chloropyrimidin-4-yl)-1-methyl-1H-pyrazole-5-carboxylate | 3.29-1 |
| 4-(5-chloropyrimidin-4-yl)-1-methyl-1H-pyrazole-5-carboxylic acid | 3.29-2 |
| methyl 4-(2,6-dimethylpyrimidin-4-yl)-1-methyl-1H-pyrazole-5-carboxylate | 3.30-1 |
| 4-(2,6-dimethylpyrimidin-4-yl)-1-methyl-1H-pyrazole-5-carboxylic acid | 3.30-2 |
| methyl 4-(6-methoxy-5-methylpyrimidin-4-yl)-1-methyl-1H-pyrazole-5-carboxylate | 3.31-1 |
| 4-(6-methoxy-5-methylpyrimidin-4-yl)-1-methyl-1H-pyrazole-5-carboxylic acid | 3.31-2 |
| methyl 1-methyl-4-(3-methylpyrazin-2-yl)-1H-pyrazole-5-carboxylate | 3.32-1 |
| 1-methyl-4-(3-methylpyrazin-2-yl)-1H-pyrazole-5-carboxylic acid | 3.32-2 |
| methyl 1-methyl-4-(5-methylpyrimidin-4-yl)-1H-pyrazole-5-carboxylate | 3.33-1 |
| 1-methyl-4-(5-methylpyrimidin-4-yl)-1H-pyrazole-5-carboxylic acid | 3.33-2 |
| methyl 4-(5-methoxypyrimidin-4-yl)-1-methyl-1H-pyrazole-5-carboxylate | 3.34-1 |

TABLE 2-7

| Compound name | Example No. |
|---|---|
| 4-(5-methoxypyrimidin-4-yl)-1-methyl-1H-pyrazole-5-carboxylic acid | 3.34-2 |
| methyl 4-(5,6-dimethylpyrimidin-4-yl)-1-methyl-1H-pyrazole-5-carboxylate | 3.35-1 |
| 4-(5,6-dimethylpyrimidin-4-yl)-1-methyl-1H-pyrazole-5-carboxylic acid | 3.35-2 |
| methyl 4-(5-fluoro-2-methylpyrimidin-4-yl)-1-methyl-1H-pyrazole-5-carboxylate | 3.36-1 |
| 4-(5-fluoro-2-methylpyrimidin-4-yl)-1-methyl-1H-pyrazole-5-carboxylic acid | 3.36-2 |
| methyl 1-methyl-4-(2,5,6-trimethylpyrimidin-4-yl)-1H-pyrazole-5-carboxylate | 3.37-1 |
| 1-methyl-4-(2,5,6-trimethylpyrimidin-4-yl)-1H-pyrazole-5-carboxylic acid | 3.37-2 |
| methyl 4-(5-fluoro-6-methylpyrimidin-4-yl)-1-methyl-1H-pyrazole-5-carboxylate | 3.38-1 |
| 4-(5-fluoro-6-methylpyrimidin-4-yl)-1-methyl-1H-pyrazole-5-carboxylic acid | 3.38-2 |
| methyl 1-methyl-4-(6-methylpyrimidin-4-yl)-1H-pyrazole-5-carboxylate | 3.39-1 |
| 1-methyl-4-(6-methylpyrimidin-4-yl)-1H-pyrazole-5-carboxylic acid | 3.39-2 |
| methyl 4-(2,6-dimethoxypyrimidin-4-yl)-1-methyl-1H-pyrazole-5-carboxylate | 3.40-1 |
| 4-(2,6-dimethoxypyrimidin-4-yl)-1-methyl-1H-pyrazole-5-carboxylic acid | 3.40-2 |
| methyl 4-(5-chloro-2-methylpyrimidin-4-yl)-1-methyl-1H-pyrazole-5-carboxylate | 3.41-1 |

TABLE 2-8

| Compound name | Example No. |
| --- | --- |
| 4-(5-chloro-2-methylpyrimidin-4-y1)-1-methyl-1H-pyrazole-5-carboxylic acid | 3.41-2 |
| methyl 4-(6-methoxypyrazin-2-y1)-1-methyl-1H-pyrazole-5-carboxylate | 3.42-1 |
| 4-(6-methoxypyrazin-2-y1)-1-methyl-1H-pyrazole-5-carboxylic acid | 3.42-2 |
| methyl 1-methyl-4-(4-methylpyrimidin-2-y1)-1H-pyrazole-5-carboxylate | 3.43-1 |
| 1-methyl-4-(4-methylpyrimidin-2-y1)-1H-pyrazole-5-carboxylic acid | 3.43-2 |
| methyl 4-(4,6-dimethylpyrimidin-2-y1)-1-methyl-1H-pyrazole-5-carboxylate | 3.44-1 |
| 4-(4,6-dimethylpyrimidin-2-y1)-1-methyl-1H-pyrazole-5-carboxylic acid | 3.44-2 |
| methyl 1-methyl-4-(6-methylpyridazin-3-y1)-1H-pyrazole-5-carboxylate | 3.45-1 |
| 1-methyl-4-(6-methylpyridazin-3-yl)-1H-pyrazole-5-carboxylic acid | 3.45-2 |
| methyl 1-methyl-4-(5-methylpyridazin-3-y1)-1H-pyrazole-5-carboxylate | 3.46-1 |
| 1-methyl-4-(5-methylpyridazin-3 -yl)-1H-pyrazole-5-carboxylic acid | 3.46-2 |
| methyl 1-methyl-4-(pyridazin-3-y1)-1H-pyrazole-5-carboxylate | 3.47-1 |
| 1-methyl-4-(pyridazin-3-y1)-1H-pyrazole-5-carboxylic acid | 3.47-2 |
| methyl 1-methyl-4-(4-methylpyridin-2-y1)-1H-pyrazole-5-carboxylate | 4.4-1 |

TABLE 2-9

| Compound name | Example No. |
| --- | --- |
| 1-methyl-4-(4-methylpyridin-2-yl)-1H-pyrazole-5-carboxylic acid | 4.4-2 |
| methyl 4-(4-methoxypyridin-2-yl)-1-methyl-1H-pyrazole-5-carboxylate | 4.5-1 |
| 4-(4-methoxypyridin-2-yl)-1-methyl-1H-pyrazole-5-carboxylic acid | 4.5-2 |
| methyl 4-(4,6-dimethylpyridin-2-yl)-1-methyl-1H-pyrazole-5-carboxylate | 4.8-1 |
| 4-(4,6-dimethylpyridin-2-yl)-1-methyl-1H-pyrazole-5-carboxylic acid | 4.8-2 |
| 4-(4-(difluoromethyl)-5-methylthiazol-2-yl)-1-methyl-1H-pyrazole-5-carboxylic acid | 4.9-1 |
| 1-methyl-4-(4-(trifluoromethyl)thiazol-2-yl)-1H-pyrazole-5-carboxylic acid | 4.10-1 |
| methyl 4-(4,5-dimethylthiazol-2-yl)-1-methyl-1H-pyrazole-5-carboxylate | 5.4-1 |
| methyl 4-(4-(difluoromethyl)-5-vinylthiazol-2-yl)-1-methyl-1H-pyrazole-5-carboxylate | 5.5-1 |
| methyl 4-(4-(difluoromethyl)-5-ethylthiazol-2-yl)-1-methyl-1H-pyrazole-5-carboxylate | 5.6-1 |
| methyl 4-(5-cyclopropyl-4-(difluoromethyl)thiazol-2-yl)-1-methyl-1H-pyrazole-5-carboxylate | 5.8-1 |
| 4-(4-cyanothiazol-2-yl)-1-methyl-1H-pyrazole-5-carboxylic acid | 5.10-1 |

TABLE 2-10

| Compound name | Example No. |
| --- | --- |
| methyl 4-(5-bromo-4-methylthiazol-2-yl)-1-methyl-1H-pyrazole-5-carboxylate | 5.11-1 |
| (E)-methyl 4-(5-(2-ethoxyyinyl)-4-methylthiazol-2-yl)-1-methyl-1H-pyrazole-5-carboxylate | 5.11-2 |
| methyl 4-(5-(2-ethoxyethyl)-4-methylthiazol-2-yl)-1-methyl-1H-pyrazole-5-carboxylate | 5.11-3 |
| methyl 4-(5-ethyl-1,3,4-thiadiazol-2-yl)-1-methyl-1H-pyrazole-5-carboxylate | 5.12-1 |
| methyl 4-(5-bromo-2-methylthiazol-4-yl)-1-methyl-1H-pyrazole-5-carboxylate | 5.13-1 |

TABLE 2-10-continued

| Compound name | Example No. |
| --- | --- |
| methyl 1-methyl-4-(3-methyl-1,2,4-thiadiazol-5-yl)-1H-pyrazole-5-carboxylate | 5.15-1 |
| methyl 4-(5-bromo-4-methylthiazol-2-yl)-1-methyl-1H-pyrazole-5-carboxylate | 5.38-1 |
| 4-(5-cyclopropyl-4-methylthiazol-2-yl)-1-methyl-1H-pyrazole-5-carboxylic acid | 5.38-2 |
| 4-(2,5-dimethylthiazol-4-yl)-1-methyl-1H-pyrazole-5-carboxylic acid | 5.39-1 |
| 4-(6-cyanopyridin-2-yl)-1-methyl-1H-pyrazole-5-carboxylic acid | 5.40-1 |
| 4-(4-cyanothiazol-2-yl)-1-methyl-1H-pyrazole-5-carboxylic acid | 5.41-1 |
| methyl 4-(5-cyclopropyl-4-methylthiazol-2-yl)-1-methyl-1H-pyrazole-5-carboxylate | 5.43-1 |

TABLE 2-11

| Compound name | Example No. |
| --- | --- |
| methyl 4-(5-acetyl-2-methylthiazol-4-yl)-1-methyl-1H-pyrazole-5-carboxylate | 5.44-1 |
| 4-(4,5-dimethylthiazol-2-yl)-1-methyl-1H-pyrazole-5-carboxylic acid | 5.45-1 |
| 1-methyl-4-(6-methylpyridin-2-yl)-1H-pyrazole-5-carbonyl chloride | 5.47-1 |

In all of the above described embodiments, when the term "compound" is used, it also refers to a "pharmaceutically acceptable salt thereof."

There may be a case in which the compound in the present invention forms an acid addition salt or a salt with a base, depending on the type of a substituent. Such salts are not particularly limited, as long as they are pharmaceutically acceptable salts. Examples of the salts include metal salts, ammonium salts, salts with organic bases, salts with inorganic acids, salts with organic acids, and salts with basic or acidic amino acids. Preferred examples of the metal salts include: alkaline metal salts, such as lithium salts, sodium salts, potassium salts, and cesium salts; alkaline-earth metal salts such as calcium salts, magnesium salts, and barium salts; and aluminum salts (wherein the salts include disodium salts and dipotassium salts, as well as mono salts). Preferred examples of the salts with organic bases include salts with methylamine, ethylamine, t-butylamine, t-octylamine, diethylamine, trimethylamine, triethylamine, cyclohexylamine, dicyclohexylamine, dibenzylamine, ethanolamine, diethanolamine, triethanolamine, piperidine, morpholine, pyridine, picoline, lysine, arginine, ornithine, ethylenediamine, N-methylglucamine, glucosamine, phenylglycinealkylester, guanidine, 2,6-lutidine, ethanolamine, diethanolamine, triethanolamine, and N,N'-dibenzylethylenediamine. Preferred examples of the salts with inorganic acids include salts with hydrochloric acid, hydrobromic acid, hydroiodic acid, nitric acid, sulfuric acid, and phosphoric acid. Preferred examples of the salts with organic acids include: salts with aliphatic monocarboxylic acids such as formic acid, acetic acid, trifluoroacetic acid, propionic acid, butyric acid, valeric acid, enanthic acid, capric acid, myristic acid, palmitic acid, stearic acid, lactic acid, sorbic acid, and mandelic acid; salts with aliphatic dicarboxylic acids such as oxalic acid, malonic acid, succinic acid, fumaric acid, maleic acid, malic acid, and tartaric acid; salts with aliphatic tricarboxylic acids such as citric acid; salts with aromatic monocarboxylic acids such as benzoic acid and salicylic acid; salts with aromatic dicarboxylic acids such as phthalic acid; salts with organic carboxylic acids such as cinnamic acid, glycolic acid, pyruvic acid, oxyl acid, salicylic acid, and N-acetyl cysteine; salts with organic sulfonic acids such as methanesulfonic acid, benzenesulfonic acid, and p-toluenesulfonic acid; and acid addition salts with acidic amino acids such as aspartic acid and glutamic acid. Preferred examples of the salts with basic amino acids include salts with arginine, lysine, and ornithine. Preferred examples of the salts with acidic amino acids include salts with aspartic acid and glutamic acid. Among these salts, pharmaceutically acceptable salts are preferable. For example, when the compound has an acidic functional group therein, examples of the salts include inorganic salts such as alkaline metal salts (e.g. sodium salts and potassium salts) and alkaline-earth metal salts (e.g. calcium salts, magnesium salts, and barium salts), and ammonium salts. When the compound has a basic functional group therein, examples of the salts include: salts with inorganic acids such as hydrochloric acid, hydrobromic acid, nitric acid, sulfuric acid, and phosphoric acid; and salts with organic acids such as acetic acid, phthalic acid, fumaric acid, oxalic acid, tartaric acid, maleic acid, citric acid, succinic acid, methanesulfonic acid and p-toluenesulfonic acid.

The above described salts can be obtained according to an ordinary method, for example, by mixing the compound in the present invention with a solution containing an appropriate amount of acid or base to form salts of interest, and then subjecting the salts to fractionation by filtration, or distilling the mixed solvent away from the reaction solution. Moreover, the compound in the present invention or a salt thereof can form a solvate with a solvent such as water, ethanol, or glycerol.

Handbook of Pharmaceutical Salts: Properties, Selection, and Use, Stahl & Wermuth (Wiley-VCH, 2002) has been published as a review book regarding salts. This book includes detailed descriptions regarding salts.

The compound in the present invention can be present in an unsolvated state or a solvated state. In the present specification, the term "solvate" means a molecular complex comprising the compound in the present invention and one or more pharmaceutically acceptable solvent molecules (e.g. water and ethanol). When the aforementioned solvent molecule is water, it is particularly referred to as a "hydrate."

Hereinafter, the descriptions regarding the compound in the present invention include the descriptions regarding the salt thereof, the solvate thereof, and a solvate of the salt.

The "prodrug" of the compound in the present invention is also included in the compound in the present invention. For instance, when a certain derivative of the compound in the present invention, which may hardly or never exhibit pharmacological activities of interest, is converted to the compound in the present invention having the pharmacological activities of interest, for example, as a result of hydrolysis or the like, following administration into or on a body, the compound before administration is referred to as a "prodrug."

A "prodrug" of the compound in the present invention can be produced, for example, by subjecting a suitable functional group present in the compound in the present invention to a known method, for example, the method described in Design of Prodrugs, H. Bundgaard (Elsevier, 1985).

Specific examples of the "prodrug" of the compound in the present invention may include the following (1) to (3), but examples are not limited thereto.

(1) Case in which the compound in the present invention is substituted with a carboxy group (—COOH): the ester thereof, namely, a compound in which the hydrogen atom of the carboxy group (—COOH) is replaced with a "$C_{1-6}$ alkyl group."

(2) Case in which the compound in the present invention is substituted with a hydroxyl group (—OH): the alkanoyloxy or the ether thereof, namely, a compound in which the hydrogen atom of the hydroxyl group (—OH) is replaced with a "$C_{2-7}$ alkanoyl group" or a "$C_{2-7}$ alkanoyloxymethyl group."

(3) Case in which the compound in the present invention is substituted with an amino group (—NH$_2$ or —NHR' (wherein R'≠H)): the amide thereof, namely, a compound in which either hydrogen atom or both hydrogen atoms of the amino group (—NH$_2$ or —NHR' (wherein R'≠H)) are replaced with "$C_{2-7}$ alkanoyl groups."

When the compound in the present invention has isomers such as a geometrical isomer, a configurational isomer, a tautomeric isomer, an optical isomer, a diastereomer, a regioisomer, or a rotational isomer, both any one isomer and a mixture thereof are included in the compound in the present invention. Moreover, when the compound in the present invention has an optical isomer, an optical isomer obtained from a racemate is also included in the compound in the present invention.

In the case of the compound in the present invention has one or more asymmetric carbon atoms, two or more isomers can be present. In addition, when the compound in the present invention comprises a "$C_{2-6}$ alkenyl group," geometrical isomer (cis/trans or Z/E) can be present. Moreover, structural isomers can be mutually converted because of low energy barrier, tautomeric isomerism may be generated. An example of such tautomeric isomerism is protonic tautomeric isomerism in a compound having an imino, keto, or oxime group.

When the compound in the present invention has a geometrical isomer, a configurational isomer, a diastereomer, a conformer or the like, these isomers can be each isolated by a known means.

Furthermore, when the compound in the present invention is an optically active substance, a racemate can be separated into a (+) form or a (−) form [D form or L form] according to an ordinary optical resolution means.

When the compound in the present invention contains an optical isomer, a diastereomer, a regioisomer, a rotational isomer, or a tautomeric isomer, each isomer can be obtained as a single compound according to a known synthetic method or separation method. Examples of the optical resolution method include known methods such as (1) a fractional recrystallization method, (2) a diastereomer method, and (3) a chiral column method.

(1) Fractional recrystallization method: This is a method which comprises binding an optical resolution agent to a racemate via an ionic bond to obtain a crystalline diastereomer, then separating this diastereomer by a fractional recrystallization method, and then subjecting the resultant to a neutralization step, as desired, so as to obtain a free optically pure compound. Examples of the optical resolution agent include (+)-mandelic acid, (−)-mandelic acid, (+)-tartaric acid, (−)-tartaric acid, (+)-1-phenethylamine, (−)-1-phenethylamine, cinchonine, (−)-cinchonidine, and brucine.

(2) Diastereomer method: This is a method which comprises binding via a covalent bond (reacting) an optical resolution agent to a racemate mixture to form a diastereomer mixture, then subjecting the diastereomer mixture to a common separation means (e.g., fractional recrystallization, silica gel column chromatography, and HPLC (high performance liquid chromatography)) to separate it into an optically pure diastereomer, and then removing the optical resolution agent by a chemical treatment such as a hydrolysis reaction, so as to obtain an optically pure optical isomer. For example, when the compound in the present invention has an intramolecular hydroxyl group or a primary or secondary amino group, the compound and an optically active organic acid (e.g., MTPA [α-methoxy-α-(trifluoromethyl)phenylacetic acid] and (−)-menthoxyacetic acid) or the like are subjected to a condensation reaction, so as to obtain a diastereomer of each ester body or amide body. On the other hand, when the compound in the present invention has a carboxy group, the compound and an optically active amine or an alcohol reagent are subjected to a condensation reaction, so as to obtain a diastereomer of each amide body or ester body. Each of the above separated diastereomers is converted to an optical isomer of the original compound by subjecting it to an acidic hydrolysis or basic hydrolysis reaction.

(3) Chiral column method: This is a method which comprises subjecting a racemate or a salt thereof to chromatography using a chiral column (optical isomer separatory column) for direct optical resolution. For example, in the case of high performance liquid chromatography (HPLC), a mixture of optical isomers is added to a chiral column of CHIRAL Series manufactured by Daicel Corporation, etc., and it is then developed by a single use of water, various buffers (e.g., a phosphate buffer), and organic solvents (e.g., ethanol, methanol, isopropanol, acetonitrile, trifluoroacetic acid, and diethylamine), or using a mixed solution thereof, thereby separating the optical isomer. In addition, for example, in the case of gas chromatography, the optical isomer can be separated using a chiral column of CP-Chirasil-DeX CB (manufactured by GL Sciences), etc.

The compound in the present invention may be a crystal. Although the crystalline form is either a single crystal or a crystalline mixture, they are included in the compound in the present invention.

The compound in the present invention may be a pharmaceutically acceptable cocrystal or a cocrystal salt. Herein, the term "cocrystal" or "cocrystal salt" means a crystalline substance composed of two or more unique solids at room temperature, which has each different physical properties (e.g. structure, melting point, melting heat, absorbency, solubility, and stability). Such a cocrystal or cocrystal salt can be produced according to a known cocrystallization method.

The compound in the present invention includes compounds labeled or substituted with isotopes (e.g. hydrogen isotopes such as $^2$H and $^3$H, carbon isotopes such as $^{11}$C, $^{13}$C, and $^{14}$C, chlorine isotopes such as $^{36}$Cl, fluorine isotopes such as $^{18}$F, iodine isotopes such as $^{123}$I and $^{125}$I, nitrogen isotopes such as $^{13}$N and $^{15}$N, oxygen isotopes such as $^{15}$O, $^{17}$O, and $^{18}$O, phosphorus isotopes such as $^{32}$P, and sulfur isotopes such as $^{35}$S).

The compound in the present invention, which is labeled or substituted with certain types of isotopes (e.g. positron emission isotopes such as $^{11}$C, $^{18}$F, $^{15}$O, and $^{13}$N), can be used, for example, as a tracer (PET tracer) in Positron Emission Tomography (PET), and thus, it is useful in the field such as medical diagnosis.

The compound in the present invention, which is labeled or substituted with certain types of isotopes, is useful for studies regarding histological distribution of drugs and/or substrates. For instance, $^3$H and $^{14}$C facilitate such labeling and substitution, and the detection means is easy. Thus, they are useful for the aforementioned study purpose.

The compound in the present invention, which is labeled with isotopes, can be obtained by a common technique known to a person skilled in the art, or by a method similar to the synthetic methods described later in Examples. In addition, instead of a non-labeled compound, the obtained isotope-labeled compound can be used in pharmacological experiments.

[Method for Producing the Compound in the Present Invention]

Hereinafter, a method for producing the compound represented by the formula (I) of the present invention will be described. The compound represented by the formula (I) that is the compound in the present invention, a salt thereof, and a solvate thereof can be easily produced by a combination of known general chemical production methods, using, as starting materials or synthetic intermediates, commercially available compounds, or compounds that can be easily obtained from such commercially available compounds according to production methods known from literature. They can be produced according to representative production methods, as described below. In addition, the below-mentioned production methods are not intended to limit the present invention.

The definitions of p, q, Z, $R^1$, $R^2$, $R^3$, $R^4$, $R^5$, $R^6$, $R^7$, $R^8$, ring A, and fused ring B, which are used in individual formulas of the below-mentioned production methods, are the same as those described in the formula (I) in the above described embodiments, unless otherwise specified. The definition of M in the production method is metal such as lithium, sodium, or potassium, unless otherwise specified. The definition of X in the production method is a halogen atom, unless otherwise specified. The definition of Y in the production method is a hydrogen atom, a hydroxyl group, $OR^4$, or chlorine, unless otherwise specified. The definition of $R^4$ in the production method is a $C_{1-6}$ alkyl group, a $C_{6-13}$ aryl group, or a $C_{7-20}$ aralkyl group, unless otherwise specified.

Individual raw material compounds used in the production of the compound of the formula (I) in the below-mentioned production methods may form salts. As such salts, the same salts as those in the above formula (I) may be included. In addition, each raw material compound used in the production of the compound of the formula (I) can be directly used as a reaction solution, or as a crude product, in the subsequent reaction. It can also be isolated from a reaction mixture according to an ordinary method, and it can be easily purified by known separation means such as extraction, concentration, neutralization, filtration, distillation, recrystallization, or chromatography.

Examples of the solvent used in the above described recrystallization include: water; alcohols such as methanol, ethanol, 2-propanol, and butanol; ethers such as diethyl ether, tetrahydrofuran, and 1,4-dioxane; hydrocarbons such as n-hexane, cyclohexane, and heptane; aromatic hydrocarbons such as benzene, toluene, and xylene; amides such as N,N-dimethylformamide, N,N-dimethylacetamide, and 1,3-dimethyl-2-imidazolidinone; halogenated hydrocarbons such as chloroform, methylene chloride, and 1,2-dichloroethane; nitriles such as acetonitrile; ketones such as acetone and diphenylketone; esters such as methyl acetate and ethyl acetate; sulfoxides such as dimethyl sulfoxide; and organic acids such as acetic acid, trifluoroacetic acid, methanesulfonic acid, and p-toluenesulfonic acid. These solvents may be used singly, or may also be used by mixing two or more solvents at a suitable ratio, for example, at a ratio of 1:1 to 1:10. Moreover, when a compound represented by a formula is commercially available product, the commercially available product may be directly used. Furthermore, a compound produced by a known method or a method equivalent thereto may also be used.

When a substituent in the formula (I) contains a variable functional group (e.g. a carboxy group, an amino group, a hydroxyl group, a carbonyl group, a mercapto group, a $C_{1-6}$ alkoxylcarbonyl group, a $C_{6-14}$ aryloxycarbonyl group, a $C_{7-20}$ aralkyloxycarbonyl group, a sulfo group (—$SO_2OH$), and a halogen atom), these functional groups are converted by a known method or a method equivalent thereto, so as to produce various compounds.

When the functional group is a "carboxy group," it can be converted according to reactions such as esterification, reduction, amidation, or conversion reaction to an optionally protected amino group.

When the functional group is an "amino group," it can be converted according to reactions such as amidation, sulfonylation, nitrosation, alkylation, arylation, or imidation.

When the functional group is a "hydroxyl group," it can be converted according to reactions such as esterification, carbamoylation, sulfonylation, alkylation, arylation, oxidation, or halogenation.

When the functional group is a "carbonyl group," it can be converted according to reactions such as reduction, oxidation, imination (including oximation and conversion to hydrazone), (thio)ketalization, conversion to alkylidene, or thiocarbonylation.

When the functional group is a "mercapto group (—SH)," it can be converted according to reactions such as alkylation or oxidation.

When the functional group is a "$C_{1-6}$ alkoxylcarbonyl group," a "$C_{6-14}$ aryloxycarbonyl group," or a "$C_{7-20}$ aralkyloxycarbonyl group," it can be converted according to reactions such as reduction or hydrolysis.

When the functional group is a "sulfo group (—$SO_2OH$)," it can be converted according to reactions such as sulfonamidation or reduction.

When the functional group is a "halogen atom," it can be converted according to, for example, various types of nucleophilic substitution reactions or various types of coupling reactions.

In each of the above described reactions, when a compound is obtained in the free state, it may be converted to salts according to an ordinary method. When the compound is obtained in the form of salts, the salts may also be converted to a free body or other salts according to an ordinary method.

Conversion of these functional groups can be carried out according to the method described, for example, in Richard C. Larock et al., Comprehensive Organic Transformations, $2^{nd}$ edition, published in October, 1999, Wiley-VCH.

Moreover, in each reaction in the method for producing the compound represented by the formula (I) of the present invention, and in each reaction in the synthesis of raw material compounds, when reactive groups such as a hydroxyl group (an alcoholic hydroxyl group, a phenolic hydroxyl group, a heterocyclic hydroxyl group, etc.), an amino group, a carboxy group, and a thiol group are used as substituents, it is also possible to appropriately protect these groups in each reaction step, and then to remove the protective groups at a suitable stage.

Examples of the protective groups for the hydroxyl group (an alcoholic hydroxyl group, a phenolic hydroxyl group, a heterocyclic hydroxyl group, etc.) that can be used herein include: $C_{1-6}$ alkyl groups including, as representative examples, methyl, ethyl, n-propyl, isopropyl, n-butyl, and tert-butyl; alkoxylalkyl groups including, as representative examples, methoxymethyl (MOM) and methoxyethoxymethyl (MEM); tetrahydropyranyl (THP) groups; aralkyl groups including, as representative examples, benzyl (Bn) and triphenylmethyl (Tr); silyl groups including, as representative examples, trimethylsilyl (TMS), triethylsilyl (TES), t-butyldimethylsilyl (TBDMS), and t-butyldiphenylsilyl (TBDPS); alkanoyl groups including, as representative examples, acetyl (Ac), ethylcarbonyl, and pivaloyl (Piv); aralkylcarbonyl groups including, as a representative example, benzylcarbonyl; aroyl groups including, as a representative example, benzoyl (Bz); alkoxylcarbonyl groups including, as representative examples, methoxycarbonyl, ethoxycarbonyl, and t-butoxycarbonyl (Boc); and aralkyloxycarbonyl groups including as a representative example, benzyloxycarbonyl (Z).

Examples of the protective groups for the amino group (—$NH_2$ group) or the imino group (—NH— group) that can be used herein include: alkanoyl groups including, as representative examples, acetyl (Ac), ethylcarbonyl, and pivaloyl (Piv); alkoxylcarbonyl groups including, as representative examples, methoxycarbonyl, ethoxycarbonyl, and t-butoxycarbonyl (Boc); allyloxycarbonyl (Alloc) groups; fluorenylmethoxycarbonyl (Fmoc) groups; phenyloxycarbonyl; aralkyloxycarbonyl groups including, as representative examples, benzyloxycarbonyl (Z), p-methoxybenzyloxycarbonyl, and p-nitrobenzyloxycarbonyl; aralkyl groups including, as representative examples, benzyl (Bn) and triphenylmethyl (Tr); aroyl groups including as a representative example, benzoyl (Bz); aralkylcarbonyl groups including as a representative example, benzylcarbonyl; sulfonyl groups including, as representative examples, methanesulfonyl (Ms), p-toluenesulfonyl (Ts), 2,4-dinitrobenzenesulfonyl (Nos), and benzenesulfonyl (Bs); 2-(trimethylsilyl)ethoxymethyl (SEM) groups; phthaloyl (Pht) groups; and N,N-dimethylaminomethylene groups.

Examples of the protective groups for the carboxy group (—COOH group) that can be used herein include: alkyl groups including, as representative examples, methyl, ethyl, n-propyl, isopropyl, n-butyl, and tert-butyl; alkenyl groups including, as a representative example, allyl; aryl groups including, as a representative example, phenyl (Ph); aralkyl groups including, as representative examples, benzyl (Bn) and triphenylmethyl (Tr); and silyl groups including, as representative examples, trimethylsilyl (TMS), triethylsilyl (TES), t-butyldimethylsilyl (TBDMS), and t-butyldiphenylsilyl (TBDPS).

Examples of the protective groups for the thiol group (—SH group) that can be used herein include: alkyl group including, as representative examples, methyl, ethyl, n-propyl, isopropyl, n-butyl, and tert-butyl; aralkyl groups including, as representative examples, benzyl (Bn) and triphenylmethyl (Tr); alkanoyl groups including, as representative examples, acetyl (Ac), ethylcarbonyl, and pivaloyl (Piv); and aroyl groups including, as a representative example, benzoyl (Bz).

A method for introducing and/or removing such protective groups can be carried out, as appropriate, depending on the type of a group to be protected or a protective group. Introduction and/or removal of protective groups can be carried out according to the method described, for example, in Greene et al., "Protective Groups in Organic Synthesis, $4^{th}$ edition, 2007, John Wiley & Sons."

When the protective groups are acyl type protective groups such as: alkanoyl groups including, as representative examples, acetyl (Ac), ethylcarbonyl, and pivaloyl (Piv); alkoxylcarbonyl groups including, as representative examples, methoxycarbonyl, ethoxycarbonyl, t-butoxycarbonyl (Boc); and aroyl groups including, as a representative example, benzoyl (Bz), as a method for removing the protective groups, the protected group is hydrolyzed using a suitable base such as an alkali metal hydroxide including lithium hydroxide, sodium hydroxide, or potassium hydroxide, so that the protective group can be removed.

When the protective groups are: alkoxylalkyl type protective groups including, as representative examples, methoxymethyl (MOM), methoxyethoxymethyl (MEM), and tetrahydropyranyl (THP); alkoxylcarbonyl type protective groups including, as a representative example, t-butoxycarbonyl (Boc); aralkyloxycarbonyl type protective groups including, as representative examples, benzyloxycarbonyl (Z) and p-methoxybenzyloxycarbonyl; or silyl type protective groups including, as representative examples, trimethylsilyl (TMS), triethylsilyl (TES), and t-butyldimethylsilyl (TBDMS), suitable acids such as acetic acid, hydrochloric acid, hydrobromic acid, sulfuric acid, phosphoric acid, trifluoroacetic acid, or trifluoromethanesulfonic acid, or a combination of these acids are used to remove the protective groups.

Moreover, the above described silyl type protective groups can also be removed using suitable fluoride ion ($F^-$) generation reagents, such as tetrabutyl ammonium fluoride or hydrogen fluoride.

Aralkyloxycarbonyl groups including, as representative examples, benzyloxycarbonyl (Z), p-methoxybenzyloxycarbonyl, and p-nitrobenzyloxycarbonyl, and aralkyl groups including, as a representative example, benzyl (Bn), can be removed by hydrolysis using, for example, a palladium-carbon (Pd—C) catalyst.

Furthermore, the above described benzyl group can also be removed by Birch reduction using metallic sodium in liquid ammonia.

The triphenylmethyl (Tr) group can be removed by using a suitable acid such as acetic acid, hydrochloric acid, hydrobromic acid, sulfuric acid, phosphoric acid, trifluoroacetic acid, or trifluoromethanesulfonic acid, or using a combination of these acids. Further, the protective group can also be removed by Birch reduction using metallic sodium or metallic lithium in liquid ammonia, or by hydrolysis using a palladium carbon catalyst.

The sulfonyl (—$SO_2$—) group can be removed, for example, by performing one-electron reduction using Na/anthracene or Na/naphthalene at a low temperature, or by performing Birch reduction using metallic sodium or metallic lithium in liquid ammonia.

Moreover, among the sulfonyl groups, a 2-nitrobenzenesulfonyl (Ns) group can be removed under mild conditions in which, for example, it is reacted with thiol in the presence of a basic reagent such as potassium carbonate or triethylamine.

The above described methods for removing protective groups are provided for illustrative purpose only. Deprotection can be carried out, for example, by applying the method described in Greene et al., "Protective Groups in Organic Synthesis, 4th edition, 2007, John Wiley & Sons," or various types of published study papers.

Reaction conditions applied to the below-mentioned production methods are determined as follows, unless otherwise specified. That is, the reaction temperature is in a range from −78° C. to a temperature at which a solvent is refluxed. When the temperature is not particularly described, it is room temperature (0° C. to 35° C.). The reaction time is a period of time in which the reaction sufficiently progresses.

Moreover, the reaction in each step of the production method can be carried out in the absence of a solvent, or after raw material compounds have been dissolved or suspended in a suitable solvent that is irrelevant to the reaction. Specific examples of such a solvent that is irrelevant to the reaction include: water; saturated hydrocarbon solvents such as cyclohexane and hexane; aromatic hydrocarbon solvents such as benzene, chlorobenzene, toluene, and xylene; alcohol solvents such as methanol, ethanol, 1-propanol, 2-propanol, tert-butyl alcohol, and 2-methoxyethanol; polar amide solvents such as N,N-dimethylformamide, N,N-dimethylacetamide, hexamethylphosphoric triamide, and 1,3-dimethyl-2-imidazolidinone; sulfoxide solvents such as dimethyl sulfoxide; nitrile solvents such as acetonitrile and propionitrile; ether solvents such as diethyl ether, diisopropyl ether, diphenyl ether, tetrahydrofuran, 1,4-dioxane, and 1,2-dimethoxyethane; ester solvents such as methyl acetate, ethyl acetate, and butyl acetate; ketone solvents such as acetone and methyl ethyl ketone; halogenated hydrocarbon solvents such as dichloromethane, chloroform, carbon tetrachloride, and 1,2-dichloroethane; basic solvents such as triethylamine, N,N-diisopropylethylamine, pyridine, and lutidine; acid anhydrides such as acetic anhydride; organic acids such as formic acid, acetic acid, propionic acid, trifluoroacetic acid, and methanesulfonic acid; and inorganic acids such as hydrochloric acid and sulfuric acid. A single type of solvent may be used alone, or two or more types of solvents may appropriately be selected depending on reaction conditions, and may be then mixed at an appropriate ratio before use.

Specific examples of the base (or deoxidizer) used in the method for producing the compound in the present invention include inorganic bases such as lithium hydroxide, sodium hydroxide, potassium hydroxide, magnesium hydroxide, lithium carbonate, sodium carbonate, potassium carbonate, cesium carbonate, calcium carbonate, and sodium hydrogen carbonate; organic bases such as triethylamine, N,N-diisopropylethylamine, tributylamine, cyclohexyldimethylamine, pyridine, lutidine, 4-dimethylaminopyridine(DMAP), N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, and imidazole; metal alkoxides such as sodium methoxide, sodium ethoxide, potassium tert-butoxide, and sodium tert-butoxide; alkali metal hydrides such as sodium hydride and potassium hydride; metal amides such as sodium amide, lithium diisopropyl amide, and lithium hexamethyl disilazide; and organic lithium reagents such as methyl lithium, n-butyl lithium, sec-butyl lithium, and tert-butyl lithium. Moreover, specific examples of the acid or acid catalyst used in the method for producing the compound in the present invention include: inorganic acids such as hydrochloric acid, sulfuric acid, nitric acid, hydrobromic acid, and phosphoric acid; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, and 10-camphorsulfonic acid; and Lewis acids such as a boron trifluoride ether complex, zinc iodide, anhydrous aluminum chloride, anhydrous zinc chloride, and anhydrous iron chloride. However, examples are not necessarily limited thereto.

The salt of the formula (I) can be produced according to a known method. For example, when the compound of the formula (I) is a basic compound, the salt thereof can be produced by adding an inorganic acid (mineral acid) such as hydrochloric acid, hydrobromic acid, nitric acid, sulfuric acid, or phosphoric acid, or an organic acid such as formic acid, acetic acid, trifluoroacetic acid, phthalic acid, fumaric acid, acid, oxalic acid, tartaric acid, maleic acid, citric acid, succinic acid, malic acid, methanesulfonic acid, benzenesulfonic acid, or p-toluenesulfonic acid, to the compound. When the compound of the formula (I) is an acidic compound, the salt thereof can be produced by adding an organic base such as ammonia, trimethylamine, triethylamine, pyridine, picoline, 2,6-lutidine, ethanolamine, diethanolamine, triethanolamine, cyclohexylamine, dicyclohexylamine, N,N-diisopropylethylamine, N,N'-dibenzylethylenediamine, or N,N-dialkylaniline, or an inorganic base such as lithium carbonate, sodium carbonate, potassium carbonate, cesium carbonate, lithium hydroxide, sodium hydroxide, potassium hydroxide, or sodium hydrogen carbonate, to the compound.

The compound represented by the formula (I) of the present invention can be obtained by a condensation reaction of a carboxylic acid derivative represented by a formula (CA) [wherein it is a carboxylic acid of a formula (CA-1), when L'=OH; it is a carboxylate of a formula (CA-2), when L'=OM; and it is an acid halide of a formula (CA-3), when L'=X] with amine represented by a formula (AM).

[Formula 105]

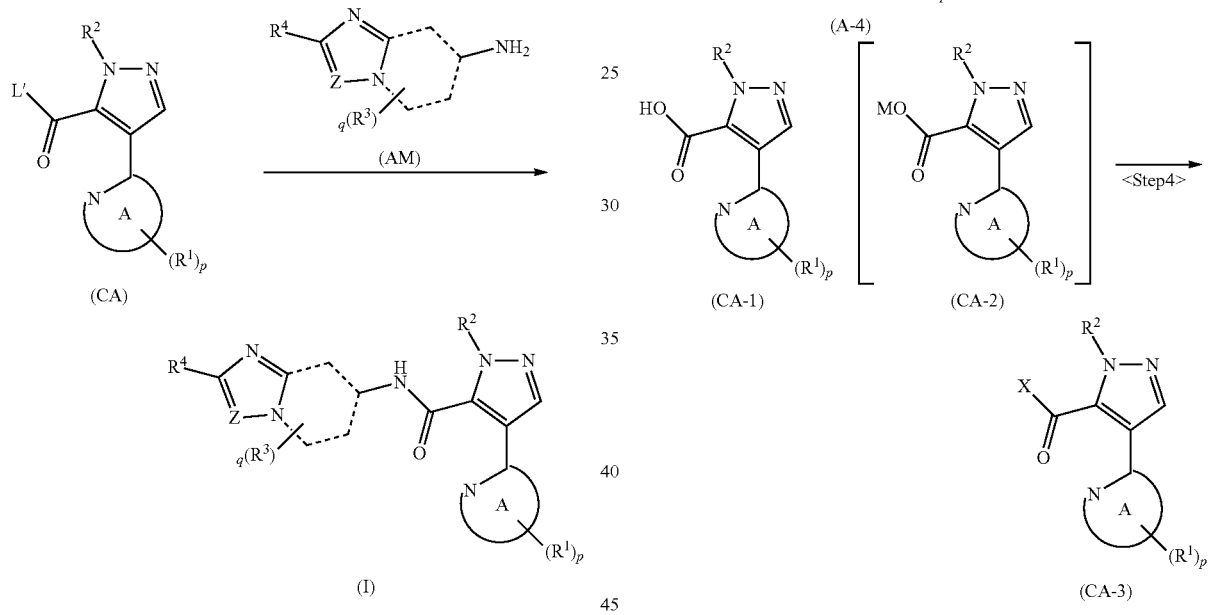

Hereinafter, methods for producing the compounds represented by the formula (CA), the formula (AM), and the formula (I) will be described.

<Production Method A>

Method for producing a carboxylic acid derivative represented by the formula (CA) [wherein it is a carboxylic acid of the formula (CA-1), when L'=OH; it is a carboxylate of the formula (CA-2), when L'=OM; and it is an acid halide of the formula (CA-3), when L'=X]:

[Formula 106]

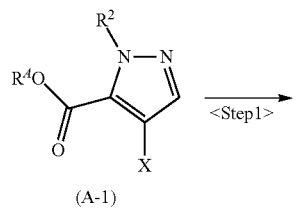

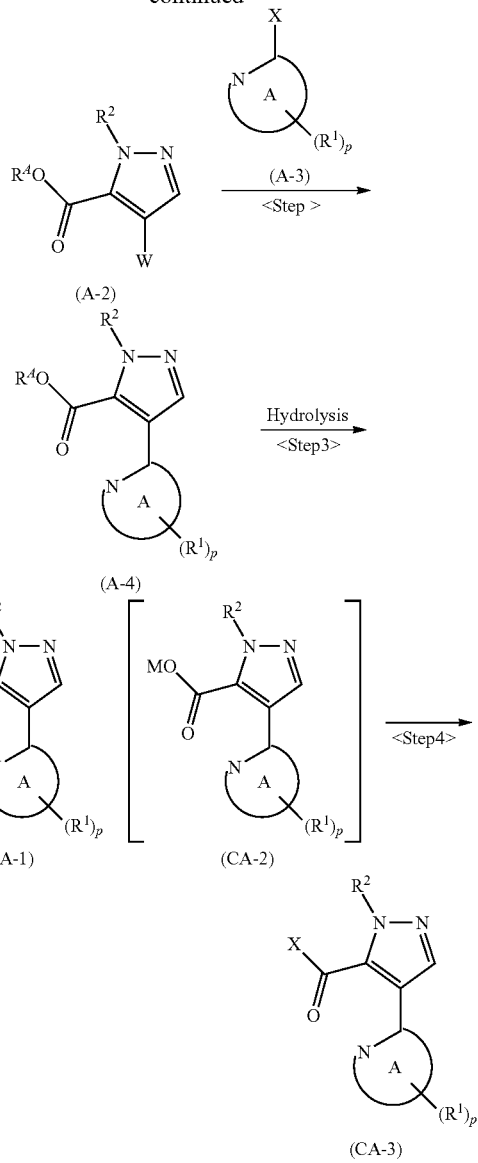

<Step 1>
<Case of W=Boronic Acid Ester>

Using the compound represented by the formula (A-1), a reaction is carried out according to a known method, for example, the method described in "The Journal of Organic Chemistry, 60, 7508-2665, 1995," in a temperature range from 0° C. to a temperature at which a solvent is refluxed, using a solvent irrelevant to the reaction, such as toluene, N,N-dimethylformamide, dimethyl sulfoxide, or 1,4-dioxane, or using a mixed solvent thereof, in the presence of a diboron ester such as bis(pinacolato)diboron or bis(neopentylglycolato)diboron, in the presence of a palladium catalyst such as palladium acetate (II), tetrakis(triphenylphosphine) palladium, tris(dibenzylideneacetone)dipalladium, [1,1'-bis(diphenylphosphino)ferrocene]dichloropalladium(II), or a [1,1'-bis(diphenylphosphino)ferrocene]dichloropalladium (II)-dichloromethane complex, in the presence or absence of a phosphine reagent such as triphenylphosphine, tris(tert-butyl)phosphine, tris(o-tolyl)phosphine, or 2-dicyclohexylphosphino-2',6'-dimethoxybiphenyl, and an organic or inorganic base such as triethylamine, N,N-diisopropylethylamine, potassium carbonate, or potassium acetate, or in the presence or absence of tetramethylammonium chloride, tetrabutylammonium chloride, etc., which is used instead of the phosphine reagent, so as to produce the boronic acid ester represented by the formula (A-2).

<Case of W=Boronic Acid>

Using the compound represented by the formula (A-1), according to a known method, for example, the method described in "Chemische Berichte, 42, 3090, 1909," trialkyl borate such as trimethyl borate or triisopropyl borate is added to a solvent irrelevant to the reaction, such as toluene, tetrahydrofuran, or 1,4-dioxane, or to a mixed solvent thereof, in the presence of alkyl lithium such as n-butyllithium or sec-butyllithium, a Grignard reagent such as isopropyl magnesium chloride, or metallic magnesium, and a reaction is then carried out in a temperature range from $-78°$ C. to room temperature. Thereafter, an acid such as hydrochloric acid or sulfuric acid is added to the reaction solution, and the reaction is then carried out in a temperature range from $0°$ C. to a temperature at which a solvent is refluxed, so as to produce the boronic acid represented by the formula (A-2).

<Case of W=Trifluoroborate>

Using the boronic acid ester or boronic acid represented by the formula (A-1), a reaction is carried out according to a known method, for example, the method described in "Chemical Reviews, 108, 288-325, 2008," in a temperature range from $0°$ C. to a temperature at which a solvent is refluxed, using a solvent irrelevant to the reaction, such as methanol, ethanol, or water, or using a mixed solvent thereof, in the presence of potassium hydrogen difluoride ($KHF_2$), so as to produce the trifluoroborate represented by the formula (A-2).

<Case of W=N-Methyliminodiacetic Acid (MIDA) Borate>

Using the boronic acid represented by the formula (A-1), a reaction is carried out according to a known method, for example, the method described in "Journal of Organometallic Chemistry, 307 (1), pp. 1-6, 1986," in a temperature range from $0°$ C. to a temperature at which a solvent is refluxed, using a solvent irrelevant to the reaction, such as benzene, toluene, xylene, or dimethyl sulfoxide, or using a mixed solvent thereof, in the presence of N-methyliminodiacetic acid (MIDA), so as to produce an N-methyliminodiacetic acid (MIDA) borate represented by the formula (A-2).

<Step 2>

Using the compound represented by the formula (A-2) obtained in <Production Method A> <Step 1> and the halogenated heteroaryl derivative represented by the formula (A-3), a reaction is carried out according to a known method, for example, the methods described in "*Jikken Kagaku Koza,* 5$^{th}$ edition, 18, Organic Compound Synthesis VI-Organic Synthesis using Metal-, pp. 327-352, 2004, Maruzen," and "Journal of Medicinal Chemistry, 48 (20), pp. 6326-6339, 2005," in a temperature range from $0°$ C. to a temperature at which a solvent is refluxed, using a solvent irrelevant to the reaction, such as toluene, xylene, N,N-dimethylformamide, N,N-dimethylacetamide, dimethoxyethane, acetonitrile (acetonitrile/water), 1,4-dioxane (1,4-dioxane/water), or tetrahydrofuran (tetrahydrofuran/water), or using a mixed solvent thereof, in the presence of a palladium catalyst such as palladium acetate (II) ($Pd(OAc)_2$), tetrakis(triphenyl phosphine) palladium(Pd ($PPh_3)_4$), tris(dibenzylidene acetone)dipalladium (($dba)_3Pd_2$), bis(dibenzylidene acetone)palladium (($dba)_2Pd$), or [1,1'-bis(diphenyl phosphino)ferrocene]dichloropalladium(II)($Pd(dppf)Cl_2$), a phosphine reagent such as triphenyl phosphine, tris(tert-butyl)phosphine, tris(o-tolyl)phosphine, 2-dicyclohexylphosphino-2',6'-dimethoxybiphenyl, or 2-dicyclohexylphosphino-2',4',6'-triisopropylbiphenyl, and an organic or inorganic base such as triethylamine, N,N-diisopropylethylamine, potassium phosphate, potassium carbonate, or cesium carbonate, so as to produce a compound represented by the formula (A-4). Otherwise, using tetramethylammonium chloride, tetrabutylammonium chloride, or the like, instead of the phosphine reagent, the compound represented by the formula (A-4) can be produced by the same method as described above.

<Step 3>

<Case of $R^A=C_{1-6}$ Alkyl Group (e.g. Methyl and Ethyl Group) or $C_{6-14}$ Aryl Group (e.g. Phenyl Group)>

Using the compound represented by the formula (A-4) obtained in <Production Method A> <Step 2>, a reaction is carried out according to a known method, for example, the method described in "*Jikken Kagaku Koza,* 4$^{th}$ edition, 22, Organic Synthesis IV, Acid, Amino Acid, and Peptide, pp. 1-43, 1992, Maruzen," in a temperature range from $0°$ C. to a temperature at which a solvent is refluxed, using a solvent inactive to the reaction, such as water, methanol, ethanol, 2-propanol, N,N-dimethylformamide, 1,4-dioxane, or tetrahydrofuran, or using a mixed solvent thereof, in the presence of a base such as lithium hydroxide, sodium hydroxide, potassium hydroxide, lithium carbonate, sodium carbonate, or potassium carbonate, so as to produce a compound represented by the formula (CA-1) or the formula (CA-2), depending on a difference in a post-treatment step after completion of the reaction.

<Case of $R^A$=Tert-Butyl Group>

Using the compound represented by the formula (A-4) obtained in <Production Method A> <Step 2>, the compound is reacted with an acid such as hydrochloric acid or trifluoroacetic acid to produce the compound represented by the formula (CA-1).

<Case of $R^A=C_{7-20}$ Aralkyl Group (e.g. Benzyl Group)>

Using the compound represented by the formula (A-4) obtained in <Production Method A> <Step 2>, a reaction is carried out according to a known method, for example, the method described in "*Jikken Kagaku Koza,* 4$^{th}$ edition, 26, Organic Synthesis VIII, Asymmetric Synthesis, Reduction, Sugar, and Labeling Compound, pp. 159-266, 1992, Maruzen," in a temperature range from $0°$ C. to a temperature at which a solvent is refluxed, using a solvent irrelevant to the reaction, such as an alcohol solvent such as methanol, ethanol, or 2-propanol, or an ether solvent such as diethyl ether, tetrahydrofuran, 1,2-dimethoxyethane, or 1,4-dioxane, or a polar solvent such as ethyl acetate or methyl acetate, or using a mixed solvent thereof, in the presence of a catalyst such as palladium-carbon (Pd—C), Raney nickel (Raney-Ni), or platinum oxide ($Pt_2O$), in a hydrogen gas atmosphere, so as to produce the compound represented by the formula (CA-1).

<Step 4>

Using the compound represented by the formula (CA-2) obtained in <Production Method A> <Step 3>, a reaction is carried out according to a known method, for example, the method described in "Journal of the American Chemical Society, 109 (24), pp. 7488-7494, 1987," in a temperature range from $0°$ C. to a temperature at which a solvent is refluxed, using a halogenating agent such as thionyl chloride, oxalyl chloride, phosphoryl chloride, sulfuryl chloride, phosphorus trichloride, phosphorus pentachloride, or phosphorus tribromide, and using a solvent inactive to the reaction, such as dioxane, tetrahydrofuran, benzene, toluene, dichloromethane, 1,2-dichloroethane, or chloroform, or using a mixed solvent thereof, in the presence or absence of a base such as triethylamine, N,N-diisopropylethylamine, or N,N-dimethylaminopyridine, so as to produce the compound represented by the formula (CA-3).

<Production Method B>

Methods for producing amines represented by a formula (AM-1) and a formula (AM-2): Case in which a fused ring B is an imidazo[1,2-a]pyridine ring (formula (AM-1)) or a 5,6,7,8-tetrahydroimidazo[1,2-a]pyridine ring (formula (AM-2)):

[Formula 107]

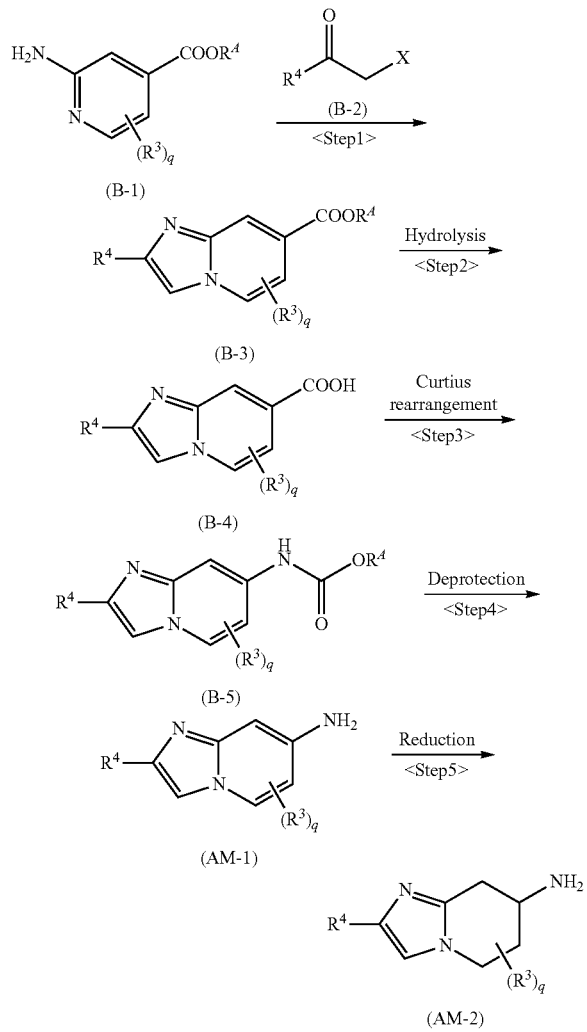

<Step 1>

Using the compound represented by the formula (B-1) and the compound represented by the formula (B-2), a reaction is carried out according to a known method, for example, the method described in "European Journal of Medicinal Chemistry, 52, pp. 137-150, 2012," in a temperature range from 0° C. to a temperature at which a solvent is refluxed, using a solvent inactive to the reaction, such as methanol, ethanol, or 2-propanol, or using a mixed solvent thereof, so as to produce a compound represented by the formula (B-3).

<Step 2>

Using the compound represented by the formula (B-3) obtained in <Production Method B> <Step 1>, a reaction is carried out according to <Production Method A> <Step 3>, so as to produce the compound represented by the formula (B-4).

<Step 3>

Using the compound represented by the formula (B-4) obtained in <Production Method B> <Step 2>, a reaction is carried out according to a known method, for example, the method described in "Strategic Applications of Named Reactions in Organic Synthesis, Elsevier Academic Press, 2005, pp. 116-117, Curtius Rearrangement," in a temperature range from 0° C. to a temperature at which a solvent is refluxed, using a solvent inactive to the reaction, such as toluene or benzene, or using a mixed solvent thereof, and using diphenylphosphoryl azide (DPPA), in the presence of a base such as triethylamine. Thereafter, the resulting compound is reacted with alcohol such as methanol, ethanol, tert-butyl alcohol, or benzyl alcohol, so as to produce the compound represented by the formula (B-5).

<Step 4>

Using the compound represented by the formula (B-5) obtained in <Production Method B> <Step 3>, the compound is reacted with a protective group (—COOR$^A$) by a method that depends on the type of the protective group, according to a known method, for example, the method described in "Protective Groups in Organic Synthesis 4$^{th}$ edition, 2007, John Wiley & Sons, Greene et al.," so as to produce the compound represented by the formula (AM-1), from which the —COOR$^A$ group is removed.

<Step 5>

Using the compound represented by the formula (AM-1) obtained in <Production Method B> <Step 4>, a reaction is carried out according to a known method, for example, the method described in "Journal of Medicinal Chemistry, 48 (10), pp. 3586-3640, 2005," in a temperature range from 0° C. to a temperature at which a solvent is refluxed, using a solvent irrelevant to the reaction, such as an alcohol solvent such as methanol, ethanol, or 2-propanol, or an ether solvent such as diethyl ether, tetrahydrofuran, 1,2-dimethoxyethane, or 1,4-dioxane, or a polar solvent such as ethyl acetate or methyl acetate, or using a mixed solvent thereof, in the presence of concentrated hydrochloric acid, in the presence of a catalyst such as platinum oxide (Pt$_2$O), and in a hydrogen gas atmosphere, so as to produce the compound represented by the formula (AM-2).

<Production Method C>

Alternative method for producing amine represented by the formula (AM-2) [the case of R$^4$=C$_{6-14}$ aryl group] and method for producing amine represented by the formula (AM-3):

[Formula 108]

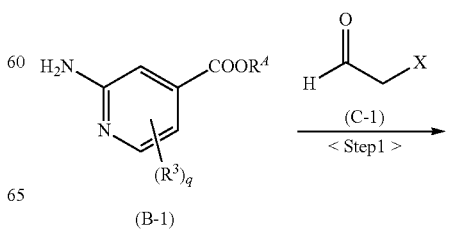

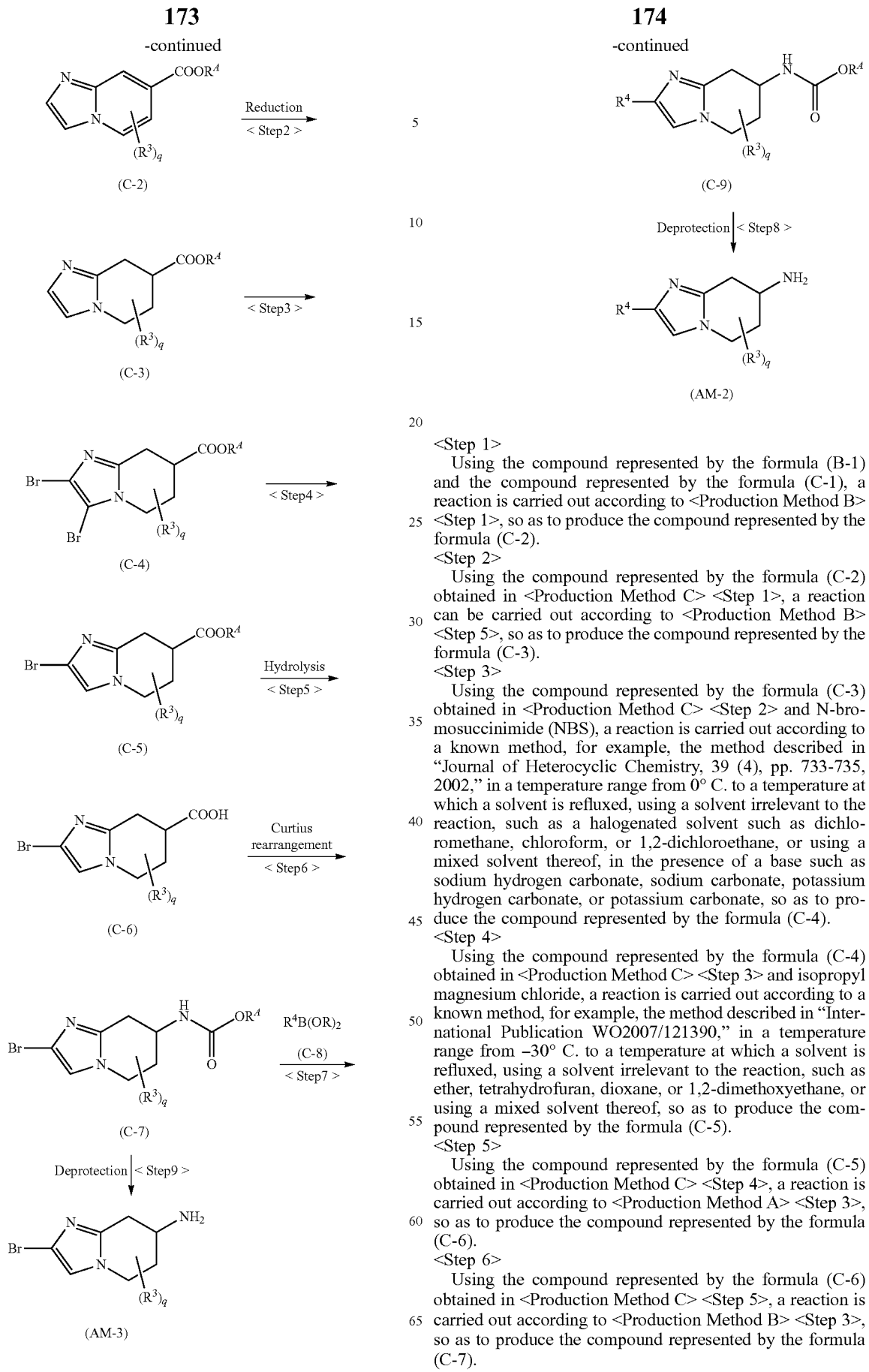

<Step 1>
Using the compound represented by the formula (B-1) and the compound represented by the formula (C-1), a reaction is carried out according to <Production Method B> <Step 1>, so as to produce the compound represented by the formula (C-2).

<Step 2>
Using the compound represented by the formula (C-2) obtained in <Production Method C> <Step 1>, a reaction can be carried out according to <Production Method B> <Step 5>, so as to produce the compound represented by the formula (C-3).

<Step 3>
Using the compound represented by the formula (C-3) obtained in <Production Method C> <Step 2> and N-bromosuccinimide (NBS), a reaction is carried out according to a known method, for example, the method described in "Journal of Heterocyclic Chemistry, 39 (4), pp. 733-735, 2002," in a temperature range from 0° C. to a temperature at which a solvent is refluxed, using a solvent irrelevant to the reaction, such as a halogenated solvent such as dichloromethane, chloroform, or 1,2-dichloroethane, or using a mixed solvent thereof, in the presence of a base such as sodium hydrogen carbonate, sodium carbonate, potassium hydrogen carbonate, or potassium carbonate, so as to produce the compound represented by the formula (C-4).

<Step 4>
Using the compound represented by the formula (C-4) obtained in <Production Method C> <Step 3> and isopropyl magnesium chloride, a reaction is carried out according to a known method, for example, the method described in "International Publication WO2007/121390," in a temperature range from −30° C. to a temperature at which a solvent is refluxed, using a solvent irrelevant to the reaction, such as ether, tetrahydrofuran, dioxane, or 1,2-dimethoxyethane, or using a mixed solvent thereof, so as to produce the compound represented by the formula (C-5).

<Step 5>
Using the compound represented by the formula (C-5) obtained in <Production Method C> <Step 4>, a reaction is carried out according to <Production Method A> <Step 3>, so as to produce the compound represented by the formula (C-6).

<Step 6>
Using the compound represented by the formula (C-6) obtained in <Production Method C> <Step 5>, a reaction is carried out according to <Production Method B> <Step 3>, so as to produce the compound represented by the formula (C-7).

<Step 7>
Using the compound represented by the formula (C-7) obtained in <Production Method C> <Step 6> and the boranic acid derivative represented by the formula (C-8), a reaction is carried out according to <Production Method A> <Step 2>, so as to produce the compound represented by the formula (C-9).
<Step 8>
Using the compound represented by the formula (C-9) obtained in <Production Method C> <Step 7>, a reaction is carried out according to <Production Method B> <Step 4>, so as to produce the compound represented by the formula (AM-2).
<Step 9>
Using the compound represented by the formula (C-7) obtained in <Production Method C> <Step 6>, a reaction is carried out according to <Production Method B> <Step 4>, so as to produce the compound represented by the formula (AM-3).
<Production Method D>
Methods for producing amines represented by a formula (AM-4) and a formula (AM-5): Case in which a fused ring B is a triazolo[1,2-a]pyridine ring (formula (AM-4)) or a 5,6,7,8-tetrahydrotriazolo[1,2-a]pyridine ring (formula (AM-5)):

<Step 1>
Using the compound represented by the formula (B-1) and the thioisocyanate compound represented by the formula (D-1), a reaction is carried out according to a known method, for example, the method described in "The Journal of Organic Chemistry, 65 (5), pp. 1566-1568, 2000," in a temperature range from 0° C. to a temperature at which a solvent is refluxed, using a solvent irrelevant to the reaction, such as ether, tetrahydrofuran, dioxane, or 1,2-dimethoxyethane, or using a mixed solvent thereof, so as to produce the compound represented by the formula (D-2).
<Step 2>
Using the compound represented by the formula (D-2) obtained in <Production Method D> <Step 1> and hydroxylamine hydrochloride, a reaction is carried out according to a known method, for example, the method described in "Synthesis, (11), pp. 1649-1652, 2003," in a temperature range from 0° C. to a temperature at which a solvent is refluxed, using a solvent irrelevant to the reaction, such as methanol, ethanol, or 2-propanol, or using a mixed solvent thereof, so as to produce the compound represented by the formula (D-3).
<Step 3>
Using the compound represented by the formula (D-3) obtained in <Production Method D> <Step 2>, isoamyl

[Formula 109]

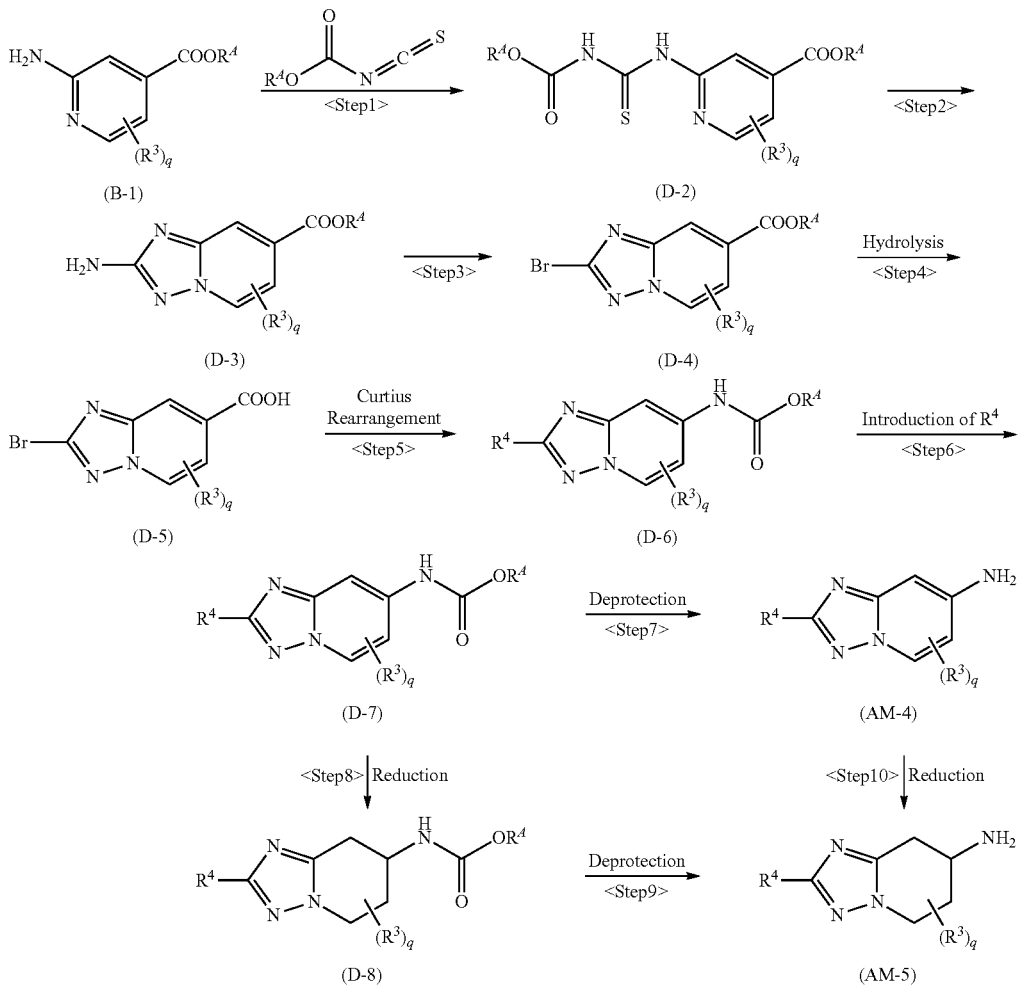

nitrile, and copper bromide (CuBr$_2$), a reaction is carried out according to a known method, for example, the method described in "The Journal of Organic Chemistry, 42 (14), pp. 2426-2431, 1977," in a temperature range from 0° C. to a temperature at which a solvent is refluxed, using a solvent irrelevant to the reaction, such as acetonitrile, or using a mixed solvent thereof, so as to produce the compound represented by the formula (D-4).

<Step 4>

Using the compound represented by the formula (D-4) obtained in <Production Method D> <Step 3>, a reaction is carried out according to <Production Method A> <Step 3>, so as to produce the compound represented by the formula (D-5).

<Step 5>

Using the compound represented by the formula (D-5) obtained in <Production Method D> <Step 4>, a reaction is carried out according to <Production Method B> <Step 3>, so as to produce the compound represented by the formula (D-6).

<Step 6>

<Case of R$^4$=C$_{6-14}$ Aryl Group or 5- to 7-Membered Monocyclic Heteroaryl Group>

Using the compound represented by the formula (D-6) obtained in <Production Method D> <Step 5> and the boranic acid derivative represented by the formula (C-8), a reaction is carried out according to <Production Method A> <Step 2>, so as to produce the compound represented by the formula (D-7).

<Case of R$^4$=3- to 14-Membered Non-Aromatic Heterocyclic Group>

Using the compound represented by the formula (D-6) obtained in <Production Method D> <Step 5> and a non-aromatic heterocyclic compound (e.g. a 3- to 8-membered ring non-aromatic heterocyclic compound such as aziridine, pyrrolidine, piperazine, piperidine, or morpholine), a reaction is carried out in the absence of a solvent at an outside temperature of approximately 100° C. to 150° C., so as to produce the compound represented by the formula (D-7).

Alternatively, using the compound represented by the formula (D-6) obtained in <Production Method D> <Step 5> and a non-aromatic heterocyclic compound (e.g. a 3- to 8-membered ring non-aromatic heterocyclic compound such as aziridine, pyrrolidine, piperazine, piperidine, or morpholine), a reaction is carried out according to a known method, for example, the method described in "Organic Synthesis, 78, p. 23, 2002," in a temperature range from 0° C. to a temperature at which a solvent is refluxed, using a solvent irrelevant to the reaction, such as toluene, xylene, N,N-dimethylformamide, N,N-dimethylacetamide, dimethoxyethane, acetonitrile (acetonitrile/water), dioxane (dioxane/water), or tetrahydrofuran (tetrahydrofuran/water), or using a mixed solvent thereof, in the presence of a Pd catalyst such as tris(dibenzylideneacetone)dipalladium ((dba)$_3$Pd$_2$), a phosphine reagent such as 4,5'-bis(diphenylphosphino)-9,9'-dimethylxanthene (XANTPHOS), and an organic or inorganic base such as triethylamine, N,N-diisopropylethylamine, potassium phosphate, potassium carbonate, or cesium carbonate, so as to produce the compound represented by the formula (D-7).

<Step 7>

Using the compound represented by the formula (D-7) obtained in <Production Method D> <Step 6>, a reaction is carried out according to <Production Method B> <Step 4>, so as to produce the compound represented by the formula (AM-4).

<Step 8>

Using the compound represented by the formula (D-7) obtained in <Production Method D> <Step 6>, a reaction is carried out according to <Production Method B> <Step 5>, so as to produce the compound represented by the formula (D-8).

<Step 9>

Using the compound represented by the formula (D-8) obtained in <Production Method D> <Step 8>, a reaction is carried out according to <Production Method B> <Step 4>, so as to produce the compound represented by the formula (AM-5).

<Step 10>

Using the compound represented by the formula (AM-4) obtained in <Production Method D> <Step 7>, a reaction is carried out according to <Production Method B> <Step 5>, so as to produce the compound represented by the formula (AM-5).

<Production Method E>

Alternative method for producing compounds represented by formula (D-7) and formula (D-8) in <Production Method D> (wherein R$^4$≠halogen atom).

[Formula 110]

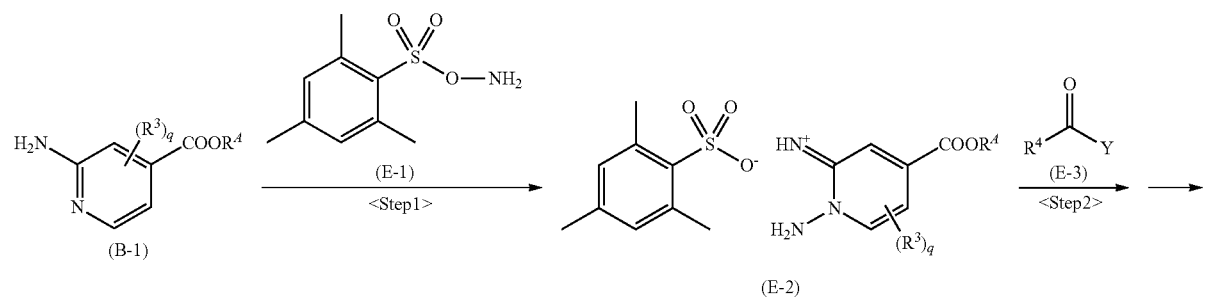

-continued

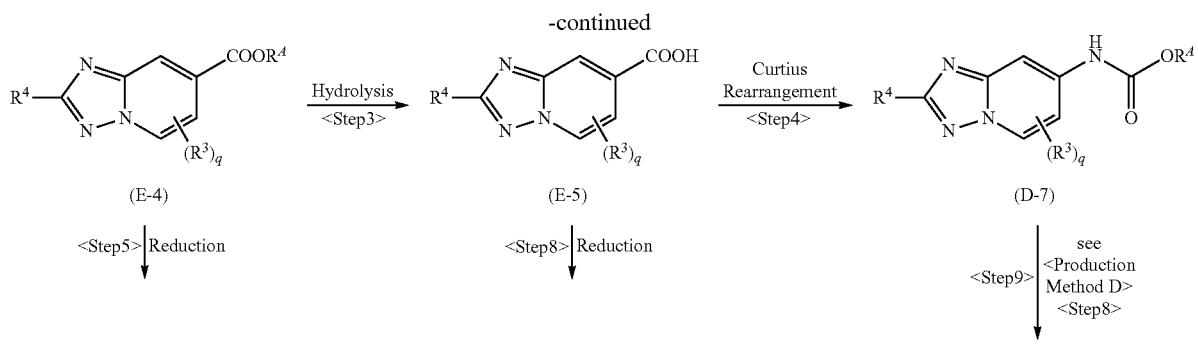

(E-4)     (E-5)     (D-7)

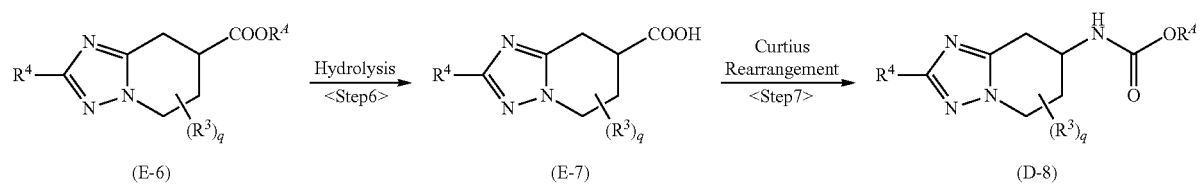

(E-6)     (E-7)     (D-8)

<Step 1>

Using the compound represented by the formula (B-1) and the compound represented by the formula (E-1), a reaction is carried out according to a known method, for example, the method described in "Journal of Heterocyclic Chemistry, 12 (1), pp. 107-110, 1975," in a temperature range from 0° C. to a temperature at which a solvent is refluxed, using a solvent irrelevant to the reaction, such as methylene chloride or chloroform, or using a mixed solvent thereof, so as to produce the compound represented by the formula (E-2).

<Step 2>

Using the compound represented by the formula (E-2) obtained in <Production Method E> <Step 1> and the compound represented by the formula (E-3) (wherein Y=H, OH, $OR^A$, or Cl), a reaction is carried out according to a known method, for example, the method described in "Journal of Heterocyclic Chemistry, 12 (1), pp. 107-110, 1975." In the case of <Y=$OR^A$, H, or Cl>, the reaction is carried out in a temperature range from 0° C. to a temperature at which a solvent is refluxed, using a solvent irrelevant to the reaction that is selected from among methylene chloride, chloroform, acetonitrile, methanol, N-methylpyrrolidone and the like, or using a mixed solvent thereof, in the presence of a base such as sodium hydroxide or sodium methoxide, so as to produce the compound represented by the formula (E-4). In the case of <Y=OH>, the reaction is carried out in a temperature range from 0° C. to a temperature at which a solvent is refluxed, in a solvent irrelevant to the reaction, such as a halogenated solvent such as dichloromethane or chloroform, an ether solvent such as diethyl ether or tetrahydrofuran, an aromatic hydrocarbon solvent such as toluene or benzene, a polar solvent such as N,N-dimethylformamide, or an alcohol solvent such as methanol, ethanol, or 2-propanol, in the presence of a condenser such as 1,3-dicyclohexylcarbodiimide (DCC), 1-ethyl-3-(3'-dimethylaminopropyl)carbodiimide hydrochloride (WSC.HCl), 1-hydroxybenzotriazole (HOBT), benzotriazol-1-yloxytris(dimethylamino)phosphonium hexafluorophosphate (BOP reagent), bis(2-oxo-3-oxazolidinyl)phosphinic chloride (BOP—Cl), 2-chloro-1,3-dimethylimidazolinium hexafluorophosphate (CIP), or 4-(4,6-dimethoxy-1,3,5-triazin-2-yl)-4-methylmorpholinium chloride (DMTMM), and in the presence or absence of a base such as triethylamine or pyridine, so as to produce the compound represented by the formula (E-4).

<Step 3>

Using the compound represented by the formula (E-4) obtained in <Production Method E> <Step 2>, a reaction is carried out according to <Production Method A> <Step 3>, so as to produce the compound represented by the formula (E-5).

<Step 4>

Using the compound represented by the formula (E-5) obtained in <Production Method E> <Step 3>, a reaction is carried out according to <Production Method B> <Step 3>, so as to produce the compound represented by the formula (D-7).

<Step 5>

Using the compound represented by the formula (E-4) obtained in <Production Method E> <Step 2>, a reaction is carried out according to <Production Method B> <Step 5>, so as to produce the compound represented by the formula (E-6).

<Step 6>

Using the compound represented by the formula (E-6) obtained in <Production Method E> <Step 5>, a reaction is carried out according to <Production Method A> <Step 3>, so as to produce the compound represented by the formula (E-7).

<Step 7>

Using the compound represented by the formula (E-7) obtained in <Production Method E> <Step 6>, a reaction is carried out according to <Production Method B> <Step 3>, so as to produce the compound represented by the formula (D-8).

<Step 8>

Using the compound represented by the formula (E-5) obtained in <Production Method E> <Step 3>, a reaction is carried out according to <Production Method B> <Step 5>, so as to produce the compound represented by the formula (E-7).

<Step 9>

Using the compound represented by the formula (D-7) obtained in <Production Method E> <Step 4>, the same reaction as that in <Production Method D> <Step 8> is carried out, so as to produce the compound represented by the formula (D-8).

<Production Method F>

Method for producing amine represented by formula (AM-6): the synthesis of an imidazolo[1,2-a]pyridine ring (AM-6) in a case in which Z=CR$^5$ and R$^5$=a halogen atom in the fused ring B (wherein R$^4$≠a halogen atom):

[Formula 111]

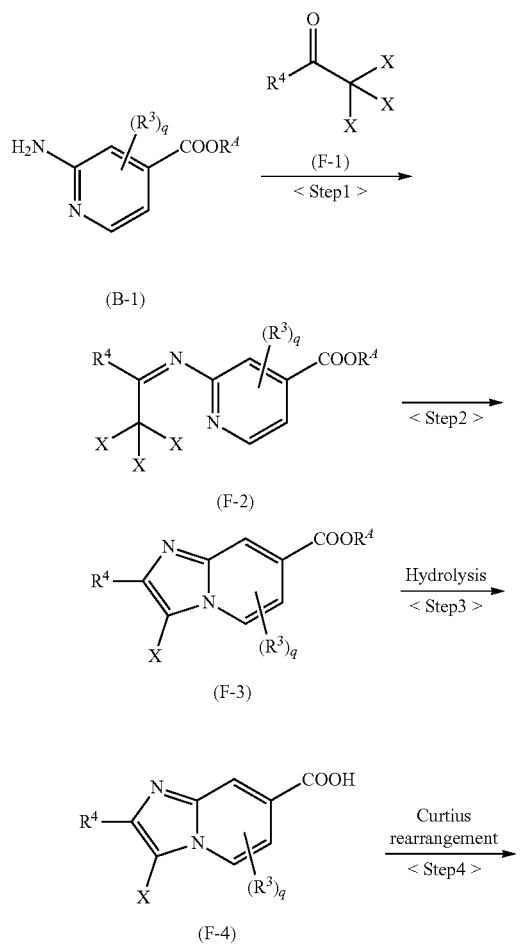

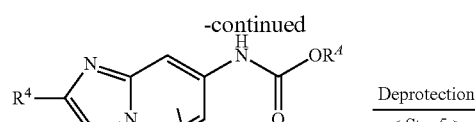

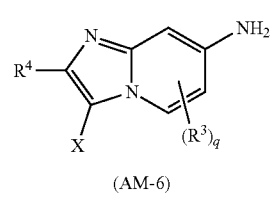

<Step 1>

Using the compound represented by the formula (B-1) and the compound represented by the formula (F-1), a reaction is carried out according to a known method, for example, the method described in "Russian Chemical Bulletin, 54, 470, 2005," in a temperature range from 0° C. to a temperature at which a solvent is refluxed, using a pyridine solvent in the presence of thionyl chloride, so as to produce the compound represented by the formula (F-2).

<Step 2>

Using the compound represented by the formula (F-2) obtained in <Production Method F> <Step 1>, a reaction is carried out according to a known method, for example, the method described in "Russian Chemical Bulletin, 54, 470, 2005," in a temperature range from 0° C. to a temperature at which a solvent is refluxed, using N-methyl-2-pyrrolidone as a solvent in the presence of trimethyl phosphite, so as to produce the compound represented by the formula (F-3).

<Step 3>

Using the compound represented by the formula (F-3) obtained in <Production Method F> <Step 2>, a reaction is carried out according to <Production Method A> <Step 3>, so as to produce the compound represented by the formula (F-4).

<Step 4>

Using the compound represented by the formula (F-4) obtained in <Production Method F> <Step 3>, a reaction is carried out according to <Production Method B> <Step 3>, so as to produce the compound represented by the formula (F-5).

<Step 5>

Using the compound represented by the formula (F-5) obtained in <Production Method F> <Step 4>, a reaction is carried out according to <Production Method B> <Step 4>, so as to produce the compound represented by the formula (AM-6).

<Production Method G>

Method for producing compound represented by formula (I): a condensation reaction of an amine represented by a formula (AM) with carboxylic acid derivatives represented by a formula (CA-1), a formula (CA-2), and a formula (CA-3).

[Formula 112]

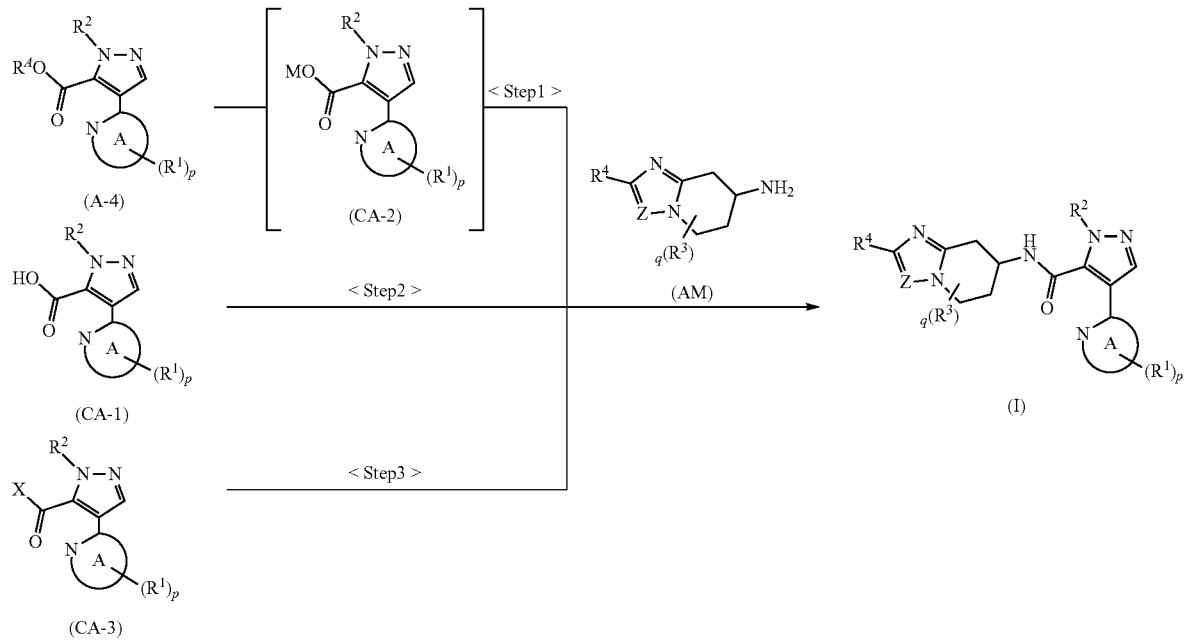

<Step 1>
The ester represented by the formula (A-4) is converted to a carboxylate (CA-2) by the method described in <Production Method A> <Step 3>. Thereafter, using the amine represented by the formula (AM), a reaction is carried out according to a known method, for example, the method described in "*Jikken Kagaku Koza*, 4$^{th}$ edition, 22, Organic Synthesis IV, Acid, Amino Acid, and Peptide, pp. 191-309, 1992, Maruzen," in a temperature range from 0° C. to a temperature at which a solvent is refluxed, in a solvent irrelevant to the reaction, such as a halogenated solvent such as dichloromethane or chloroform, an ether solvent such as diethyl ether or tetrahydrofuran, an aromatic hydrocarbon solvent such as toluene or benzene, a polar solvent such as N,N-dimethylformamide, or an alcohol solvent such as methanol, ethanol, or 2-propanol, in the presence of a condenser such as 2-(1H-7-azabenzotriazol-1-yl)-1,1,3,3-tetramethyluronium hexafluorophosphate methanaminium (HATU), and in the presence or absence of a base such as N,N-diisopropylethylamine, triethylamine, or pyridine, so as to produce the compound represented by the formula (I).

<Step 2>
Using the carboxylic acid represented by the formula (CA-1) and the amine represented by the formula (AM), a reaction is carried out according to a known method, for example, the method described in "*Jikken Kagaku Koza*, 4$^{th}$ edition, 22, Organic Synthesis IV, Acid, Amino Acid, and Peptide, pp. 191-309, 1992, Maruzen," in a temperature range from 0° C. to a temperature at which a solvent is refluxed, in a solvent irrelevant to the reaction, such as a halogenated solvent such as dichloromethane or chloroform, an ether solvent such as diethyl ether or tetrahydrofuran, an aromatic hydrocarbon solvent such as toluene or benzene, a polar solvent such as N,N-dimethylformamide, or an alcohol solvent such as methanol, ethanol, or 2-propanol, in the presence of a condenser such as 1,3-dicyclohexylcarbodiimide (DCC), 1-ethyl-3-(3'-dimethylaminopropyl)carbodiimide hydrochloride (WSC.HCl), 1-hydroxybenzotriazole (HOBT), benzotriazol-1-yloxytris(dimethylamino)phosphonium hexafluorophosphate (BOP reagent), bis(2-oxo-3-oxazolidinyl)phosphinic chloride (BOP—Cl), 2-chloro-1,3-dimethylimidazolinium hexafluorophosphate (CIP), 4-(4,6-dimethoxy-1,3,5-triazin-2-yl)-4-methylmorpholinium chloride (DMTMM), polyphosphoric acid (PPA), or 2-(1H-7-azabenzotriazol-1-yl)-1,1,3,3-tetramethyluronium hexafluorophosphate methanaminium (HATU), and in the presence or absence of a base such as triethylamine, N,N-diisopropylethylamine, or pyridine, so as to produce the compound represented by the formula (I).

Otherwise, as an alternative method, using the carboxylic acid represented by the formula (CA-1) and the amine represented by the formula (AM), a reaction is carried out according to a known method, for example, the method described in "International Publication No. WO2005/034867" or "Bioorganic & Medicinal Chemistry Letters, 14 (4), pp. 983-988, 2004," in a temperature range from 0° C. to a temperature at which a solvent is refluxed, in a solvent irrelevant to the reaction, such as pyridine, in the presence of phosphoryl chloride, so as to produce the compound represented by the formula (I).

<Step 3>
Using the acid halide represented by the formula (CA-3) and the amine represented by the formula (AM), a reaction is carried out according to a known method, for example, the method described in "*Jikken Kagaku Koza*, 4$^{th}$ edition, 22, Organic Synthesis IV, Acid, Amino Acid, and Peptide, pp. 144-146, 1992, Maruzen," in a temperature range from 0° C. to a temperature at which a solvent is refluxed, in a solvent irrelevant to the reaction, such as a halogenated solvent such as dichloromethane, chloroform, or 1,2-dichloroethane, an ether solvent such as diethyl ether, tetrahydrofuran, or 1,4-dioxane, an aromatic hydrocarbon solvent such as toluene or benzene, or a polar solvent such as N,N-dimethylformamide, in the presence of a base such as triethylamine, N,N-diisopropylethylamine, pyridine, or 4-dimethylaminopyridine, so as to produce the compound represented by the formula (I).

<Production Method H>

Method for producing compound represented by formula (I): a synthetic method from formula (I''') (in case of $R^4$=halogen) to formula (I).

[Formula 113]

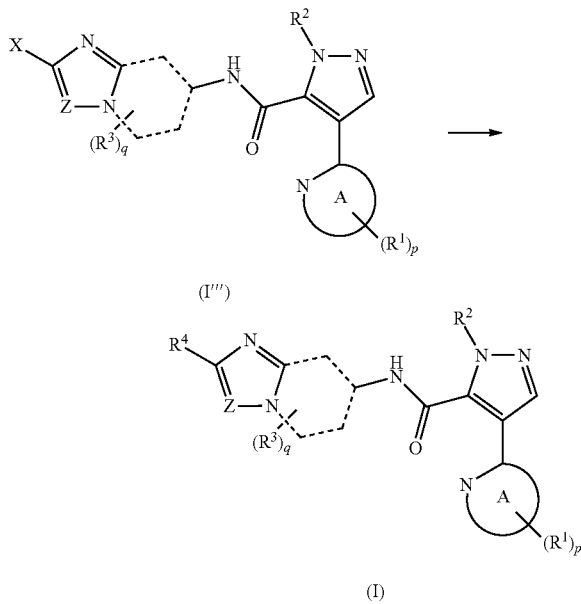

(I''')

(I)

<Case of $R^4$=a $C_{6-14}$ Aryl Group or a 5- to 7-Membered Monocyclic Heteroaryl Group>

Using the compound represented by the formula (I''') and the boranic acid derivative represented by the formula (C-8), a reaction is carried out according to <Production Method A> <Step 2>, so as to produce the compound represented by the formula (I).

<Case of $R^4$=a 3- to 14-Membered Non-Aromatic Heterocyclic Group>

Using the compound represented by the formula (I''') and a non-aromatic heterocyclic compound (e.g. a 3- to 8-membered ring non-aromatic heterocyclic compound such as aziridine, pyrrolidine, piperazine, piperidine, or morpholine), a reaction is carried out according to <Production Method D> <Step 6> <Case of $R^4$=a 3- to 14-membered non-aromatic heterocyclic group>, so as to produce the compound represented by the formula (I).

<Production Method I>

Method for producing compound represented by formula (I): a method comprising performing a condensation reaction between an amine represented by a formula (AM) and carboxylic acid derivatives represented by a formula (CA-1-2), a formula (CA-2-2), and a formula (CA-3-2), and then introducing Het that corresponds to a ring A portion into the reaction product.

[Formula 114]

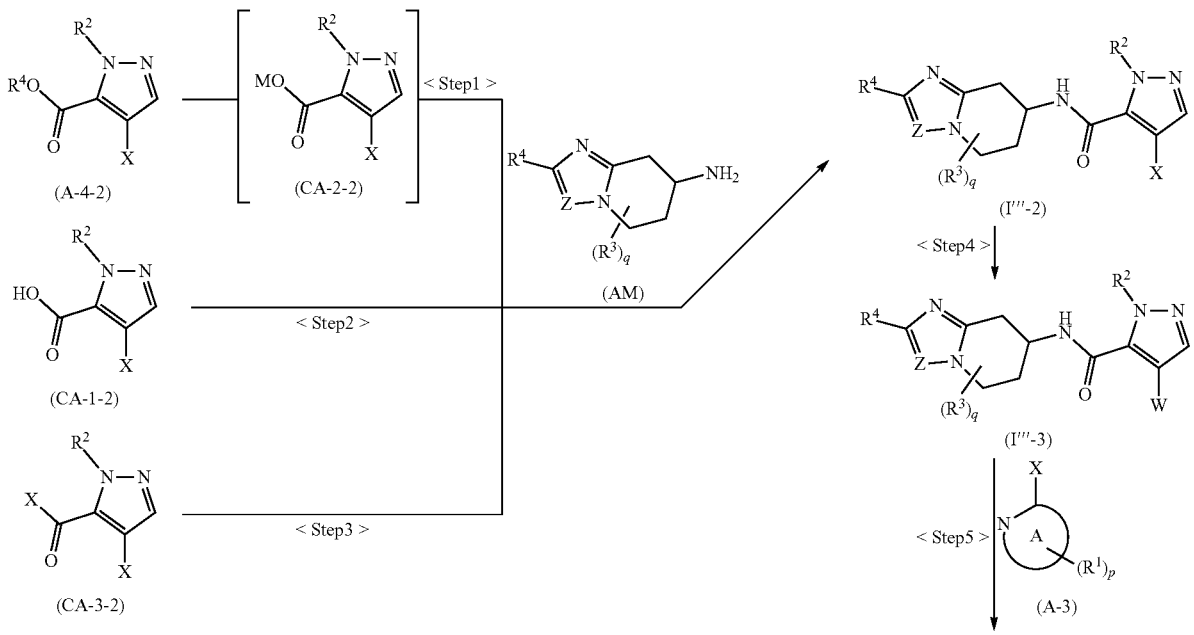

-continued

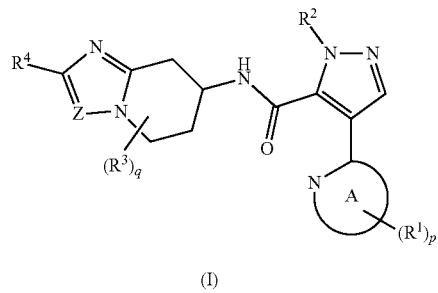

(I)

<Step 1>

The ester represented by the formula (A-4-2) is converted to the carboxylate represented by the formula (CA-2-2) by performing a reaction according to <Production Method A> <Step 3>. Thereafter, using the amine represented by the formula (AM), a reaction is carried out according to <Production Method G> <Step 1>, so as to produce the compound represented by the formula (I'''-2).

<Step 2>

Using the carboxylic acid represented by the formula (CA-1-2) and the amine represented by the formula (AM), a reaction is carried out according to <Production Method G> <Step 2>, so as to produce the compound represented by the formula (I'''-2).

<Step 3>

Using the acid halide represented by the formula (CA-3-2) and the amine represented by the formula (AM), a reaction is carried out according to <Production Method G> <Step 3>, so as to produce the compound represented by the formula (I'''-2).

<Step 4>

Using the compound represented by the formula (I'''-2) obtained in <Production Method I> <Step 1>, or <Production Method I> <Step 2>, or <Production Method I> <Step 3>, a reaction is carried out according to <Production Method A> <Step 1>, so as to produce the compound represented by the formula (I'''-3).

<Step 5>

Using the compound represented by the formula (I'''-3) obtained in <Production Method I> <Step 4> and the compound represented by the formula (A-3), a reaction is carried out according to <Production Method A> <Step 2>, so as to produce the compound represented by the formula (I).

<Production Method J>

Alternative method for producing compound represented by formula (I'''-3) in <Production Method I>.

[Formula 115]

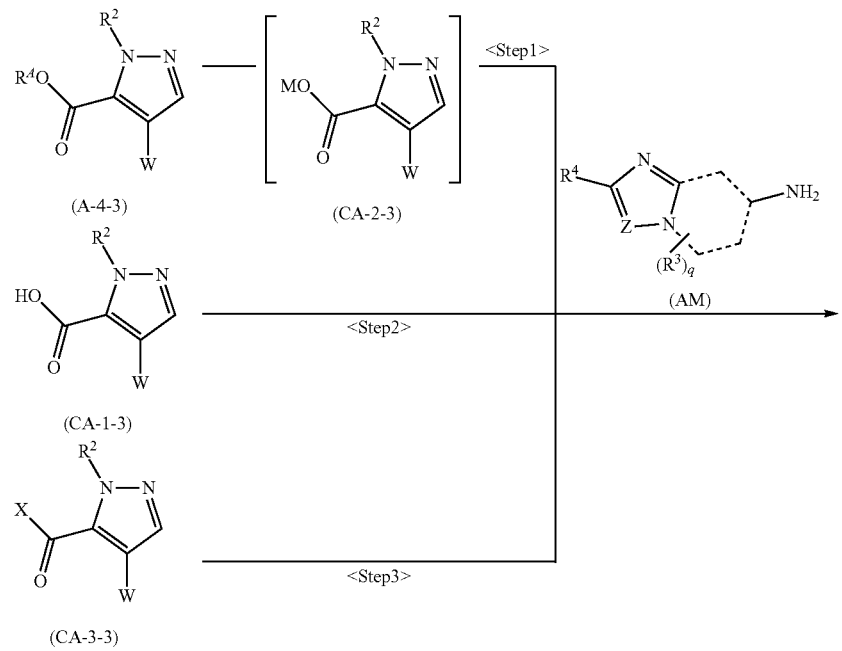

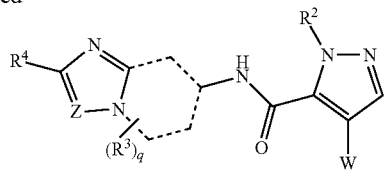

(I'''-3)

<Step 1>
The ester represented by the formula (A-4-3) is converted to the carboxylate represented by the formula (CA-2-3) by performing a reaction according to <Production Method A> <Step 3>. Thereafter, using the amine represented by the formula (AM), a reaction is carried out according to <Production Method G> <Step 1>, so as to produce the compound represented by the formula (I'''-3).

<Step 2>
Using the carboxylic acid represented by the formula (CA-1-3) and the amine represented by the formula (AM), a reaction is carried out according to <Production Method G> <Step 2>, so as to produce the compound represented by the formula (I'''-3).

<Step 3>
Using the acid halide represented by the formula (CA-3-3) and the amine represented by the formula (AM), a reaction is carried out according to <Production Method G> <Step 3>, so as to produce the compound represented by the formula (I''-3).

[Combination Agent Containing the Compound in the Present Invention]

The compound or pharmaceutical composition of the present invention can be used in combination with other drugs or agents according to a common method applied in medical sites. Examples of a drug that can be used in combination with the compound in the present invention include (A) therapeutic agents for mental diseases, and in particular, schizophrenia, or for bipolar disorder, obsessive-compulsive disorder, major depression, Parkinson's disease, Huntington's disease, Alzheimer's disease, cognitive function disorder and defect of memory, and (B) therapeutic agents for diseases occurring together with schizophrenia.

Examples of the above described agent (A) include (1) atypical antipsychotic agents [specifically, olanzapine, quetiapine, clozapine, ziprasidone, risperidone, paliperidone, perospirone, blonanserin, lurasidone, aripiprazole, sertindole, amisulpride, iloperidone, bifeprunox, asenapine, melperone, brexpiprazole, zotepine, etc.], (2) typical antipsychotic agents [specifically, chlorpromazine, prochlorperazine, perphenazine, levomepromazine, fluphenazine, thioridazine, propericiazine, spiperone, moperone, haloperidol, timiperone, bromperidol, pimozide, floropipamide, sulpiride, tiapride, sultopride, nemonapride, oxypertine, etc.], (3) selective serotonin reuptake inhibitors (SSRI) [specifically, escitalopram, citalopram, paroxetine, sertraline, fluvoxamine, fluoxetine, etc.], (4) selective serotonin/noradrenalin reuptake inhibitors (SNRI) [specifically, milnacipran, duloxetine, venlafaxine, nefazodone, etc.], (5) selective noradrenalin/dopamine reuptake inhibitors (NDRI) [specifically, bupropion etc.], (6) noradrenergic and specific serotonergic antidepressants (NaSSA) [specifically, mirtazapine etc.], (7) triazolopyridine antidepressants (SARI) [specifically, trazodone etc.], (8) tetracyclic antidepressants [specifically, setiptiline, mianserin, maprotiline, etc.], (9) tricyclic antidepressants [specifically, amitriptyline, trimipramine, imipramine, nortriptyline, clomipramine, lofepramine, amoxapine, dosulepin, etc.], (10) other antidepressants [specifically, NS-2359, Lu AA21004, DOV21947, etc.], (11) α7 nicotine receptor agonists, (12) α7 nicotine receptor activity modulators, (13) α7 nicotine receptor partial modulators [specifically, SSR-180711, PNU-120596, etc.], (14) other PDE inhibitors [PDE1 inhibitor, PDE2 inhibitor, PDE4 inhibitor, PDE5 inhibitor, PDE7 inhibitor, PDE9 inhibitor, etc.], (15) NK2 antagonists, (16) NK3 antagonists, (17) muscarinic M1 acetylcholine receptor activity modulators, (18) muscarinic M2 acetylcholine receptor activity modulators, (19) adenosine receptor modulators, (20) muscarinic M4 acetylcholine receptor activity modulators, (21) muscarinic M5 acetylcholine receptor activity modulators, (22) adenosine receptor modulators, (23) glycine transporter 1 (GlyT1) inhibitors [specifically, ALX5407, SSR504734, etc.], (24) glutamate enhancers [specifically, ampakine], (25) NMDA receptor inhibitors [specifically, memantine hydrochloride etc.], (26) metabolic glutamate receptor modulators (mGlu) [specifically, CDPPB, MPEP, etc.], (27) anti-anxiety agents ((i) benzodiazepine anti-anxiety agents [specifically, chlordiazepoxide, diazepam, oxazolam, medazepam, cloxazolam, lorazepam, clorazepate dipotassium, prazepam, bromazepam, fludiazepam, mexazolam, alprazolam, flutoprazepam, flutazolam, ethyl loflazepate, etc.], (ii) thienodiazepine anti-anxiety agents [specifically, etizolam, clotiazepam, etc.], and (iii) serotonin 5-HT1A agonists [specifically, tandospirone etc.]), (28) sleep inducing drugs ((i) benzodiazepine sleep inducing drugs [specifically, nitrazepam, estazolam, flurazepam hydrochloride, nimetazepam, flurazepam, haloxazolam, flunitrazepam, rilmazafone hydrochloride, lormetazepam, triazolam, etc.], (ii) thienodiazepine sleep inducing drugs [specifically, brotizolam etc.], (iii) non-benzodiazepine sleep inducing drugs [specifically, zolpidem etc.], (iv) melatonin receptor agonists [specifically, ramelteon etc.]), (v) cyclopyrrolone sleep inducing drugs [specifically, zopiclone etc.], (29) β amyloid vaccines, (30) β amyloid decomposing enzymes, etc., (31) cerebral function activators [specifically, aniracetam, nicergoline, etc.], (32) cannabinoid modulators, (33) choline esterase inhibitors [specifically, donepezil hydrochloride, rivastigmine, galantamine hydrobromide, etc.], (34) MAO-B inhibitors [specifically, rasagiline etc.] (35) Parkinson's disease-treating agents ((i) dopamine receptor agonists [specifically, levodopa, amantadine hydrochloride, bromocriptine mesilate, pergolide mesilate, cabergoline, talipexole hydrochloride, pramipexole hydrochloride hydrate, selegiline hydrochloride, ropinirole hydrochloride, etc.], (ii) monoamine oxidase inhibitors [specifically, deprenyl, selegiline, remacemide, riluzole, etc.], (iii) anticholinergic drugs [specifically, trihexyphenidyl, profenamine, biperiden, piroheptine hydrochloride, methixene hydrochloride, mazaticol hydrochloride, etc.], (iv) COMT inhibitors [specifically, entacapone etc.], (v) therapeutic agents for amyotrophic lateral sclerosis [specifically, riluzole, neurotrophic factors, etc.], (vi) apoptosis inhibitors [specifically, CPI-1189, IDN-6556, CEP-1347, etc.], and (vii) nerve differentiation/regeneration promoters [specifically, leteprinim, xaliproden; SR-57746-A, SB-216763, etc.]).

On the other hand, examples of the above described agent (B) include (36) therapeutic agents for diabetes ((i) PPARγ stimulants (agonists and inhibitors) [specifically, pioglitazone, rosiglitazone, troglitazone, ciglitazone, darglitazone, englitazone, netoglitazone, etc.], (ii) insulin secretion promoters [(a) sulfonylurea agents (specifically, tolbutamide, acetohexamide, chlorpropamide, glibenclamide, gliclazide, glipizide, glimepiride, glipentide, gliquidone, glisolamide, tolazamide, etc.), (b) non-sulfonylurea agents etc.], (iii) rapid-acting insulin secretion promoters (specifically, nateglinide, mitiglinide, repaglinide, etc.), (iv) α-glucosidase inhibitors [specifically, acarbose, voglibose, miglitol, camiglibose, adiposin, emiglitate, pradimicin-Q, salbostatin, etc.], (v) insulin resistance-improving agents [specifically, (a) PPARγ stimulants, (b) PTP-1B inhibitors, (c) DPP-4 inhibitors [specifically, sitagliptin, vildagliptin, alogliptin, saxagliptin, NVP-DPP-728, etc.], (d) GLP-1 and GLP-1 agonists [specifically, exenatide, liraglutide, etc.], (e) 11β-HSD inhibitors and the like, (f) GPR40 agonists, (g) GPR119 agonists, and (h) GPR120 agonists], (vi) hepatic gluconeogenesis suppressants [specifically, glucagon antagonists etc.], (vii) biguanide agents [specifically, metformin, buformin, phenformin, etc.], (viii) insulin or insulin derivatives [specifically, insulin zinc suspension, insulin lispro, insulin aspart, regular insulin, NPH insulin, insulin glargine, insulin detemir, mix-type insulin, etc.], (ix) α2 antagonists [specifically, midaglizole, isaglidole, deriglidole, idazoxan, efaroxan, etc.]), (37) antiobestic drugs ((i) adrenalin β3 receptor agonists [specifically, KRP-204, TRK-380/TAC-301, etc.], (ii) CB-1 receptor antagonists [specifically, rimonabant, SR-147778, BAY-65-2520, etc.], (iii) neuropeptide Y (NPY) receptor antagonists [specifically, S-2367 etc.], (iv) anti-feeding drugs [monoamine reuptake inhibitors [specifically, sibutramine, mazindol, etc.]], (v) lipase inhibitors [specifically, orlistat, cetilistat, etc.], and (vi) peptide YY (PYY) receptor antagonists, etc.), (38) hyperlipidemia-treating agents such as cholesterol-reducing agents ((i) ω3 fatty acids [specifically, ethyl icosapentate (EPA-E preparations, for example, product name: Epadel (registered trademark)), docosahexaenoic acid (DHA), a mixed preparation of ethyl icosapentate and ethyl docosahexaenoate (e.g. product name: LOVAZA™ and Omacor (registered trademark)), etc.], (ii) HMG-CoA reductase inhibitors [specifically, atorvastatin, simvastatin, pitavastatin, itavastatin, fluvastatin, lovastatin, pravastatin, rivastatin, rosuvastatin, etc.] (iii) HMG-CoA synthetase inhibitors, (iv) cholesterol absorption inhibitors [specifically, ezetimibe], (v) acyl-CoA cholesterol acyl transferase (ACAT) inhibitors, (vi) CETP inhibitors, (vii) squalene synthetase inhibitors, (viii) antioxidants [specifically, probucol etc.], (ix) PPARα agonists [specifically, clofibrate, etofibrate, fenofibrate, bezafibrate, ciprofibrate, gemfibrozil, KRP-101, etc.], (x) PPARδ agonists, (xi) LXR agonists, (xii) FXR agonists [specifically, INT-747 etc.], (xiii) MTTP inhibitors, (xiv) squalene epoxidase inhibitors, etc.), (39) antihypertensive agents ((i) diuretics [specifically, trichlormethiazide, hydrochlorothiazide, mefruside, indapamide, meticrane, chlorthalidone, tripamide, furosemide, torasemide, bumetanide, ethacrynic acid, spironolactone, triamteren, eplerenone, etc.], (ii) calcium receptor antagonists [specifically, amlodipine, felodipine, nicardipine, nifedipine, nimodipine, nitrendipine, nilvadipine, aranidipine, azelnidipine, manidipine, barnidipine, efonidipine, cilnidipine, benidipine, diltiazem, etc.], (iii) angiotensin converting enzyme inhibitors (ACEI) [specifically, captopril, lisinopril, enalapril, delapril, perindopril, benazepril, trandolapril, quinapril, alacepril, imidapril, temocapril, cilazapril, etc.], (iv) angiotensin receptor blockers (ARB) [specifically, losartan, olmesartan, telmisartan, valsartan, candesartan cilexetil, irbesartan, etc.], (v) direct renin inhibitors [specifically, aliskiren etc.], (vi) a receptor blockers [specifically, tolazoline, phentolamine, doxazosin, prazosin, bunazosin, terazosin, urapidil, etc.], (vii) β receptor blockers [specifically, bopindolol, pindolol, timolol, dichloroisoprenaline, alprenolol, carteolol, indenolol, bunitrolol, penbutolol, propranolol, nadolol, nipradilol, tilisolol, acebutolol, celiprolol, metoprolol, atenolol, bisoprolol, betaxolol, practolol, bevantolol, butoxamine, carvedilol, amosulalol, arotinolol, labetalol, etc.], (viii) $\alpha_1\beta$ blockers [specifically, carvedilol, labetalol, arotinolol, bevantolol, etc.], and (ix) $\alpha_2$ receptor stimulants [specifically, clonidine, methyldopa, guanfacine, etc.]), (40) non-steroidal anti-inflammatory agents [specifically, meloxicam, teoxicam, indomethacin, ibuprofen, celecoxib, rofecoxib, aspirin, indomethacin, etc.], (41) disease-modifying antirheumatic drugs (DMARDs), (42) anti-cytokine agents [specifically, TNF inhibitors and MAP kinase inhibitors], (43) steroid drugs [specifically, dexamethasone, hexestrol, cortisone acetate, etc.], (44) sex hormones or derivatives thereof [specifically, progesterone, estradiol, estradiol benzoate, etc.], and (45) parathyroid hormone (PTH).

By using the drug of the present invention in combination with the existing drugs on the above described diseases, it is possible to reduce the doses of the existing drugs, and it is also possible to reduce the adverse drug reactions of the existing drugs. Naturally, application of the combined-use method using the present drug is not limited to the above described diseases, and the combined drugs are not limited to the above exemplified compounds.

The administration form of the compound in the present invention and the combined drug is not particularly limited. It is appropriate if the compound in the present invention may be combined with the combined drug upon administration. Examples of such an administration form include:

(1) administration of a single preparation obtained by simultaneous formulation of the compound in the present invention and the combined drug, (2) simultaneous administration of two types of preparations obtained by separately formulating the compound in the present invention and the combined drug via a single administration route, (3) time-lag administration of two types of preparations obtained by separately formulating the compound in the present invention and the combined drug via a single administration route, (4) simultaneous administration of two types of preparations obtained by separately formulating the compound in the present invention and the combined drug via different administration routes, and (5) time-lag administration of two types of preparations obtained by separately formulating the compound in the present invention and the combined drug via different administration routes (for example, administration in the order of the compound in the present invention and the combined drug, or in an opposite order).

Hereinafter, these administration forms are collectively abbreviated as the "combination agent of the present invention."

Upon administration of the combination agent of the present invention, the combined drug and the compound in the present invention may be administered at the same time. Otherwise, after administration of the combined drug, the compound in the present invention may be administered, or after administration of the compound in the present invention, the combined drug may be administered. In the case of time-lag administration, such a time lag is different depending on an active ingredient to be administered, dosage form, and administration method. For example, when the combined drug is administered in advance, there is applied a method which comprises administering the compound in the present invention within 1 minute to 3 days, preferably within 10 minutes to 1 day, and more preferably within 15 minutes to 1 hour, after administration of the combined drug. When the compound in the present invention is administered in advance, there is applied a method which comprises administering the combined drug within 1 minute to 1 day, preferably within 10 minutes to 6 hours, and more preferably within 15 minutes to 1 hour, after administration of the compound in the present invention.

The amount of the combined drug is not particularly limited, as long as it does not cause a problem regarding adverse drug reactions. The daily dose of the combined drug is different depending on administration target, administration route, target disease, symptoms, etc. For example, when such a combined drug is administered to a schizophrenia patient (adult; body weight: approximately 60 kg) via oral administration, it is administered at a single dose of generally approximately 0.1 to approximately 20 mg/kg body weight, preferably approximately 0.2 to 10 mg/kg body weight, and more preferably approximately 0.5 to approximately 10 mg/kg body weight. It is desirable to administer this dose once or divided over several administrations (e.g. three times) per day.

When the compound in the present invention is used in combination with a combined drug, the amounts of both agents can be reduced within a safe range, while taking into consideration the opposite effects of the agents.

The combination agent of the present invention has low toxicity, and for example, the compound in the present invention, or (and) the above described combined drug can be mixed with a pharmacologically acceptable carrier according to a known method, so as to prepare a pharmaceutical composition, for example, a tablet (including a sugar-coated tablet and a film-coated tablet), a powder agent, a granule, a capsule (including a soft capsule), a liquid agent, an injection, a suppository, a sustained-release agent, etc. These agents can be safely administered via oral or parenteral administration.

As a pharmacologically acceptable carrier that may be used in the production of the combination agent of the present invention, the same carriers as those used in the above described pharmaceutical composition of the present invention can be used.

The mixing ratio between the compound in the present invention and the combined drug in the combination agent of the present invention can be selected, as appropriate, depending on administration target, administration route, disease, etc. It may also be possible to use the above described combined drug by mixing two or more types of combined drugs at an appropriate ratio.

The dose of the combined drug can be selected, as appropriate, considering a clinically used dose as a standard. In addition, the mixing ratio between the compound in the present invention and the combined drug can be selected, as appropriate, depending on administration target, administration route, target disease, symptoms, combination, etc. For instance, when the administration target is a human, the combined drug may be used at a ratio of 0.01 to 100 parts by weight, based on 1 part by weight of the compound in the present invention. For instance, the content of the compound in the present invention in the combination agent of the present invention is different depending on the form of a preparation. The compound in the present invention is used at a weight percentage of generally approximately 0.01% to 99.9%, preferably approximately 0.1% to 50%, and more preferably approximately 0.5% to 20%, based on the total weight of the preparation.

The content of the combined drug in the combination agent of the present invention is different depending on the form of a preparation. The combined drug is used at a weight percentage of generally approximately 0.01% to 99.9%, preferably approximately 0.1% to 50%, and more preferably approximately 0.5% to 20%, based on the total weight of the preparation.

The content of an additive such as a carrier in the combination agent of the present invention is different depending on the form of a preparation. The additive is used at a weight percentage of generally approximately 1% to 99.99%, and preferably approximately 10% to 90%, based on the total weight of the preparation.

Even when the compound in the present invention and the combined drug are formulated separately, the same contents as those described above may be applied.

Since the dose is fluctuated depending on various conditions, as described above, there is a case in which a dose lower than the aforementioned dose is sufficient. On the other hand, there is also a case in which a dose higher than the aforementioned dose range needs to be administered.

The compound in the present invention can be administered alone or in a combination with a pharmaceutically acceptable carrier, once or divided over multiple administrations. Examples of a suitable pharmaceutical carrier include an inactive solid diluent or filler, a sterilized aqueous solution, and various organic solvents. Then, a pharmaceutical composition formed from these substances can be easily administered in various administration forms such as a tablet, a powder agent, a lozenge, a liquid preparation, syrup, or injection. Such a pharmaceutical composition may comprise additional components such as a flavor, a binder, and an excipient, depending on the situation. Accordingly, the compound in the present invention can be formulated into a form suitable for oral, buccal, nasal, parenteral (e.g. intravenous, intramuscular, or subcutaneous), transdermal (e.g. patch) or rectal administration, or inhalation or insufflation administration.

[Formulation of Preventive and/or Therapeutic Agents of the Present Invention]

The pharmaceutical agent of the present invention is administered in the form of a pharmaceutical composition.

The pharmaceutical composition of the present invention may comprise at least one compound represented by the formula (I) of the present invention, and it is prepared by combining the compound in the present invention with pharmaceutically acceptable additives. More specifically, various dosage forms can be prepared by appropriately combining the compound in the present invention with excipients (e.g. lactose, sucrose, mannit, crystalline cellulose, silicic acid, corn starch, and potato starch), binders (e.g. celluloses (hydroxypropyl cellulose (HPC) and hydroxypropylmethyl cellulose (HPMC)), and crystalline cellulose, sugars (lactose, mannit, sucrose, sorbitol, erythritol, and xylitol), starches (corn starch and potato starch), pregelatinized starch, dextrin, polyvinyl pyrrolidone (PVP), macrogol, and polyvinyl alcohol (PVA)), lubricants (e.g.

magnesium stearate, calcium stearate, talc, and carboxymethyl cellulose), disintegrators (e.g. starches (corn starch and potato starch), carboxymethyl starch sodium, carmellose, carmellose calcium, croscarmellose sodium, and crospovidone), coating agents (e.g. celluloses (hydroxypropyl cellulose (HPC), hydroxypropylmethyl cellulose (HPMC), aminoalkyl methacrylate copolymer E, and methacrylic acid copolymer-LD), plasticizers (e.g. triethyl citrate and macrogol), masking agents (e.g. titanium oxide), coloring agents, flavoring agents, antiseptics (e.g. benzalkonium chloride and p-oxybenzoic acid ester), isotonizing agents (e.g. glycerin, sodium chloride, calcium chloride, mannitol, and glucose), pH adjusters (e.g. sodium hydroxide, potassium hydroxide, sodium carbonate, hydrochloric acid, sulfuric acid, and buffers such as a phosphate buffer), stabilizers (e.g. sugar, sugar alcohol, and xanthan gum), dispersants, antioxidants (e.g. ascorbic acid, butylhydroxyanisole (BHA), propyl gallate, and dl-α-tocopherol), buffering agents, preservatives (e.g. paraben, benzyl alcohol, and benzalkonium chloride), aromatics (e.g. vaniline, l-menthol, and rose oil), solubilizers (e.g. polyoxyethylene hydrogenated castor oil, polysorbate 80, polyethylene glycol, phospholipid cholesterol, and triethanolamine), absorption promoters (e.g. sodium glycolate, sodium edetate, sodium caprylate, acylcarnitines, and limonene), gelatinizers, suspending agents, emulsifiers, or commonly used suitable additives or solvents.

Various dosage forms include a tablet, a capsule, a granule, a powder agent, a pill, an aerosol, an inhalant, an ointment, a patch, a suppository, an injection, a troche, a liquid preparation, a spirit, a suspension, an extract, and an elixir. In addition, the pharmaceutical composition of the present invention can be administered to a patient, via oral administration, subcutaneous administration, intramuscular administration, intranasal administration, transdermal administration, intravenous administration, intraarterial administration, perineural administration, epidural administration, intrathecal administration, intraventricular administration, intrarectal administration, inhalation, etc.

The compound in the present invention can be formulated into an injection administered via parenteral administration, which includes the use of a common catheter technique or infusion. To such an injection preparation, a preservative is added, and it can be provided in a unit administration form, for example, in an ampule or in a multiple-dose container. Such a preparation can take a form such as a suspension agent in an oily or aqueous vehicle, a liquid agent, or an emulsion, and it may comprise agents for drug formulation, such as a suspending agent, a stabilizer, and/or a dispersant. Otherwise, an active ingredient can be in a powdery form, which can be reconstituted with a suitable vehicle, such as a sterilized pyrogen-removed water, before use.

When a product solution is necessary, such a product solution can be produced by dissolving an isolated inclusion complex in water (or another aqueous medium) that is in an amount sufficient for generation of a solution with strength necessary for oral or parenteral administration to a patient. Such a compound can be formulated into a fast dissolving dosage form (fddf), which is designed such that an active ingredient thereof is released in an oral cavity. Such a preparation is formulated using a matrix comprising fast dissolving gelatin as a base in many cases. Such a dosage form is well known, and it can be used to deliver a wide range of drugs. Almost all of such fast dissolving dosage forms utilize gelatin as a carrier or a structure-forming agent. Typically, gelatin is used to impart to a dosage form, sufficient strength for preventing the preparation from being broken when it is removed from a package. Once such gelatin is put into the mouth, the dosage form thereof can be immediately decomposed. Otherwise, in order to obtain the same effects as described above, various types of starches can be used.

The compound in the present invention can also be formulated into a rectal composition such as a suppository or retention enema, wherein the rectal composition comprises, for example, a common suppository base such as cacao butter or other glycerides.

In the case of administration via intranasal administration or inhalation, the compound in the present invention is conveniently delivered in the form of a solution or a suspension from a pump spray container that is compressed by a patient or is delivered by a pump, or in the form of an aerosol spray presentation delivered from a pressurized container or a nebulizer using a suitable spraying agent such as dichlorodifluoromethane, trichlorofluoromethane, dichlorotetrafluoroethane, carbon dioxide or another suitable gas. In the case of pressurized aerosol, the dosage unit can be determined by providing a valve for delivering the measured amount. A pressurized container or a nebulizer may comprise a solution or a suspension of an active compound. A capsule agent and a cartridge agent (for example, produced from gelatin), which are used with an inhalator or a filler, can be formulated from a mixed powder of the compound in the present invention and a suitable powder base such as lactose or starch.

With regard to an aerosol preparation for treating the aforementioned condition in an average adult, the measured dose or "one puff" of aerosol is determined such that it comprises preferably approximately 20 mg to approximately 1000 mg of the compound in the present invention. The total daily dose of aerosol is determined in the range from approximately 100 mg to approximately 10 mg. The aerosol preparation is administered several times, for example, 2, 3, 4 or 8 times per day, for example at 1, 2 or 3 doses every administration.

The content of the compound in the present invention in the pharmaceutical composition of the present invention is different depending on dosage form, the dose of the compound in the present invention, etc. For example, the compound in the present invention is used at a weight percentage of approximately 0.01% to 100%, and preferably 0.1% to 95%, based on the total weight of the composition.

In order to treat the aforementioned condition, the dose of the compound in the present invention is different depending on administration target, administration route (oral, parenteral, rectal, buccal, etc.), target disease, symptoms, and the like. For example, in the case of oral administration to a schizophrenia patient (adult; body weight: approximately 60 kg), the compound in the present invention is administered at a dose of generally approximately 0.1 to approximately 20 mg/kg body weight, preferably approximately 0.2 to 10 mg/kg body weight, and more preferably approximately 0.5 to approximately 10 mg/kg body weight, per administration. This dose is desirably administered once or divided over several administrations (for example, three times) per day.

Pharmacological Experimental Examples

The present invention will be specifically described in the following experimental examples. However, these experimental examples are not intended to limit the present invention.

The following Pharmacological Experimental Examples 1 to 7 provide methods for examining the effectiveness of the compound in the present invention.

Pharmacological Experimental Example 1

In Vitro Evaluation of Compounds (Evaluation of Enzyme Inhibitory Activity: Human PDE10 Inhibitory Effect)

IMAP TR-FRET Phosphodiersterase Evaluation Assay Kit (Molecular Device) was used for the measurement. Ten µL of a diluted test compound having each concentration and 5 µL of the enzyme PDE10 (BPA Bioscience) that had been diluted to 2 ng/mL with 1×IMAP Reaction Buffer (prepared with 5× included with the kit, 10 mM Tris-HCl, pH=7.2, 10 mM $MgCl_2$, 0.05% $NaN_3$, and 0.1% BSA) containing 0.1% BSA were added to a 384-well plate (Corning). The obtained mixture was then pre-incubated at room temperature for 5 minutes. Thereafter, 5 µL of cAMP substrate solution which was included with the kit and diluted to 400 nM with 1×IMAP Reaction Buffer containing 0.1% BSA, was added to the reaction solution, and the obtained mixture was reacted at room temperature for 60 minutes. Thereafter, 60 µL of an IMAP TR-FRET Binding solution included with the kit was further added to the reaction solution, and the obtained mixture was then left for 3 hours or more. Subsequently, using ARVO SX (PerkinElmer), the fluorescent intensity of Terbium (Emission=490 nm) and TR-FRET (Emission=520 nm) in the reaction solution were measured at an excitation wavelength of 340 nm, so as to calculate the amount of the generated 5'-AMP. The count of a well to which a solvent had been added instead of the test compound was set at 0%, and the count of a well to which the enzyme PDE10 had not been added was set at 100%. Thus, the inhibitory activity of each test compound was calculated.

The PDE10 inhibitory activity of the test compound was indicated with an $IC_{50}$ value. The compound in the present invention having an $IC_{50}$ value of 5 to 100 nmol/L was indicated with +, and the compound in the present invention having an $IC_{50}$ value of less than 5 nmol/L was indicated with ++. The test compounds are shown in Table 3 (Table 3-1 and Table 3-2).

TABLE 3-1

| Example | $IC_{50}$ value |
|---|---|
| 1.1 | ++ |
| 1.2 | ++ |
| 1.3 | ++ |
| 1.4 | ++ |
| 1.5 | ++ |
| 1.6 | ++ |
| 1.7 | ++ |
| 2.1 | ++ |
| 2.2 | ++ |
| 2.3 | ++ |
| 2.4 | ++ |
| 2.5 | ++ |
| 2.6 | ++ |
| 2.7 | ++ |
| 2.8 | ++ |
| 2.9 | ++ |
| 2.10 | ++ |
| 2.11 | ++ |
| 2.12 | ++ |
| 2.13 | ++ |
| 2.14 | ++ |
| 2.15 | ++ |
| 2.16 | + |

TABLE 3-1-continued

| Example | $IC_{50}$ value |
|---|---|
| 2.17 | + |
| 2.18 | + |
| 2.19 | ++ |
| 2.20 | ++ |
| 2.21 | + |
| 2.22 | ++ |
| 2.23 | + |
| 2.24 | + |
| 2.25 | + |
| 2.26 | + |
| 2.27 | + |
| 2.28 | ++ |
| 2.29 | ++ |
| 3.1 | ++ |
| 3.2 | ++ |
| 3.3 | ++ |
| 3.4 | ++ |
| 3.5 | ++ |
| 3.6 | ++ |
| 3.7 | ++ |
| 3.8 | ++ |
| 3.9 | ++ |
| 3.10 | ++ |
| 3.11 | ++ |
| 3.12 | ++ |
| 3.13 | ++ |
| 3.14 | ++ |
| 3.15 | ++ |
| 3.16 | ++ |
| 3.17 | ++ |
| 3.18 | ++ |
| 3.19 | ++ |
| 3.20 | ++ |
| 3.21 | + |
| 3.22 | ++ |
| 3.23 | ++ |
| 3.24 | ++ |
| 3.25 | ++ |
| 3.26 | ++ |
| 3.27 | ++ |
| 3.28 | ++ |
| 3.29 | ++ |
| 3.30 | ++ |
| 3.31 | ++ |
| 3.32 | ++ |
| 3.33 | ++ |
| 3.34 | ++ |
| 3.35 | ++ |
| 3.36 | ++ |
| 3.37 | ++ |
| 3.38 | ++ |
| 3.39 | ++ |
| 3.40 | ++ |
| 3.41 | ++ |
| 3.42 | ++ |
| 3.43 | ++ |
| 3.44 | ++ |
| 3.45 | ++ |
| 3.46 | ++ |
| 3.47 | ++ |
| 3.48 | ++ |
| 3.49 | ++ |
| 3.50 | ++ |
| 3.51 | ++ |
| 3.52 | ++ |
| 3.53 | ++ |
| 3.54 | ++ |
| 4.1 | ++ |
| 4.2 | ++ |

TABLE 3-2

| Example | IC$_{50}$ |
|---|---|
| 4.3 | ++ |
| 4.4 | ++ |
| 4.5 | ++ |
| 4.6 | ++ |
| 4.7 | ++ |
| 4.8 | ++ |
| 4.9 | ++ |
| 4.10 | ++ |
| 4.11 | ++ |
| 4.12 | ++ |
| 4.13 | ++ |
| 3.14 | ++ |
| 4.15 | ++ |
| 4.16 | ++ |
| 4.17 | ++ |
| 4.18 | ++ |
| 4.19 | ++ |
| 4.20 | ++ |
| 4.21 | ++ |
| 4.22 | ++ |
| 4.23 | ++ |
| 4.24 | ++ |
| 4.25 | ++ |
| 4.26 | ++ |
| 4.27 | ++ |
| 4.28 | ++ |
| 4.29 | ++ |
| 4.30 | ++ |
| 4.31 | ++ |
| 4.32 | ++ |
| 4.33 | ++ |
| 4.34 | ++ |
| 4.35 | ++ |
| 4.36 | + |
| 5.1 | ++ |
| 5.2 | + |
| 5.3 | ++ |
| 5.4 | ++ |
| 5.5 | ++ |
| 5.6 | ++ |
| 5.7 | ++ |
| 5.8 | + |
| 5.9 | + |
| 5.10 | + |
| 5.11 | + |
| 5.12 | + |
| 5.13 | + |
| 5.14 | + |
| 5.15 | + |
| 5.16 | + |
| 5.17 | ++ |
| 5.18 | + |
| 5.19 | + |
| 5.20 | + |
| 5.21 | + |
| 5.22 | + |
| 5.23 | + |
| 5.24 | + |
| 5.25 | + |
| 5.26 | + |
| 5.27 | + |
| 5.28 | + |
| 5.29 | ++ |
| 5.30 | + |
| 5.31 | + |
| 5.32 | + |
| 5.33 | + |
| 5.34 | ++ |
| 5.35 | + |
| 5.36 | ++ |
| 5.37 | + |
| 5.38 | + |
| 5.39 | + |
| 5.40 | + |
| 5.41 | + |
| 5.42 | + |
| 5.43 | + |
| 5.44 | + |
| 5.45 | ++ |
| 5.46 | ++ |
| 5.47 | + |

The effectiveness of the compound in the present invention as a therapeutic agent for mental disorder and neurodegenerative disorder will be demonstrated by the following Pharmacological Experimental Example 2 (an experiment regarding suppression of locomotor activity by oral administration of a test compound to rats 30 minutes before administration of MK-801).

Pharmacological Experimental Example 2

Evaluation of MK-801-Induced Locomotor Activity (Animals)

Male Sprague-Dawley rats were purchased. After the animals had arrived at a rearing facility, they were subjected to habituation for at least one week and were then used in the experiment. The animals were reared in a laboratory in which temperature and humidity were controlled, under a light-dark cycle of 12:12 hours. The animals were freely fed with diet and water.

(Administration of Drug)

The test compound was suspended in a 0.5 w/v % Methyl Cellulose 400 Solution (Wako Pure Chemical Industries, Ltd., Japan), and it was then administered to the rats via oral administration (p.o.). (+)-MK-801 hydrogen maleate ((5R,10S)-(+)-5-methyl-10,11-dihydro-5H-dibenzo[a,d]cyclohepten-5,10-imine hydrogen maleate, Sigma-Aldrich, St. Louis, Mo.) was dissolved in a physiological saline, and it was then administered to the rats via subcutaneous administration (s.c.). To the rats, the test compound was administered at a volume of 5 mL/kg body weight, and MK-801 was administered at a volume of 1 mL/kg body weight.

(Antagonism on the Increase of Locomotor Activity Induced by MK-801)

Evaluation of the increase of locomotor activity in rodents caused by psychostimulants (e.g., amphetamine, cocaine, methanephetamine, MK-801, and phencyclidine) has been widely used as an animal models for schizophrenia (Schizophrenia Bulletin 2010, vol. 36: 1066-1072; Psychopharmacology 1999, vol. 145: 237-250). The antagonism of a test compound on the increase of locomotor activity in rats, which had been induced by MK-801, was examined Before the test, male Sprague-Dawley rats (approximately 300 g) were habituated for 60 minutes or more in a breeding cage in a room, in which the measurement was to be carried out. After the habituation, either a solvent or a compound (0.3 or 1 mg/kg body weight) was administered to the animals via oral administration, and thereafter, the animals were immediately returned into the breeding cage. Sixty minutes after administration of the test compound, the animals were removed from the breeding cage again, and a solvent (a physiological saline) or MK-801 (0.2 mg/kg body weight) was administered to the animals via subcutaneous administration. Immediately after the administration, the animals were placed in a locomotor activity measurement chamber equipped with an infrared sensor (Muromachi Kikai Co., Ltd., Japan), and the measurement was then started. Locomotor activity was counted every 10 minutes. The cumulative count for 120 minutes after administration of MK-801 was calculated for each treatment group. All data are shown as a mean value and a standard error of the mean value. Statistical analysis was carried out, by applying a Student's t-test for a comparison between a control group and a single MK-801 administration group (there was a significant difference when $p<0.05$), and by applying a Dunnett's test for a comparison between a single MK-801 administration group and a test compound administration group (there was a significant difference when $p<0.05$).

Pharmacological Experimental Example 3

Solubility Test (1) DMSO Precipitation Solubility (Kinetic Solubility)

A DMSO solution of the compound in the present invention (10 mM) was added to a 50 mM phosphate buffer (pH 7.4) to a final concentration of 100 µM. The obtained solution was incubated at room temperature for 1.5 hours, while being stirred at 600 rpm, and the resulting solution was then filtered through a filter plate (4 µm, MultiScreen Solubility Filter Plate (Millipore)). Thereafter, using a plate reader (Powerscan HT (Dainippon Pharma Co., Ltd.)), the absorbance of the filtrate was measured at a maximum absorption wavelength. At the same time, DMSO solutions, to which test compounds each having a known concentration (1, 3, 10, 30, and 100 µM) had been added, were used as calibration curve standard solutions, and the absorbance of each standard solution was then measured, so as to prepare a calibration curve. Based on the absorbance values of the filtrate and the standard solution, the solubility (µM) of the compound was calculated.

(2) Crystal Solubility (Thermodynamic Solubility)

The compound in the present invention was added to water to a concentration of 1 mg/mL. The obtained solution was left at rest at 37° C. for 24 hours, and was then centrifuged. The obtained supernatant was analyzed by HPLC, a peak was then detected at a maximum absorption wavelength, and a peak area was then measured. Likewise, using DMSO solutions, to which test compounds each having a known concentration (0.03, 0.1, 0.3, 1, 3, and 10 µg/mL) had been added as calibration curve standard solutions, each peak area was measured, and the solubility (µg/mL) of the compound was calculated based on the peak area of the calibration curve.

Pharmacological Experimental Example 4

Metabolic Stability Test

A DMSO solution of the compound in the present invention (10 mM) was added to a hepatic microsome solution (human, mouse; XenoTech) and an NADPH generation solution (water containing β-NADP, Glucose-6-Phosphate, G-6-PDH (Y), and $MgCl_2$) to a final concentration of 1 µM. This solution was incubated at 37° C. for 20 minutes, and the reaction was then terminated with adding acetonitrile. The reaction solution was subjected to centrifugal filtration using a filter plate (MultiScreenHTS-HV Plate (Millipore)), and the test compound in the filtrate was then measured using high performance liquid chromatography/mass spectrometry. Likewise, a sample with a reaction time of 0 minute was measured as a control, and a decomposition rate (%) was then calculated based on the ratio of the microsome reaction sample and the control.

Pharmacological Experimental Example 5 hERG Inhibition Test According to Patch-Clamp Method

The effect of the test compound on an hERG (human ether-a-go-go related gene) channel was measured using a fully-automated patch-clamp system (Patchliner (Nanion)). In order to confirm the hERG $I_{Kr}$ current of cells (hERG-HEK (Upstate)), a membrane potential was kept at −80 mV, and depolarization pulse was periodically added thereto. After the generated current had been stabilized, a test compound was added. The effect of the test compound on the hERG channel was confirmed based on a change in a tail current induced by repolarization pulse performed at −40 mV for 0.5 seconds, after the depolarization pulse at 40 mV for 0.5 seconds. Stimulation was given at a frequency of once every 10 seconds. The measurement was carried out at room temperature. The hERG channel inhibitory rate was calculated as a reduction rate (suppression rate) of the tail current two minutes after application of the test compound, comparison with the maximum tail current before application of the test compound.

Calculation of such a suppression rate shows the possibility of inducing QT extension caused by the drug and the subsequent fatal adverse drug reactions (ventricular tachycardia, sudden death, etc.).

Pharmacological Experimental Example 6

Pharmacokinetics Test (Mouse Cassette PK)

The the compound in the present invention was administered to 7- or 8-week-old male C57BL/6J Jcl mice at a single oral dose of 1 mg/kg (administered solvent: DMSO: Tween 80:ultrapure water=1:1:8; 10 mL/kg). Thereafter, 0.25, 0.5, 1, or 2 hours later, blood was collected from the abdominal portion of vena cava of each mouse. The collected blood was centrifuged (3000 rpm, 15 minutes, and 4° C.), and using the obtained plasma, the test compound in the plasma was measured by high performance liquid chromatography/mass spectrometry. Likewise, standard solutions, to which test compounds each having a known concentration (0.01, 0.02, 0.05, 0.1, 0.2, 0.5, and 1 µg/mL) had been added, were measured, and a calibration curve was prepared. The plasma concentrations (µg/mL) were calculated from the prepared calibration curve, and the highest plasma concentration was defined as Cmax (µg/mL).

Pharmacological Experimental Example 7

Protein Binding Test

A DMSO solution of the compound in the present invention (10 mM) was added to normal plasma (human and rat) to a final concentration of 10 µM. Dialysis was carried out at 37° C. for 4 hours in a simple equilibrium dialyzer (RED Device (Linden Bioscience)). Thereafter, the inner solution (plasma side) and the outer solution (PBS side) of a dialysis membrane were subjected to high performance liquid chromatography/mass spectrometry, so that the test compound in the sample was measured. A non-binding percentage (%) was calculated based on the ratio between the PBS side and the plasma side, and a protein binding percentage (%) was then calculated from 100-non-binding percentage (%).

Pharmacological Experimental Example 8

Safety Test

The compound in the present invention was administered to mice or rats in a single dose via oral administration. No animal died, and significant behavior abnormality was not observed. Thus, the safety of the compound in the present invention was demonstrated.

The above results demonstrated that the compound in the present invention has an excellent PDE10 inhibitory effect. In addition, no abnormality was observed in the safety study, and thus, it was also demonstrated that the compound in the present invention has low toxicity.

Moreover, as a result of the above described tests, the compound in the present invention was confirmed to be favorable in terms of one of solubility, metabolic stability, pharmacokinetics, the avoidance of hERG channel inhibitory effect, etc.

Therefore, it is anticipated that the compound in the present invention will be used as a selective PDE10 inhibitor in agents for preventing and/or treating diseases such as certain types of mental disorders and conditions, such as mental disorder, paranoid disorder, and drug-induced psychosis, anxiety disorders such as panic disorder and obsessive-compulsive disorder, motor disorders including Parkinson's disease and Huntington's disease, mood disorder, neurodegenerative disorder, disorder involving deficits in attention and/or cognition, obesity, and drug addiction.

The compound in the present invention is anticipated to exhibit promising preventive or therapeutic effects on various types of diseases, as described below. Specifically, the present compound is anticipated to exhibit promising therapeutic effects on (1) paranoid, disorganized, catatonic, undifferentiated, or residual schizophrenia, (2) schizophreniform disorder, (3) paranoid or depressive schizoaffective disorder, (4) paranoid disorder, (5) substance-induced mental disorder, (6) psychosis induced by alcohol, amphetamine, *cannabis*, cocaine, a hallucinatory drug, an inhalant, opioid, or phencyclidine, (7) paranoic personality disorder, (8) schizotypal personality disorder, (9) Huntington's disease, (10) dyskinesia associated with dopamine agonist therapy, (11) Parkinson's disease, (12) restless legs syndrome, (13) essential tremor, (14) obsessive-compulsive disorder, (15) Tourette's syndrome, (16) tic disorder, (17) panic disorder, (18) agoraphobia, (19) specific phobias, (20) social phobias, (21) posttraumatic stress disorder, (22) acute stress disorder, (23) generalized anxiety disorder, (24) dementia; Alzheimer's disease, multiple cerebral infarction, alcoholic dementia or other drug-related dementia, dementia associated with intracranial tumor or brain damage, dementia associated with Huntington's disease or Parkinson's disease, AIDS-related dementia, or frontotemporal dementia, (25) delirium, (26) amnestic disorder, (27) mental retardation, (28) learning disorder; dyslexia, mathematics disorder, or disorder of written expression, (29) attention-deficit hyperactivity disorder, (30) age-related cognitive decline, (31) major depressive episode (mild level, moderate level, or severe level type), manic episode, mixed affective episode, or hypomanic episode, (32) atypical depression, (33) melancholic depression, (34) catatonic depression, (35) postpartum mood episode, (36) postapoplectic depression, (37) major depressive disorder, (38) dysthymic disorder/dysthymia, (39) minor depressive disorder, (40) premenstrual dysphoric disorder, (41) postschizophrenic depressive disorder, (42) major depressive disorder occurring with paranoid disorder or mental disorder such as schizophrenia, (43) bipolar disorder; bipolar disorder type I and bipolar disorder type II, (44) cyclothymic disorder, (45) neurodegeneration associated with brain damage, (46) neurodegeneration associated with stroke or neurodegeneration associated with cerebral infarction, (47) hypoglycemia-induced neurodegeneration, (48) neurodegeneration associated with epileptic seizure, (49) neurodegeneration associated with neurotoxic addiction, (50) multiple system atrophy, (51) neurodegeneration of striatal medium-sized spiny neurons, and the like.

EXAMPLES

Hereinafter, the present invention will be described more in detail in the following examples. However, these examples are not intended to limit the present invention.

For the measurement of nuclear magnetic resonance (NMR) spectra, JEOL JNM-ECX 400 (JEOL JNM-ECX 400) FT-NMR (manufactured by JEOL Ltd.) and JEOL JNM-ECX 300 (JEOL JNM-ECX 300) FT-NMR (manufactured by JEOL Ltd.) were used. LC-Mass was measured by any of the following methods. Waters FractionLynx MS System (manufactured by Waters) was used, and SunFire Column (4.6 mm×5 cm, 5 µm) manufactured by Waters was used as a column. Regarding a mobile phase, the following gradient conditions were applied. That is, [Method A] methanol:0.05% acetic acid aqueous solution=10:90 (0 minute)-100:0 (5 minutes)-100:0 (7 minutes), or [Method B] methanol:0.05% trifluoroacetic acid aqueous solution=10:90 (0 minute)-100:0 (5 minutes)-100:0 (7 minutes). UPLC/MS was measured using Waters UPLC-ZQ MS System (manufactured by Waters), and using MGIII-H (2.1 mm×5 cm, 3 µm) manufactured by Shiseido Co., Ltd., as a column. Regarding a mobile phase, the following gradient conditions were applied: [Method C] methanol:0.05% trifluoroacetic acid aqueous solution=5:95 (0 minute)-100:0 (1 minute)-100:0 (2 minutes). As a fractionation system, gradient conditions, which were appropriately altered depending on compounds, were used. As a microwave, Microwave Reactor (Initiator™) manufactured by Biotage® was used.

Example 1.1

Synthesis of 1-methyl-4-(5-methylpyridin-2-yl)-N-(2-phenylimidazo[1,2-a]pyridin-7-yl)-1H-pyrazole-5-carboxamide <Step 1> Synthesis of methyl 4-(5,5-dimethyl-1,3,2-dioxaborinan-2-yl)-1-methyl-1H-pyrazole-5-carboxylate A 1,1'-bis(diphenylphosphino)ferrocene-palladium(II) dichloride dichloromethane complex (0.37 g) and potassium acetate (3.5 g) were added to a dimethyl sulfoxide (10 ml) solution of 4-bromo-1-methyl-1H-pyrazole-5-carboxylate (2.0 g) and 5,5,5',5'-tetramethyl-2,2'-bi(1,3,2-dioxaborinane) (4.1 g). The obtained mixture was stirred in a nitrogen atmosphere at 100° C. for 4 hours. Thereafter, the reaction solution was cooled, and water (50 ml) was then added thereto, followed by extraction with ethyl acetate (100 ml) twice. Organic layers were gathered. The gathered organic layer was successively washed with water and a saturated saline, and was then dried over anhydrous sodium sulfate. The solvent was distilled away under reduced pressure, and the obtained residue was then purified by silica gel column chromatography (silica gel:eluent; heptane:ethyl acetate=90:10-40:60), so as to obtain the title compound (1.0 g) in the form of a brown liquid.

<Step 2> Synthesis of methyl 1-methyl-4-(5-methylpyridin-2-yl)-1H-pyrazole-5-carboxylate An aqueous solution (0.5 ml) of potassium carbonate (246 mg) was added to a 1,4-dioxane (1 ml) solution of the methyl 4-(5,5-dimethyl-1,3,2-dioxaborinan)-2-yl)-1-methyl-1H-pyrazole-5-carboxylate (150 mg) obtained in (Example 1.1) <Step 1>, 2-bromo-5-methylpyridine (102 mg), bis(dibenzylideneacetone)palladium (17 mg), and 2-dicyclohexylphosphino-2,4,6-triisopropyl-1,1'-biphenyl (57 mg). The obtained mixture was stirred in a nitrogen atmosphere at 100° C. for 1 hour. Thereafter, the reaction solution was extracted with ethyl acetate. The extract was washed with a saturated saline, and was then dried over anhydrous sodium sulfate. The solvent was distilled away under reduced pressure, and the obtained residue was then purified by silica gel column chromatography (silica gel:eluent; heptane:ethyl acetate=100:0-40:60), so as to obtain the title compound (110 mg) in the form of a yellow liquid.

<Step 3> Synthesis of 1-methyl-4-(5-methylpyridin-2-yl)-1H-pyrazole-5-carboxylic acid An aqueous solution (1.3 ml) of sodium hydroxide (50 mg) was added to a methanol (1.3 ml) solution of the methyl 1-methyl-4-(5-methylpyridin-2-yl)-1H-pyrazole-5-carboxylate (100 mg) obtained in (Example 1.1) <Step 2>. The obtained mixture was stirred at 70° C. for 1 hour. Thereafter, 1 N hydrochloric acid was added to the reaction solution to adjust the pH value to pH 5, and the reaction mixture was then extracted with methylene chloride three times. The organic layer was successively washed with water and a saturated saline, and was then dried over anhydrous sodium sulfate. The solvent was distilled away under reduced pressure, and a mixed solution of diethyl ether and heptane (1:1) was added to the obtained residue to solidify it, so as to obtain the title compound (74 mg) in the form of a white solid.

<Step 4> Synthesis of 1-methyl-4-(5-methylpyridin-2-yl)-N-(2-phenylimidazo[1,2-a]pyridin-7-yl)-1H-pyrazole-5-carboxamide Diisopropylethylamine (0.071 ml) was added to an N,N-dimethylformamide (1 ml) solution of 2-phenylimidazo[1,2-a]pyridin-7-amine hydrochloride (25 mg), the 1-methyl-4-(5-methylpyridin-2-yl)-1H-pyrazole-5-carboxylic acid (27 mg) obtained in (Example 1.1) <Step 3>, and O-(7-azabenzotriazol-1-yl)-N,N,N',N'-tetramethyluronium hexafluorophosphate (58 mg). The obtained mixture was stirred at room temperature for 14 hours. Thereafter, the reaction solution was fractionated and purified by LC/MS, so as to obtain the title compound (13 mg) in the form of a white solid.

Example 1.2

Synthesis of 1-methyl-4-(4-methylthiazol-2-yl)-N-(2-phenylimidazo[1,2-a]pyridin-7-yl)-1H-pyrazole-5-carboxamide <Step 1> Synthesis of methyl 1-methyl-4-(4-methylthiazol-2-yl)-1H-pyrazole-5-carboxylate Using 2-bromo-4-methylthiazole (106 mg), the title compound (110 mg) was obtained in a white amorphous form by the same method as that of (Example 1.1) <Step 2> or a method equivalent thereto.

<Step 2> Synthesis of 1-methyl-4-(4-methylthiazol-2-yl)-1H-pyrazole-5-carboxylic acid Using the methyl 1-methyl-4-(4-methylthiazol-2-yl)-1H-pyrazole-5-carboxylate (100 mg) obtained in (Example 1.2) <Step 1>, the title compound (58 mg) was obtained in the form of a beige solid by the same method as that of (Example 1.1) <Step 3> or a method equivalent thereto.

<Step 3> Synthesis of 1-methyl-4-(4-methylthiazol-2-yl)-N-(2-phenylimidazo[1,2-a]pyridin-7-yl)-1H-pyrazole-5-carboxamide Using the 1-methyl-4-(4-methylthiazol-2-yl)-1H-pyrazole-5-carboxylic acid (27 mg) obtained in (Example 1.2) <Step 2>, the title compound (6.0 mg) was obtained in the form of a light yellow solid by the same method as that of (Example 1.1) <Step 4> or a method equivalent thereto.

Example 1.3

Synthesis of 4-(4-(difluoromethyl)thiazol-2-yl)-1-methyl-N-(2-phenylimidazo[1,2-a]pyridin-7-yl)-1H-pyrazole-5-carboxamide <Step 1> Synthesis of methyl 4-(4-(difluoromethyl)thiazol-2-yl)-1-methyl-1H-pyrazole-5-carboxylate Using 2-bromo-4-(difluoromethyl)thiazole (600 mg), the title compound (590 mg) was obtained in a light brown amorphous form by the same method as that of (Example 1.1) <Step 2> or a method equivalent thereto.

<Step 2> Synthesis of 4-(4-(difluoromethyl)thiazol-2-yl)-1-methyl-N-(2-phenylimidazo[1,2-a]pyridin-7-yl)-1H-pyrazole-5-carboxamide An aqueous solution (0.28 ml) of 1 N sodium hydroxide was added to a methanol (1.4 ml) solution of the methyl 4-(4-(difluoromethyl)thiazol-2-yl)-1-methyl-1H-pyrazole-5-carboxylate (30 mg) obtained in (Example 1.3) <Step 1>. The obtained mixture was stirred at 60° C. for 30 minutes. Thereafter, the solvent was distilled away under reduced pressure, and the obtained residue was then subjected to azeotropy with toluene (10 ml). Subsequently, diisopropylethylamine (0.15 ml) and O-(benzotriazol-1-yl)-N,N,N',N'-tetramethyluronium tetrafluoroborate (138 mg) were added to an N,N-dimethylformamide (0.72 ml) solution of the obtained residue, and the thus obtained mixture was then stirred in a nitrogen atmosphere at room temperature for 30 minutes. Thereafter, 2-phenylimidazo[1,2-a]pyridin-7-amine (30 mg) was added to the reaction solution, and the mixture was then stirred for 18 hours 15 minutes. Thereafter, the reaction solution was fractionated and purified by LC/MS, so as to obtain the title compound (28 mg) in the form of a brown solid.

Example 1.4

Synthesis of 4-(4-(difluoromethyl)-5-methylthiazol-2-yl)-1-methyl-N-(2-phenylimidazo[1,2-a]pyridin-7-yl)-1H-pyrazole-5-carboxamide <Step 1> Synthesis of methyl 4-(5-bromo-4-(difluoromethyl)thiazol-2-yl)-1-methyl-1H-pyrazole-5-carboxylate N-bromosuccinimide (391 mg) was added to an N,N-dimethylformamide (3.6 ml) solution of the methyl 4-(4-(difluoromethyl)thiazol-2-yl)-1-methyl-1H-pyrazole-5-carboxylate (200 mg) obtained in (Example 1.3) <Step 1>, and the obtained mixture was then stirred in a nitrogen atmosphere at 80° C. for 40 minutes. Thereafter, N-bromosuccinimide (391 mg) was further added to the reaction solution, and the obtained mixture was then stirred in a nitrogen atmosphere at 80° C. for 15 hours. Thereafter, a sodium thiosulfate aqueous solution (40 ml) and a saturated sodium hydrogen carbonate aqueous solution (60 ml) were successively added to the reaction solution, and the reaction mixture was then extracted with ethyl acetate (60 ml) twice. Organic layers were gathered. The gathered organic layer was washed with a saturated saline (100 ml) three times, and was then dried over anhydrous sodium sulfate. The solvent was distilled away under reduced pressure, and the obtained residue was then dried under reduced pressure, so as to obtain the title compound (274 mg) in the form of a brown solid.

<Step 2> Synthesis of methyl 4-(4-(difluoromethyl)-5-methylthiazol-2-yl)-1-methyl-1H-pyrazole-5-carboxylate Toluene (19 ml) and water (1.7 ml) were added to a mixture of the methyl 4-(5-bromo-4-(difluoromethyl)thiazol-2-yl)-1-methyl-1H-pyrazole-5-carboxylate (270 mg) obtained in (Example 1.4) <Step 1>, 2,4,6-trimethoxyboroxin (289 mg), palladium acetate (II) (86 mg), tricyclohexylphosphine (251 mg), and potassium phosphate (651 mg). The obtained mixture was stirred in a nitrogen atmosphere at 110° C. for 35 minutes. Thereafter, the solvent was distilled away under reduced pressure, and the obtained residue was then purified by silica gel column chromatography (silica gel:eluent; heptane:ethyl acetate=92:8-40:60), so as to obtain the title compound (142 mg) in the form of a brown solid.

<Step 3> Synthesis of 4-(4-(difluoromethyl)-5-methylthiazol-2-yl)-1-methyl-N-(2-phenylimidazo[1,2-a]pyridin-7-yl)-1H-pyrazole-5-carboxamide Using the methyl 4-(4-(difluoromethyl)-5-methylthiazol-2-yl)-1-methyl-1H-pyrazole-5-carboxylate (27 mg) obtained in (Example 1.4) <Step 2>, the title compound (4.3 mg) was obtained in the form of a brown solid by the same method as that of (Example 1.3) <Step 2> or a method equivalent thereto.

Example 1.5

Synthesis of 1-methyl-N-(2-phenylimidazo[1,2-a]pyridin-7-yl)-4-(4-(trifluoromethyl)thiazol-2-yl)-1H-pyrazole-5-carboxamide <Step 1> Synthesis of methyl 1-methyl-4-(4-(trifluoromethyl)thiazol-2-yl)-1H-pyrazole-5-carboxylate Using 2-bromo-4-(trifluoromethyl)thiazole (291 mg), the title compound (259 mg) was obtained in the form of a light brown solid by the same method as that of (Example 1.1) <Step 2> or a method equivalent thereto.

<Step 2> Synthesis of 1-methyl-N-(2-phenylimidazo[1,2-a]pyridin-7-yl)-4-(4-(trifluoromethyl)thiazol-2-yl)-1H-pyrazole-5-carboxamide Using the methyl 1-methyl-4-(4-(trifluoromethyl)thiazol-2-yl)-1H-pyrazole-5-carboxylate (33 mg) obtained in (Example 1.5) <Step 1>, the title compound (5.9 mg) was obtained in the form of a white solid by the same method as that of (Example 1.3) <Step 2> or a method equivalent thereto.

Example 1.6

Synthesis of 1-methyl-N-(2-phenylimidazo[1,2-a]pyridin-7-yl)-4-(6-(trifluoromethyl)pyridin-2-yl)-1H-pyrazole-5-carboxamide <Step 1> Synthesis of methyl 1-methyl-4-(6-(trifluoromethyl)pyridin-2-yl)-1H-pyrazole-5-carboxylate Using 2-bromo-6-(trifluoromethyl)pyridine (269 mg), the title compound (220 mg) was obtained in the form of a colorless liquid by the same method as that of (Example 1.1) <Step 2> or a method equivalent thereto.

<Step 2> Synthesis of 1-methyl-N-(2-phenylimidazo[1,2-a]pyridin-7-yl)-4-(6-(trifluoromethyl)pyridin-2-yl)-1H-pyrazole-5-carboxamide Using the methyl 1-methyl-4-(6-(trifluoromethyl)pyridin-2-yl)-1H-pyrazole-5-carboxylate (33 mg) obtained in (Example 1.6) <Step 1>, the title compound (2.4 mg) was obtained in the form of a brown solid by the same method as that of (Example 1.3) <Step 2> or a method equivalent thereto.

Example 1.7

Synthesis of 4-(5-chloro-4-(difluoromethyl)thiazol-2-yl)-1-methyl-N-(2-phenylimidazo[1,2-a]pyridin-7-yl)-1H-pyrazole-5-carboxamide <Step 1> Synthesis of methyl 4-(5-chloro-4-(difluoromethyl)thiazol-2-yl)-1-methyl-1H-pyrazole-5-carboxylate Using the methyl 4-(4-(difluoromethyl)thiazol-2-yl)-1-methyl-1H-pyrazole-5-carboxylate (300 mg) obtained in (Example 1.3) <Step 1> and N-chlorosuccinimide (440 mg), the title compound (465 mg) was obtained in the form of a brown solid by the same method as that of (Example 1.4) <Step 1> or a method equivalent thereto.

<Step 2> Synthesis of 4-(5-chloro-4-(difluoromethyl)thiazol-2-yl)-1-methyl-1H-pyrazole-5-carboxylic acid Using the methyl 4-(5-chloro-4-(difluoromethyl)thiazol-2-yl)-1-methyl-1H-pyrazole-5-carboxylate (460 mg) obtained in (Example 1.7) <Step 1>, the title compound (306 mg) was obtained in the form of a brown solid by the same method as that of (Example 1.1) <Step 3> or a method equivalent thereto.

<Step 3> Synthesis of 4-(5-chloro-4-(difluoromethyl)thiazol-2-yl)-1-methyl-N-(2-phenylimidazo[1,2-a]pyridin-7-yl)-1H-pyrazole-5-carboxamide Diisopropylethylamine (0.30 ml) and O-(benzotriazol-1-yl)-N,N,N',N'-tetramethyluronium tetrafluoroborate (276 mg) were added to an N,N-dimethylformamide (0.72 ml) solution of the 4-(5-chloro-4-(difluoromethyl)thiazol-2-yl)-1-methyl-1H-pyrazole-5-carboxylic acid (42 mg) obtained in (Example 1.7) <Step 2>. The obtained mixture was stirred in a nitrogen atmosphere at room temperature for 30 minutes. Thereafter, 2-phenylimidazo[1,2-a]pyridin-7-amine (30 mg) was added to the reaction solution, and the obtained mixture was then stirred at 60° C. for 1 hour. Thereafter, the reaction solution was fractionated and purified by LC/MS to obtain the title compound (1 mg) in the form of a light brown solid.

Example 2.1

Synthesis of 1-methyl-4-(4-methylthiazol-2-yl)-N-(2-phenyl-5,6,7,8-tetrahydroimidazo[1,2-a]pyridin-7-yl)-1H-pyrazole-5-carboxamide <Step 1> Synthesis of 2-phenyl-5,6,7,8-tetrahydroimidazo[1,2-a]pyridin-7-amine hydrochloride Concentrated hydrochloric acid (0.11 ml) and platinum (IV) dioxide (83 mg) were added to a methanol (183 ml) solution of 2-phenylimidazo[1,2-a]pyridin-7-amine hydrochloride (900 mg), and the obtained mixture was then stirred in a hydrogen atmosphere for 4 hours. Thereafter, platinum (IV) dioxide (83 mg) was added to the reaction solution, and the obtained mixture was further stirred in a hydrogen atmosphere for 14 hours 30 minutes. Thereafter, the reaction solution was filtered with Celite, and was then washed with methanol (15 ml). The filtrate was concentrated under reduced pressure, and diethyl ether (3.6 ml) was then added to the obtained residue to solidify it, so as to obtain the title compound (733 mg) in the form of a gray solid.

<Step 2> Synthesis of 1-methyl-4-(4-methylthiazol-2-yl)-N-(2-phenyl-5,6,7,8-tetrahydroimidazo[1,2-a]pyridin-7-yl)-1H-pyrazole-5-carboxamide Diisopropylethylamine (70 µl) was added to a N,N-dimethylformamide (1 ml) solution of the 1-methyl-4-(4-methylthiazol-2-yl)-1H-pyrazole-5-carboxylic acid (22 mg) obtained in (Example 1.2) <Step 2>, the 2-phenyl-5,6,7,8-tetrahydroimidazo[1,2-a]pyridin-7-amine (25 mg) obtained in (Example 2.1) <Step 1>, and O-(7-azabenzotriazol-1-yl)-N,N,N',N'-tetramethyluronium hexafluorophosphate (57 mg). The obtained mixture was stirred at room temperature for 2 hours, and then at 60° C. for 1 hour. Thereafter, water (5 ml) was added to the reaction solution, and the reaction mixture was then extracted with ethyl acetate (10 ml). The organic layer was washed with a saturated saline, and was then dried over anhydrous sodium sulfate. The solvent was distilled away under reduced pressure, and the obtained residue was then purified by silica gel column chromatography (silica gel:eluent; heptane:ethyl acetate=90:10-20:80), so as to obtain the title compound (14 mg) in a white amorphous form.

Example 2.2

Synthesis of 4-(4,5-dimethylthiazol-2-yl)-1-methyl-N-(2-phenyl-5,6,7,8-tetrahydroimidazo[1,2-a]pyridin-7-yl)-1H-pyrazole-5-carboxamide <Step 1> Synthesis of methyl 4-(4,5-dimethylthiazol-2-yl)-1-methyl-1H-pyrazole-5-carboxylate Using 2-bromo-4,5-dimethylthiazole (274 mg), the title compound (170 mg) was obtained in the form of a white solid by the same method as that of (Example 1.1) <Step 2> or a method equivalent thereto.

<Step 2> Synthesis of sodium 4-(4,5-dimethylthiazol-2-yl)-1-methyl-1H-pyrazole-5-carboxylate An aqueous solution (1 ml) of sodium hydroxide (9.6 mg) was added to a methanol (1 ml) solution of the methyl 4-(4,5-dimethylthiazol-2-yl)-1-methyl-1H-pyrazole-5-carboxylate (30 mg) obtained in (Example 2.2) <Step 1>, and the obtained mixture was then heated to reflux for 15 minutes. Thereafter, the solvent was distilled away under reduced pressure, and the residue was then subjected to azeotropy with toluene, so as to obtain a crude product of the title compound.

<Step 3> Synthesis of 4-(4,5-dimethylthiazol-2-yl)-1-methyl-N-(2-phenyl-5,6,7,8-tetrahydroimidazo[1,2-a]pyridin-7-yl)-1H-pyrazole-5-carboxamide Using the sodium 4-(4,5-dimethylthiazol-2-yl)-1-methyl-1H-pyrazole-5-carboxylate (31 mg) obtained in (Example 2.2) <Step 2>, the title compound (19 mg) was obtained in the form of a white solid by the same method as that of (Example 2.1) <Step 2> or a method equivalent thereto.

Example 2.3

Synthesis of 1-methyl-N-(2-phenyl-5,6,7,8-tetrahydroimidazo[1,2-a]pyridin-7-yl)-4-(4-(trifluoromethyl)thiazol-2-yl)-1H-pyrazole-5-carboxamide A 1 N sodium hydroxide aqueous solution (0.33 ml) was added to a methanol (1.6 ml) solution of the methyl 1-methyl-4-(4-(trifluoromethyl)thiazol-2-yl)-1H-pyrazole-5-carboxylate (71 mg) obtained in (Example 1.5) <Step 1>, and the obtained mixture was then stirred at 60° C. for 30 minutes. Thereafter, the solvent was distilled away under reduced pressure, and the obtained residue was then subjected to azeotropy with toluene (10 ml). Diisopropylethylamine (0.17 ml), O-(benzotriazol-1-yl)-N,N,N',N'-tetramethyluronium tetrafluoroborate (187 mg), and the 2-phenyl-5,6,7,8-tetrahydroimidazo[1,2-a]pyridin-7-amine hydrochloride (35 mg) obtained in (Example 2.1) <Step 1> were added to an N,N-dimethylformamide (0.82 ml) solution of the obtained residue, and the obtained mixture was then stirred in a nitrogen atmosphere. Thereafter, the reaction solution was fractionated and purified by LC/MS to obtain the title compound (13 mg) in the form of an orange solid.

Example 2.4

Synthesis of 4-(4-(difluoromethyl)thiazol-2-yl)-1-methyl-N-(2-phenyl-5,6,7,8-tetrahydroimidazo[1,2-a]pyridin-7-yl)-1H-pyrazole-5-carboxamide Using the methyl 4-(4-(difluoromethyl)thiazol-2-yl)-1-methyl-1H-pyrazole-5-carboxylate (46 mg) obtained in (Example 1.3) <Step 1>, the title compound (69 mg) was obtained in the form of a light brown solid by the same method as that of (Example 2.3) or a method equivalent thereto.

Example 2.5

Synthesis of 4-(5-chloro-4-(difluoromethyl)thiazol-2-yl)-1-methyl-N-(2-phenyl-5,6,7,8-tetrahydroimidazo[1,2-a]pyridin-7-yl)-1H-pyrazole-5-carboxamide Using the 4-(5-chloro-4-(difluoromethyl)thiazol-2-yl)-1-methyl-1H-pyrazole-5-carboxylic acid (50 mg) obtained in (Example 1.7) <Step 2>, the title compound (12 mg) was obtained in the form of a brown solid by the same method as that of (Example 2.1) <Step 2> or a method equivalent thereto.

Example 2.6

Synthesis of 4-(4-(difluoromethyl)-5-methylthiazol-2-yl)-1-methyl-N-(2-phenyl-5,6,7,8-tetrahydroimidazo[1,2-a]pyridin-7-yl)-1H-pyrazole-5-carboxamide Using the methyl 4-(4-(difluoromethyl)-5-methylthiazol-2-yl)-1-methyl-1H-pyrazole-5-carboxylate (32 mg) obtained in (Example 1.4) <Step 2>, the title compound (22 mg) was obtained in the form of a brown solid by the same method as that of (Example 2.3) or a method equivalent thereto.

Example 2.7

Synthesis of 4-(4-(difluoromethyl)-5-methylthiazol-2-yl)-N-(2-(3-fluorophenyl)-5,6,7,8-tetrahydroimidazo[1,2-a]pyridin-7-yl)-1-methyl-1H-pyrazole-5-carboxamide <Step 1> Synthesis of methyl 2,3-dibromo-5,6,7,8-tetrahydroimidazo[1,2-a]pyridine-7-carboxylate N-bromosuccinimide (9 g) was added to a methylene chloride (200 ml) suspension of methyl 5,6,7,8-tetrahydroimidazo[1,2-a]pyridine-7-carboxylate hydrochloride (10 g) and sodium hydrogen carbonate (16 g) over 5 minutes, while keeping the temperature at 5° C. or less. The obtained mixture was stirred for 10 minutes at the same temperature as described above, and N-bromosuccinimide (9 g) was then added to the reaction solution at a temperature of 5° C. or less. The obtained mixture was stirred at 3° C. for 30 minutes. Thereafter, water (200 ml) was added to the reaction solution, and the mixture was then stirred. Subsequently, an organic layer was separated from a water layer, and the water layer was then extracted with methylene chloride (200 ml) again. Organic layers were gathered. The gathered organic layer was washed with a saturated saline, and the solvent was then distilled away under reduced pressure. The obtained residue was purified by silica gel column chromatography (silica gel:eluent; heptane:ethyl acetate=60:40-30:70), and the obtained fraction was then concentrated. The obtained residue was washed with methyl tert-butyl ether, and the filtrate was then concentrated under reduced pressure, so as to obtain the title compound (14 g) in the form of a yellow solid.

<Step 2> Synthesis of methyl 2-bromo-5,6,7,8-tetrahydroimidazo[1,2-a]pyridine-7-carboxylate A tetrahydrofuran (150 ml) solution of the methyl 2,3-dibromo-5,6,7,8-tetrahydroimidazo[1,2-a]pyridine-7-carboxylate (13 g) obtained in (Example 2.7) <Step 1> was cooled to −35° C. Thereafter, isopropylmagnesium bromide (95 ml, 1 M tetrahydrofuran solution) was added to the solution over 20 minutes, while keeping the temperature at −30° C. or less, and the reaction solution was then stirred at −35° C. for 30 minutes. Thereafter, water (350 ml) and ethyl acetate (250 ml) were added to the reaction solution, and insoluble matters were then removed by filtration with Celite. Subsequently, the filtrate was separated into an organic layer and a water layer. The water layer was extracted with ethyl acetate (250 ml), and the organic layers were then gathered. The gathered organic layer was washed with a saturated saline, and the solvent was then distilled away under reduced pressure. The obtained residue was purified by silica gel column chromatography (silica gel:eluent; heptane:ethyl acetate=70:30-30:70), so as to obtain the title compound (6.8 g) in the form of a white solid.

<Step 3> Synthesis of 2-bromo-5,6,7,8-tetrahydroimidazo[1,2-a]pyridine-7-carboxylic acid A 1 N sodium hydroxide aqueous solution (23 ml) was added to a methanol (23 ml) solution of the methyl 2-bromo-5,6,7,8-tetrahydroimidazo[1,2-a]pyridine-7-carboxylate (6.3 g) obtained in (Example 2.7) <Step 2>, and the obtained mixture was then stirred at 40° C. for 1 hour. Thereafter, 1 N hydrochloric acid (23 ml) was added to the reaction solution, and the generated solid was then collected by filtration, followed by washing with water (20 ml). The obtained solid was subjected to azeotropy with toluene, and was then dried under reduced pressure, so as to obtain the title compound (3.5 g) in the form of a beige solid.

<Step 4> Synthesis of tert-butyl (2-bromo-5,6,7,8-tetrahydroimidazo[1,2-a]pyridin-7-yl)carbamate Molecular Sieves 4A (6 g) was added to a tert-butanol (45 ml) solution of the 2-bromo-5,6,7,8-tetrahydroimidazo[1,2-a]pyridine-7-carboxylic acid (3.1 g) obtained in (Example 2.7) <Step 3> and triethylamine (9.7 ml), and the obtained mixture was then stirred at room temperature for 30 minutes. Thereafter, diphenyl phosphate azide (3.8 ml) was added to the reaction solution, and the obtained mixture was stirred for 30 minutes and then at 110° C. for 4 hours. Thereafter, the reaction solution was filtered with Celite, and insoluble matters were then washed with ethyl acetate. After that, ethyl acetate (100 ml) was added to the filtrate, and the obtained mixture was successively washed with a saturated ammonium chloride aqueous solution (25 ml) three times, a saturated sodium hydrogen carbonate aqueous solution (25 ml) twice, and a saturated saline. Then, the solvent was distilled away under reduced pressure. Methylene chloride was added to the obtained residue, and precipitated white insoluble matters were then removed by suction filtration. The filtrate was concentrated under reduced pressure, and the obtained residue was then purified by silica gel column chromatography (silica gel:eluent; heptane:ethyl acetate=60:40-20:80), so as to obtain the title compound (1.3 g) in the form of a white solid.

<Step 5> Synthesis of tert-butyl (2-(3-fluorophenyl)-5,6,7,8-tetrahydroimidazo[1,2-a]pyridin-7-yl) carbamate A dimethoxyethane (3 ml) and an aqueous solution (1 ml), which contained the tert-butyl (2-bromo-5,6,7,8-tetrahydroimidazo[1,2-a]pyridin-7-yl)carbamate (150 mg) obtained in (Example 2.7) <Step 4>, (3-fluorophenyl)boronic acid (80 mg), tetrakis(triphenylphosphine) palladium (44 mg), and cesium carbonate (464 mg), were heated to reflux for 2 hours 30 minutes. Thereafter, the reaction solution was diluted with ethyl acetate (30 ml). The thus diluted solution was successively washed with water (25 ml) twice and a saturated saline (20 ml), and was then dried over anhydrous sodium sulfate. The solvent was distilled away under reduced pressure, and the obtained residue was then purified by silica gel column chromatography (silica gel: eluent; heptane:ethyl acetate=50:50), so as to obtain the title compound (118 mg) in the form of a white solid.

<Step 6> Synthesis of 2-(3-fluorophenyl)-5,6,7,8-tetrahydroimidazo[1,2-a]pyridin-7-amine hydrochloride A 4 N hydrochloric acid-1,4-dioxane solution (5 ml) was added to the tert-butyl (2-(3-fluorophenyl)-5,6,7,8-tetrahydroimidazo[1,2-a]pyridin-7-yl)carbamate (116 mg) obtained in (Example 2.7) <Step 5>, and the obtained mixture was then stirred for 1 hour. Thereafter, the solvent was distilled away under reduced pressure, and the title compound (133 mg) was obtained in the form of a colorless solid.

<Step 7> Synthesis of 4-(4-(difluoromethyl)-5-methylthiazol-2-yl)-N-(2-(3-fluorophenyl)-5,6,7,8-tetrahydroimidazo[1,2-a]pyridin-7-yl)-1-methyl-1H-pyrazole-5-carboxamide Using the methyl 4-(4-(difluoromethyl)-5-methylthiazol-2-yl)-1-methyl-1H-pyrazole-5-carboxylate (30 mg) obtained in (Example 1.4) <Step 2> and a free form (20 mg) of the 2-(3-fluorophenyl)-5,6,7,8-tetrahydroimidazo[1,2-a]pyridin-7-amine hydrochloride obtained in (Example 2.7) <Step 6>, the title compound (3 mg) was obtained in the form of a brown solid by the same method as that of (Example 2.1) <Step 2> or a method equivalent thereto.

Example 2.8

Synthesis of N-(2-(3-fluorophenyl)-5,6,7,8-tetrahydroimidazo[1,2-a]pyridin-7-yl)-1-methyl-4-(4-(trifluoromethyl)thiazol-2-yl)-1H-pyrazole-5-carboxamide <Step 1> Synthesis of 1-methyl-4-(4-(trifluoromethyl)thiazol-2-yl)-1H-pyrazole-5-carboxylic acid Using the methyl 1-methyl-4-(4-(trifluoromethyl)thiazol-2-yl)-1H-pyrazole-5-carboxylate (210 mg) obtained in (Example 1.5) <Step 1>, the title compound (173 mg) was obtained in the form of a whitish brown solid by the same method as that of (Example 1.1) <Step 3> or a method equivalent thereto.

<Step 2> Synthesis of N-(2-(3-fluorophenyl)-5,6,7, 8-tetrahydroimidazo[1,2-a]pyridin-7-yl)-1-methyl-4-(4-(trifluoromethyl)thiazol-2-yl)-1H-pyrazole-5-carboxamide Using the 2-(3-fluorophenyl)-5,6,7,8-tetrahydroimidazo[1,2-a]pyridin-7-amine hydrochloride (48 mg) obtained in (Example 2.7) <Step 6> and the 1-methyl-4-(4-(trifluoromethyl)thiazol-2-yl)-1H-pyrazole-5-carboxylic acid (50 mg) obtained in (Example 2.8) <Step 1>, the title compound (6.1 mg) was obtained in the form of a colorless solid by the same method as that of (Example 2.1) <Step 2> or a method equivalent thereto.

Example 2.9

Synthesis of 1-methyl-4-(6-methylpyridin-2-yl)-N-(2-phenyl-5,6,7,8-tetrahydroimidazo[1,2-a]pyridin-7-yl)-1H-pyrazole-5-carboxamide <Step 1> Synthesis of methyl 1-methyl-4-(6-methylpyridin-2-yl)-1H-pyrazole-5-carboxylate Using 2-bromo-6-methylpyridine (273 mg), the title compound (427 mg) was obtained in the form of a colorless liquid by the same method as that of (Example 1.1) <Step 2> or a method equivalent thereto.

<Step 2> Synthesis of 1-methyl-4-(6-methylpyridin-2-yl)-N-(2-phenyl-5,6,7,8-tetrahydroimidazo[1, 2-a]pyridin-7-yl)-1H-pyrazole-5-carboxamide Using the methyl 1-methyl-4-(6-methylpyridin-2-yl)-1H-pyrazole-5-carboxylate (30 mg) obtained in (Example 2.9) <Step 1>, the corresponding sodium salts were obtained by the same method as that of (Example 2.2) <Step 2> or a method equivalent thereto. Using the obtained sodium salts (31 mg) and the 2-phenyl-5,6,7,8-tetrahydroimidazo[1,2-a]pyridin-7-amine hydrochloride (32 mg) obtained in (Example 2.2) <Step 1>, the title compound (22 mg) was obtained in the form of a colorless rubbery substance by the same method as that of (Example 2.1) <Step 2> or a method equivalent thereto.

Example 2.10

Synthesis of 1-methyl-4-(5-methyl-1,3,4-thiadiazol-2-yl)-N-(2-phenyl-5,6,7,8-tetrahydroimidazo[1,2-a]pyridin-7-yl)-1H-pyrazole-5-carboxamide <Step 1> Synthesis of methyl 1-methyl-4-(5-methyl-1,3,4-thiadiazol-2-yl)-1H-pyrazole-5-carboxylate Using 2-bromo-5-methyl-1,3,4-thiadiazole (320 mg), the title compound (100 mg) was obtained in the form of a yellow solid by the same method as that of (Example 1.1) <Step 2> or a method equivalent thereto.

<Step 2> Synthesis of 1-methyl-4-(5-methyl-1,3,4-thiadiazol-2-yl)-1H-pyrazole-5-carboxylic acid Using the methyl 1-methyl-4-(5-methyl-1,3,4-thiadiazol-2-yl)-1H-pyrazole-5-carboxylate (100 mg) obtained in (Example 2.10) <Step 1>, the title compound (80 mg) was obtained in the form of a light orange solid by the same method as that of (Example 1.1) <Step 3> or a method equivalent thereto.

<Step 3> Synthesis of 1-methyl-4-(5-methyl-1,3,4-thiadiazol-2-yl)-N-(2-phenyl-5,6,7,8-tetrahydroimidazo[1,2-a]pyridin-7-yl)-1H-pyrazole-5-carboxamide Using the 1-methyl-4-(5-methyl-1,3,4-thiadiazol-2-yl)-1H-pyrazole-5-carboxylic acid (22 mg) obtained in (Example 2.10) <Step 2>, the title compound (15 mg) was obtained in a white amorphous form by the same method as that of (Example 2.1) <Step 2> or a method equivalent thereto.

Example 2.11

Synthesis of 4-(6-methoxypyridin-2-yl)-1-methyl-N-(2-phenyl-5,6,7,8-tetrahydroimidazo[1,2-a]pyridin-7-yl)-1H-pyrazole-5-carboxamide <Step 1> Synthesis of methyl 4-(6-methoxypyridin-2-yl)-1-methyl-1H-pyrazole-5-carboxylate Using 2-bromo-6-methoxypyridine (336 mg), the title compound (263 mg) was obtained in the form of a colorless liquid by the same method as that of (Example 1.1) <Step 2> or a method equivalent thereto.

<Step 2> Synthesis of sodium 4-(6-methoxypyridin-2-yl)-1-methyl-1H-pyrazole-5-carboxylate Using the methyl 4-(6-methoxypyridin-2-yl)-1-methyl-1H-pyrazole-5-carboxylate (30 mg) obtained in (Example 2.11) <Step 1>, the title compound (50 mg) was obtained in the form of a colorless solid by the same method as that of (Example 2.2) <Step 2> or a method equivalent thereto.

<Step 3> Synthesis of 4-(6-methoxypyridin-2-yl)-1-methyl-N-(2-phenyl-5,6,7,8-tetrahydroimidazo[1,2-a]pyridin-7-yl)-1H-pyrazole-5-carboxamide Using the sodium 4-(6-methoxypyridin-2-yl)-1-methyl-1H-pyrazole-5-carboxylate (31 mg) obtained in (Example 2.11) <Step 2>, the title compound (22 mg) was obtained in the form of a colorless solid by the same method as that of (Example 2.1) <Step 2> or a method equivalent thereto.

Example 2.12

Synthesis of 1-methyl-4-(2-methylthiazol-4-yl)-N-(2-phenyl-5,6,7,8-tetrahydroimidazo[1,2-a]pyridin-7-yl)-1H-pyrazole-5-carboxamide <Step 1> Synthesis of methyl 1-methyl-4-(2-methylthiazol-4-yl)-1H-pyrazole-5-carboxylate Using 4-bromo-2-methylthiazole (254 mg), the title compound (180 mg) was obtained in the form of a whitish brown solid by the same method as that of (Example 1.1) <Step 2> or a method equivalent thereto.

<Step 2> Synthesis of 1-methyl-4-(2-methylthiazol-4-yl)-N-(2-phenyl-5,6,7,8-tetrahydroimidazo[1,2-a]pyridin-7-yl)-1H-pyrazole-5-carboxamide Using the methyl 1-methyl-4-(2-methylthiazol-4-yl)-1H-pyrazole-5-carboxylate (30 mg) obtained in (Example 2.12)

<Step 1>, the corresponding sodium salts were obtained by the same method as that of (Example 2.2) <Step 2> or a method equivalent thereto. Using the obtained sodium salts (31 mg), the title compound (21 mg) was obtained in the form of a white solid by the same method as that of (Example 2.1) <Step 2> or a method equivalent thereto.

Example 2.13

Synthesis of 1-methyl-4-(6-methylpyrazin-2-yl)-N-(2-phenyl-5,6,7,8-tetrahydroimidazo[1,2-a]pyridin-7-yl)-1H-pyrazole-5-carboxamide <Step 1> Synthesis of methyl 1-methyl-4-(6-methylpyrazin-2-yl)-1H-pyrazole-5-carboxylate Using 2-bromo-6-methylpyrazine (309 mg), the title compound (281 mg) was obtained in the form of a yellow solid by the same method as that of (Example 1.1) <Step 2> or a method equivalent thereto.

<Step 2> Synthesis of sodium 1-methyl-4-(6-methylpyrazin-2-yl)-1H-pyrazole-5-carboxylate Using the methyl 1-methyl-4-(6-methylpyrazin-2-yl)-1H-pyrazole-5-carboxylate (53 mg) obtained in (Example 2.13) <Step 1>, the title compound (80 mg) was obtained in the form of a colorless solid by the same method as that of (Example 2.2) <Step 2> or a method equivalent thereto.

<Step 3> Synthesis of 1-methyl-4-(6-methylpyrazin-2-yl)-N-(2-phenyl-5,6,7,8-tetrahydroimidazo[1,2-a]pyridin-7-yl)-1H-pyrazole-5-carboxamide Using the sodium 1-methyl-4-(6-methylpyrazin-2-yl)-1H-pyrazole-5-carboxylate (27 mg) obtained in (Example 2.13) <Step 2>, the title compound (13 mg) was obtained in the form of a colorless solid by the same method as that of (Example 2.1) <Step 2> or a method equivalent thereto.

Example 2.14

Synthesis of 4-(3-isopropyl-1,2,4-thiadiazol-5-yl)-1-methyl-N-(2-phenyl-5,6,7,8-tetrahydroimidazo[1,2-a]pyridin-7-yl)-1H-pyrazole-5-carboxamide <Step 1> Synthesis of methyl-4-(3-isopropyl-1,2,4-thiadiazol-5-yl)-1-methyl-1H-pyrazole-5-carboxylate Using 5-bromo-3-isopropyl-1,2,4-thiadiazole (295 mg), the title compound (140 mg) was obtained in the form of a light orange solid by the same method as that of (Example 1.1) <Step 3> or a method equivalent thereto.

<Step 2> Synthesis of 4-(3-isopropyl-1,2,4-thiadiazol-5-yl)-1-methyl-N-(2-phenyl-5,6,7,8-tetrahydroimidazo[1,2-a]pyridin-7-yl)-1H-pyrazole-5-carboxamide Using the methyl-4-(3-isopropyl-1,2,4-thiadiazol-5-yl)-1-methyl-1H-pyrazole-5-carboxylate (30 mg) obtained in (Example 2.14) <Step 1>, the corresponding sodium salts were obtained by the same method as that of (Example 2.2) <Step 2> or a method equivalent thereto. Using the obtained sodium salts (30 mg), the title compound (10 mg) was

Example 2.15

Synthesis of 1-methyl-4-(5-methylthiazol-2-yl)-N-(2-phenyl-5,6,7,8-tetrahydroimidazo[1,2-a]pyridin-7-yl)-1H-pyrazole-5-carboxamide <Step 1> Synthesis of methyl 1-methyl-4-(5-methylthiazol-2-yl)-1H-pyrazole-5-carboxylate Using 2-bromo-5-methylthiazole (318 mg), the title compound (150 mg) was obtained in the form of a light brown liquid by the same method as that of (Example 1.1) <Step 2> or a method equivalent thereto.

<Step 2> Synthesis of 1-methyl-4-(5-methylthiazol-2-yl)-N-(2-phenyl-5,6,7,8-tetrahydroimidazo[1,2-a]pyridin-7-yl)-1H-pyrazole-5-carboxamide Using the methyl-1-methyl-4-(5-methylthiazol-2-yl)-1H-pyrazole-5-carboxylate (30 mg) obtained by (Example 2.15) <Step 1>, the corresponding sodium salts were obtained by the same method as that of (Example 2.2) <Step 2> or a method equivalent thereto. Using the obtained sodium salts (31 mg), the title compound (20 mg) was obtained in the form of a white solid by the same method as that of (Example 2.1) <Step 2> or a method equivalent thereto.

Example 2.16

Synthesis of 1-methyl-4-(4-methylpyrimidin-2-yl)-N-(2-phenyl-5,6,7,8-tetrahydroimidazo[1,2-a]pyridin-7-yl)-1H-pyrazole-5-carboxamide <Step 1> Synthesis of methyl 1-methyl-4-(4-methylpyrimidin-2-yl)-1H-pyrazole-5-carboxylate Using 2-bromo-4-methylpyrimidine (113 mg), the title compound (126 mg) was obtained in the form of a yellow solid by the same method as that of (Example 1.1) <Step 2> or a method equivalent thereto.

<Step 2> Synthesis of sodium 1-methyl-4-(4-methylpyrimidin-2-yl)-1H-pyrazole-5-carboxylate Using the methyl 1-methyl-4-(4-methylpyrimidin-2-yl)-1H-pyrazole-5-carboxylate (37 mg) obtained in (Example 2.16) <Step 1>, the title compound (56 mg) was obtained in the form of a colorless solid by the same method as that of (Example 2.2) <Step 2> or a method equivalent thereto.

<Step 3> Synthesis of 1-methyl-4-(4-methylpyrimidin-2-yl)-N-(2-phenyl-5,6,7,8-tetrahydroimidazo[1,2-a]pyridin-7-yl)-1H-pyrazole-5-carboxamide Using the sodium 1-methyl-4-(4-methylpyrimidin-2-yl)-1H-pyrazole-5-carboxylate (19 mg) obtained in (Example 2.16) <Step 2>, the title compound (8.7 mg) was obtained in the form of a colorless solid by the same method as that of (Example 2.1) <Step 2> or a method equivalent thereto.

Example 2.17

Synthesis of 1-methyl-4-(1-methyl-1H-imidazol-4-yl)-N-(2-phenyl-5,6,7,8-tetrahydroimidazo[1,2-a]pyridin-7-yl)-1H-pyrazole-5-carboxamide <Step 1> Synthesis of methyl 1-methyl-4-(1-methyl-1H-imidazol-4-yl)-1H-pyrazole-5-carboxylate Using 4-bromo-1-methyl-1H-imidazole (249 mg), the title compound (110 mg) was obtained in the form of a white solid by the same method as that of (Example 1.1) <Step 2> or a method equivalent thereto.

<Step 2> Synthesis of 1-methyl-4-(1-methyl-1H-imidazol-4-yl)-N-(2-phenyl-5,6,7,8-tetrahydroimidazo[1,2-a]pyridin-7-yl)-1H-pyrazole-5-carboxamide Using the methyl 1-methyl-4-(1-methyl-1H-imidazol-4-yl)-1H-pyrazole-5-carboxylate (30 mg) obtained in (Example 2.17) <Step 1>, the corresponding sodium salts were obtained by the same method as that of (Example 2.2) <Step 2> or a method equivalent thereto. Using the obtained sodium salts (31 mg), the title compound (9.9 mg) was obtained in the form of a white solid by the same method as that of (Example 2.1) <Step 2> or a method equivalent thereto.

Example 2.18

Synthesis of N-(2-(2,5-difluorophenyl)-5,6,7,8-tetrahydroimidazo[1,2-a]pyridin-7-yl)-1-methyl-4-(5-methyl-1,3,4-thiadiazol-2-yl)-1H-pyrazole-5-carboxamide <Step 1> Synthesis of methyl 2-(2,5-difluorophenyl)imidazo[1,2-a]pyridine-7-carboxylate 2-Bromo-1-(2,5-difluorophenyl)ethanone (1.5 g) was added to an ethanol (8.2 ml) solution of methyl 2-aminoisonicotinate (1.0 g), and the obtained mixture was then stirred in a nitrogen atmosphere at 60° C. for 18 hours. Thereafter, 2-bromo-1-(2,5-difluorophenyl)ethanone (0.77 g) was added to the reaction solution, and the obtained mixture was then stirred for 6 hours at the same temperature as described above. Thereafter, the reaction solution was concentrated under reduced pressure, and ethyl acetate (10 ml) was then added to the obtained residue. The precipitated solid was collected by filtration, and it was washed with ethyl acetate (15 ml) and heptane (6 ml) and was then dried, so as to obtain the title compound (2.5 g) in the form of a pink solid.

<Step 2> Synthesis of 2-(2,5-difluorophenyl)imidazo[1,2-a]pyridine-7-carboxylic acid Using the methyl 2-(2,5-difluorophenyl)imidazo[1,2-a]pyridine-7-carboxylate (2.4 g) obtained in (Example 2.18) <Step 1>, the title compound (1.2 g) was obtained in the form of a light yellow solid by the same method as that of (Example 2.7) <Step 3> or a method equivalent thereto.

<Step 3> Synthesis of tert-butyl (2-(2,5-difluorophenyl)imidazo[1,2-a]pyridin-7-yl)carbamate Using the 2-(2,5-difluorophenyl)imidazo[1,2-a]pyridine-7-carboxylic acid (1.2 g) obtained in (Example 2.18) <Step 2>, the title compound (786 mg) was obtained in the form of a yellow solid by the same method as that of (Example 2.7) <Step 4> or a method equivalent thereto.

<Step 4> Synthesis of 2-(2,5-difluorophenyl)imidazo[1,2-a]pyridin-7-amine hydrochloride Using the tert-butyl (2-(2,5-difluorophenyl)imidazo[1,2-a]pyridin-7-yl)carbamate (780 mg) obtained in (Example 2.18) <Step 3>, the title compound (886 mg) was obtained in the form of a light yellow solid by the same method as that of (Example 2.7) <Step 6> or a method equivalent thereto.

<Step 5> Synthesis of 2-(2,5-difluorophenyl)-5,6,7,8-tetrahydroimidazo[1,2-a]pyridin-7-amine Concentrated hydrochloric acid (0.095 ml) and platinum dioxide (0.11 g) were added to a methanol (31 ml) solution of the 2-(2,5-difluorophenyl)imidazo[1,2-a]pyridin-7-yl)amine hydrochloride (0.88 g) obtained in (Example 2.18) <Step 4>, and the obtained mixture was then stirred in a hydrogen atmosphere for 5 hours 30 minutes. Thereafter, platinum dioxide (0.14 g) was added to the reaction solution, and the obtained mixture was then stirred in a hydrogen atmosphere for 2.5 hours. Thereafter, the reaction solution was filtered with Celite, and was then washed with methanol (30 ml). The filtrate was concentrated under reduced pressure, and the obtained residue was then purified by silica gel column chromatography (NH silica gel:eluent; heptane:ethyl acetate=1:4-methylene chloride:methanol=20:1), so as to obtain the title compound (0.44 g) in the form of a colorless solid.

<Step 6> Synthesis of N-(2-(2,5-difluorophenyl)-5,6,7,8-tetrahydroimidazo[1,2-a]pyridin-7-yl)-1-methyl-4-(5-methyl-1,3,4-thiadiazol-2-yl)-1H-pyrazole-5-carboxamide Using the 2-(2,5-difluorophenyl)-5,6,7,8-tetrahydroimidazo[1,2-a]pyridin-7-amine (30 mg) obtained in (Example 2.18) <Step 5> and the 1-methyl-4-(5-methyl-1,3,4-thiazol-2-yl)-1H-pyrazole-5-carboxylic acid (32 mg) obtained in (Example 2.10) <Step 2>, the title compound (43 mg) was obtained in the form of a colorless solid by the same method as that of (Example 2.1) <Step 2> or a method equivalent thereto.

Example 2.19

Synthesis of N-(3-fluoro-2-phenyl-5,6,7,8-tetrahydroimidazo[1,2-a]pyridin-7-yl)-1-methyl-4-(4-(trifluoromethyl)thiazol-2-yl)-1H-pyrazole-5-carboxamide <Step 1> Synthesis of (Z)-methyl 2-((2,2,2-trifluoro-1-phenylethylidene)amino)isonicotinate Thionyl chloride (2.2 ml) was added at 0° C. to a pyridine (4.8 ml) solution of 2,2,2-trifluoro-1-phenylethanone (5.1 g) and 2-aminopyridine-4-carboxylic acid methyl ester (4.5 g). The temperature of the reaction solution was increased to room temperature, and the reaction solution was then stirred for 1 hour. Thereafter, the reaction solution was poured into a 1 N sodium hydroxide aqueous solution, and the mixed solution was then extracted with ethyl acetate. Organic layers were gathered, and the gathered organic layer was then dried over anhydrous sodium sulfate. After that, the solvent was distilled away under reduced pressure. The obtained residue was purified by silica gel column chromatography (silica gel: eluent; heptane:ethyl acetate=2:1-1:1), so as to obtain the title compound (2.5 g) in the form of a yellow liquid.

<Step 2> Synthesis of methyl 3-fluoro-2-phenylimidazo[1,2-a]pyridine-7-carboxylate Trimethyl phosphite (1.9 ml) was added to an N-methylpyrrolidone (10 ml) solution of the (Z)-methyl 2-((2,2,2-trifluoro-1-phenylethylidene)amino)isonicotinate (2.5 g) obtained in (Example 2.19) <Step 1>, and the obtained mixture was then stirred in microwave at 150° C. for 60 minutes. Thereafter, water was added to the reaction solution, and the mixed solution was then extracted with ethyl acetate. Organic layers were gathered, and the gathered organic layer was then dried over sodium sulfate. The solvent was distilled away under reduced pressure, and the obtained residue was then purified by silica gel column chromatography (silica gel: eluent; heptane:ethyl acetate=90:10-50:50), so as to obtain the title compound (1.9 g) in the form of a brown solid.

<Step 3> Synthesis of methyl 3-fluoro-2-phenyl-5,6,7,8-tetrahydroimidazo[1,2-a]pyridine-7-carboxylate A palladium carbon-ethylenediamine complex (0.6 g) was added to a methanol (120 ml) solution of the methyl 3-fluoro-2-phenylimidazo[1,2-a]pyridine-7-carboxylate (0.6 g) obtained in (Example 2.19) <Step 2> and concentrated hydrochloric acid (0.6 ml), and the obtained mixture was then stirred in a hydrogen atmosphere for 7 hours. Thereafter, the reaction solution was filtered with Celite, and the filtrate was then concentrated under reduced pressure. The obtained residue was purified by silica gel column chromatography (silica gel:eluent; heptane:ethyl acetate=2:1-1:1), so as to obtain a crude product (123 mg) containing the title compound in the form of a yellow solid.

<Step 4> Synthesis of 3-fluoro-2-phenyl-5,6,7,8-tetrahydroimidazo[1,2-a]pyridine-7-carboxylic acid Using the crude product (123 mg) containing the methyl 3-fluoro-2-phenylimidazo[1,2-a]pyridine-7-carboxylate obtained in (Example 2.19) <Step 3>, a crude product (200 mg) containing the title compound was obtained in the form of a colorless solid by the same method as that of (Example 2.7) <Step 3> or a method equivalent thereto.

<Step 5> Synthesis of tert-butyl (3-fluoro-2-phenyl-5,6,7,8-tetrahydroimidazo[1,2-a]pyridin-7-yl)carbamate Using the 3-fluoro-2-phenyl-5,6,7,8-tetrahydroimidazo[1,2-a]pyridine-7-carboxylic acid (133 mg) obtained in (Example 2.19) <Step 4>, the title compound (52 mg) was obtained in the form of a colorless solid by the same method as that of (Example 2.7) <Step 4> or a method equivalent thereto.

<Step 6> Synthesis of 3-fluoro-2-phenyl-5,6,7,8-tetrahydroimidazo[1,2-a]pyridin-7-amine hydrochloride Using the tert-butyl (3-fluoro-2-phenyl-5,6,7,8-tetrahydroimidazo[1,2-a]pyridin-7-yl)carbamate (52 mg) obtained in (Example 2.19) <Step 5>, the title compound (41 mg) was obtained in the form of a colorless solid by the same method as that of (Example 2.7) <Step 6> or a method equivalent thereto.

<Step 7> Synthesis of sodium 1-methyl-4-(4-(trifluoromethyl)thiazol-2-yl)-1H-pyrazole-5-carboxylate Sodium hydroxide (3.5 mg) was added to a mixed solution of water (1 ml) and methanol (1 ml) containing the methyl 1-methyl-4-(4-(trifluoromethyl)thiazol-2-yl)-1H-pyrazole-5-carboxylate (13 mg) obtained in (Example 1.5) <Step 1>, and the obtained mixture was then stirred at 70° C. for 30 minutes. Thereafter, the reaction solution was subjected to azeotropy with toluene, so as to obtain the title compound (20 mg) in the form of a colorless solid.

<Step 8> Synthesis of N-(3-fluoro-2-phenyl-5,6,7,8-tetrahydroimidazo[1,2-a]pyridin-7-yl)-1-methyl-4-(4-(trifluoromethyl)thiazol-2-yl)-1H-pyrazole-5-carboxamide Using the 3-fluoro-2-phenyl-5,6,7,8-tetrahydroimidazo[1,2-a]pyridin-7-amine hydrochloride (12 mg) obtained in (Example 2.19) <Step 6> and the sodium 1-methyl-4-(4-(trifluoromethyl)thiazol-2-yl)-1H-pyrazole-5-carboxylate (13 mg) obtained in (Example 2.19) <Step 7>, the title compound (7.5 mg) was obtained in the form of a colorless solid by the same method as that of (Example 2.1) <Step 2> or a method equivalent thereto.

Example 2.20

Synthesis of 4-(4-(difluoromethyl)thiazol-2-yl)-N-(2-(3-fluorophenyl)-5,6,7,8-tetrahydroimidazo[1,2-a]pyridin-7-yl)-1-methyl-1H-pyrazole-5-carboxamide Using the 4-(4-(difluoromethyl)thiazol-2-yl)-1-methyl-1H-pyrazole-5-carboxylic acid (9.8 mg) obtained in (Example 3.12) <Step 1> and the 2-(3-fluorophenyl)-5,6,7,8-tetrahydroimidazo[1,2-a]pyridin-7-amine (8.0 mg) obtained in (Example 2.7) <Step 6>, the title compound (8 mg) was obtained in the form of a white solid by the same method as that of (Example 2.1) <Step 2> or a method equivalent thereto.

The compounds of (Example 2.21) and (Example 2.22) were synthesized by the same method as that of (Example 2.1) <Step 2> or (Example 2.3), or a method equivalent thereto, using the corresponding carboxylic acid or sodium salts.

Example 2.21

1-methyl-4-(5-methylpyridin-2-yl)-N-(2-phenyl-5,6,7,8-tetrahydroimidazo[1,2-a]pyridin-7-yl)-1H-pyrazole-5-carboxamide Example 2.22

1-methyl-4-(4-methylpyridin-2-yl)-N-(2-phenyl-5,6,7,8-tetrahydroimidazo[1,2-a]pyridin-7-yl)-1H-pyrazole-5-carboxamide The compounds of (Example 2.23) and (Example 2.24) were synthesized by the same method as that of (Example 2.3) or a method equivalent thereto, using the corresponding sodium salts of carboxylic acid and the 2-(3-fluorophenyl)-5,6,7,8-tetrahydroimidazo[1,2-a]pyridin-7-amine hydrochloride obtained in (Example 2.7) <Step 6>.

Example 2.23

N-(2-(3-fluorophenyl)-5,6,7,8-tetrahydroimidazo[1,2-a]pyridin-7-yl)-1-methyl-4-(4-methylpyrimidin-2-yl)-1H-pyrazole-5-carboxamide Example 2.24

N-(2-(3-fluorophenyl)-5,6,7,8-tetrahydroimidazo[1,2-a]pyridin-7-yl)-1-methyl-4-(6-methylpyrazin-2-yl)-1H-pyrazole-5-carboxamide Example 2.25

Synthesis of 1-methyl-N-(2-phenyl-5,6,7,8-tetrahydroimidazo[1,2-a]pyridin-7-yl)-4-(thiazol-4-yl)-1H-pyrazole-5-carboxamide <Step 1> Synthesis of methyl 1-methyl-4-(thiazol-4-yl)-1H-pyrazole-5-carboxylate Using 4-bromothiazole (195 mg), the title compound (167 mg) was obtained in the form of a light yellow solid by the same method as that of (Example 1.1.) <Step 2> or a method equivalent thereto.

<Step 2> Synthesis of 1-methyl-N-(2-phenyl-5,6,7,8-tetrahydroimidazo[1,2-a]pyridin-7-yl)-4-(thiazol-4-yl)-1H-pyrazole-5-carboxamide Using the methyl 1-methyl-4-(thiazol-4-yl)-1H-pyrazole-5-carboxylate (39 mg) obtained in (Example 2.25) <Step 1>, the title compound (18 mg) was obtained in the form of a brown solid by the same method as that of (Example 2.3) or a method equivalent thereto.

Example 2.26

Synthesis of 1-methyl-N-(2-phenyl-5,6,7,8-tetrahydroimidazo[1,2-a]pyridin-7-yl)-4-(thiazol-2-yl)-1H-pyrazole-5-carboxamide <Step 1> Synthesis of methyl 1-methyl-4-(thiazol-2-yl)-1H-pyrazole-5-carboxylate Using 2-bromothiazole (195 mg), the title compound (133 mg) was obtained in the form of a brown solid by the same method as that of (Example 1.1.) <Step 2> or a method equivalent thereto.

<Step 2> Synthesis of 1-methyl-N-(2-phenyl-5,6,7,8-tetrahydroimidazo[1,2-a]pyridin-7-yl)-4-(thiazol-2-yl)-1H-pyrazole-5-carboxamide Using the methyl 1-methyl-4-(thiazol-2-yl)-1H-pyrazole-5-carboxylate (39 mg) obtained in (Example 2.26) <Step 1>, the title compound (16 mg) was obtained in the form of a brown solid by the same method as that of (Example 2.3) or a method equivalent thereto.

Example 2.27

Synthesis of 4-(4-(tert-butyl)thiazol-2-yl)-1-methyl-N-(2-phenyl-5,6,7,8-tetrahydroimidazo[1,2-a]pyridin-7-yl)-1H-pyrazole-5-carboxamide <Step 1> Synthesis of methyl 4-(4-(tert-butyl)thiazol-2-yl)-1-methyl-1H-pyrazole-5-carboxylate Using 2-bromo-4-(tert-butyl)thiazole (262 mg), the title compound (190 mg) was obtained in the form of a light orange solid by the same method as that of (Example 1.1) <Step 2> or a method equivalent thereto.

<Step 2> Synthesis of 4-(4-(tert-butyl)thiazol-2-yl)-1-methyl-N-(2-phenyl-5,6,7,8-tetrahydroimidazo[1,2-a]pyridin-7-yl)-1H-pyrazole-5-carboxamide Using the methyl 4-(4-(tert-butyl)thiazol-2-yl)-1-methyl-1H-pyrazole-5-carboxylate (30 mg) obtained in (Example 2.27) <Step 1>, the title compound (30 mg) was obtained in the form of a white solid by the same method as that of (Example 2.3) or a method equivalent thereto.

Example 2.28

Synthesis of 4-(4-(difluoromethyl)thiazol-2-yl)-N-(2-(4-fluorophenyl)-5,6,7,8-tetrahydroimidazo[1,2-a]pyridin-7-yl)-1-methyl-1H-pyrazole-5-carboxamide <Step 1> Synthesis of 2-(4-fluorophenyl)-5,6,7,8-tetrahydroimidazo[1,2-a]pyridin-7-amine Using 2-(4-fluorophenyl)-imidazo[1,2-a]pyridin-7-amine hydrochloride (430 mg), the title compound (75 mg) was obtained in the form of a light orange solid by the same method as that of (Example 2.1) <Step 1> or a method equivalent thereto.

<Step 2> Synthesis of 4-(4-(difluoromethyl)thiazol-2-yl)-N-(2-(4-fluorophenyl)-5,6,7,8-tetrahydroimidazo[1,2-a]pyridin-7-yl)-1-methyl-1H-pyrazole-5-carboxamide Using the methyl 4-(4-(difluoromethyl)thiazol-2-yl)-1-methyl-1H-pyrazole-5-carboxylate (5.0 mg) obtained in (Example 1.3) <Step 1> and the 2-(4-fluorophenyl)-5,6,7,8-tetrahydroimidazo[1,2-a]pyridin-7-amine (3.5 mg) obtained in (Example 2.28) <Step 1>, the title compound (1.4 mg) was obtained in the form of a brown solid by the same method as that of (Example 2.3) or a method equivalent thereto.

Example 2.29

Synthesis of N-(2-(4-fluorophenyl)-5,6,7,8-tetrahydroimidazo[1,2-a]pyridin-7-yl)-1-methyl-4-(4-(trifluoromethyl)thiazol-2-yl)-1H-pyrazole-5-carboxamide Using the corresponding hydrochloride (19 mg) of the 2-(4-fluorophenyl)-5,6,7,8-tetrahydroimidazo[1,2-a]pyridin-7-amine obtained in (Example 2.28) <Step 1> and the 1-methyl-4-(4-(trifluoromethyl)thiazol-2-yl)-1H-pyrazole-5-carboxylic acid (20 mg) obtained in (Example 2.8) <Step 1>, the title compound (4.6 mg) was obtained in the form of a colorless solid by the same method as that of (Example 2.1) <Step 2> or a method equivalent thereto.

Example 3.1

Synthesis of N-(6-fluoro-2-phenyl-[1,2,4]triazolo[1,5-a]pyridin-7-yl)-1-methyl-4-(3-methylpyridin-2-yl)-1H-pyrazole-5-carboxamide <Step 1> Synthesis of methyl 1-methyl-4-(4,4,5,5-tetramethyl-1,3,2-dioxaborolan-2-yl)-1H-pyrazole-5-carboxylate 4,4,4',4',5,5,5',5'-Octamethyl-2,2'-bi(1,3,2-dioxaborolane) (1.9 g), potassium acetate (1.1 g), and 1,1'-bis(diphenylphosphino)ferrocene-palladium(II) dichloride (0.28 g) were added to a dimethyl sulfoxide (15 ml) solution of methyl 4-iodo-1-methyl-1H-pyrazole-5-carboxylate (1.0 g), and the obtained mixture was then stirred in a nitrogen atmosphere at 100° C. for 45 minutes. Thereafter, the reaction solution was subjected to suction filtration using Celite, and was then washed with ethyl acetate (100 ml) and water (50 ml). After that, a saturated sodium hydrogen carbonate aqueous solution (50 ml) was added to the filtrate, and a water layer was separated from an organic layer. The organic layer was successively washed with a saturated ammonium chloride aqueous solution (50 ml) twice, water (100 ml) three times, and a saturated saline (100 ml). The organic layer was dried over anhydrous sodium sulfate. The solvent was distilled away under reduced pressure, and the obtained residue was then purified by silica gel column chromatography (silica gel: eluent; heptane:ethyl acetate=90:10-0:100), so as to obtain the title compound (0.30 g) in a yellow amorphous form.

<Step 2> Synthesis of methyl 1-methyl-4-(3-methylpyridin-2-yl)-1H-pyrazole-5-carboxylate Using the methyl 1-methyl-4-(4,4,5,5-tetramethyl-1,3,2-dioxaborolan-2-yl)-1H-pyrazole-5-carboxylate (1.4 g) obtained in (Example 3.1) <Step 1> and 2-bromo-3-methylpyridine (1.1 g), the title compound (0.54 g) was obtained in the form of a yellow liquid by the same method as that of (Example 1.1) <Step 2> or a method equivalent thereto.

<Step 3> Synthesis of 1-methyl-4-(3-methylpyridin-2-yl)-1H-pyrazole-5-carboxylic acid Using the methyl 1-methyl-4-(3-methylpyridin-2-yl)-1H-pyrazole-5-carboxylate (537 mg) obtained in (Example 3.1) <Step 2>, the title compound (439 mg) was obtained in the form of a light brown solid by the same method as that of (Example 1.1) <Step 3> or a method equivalent thereto.

<Step 4> Synthesis of (N-(6-fluoro-2-phenyl-[1,2,4]triazolo[1,5-a]pyridin-7-yl)-1-methyl-4-(3-methylpyridin-2-yl)-1H-pyrazole-5-carboxamide Phosphorus oxychloride (0.011 ml) was added at 0° C. to a pyridine (0.5 ml) solution of the methyl 1-methyl-4-(3-methylpyridin-2-yl)-1H-pyrazole-5-carboxylic acid (16 mg) obtained in (Example 3.1) <Step 3> and 6-fluoro-2-phenyl-[1,2,4]triazolo[1,5-a]pyridin-7-amine hydrochloride (obtained according to the method described in International Publication No. WO2012/076430, p. 80, Example 30-h) (13 mg). The obtained mixture was stirred at the same temperature as described above for 30 minutes. Thereafter, water was added to the reaction solution, and the precipitated solid was collected by suction filtration and was then washed with methanol, so as to obtain the title compound (18 mg) in the form of a colorless solid.

Example 3.2

Synthesis of N-(6-fluoro-2-phenyl-[1,2,4]triazolo[1,5-a]pyridin-7-yl)-1-methyl-4-(5-methylpyrazin-2-yl)-1H-pyrazole-5-carboxamide <Step 1> Synthesis of 1-methyl-4-(5-methylpyrazin-2-yl)-1H-pyrazole-5-carboxylic acid Using 2-bromo-5-methylpyrazine (312 mg), the title compound (85 mg) was obtained in the form of a gray solid by the same methods as those of (Example 3.1) <Step 2> and (Example 1.1) <Step 3>, or methods equivalent thereto.

<Step 2> Synthesis of N-(6-fluoro-2-phenyl-[1,2,4]triazolo[1,5-a]pyridin-7-yl)-1-methyl-4-(5-methylpyrazin-2-yl)-1H-pyrazole-5-carboxamide Using the 1-methyl-4-(5-methylpyrazin-2-yl)-1H-pyrazole-5-carboxylic acid (18 mg) obtained in (Example 3.2) <Step 1>, the title compound (4.4 mg) was obtained in the form of a gray solid by the same method as that of (Example 3.1) <Step 4> or a method equivalent thereto.

Example 3.3

Synthesis of N-(6-fluoro-2-phenyl-[1,2,4]triazolo[1,5-a]pyridin-7-yl)-1-methyl-4-(6-methylpyridin-2-yl)-1H-pyrazole-5-carboxamide <Step 1> Synthesis of 1-methyl-4-(6-methylpyridin-2-yl)-1H-pyrazole-5-carboxylic acid Using the methyl 1-methyl-4-(6-methylpyridin-2-yl)-1H-pyrazole-5-carboxylate (427 mg) obtained in (Example 2.9) <Step 1>, the title compound (206 mg) was obtained in the form of a colorless solid by the same method as that of (Example 1.1) <Step 3> or a method equivalent thereto.

<Step 2> Synthesis of N-(6-fluoro-2-phenyl-[1,2,4]triazolo[1,5-a]pyridin-7-yl)-1-methyl-4-(6-methylpyridin-2-yl)-1H-pyrazole-5-carboxamide Using the 1-methyl-4-(6-methylpyridin-2-yl)-1H-pyrazole-5-carboxylic acid (18 mg) obtained in (Example 3.3) <Step 1>, the title compound (1.6 mg) was obtained in the form of a brown solid by the same method as that of (Example 3.1) <Step 4> or a method equivalent thereto.

Example 3.4

Synthesis of N-(6-fluoro-2-phenyl-[1,2,4]triazolo[1,5-a]pyridin-7-yl)-4-(4-fluoropyridin-2-yl)-1-methyl-1H-pyrazole-5-carboxamide <Step 1> Synthesis of sodium 4-(4-fluoropyridin-2-yl)-1-methyl-1H-pyrazole-5-carboxylate Using 2-bromo-4-fluoropyridine (331 mg), the title compound (361 mg) was obtained in the form of a brown solid by the same methods as those of (Example 3.1) <Step 2> and (Example 2.2) <Step 2>, or methods equivalent thereto.

<Step 2> Synthesis of N-(6-fluoro-2-phenyl-[1,2,4]triazolo[1,5-a]pyridin-7-yl)-4-(4-fluoropyridin-2-yl)-1-methyl-1H-pyrazole-5-carboxamide Using the sodium 4-(4-fluoropyridin-2-yl)-1-methyl-1H-pyrazole-5-carboxylate (21 mg) obtained in (Example 3.4) <Step 1>, the title compound (2.8 mg) was obtained in the form of a colorless solid by the same method as that of (Example 3.1) <Step 4> or a method equivalent thereto.

Example 3.5

Synthesis of N-(6-fluoro-2-phenyl-[1,2,4]triazolo[1,5-a]pyridin-7-yl)-1-methyl-4-(4-methylpyridin-2-yl)-1H-pyrazole-5-carboxamide <Step 1> Synthesis of sodium 1-methyl-4-(4-methylpyridin-2-yl)-1H-pyrazole-5-carboxylate Using 2-bromo-4-methylpyridine (310 mg), the title compound (300 mg) was obtained in the form of a brown solid by the same methods as those of (Example 3.1) <Step 2> and (Example 2.2) <Step 2>, or methods equivalent thereto.

<Step 2> Synthesis of N-(6-fluoro-2-phenyl-[1,2,4]triazolo[1,5-a]pyridin-7-yl)-1-methyl-4-(4-methylpyridin-2-yl)-1H-pyrazole-5-carboxamide Using the sodium 1-methyl-4-(4-methylpyridin-2-yl)-1H-pyrazole-5-carboxylate (20 mg) obtained in (Example 3.5) <Step 1>, the title compound (1.3 mg) was obtained in the form of a colorless solid by the same method as that of (Example 3.1) <Step 4> or a method equivalent thereto.

Example 3.6

Synthesis of N-(6-fluoro-2-phenyl-[1,2,4]triazolo[1,5-a]pyridin-7-yl)-1-methyl-4-(4-(trifluoromethyl)thiazol-2-yl)-1H-pyrazole-5-carboxamide <Step 1> Synthesis of 1-methyl-4-(4-(trifluoromethyl)thiazol-2-yl)-1H-pyrazole-5-carboxylic acid Using the methyl 1-methyl-4-(4-(trifluoromethyl)thiazol-2-yl)-1H-pyrazole-5-carboxylate (210 mg) obtained in (Example 1.5) <Step 1>, the title compound (173 mg) was obtained in the form of a whitish brown solid by the same method as that of (Example 1.1) <Step 3> or a method equivalent thereto.

<Step 2> Synthesis of N-(6-fluoro-2-phenyl-[1,2,4]triazolo[1,5-a]pyridin-7-yl)-1-methyl-4-(4-(trifluoromethyl)thiazol-2-yl)-1H-pyrazole-5-carboxamide Using the 1-methyl-4-(4-(trifluoromethyl)thiazol-2-yl)-1H-pyrazole-5-carboxylic acid (17 mg) obtained in (Example 3.6) <Step 1>, the title compound (5.0 mg) was obtained in the form of a white solid by the same method as that of (Example 3.1) <Step 4> or a method equivalent thereto.

Example 3.7

Synthesis of N-(6-fluoro-2-phenyl-[1,2,4]triazolo[1,5-a]pyridin-7-yl)-4-(3-methoxypyridin-2-yl)-1-methyl-1H-pyrazole-5-carboxamide <Step 1> Synthesis of sodium 4-(3-methoxypyridin-2-yl)-1-methyl-1H-pyrazole-5-carboxylate Using 2-bromo-3-methoxypyridine (339 mg), the title compound (469 mg) was obtained in the form of a gray solid by the same methods as those of (Example 3.1) <Step 2> and (Example 2.2) <Step 2>, or methods equivalent thereto.

<Step 2> Synthesis of N-(6-fluoro-2-phenyl-[1,2,4]triazolo[1,5-a]pyridin-7-yl)-4-(3-methoxypyridin-2-yl)-1-methyl-1H-pyrazole-5-carboxamide Using the sodium 4-(3-methoxypyridin-2-yl)-1-methyl-1H-pyrazole-5-carboxylate (21 mg) obtained in (Example 3.7) <Step 1>, the title compound (6.5 mg) was obtained in the form of a colorless solid by the same method as that of (Example 3.1) <Step 4> or a method equivalent thereto.

Example 3.8

Synthesis of N-(6-fluoro-2-phenyl-[1,2,4]triazolo[1,5-a]pyridin-7-yl)-4-(5-fluoropyridin-2-yl)-1-methyl-1H-pyrazole-5-carboxamide <Step 1> Synthesis of sodium 4-(5-fluoropyridin-2-yl)-1-methyl-1H-pyrazole-5-carboxylate Using 2-bromo-5-fluoropyridine (317 mg), the title compound (418 mg) was obtained in the form of a brown solid by the same methods as those of (Example 3.1) <Step 2> and (Example 2.2) <Step 2>, or methods equivalent thereto.

<Step 2> Synthesis of N-(6-fluoro-2-phenyl-[1,2,4]triazolo[1,5-a]pyridin-7-yl)-4-(5-fluoropyridin-2-yl)-1-methyl-1H-pyrazole-5-carboxamide Using the sodium 4-(5-fluoropyridin-2-yl)-1-methyl-1H-pyrazole-5-carboxylate (24 mg) obtained in (Example 3.8) <Step 1>, the title compound (1.3 mg) was obtained in the form of a colorless solid by the same method as that of (Example 3.1) <Step 4> or a method equivalent thereto.

Example 3.9

Synthesis of N-(6-fluoro-2-phenyl-[1,2,4]triazolo[1,5-a]pyridin-7-yl)-1-methyl-4-(6-methylpyrazin-2-yl)-1H-pyrazole-5-carboxamide <Step 1> Synthesis of methyl 1-methyl-4-(6-methylpyrazin-2-yl)-1H-pyrazole-5-carboxylate Using 2-bromo-6-methylpyrazine (275 mg), the title compound (228 mg) was obtained in the form of a light yellow liquid by the same method as that of (Example 1.1) <Step 2> or a method equivalent thereto.

<Step 2> Synthesis of 1-methyl-4-(6-methylpyrazin-2-yl)-1H-pyrazole-5-carboxylic acid Using the methyl 1-methyl-4-(6-methylpyrazin-2-yl)-1H-pyrazole-5-carboxylate (225 mg) obtained in (Example 3.9) <Step 1>, the title compound (184 mg) was obtained in the form of a white solid by the same method as that of (Example 1.1) <Step 3> or a method equivalent thereto.

<Step 3> Synthesis of N-(6-fluoro-2-phenyl-[1,2,4]triazolo[1,5-a]pyridin-7-yl)-1-methyl-4-(6-methylpyrazin-2-yl)-1H-pyrazole-5-carboxamide Using the 1-methyl-4-(6-methylpyrazin-2-yl)-1H-pyrazole-5-carboxylic acid (16 mg) obtained in (Example 3.9) <Step 2>, the title compound (3.1 mg) was obtained in the form of an orange solid by the same method as that of (Example 3.1) <Step 4> or a method equivalent thereto.

Example 3.10

Synthesis of N-(6-fluoro-2-phenyl-[1,2,4]triazolo[1,5-a]pyridin-7-yl)-1-methyl-4-(6-(trifluoromethyl)pyridin-2-yl)-1H-pyrazole-5-carboxamide <Step 1> Synthesis of 1-methyl-4-(6-(trifluoromethyl)pyridin-2-yl)-1H-pyrazole-5-carboxylic acid Using the methyl 1-methyl-4-(6-(trifluoromethyl)pyridin-2-yl)-1H-pyrazole-5-carboxylate (556 mg) obtained in (Example 1.6) <Step 1>, the title compound (160 mg) was obtained in the form of a colorless solid by the same method as that of (Example 1.1) <Step 3> or a method equivalent thereto.

<Step 2> Synthesis of N-(6-fluoro-2-phenyl-[1,2,4]triazolo[1,5-a]pyridin-7-yl)-1-methyl-4-(6-(trifluoromethyl)pyridin-2-yl)-1H-pyrazole-5-carboxamide Using the 1-methyl-4-(6-(trifluoromethyl)pyridin-2-yl)-1H-pyrazole-5-carboxylic acid (10 mg) obtained in (Example 3.10) <Step 1>, the title compound (2.0 mg) was obtained in the form of a white solid by the same method as that of (Example 3.1) <Step 4> or a method equivalent thereto.

Example 3.11

Synthesis of 4-(4,6-dimethylpyridin-2-yl)-N-(6-fluoro-2-phenyl-[1,2,4]triazolo[1,5-a]pyridin-7-yl)-1-methyl-1H-pyrazole-5-carboxamide <Step 1> Synthesis of sodium 4-(4,6-dimethylpyridin-2-yl)-1-methyl-1H-pyrazole-5-carboxylate Using 2-bromo-4,6-dimethylpyridine (252 mg), the title compound (191 mg) was obtained in the form of a brown solid by the same methods as those of (Example 3.1) <Step 2> and (Example 2.2) <Step 2>, or methods equivalent thereto.

<Step 2> Synthesis of 4-(4,6-dimethylpyridin-2-yl)-N-(6-fluoro-2-phenyl-[1,2,4]triazolo[1,5-a]pyridin-7-yl)-1-methyl-1H-pyrazole-5-carboxamide Using the sodium 4-(4,6-dimethylpyridin-2-yl)-1-methyl-1H-pyrazole-5-carboxylate (139 mg) obtained in (Example 3.11) <Step 1>, the title compound (35.4 mg) was obtained in the form of a colorless solid by the same method as that of (Example 3.1) <Step 4> or a method equivalent thereto.

Example 3.12

Synthesis of 4-(4-(difluoromethyl)thiazol-2-yl)-N-(6-fluoro-2-phenyl-[1,2,4]triazolo[1,5-a]pyridin-7-yl)-1-methyl-1H-pyrazole-5-carboxamide <Step 1> Synthesis of 4-(4-(difluoromethyl)thiazol-2-yl)-1-methyl-1H-pyrazole-5-carboxylic acid Using the methyl 4-(4-(difluoromethyl)thiazol-2-yl)-1-methyl-1H-pyrazole-5-carboxylate (60 mg) obtained in (Example 1.3) <Step 1>, the title compound (57 mg) was obtained in the form of a beige solid by the same method as that of (Example 1.1) <Step 3> or a method equivalent thereto.

<Step 2> Synthesis of 4-(4-(difluoromethyl)thiazol-2-yl)-N-(6-fluoro-2-phenyl-[1,2,4]triazolo[1,5-a]pyridin-7-yl)-1-methyl-1H-pyrazole-5-carboxamide Using the 4-(4-(difluoromethyl)thiazol-2-yl)-1-methyl-1H-pyrazole-5-carboxylic acid (12 mg) obtained in (Example 3.12) <Step 1>, the title compound (3.5 mg) was obtained in the form of a colorless solid by the same method as that of (Example 3.1) <Step 4> or a method equivalent thereto.

Example 3.13

Synthesis of 4-(3-cyanopyridin-2-yl)-N-(6-fluoro-2-phenyl-[1,2,4]triazolo[1,5-a]pyridin-7-yl)-1-methyl-1H-pyrazole-5-carboxamide <Step 1> Synthesis of methyl 4-(3-cyanopyridin-2-yl)-1-methyl-1H-pyrazole-5-carboxylate Using 2-chloronicotinonitrile (780 mg), the title compound (2.0 g) was obtained in the form of a black liquid by the same method as that of (Example 3.1) <Step 2> or a method equivalent thereto.

<Step 2> Synthesis of 4-(3-cyanopyridin-2-yl)-1-methyl-1H-pyrazole-5-carboxylic acid Using the methyl 4-(3-cyanopyridin-2-yl)-1-methyl-1H-pyrazole-5-carboxylate (930 mg) obtained in (Example 3.13) <Step 1>, the title compound (456 mg) was obtained in the form of a brown solid by the same method as that of (Example 3.1) <Step 3> or a method equivalent thereto.

<Step 3> Synthesis of 4-(3-cyanopyridin-2-yl)-N-(6-fluoro-2-phenyl-[1,2,4]triazolo[1,5-a]pyridin-7-yl)-1-methyl-1H-pyrazole-5-carboxamide Using the 4-(3-cyanopyridin-2-1-yl)-1-methyl-1H-pyrazole-5-carboxylic acid (19 mg) obtained in (Example 3.13) <Step 2>, the title compound (11 mg) was obtained in the form of a colorless solid by the same method as that of (Example 3.1) <Step 4> or a method equivalent thereto.

Example 3.14

Synthesis of 4-(3,6-dimethylpyrazin-2-yl)-N-(6-fluoro-2-phenyl-[1,2,4]triazolo[1,5-a]pyridin-7-yl)-1-methyl-1H-pyrazole-5-carboxamide <Step 1> Synthesis of methyl 4-(3,6-dimethylpyrazin-2-yl)-1-methyl-1H-pyrazole-5-carboxylate Using 3-chloro-2,5-dimethylpyrazine (0.80 g), the title compound (1.2 g) was obtained in the form of a black liquid by the same method as that of (Example 3.1) <Step 2> or a method equivalent thereto.

<Step 2> Synthesis of 4-(3,6-dimethylpyrazin-2-yl)-1-methyl-1H-pyrazole-5-carboxylic acid Using the methyl 4-(3,6-dimethylpyrazin-2-yl)-1-methyl-1H-pyrazole-5-carboxylate (930 mg) obtained in (Example 3.14) <Step 1>, the title compound (199 mg) was obtained in the form of a colorless solid by the same method as that of (Example 1.1) <Step 3> or a method equivalent thereto.

<Step 3> Synthesis of 4-(3,6-dimethylpyrazin-2-yl)-N-(6-fluoro-2-phenyl-[1,2,4]triazolo[1,5-a]pyridin-7-yl)-1-methyl-1H-pyrazole-5-carboxamide Using the 4-(3,6-dimethylpyrazin-2-yl)-1-methyl-1H-pyrazole-5-carboxylic acid (19 mg) obtained in (Example 3.14) <Step 2>, the title compound (9.3 mg) was obtained in the form of a colorless solid by the same method as that of (Example 3.1) <Step 4> or a method equivalent thereto.

Example 3.15

Synthesis of 4-(4-(difluoromethyl)thiazol-2-yl)-1-methyl-N-(2-phenyl-[1,2,4]triazolo[1,5-a]pyridin-7-yl)-1H-pyrazole-5-carboxamide <Step 1> Synthesis of methyl 2-amino-[1,2,4]triazolo[1,5-a]pyridine-7-carboxylate Ethoxycarbonyl isothiocyanate (8.6 g) was added to a 1,4-dioxane (100 ml) solution of methyl 2-aminoisonicotinate (9.0 g), and the obtained mixture was then stirred for 90 minutes. Thereafter, the solvent was distilled away under reduced pressure, and the obtained residue was then added to a mixed solution of diisopropylethylamine (34 ml), methanol (40 ml) and ethanol (70 ml) containing hydroxyamine hydrochloride (22 g). The obtained mixture was stirred under heating at 60° C. for 15 hours. Thereafter, the precipitated solid was collected by filtration, and was then washed with ethanol (30 ml), so as to obtain the title compound (9.8 g) in the form of a white solid.

<Step 2> Synthesis of methyl 2-bromo-[1,2,4]triazolo[1,5-a]pyridine-7-carboxylate An acetonitrile (560 ml) suspension of tert-butyl nitrile (10.7 g) and copper(II) bromide (23.3 g) was stirred at 70° C. for 10 minutes. Thereafter, the methyl 2-amino-[1,2,4]triazolo[1,5-a]pyridine-7-carboxylate (14.3 g) obtained in (Example 3.15) <Step 1> was added to the reaction solution at the same temperature as described above over 20 minutes, and the obtained mixture was then stirred under heating at 75° C. for 1 hour. Thereafter, ethyl acetate (500 ml) and water (500 ml) were added to the reaction solution, and insoluble matters were then removed by Celite. After that, the Celite was washed with ethyl acetate (250 ml). The filtrate was separated into a water layer and an organic layer, and the water layer was then extracted with ethyl acetate (250 ml). Organic layers were combined, and the combined organic layer was successively washed with a 5% ammonia aqueous solution (300 ml) twice and water (300 ml). The solvent was distilled away under reduced pressure, so as to obtain a crude product of the title compound (11.5 g) in the form of a beige solid.

<Step 3> Synthesis of 2-bromo-[1,2,4]triazolo[1,5-a]pyridine-7-carboxylic acid

A 1 N sodium hydroxide aqueous solution (150 ml) was added to a methanol (150 ml) suspension of the methyl 2-bromo-[1,2,4]triazolo[1,5-a]pyridine-7-carboxylate (10 g) obtained in (Example 3.15) <Step 2>, and the obtained mixture was then stirred for 30 minutes. Thereafter, about half of the solvent was distilled away under reduced pressure, and the residue was then adjusted to pH 4 by addition of 3 N hydrochloric acid (50 ml). The precipitated solid was collected by filtration, and was then successively washed with water (50 ml) and methyl tert-butyl ether (20 ml). The obtained solid was subjected to azeotropy with toluene to obtain the title compound (9.0 g) in the form of a white solid.

<Step 4> Synthesis of tert-butyl (2-bromo-[1,2,4]triazolo[1,5-a]pyridin-7-yl)carbamate Triethylamine (0.39 ml), MS4A (1.5 g), and diphenyl phosphate azide (0.18 ml) were added to a tert-butanol (5 ml) solution of the 2-bromo-[1,2,4]triazolo[1,5-a]pyridine-7-carboxylate (0.17 g) obtained in (Example 3.15) <Step 3>. The obtained mixture was stirred at room temperature for 1 hour, and then at 100° C. for 2 hours. Thereafter, ethyl acetate (50 ml) was added to the reaction solution, and the mixed solution was then filtered with Celite. The filtrate was washed with a saturated sodium hydrogen carbonate aqueous solution (20 ml), and was then dried over anhydrous sodium sulfate. The solvent was distilled away under reduced pressure, and the obtained residue was then purified by silica gel column chromatography (silica gel:eluent; heptane:ethyl acetate=75:25-50:50), so as to obtain the title compound (0.15 g) in a white amorphous form.

<Step 5> Synthesis of 2-bromo-[1,2,4]triazolo[1,5-a]pyridin-7-amine hydrochloride A suspension of 4 N hydrochloric acid-1,4-dioxane (8 ml) and 1,4-dioxane (8 ml) containing the tert-butyl (2-bromo-[1,2,4]triazolo[1,5-a]pyridin-7-yl)carbamate (400 mg) obtained in (Example 3.15) <Step 4> was heated to reflux for 40 minutes. Thereafter, the precipitated solid was collected by filtration, and was then washed with 1,4-dioxane (15 ml). The obtained solid was dried to obtain the title compound (279 mg) in the form of a white solid.

<Step 6> Synthesis of N-(2-bromo-[1,2,4]triazolo[1,5-a]pyridin-7-yl)-4-(4-(difluoromethyl)thiazol-2-yl)-1-methyl-1H-pyrazole-5-carboxamide Propylphosphonic anhydride (1.2 ml, a 50% ethyl acetate solution) and diisopropylethylamine (0.42 ml) were added to a tetrahydrofuran (12 ml) solution of the 4-(4-(difluoromethyl)thiazole-2-yl)-1 methyl-1H-pyrazole-5-carboxylic acid (156 mg) obtained in (Example 3.12) <Step 1> and the 2-bromo-[1,2,4]triazolo[1,5-a]pyridin-7-amine hydrochloride (150 mg) obtained in (Example 3.15) <Step 5>, and the obtained mixture was then stirred under heating at 100° C. for 12 hours. The reaction solution was poured into water (30 ml), and the mixed solution was then extracted with ethyl acetate (10 ml) three times. Organic layers were combined. The combined organic layer was washed with water (5 ml), and was then dried over anhydrous sodium sulfate. The solvent was distilled away under reduced pressure, and the obtained residue was then purified by silica gel column chromatography (silica gel:eluent; heptane:ethyl acetate=90:10-50:50), so as to obtain the title compound (254 mg) in the form of a white solid.

<Step 7> Synthesis of 4-(4-(difluoromethyl)thiazol-2-yl)-1-methyl-N-(2-phenyl-[1,2,4]triazolo[1,5-a]pyridin-7-yl)-1H-pyrazole-5-carboxamide Dimethoxyethane (1 ml) and water (0.5 ml), which contained the N-(2-bromo-[1,2,4]triazolo[1,5-a]pyridin-7-yl)-4-(4-(difluoromethyl)thiazol-2-yl)-1-methyl-1H-pyrazole-5-carboxamide (20 mg) obtained in (Example 3.15) <Step 6>, phenylboronic acid (6.4 mg), cesium carbonate (43 mg), and tetrakis(triphenylphosphine) palladium (5.1 mg), were stirred under heating at 100° C. for 3 hours. Thereafter, the reaction solution was cooled to room temperature. Water (20 ml) and ethyl acetate (10 ml) were added to the reaction solution, and an organic layer was separated from a water layer, followed by extraction with ethyl acetate (5 ml) twice. Organic layers were combined, and the combined organic layer was washed with water (10 ml) and was then dried over anhydrous sodium sulfate. The solvent was distilled away under reduced pressure, and the obtained residue was purified by preparative thin-layer chromatography (silica gel:eluent; heptane:ethyl acetate=0:100), so as to obtain the title compound (1.4 mg) in the form of a white solid.

Example 3.16

Synthesis of 4-(4-(difluoromethyl)thiazol-2-yl)-N-(2-(2-methoxyphenyl)-[1,2,4]triazolo[1,5-a]pyridin-7-yl)-1-methyl-1H-pyrazole-5-carboxamide Using 2-methoxyphenylboronic acid (8.0 mg), the title compound (11 mg) was obtained in the form of a yellow solid by the same method as that of (Example 3.15) <Step 7> or a method equivalent thereto.

Example 3.17

Synthesis of 4-(4-(difluoromethyl)thiazol-2-yl)-N-(2-(3-fluorophenyl)-[1,2,4]triazolo[1,5-a]pyridin-7-yl)-1-methyl-1H-pyrazole-5-carboxamide Using 3-fluorophenylboronic acid (11 mg), the title compound (1.1 mg) was obtained in the form of a light yellow solid by the same method as that of (Example 3.15) <Step 7> or a method equivalent thereto.

Example 3.18

Synthesis of 4-(4-ethylthiazol-2-yl)-1-methyl-N-(2-phenyl-[1,2,4]triazolo[1,5-a]pyridin-7-yl)-1H-pyrazole-5-carboxamide <Step 1> Synthesis of methyl 4-(4-ethylthiazol-2-yl)-1-methyl-1H-pyrazole-5-carboxylate Using 2-bromo-4-ethylthiazole (251 mg), the title compound (126 mg) was obtained in the form of a light brown solid by the same method as that of (Example 1.1) <Step 2> or a method equivalent thereto.

<Step 2> Synthesis of 4-(4-ethylthiazol-2-yl)-1-methyl-1H-pyrazole-5-carboxylic acid Using the methyl 4-(4-ethylthiazol-2-yl)-1-methyl-1H-pyrazole-5-carboxylate (120 mg) obtained in (Example 3.18) <Step 1>, the title compound (24 mg) was obtained in the form of a white solid by the same method as that of (Example 1.1) <Step 3> or a method equivalent thereto.

<Step 3> Synthesis of 1-amino-4-(methoxycarbonyl)pyridin-2(1H)-iminium 2,4,6-trimethylbenzenesulfonate 70% Perchloric acid (18.9 ml) was added to a 1,4-dioxane (26 ml) solution of (Z)-ethyl N-(mesitylsulfonyl)oxyacetimidate (11.7 g) at 4° C. over 20 minutes. Thereafter, the reaction solution was stirred at 3° C. for 30 minutes, and it was then poured into water (100 ml). The precipitated solid was collected by filtration, and was then washed with water (45 ml) to obtain a white solid as a crude product. Methyl 2-aminoisonicotinate (5 g) was added to methylene chloride (35 ml), and the obtained mixture was then cooled to 3° C. The obtained crude product was dissolved in methylene chloride (40 ml), and only an organic layer was added to a methylene chloride solution of 2-aminoisonicotinate. The obtained mixture was stirred at 3° C. for 30 minutes. Thereafter, methyl tert-butyl ether (50 ml) was added to the reaction solution, and the precipitated solid was collected by filtration. The collected solid was washed with methyl tert-butyl ether (20 ml), and was then dried at 45° C., so as to obtain the title compound (10.7 g) in the form of a light yellow solid.

<Step 4> Synthesis of 2-phenyl-[1,2,4]triazolo[1,5-a]pyridine-7-carboxylic acid

Sodium methoxide (10.9 ml, a 5 M methanol solution) and benzaldehyde (3.3 ml) were added to a methanol (100 ml) solution of the 1-amino-4-(methoxycarbonyl)pyridin-2(1H)-iminium 2,4,6-trimethylbenzenesulfonate (10 g) obtained in (Example 3.18) <Step 3>, and the obtained mixture was then stirred for 1 hour. Thereafter, water (5 ml) was added to the reaction solution, and the mixed solution was then stirred at 40° C. for 30 minutes. Thereafter, methanol was distilled away under reduced pressure, water (50 ml) and methyl tert-butyl ether (50 ml) were then added to the residue, followed by stirring the mixture. An organic layer was separated from a water layer, and the water layer was then washed with methyl tert-butyl ether (50 ml) again. The water layer was adjusted to pH 4 by addition of 4 N hydrochloric acid (10 ml), and a mixed solution of methylene chloride and methanol (95:5, 50 ml) was then added thereto. Insoluble substances were removed by filtration, and an organic layer was then separated from a water layer. The water layer was extracted with a mixed solution of methylene chloride and methanol (95:5, 50 ml) twice. Organic layers were then combined, and the solvent was then distilled away under reduced pressure. The obtained residue was successively triturated with methyl tert-butyl ether (50 ml) and methanol (50 ml). The obtained solid was washed with methanol (20 ml), and was then dried at 50° C. under reduced pressure, so as to obtain the title compound (3.2 g) in the form of a brown solid.

<Step 5> Synthesis of tert-butyl (2-phenyl-[1,2,4]triazolo[1,5-a]pyridin-7-yl)carbamate Using the 2-phenyl-[1,2,4]triazolo[1,5-a]pyridine-7-carboxylic acid (150 mg) obtained in (Example 3.18) <Step 4>, the title compound (139 mg) was obtained in the form of a white solid by the same method as that of (Example 3.15) <Step 4> or a method equivalent thereto.

<Step 6> Synthesis of 2-phenyl-[1,2,4]triazolo[1,5-a]pyridin-7-amine hydrochloride Using the tert-butyl (2-phenyl-[1,2,4]triazolo[1,5-a]pyridin-7-yl)carbamate (130 mg) obtained in (Example 3.18) <Step 5>, the title compound (94 mg) was obtained in the form of a white solid by the same method as that of (Example 3.15) <Step 5> or a method equivalent thereto.

<Step 7> Synthesis of 4-(4-ethylthiazol-2-yl)-1-methyl-N-(2-phenyl-[1,2,4]triazolo[1,5-a]pyridin-7-yl)-1H-pyrazole-5-carboxamide Using the 4-(4-ethylthiazol-2-yl)-1-methyl-1H-pyrazole-5-carboxylic acid (19 mg) obtained in (Example 3.18) <Step 2> and the 2-phenyl-[1,2,4]triazolo[1,5-a]pyridin-7-amine hydrochloride (17 mg) obtained in (Example 3.18) <Step 6>, the title compound (6.7 mg) was obtained in the form of a colorless solid by the same method as that of (Example 3.15) <Step 6> or a method equivalent thereto.

Example 3.19

Synthesis of 4-(4-(difluoromethyl)thiazol-2-yl)-N-((2S,6R)-2,6-dimethylmorpholino)-[1,2,4]triazolo[1,5-a]pyridin-7-yl)-1-methyl-1H-pyrazole-5-carboxamide A (2R,6S)-2,6-dimethylmorpholine (0.5 ml) solution of the N-(2-bromo-[1,2,4]triazolo[1,5-a]pyridin-7-yl)-4-(4-(difluoromethyl)thiazol-2-yl)-1-methyl-1H-pyrazole-5-carboxamide (30 mg) obtained in (Example 3.15) <Step 6> was heated by microwave at 150° C. for 1 hour. Thereafter, the reaction solution was diluted with ethyl acetate (20 ml). The diluted solution was washed with water (15 ml) twice and a saturated saline (10 ml), and was then dried over anhydrous sodium sulfate. The solvent was distilled away under reduced pressure, and the obtained residue was then purified by silica gel column chromatography (silica gel:eluent; heptane:ethyl acetate=25:75), so as to obtain the title compound (27 mg) in the form of a light yellow solid.

Example 3.20

Synthesis of 4-(5-chloro-4-(difluoromethyl)thiazol-2-yl)-1-methyl-N-(2-phenyl-[1,2,4]triazolo[1,5-a]pyridin-7-yl)-1H-pyrazole-5-carboxamide Using the 4-(4-(difluoromethyl)thiazol-2-yl)-1-methyl-N-(2-phenyl-[1,2,4]triazolo[1,5-a]pyridin-7-yl)-1H-pyrazole-5-carboxamide (8.0 mg) obtained in (Example 3.15) <Step 7> and N-chlorosuccinimide (2.1 mg), the title compound (1.1 mg) was obtained in the form of a light yellow solid by the same method as that of (Example 1.4) <Step 1> or a method equivalent thereto.

Example 3.21

Synthesis of N-(5-chloro-2-(2-methoxyphenyl)-[1,2,4]triazolo[1,5-a]pyridin-7-yl)-4-(5-chloro-4-(difluoromethyl)thiazol-2-yl)-1-methyl-1H-pyrazole-5-carboxamide Using the 4-(4-(difluoromethyl)thiazol-2-yl)-N-(2-(2-methoxyphenyl-[1,2,4]triazolo[1,5-a]pyridin-7-yl)-1-methyl-1H-pyrazole-5-carboxamide (5 mg) obtained in (Example 3.16) and N-chlorosuccinimide (1.7 mg), the title compound (1.2 mg) was obtained in the form of an orange solid by the same method as that of (Example 1.4) <Step 1> or a method equivalent thereto.

Example 3.22

Synthesis of 4-(2,5-dimethylpyrimidin-4-yl)-N-(6-fluoro-2-phenyl-[1,2,4]triazolo[1,5-a]pyridin-7-yl)-1-methyl-1H-pyrazole-5-carboxamide <Step 1> Synthesis of methyl 4-(2,5-dimethylpyrimidin-4-yl)-1-methyl-1H-pyrazole-5-carboxylate 4,4,5,5-Tetramethyl-1,3,2-dioxaborolane (1.5 ml) was added to a 1,4-dioxane (19 ml) solution of methyl 4-bromo-1-methyl-1H-pyrazole-5-carboxylate (1.9 g), 2-dicyclohexylphosphino-2',6'-dimethoxy-1,1'-biphenyl (0.15 g), Tris(dibenzylideneacetone)dipalladium(0) (0.16 g), and triethylamine (3.7 ml). The obtained mixture was stirred in a nitrogen atmosphere at 100° C. for 30 minutes. Thereafter, 4,4,5,5-tetramethyl-1,3,2-dioxaborolane (1.5 ml) was added to the reaction solution, and the obtained mixture was then stirred for 30 minutes at the same temperature as described above. Thereafter, an aqueous solution (3.9 ml) of potassium carbonate (3.6 g) and a 1,4-dioxane (4 ml) solution of 4-chloro-2,5-dimethylpyrimidine (1.0 g) were successively added to the reaction solution, and the obtained mixture was then stirred at the same temperature as described above for 1 hour. Thereafter, water was added to the reaction solution, and the mixed solution was extracted with ethyl acetate and was then dried over anhydrous sodium sulfate. The solvent was distilled away under reduced pressure, and the obtained residue was purified by silica gel column chromatography (silica gel:eluent; heptane:ethyl acetate=3:1-1:1-0:1), so as to obtain the title compound (1.9 g) in the form of an orange liquid.

<Step 2> Synthesis of 4-(2,5-dimethylpyrimidin-4-yl)-1-methyl-1H-pyrazole-5-carboxylic acid Sodium hydroxide (0.31 g) was added to a mixed solution of methanol (15 ml) and water (15 ml) containing the methyl 4-(2,5-dimethylpyrimidin-4-yl)-1-methyl-1H-pyrazole-5-carboxylate (1.9 g) obtained in (Example 3.22) <Step 1>, and the obtained mixture was then stirred at 50° C. for 1 hour. Thereafter, methanol was distilled away from the reaction solution under reduced pressure, and the residue was then adjusted to pH 5-6 by addition of 1 N hydrochloric acid. Thereafter, water was distilled away under reduced pressure. The obtained residue was washed with methylene chloride, and the filtrate was then concentrated under reduced pressure, so as to obtain the title compound (0.94 g) in the form of a yellow solid.

<Step 3> Synthesis of 4-(2,5-dimethylpyrimidin-4-yl)-N-(6-fluoro-2-phenyl-[1,2,4]triazolo[1,5-a]pyridin-7-yl)-1-methyl-1H-pyrazole-5-carboxamide An N-methylpyrrolidone (7.7 ml) solution of the 4-(2,5-dimethylpyrimidin-4-yl)-1-methyl-1H-pyrazole-5-carboxylic acid (715 mg) obtained in (Example 3.22) <Step 2>, 6-fluoro-2-phenyl-[1,2,4]triazolo[1,5-a]pyridin-7-amine hydrochloride (obtained according to the method described in International Publication No. WO2012/076430, p. 80, Example 30-h) (815 mg), 2-(1H-7-azabenzotriazol-1-yl)-1,1,3,3-tetramethyluroniumhexafluorophosphate methanaminium (2.34 g), and diisopropylethylamine (2.69 ml) was stirred at 80° C. for 3 hours. Thereafter, water was added to the reaction solution, and the mixed solution was then extracted with ethyl acetate. Organic layers were combined, and the combined organic layer was then dried over anhydrous sodium sulfate. Subsequently, the solvent was distilled away under reduced pressure, and the obtained residue was then purified by silica gel column chromatography (NH silica gel:eluent; heptane:ethyl acetate=3:1-1:1). The obtained fraction was concentrated under reduced pressure. The obtained residue (solid) was triturated with methanol to obtain the title compound (377 mg) in the form of a colorless solid.

Example 3.23

Synthesis of 4-(5-cyanopyridin-2-yl)-N-(6-fluoro-2-phenyl-[1,2,4]triazolo[1,5-a]pyridin-7-yl)-1-methyl-1H-pyrazole-5-carboxamide <Step 1> Synthesis of 4-(5-cyanopyrimidin-2-yl)-1-methyl-1H-pyrazole-5-carboxylic acid Using 4-iodo-1-methyl-1H-pyrazole-5-carboxylic acid (1.0 g) and 6-bromonicotinonitrile (0.73 g), the title compound (72 mg) was obtained in the form of a colorless solid by the same method as that of (Example 3.22) <Step 1> or a method equivalent thereto.

<Step 2> Synthesis of 4-(5-cyanopyridin-2-yl)-N-(6-fluoro-2-phenyl-[1,2,4]triazolo[1,5-a]pyridin-7-yl)-1-methyl-1H-pyrazole-5-carboxamide Using the 4-(5-cyanopyrimidin-2-yl)-1-methyl-1H-pyrazole-5-carboxylic acid (20 mg) obtained in (Example 3.23) <Step 1>, the title compound (4.3 mg) was obtained in the form of a colorless solid by the same method as that of (Example 3.1) <Step 4> or a method equivalent thereto.

Example 3.24

Synthesis of N-(6-fluoro-2-phenyl-[1,2,4]triazolo[1,5-a]pyridin-7-yl)-1-methyl-4-(4-methylpyridazin-3-yl)-1H-pyrazole-5-carboxamide <Step 1> Synthesis of methyl 1-methyl-4-(4-methylpyridazin-3-yl)-1H-pyrazole-5-carboxylate Using 3-chloro-4-methylpyridazine (0.41 g), a crude product (2.0 g) containing the title compound was obtained in the form of a black liquid by the same method as that of (Example 3.22) <Step 1> or a method equivalent thereto.

<Step 2> Synthesis of 1-methyl-4-(4-methylpyridazin-3-yl)-1H-pyrazole-5-carboxylic acid Using the methyl 1-methyl-4-(4-methylpyridazin-3-yl)-1H-pyrazole-5-carboxylate (1.06 g) obtained in (Example 3.24) <Step 1>, the title compound (300 mg) was obtained in the form of a colorless solid by the same method as that of (Example 3.22) <Step 2> or a method equivalent thereto.

<Step 3> Synthesis of N-(6-fluoro-2-phenyl-[1,2,4]triazolo[1,5-a]pyridin-7-yl)-1-methyl-4-(4-methylpyridazin-3-yl)-1H-pyrazole-5-carboxamide Using the 1-methyl-4-(4-methylpyridazin-3-yl)-1H-pyrazole-5-carboxylic acid (37 mg) obtained in (Example 3.24) <Step 2>, the title compound (5.4 mg) was obtained in the form of a brown solid by the same method as that of (Example 3.22) <Step 3> or a method equivalent thereto.

Example 3.25

Synthesis of N-(6-fluoro-2-phenyl-[1,2,4]triazolo[1,5-a]pyridin-7-yl)-1-methyl-4-(2-methylpyrimidin-4-yl)-1H-pyrazole-5-carboxamide <Step 1> Synthesis of methyl 1-methyl-4-(2-methylpyrimidin-4-yl)-1H-pyrazole-5-carboxylate Using 4-chloro-2-methylpyrimidine (0.94 g), the title compound (1.26 g) was obtained in the form of a yellow oily substance by the same method as that of (Example 3.22) <Step 1> or a method equivalent thereto.

<Step 2> Synthesis of 1-methyl-4-(2-methylpyrimidin-4-yl)-1H-pyrazole-5-carboxylic acid Using the methyl 1-methyl-4-(2-methylpyrimidin-4-yl)-1H-pyrazole-5-carboxylate (1.26 g) obtained in (Example 3.25) <Step 1>, the title compound (682 mg) was obtained in the form of a colorless solid by the same method as that of (Example 3.22) <Step 2> or a method equivalent thereto.

<Step 3> Synthesis of N-(6-fluoro-2-phenyl-[1,2,4]triazolo[1,5-a]pyridin-7-yl)-1-methyl-4-(2-methylpyrimidin-4-yl)-1H-pyrazole-5-carboxamide Using the 1-methyl-4-(2-methylpyrimidin-4-yl)-1H-pyrazole-5-carboxylic acid (300 mg) obtained in (Example 3.25) <Step 2>, the title compound (284 mg) was obtained in the form of a gray solid by the same method as that of (Example 3.22) <Step 3> or a method equivalent thereto.

Example 3.26

Synthesis of N-(6-fluoro-2-phenyl-[1,2,4]triazolo[1,5-a]pyridin-7-yl)-4-(2-methoxypyrimidin-4-yl)-1-methyl-1H-pyrazole-5-carboxamide <Step 1> Synthesis of methyl 4-(2-methoxypyrimidin-4-yl)-1-methyl-1H-pyrazole-5-carboxylate Using 4-bromo-2-methoxypyrimidine (1.38 g), the title compound (1.73 g) was obtained in the form of an orange oily substance by the same method as that of (Example 3.22) <Step 1> or a method equivalent thereto.

<Step 2> Synthesis of 4-(2-methoxypyrimidin-4-yl)-1-methyl-1H-pyrazole-5-carboxylic acid Using the methyl 4-(2-methoxypyrimidin-4-yl)-1-methyl-1H-pyrazole-5-carboxylate (1.73 g) obtained in (Example 3.26) <Step 1>, the title compound (308 mg) was obtained in the form of a colorless solid by the same method as that of (Example 3.22) <Step 2> or a method equivalent thereto.

<Step 3> Synthesis of N-(6-fluoro-2-phenyl-[1,2,4]triazolo[1,5-a]pyridin-7-yl)-4-(2-methoxypyrimidin-4-yl)-1-methyl-1H-pyrazole-5-carboxamide Using the 4-(2-methoxypyrimidin-4-yl)-1-methyl-1H-pyrazole-5-carboxylic acid (270 mg) obtained in (Example 3.26) <Step 2>, the title compound (200 mg) was obtained in the form of a brown solid by the same method as that of (Example 3.22) <Step 3> or a method equivalent thereto.

Example 3.27

Synthesis of 4-(5-fluoro-2-methoxypyrimidin-4-yl)-N-(6-fluoro-2-phenyl-[1,2,4]triazolo[1,5-a]pyridin-7-yl)-1-methyl-1H-pyrazole-5-carboxamide <Step 1> Synthesis of methyl 4-(5-fluoro-2-methoxypyrimidin-4-yl)-1-methyl-1H-pyrazole-5-carboxylate Using 4-chloro-5-fluoro-2-methoxypyrimidine (1.5 g), the title compound (1.6 g) was obtained in the form of a light yellow liquid by the same method as that of (Example 3.22) <Step 1> or a method equivalent thereto.

<Step 2> Synthesis of 4-(5-fluoro-2-methoxypyrimidin-4-yl)-1-methyl-1H-pyrazole-5-carboxylic acid Using the methyl 4-(5-fluoro-2-methoxypyrimidin-4-yl)-1-methyl-1H-pyrazole-5-carboxylate (1.6 g) obtained in (Example 3.27) <Step 1>, the title compound (0.65 g) was obtained in the form of a colorless solid by the same method as that of (Example 3.22) <Step 2> or a method equivalent thereto.

<Step 3> Synthesis of 4-(5-fluoro-2-methoxypyrimidin-4-yl)-N-(6-fluoro-2-phenyl-[1,2,4]triazolo[1,5-a]pyridin-7-yl)-1-methyl-1H-pyrazole-5-carboxamide Using the 4-(5-fluoro-2-methoxypyrimidin-4-yl)-1-methyl-1H-pyrazole-5-carboxylic acid (381 mg) obtained in (Example 3.27) <Step 2>, the title compound (62.6 mg) was obtained in the form of a light yellow solid by the same method as that of (Example 3.22) <Step 3> or a method equivalent thereto.

Example 3.28

Synthesis of N-(6-fluoro-2-phenyl-[1,2,4]triazolo[1,5-a]pyridin-7-yl)-4-(3-methoxypyrazin-2-yl)-1-methyl-1H-pyrazole-5-carboxamide <Step 1> Synthesis of methyl 4-(3-methoxypyrazin-2-yl)-1-methyl-1H-pyrazole-5-carboxylate Using 2-chloro-3-methoxypyrazine (2.11 g), the title compound (2.69 g) was obtained in the form of a light brown oily substance by the same method as that of (Example 3.22) <Step 1> or a method equivalent thereto.

<Step 2> Synthesis of 4-(3-methoxypyrazin-2-yl)-1-methyl-1H-pyrazole-5-carboxylic acid Using the methyl 4-(3-methoxypyrazin-2-yl)-1-methyl-1H-pyrazole-5-carboxylate (1.6 g) obtained in (Example 3.28) <Step 1>, the title compound (0.44 g) was obtained in the form of a white solid by the same method as that of (Example 3.22) <Step 2> or a method equivalent thereto.

<Step 3> Synthesis of N-(6-fluoro-2-phenyl-[1,2,4] triazolo[1,5-a]pyridin-7-yl)-4-(3-methoxypyrazin-2-yl)-1-methyl-1H-pyrazole-5-carboxamide Using the 4-(3-methoxypyrazin-2-yl)-1-methyl-1H-pyrazole-5-carboxylic acid (372 mg) obtained in (Example 3.28) <Step 2>, the title compound (89 mg) was obtained in the form of a brown solid by the same method as that of (Example 3.22) <Step 3> or a method equivalent thereto.

Example 3.29

Synthesis of 4-(5-chloropyrimidin-4-yl)-N-(6-fluoro-2-phenyl-[1,2,4]triazolo[1,5-a]pyridin-7-yl)-1-methyl-1H-pyrazole-5-carboxamide <Step 1> Synthesis of methyl 4-(5-chloropyrimidin-4-yl)-1-methyl-1H-pyrazole-5-carboxylate Using 4,5-dichloropyrimidine (0.54 g), the title compound (0.46 g) was obtained in the form of a brown liquid by the same method as that of (Example 3.22) <Step 1> or a method equivalent thereto.

<Step 2> Synthesis of 4-(5-chloropyrimidin-4-yl)-1-methyl-1H-pyrazole-5-carboxylic acid Using the methyl 4-(5-chloropyrimidin-4-yl)-1-methyl-1H-pyrazole-5-carboxylate (0.45 g) obtained in (Example 3.29) <Step 1>, the title compound (0.30 g) was obtained in the form of a white solid by the same method as that of (Example 3.22) <Step 2> or a method equivalent thereto.

<Step 3> Synthesis of 4-(5-chloropyrimidin-4-yl)-N-(6-fluoro-2-phenyl-[1,2,4]triazolo[1,5-a]pyridin-7-yl)-1-methyl-1H-pyrazole-5-carboxamide Using the 4-(5-chloropyrimidin-4-yl)-1-methyl-1H-pyrazole-5-carboxylic acid (270 mg) obtained in (Example 3.29) <Step 2>, the title compound (260 mg) was obtained in the form of a brown solid by the same method as that of (Example 3.22) <Step 3> or a method equivalent thereto.

Example 3.30

Synthesis of 4-(2,6-dimethylpyrimidin-4-yl)-N-(6-fluoro-2-phenyl-[1,2,4]triazolo[1,5-a]pyridin-7-yl)-1-methyl-1H-pyrazole-5-carboxamide <Step 1> Synthesis of methyl 4-(2,6-dimethylpyrimidin-4-yl)-1-methyl-1H-pyrazole-5-carboxylate Using 4-chloro-2,6-dimethylpyrimidine (1.17 g), the title compound (2.05 g) was obtained in the form of an orange liquid by the same method as that of (Example 3.22) <Step 1> or a method equivalent thereto.

<Step 2> Synthesis of 4-(2,6-dimethylpyrimidin-4-yl)-1-methyl-1H-pyrazole-5-carboxylic acid Using the methyl 4-(2,6-dimethylpyrimidin-4-yl)-1-methyl-1H-pyrazole-5-carboxylate (2.05 g) obtained in (Example 3.30) <Step 1>, the title compound (666 mg) was obtained in the form of a colorless solid by the same method as that of (Example 3.22) <Step 2> or a method equivalent thereto.

<Step 3> Synthesis of 4-(2,6-dimethylpyrimidin-4-yl)-N-(6-fluoro-2-phenyl-[1,2,4]triazolo[1,5-a]pyridin-7-yl)-1-methyl-1H-pyrazole-5-carboxamide Using the 4-(2,6-dimethylpyrimidin-4-yl)-1-methyl-1H-pyrazole-5-carboxylic acid (300 mg) obtained in (Example 3.30) <Step 2>, the title compound (290 mg) was obtained in the form of a brown solid by the same method as that of (Example 3.22) <Step 3> or a method equivalent thereto.

Example 3.31

Synthesis of N-(6-fluoro-2-phenyl-[1,2,4]triazolo[1,5-a]pyridin-7-yl)-4-(6-methoxy-5-methylpyrimidin-4-yl)-1-methyl-1H-pyrazole-5-carboxamide <Step 1> Synthesis of methyl 4-(6-methoxy-5-methylpyrimidin-4-yl)-1-methyl-1H-pyrazole-5-carboxylate Using 4-chloro-6-methoxy-5-methylpyrimidine (1.16 g), the title compound (2.72 g) was obtained in the form of an orange oily substance by the same method as that of (Example 3.22) <Step 1> or a method equivalent thereto.

<Step 2> Synthesis of 4-(6-methoxy-5-methylpyrimidin-4-yl)-1-methyl-1H-pyrazole-5-carboxylic acid Using the methyl 4-(6-methoxy-5-methylpyrimidin-4-yl)-1-methyl-1H-pyrazole-5-carboxylate (2.39 g) obtained in (Example 3.31) <Step 1>, the title compound (814 mg) was obtained in the form of a colorless solid by the same method as that of (Example 3.22) <Step 2> or a method equivalent thereto.

<Step 3> Synthesis of N-(6-fluoro-2-phenyl-[1,2,4] triazolo[1,5-a]pyridin-7-yl)-4-(6-methoxy-5-methylpyrimidin-4-yl)-1-methyl-1H-pyrazole-5-carboxamide Using the 4-(6-methoxy-5-methylpyrimidin-4-yl)-1-methyl-1H-pyrazole-5-carboxylic acid (300 mg) obtained in (Example 3.31) <Step 2>, the title compound (263 mg) was obtained in the form of a brown solid by the same method as that of (Example 3.22) <Step 3> or a method equivalent thereto.

Example 3.32

Synthesis of N-(6-fluoro-2-phenyl-[1,2,4]triazolo[1,5-a]pyridin-7-yl)-1-methyl-4-(3-methylpyrazin-2-yl)-1H-pyrazole-5-carboxamide <Step 1> Synthesis of methyl 1-methyl-4-(3-methylpyrazin-2-yl)-1H-pyrazole-5-carboxylate Using 2-iodo-3-methylpyrazine (1.2 g), the title compound (1.2 g) was obtained in the form of a green liquid by the same method as that of (Example 3.22) <Step 1> or a method equivalent thereto.

<Step 2> Synthesis of 1-methyl-4-(3-methyl-
pyrazin-2-yl)-1H-pyrazole-5-carboxylic acid Using the methyl 1-methyl-4-(3-methylpyrazin-2-yl)-1H-pyrazole-5-carboxylate (1.2 g) obtained in (Example 3.32) <Step 1>, the title compound (0.55 g) was obtained in the form of a brown solid by the same method as that of (Example 3.22) <Step 2> or a method equivalent thereto.

<Step 3> Synthesis of N-(6-fluoro-2-phenyl-[1,2,4]
triazolo[1,5-a]pyridin-7-yl)-1-methyl-4-(3-methyl-
pyrazin-2-yl)-1H-pyrazole-5-carboxamide Using the 1-methyl-4-(3-methylpyrazin-2-yl)-1H-pyrazole-5-carboxylic acid (420 mg) obtained in (Example 3.32) <Step 2>, the title compound (179 mg) was obtained in the form of a brown solid by the same method as that of (Example 3.22) <Step 3> or a method equivalent thereto.

Example 3.33

Synthesis of N-(6-fluoro-2-phenyl-[1,2,4]triazolo[1,
5-a]pyridin-7-yl)-1-methyl-4-(5-methylpyrimidin-4-
yl)-1H-pyrazole-5-carboxamide <Step 1> Synthesis of methyl 1-methyl-4-(5-meth-
ylpyrimidin-4-yl)-1H-pyrazole-5-carboxylate Using 4-chloro-5-methylpyrimidine (0.52 g), the title compound (0.16 g) was obtained in the form of a brown oily substance by the same method as that of (Example 3.22) <Step 1> or a method equivalent thereto.

<Step 2> Synthesis of 1-methyl-4-(5-methylpyrimi-
din-4-yl)-1H-pyrazole-5-carboxylic acid Using the methyl 1-methyl-4-(5-methylpyrimidin-4-yl)-1H-pyrazole-5-carboxylate (155 mg) obtained in (Example 3.33) <Step 1>, the title compound (175 mg) was obtained in the form of a light yellow solid by the same method as that of (Example 3.22) <Step 2> or a method equivalent thereto.

<Step 3> Synthesis of N-(6-fluoro-2-phenyl-[1,2,4]
triazolo[1,5-a]pyridin-7-yl)-1-methyl-4-(5-methylpy-
rimidin-4-yl)-1H-pyrazole-5-carboxamide Using the 1-methyl-4-(5-methylpyrimidin-4-yl)-1H-pyrazole-5-carboxylic acid (129 mg) obtained in (Example 3.33) <Step 2>, the title compound (13.3 mg) was obtained in the form of a colorless solid by the same method as that of (Example 3.1) <Step 4> or a method equivalent thereto.

Example 3.34

Synthesis of N-(6-fluoro-2-phenyl-[1,2,4]triazolo[1,
5-a]pyridin-7-yl)-4-(5-methoxypyrimidin-4-yl)-1-
methyl-1H-pyrazole-5-carboxamide <Step 1> Synthesis of methyl 4-(5-methoxypyrimi-
din-4-yl)-1-methyl-1H-pyrazole-5-carboxylate Using 4-chloro-5-methoxypyrimidine (0.31 g), the title compound (0.43 g) was obtained in the form of a white solid by the same method as that of (Example 3.22) <Step 1> or a method equivalent thereto.

<Step 2> Synthesis of 4-(5-methoxypyrimidin-4-
yl)-1-methyl-1H-pyrazole-5-carboxylic acid Using the methyl (4-(5-methoxypyrimidin-4-yl)-1-methyl-1H-pyrazole-5-carboxylate (0.42 g) obtained in (Example 3.34) <Step 1>, the title compound (290 mg) was obtained in the form of a white solid by the same method as that of (Example 3.22) <Step 2> or a method equivalent thereto.

<Step 3> Synthesis of N-(6-fluoro-2-phenyl-[1,2,4]
triazolo[1,5-a]pyridin-7-yl)-4-(5-methoxypyrimidin-
4-yl)-1-methyl-1H-pyrazole-5-carboxamide Using the 4-(5-methoxypyrimidin-4-yl)-1-methyl-1H-pyrazole-5-carboxylic acid (265 mg) obtained in (Example 3.34) <Step 2>, the title compound (220 mg) was obtained in the form of a light brown solid by the same method as that of (Example 3.22) <Step 3> or a method equivalent thereto.

Example 3.35

Synthesis of 4-(5,6-dimethylpyrimidin-4-yl)-N-(6-
fluoro-2-phenyl-[1,2,4]triazolo[1,5-a]pyridin-7-yl)-
1-methyl-1H-pyrazole-5-carboxamide <Step 1> Synthesis of methyl 4-(5,6-dimethylpy-
rimidin-4-yl)-1-methyl-1H-pyrazole-5-carboxylate Using 4-chloro-5,6-dimethylpyrimidine (94 mg), the title compound (71 mg) was obtained in the form of a white solid by the same method as that of (Example 3.22) <Step 1> or a method equivalent thereto.

<Step 2> Synthesis of 4-(5,6-dimethylpyrimidin-4-
yl)-1-methyl-1H-pyrazole-5-carboxylic acid Using the methyl 4-(5,6-dimethylpyrimidin-4-yl)-1-methyl-1H-pyrazole-5-carboxylate (1.7 g) obtained in (Example 3.35) <Step 1>, the title compound (1.2 g) was obtained in the form of a light yellow solid by the same method as that of (Example 3.22) <Step 2> or a method equivalent thereto.

<Step 3> Synthesis of 4-(5,6-dimethylpyrimidin-4-
yl)-N-(6-fluoro-2-phenyl-[1,2,4]triazolo[1,5-a]pyri-
din-7-yl)-1-methyl-1H-pyrazole-5-carboxamide Using the 4-(5,6-dimethylpyrimidin-4-yl)-1-methyl-1H-pyrazole-5-carboxylic acid (400 mg) obtained in (Example 3.35) <Step 2>, the title compound (260 mg) was obtained in the form of a light brown solid by the same method as that of (Example 3.22) <Step 3> or a method equivalent thereto.

Example 3.36

Synthesis of 4-(5-fluoro-2-methylpyrimidin-4-yl)-N-
(6-fluoro-2-phenyl-[1,2,4]triazolo[1,5-a]pyridin-7-
yl)-1-methyl-1H-pyrazole-5-carboxamide <Step 1> Synthesis of methyl 4-(5-fluoro-2-methyl-
pyrimidin-4-yl)-1-methyl-1H-pyrazole-5-carboxylate Using 4-chloro-5-fluoro-2-methylpyrimidine (0.75 g), the title compound (1.35 g) was obtained in the form of an <Step 2> Synthesis of 4-(5-fluoro-2-methylpyrimidin-4-yl)-1-methyl-1H-pyrazole-5-carboxylic acid Using the methyl 4-(5-fluoro-2-methylpyrimidin-4-yl)-1-methyl-1H-pyrazole-5-carboxylate (1.35 g) obtained in (Example 3.36) <Step 1>, the title compound (0.869 g) was obtained in the form of a light brown solid by the same method as that of (Example 3.22) <Step 2> or a method equivalent thereto.

<Step 3> Synthesis of 4-(5-fluoro-2-methylpyrimidin-4-yl)-N-(6-fluoro-2-phenyl-[1,2,4]triazolo[1,5-a]pyridin-7-yl)-1-methyl-1H-pyrazole-5-carboxamide Using the 4-(5-fluoro-2-methylpyrimidin-4-yl)-1-methyl-1H-pyrazole-5-carboxylic acid (450 mg) obtained in (Example 3.36) <Step 2>, the title compound (350 mg) was obtained in the form of a brown solid by the same method as that of (Example 3.22) <Step 3> or a method equivalent thereto.

Example 3.37

Synthesis of N-(6-fluoro-2-phenyl-[1,2,4]triazolo[1,5-a]pyridin-7-yl)-1-methyl-4-(2,5,6-trimethylpyrimidin-4-yl)-1H-pyrazole-5-carboxamide <Step 1> Synthesis of methyl 1-methyl-4-(2,5,6-trimethylpyrimidin-4-yl)-1H-pyrazole-5-carboxylate Using 4-chloro-2,5,6-trimethylpyrimidine (1.0 g), the title compound (1.1 g) was obtained in the form of a brown liquid by the same method as that of (Example 3.22) <Step 1> or a method equivalent thereto.

<Step 2> Synthesis of 1-methyl-4-(2,5,6-trimethylpyrimidin-4-yl)-1H-pyrazole-5-carboxylic acid Using the methyl 1-methyl-4-(2,5,6-trimethylpyrimidin-4-yl)-1H-pyrazole-5-carboxylate (1.1 g) obtained in (Example 3.37) <Step 1>, the title compound (0.48 g) was obtained in the form of a colorless solid by the same method as that of (Example 3.22) <Step 2> or a method equivalent thereto.

<Step 3> Synthesis of N-(6-fluoro-2-phenyl-[1,2,4]triazolo[1,5-a]pyridin-7-yl)-1-methyl-4-(2,5,6-trimethylpyrimidin-4-yl)-1H-pyrazole-5-carboxamide Using the 1-methyl-4-(2,5,6-trimethylpyrimidin-4-yl)-1H-pyrazole-5-carboxylic acid (373 mg) obtained in (Example 3.37) <Step 2>, the title compound (182 mg) was obtained in the form of a light brown solid by the same method as that of (Example 3.22) <Step 3> or a method equivalent thereto.

Example 3.38

Synthesis of N-(6-fluoro-2-phenyl-[1,2,4]triazolo[1,5-a]pyridin-7-yl)-4-(5-fluoro-6-methylpyrimidin-4-yl)-1-methyl-1H-pyrazole-5-carboxamide <Step 1> Synthesis of methyl 4-(5-fluoro-6-methylpyrimidin-4-yl)-1-methyl-1H-pyrazole-5-carboxylate Using 4-chloro-5-fluoro-6-methylpyrimidine (150 mg), the title compound (103 mg) was obtained in the form of a orange liquid by the same method as that of (Example 3.22) <Step 1> or a method equivalent thereto.

<Step 2> Synthesis of 4-(5-fluoro-6-methylpyrimidin-4-yl)-1-methyl-1H-pyrazole-5-carboxylic acid Using the methyl 4-(5-fluoro-6-methylpyrimidin-4-yl)-1-methyl-1H-pyrazole-5-carboxylate (101 mg) obtained in (Example 3.38) <Step 1>, the title compound (71.5 mg) was obtained in the form of a white solid by the same method as that of (Example 3.22) <Step 2> or a method equivalent thereto.

<Step 3> Synthesis of N-(6-fluoro-2-phenyl-[1,2,4]triazolo[1,5-a]pyridin-7-yl)-4-(5-fluoro-6-methylpyrimidin-4-yl)-1-methyl-1H-pyrazole-5-carboxamide Using the 4-(5-fluoro-6-methylpyrimidin-4-yl)-1-methyl-1H-pyrazole-5-carboxylic acid (66 mg) obtained in (Example 3.38) <Step 2>, the title compound (38 mg) was obtained in the form of a brown solid by the same method as that of (Example 3.22) <Step 3> or a method equivalent thereto.

Example 3.39

Synthesis of N-(6-fluoro-2-phenyl-[1,2,4]triazolo[1,5-a]pyridin-7-yl)-1-methyl-4-(6-methylpyrimidin-4-yl)-1H-pyrazole-5-carboxamide <Step 1> Synthesis of methyl 1-methyl-4-(6-methylpyrimidin-4-yl)-1H-pyrazole-5-carboxylate Using 4-chloro-6-methylpyrimidine (1.88 g), the title compound (665 mg) was obtained in the form of a light brown solid by the same method as that of (Example 3.22) <Step 1> or a method equivalent thereto.

<Step 2> Synthesis of 1-methyl-4-(6-methylpyrimidin-4-yl)-1H-pyrazole-5-carboxylic acid Using the methyl 1-methyl-4-(6-methylpyrimidin-4-yl)-1H-pyrazole-5-carboxylate (655 mg) obtained in (Example 3.39) <Step 1>, the title compound (564 mg) was obtained in the form of a white solid by the same method as that of (Example 3.22) <Step 2> or a method equivalent thereto.

<Step 3> Synthesis of N-(6-fluoro-2-phenyl-[1,2,4]triazolo[1,5-a]pyridin-7-yl)-1-methyl-4-(6-methylpyrimidin-4-yl)-1H-pyrazole-5-carboxamide Using the 1-methyl-4-(6-methylpyrimidin-4-yl)-1H-pyrazole-5-carboxylic acid (346 mg) obtained in (Example 3.39) <Step 2>, the title compound (392 mg) was obtained in the form of a black solid by the same method as that of (Example 3.22) <Step 3> or a method equivalent thereto.

Example 3.40

Synthesis of 4-(2,6-dimethoxypyrimidin-4-yl)-N-(6-fluoro-2-phenyl-[1,2,4]triazolo[1,5-a]pyridin-7-yl)-1-methyl-1H-pyrazole-5-carboxamide <Step 1> Synthesis of methyl 4-(2,6-dimethoxypyrimidin-4-yl)-1-methyl-1H-pyrazole-5-carboxylate Using 4-chloro-2,6-dimethoxypyrimidine (1.28 g), the title compound (2.53 g) was obtained in the form of an

245 orange liquid by the same method as that of (Example 3.22) <Step 1> or a method equivalent thereto.

<Step 2> Synthesis of 4-(2,6-dimethoxypyrimidin-4-yl)-1-methyl-1H-pyrazole-5-carboxylic acid Using the methyl 4-(2,6-dimethoxypyrimidin-4-yl)-1-methyl-1H-pyrazole-5-carboxylate (2.53 g) obtained in (Example 3.40) <Step 1>, the title compound (988 mg) was obtained in the form of a colorless solid by the same method as that of (Example 3.22) <Step 2> or a method equivalent thereto.

<Step 3> Synthesis of 4-(2,6-dimethoxypyrimidin-4-yl)-N-(6-fluoro-2-phenyl-[1,2,4]triazolo[1,5-a]pyridin-7-yl)-1-methyl-1H-pyrazole-5-carboxamide Using the 4-(2,6-dimethoxypyrimidin-4-yl)-1-methyl-1H-pyrazole-5-carboxylic acid (360 mg) obtained in (Example 3.40) <Step 2>, the title compound (266 mg) was obtained in the form of a brown solid by the same method as that of (Example 3.22) <Step 3> or a method equivalent thereto.

Example 3.41

Synthesis of 4-(5-chloro-2-methylpyrimidin-4-yl)-N-(6-fluoro-2-phenyl-[1,2,4]triazolo[1,5-a]pyridin-7-yl)-1-methyl-1H-pyrazole-5-carboxamide <Step 1> Synthesis of methyl 4-(5-chloro-2-methylpyrimidin-4-yl)-1-methyl-1H-pyrazole-5-carboxylate Using 4,5-dichloro-2-methylpyrimidine (180 mg), the title compound (50 mg) was obtained in the form of a yellow liquid by the same method as that of (Example 3.22) <Step 1> or a method equivalent thereto.

<Step 2> Synthesis of 4-(5-chloro-2-methylpyrimidin-4-yl)-1-methyl-1H-pyrazole-5-carboxylic acid Using the methyl 4-(5-chloro-2-methylpyrimidin-4-yl)-1-methyl-1H-pyrazole-5-carboxylate (50 mg) obtained in (Example 3.41) <Step 1>, the title compound (32 mg) was obtained in the form of a brown solid by the same method as that of (Example 3.22) <Step 2> or a method equivalent thereto.

<Step 3> Synthesis of 4-(5-chloro-2-methylpyrimidin-4-yl)-N-(6-fluoro-2-phenyl-[1,2,4]triazolo[1,5-a]pyridin-7-yl)-1-methyl-1H-pyrazole-5-carboxamide Using the 4-(5-chloro-2-methylpyrimidin-4-yl)-1-methyl-1H-pyrazole-5-carboxylic acid (21 mg) obtained in (Example 3.41) <Step 2>, the title compound (1.3 mg) was obtained in the form of a light brown solid by the same method as that of (Example 3.22) <Step 3> or a method equivalent thereto.

246

Example 3.42

Synthesis of N-(6-fluoro-2-phenyl-[1,2,4]triazolo[1,5-a]pyridin-7-yl)-4-(6-methoxypyrazin-2-yl)-1-methyl-1H-pyrazole-5-carboxamide <Step 1> Synthesis of methyl 4-(6-methoxypyrazin-2-yl)-1-methyl-1H-pyrazole-5-carboxylate Using 2-chloro-6-methoxypyrazine (1.0 g), the title compound (1.7 g) was obtained in the form of a yellow liquid by the same method as that of (Example 3.22) <Step 1> or a method equivalent thereto.

<Step 2> Synthesis of 4-(6-methoxypyrazin-2-yl)-1-methyl-1H-pyrazole-5-carboxylic acid Using the methyl 4-(6-methoxypyrazin-2-yl)-1-methyl-1H-pyrazole-5-carboxylate (1.5 g) obtained in (Example 3.42) <Step 1>, the title compound (0.44 g) was obtained in the form of a white solid by the same method as that of (Example 3.22) <Step 2> or a method equivalent thereto.

<Step 3> Synthesis of N-(6-fluoro-2-phenyl-[1,2,4]triazolo[1,5-a]pyridin-7-yl)-4-(6-methoxypyrazin-2-yl)-1-methyl-1H-pyrazole-5-carboxamide Using the 4-(6-methoxypyrazin-2-yl)-1-methyl-1H-pyrazole-5-carboxylic acid (380 mg) obtained in (Example 3.42) <Step 2>, the title compound (62 mg) was obtained in the form of a yellow solid by the same method as that of (Example 3.22) <Step 3> or a method equivalent thereto.

Example 3.43

Synthesis of N-(6-fluoro-2-phenyl-[1,2,4]triazolo[1,5-a]pyridin-7-yl)-1-methyl-4-(4-methylpyrimidin-2-yl)-1H-pyrazole-5-carboxamide <Step 1> Synthesis of methyl 1-methyl-4-(4-methylpyrimidin-2-yl)-1H-pyrazole-5-carboxylate Using 2-chloro-4-methylpyrimidine (0.92 g), the title compound (1.0 g) was obtained in the form of an orange liquid by the same method as that of (Example 3.22) <Step 1> or a method equivalent thereto.

<Step 2> Synthesis of 1-methyl-4-(4-methylpyrimidin-2-yl)-1H-pyrazole-5-carboxylic acid Using the methyl 1-methyl-4-(4-methylpyrimidin-2-yl)-1H-pyrazole-5-carboxylate (1.0 g) obtained in (Example 3.43) <Step 1>, the title compound (0.40 g) was obtained in the form of a brown solid by the same method as that of (Example 3.22) <Step 2> or a method equivalent thereto.

<Step 3> Synthesis of N-(6-fluoro-2-phenyl-[1,2,4]triazolo[1,5-a]pyridin-7-yl)-1-methyl-4-(4-methylpyrimidin-2-yl)-1H-pyrazole-5-carboxamide Using the 1-methyl-4-(4-methylpyrimidin-2-yl)-1H-pyrazole-5-carboxylic acid (346 mg) obtained in (Example 3.43) <Step 2>, the title compound (398 mg) was obtained in the form of a brown solid by the same method as that of (Example 3.22) <Step 3> or a method equivalent thereto.

Example 3.44

Synthesis of 4-(4,6-dimethylpyrimidin-2-yl)-N-(6-fluoro-2-phenyl-[1,2,4]triazolo[1,5-a]pyridin-7-yl)-1-methyl-1H-pyrazole-5-carboxamide <Step 1> Synthesis of methyl 4-(4,6-dimethylpyrimidin-2-yl)-1-methyl-1H-pyrazole-5-carboxylate Using 2-chloro-4,6-dimethylpyrimidine (1.6 g), the title compound (0.47 g) was obtained in the form of an orange liquid by the same method as that of (Example 3.22) <Step 1> or a method equivalent thereto.

<Step 2> Synthesis of 4-(4,6-dimethylpyrimidin-2-yl)-1-methyl-1H-pyrazole-5-carboxylic acid Using the methyl 4-(4,6-dimethylpyrimidin-2-yl)-1-methyl-1H-pyrazole-5-carboxylate (460 mg) obtained in (Example 3.44) <Step 1>, the title compound (288 mg) was obtained in the form of a white solid by the same method as that of (Example 3.22) <Step 2> or a method equivalent thereto.

<Step 3> Synthesis of 4-(4,6-dimethylpyrimidin-2-yl)-N-(6-fluoro-2-phenyl-[1,2,4]triazolo[1,5-a]pyridin-7-yl)-1-methyl-1H-pyrazole-5-carboxamide Using the 4-(4,6-dimethylpyrimidin-2-yl)-1-methyl-1H-pyrazole-5-carboxylic acid (250 mg) obtained in (Example 3.44) <Step 2>, the title compound (280 mg) was obtained in the form of a brown solid by the same method as that of (Example 3.22) <Step 3> or a method equivalent thereto.

Example 3.45

Synthesis of N-(6-fluoro-2-phenyl-[1,2,4]triazolo[1,5-a]pyridin-7-yl)-1-methyl-4-(6-methylpyridazin-3-yl)-1H-pyrazole-5-carboxamide <Step 1> Synthesis of methyl 1-methyl-4-(6-methylpyridazin-3-yl)-1H-pyrazole-5-carboxylate Using 3-chloro-6-methylpyridazine (0.94 g), the title compound (0.65 g) was obtained in the form of an orange oily substance by the same method as that of (Example 3.22) <Step 1> or a method equivalent thereto.

<Step 2> Synthesis of 1-methyl-4-(6-methylpyridazin-3-yl)-1H-pyrazole-5-carboxylic acid Using the methyl 1-methyl-4-(6-methylpyridazin-3-yl)-1H-pyrazole-5-carboxylate (0.6 g) obtained in (Example 3.45) <Step 1>, the title compound (0.35 g) was obtained in the form of a white solid by the same method as that of (Example 3.22) <Step 2> or a method equivalent thereto.

<Step 3> Synthesis of N-(6-fluoro-2-phenyl-[1,2,4]triazolo[1,5-a]pyridin-7-yl)-1-methyl-4-(6-methylpyridazin-3-yl)-1H-pyrazole-5-carboxamide Using the 1-methyl-4-(6-methylpyridazin-3-yl)-1H-pyrazole-5-carboxylic acid (170 mg) obtained in (Example 3.45) <Step 2>, the title compound (186 mg) was obtained in the form of a white solid by the same method as that of (Example 3.22) <Step 3> or a method equivalent thereto.

Example 3.46

Synthesis of N-(6-fluoro-2-phenyl-[1,2,4]triazolo[1,5-a]pyridin-7-yl)-1-methyl-4-(5-methylpyridazin-3-yl)-1H-pyrazole-5-carboxamide <Step 1> Synthesis of methyl 1-methyl-4-(5-methylpyridazin-3-yl)-1H-pyrazole-5-carboxylate Using 3-chloro-5-methylpyridazine (0.94 g), the title compound (0.45 g) was obtained in the form of an orange oily substance by the same method as that of (Example 3.22) <Step 1> or a method equivalent thereto.

<Step 2> Synthesis of 1-methyl-4-(5-methylpyridazin-3-yl)-1H-pyrazole-5-carboxylic acid Using the methyl 1-methyl-4-(5-methylpyridazin-3-yl)-1H-pyrazole-5-carboxylate (400 mg) obtained in (Example 3.46) <Step 1>, the title compound (49 mg) was obtained in the form of a red solid by the same method as that of (Example 3.22) <Step 2> or a method equivalent thereto.

<Step 3> Synthesis of N-(6-fluoro-2-phenyl-[1,2,4]triazolo[1,5-a]pyridin-7-yl)-1-methyl-4-(5-methylpyridazin-3-yl)-1H-pyrazole-5-carboxamide Using the 1-methyl-4-(5-methylpyridazin-3-yl)-1H-pyrazole-5-carboxylic acid (50 mg) obtained in (Example 3.46) <Step 2>, the title compound (51 mg) was obtained in the form of a white solid by the same method as that of (Example 3.22) <Step 3> or a method equivalent thereto.

Example 3.47

Synthesis of N-(6-fluoro-2-phenyl-[1,2,4]triazolo[1,5-a]pyridin-7-yl)-1-methyl-4-(pyridazin-3-yl)-1H-pyrazole-5-carboxamide <Step 1> Synthesis of methyl 1-methyl-4-(pyridazin-3-yl)-1H-pyrazole-5-carboxylate Using 3-chloropyridazine (0.5 g), the title compound (0.3 g) was obtained in the form of a red oily substance by the same method as that of (Example 3.22) <Step 1> or a method equivalent thereto.

<Step 2> Synthesis of 1-methyl-4-(pyridazin-3-yl)-1H-pyrazole-5-carboxylic acid

Using the methyl 1-methyl-4-(pyridazin-3-yl)-1H-pyrazole-5-carboxylate (300 mg) obtained in (Example 3.47) <Step 1>, the title compound (96 mg) was obtained in the form of a red solid by the same method as that of (Example 3.22) <Step 2> or a method equivalent thereto.

<Step 3> Synthesis of N-(6-fluoro-2-phenyl-[1,2,4]triazolo[1,5-a]pyridin-7-yl)-1-methyl-4-(pyridazin-3-yl)-1H-pyrazole-5-carboxamide Using the 1-methyl-4-(pyridazin-3-yl)-1H-pyrazole-5-carboxylic acid (90 mg) obtained in (Example 3.47) <Step 2>, the title compound (98 mg) was obtained in the form of a white solid by the same method as that of (Example 3.22) <Step 3> or a method equivalent thereto.

Example 3.48

Synthesis of N-(6-fluoro-2-phenyl-[1,2,4]triazolo[1,5-a]pyridin-7-yl)-1-methyl-4-(1-methyl-1H-imidazol-4-yl)-1H-pyrazole-5-carboxamide Using the methyl 1-methyl-4-(1-methyl-1H-imidazol-4-yl)-1H-pyrazole-5-carboxylate (50 mg) obtained in (Example 2.17) <Step 1>, the corresponding sodium salts were obtained by the same method as that of (Example 2.2) <Step 2> or a method equivalent thereto. Using the obtained sodium salts (50 mg), the title compound (12 mg) was obtained in the form of a brown solid by the same method as that of (Example 3.22) <Step 3> or a method equivalent thereto.

Example 3.49

Synthesis of 4-(2,5-dimethylpyrimidin-4-yl)-N-(6-fluoro-2-(pyridin-3-yl)-[1,2,4]triazolo[1,5-a]pyridin-7-yl)-1-methyl-1H-pyrazole-5-carboxamide <Step 1> Synthesis of N-(2-bromo-6-fluoro-[1,2,4]triazolo[1,5-a]pyridin-7-yl)-4-(2,5-dimethylpyrimidin-4-yl)-1-methyl-1H-pyrazole-5-carboxamide Using the 2-bromo-6-fluoro-[1,2,4]triazolo[1,5-a]pyridin-7-amine hydrochloride (2.3 g) obtained in (Example 4.24) <Step 1> and the 4-(2,5-dimethylpyrimidin-4-yl)-1H-pyrazole-5-carboxylic acid (2.0 g) obtained in (Example 3.22) <Step 2>, the title compound (2.3 g) was obtained in the form of a beige solid by the same method as that of (Example 3.22) <Step 3> or a method equivalent thereto.

<Step 2> Synthesis of 4-(2,5-dimethylpyrimidin-4-yl)-N-(6-fluoro-2-(pyridin-3-yl)-[1,2,4]triazolo[1,5-a]pyridin-7-yl)-1-methyl-1H-pyrazole-5-carboxamide Using the N-(2-bromo-6-fluoro-[1,2,4]triazolo[1,5-a]pyridin-7-yl)-4-(2,5-dimethylpyrimidin-4-yl)-1-methyl-1H-pyrazole-5-carboxamide (500 mg) obtained in (Example 3.49) <Step 1> and 3-pyridineboronic acid (414 mg), the title compound (15 mg) was obtained in the form of a colorless solid by the same method as that of (Example 3.15) <Step 7> or a method equivalent thereto.

Example 3.50

Synthesis of 4-(2,5-dimethylpyrimidin-4-yl)-N-(6-fluoro-2-(o-tolyl)-[1,2,4]triazolo[1,5-a]pyridin-7-yl)-1-methyl-1H-pyrazole-5-carboxamide Using the N-(2-bromo-6-fluoro-[1,2,4]triazolo[1,5-a]pyridin-7-yl)-4-(2,5-dimethylpyrimidin-4-yl)-1-methyl-1H-pyrazole-5-carboxamide (100 mg) obtained in (Example 3.49) <Step 1> and o-tolylboronic acid (55 mg), the title compound (24 mg) was obtained in the form of a white solid by the same method as that of (Example 3.15) <Step 7> or a method equivalent thereto.

Using the corresponding carboxylic acid or sodium salts, the compounds of (Example 3.51) to (Example 3.53) were synthesized by the same method as that of (Example 3.1) <Step 4> or a method equivalent thereto.

Example 3.51

N-(6-fluoro-2-phenyl-[1,2,4]triazolo[1,5-a]pyridin-7-yl)-1-methyl-4-(5-methylpyridin-2-yl)-1H-pyrazole-5-carboxamide

Example 3.52

N-(6-fluoro-2-phenyl-[1,2,4]triazolo[1,5-a]pyridin-7-yl)-4-(4-methoxypyridin-2-yl)-1-methyl-1H-pyrazole-5-carboxamide

Example 3.53

4-(4,6-dimethylpyridin-2-yl)-N-(6-fluoro-2-phenyl-[1,2,4]triazolo[1,5-a]pyridin-7-yl)-1-methyl-1H-pyrazole-5-carboxamide 2,2,2-trifluoroacetate

Example 3.54

Synthesis of 4-(4,6-dimethylpyridin-2-yl)-N-(6-fluoro-2-(4-fluorophenyl)-[1,2,4]triazolo[1,5-a]pyridin-7-yl)-1-methyl-1H-pyrazole-5-carboxamide <Step 1> Synthesis of tert-butyl (6-fluoro-2-(4-fluorophenyl)-[1,2,4]triazolo[1,5-a]pyridin-7-yl)carbamate Using the tert-butyl (2-bromo-6-fluoro-[1,2,4]triazolo[1,5-a]pyridin-7-yl)carbamate (180 mg) obtained in (Example 4.11) <Step 4> and 4-fluoroboronic acid (114 mg), the title compound (123 mg) was obtained in the form of a white solid by the same method as that of (Example 3.15) <Step 7> or a method equivalent thereto.

<Step 2> Synthesis of 6-fluoro-2-(4-fluorophenyl)-[1,2,4]triazolo[1,5-a]pyridin-7-amine Using the tert-butyl (6-fluoro-2-(4-fluorophenyl)-[1,2,4]triazolo[1,5-a]pyridin-7-yl)carbamate (105 mg) obtained in (Example 3.54) <Step 1>, the title compound (34 mg) was obtained in the form of a colorless solid by the same method as that of (Example 3.15) <Step 5> or a method equivalent thereto.

<Step 3> Synthesis of 4-(4,6-dimethylpyridin-2-yl)-N-(6-fluoro-2-(4-fluorophenyl)-[1,2,4]triazolo[1,5-a]pyridin-7-yl)-1-methyl-1H-pyrazole-5-carboxamide Using the 6-fluoro-2-(4-fluorophenyl)-[1,2,4]triazolo[1,5-a]pyridin-7-amine (7 mg) obtained in (Example 3.54) <Step 2> and the sodium 4-(4,6-dimethylpyridin-2-yl)-1-methyl-1H-pyrazole-5-carboxylate (11 mg) obtained in (Example 3.11) <Step 1>, the title compound (1.4 mg) was obtained in the form of a colorless solid by the same method as that of (Example 3.1) <Step 4> or a method equivalent thereto.

Example 4.1

Synthesis of (S)-4-(4-(difluoromethyl)thiazol-2-yl)-1-methyl-N-(2-(2-methylpyrrolidin-1-yl)-[1,2,4]triazolo[1,5-a]pyridin-7-yl)-1H-pyrazole-5-carboxamide An (S)-2-methylpyrrolidine (0.5 ml) solution of the N-(2-bromo-[1,2,4]triazolo[1,5-a]pyridin-7-yl)-4-(4-(difluoromethyl)thiazol-2-yl)-1-methyl-1H-pyrazole-5-carboxamide (30 mg) synthesized in (Example 3.15) <Step 6> was stirred under microwave heating at 150° C. for 1 hour. Thereafter, ethyl acetate (20 ml) was added to the reaction solution, and the mixed solution was successively washed with water (15 ml) twice and with a saturated saline (10 ml) once, and was then dried over anhydrous sodium sulfate. The solvent was distilled away under reduced pressure, and the obtained residue was then purified by silica gel column chromatography (silica gel:eluent; heptane:ethyl acetate=40:60), so as to obtain the title compound (13 mg) in the form of a light yellow solid.

Example 4.2

Synthesis of (S)-4-(5-chloro-4-(difluoromethyl)thiazol-2-yl)-1-methyl-N-(2-(2-methylpyrrolidin-1-yl)-[1,2,4]triazolo[1,5-a]pyridin-7-yl)-1H-pyrazole-5-carboxamide Using the (S)-4-(4-(difluoromethyl)thiazol-2-yl)-1-methyl-N-(2-(2-methylpyrrolidin-1-yl)-[1,2,4]triazolo[1,5-a]pyridin-7-yl)-1H-pyrazole-5-carboxamide (11 mg) obtained in (Example 4.1) and N-chlorosuccinimide (3.5 mg), the title compound (5.5 mg) was obtained in the form of a white solid by the same method as that of (Example 1.4) <Step 1> or a method equivalent thereto.

Example 4.3

Synthesis of (S)-1-methyl-N-(2-(2-methylpyrrolidin-1-yl)-[1,2,4]triazolo[1,5-a]pyridin-7-yl)-4-(6-(trifluoromethyl)pyridin-2-yl)-1H-pyrazole-5-carboxamide <Step 1> Synthesis of (S)-2-(2-methylpyrrolidin-1-yl)-[1,2,4]triazolo[1,5-a]pyridin-7-amine Using the 2-bromo-[1,2,4]triazolo[1,5-a]pyridin-7-amine hydrochloride (750 mg) obtained in (Example 3.15) <Step 5>, the title compound (450 mg) was obtained in the form of a light yellow solid by the same method as that of (Example 4.1) or a method equivalent thereto.

<Step 2> Synthesis of (S)-1-methyl-N-(2-(2-methylpyrrolidin-1-yl)-[1,2,4]triazolo[1,5-a]pyridin-7-yl)-4-(6-(trifluoromethyl)pyridin-2-yl)-1H-pyrazole-5-carboxamide Oxalyl chloride (0.52 ml) and N,N-dimethylformamide (5 μl) were added to a methylene chloride (5 ml) solution of the 1-methyl-4-(6-(trifluoromethyl)pyridin-2-yl)-1H-pyrazole-5-carboxylic acid (160 mg) obtained in (Example 3.10) <Step 1>, and the obtained mixture was then stirred at room temperature for 1 hour. Thereafter, the solvent was distilled away under reduced pressure, and a crude product (175 mg) was obtained in the form of a yellow liquid. To a methylene chloride (1 ml) solution of the obtained crude product (42 mg), pyridine (35 μl) and a methylene chloride (1 ml) solution of the (S)-2-(2-methylpyrrolidin-1-yl)-[1,2,4]triazolo[1,5-a]pyridin-7-amine (26 mg) obtained in (Example 4.3) <Step 1>, and the obtained mixture was then stirred for 16 hours. Thereafter, the solvent was distilled away under reduced pressure, and the obtained residue was then purified by LC/MS, so as to obtain the title compound (36 mg) in the form of a white solid.

Example 4.4

Synthesis of (S)-1-methyl-4-(4-methylpyridin-2-yl)-N-(2-(2-methylpyrrolidin-1-yl)-[1,2,4]triazolo[1,5-a]pyridin-7-yl)-1H-pyrazole-5-carboxamide <Step 1> Synthesis of methyl 1-methyl-4-(4-methylpyridin-2-yl)-1H-pyrazole-5-carboxylate Using 2-bromo-4-methylpyridine (273 mg), the title compound (233 mg) was obtained in the form of a yellow liquid by the same method as that of (Example 1.1) <Step 2> or a method equivalent thereto.

<Step 2> Synthesis of 1-methyl-4-(4-methylpyridin-2-yl)-1H-pyrazole-5-carboxylic acid Using the methyl 1-methyl-4-(4-methylpyridin-2-yl)-1H-pyrazole-5-carboxylate (230 mg) obtained in (Example 4.4) <Step 1>, the title compound (121 mg) was obtained in the form of a white solid by the same method as that of (Example 1.1) <Step 3> or a method equivalent thereto.

<Step 3> Synthesis of (S)-1-methyl-4-(4-methylpyridin-2-yl)-N-(2-(2-methylpyrrolidin-1-yl)-[1,2,4]triazolo[1,5-a]pyridin-7-yl)-1H-pyrazole-5-carboxamide Using the 1-methyl-4-(4-methylpyridin-2-yl)-1H-pyrazole-5-carboxylic acid obtained in (Example 4.4) <Step 2>, the title compound (28 mg) was obtained in the form of a white solid by the same method as that of (Example 4.3) <Step 2> or a method equivalent thereto.

Example 4.5

Synthesis of (S)-4-(4-methoxypyridin-2-yl)-1-methyl-N-(2-(2-methylpyrrolidin-1-yl)-[1,2,4]triazolo[1,5-a]pyridin-7-yl)-1H-pyrazole-5-carboxamide <Step 1> Synthesis of methyl 4-(4-methoxypyridin-2-yl)-1-methyl-1H-pyrazole-5-carboxylate Using 2-bromo-4-methoxypyridine (298 mg), the title compound (186 mg) was obtained in the form of a yellow liquid by the same method as that of (Example 1.1) <Step 2> or a method equivalent thereto.

<Step 2> Synthesis of 4-(4-methoxypyridin-2-yl)-1-methyl-1H-pyrazole-5-carboxylic acid Using the methyl 4-(4-methoxypyridin-2-yl)-1-methyl-1H-pyrazole-5-carboxylate (185 mg) obtained in (Example 4.5) <Step 1>, the title compound (138 mg) was obtained in the form of a red solid by the same method as that of (Example 1.1) <Step 3> or a method equivalent thereto.

<Step 3> Synthesis of (S)-4-(4-methoxypyridin-2-yl)-1-methyl-N-(2-(2-methylpyrrolidin-1-yl)-[1,2,4]triazolo[1,5-a]pyridin-7-yl)-1H-pyrazole-5-carboxamide Using the 4-(4-methoxypyridin-2-yl)-1-methyl-1H-pyrazole-5-carboxylic acid obtained in (Example 4.5) <Step 2>, the title compound (18 mg) was obtained in the form of a colorless solid by the same method as that of (Example 4.3) <Step 2> or a method equivalent thereto.

Example 4.6

Synthesis of (S)-1-methyl-4-(6-methylpyrazin-2-yl)-N-(2-(2-methylpyrrolidin-1-yl)-[1,2,4]triazolo[1,5-a]pyridin-7-yl)-1H-pyrazole-5-carboxamide Using the 1-methyl-4-(6-methylpyrazin-2-yl)-1H-pyrazole-5-carboxylic acid obtained in (Example 3.9) <Step 2>, the title compound (21 mg) was obtained in the form of a colorless solid by the same method as that of (Example 4.3) <Step 2> or a method equivalent thereto.

Example 4.7

Synthesis of (S)-1-methyl-4-(6-methylpyridin-2-yl)-N-(2-(2-methylpyrrolidin-1-yl)-[1,2,4]triazolo[1,5-a]pyridin-7-yl)-1H-pyrazole-5-carboxamide Using the 1-methyl-4-(6-methylpyridin-2-yl)-1H-pyrazole-5-carboxylic acid obtained in (Example 3.3) <Step 2>, the title compound (17 mg) was obtained in the form of a white solid by the same method as that of (Example 4.3) <Step 2> or a method equivalent thereto.

Example 4.8

Synthesis of (S)-4-(4,6-dimethylpyridin-2-yl)-1-methyl-N-(2-(2-methylpyrrolidin-1-yl)-[1,2,4]triazolo[1,5-a]pyridin-7-yl)-1H-pyrazole-5-carboxamide <Step 1> Synthesis of methyl 4-(4,6-dimethylpyridin-2-yl)-1-methyl-1H-pyrazole-5-carboxylate Using 2-bromo-4,6-dimethylpyridine (295 mg), the title compound (310 mg) was obtained in the form of a yellow liquid by the same method as that of (Example 1.1) <Step 2> or a method equivalent thereto.

<Step 2> Synthesis of 4-(4,6-dimethylpyridin-2-yl)-1-methyl-1H-pyrazole-5-carboxylic acid Using the methyl 4-(4,6-dimethylpyridin-2-yl)-1-methyl-1H-pyrazole-5-carboxylate (310 mg) obtained in (Example 4.8) <Step 1>, the title compound (141 mg) was obtained in the form of a colorless solid by the same method as that of (Example 1.1) <Step 3> or a method equivalent thereto.

<Step 3> Synthesis of (S)-4-(4,6-dimethylpyridin-2-yl)-1-methyl-N-(2-(2-methylpyrrolidin-1-yl)-[1,2,4]triazolo[1,5-a]pyridin-7-yl)-1H-pyrazole-5-carboxamide Using the 4-(4,6-dimethylpyridin-2-yl)-1-methyl-1H-pyrazole-5-carboxylic acid obtained in (Example 4.8) <Step 2>, the title compound (10 mg) was obtained in the form of a yellow solid by the same method as that of (Example 4.3) <Step 2> or a method equivalent thereto.

Example 4.9

Synthesis of (S)-4-(4-(difluoromethyl)-5-methylthiazol-2-yl)-1-methyl-N-(2-(2-methylpyrrolidin-1-yl)-[1,2,4]triazolo[1,5-a]pyridin-7-yl)-1H-pyrazole-5-carboxamide <Step 1> Synthesis of 4-(4-(difluoromethyl)-5-methylthiazol-2-yl)-1-methyl-1H-pyrazole-5-carboxylic acid Using the methyl 4-(4-(difluoromethyl)-5-methylthiazol-2-yl)-1-methyl-1H-pyrazole-5-carboxylate (90 mg) obtained in (Example 1.4) <Step 2>, the title compound (64 mg) was obtained in the form of a white solid by the same method as that of (Example 1.1) <Step 3> or a method equivalent thereto.

<Step 2> Synthesis of (S)-4-(4-(difluoromethyl)-5-methylthiazol-2-yl)-1-methyl-N-(2-(2-methylpyrrolidin-1-yl)-[1,2,4]triazolo[1,5-a]pyridin-7-yl)-1H-pyrazole-5-carboxamide Using the 4-(4-(difluoromethyl)-5-methylthiazol-2-yl)-1-methyl-1H-pyrazole-5-carboxylic acid obtained in (Example 4.9) <Step 1>, the title compound (21 mg) was obtained in the form of a white solid by the same method as that of (Example 4.3) <Step 2> or a method equivalent thereto.

Example 4.10

Synthesis of (S)-1-methyl-N-(2-(2-methylpyrrolidin-1-yl)-[1,2,4]triazolo[1,5-a]pyridin-7-yl)-4-(4-(trifluoromethylthiazol-2-yl)-1H-pyrazole-5-carboxamide <Step 1> Synthesis of 1-methyl-4-(4-(trifluoromethyl)thiazol-2-yl)-1H-pyrazole-5-carboxylic acid Using the methyl 4-(4-(difluoromethyl)-5-methylthiazol-2-yl)-1-methyl-1H-pyrazole-5-carboxylate (210 mg) obtained in (Example 1.5) <Step 1>, the title compound (173 mg) was obtained in the form of a whitish brown solid by the same method as that of (Example 1.1) <Step 3> or a method equivalent thereto.

<Step 2> Synthesis of (S)-1-methyl-N-(2-(2-methylpyrrolidin-1-yl)-[1,2,4]triazolo[1,5-a]pyridin-7-yl)-4-(4-(trifluoromethylthiazol-2-yl)-1H-pyrazole-5-carboxamide Using the 1-methyl-4-(4-(trifluoromethyl)thiazol-2-yl)-1H-pyrazole-5-carboxylic acid obtained in (Example 4.10) <Step 1>, the title compound (14 mg) was obtained in the form of a white solid by the same method as that of (Example 4.3) <Step 2> or a method equivalent thereto.

Example 4.11

Synthesis of (R)—N-(6-fluoro-2-(2-(trifluoromethyl)pyrrolidin-1-yl)-[1,2,4]triazolo[1,5-a]pyridin-7-yl)-1-methyl-4-(6-methylpyridin-2-yl)-1H-pyrazole-5-carboxamide <Step 1> Synthesis of methyl 2-amino-6-fluoro-[1,2,4]triazolo[1,5-a]pyridine-7-carboxylate Using methyl 2-amino-5-fluoroisonicotinate, the title compound was obtained in the form of a yellow solid by the same method as that of (Example 3.15) <Step 1> or a method equivalent thereto.

<Step 2> Synthesis of methyl 2-bromo-6-fluoro-[1,2,4]triazolo[1,5-a]pyridine-7-carboxylate Using the methyl 2-amino-6-fluoro-[1,2,4]triazolo[1,5-a]pyridine-7-carboxylate (10 g) obtained in (Example 4.11) <Step 1>, the title compound (5.5 g) was obtained in the form of a brown solid by the same method as that of (Example 3.15) <Step 2> or a method equivalent thereto.

<Step 3> Synthesis of 2-bromo-6-fluoro-[1,2,4]triazolo[1,5-a]pyridine-7-carboxylic acid Using the methyl 2-bromo-6-fluoro-[1,2,4]triazolo[1,5-a]pyridine-7-carboxylate (5.56 g) obtained in (Example 4.11) <Step 2>, the title compound (2.15 g) was obtained in the form of a brown solid by the same method as that of (Example 3.15) <Step 3> or a method equivalent thereto.

<Step 4> Synthesis of tert-butyl (2-bromo-6-fluoro-[1,2,4]triazolo[1,5-a]pyridin-7-yl)carbamate Using the 2-bromo-6-fluoro-[1,2,4]triazolo[1,5-a]pyridine-7-carboxylic acid (2.15 g) obtained in (Example 4.11) <Step 3>, the title compound (2.52 g) was obtained in the form of an orange solid by the same method as that of (Example 3.15) <Step 3> or a method equivalent thereto.

<Step 5> Synthesis of (R)-tert-butyl (6-fluoro-2-(2-(trifluoromethyl)pyrrolidin-1-yl)-[1,2,4]triazolo[1,5-a]pyridin-7-yl)carbamate A 1,4-dioxane (5.5 ml) solution of the tert-butyl (2-bromo-6-fluoro-[1,2,4]triazolo[1,5-a]pyridin-7-yl)carbamate (110 mg) obtained in (Example 4.11) <Step 4>, tris(dibenzylideneacetone)dipalladium(0) (48 mg), 4,5-bis(diphenylphosphino)-9,9-dimethylxanthene (61 mg), cesium carbonate (162 mg), and (R)-2-(trifluoromethyl)pyrrolidine (231 mg) was purged with nitrogen gas, and it was then stirred under heating at 110° C. for 12 hours. Thereafter, water and ethyl acetate were added to the reaction solution, and the mixed solution was then extracted with ethyl acetate (10 ml) three times. The solvent was distilled away under reduced pressure, and the obtained residue was then purified by silica gel column chromatography (silica gel:eluent; heptane:ethyl acetate=5:1-1:1), so as to obtain the title compound (75 mg) in the form of a white solid.

<Step 6> Synthesis of (R)-6-fluoro-2-(2-(trifluoromethyl)pyrrolidin-1-yl)-[1,2,4]triazolo[1,5-a]pyridin-7-amine Using the (R)-tert-butyl (6-fluoro-2-(2-(trifluoromethyl)pyrrolidin-1-yl)-[1,2,4]triazolo[1,5-a]pyridin-7- yl)carbamate (73 mg) obtained in (Example 4.11) <Step 5>, the title compound (41 mg) was obtained in the form of a white solid by the same method as that of (Example 3.15) <Step 5> or a method equivalent thereto.

<Step 7> Synthesis of (R)—N-(6-fluoro-2-(2-(trifluoromethyl)pyrrolidin-1-yl)-[1,2,4]triazolo[1,5-a]pyridin-7-yl)-1-methyl-4-(6-methylpyridin-2-yl)-1H-pyrazole-5-carboxamide Using the 1-methyl-4-(6-methylpyridin-2-yl)-1H-pyrazole-5-carboxylic acid (3.8 mg) obtained in (Example 3.3) <Step 2> and the (R)-6-fluoro-2-(2-(trifluoromethyl)pyrrolidin-1-yl)-[1,2,4]triazolo[1,5-a]pyridin-7-amine (5 mg) obtained in (Example 4.11) <Step 6>, the title compound (1.1 mg) was obtained in the form of a brown solid by the same method as that of (Example 3.1) <Step 4> or a method equivalent thereto.

Example 4.12

Synthesis of (R)-4-(4-(difluoromethyl)thiazol-2-yl)-N-(2-(3-fluoropyrrolidin-1-yl)-[1,2,4]triazolo[1,5-a]pyridin-7-yl)-1-methyl-1H-pyrazole-5-carboxamide Using (R)-3-fluoropyrrolidine hydrochloride (179 mg), the title compound (4.4 mg) was obtained in the form of a light brown solid by the same method as that of (Example 4.1) or a method equivalent thereto.

Example 4.13

Synthesis of (R)—N-(2-(3-fluoropyrrolidin-1-yl)-[1,2,4]triazolo[1,5-a]pyridin-7-yl)-1-methyl-4-(4-(trifluoromethyl)thiazol-2-yl)-1H-pyrazole-5-carboxamide <Step 1> Synthesis of (R)-2-(3-fluoropyrrolidin-1-yl)-[1,2,4]triazolo[1,5-a]pyridin-7-amine Using the 2-bromo-[1,2,4]triazolo[1,5-a]pyridin-7-amine hydrochloride (700 mg) obtained in (Example 3.15) <Step 5> and (R)-3-fluoropyrrolidine hydrochloride (5 g), the title compound (160 mg) was obtained in the form of a beige solid by the same method as that of (Example 4.1) or a method equivalent thereto.

<Step 2> Synthesis of (R)—N-(2-(3-fluoropyrrolidin-1-yl)-[1,2,4]triazolo[1,5-a]pyridin-7-yl)-1-methyl-4-(4-(trifluoromethyl)thiazol-2-yl)-1H-pyrazole-5-carboxamide Using the 1-methyl-4-(4-(trifluoromethyl)thiazol-2-yl)-1H-pyrazole-5-carboxylic acid obtained in (Example 4.10) <Step 1> and the (R)-2-(3-fluoropyrrolidin-1-yl)-[1,2,4]triazolo[1,5-a]pyridin-7-amine (20 mg) obtained in (Example 4.13) <Step 1>, the title compound (13 mg) was obtained in the form of a white solid by the same method as that of (Example 4.3) <Step 2> or a method equivalent thereto.

Example 4.14

Synthesis of (R)-4-(4-(difluoromethyl)-5-methylthiazol-2-yl)N-(2-(3-fluoropyrrolidin-1-yl)-[1,2,4]triazolo[1,5-a]pyridin-7-yl)-1-methyl-1H-pyrazole-5-carboxamide Using the 4-(4-(difluoromethyl)-5-methylthiazol-2-yl)-1-methyl-1H-pyrazole-5-carboxylic acid obtained in (Example 4.9) <Step 1> and the (R)-2-(3-fluoropyrrolidin-1-yl)-[1,2,4]triazolo[1,5-a]pyridin-7-amine (20 mg) obtained in (Example 4.13) <Step 1>, the title compound (19 mg) was obtained in the form of a white solid by the same method as that of (Example 4.3) <Step 2> or a method equivalent thereto.

Example 4.15

Synthesis of (S)-4-(4-(difluoromethyl)thiazol-2-yl)-N-(2-(3-fluoropyrrolidin-1-yl)-[1,2,4]triazolo[1,5-a]pyridin-7-yl)-1-methyl-1H-pyrazole-5-carboxamide Using (S)-3-fluoropyrrolidine hydrochloride (179 mg), the title compound (4.3 mg) was obtained in the form of a Example 4.16

Synthesis of (S)—N-(2-(3-fluoropyrrolidin-1-yl)-[1,2,4]triazolo[1,5-a]pyridin-7-yl)-1-methyl-4-(6-(trifluoromethyl)pyridin-2-yl)-1H-pyrazole-5-carboxamide <Step 1> Synthesis of (S)-(2-(3-fluoropyrrolidin-1-yl)-[1,2,4]triazolo[1,5-a]pyridin-7-amine Using the 2-bromo-[1,2,4]triazolo[1,5-a]pyridin-7-amine hydrochloride (700 mg) obtained in (Example 3.15) <Step 5> and (R)-3-fluoropyrrolidine hydrochloride (4.5 g), the title compound (240 mg) was obtained in the form of a white solid by the same method as that of (Example 4.1) or a method equivalent thereto.

<Step 2> Synthesis of (S)—N-(2-(3-fluoropyrrolidin-1-yl)-[1,2,4]triazolo[1,5-a]pyridin-7-yl)-1-methyl-4-(6-(trifluoromethyl)pyridin-2-yl)-1H-pyrazole-5-carboxamide Using the 1-methyl-4-(6-(trifluoromethyl)pyridin-2-yl)-1H-pyrazole-5-carboxylic acid obtained in (Example 3.10) <Step 1> and the (S)-2-(3-fluoropyrrolidin-1-yl)-[1,2,4]triazolo[1,5-a]pyridin-7-amine (20 mg) obtained in (Example 4.16) <Step 1>, the title compound (9.3 mg) was obtained by the same method as that of (Example 4.3) <Step 2> or a method equivalent thereto.

Example 4.17

Synthesis of (S)—N-(2-(3-fluoropyrrolidin-1-yl)-[1,2,4]triazolo[1,5-a]pyridin-7-yl)-1-methyl-4-(4-methylpyridin-2-yl)-1H-pyrazole-5-carboxamide Using the 1-methyl-4-(4-methylpyridin-2-yl)-1H-pyrazole-5-carboxylic acid obtained in (Example 4.4) <Step 2> and the (S)-2-(3-fluoropyrrolidin-1-yl)-[1,2,4]triazolo[1,5-a]pyridin-7-amine (20 mg) obtained in (Example 4.16) <Step 1>, the title compound (7.6 mg) was obtained by the same method as that of (Example 4.3) <Step 2> or a method equivalent thereto.

Example 4.18

Synthesis of (S)—N-(2-(3-fluoropyrrolidin-1-yl)-[1,2,4]triazolo[1,5-a]pyridin-7-yl)-4-(4-methoxypyridin-2-yl)-1-methyl-1H-pyrazole-5-carboxamide Using the 4-(4-methoxypyridin-2-yl)-1-methyl-1H-pyrazole-5-carboxylic acid obtained in (Example 4.5) <Step 2> and the (S)-2-(3-fluoropyrrolidin-1-yl)-[1,2,4]triazolo[1,5-a]pyridin-7-amine (20 mg) obtained in (Example 4.16) <Step 1>, the title compound (1.0 mg) was obtained by the same method as that of (Example 4.3) <Step 2> or a method equivalent thereto.

Example 4.19

Synthesis of (S)—N-(2-(3-fluoropyrrolidin-1-yl)-[1,2,4]triazolo[1,5-a]pyridin-7-yl)-1-methyl-4-(6-methylpyrazin-2-yl)-1H-pyrazole-5-carboxamide Using the 1-methyl-4-(6-methylpyrazin-2-yl)-1H-pyrazole-5-carboxylic acid obtained in (Example 3.9) <Step 2> and the (S)-2-(3-fluoropyrrolidin-1-yl)-[1,2,4]triazolo[1,5-a]pyridin-7-amine (20 mg) obtained in (Example 4.16) <Step 1>, the title compound (3.2 mg) was obtained by the same method as that of (Example 4.3) <Step 2> or a method equivalent thereto.

Example 4.20

Synthesis of (S)-4-(4,6-dimethylpyridin-2-yl)-N-(2-(3-fluoropyrrolidin-1-yl)-[1,2,4]triazolo[1,5-a]pyridin-7-yl)-1-methyl-1H-pyrazole-5-carboxamide Using the 4-(4,6-dimethylpyridin-2-yl)-1-methyl-1H-pyrazole-5-carboxylic acid obtained in (Example 4.8) <Step 2> and the (S)-2-(3-fluoropyrrolidin-1-yl)-[1,2,4]triazolo[1,5-a]pyridin-7-amine (20 mg) obtained in (Example 4.16) <Step 1>, the title compound (4.8 mg) was obtained by the same method as that of (Example 4.3) <Step 2> or a method equivalent thereto.

Example 4.21

Synthesis of (S)—N-(2-(3-fluoropyrrolidin-1-yl)-[1,2,4]triazolo[1,5-a]pyridin-7-yl)-1-methyl-4-(6-methylpyridin-2-yl)-1H-pyrazole-5-carboxamide Using the 1-methyl-4-(6-methylpyridin-2-yl)-1H-pyrazole-5-carboxylic acid obtained in (Example 3.3) <Step 2> and the (S)-2-(3-fluoropyrrolidin-1-yl)-[1,2,4]triazolo[1,5-a]pyridin-7-amine (20 mg) obtained in (Example 4.16) <Step 1>, the title compound (1.9 mg) was obtained by the same method as that of (Example 4.3) <Step 2> or a method equivalent thereto.

Example 4.22

Synthesis of (S)—N-(2-(3-fluoropyrrolidin-1-yl)-[1,2,4]triazolo[1,5-a]pyridin-7-yl)-1-methyl-4-(4-(trifluoromethyl)thiazol-2-yl)-1H-pyrazole-5-carboxamide Using the 1-methyl-4-(4-(trifluoromethyl)methylthiazol-2-yl)-1H-pyrazole-5-carboxylic acid obtained in (Example 4.10) <Step 1> and the (S)-2-(3-fluoropyrrolidin-1-yl)-[1,2,4]triazolo[1,5-a]pyridin-7-amine (20 mg) obtained in (Example 4.16) <Step 1>, the title compound (11 mg) was obtained by the same method as that of (Example 4.3) <Step 2> or a method equivalent thereto.

Example 4.23

Synthesis of (S)-4-(4-(difluoromethyl)-5-methylthiazol-2-yl)-N-(2-(3-fluoropyrrolidin-1-yl)-[1,2,4]triazolo[1,5-a]pyridin-7-yl)-1-methyl-1H-pyrazole-5-carboxamide Using the 4-(4-(difluoromethyl)-5-methylthiazol-2-yl)-1-methyl-1H-pyrazole-5-carboxylic acid obtained in (Example 4.9) <Step 1> and the (S)-2-(3-fluoropyrrolidin-1-yl)-[1,2,4]triazolo[1,5-a]pyridin-7-amine (20 mg) obtained in (Example 4.16) <Step 1>, the title compound (47 mg) was obtained by the same method as that of (Example 4.3) <Step 2> or a method equivalent thereto.

Example 4.24

Synthesis of (S)-4-(4,6-dimethylpyridin-2-yl)-N-(6-fluoro-2-(3-fluoropyrrolidin-1-yl)-[1,2,4]triazolo[1,5-a]pyridin-7-yl)-1-methyl-1H-pyrazole-5-carboxamide

<Step 1> Synthesis of 2-bromo-6-fluoro-[1,2,4]triazolo[1,5-a]pyridin-7-amine hydrochloride Using the tert-butyl (2-bromo-6-fluoro-[1,2,4]triazolo[1,5-a]pyridin-7-yl)carbamate (200 mg) obtained in (Example 4.11) <Step 4>, the title compound (154 mg) was obtained in the form of a white solid by the same method as that of (Example 3.15) <Step 5> or a method equivalent thereto.

<Step 2> Synthesis of (S)-6-fluoro-2-(3-fluoropyrrolidin-1-yl)-[1,2,4]triazolo[1,5-a]pyridin-7-amine Using the 2-bromo-6-fluoro-[1,2,4]triazolo[1,5-a]pyridin-7-amine hydrochloride (100 mg) obtained in (Example 4.24) <Step 1> and (S)-3-fluoropyrrolidine hydrochloride (469 mg), the title compound (15.5 mg) was obtained in the form of a beige solid by the same method as that of (Example 4.1) or a method equivalent thereto.

<Step 3> Synthesis of (S)-4-(4,6-dimethylpyridin-2-yl)-N-(6-fluoro-2-(3-fluoropyrrolidin-1-yl)-[1,2,4]triazolo[1,5-a]pyridin-7-yl)-1-methyl-1H-pyrazole-5-carboxamide Using the (S)-6-fluoro-2-(3-fluoropyrrolidin-1-yl)-[1,2,4]triazolo[1,5-a]pyridin-7-amine (11 mg) obtained in (Example 4.24) <Step 2> and the 4-(4,6-dimethylpyridin-2-yl)-1-methyl-1H-pyrazole-5-carboxylic acid (10 mg) obtained in (Example 4.8) <Step 2>, the title compound (3.0 mg) was obtained in the form of a whitish brown solid by the same method as that of (Example 3.1) <Step 4> or a method equivalent thereto.

Example 4.25

Synthesis of 4-(4-(difluoromethyl)thiazol-2-yl)-1-methyl-N-(2-(pyrrolidin-1-yl)-[1,2,4]triazolo[1,5-a]pyridin-7-yl)-1H-pyrazole-5-carboxamide Using pyrrolidine (0.4 ml), the title compound (18 mg) was obtained in the form of a light yellow solid by the same method as that of (Example 4.1) or a method equivalent thereto.

Example 4.26

Synthesis of 4-(5-chloro-4-(difluoromethyl)thiazol-2-yl)-1-methyl-N-(2-(pyrrolidin-1-yl)-[1,2,4]triazolo[1,5-a]pyridin-7-yl)-1H-pyrazole-5-carboxamide Using the 4-(4-(difluoromethyl)thiazol-2-yl)-1-methyl-N-(2-(pyrrolidin-1-yl)-[1,2,4]triazolo[1,5-a]pyridin-7-yl)-1-methyl-1H-pyrazole-5-carboxamide (15 mg) obtained in (Example 4.25) and N-chlorosuccinimide (5.4 mg), the title compound (2.3 mg) was obtained in the form of a light yellow solid by the same method as that of (Example 1.4) <Step 1> or a method equivalent thereto.

Example 4.27

Synthesis of 1-methyl-N-(2-(pyrrolidin-1-yl)-[1,2,4]triazolo[1,5-a]pyridin-7-yl)-4-(6-(trifluoromethyl)pyridin-2-yl)-1H-pyrazole-5-carboxamide

<Step 1> Synthesis of 2-(pyrrolidin-1-yl)-[1,2,4]triazolo[1,5-a]pyridin-7-amine hydrochloride The tert-butyl (2-bromo-[1,2,4]triazolo[1,5-a]pyridin-7-yl)carbamate (75 mg) obtained in (Example 3.15) <Step 4> and pyrrolidine (1 ml) were stirred under microwave heating at 150° C. for 1 hour. Thereafter, ethyl acetate (10 ml) and water (3 ml) were added to the reaction solution. An organic layer was separated, and was then dried over anhydrous sodium sulfate. The solvent was distilled away under reduced pressure. Thereafter, potassium hydroxide (134 mg) was added to an ethanol (2 ml) solution of the obtained residue, and the obtained mixture was then heated to reflux for 16 hours. Thereafter, the solvent was distilled away under reduced pressure, and potassium hydroxide (134 mg) was added to an ethylene glycol (2 ml) solution of the obtained residue, followed by heating the obtained mixture at 155° C. for 2 hours. The solvent was distilled away under reduced pressure, and ethyl acetate (10 ml) and water (3 ml) were then added to the obtained residue. An organic layer was separated, and was then dried over anhydrous sodium sulfate. The solvent was distilled away under reduced pressure, and the obtained residue was then purified by silica gel column chromatography (silica gel: eluent; heptane:ethyl acetate=50:50-0:100) to obtain a crude product. The obtained crude product was dissolved in 4 N hydrochloric acid-ethyl acetate (1 ml), and the precipitated solid was then collected by filtration, so as to obtain the title compound (16 mg) in the form of a yellow solid.

<Step 2> Synthesis of 1-methyl-N-(2-(pyrrolidin-1-yl)-[1,2,4]triazolo[1,5-a]pyridin-7-yl)-4-(6-(trifluoromethyl)pyridin-2-yl)-1H-pyrazole-5-carboxamide Using the methyl 1-methyl-4-(6-(trifluoromethyl)pyridin-2-yl)-1H-pyrazole-5-carboxylate (20 mg) obtained in (Example 1.6) <Step 1> and the 2-(pyrrolidin-1-yl)-[1,2,4]triazolo[1,5-a]pyridin-7-amine hydrochloride (14 mg) obtained in (Example 4.27) <Step 1>, the title compound (5.2 mg) was obtained in the form of a light brown solid by the same method as that of (Example 3.15) <Step 6> or a method equivalent thereto.

Example 4.28

Synthesis of 4-(4-methoxypyridin-2-yl)-1-methyl-N-(2-(pyrrolidin-1-yl)-[1,2,4]triazolo[1,5-a]pyridin-7-yl)-1H-pyrazole-5-carboxamide

<Step 1> Synthesis of 2-(pyrrolidin-1-yl)-[1,2,4]triazolo[1,5-a]pyridin-7-amine Using the 2-bromo-[1,2,4]triazolo[1,5-a]pyridin-7-amine hydrochloride (90 mg) obtained in (Example 3.15) <Step 5> and pyrrolidine (0.6 ml), the title compound (64 mg) was obtained in the form of a light brown solid by the same method as that of (Example 4.1) or a method equivalent thereto.

<Step 2> Synthesis of 4-(4-methoxypyridin-2-yl)-1-methyl-N-(2-(pyrrolidin-1-yl)-[1,2,4]triazolo[1,5-a]pyridin-7-yl)-1H-pyrazole-5-carboxamide Using the 4-(4-methoxypyridin-2-yl)-1-methyl-1H-pyrazole-5-carboxylic acid obtained in (Example 4.5) <Step 2> and the 2-(pyrrolidin-1-yl)-[1,2,4]triazolo[1,5-a]pyridin-7-amine (24 mg) obtained in (Example 4.28) <Step 1>, the title compound (19 mg) was obtained in the form of a colorless solid by the same method as that of (Example 4.3) <Step 2> or a method equivalent thereto.

Example 4.29

Synthesis of 1-methyl-4-(6-methylpyrazin-2-yl)-N-(2-(pyrrolidin-1-yl)-[1,2,4]triazolo[1,5-a]pyridin-7-yl)-1H-pyrazole-5-carboxamide Using the 1-methyl-4-(6-methylpyrazin-2-yl)-1H-pyrazole-5-carboxylic acid obtained in (Example 3.9) <Step 2> and the 2-(pyrrolidin-1-yl)-[1,2,4]triazolo[1,5-a]pyridin-7-amine (35 mg) obtained in (Example 4.28) <Step 1>, the title compound (9.3 mg) was obtained in the form of a colorless solid by the same method as that of (Example 4.3) <Step 2> or a method equivalent thereto.

Example 4.30

Synthesis of 1-methyl-4-(4-methylpyridin-2-yl)-N-(2-(pyrrolidin-1-yl)-[1,2,4]triazolo[1,5-a]pyridin-7-yl)-1H-pyrazole-5-carboxamide Using the 1-methyl-4-(6-methylpyrazin-2-yl)-1H-pyrazole-5-carboxylic acid obtained in (Example 4.4) <Step 2> and the 2-(pyrrolidin-1-yl)-[1,2,4]triazolo[1,5-a]pyridin-7-amine (22 mg) obtained in (Example 4.28) <Step 1>, the title compound (14 mg) was obtained in the form of a light brown solid by the same method as that of (Example 4.3) <Step 2> or a method equivalent thereto.

Example 4.31

Synthesis of 1-methyl-4-(6-methylpyridin-2-yl)-N-(2-(pyrrolidin-1-yl)-[1,2,4]triazolo[1,5-a]pyridin-7-yl)-1H-pyrazole-5-carboxamide Using the 1-methyl-4-(6-methylpyridin-2-yl)-1H-pyrazole-5-carboxylic acid obtained in (Example 3.3) <Step 2> and the 2-(pyrrolidin-1-yl)-[1,2,4]triazolo[1,5-a]pyridin-7-amine (31 mg) obtained in (Example 4.28) <Step 1>, the title compound (18 mg) was obtained in the form of a light yellow solid by the same method as that of (Example 4.3) <Step 2> or a method equivalent thereto.

Example 4.32

Synthesis of 4-(4,6-dimethylpyridin-2-yl)-1-methyl-N-(2-(pyrrolidin-1-yl)-[1,2,4]triazolo[1,5-a]pyridin-7-yl)-1H-pyrazole-5-carboxamide Using the 1-methyl-4-(6-methylpyridin-2-yl)-1H-pyrazole-5-carboxylic acid obtained in (Example 4.8) <Step 2> and the 2-(pyrrolidin-1-yl)-[1,2,4]triazolo[1,5-a]pyridin-7-amine (21 mg) obtained in (Example 4.28) <Step 1>, the title compound (3.4 mg) was obtained in the form of a white solid by the same method as that of (Example 4.3) <Step 2> or a method equivalent thereto.

Example 4.33

Synthesis of 4-(4-(difluoromethyl)-5-methylthiazol-2-yl)-1-methyl-N-(2-(pyrrolidin-1-yl)-[1,2,4]triazolo[1,5-a]pyridin-7-yl)-1H-pyrazole-5-carboxamide Using the 4-(4-(difluoromethyl)-5-methylthiazol-2-yl)-1-methyl-1H-pyrazole-5-carboxylic acid obtained in (Example 4.9) <Step 1> and the 2-(pyrrolidin-1-yl)-[1,2,4]triazolo[1,5-a]pyridin-7-amine (15 mg) obtained in (Example 4.28) <Step 1>, the title compound (10 mg) was obtained in the form of a white solid by the same method as that of (Example 4.3) <Step 2> or a method equivalent thereto.

Example 4.34

Synthesis of 1-methyl-N-(2-(pyrrolidin-1-yl)-[1,2,4]triazolo[1,5-a]pyridin-7-yl)-4-(4-(trifluoromethyl)thiazol-2-yl)-1H-pyrazole-5-carboxamide Using the 1-methyl-4-(4-(trifluoromethyl)methylthiazol-2-yl)-1H-pyrazole-5-carboxylic acid obtained in (Example 4.10) <Step 1> and the 2-(pyrrolidin-1-yl)-[1,2,4]triazolo[1,5-a]pyridin-7-amine (12 mg) obtained in (Example 4.28) <Step 1>, the title compound (5.1 mg) was obtained in the form of a white solid by the same method as that of (Example 4.3) <Step 2> or a method equivalent thereto.

Example 4.35

Synthesis of 4-(2,5-dimethylpyrimidin-4-yl)-N-(6-fluoro-2-(pyrrolidin-1-yl)-[1,2,4]triazolo[1,5-a]pyridin-7-yl)-1-methyl-1H-pyrazole-5-carboxamide A pyrrolidine (3 ml) solution of the N-(2-bromo-6-fluoro-[1,2,4]triazolo[1,5-a]pyridin-7-yl)-4-(2,5-dimethylpyrimidin-4-yl)-1-methyl-1H-pyrazole-5-carboxamide (500 mg) obtained in (Example 3.49) <Step 1> was heated at 100° C. for 5 hours. Thereafter, the reaction solution was diluted with water, and was then washed with ethyl acetate. The water layer was adjusted to neutral with 1 N hydrochloric acid, and was then extracted with ethyl acetate. The solvent was distilled away under reduced pressure, and the obtained residue was then purified by silica gel column chromatography (NH silica gel:eluent; heptane:ethyl acetate=75:25-0: 100) to obtain a crude product. Methanol was added to the obtained crude product, followed by collection by filtration, so as to obtain the title compound (82 mg) in the form of a yellow solid.

Example 4.36

Synthesis of 4-(5-chloro-4-(difluoromethyl)thiazol-2-yl)-N-(2-((2S,6R)-2,6-dimethylmorpholino)-[1,2,4]triazolo[1,5-a]pyridin-7-yl)-1-methyl-1H-pyrazole-5-carboxamide Using the 4-(4-(difluoromethyl)thiazol-2-yl)-N-((2S,6R)-2,6-dimethylmorpholino)-[1,2,4]triazolo[1,5-a]pyridin-7-yl)-1-methyl-1H-pyrazole-5-carboxamide (24 mg) obtained in (Example 3.19) and N-chlorosuccinimide (7.1 mg), the title compound (12 mg) was obtained in the form of a white

Example 5.1

Synthesis of 4-(4-(difluoromethyl)-5-methylthiazol-2-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of 2-phenyl-5,6,7,8-tetrahydro-[1,2,4]triazolo[1,5-a]pyridine-7-carboxylic acid 10% Palladium-carbon (3 g) and concentrated hydrochloric acid (3.1 ml) were added to a mixed solution of methanol (200 ml) and methylene chloride (150 ml) containing the 2-phenyl-[1,2,4]triazolo[1,5-a]pyridine-7-carboxylic acid (3 g) obtained in (Example 3.18) <Step 4>, and the obtained mixture was then stirred in a hydrogen atmosphere for 15 hours. Thereafter, the reaction solution was heated to 40° C., and then, it was further stirred for 4 hours. Thereafter, the reaction solution was filtered with Celite, and was then washed with methanol. The filtrate was concentrated under reduced pressure, and the solvent was then distilled away. After that, methanol (20 ml) and a 4 N sodium hydroxide aqueous solution (9 ml) were added to the residue, and the obtained mixture was then stirred at 50° C. for 30 minutes. Thereafter, the solvent was distilled away under reduced pressure, and a 1 N hydrochloric acid aqueous solution (9 ml) was then added to the residue. The generated solid was collected by filtration, and was then washed with water (10 ml). The obtained solid was dried under reduced pressure at 45° C. for 15 hours, so as to obtain the title compound (2.4 g) in the form of a white solid.

<Step 2> Synthesis of tert-butyl (2-phenyl-5,6,7,8-tetrahydro-[1,2,4]triazolo[1,5-a]pyridin-7-yl)-carbamate Using the 2-phenyl-5,6,7,8-tetrahydro-[1,2,4]triazolo[1,5-a]pyridine-7-carboxylic acid (2 g) obtained in (Example 5.1) <Step 1>, the title compound (2 g) was obtained in the form of a white solid by the same method as that of (Example 3.18) <Step 5> or a method equivalent thereto.

<Step 3> Synthesis of 2-phenyl-5,6,7,8-tetrahydro-[1,2,4]triazolo[1,5-a]pyridin-7-amine hydrochloride Using the tert-butyl (2-phenyl-5,6,7,8-tetrahydro-[1,2,4]triazolo[1,5-a]pyridine-7-carbamate (1.9 g) obtained in (Example 5.1) <Step 2>, the title compound (1.7 g) was obtained in the form of a white solid by the same method as that of (Example 3.18) <Step 6> or a method equivalent thereto.

<Step 4> Synthesis of 4-(4-(difluoromethyl)-5-methylthiazol-2-yl)-1-methyl-N-(2-phenyl-5,6,7,8-tetrahydro-[1,2,4]triazolo[1,5-a]pyridin-7-yl)-1H-pyrazole-5-carboxamide Using the 2-phenyl-5,6,7,8-tetrahydro-[1,2,4]triazolo[1,5-a]pyridin-7-amine hydrochloride (17 mg) obtained in (Example 5.1) <Step 3> and the methyl 4-(4-(difluoromethyl)-5-methylthiazol-2-yl)-1-methyl-1H-pyrazole-5-carboxylate (21 mg) obtained in (Example 1.4) <Step 2>, the title compound (14 mg) was obtained in the form of a colorless solid by the same method as that of (Example 2.3) or a method equivalent thereto.

Example 5.2

Synthesis of 4-(4-(difluoromethyl)thiazol-2-yl)-N-(2-(4-fluorophenyl)-5,6,7,8-tetrahydro-[1,2,4]triazolo[1,5-a]pyridin-7-yl)-1-methyl-1H-pyrazole-5-carboxamide <Step 1> Synthesis of 2-(4-fluorophenyl)-5,6,7,8-tetrahydro-[1,2,4]triazolo[1,5-a]pyridine-7-carboxylic acid Using 4-fluorobenzaldehyde (1.82 g), the title compound (1.93 g) was obtained in the form of an orange solid by the same method as that of (Example 3.18) <Step 4> or a method equivalent thereto.

<Step 2> Synthesis of sodium 2-(4-fluorophenyl)-5,6,7,8-tetrahydro-[1,2,4]triazolo[1,5-a]pyridine-7-carboxylate Using a methanol (194 ml) solution of the 2-(4-fluorophenyl)-5,6,7,8-tetrahydro-[1,2,4]triazolo[1,5-a]pyridine-7-carboxylic acid (1 g) obtained in (Example 5.2) <Step 1>, a crude product (1.96 g) containing the title compound was obtained in the form of a brown solid by the same method as that of (Example 5.1) <Step 1> or a method equivalent thereto.

<Step 3> Synthesis of 2-(4-fluorophenyl)-5,6,7,8-tetrahydro-[1,2,4]triazolo[1,5-a]pyridine-7-carboxylic acid Concentrated hydrochloric acid (0.16 ml) was added to an aqueous solution (2 ml) of the sodium 2-(4-fluorophenyl)-5,6,7,8-tetrahydro-[1,2,4]triazolo[1,5-a]pyridine-7-carboxylate (530 mg) obtained in (Example 5.2) <Step 2>, and the obtained mixture was then stirred for 15 minutes. Thereafter, the precipitated solid was collected by filtration, so as to obtain the title compound (196 mg) in the form of a whitish brown solid.

<Step 4> Synthesis of tert-butyl (2-(4-fluorophenyl)-5,6,7,8-tetrahydro-[1,2,4]triazolo[1,5-a]pyridin-7-yl)carbamate Using the 2-(4-fluorophenyl)-5,6,7,8-tetrahydro-[1,2,4]triazolo[1,5-a]pyridine-7-carboxylic acid (160 mg) obtained in (Example 5.2) <Step 3>, the title compound (154 mg) was obtained in the form of a light yellow solid by the same method as that of (Example 2.7) <Step 4> or a method equivalent thereto.

<Step 5> Synthesis of (2-(4-fluorophenyl)-5,6,7,8-tetrahydro-[1,2,4]triazolo[1,5-a]pyridin-7-amine hydrochloride Using the tert-butyl (2-(4-fluorophenyl)-5,6,7,8-tetrahydro-[1,2,4]triazolo[1,5-a]pyridin-7-yl)carbamate (150 mg) obtained in (Example 5.2) <Step 4>, a crude product (155 mg) containing the title compound was obtained in the form of a light yellow solid by the same method as that of (Example 2.7) <Step 6> or a method equivalent thereto.

<Step 6> Synthesis of 4-(4-(difluoromethyl)thiazol-2-yl)-N-(2-(4-fluorophenyl)-5,6,7,8-tetrahydro-[1,2,4]triazolo[1,5-a]pyridin-7-yl)-1-methyl-1H-pyrazole-5-carboxamide Using the 4-(4-(difluoromethyl)thiazole)-1 methyl-1H-pyrazole-5-carboxylic acid (20 mg) obtained in (Example 3.12) <Step 1> and the (2-(4-fluorophenyl)-5,6,7,8-tetrahydro-[1,2,4]triazolo[1,5-a]pyridin-7-amine hydrochloride (27 mg) obtained in (Example 5.2) <Step 5>, the title compound (29 mg) was obtained in the form of a colorless solid by the same method as that of (Example 1.1) <Step 4> or a method equivalent thereto.

Example 5.3

Synthesis of 4-(5-chloro-4-(difluoromethyl)thiazol-2-yl)-N-(2-(4-fluorophenyl)-5,6,7,8-tetrahydro-[1,2,4]triazolo[1,5-a]pyridin-7-yl)-1-methyl-1H-pyrazole-5-carboxamide Using the 4-(4-(difluoromethyl)thiazol-2-yl)-N-(2-(4-fluorophenyl)-5,6,7,8-tetrahydro-[1,2,4]triazolo[1,5-a]pyridin-7-yl)-1-methyl-1H-pyrazole-5-carboxamide (8 mg) obtained in (Example 5.2) <Step 6> and N-chlorosuccinimide (14 mg), the title compound (5.7 mg) was obtained in the form of a colorless solid by the same method as that of (Example 1.4) <Step 1> or a method equivalent thereto.

Example 5.4

Synthesis of 4-(4,5-dimethylthiazol-2-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of methyl 4-(4,5-dimethylthiazol-2-yl)-1-methyl-1H-pyrazole-5-carboxylate Using 2-bromo-4,5-dimethylthiazole (274 mg), the title compound (170 mg) was obtained in the form of a white solid by the same method as that of (Example 1.1) <Step 2> or a method equivalent thereto.

<Step 2> Synthesis of 4-(4,5-dimethylthiazol-2-yl)-1-methyl-N-(2-phenyl-5,6,7,8-tetrahydro-[1,2,4]triazolo[1,5-a]pyridin-7-yl)-1H-pyrazole-5-carboxamide Using the methyl 4-(4,5-dimethylthiazol-2-yl)-1-methyl-1H-pyrazole-5-carboxylate (30 mg) obtained in (Example 5.4) <Step 1> and the 2-phenyl-5,6,7,8-tetrahydro-(1,2,4)triazolo(1,5-a)pyridin-7-amine hydrochloride (20 mg) obtained in (Example 5.1) <Step 3>, the title compound (21 mg) was obtained in the form of a colorless solid by the same method as that of (Example 2.3) or a method equivalent thereto.

Example 5.5

Synthesis of 4-(4-(difluoromethyl)-5-vinylthylthiazol-2-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of methyl 4-(4-(difluoromethyl)-5-vinylthiazol-2-yl)-1-methyl-1H-pyrazole-5-carboxylate Potassium trifluorovinylborate (172 mg), 1,1'-bis(diphenylphosphino)ferrocene-palladium(II) dichloride (31 mg), and triethylamine (59.4 μl) were added to an ethanol (2.1 ml) solution of the methyl 4-(5-bromo-4-(difluoromethyl)thiazol-2-yl)-1-methyl-1H-pyrazole-5-carboxylate (150 mg) obtained in (Example 1.4) <Step 1>, and the obtained mixture was then stirred in a nitrogen atmosphere at 100° C. for 17 hours. Thereafter, potassium trifluoro(vinyl)borate (342 mg), 1,1'-bis(diphenylphosphino)ferrocene-palladium (II) dichloride (62 mg), and triethylamine (59.4 μl) were added to the reaction solution, and the obtained mixture was stirred again in a nitrogen atmosphere at 100° C. for 2 hours 40 minutes. Thereafter, ethyl acetate (100 ml) and a saturated saline (50 ml) were added to the reaction solution. An organic layer was extracted, and was then dried over anhydrous sodium sulfate. The solvent was distilled away under reduced pressure, and the obtained residue was then purified by silica gel column chromatography (silica gel:eluent; heptane:ethyl acetate=95:5-50:50), so as to obtain the title compound (74 mg) in the form of a colorless solid.

<Step 2> Synthesis of 4-(4-(difluoromethyl)-5-vinylthylthiazol-2-yl)-1-methyl-N-(2-phenyl-5,6,7,8-tetrahydro-[1,2,4]triazolo[1,5-a]pyridin-7-yl)-1H-pyrazole-5-carboxamide Using the methyl 4-(4-(difluoromethyl)-5-vinylthiazol-2-yl)-1-methyl-1H-pyrazole-5-carboxylate (21 mg) obtained in (Example 5.5) <Step 1> and the 2-phenyl-5,6,7,8-tetrahydro-[1,2,4]triazolo[1,5-a]pyridin-7-amine hydrochloride (15 mg) obtained in (Example 5.1) <Step 3>, the title compound (15 mg) was obtained in the form of a colorless solid by the same method as that of (Example 2.3) or a method equivalent thereto.

Example 5.6

Synthesis of 4-(4-(difluoromethyl)-5-ethylthylthiazol-2-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of methyl 4-(4-(difluoromethyl)-5-ethylthiazol-2-yl)-1-methyl-1H-pyrazole-5-carboxylate Using the methyl 4-(4-(difluoromethyl)-5-vinylthiazol-2-yl)-1-methyl-1H-pyrazole-5-carboxylate (50 mg) obtained in (Example 5.5) <Step 1>, the title compound (43 mg) was obtained in the form of a light yellow solid by the same method as that of (Example 5.1) <Step 1> or a method equivalent thereto.

<Step 2> Synthesis of 4-(4-(difluoromethyl)-5-ethylthylthiazol-2-yl)-1-methyl-N-(2-phenyl-5,6,7,8-tetrahydro-[1,2,4]triazolo[1,5-a]pyridin-7-yl)-1H-pyrazole-5-carboxamide Using the methyl 4-(4-(difluoromethyl)-5-ethylthiazol-2-yl)-1-methyl-1H-pyrazole-5-carboxylate (22 mg) obtained in (Example 5.6) <Step 1> and the 2-phenyl-5,6,7,8-tetrahydro-[1,2,4]triazolo[1,5-a]pyridin-7-amine hydrochloride (17 mg) obtained in (Example 5.1) <Step 3>, the title compound (22 mg) was obtained in the form of a light brown solid by the same method as that of (Example 2.3) or a method equivalent thereto.

Example 5.7

Synthesis of 4-(5-bromo-4-methylthiazol-2-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of 1-methyl-4-(4-methylthiazol-2-yl)-N-(2-phenyl-5,6,7,8-tetrahydro-[1,2,4]triazolo[1,5-a]pyridin-7-yl)-1H-pyrazole-5-carboxamide Using the methyl 1-methyl-4-(4-methylthiazol-2-yl)-1H-pyrazole-5-carboxylate (25 mg) obtained in (Example 1.2) <Step 1> and the 2-phenyl-5,6,7,8-tetrahydro-[1,2,4]triazolo[1,5-a]pyridin-7-amine hydrochloride (26 mg) obtained in (Example 5.1) <Step 3>, the title compound (26 mg) was obtained in a white amorphous form by the same method as that of (Example 2.3) or a method equivalent thereto.

<Step 2> Synthesis of 4-(5-bromo-4-methylthiazol-2-yl)-1-methyl-N-(2-phenyl-5,6,7,8-tetrahydro-[1,2,4]triazolo[1,5-a]pyridin-7-yl)-1H-pyrazole-5-carboxamide Using the 1-methyl-4-(4-methylthiazol-2-yl)-N-(2-phenyl)-5,6,7,8-tetrahydro-[1,2,4]triazolo[1,5-a]pyridin-7-yl)-1H-pyrazole-5-carboxamide (15 mg) obtained in (Example 5.7) <Step 1>, the title compound (18 mg) was obtained in the form of a colorless solid by the same method as that of (Example 1.4) <Step 1> or a method equivalent thereto.

Example 5.8

Synthesis of 4-(5-cyclopropyl-4-(difluoromethyl)thylthiazol-2-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of methyl 4-(5-cyclopropyl-4-(difluoromethyl)thiazol-2-yl)-1-methyl-1H-pyrazole-5-carboxylate Cyclopropylboronic acid (61 mg), palladium acetate (11 mg), phosphoric acid potassium salts (203 mg), water (0.53 ml), and tricyclohexylphosphine (27 mg) were added to a toluene (6 ml) solution of the methyl 4-(5-bromo-4-(difluoromethyl)thiazol-2-yl)-1-methyl-1H-pyrazole-5-carboxylate (84 mg) obtained in (Example 1.4) <Step 1>, and the obtained mixture was then stirred in a nitrogen atmosphere at 100° C. for 1.5 hours. Thereafter, ethyl acetate (50 ml) and a saturated sodium hydrogen carbonate aqueous solution (30 ml) were added to the reaction solution. After extraction of organic layers, water layers were extracted with ethyl acetate (50 ml). The organic layers were combined. The combined organic layer was washed with a saturated saline, and was then dried over anhydrous sodium sulfate. The solvent was distilled away under reduced pressure, and the obtained residue was then purified by silica gel column chromatography (silica gel:eluent; heptane:ethyl acetate=93:7-40:60), so as to obtain the title compound (62 mg) in the form of a light brown solid.

<Step 2> Synthesis of 4-(5-cyclopropyl-4-(difluoromethyl)thylthiazol-2-yl)-1-methyl-N-(2-phenyl-5,6,7,8-tetrahydro-[1,2,4]triazolo[1,5-a]pyridin-7-yl)-1H-pyrazole-5-carboxamide Using the methyl 4-(5-cyclopropyl-4-(difluoromethyl)thiazol-2-yl)-1-methyl-1H-pyrazole-5-carboxylate (22 mg) obtained in (Example 5.8) <Step 1> and the 2-phenyl-5,6,7,8-tetrahydro-[1,2,4]triazolo[1,5-a]pyridin-7-amine hydrochloride (15 mg) obtained in (Example 5.1) <Step 3>, the title compound (16 mg) was obtained in the form of a colorless solid by the same method as that of (Example 2.3) or a method equivalent thereto.

Example 5.9

Synthesis of 1-methyl-N-(2-phenyl-5,6,7,8-tetrahydro-[1,2,4]triazolo[1,5-a]pyridin-7-yl)-4-(4-(trifluoromethyl)thylthiazol-2-yl)-1H-pyrazole-5-carboxamide Using the methyl 1-methyl-4-(4-(trifluoromethyl)thiazol-2-yl)-1H-pyrazole-5-carboxylate (25 mg) obtained in (Example 1.5) <Step 1> and the 2-phenyl-5,6,7,8-tetrahydro-[1,2,4]triazolo[1,5-a]pyridin-7-amine hydrochloride (22 mg) obtained in (Example 5.1) <Step 3>, the title compound (20 mg) was obtained in a white amorphous form by the same method as that of (Example 2.3) or a method equivalent thereto.

Example 5.10

Synthesis of 4-(4-cyanothiazol-2-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of 4-(4-cyanothiazol-2-yl)-1-methyl-1H-pyrazole-5-carboxylic acid Using 2-bromothiazole-4-carbonitrile (150 mg), the title compound (59 mg) was obtained in the form of a thick gray solid by the same method as that of (Example 1.1) <Step 2> or a method equivalent thereto.

<Step 2> Synthesis of 4-(4-cyanothiazol-2-yl)-1-methyl-N-(2-phenyl-5,6,7,8-tetrahydro-[1,2,4]triazolo[1,5-a]pyridin-7-yl)-1H-pyrazole-5-carboxamide Using the 4-(4-cyanothiazol-2-yl)-1-methyl-1H-pyrazole-5-carboxylic acid (12 mg) obtained in (Example 5.10) <Step 1> and the 2-phenyl-5,6,7,8-tetrahydro-[1,2,4]triazolo[1,5-a]pyridin-7-amine hydrochloride (13 mg) obtained in (Example 5.1) <Step 3>, the title compound (11 mg) was obtained in the form of a gray solid by the same method as that of (Example 1.1) <Step 4> or a method equivalent thereto.

Example 5.11

Synthesis of 4-(5-(2-ethoxyethyl)-4-methylthiazol-2-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of methyl 4-(5-bromo-4-methylthiazol-2-yl)-1-methyl-1H-pyrazole-5-carboxylate Using the methyl 1-methyl-4 (4-methylthiazol-2-yl)-1H-pyrazole-5-carboxylate (100 mg) obtained in (Example 1.2) <Step 1>, the title compound (129 mg) was obtained in the form of a brown solid by the same method as that of (Example 1.4) <Step 1> or a method equivalent thereto.

<Step 2> Synthesis of (E)-methyl 4-(5-(2-ethoxyvinyl)-4-methylthiazol-2-yl)-1-methyl-1H-pyrazole-5-carboxylate (E)-2-(2-ethoxyvinyl)-4,4,5,5-tetramethyl-1,3,2-dioxaborolane (63 mg), palladium acetate (7.1 mg), tripotassium phosphate (67 mg), 2-dicyclohexylphosphino-2',6'-dimethoxy-1,1'-biphenyl (26 mg), and water (0.35 ml) were added to an acetonitrile (4.0 ml) solution of the methyl 4-(5-bromo-4-methylthiazol-2-yl)-1-methyl-1H-pyrazole-5-carboxylate (50 mg) obtained in (Example 5.11) <Step 1>, and the obtained mixture was then stirred under heating in a nitrogen atmosphere for 2 hours at 90° C. Thereafter, ethyl acetate (50 ml) and a saturated sodium hydrogen carbonate aqueous solution (30 ml) were added to the reaction solution. After extraction of organic layers, water layers were extracted with ethyl acetate (50 ml). The organic layers were combined. The combined organic layer was washed with a saturated saline, and was then dried over anhydrous sodium sulfate. The solvent was distilled away under reduced pressure, and the obtained residue was then purified by silica gel column chromatography (silica gel: eluent; heptane:ethyl acetate=92:8-40:60), so as to obtain the title compound (31 mg) in the form of a yellow solid.

<Step 3> Synthesis of methyl 4-(5-(2-ethoxyethyl)-4-methylthiazol-2-yl)-1-methyl-1H-pyrazole-5-carboxylate Using the (E)-methyl 4-(5-(2-ethoxyvinyl)-4-methylthiazol-2-yl)-1-methyl-1H-pyrazole-5-carboxylate (27 mg) obtained in (Example 5.11) <Step 2>, the title compound (26 mg) was obtained in a yellow amorphous form by the same method as that of (Example 5.1) <Step 1> or a method equivalent thereto.

<Step 4> Synthesis of 4-(5-(2-ethoxyethyl)-4-methylthiazol-2-yl)-1-methyl-N-(2-phenyl-5,6,7,8-tetrahydro-[1,2,4]triazolo[1,5-a]pyridin-7-yl)-1H-pyrazole-5-carboxamide Using the methyl 4-(5-(2-ethoxyethyl)-4-methylthiazol-2-yl)-1-methyl-1H-pyrazole-5-carboxylate (14 mg) obtained in (Example 5.11) <Step 3> and the 2-phenyl-5,6,7,8-tetrahydro-[1,2,4]triazolo[1,5-a]pyridin-7-amine hydrochloride (10 mg) obtained in (Example 5.1) <Step 3>, the title compound (4.0 mg) was obtained in the form of a light yellow solid by the same method as that of (Example 2.3) or a method equivalent thereto.

Example 5.12

Synthesis of 4-(5-ethyl-1,3,4-thiadiazol-2-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of methyl 4-(5-ethyl-1,3,4-thiadiazol-2-yl)-1-methyl-1H-pyrazole-5-carboxylate Using 2-bromo-5-ethyl-1,3,4-thiadiazole (230 mg), the title compound (28 mg) was obtained in the form of a light yellow solid by the same method as that of (Example 1.1) <Step 2> or a method equivalent thereto.

<Step 2> Synthesis of 4-(5-ethyl-1,3,4-thiadiazol-2-yl)-1-methyl-N-(2-phenyl-5,6,7,8-tetrahydro-[1,2,4]triazolo[1,5-a]pyridin-7-yl)-1H-pyrazole-5-carboxamide Using the methyl 4-(5-ethyl-1,3,4-thiadiazol-2-yl)-1-methyl-1H-pyrazole-5-carboxylate (20 mg) obtained in (Example 5.12) <Step 1> and the 2-phenyl-5,6,7,8-tetrahydro-[1,2,4]triazolo[1,5-a]pyridin-7-amine hydrochloride (20 mg) obtained in (Example 5.1) <Step 3>, the title compound (16 mg) was obtained in the form of a white solid by the same method as that of (Example 2.3) or a method equivalent thereto.

Example 5.13

Synthesis of 4-(5-bromo-2-methylthiazol-4-yl)-1-methyl-N-(2-phenyl)-5,6,7,8-tetrahydro-[1,2,4]triazolo[1,5-a]pyridin-7-yl)-1H-pyrazole-5-carboxamide <Step 1> Synthesis of methyl 4-(5-bromo-2-methylthiazol-4-yl)-1-methyl-1H-pyrazole-5-carboxylate Using the methyl 1-methyl-4-(2-methylthiazol-4-yl)-1H-pyrazole-5-carboxylate (40 mg) obtained in (Example 2.12) <Step 1>, the title compound (51 mg) was obtained in the form of a brown solid by the same method as that of (Example 1.4) <Step 1> or a method equivalent thereto.

<Step 2> Synthesis of 4-(5-bromo-2-methylthiazol-4-yl)-1-methyl-N-(2-phenyl-5,6,7,8-tetrahydro-[1,2,4]triazolo[1,5-a]pyridin-7-yl)-1H-pyrazole-5-carboxamide Using the methyl 4-(5-bromo-2-methylthiazol-4-yl)-1-methyl-1H-pyrazole-5-carboxylate (25 mg) obtained in (Example 5.13) <Step 1> and the 2-phenyl-5,6,7,8-tetrahydro-[1,2,4]triazolo[1,5-a]pyridin-7-amine hydrochloride (20 mg) obtained in (Example 5.1) <Step 3>, the title compound (10 mg) was obtained in a light yellow amorphous form by the same method as that of (Example 2.3) or a method equivalent thereto.

Example 5.14

Synthesis of 4-(3,6-dimethylpyrazin-2-yl)-1-methyl-N-(2-phenyl-5,6,7,8-tetrahydro-[1,2,4]triazolo[1,5-a]pyridin-7-yl)-1H-pyrazole-5-carboxamide Using the 4-(3,6-dimethylpyrazin-2-yl)-1-methyl-1H-pyrazole-5-carboxylic acid (17 mg) obtained in (Example 3.14) <Step 2> and the 2-phenyl-5,6,7,8-tetrahydro-[1,2,4]triazolo[1,5-a]pyridin-7-amine hydrochloride (15 mg) obtained in (Example 5.1) <Step 3>, the title compound (11 mg) was obtained in the form of a colorless solid by the same method as that of (Example 1.1) <Step 4> or a method equivalent thereto.

Example 5.15

Synthesis of 1-methyl-4-(3-methyl-1,2,4-thiadiazol-5-yl)-N-(2-phenyl-5,6,7,8-tetrahydro-[1,2,4]triazolo[1,5-a]pyridin-7-yl)-1H-pyrazole-5-carboxamide <Step 1> Synthesis of methyl 1-methyl-4-(3-methyl-1,2,4-thiadiazol-5-yl)-1H-pyrazole-5-carboxylate Using 5-bromo-3-methyl-1,2,4-thiadiazole (213 mg), the title compound (140 mg) was obtained in the form of a light yellow solid by the same method as that of (Example 1.1) <Step 2> or a method equivalent thereto.

<Step 2> Synthesis of 1-methyl-4-(3-methyl-1,2,4-thiadiazol-5-yl)-N-(2-phenyl-5,6,7,8-tetrahydro-[1,2,4]triazolo[1,5-a]pyridin-7-yl)-1H-pyrazole-5-carboxamide Using the methyl 1-methyl-4-(3-methyl-1,2,4-thiadiazol-5-yl)-1H-pyrazole-5-carboxylate (21 mg) obtained in (Example 5.15) <Step 1> and the 2-phenyl-5,6,7,8-tetrahydro-[1,2,4]triazolo[1,5-a]pyridin-7-amine hydrochloride (20 mg) obtained in (Example 5.1) <Step 3>, the title compound (10 mg) was obtained in the form of a light brown solid by the same method as that of (Example 2.3) or a method equivalent thereto.

Example 5.16

Synthesis of 4-(4-(difluoromethyl)thiazol-2-yl)-N-((2R)-2-(methoxymethyl)pyrrolidin-1-yl)-5,6,7,8-tetrahydro-[1,2,4]triazolo[1,5-a]pyridin-7-yl)-1-methyl-1H-pyrazole-5-carboxamide <Step 1> Synthesis of methyl 2-amino-[1,2,4]triazolo[1,5-a]pyridine-7-carboxylate Ethoxycarbonyl isothiocyanate (9.0 g) was added to a 1,4-dioxane (100 ml) suspension of 2-aminopyridine-4-carboxylic acid methyl ester (10 g) at an internal temperature of 19° C. to 23° C. over 20 minutes. The obtained mixture was stirred for 90 minutes at the same temperature as described above, and was then concentrated under reduced pressure to obtain a crude product. The obtained crude product was added to a mixed suspension of methanol (70 ml) and ethanol (70 ml) containing hydroxyamine hydrochloride (22.8 g) and diisopropylethylamine (34 ml), and thereafter, the reaction solution was stirred at room temperature for 67 hours, at 60° C. for 5 hours, and again, at room temperature for 20 hours. Thereafter, the generated solid was collected, and it was washed with ethanol (30 ml) and was then dried, so as to obtain the title compound (11.3 g) in the form of a white solid.

<Step 2> Synthesis of methyl 2-amino-5,6,7,8-tetrahydro-[1,2,4]triazolo[1,5-a]pyridine-7-carboxylate Platinum(IV) oxide (3 g) was added to a mixed solution of methanol (200 ml), methylene chloride (200 ml), and concentrated hydrochloric acid (3.9 ml) containing the methyl 2-amino-[1,2,4]triazolo[1,5-a]pyridine-7-carboxylate (3.0 g) obtained in (Example 5.16) <Step 1>. The obtained mixture was stirred in a hydrogen atmosphere for 66 hours at room temperature. Thereafter, the reaction solution was filtered with Celite, and was then washed with methanol (80 ml). The filtrate was combined with the washing solution, and the thus mixed solution was then concentrated under reduced pressure. The obtained residue was subjected to azeotropy with methanol (20 ml) four times, so as to obtain the title compound (3.3 g) in the form of a light brown solid.

<Step 3> Synthesis of methyl 2-bromo-5,6,7,8-tetrahydro-[1,2,4]triazolo[1,5-a]pyridine-7-carboxylate Tert-butyl nitrite (2.3 ml) was added to an acetonitrile (80 ml) suspension of copper(II) bromide (4.2 g), and the obtained mixture was then heated at 85° C. Thereafter, the methyl 2-amino-5,6,7,8-tetrahydro-[1,2,4]triazolo[1,5-a]pyridine-7-carboxylate (2.4 g) obtained in (Example 5.16) <Step 2> was added to the reaction solution over 30 minutes, and the obtained mixture was then heated at the same temperature as described above for 2 hours 30 minutes. Thereafter, the reaction solution was cooled to room temperature, and ethyl acetate (150 ml) and water (150 ml) were then added thereto. The mixed solution was filtered with Celite, and organic layers were then separated. After extraction of water layers with ethyl acetate, organic layers were combined, and were then dried over anhydrous sodium sulfate. The solvent was distilled away under reduced pressure, so that a crude product of the title compound (2.7 g) was obtained in the form of a brown solid.

<Step 4> Synthesis of 2-bromo-5,6,7,8-tetrahydro-[1,2,4]triazolo[1,5-a]pyridine-7-carboxylic acid A 2 N sodium hydroxide aqueous solution (6.9 ml) was added to a mixed solution of methanol (20 ml) and water (10 ml) containing the methyl 2-bromo-5,6,7,8-tetrahydro-[1,2,4]triazolo[1,5-a]pyridine-7-carboxylate (2.4 g) obtained in (Example 5.16) <Step 3>. The obtained mixture was stirred for 1 hour 30 minutes. Thereafter, methanol was distilled away under reduced pressure, and the obtained aqueous solution was then washed with ethyl acetate (2 ml). Insoluble substances were removed by filtration. The filtrate was adjusted to pH 1 with concentrated hydrochloric acid, and was then extracted with a mixed solution (50 ml) of 20% isopropanol and methylene chloride five times. The organic layer was dried over anhydrous sodium sulfate, and the solvent was then distilled away under reduced pressure, so as to obtain a crude product (1.87 g) of the title compound in the form of a yellow solid.

<Step 5> Synthesis of tert-butyl (2-bromo-5,6,7,8-tetrahydro-[1,2,4]triazolo[1,5-a]pyridin-7-carbamate Using the 2-bromo-5,6,7,8-tetrahydro-[1,2,4]triazolo[1,5-a]pyridine-7-carboxylic acid (1.8 g) obtained in (Example 5.16) <Step 4>, the title compound (2.0 g) was obtained in a white amorphous form by the same method as that of (Example 3.15) <Step 4> or a method equivalent thereto.

<Step 6> Synthesis of 2-bromo-5,6,7,8-tetrahydro-[1,2,4]triazolo[1,5-a]pyridin-7-amine hydrochloride Using the tert-butyl (2-bromo-5,6,7,8-tetrahydro-[1,2,4]triazolo[1,5-a]pyridin-7-carbamate (500 mg) obtained in (Example 5.16) <Step 5>, a crude product (420 mg) containing the title compound was obtained in the form of a white solid by the same method as that of (Example 3.15) <Step 5> or a method equivalent thereto.

<Step 7> Synthesis of N-(2-bromo-5,6,7,8-tetrahydro-[1,2,4]triazolo[1,5-a]pyridin-7-yl)-4-(4-(difluoromethyl)thiazol-2-yl)-1-methyl-1H-pyrazole-5-carboxamide Using the 4-(4-(difluoromethyl)thiazole)-1-methyl-1H-pyrazole-5-carboxylic acid (50 mg) obtained in (Example 3.12) <Step 1> and the 2-bromo-5,6,7,8-tetrahydro-[1,2,4]triazolo[1,5-a]pyridin-7-amine hydrochloride (49 mg) obtained in (Example 5.16) <Step 6>, the title compound (81 mg) was obtained in the form of a white solid by the same method as that of (Example 1.1) <Step 4> or a method equivalent thereto.

<Step 8> Synthesis of 4-(4-(difluoromethyl)thiazol-2-yl)-N-((2R)-2-(methoxymethyl)pyrrolidin-1-yl)-5,6,7,8-tetrahydro-[1,2,4]triazolo[1,5-a]pyridin-7-yl)-1-methyl-1H-pyrazole-5-carboxamide The N-(2-bromo-5,6,7,8-tetrahydro-[1,2,4]triazolo[1,5-a]pyridin-7-yl)-4-(4-(difluoromethyl)thiazol-2-yl)-1-methyl-1H-pyrazole-5-carboxamide (20 mg) obtained in (Example 5.16) <Step 7> and (R)-2-(methoxymethyl)pyrrolidine (0.5 ml) were heated at 150° C. for 4 days. Thereafter, ethyl acetate (50 ml) and a saturated saline (20 ml) were added to the reaction solution, and an organic layer was then extracted. The obtained organic layer was dried over sodium sulfate. The solvent was distilled away under reduced pressure, and the obtained residue was then purified by preparative thin-layer chromatography (silica gel:eluent; ethyl acetate), so as to obtain the title compound (2.1 mg) in a yellow amorphous form.

The compounds of (Example 5.17) to (Example 5.27) were synthesized using the 2-phenyl-5,6,7,8-tetrahydro-[1,2,4]triazolo[1,5-a]pyridin-7-amine hydrochloride obtained in (Example 5.1) <Step 3> and the corresponding carboxylic acid or the sodium salts thereof by the same method as that of (Example 1.1) <Step 4> or a method equivalent thereto.

Example 5.17

4-(4-(difluoromethyl)thiazol-2-yl)-1-methyl-N-(2-phenyl-5,6,7,8-tetrahydro-[1,2,4]triazolo[1,5-a]pyridin-7-yl)-1H-pyrazole-5-carboxamide

Example 5.18

1-methyl-4-(4-methylthiazol-2-yl)-N-(2-phenyl-5,6,7,8-tetrahydro-[1,2,4]triazolo[1,5-a]pyridin-7-yl)-1H-pyrazole-5-carboxamide

Example 5.19

1-methyl-4-(6-methylpyridin-2-yl)-N-(2-phenyl-5,6,7,8-tetrahydro-[1,2,4]triazolo[1,5-a]pyridin-7-yl)-1H-pyrazole-5-carboxamide

Example 5.20

1-methyl-4-(4-methylpyridin-2-yl)-N-(2-phenyl-5,6,7,8-tetrahydro-[1,2,4]triazolo[1,5-a]pyridin-7-yl)-1H-pyrazole-5-carboxamide

Example 5.21

1-methyl-N-(2-phenyl-5,6,7,8-tetrahydro-[1,2,4]triazolo[1,5-a]pyridin-7-yl)-4-(6-(trifluoromethyl)pyridin-2-yl)-1H-pyrazole-5-carboxamide

Example 5.22

1-methyl-4-(3-methylpyridin-2-yl)-N-(2-phenyl-5,6,7,8-tetrahydro-[1,2,4]triazolo[1,5-a]pyridin-7-yl)-1H-pyrazole-5-carboxamide

Example 5.23

4-(4-fluoropyridin-2-yl)-1-methyl-N-(2-phenyl-5,6,7,8-tetrahydro-[1,2,4]triazolo[1,5-a]pyridin-7-yl)-1H-pyrazole-5-carboxamide

Example 5.24

4-(5-fluoropyridin-2-yl)-1-methyl-N-(2-phenyl-5,6,7,8-tetrahydro-[1,2,4]triazolo[1,5-a]pyridin-7-yl)-1H-pyrazole-5-carboxamide

Example 5.25

4-(4-methoxypyridin-2-yl)-1-methyl-N-(2-phenyl-5,6,7,8-tetrahydro-[1,2,4]triazolo[1,5-a]pyridin-7-yl)-1H-pyrazole-5-carboxamide

Example 5.26

1-methyl-4-(5-methylpyridin-2-yl)-N-(2-phenyl-5,6,7,8-tetrahydro-[1,2,4]triazolo[1,5-a]pyridin-7-yl)-1H-pyrazole-5-carboxamide

Example 5.27

4-(3-cyanopyridin-2-yl)-1-methyl-N-(2-phenyl-5,6,7,8-tetrahydro-[1,2,4]triazolo[1,5-a]pyridin-7-yl)-1H-pyrazole-5-carboxamide

Example 5.28

Synthesis of 4-(2,5-dimethylthiazol-4-yl)-N-(2-(4-fluorophenyl)-5,6,7,8-tetrahydro-[1,2,4]triazolo[1,5-a]pyridin-7-yl)-1-methyl-1H-pyrazole-5-carboxamide Using the after-mentioned 4-(2,5-dimethylthiazol-4-yl)-1-methyl-1H-pyrazole-5-carboxylic acid (12 mg), which will be obtained in (Example 5.39) <Step 1>, and the 2-(4-fluorophenyl)-5,6,7,8-tetrahydro-[1,2,4]triazolo[1,5-a]pyridin-7-amine hydrochloride (14 mg) obtained in (Example 5.2) <Step 5>, the title compound (7.8 mg) was obtained in a yellow amorphous form by the same method as that of (Example 1.1) <Step 4> or a method equivalent thereto.

Example 5.29

Synthesis of 4-(5-chloro-4-(difluoromethyl)thiazol-2-yl)-1-methyl-N-(2-phenyl-5,6,7,8-tetrahydro-[1,2,4]triazolo[1,5-a]pyridin-7-yl)-1H-pyrazole-5-carboxamide Using the 4-(4-(difluoromethyl)thiazol-2-yl)-1-methyl-N-(2-phenyl-5,6,7,8-tetrahydro-[1,2,4]triazolo[1,5-a]pyridin-7-yl)-1H-pyrazole-5-carboxamide (56 mg) obtained in (Example 5.17) and N-chlorosuccinimide (99 mg), the title compound (40 mg) was obtained in the form of a colorless solid by the same method as that of (Example 1.4) <Step 1> or a method equivalent thereto.

Example 5.30

Synthesis of 4-(5-acetyl-2-methylthiazol-4-yl)-1-methyl-N-(2-phenyl-5,6,7,8-tetrahydro-[1,2,4]triazolo[1,5-a]pyridin-7-yl)-1H-pyrazole-5-carboxamide An N,N-dimethylformamide (1 ml) solution of the 4-(5-bromo-2-methylthiazol-4-yl)-1-methyl-N-(2-phenyl-5,6,7,8-tetrahydro-[1,2,4]triazolo[1,5-a]pyridin-7-yl)-1H-pyrazole-5-carboxamide (40 mg) obtained in (Example 5.13) <Step 2>, tributyl(1-ethoxyvinyl)stannane (58 mg), and 1,1'-bis(diphenylphosphino)ferrocene palladium(II) dichloride (5.9 mg) was stirred in microwave at 100° C. for 40 minutes. Thereafter, 1 N hydrochloric acid (0.3 ml) was added to the reaction solution, and the obtained mixture was then stirred for 1 hour. Thereafter, ethyl acetate (50 ml) and a saturated sodium hydrogen carbonate aqueous solution (20 ml) were added to the reaction solution. The organic layer was washed with water (20 ml) twice, and was then dried over sodium sulfate. The solvent was distilled away under reduced pressure, and the obtained residue was then purified by silica gel column chromatography (silica gel:eluent; heptane:ethyl acetate=50:50-0:100), so as to obtain the title compound (18 mg) in a light yellow amorphous form.

Example 5.31

Synthesis of 4-(5-(1-hydroxyethyl)-2-methylthiazol-4-yl)-1-methyl-N-(2-phenyl-5,6,7,8-tetrahydro-[1,2,4]triazolo[1,5-a]pyridin-7-yl)-1H-pyrazole-5-carboxamide Methylmagnesium bromide (0.17 ml, a 3 M diethyl ether solution) was added to a tetrahydrofuran (2 ml) solution of cerium(III) chloride (128 mg) in a dry ice-acetone bath, and the obtained mixture was then stirred for 30 minutes. Thereafter, the reaction solution was warmed in the ice cold. A tetrahydrofuran solution of the 4-(5-acetyl-2-methylthiazol- 4-yl)-1-methyl-N-(2-phenyl-5,6,7,8-tetrahydro-[1,2,4]triazolo[1,5-a]pyridin-7-yl)-1H-pyrazole-5-carboxamide (12 mg) obtained in (Example 5.30) was added to the reaction solution, and the obtained mixture was then warmed to room temperature. The obtained mixture was stirred at room temperature for 1 hour, and then at 40° C. for 2 hours. Thereafter, water (10 ml) was added to the reaction solution, and the mixed solution was extracted with ethyl acetate (30 ml) and was then dried over sodium sulfate. The solvent was distilled away under reduced pressure, and sodium borohydride (0.98 mg) was then added to a methanol (1 ml) solution of the obtained residue, followed by stirring the mixture for 1 hour. Thereafter, water (20 ml) and ethyl acetate (50 ml) were added to the reaction solution. The organic layer was extracted, and was then dried over anhydrous sodium sulfate. The solvent was distilled away under reduced pressure, and the obtained residue was then purified by preparative thin-layer chromatography (silica gel:eluent; ethyl acetate:methanol=95:5), so as to obtain the title compound (1.3 mg) in a light yellow amorphous form.

Example 5.32

Synthesis of 4-(4-(difluoromethyl)thiazol-2-yl)-N-(2-(2-fluorophenyl)-5,6,7,8-tetrahydro-[1,2,4]triazolo[1,5-a]pyridin-7-yl)-1-methyl-1H-pyrazole-5-carboxamide Using the N-(2-bromo-5,6,7,8-tetrahydro-[1,2,4]triazolo[1,5-a]pyridin-7-yl)-4-(4-(difluoromethyl)thiazol-2-yl)-1-methyl-1H-pyrazole-5-carboxamide (20 mg) obtained in (Example 5.16) <Step 7> and (2-fluorophenyl)boronic acid (6.7 mg), the title compound (13 mg) was obtained in a light yellow amorphous form by the same method as that of (Example 3.15) <Step 7> or a method equivalent thereto.

Example 5.33

Synthesis of 4-(4-(difluoromethyl)thiazol-2-yl)-N-(2-(3-fluorophenyl)-5,6,7,8-tetrahydro-[1,2,4]triazolo[1,5-a]pyridin-7-yl)-1-methyl-1H-pyrazole-5-carboxamide <Step 1> Synthesis of (2-(3-fluorophenyl)-5,6,7,8-tetrahydro-[1,2,4]triazolo[1,5-a]pyridin-7-amine hydrochloride Using 3-fluorobenzaldehyde, the title compound was obtained by applying the same methods as those of (Example 3.18) <Step 4>, (Example 5.1) <Step 1>, (Example 2.7) <Step 4>, and (Example 2.7) <Step 6>, successively, or methods equivalent thereto.

<Step 2> Synthesis of 4-(4-(difluoromethyl)thiazol-2-yl)-N-(2-(3-fluorophenyl)-5,6,7,8-tetrahydro-[1,2,4]triazolo[1,5-a]pyridin-7-yl)-1-methyl-1H-pyrazole-5-carboxamide Using the (2-(3-fluorophenyl)-5,6,7,8-tetrahydro-[1,2,4]triazolo[1,5-a]pyridine-7-amine hydrochloride (27 mg) obtained in (Example 5.33) <Step 1> and the 4-(4-difluoromethyl)thiazol-2-yl)-1 methyl-1H-pyrazole-5-carboxylic acid (20 mg) obtained in (Example 3.12) <Step 1>, the title compound (28 mg) was obtained in the form of a light brown solid by the same method as that of (Example 1.1) <Step 4> or a method equivalent thereto.

Example 5.34

Synthesis of 4-(4-(difluoromethyl)thiazol-2-yl)-N-(2-(2-methoxyphenyl)-5,6,7,8-tetrahydro-[1,2,4]triazolo[1,5-a]pyridin-7-yl)-1-methyl-1H-pyrazole-5-carboxamide Using the N-(2-bromo-5,6,7,8-tetrahydro-[1,2,4]triazolo[1,5-a]pyridin-7-yl)-4-(4-(difluoromethyl)thiazol-2-yl)-1-methyl-1H-pyrazole-5-carboxamide (20 mg) obtained in (Example 5.16) <Step 7> and (2-methoxyphenyl)boronic acid (7.3 mg), the title compound (16 mg) was obtained in a white amorphous form by the same method as that of (Example 3.15) <Step 7> or a method equivalent thereto.

Example 5.35

Synthesis of 4-(5-cyclopropyl-4-(difluoromethyl)thiazol-2-yl)-N-(2-(4-fluorophenyl)-5,6,7,8-tetrahydro-[1,2,4]triazolo[1,5-a]pyridin-7-yl)-1-methyl-1H-pyrazole-5-carboxamide Using the methyl 4-(5-cyclopropyl-4-(difluoromethyl)thiazol-2-yl)-1-methyl-1H-pyrazole-5-carboxylate (20 mg) obtained in (Example 5.8) <Step 1> and the (2-(4-fluorophenyl)-5,6,7,8-tetrahydro-[1,2,4]triazolo[1,5-a]pyridin-7-amine hydrochloride (14 mg) obtained in (Example 5.2) <Step 5>, the title compound (10 mg) was obtained in the form of a light yellow solid by the same method as that of (Example 1.3) <Step 2> or a method equivalent thereto.

Example 5.36

Synthesis of 4-(4-(difluoromethyl)-5-methylthiazol-2-yl)-N-(2-(4-fluorophenyl)-5,6,7,8-tetrahydro-[1,2,4]triazolo[1,5-a]pyridin-7-yl)-1-methyl-1H-pyrazole-5-carboxamide Using the methyl 4-(4-(difluoromethyl)-5-methylthiazol-2-yl)-1-methyl-1H-pyrazole-5-carboxylate (21 mg) obtained in (Example 1.4) <Step 2> and the 2-(4-fluorophenyl)-5,6,7,8-tetrahydro-[1,2,4]triazolo[1,5-a]pyridin-7-amine hydrochloride (18 mg) obtained in (Example 5.2) <Step 5>, the title compound (10 mg) was obtained in the form of a colorless solid by the same method as that of (Example 1.3) <Step 2> or a method equivalent thereto.

Example 5.37

Synthesis of 4-(5-chloro-4-(difluoromethyl)thiazol-2-yl)-N-(2-(3-fluorophenyl)-5,6,7,8-tetrahydro-[1,2,4]triazolo[1,5-a]pyridin-7-yl)-1-methyl-1H-pyrazole-5-carboxamide Using the 4-(4-(difluoromethyl)thiazol-2-yl)-N-(2-(3-fluorophenyl)-5,6,7,8-tetrahydro-[1,2,4]triazolo[1,5-a]pyridin-7-yl)-1-methyl-1H-pyrazole-5-carboxamide (10 mg) obtained in (Example 5.33) and N-chlorosuccinimide (17 mg), the title compound (7.1 mg) was obtained in the form of a colorless solid by the same method as that of (Example 1.4) <Step 1> or a method equivalent thereto.

Example 5.38

Synthesis of 4-(5-cyclopropyl-4-methylthiazol-2-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of methyl 4-(5-bromo-4-methylthiazol-2-yl)-1-methyl-1H-pyrazole-5-carboxylate Using the methyl 1-methyl-4-(4-methylthiazol-2-yl)-1H-pyrazole-5-carboxylate (100 mg) obtained in (Example 1.2)

<Step 1>, the title compound (129 mg) was obtained in the form of a brown solid by the same method as that of (Example 1.4) <Step 1> or a method equivalent thereto.

<Step 2> Synthesis of 4-(5-cyclopropyl-4-methyl-thiazol-2-yl)-1-methyl-1H-pyrazole-5-carboxylic acid Using the methyl 4-(5-bromo-4-methylthiazol-2-yl)-1-methyl-1H-pyrazole-5-carboxylate (25 mg) obtained in (Example 5.38) <Step 1>, the title compound (20 mg) was obtained in the form of a yellow solid by the same method as that of (Example 5.8) <Step 1> or a method equivalent thereto.

<Step 3> Synthesis of 4-(5-cyclopropyl-4-methyl-thiazol-2-yl)-1-methyl-N-(2-phenyl-5,6,7,8-tetra-hydro-[1,2,4]triazolo[1,5-a]pyridin-7-yl)-1H-pyrazole-5-carboxamide Using the 4-(5-cyclopropyl-4-methylthiazol-2-yl)-1-methyl-1H-pyrazole-5-carboxylic acid (20 mg) obtained in (Example 5.38) <Step 2> and a free form (16 mg) of the 2-phenyl-5,6,7,8-tetrahydro-[1,2,4]triazolo[1,5-a]pyridin-7-amine hydrochloride obtained in (Example 5.1) <Step 3>, the title compound (9.7 mg) was obtained in the form of a white solid by the same method as that of (Example 1.1) <Step 4> or a method equivalent thereto.

Example 5.39

Synthesis of 4-(2,5-dimethylthiazol-4-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of 4-(2,5-dimethylthiazol-4-yl)-1-methyl-1H-pyrazole-5-carboxylic acid Using 4-bromo-2,5-dimethylthiazole (61 mg), the title compound (28 mg) was obtained in the form of a light brown solid by the same methods as those of (Example 1.1) <Step 2> and (Example 1.1) <Step 3>, or methods equivalent thereto.

<Step 2> Synthesis of 4-(2,5-dimethylthiazol-4-yl)-1-methyl-N-(2-phenyl-5,6,7,8-tetrahydro-[1,2,4]triazolo[1,5-a]pyridin-7-yl)-1H-pyrazole-5-carbox-amide Using the 4-(2,5-dimethylthiazol-4-yl)-1-methyl-1H-pyrazole-5-carboxylic acid (13 mg) obtained in (Example 5.39) <Step 1> and the 2-phenyl-5,6,7,8-tetrahydro-[1,2,4]triazolo[1,5-a]pyridin-7-amine hydrochloride (14 mg) obtained in (Example 5.1) <Step 3>, the title compound (11 mg) was obtained in a light yellow amorphous form by the same method as that of (Example 1.1) <Step 4> or a method equivalent thereto.

Example 5.40

Synthesis of 4-(6-cyanopyridin-2-yl)-1-methyl-N-(2-phenyl-5,6,7,8-tetrahydro-[1,2,4]triazolo[1,5-a]pyridin-7-yl)-1H-pyrazole-5-carboxamide <Step 1> Synthesis of 4-(6-cyanopyridin-2-yl)-1-methyl-1H-pyrazole-5-carboxylic acid Using 6-bromopicolinonitrile (0.73 g) and 4-iodo-1-methyl-1H-pyrazole-5-carboxylic acid (1 g), the title compound (4.7 mg) was obtained in the form of a colorless solid by the same method as that of (Example 3.22) <Step 1> or a method equivalent thereto.

<Step 2> Synthesis of 4-(6-cyanopyridin-2-yl)-1-methyl-N-(2-phenyl-5,6,7,8-tetrahydro-[1,2,4]triazolo[1,5-a]pyridin-7-yl)-1H-pyrazole-5-carboxamide Using the 4-(6-cyanopyridin-2-yl)-1-methyl-1H-pyrazole-5-carboxylic acid (15 mg) obtained in (Example 5.40) <Step 1> and the 2-phenyl-5,6,7,8-tetrahydro-[1,2,4]triazolo[1,5-a]pyridin-7-amine hydrochloride (20 mg) obtained in (Example 5.1) <Step 3>, the title compound (1.8 mg) was obtained in the form of a colorless solid by the same method as that of (Example 1.1) <Step 4> or a method equivalent thereto.

Example 5.41

Synthesis of 4-(4-cyanothiazol-2-yl)-N-(2-(4-fluoro-phenyl)-5,6,7,8-tetrahydro-[1,2,4]triazolo[1,5-a]pyri-din-7-yl)-1-methyl-1H-pyrazole-5-carboxamide <Step 1> Synthesis of 4-(4-cyanothiazol-2-yl)-1-methyl-1H-pyrazole-5-carboxylic acid Using 2-bromothiazole-4-carbonitrile (150 mg), the title compound (59 mg) was obtained in the form of a thick gray solid by the same method as that of (Example 1.1) <Step 2> or a method equivalent thereto.

<Step 2> Synthesis of 4-(4-cyanothiazol-2-yl)-N-(2-(4-fluorophenyl)-5,6,7,8-tetrahydro-[1,2,4]tri-azolo[1,5-a]pyridin-7-yl)-1-methyl-1H-pyrazole-5-carboxamide Using the 4-(4-cyanothiazol-2-yl)-1-methyl-1H-pyrazole-5-carboxylic acid (13 mg) obtained in (Example 5.41) <Step 1> and the (2-(4-fluorophenyl)-5,6,7,8-tetrahydro-[1,2,4]tri-azolo[1,5-a]pyridin-7-amine hydrochloride (15 mg) obtained in (Example 5.2) <Step 5>, the title compound (7.6 mg) was obtained in the form of a gray solid by the same method as that of (Example 1.1) <Step 4> or a method equivalent thereto.

Example 5.42

Synthesis of 4-(5-cyclopropyl-4-(difluoromethyl) thiazol-2-yl)-N-(2-(3-fluorophenyl)-5,6,7,8-tetra-hydro-[1,2,4]triazolo[1,5-a]pyridin-7-yl)-1-methyl-1H-pyrazole-5-carboxamide Using the 2-(3-fluorophenyl)-5,6,7,8-tetrahydro-[1,2,4] triazolo[1,5-a]pyridin-7-amine hydrochloride (23 mg) obtained in (Example 5.33) <Step 1> and the methyl 4-(5-cyclopropyl-4-(difluoromethyl)thiazol-2-yl)-1-methyl-1H-pyrazole-5-carboxylate obtained in (Example 5.8) <Step 1>, the title compound (16 mg) was obtained in the form of a gray solid by the same method as that of (Example 1.3) <Step 2> or a method equivalent thereto.

Example 5.43

Synthesis of 4-(5-cyclopropyl-4-methylthiazol-2-yl)-N-(2-(4-fluorophenyl)-5,6,7,8-tetrahydro-[1,2,4] triazolo[1,5-a]pyridin-7-yl)-1-methyl-1H-pyrazole-5-carboxamide <Step 1> Synthesis of methyl 4-(5-cyclopropyl-4-methylthiazol-2-yl)-1-methyl-1H-pyrazole-5-car-boxylate Using the methyl 4-(5-bromo-4-methylthiazol-2-yl)-1-methyl-1H-pyrazole-5-carboxylate (20 mg) obtained in (Example 5.11) <Step 1>, the title compound (11 mg) was obtained in the form of an orange solid by the same method as that of (Example 5.8) <Step 1> or a method equivalent thereto.

<Step 2> Synthesis of 4-(5-cyclopropyl-4-methyl-thiazol-2-yl)-N-(2-(4-fluorophenyl)-5,6,7,8-tetrahydro-[1,2,4]triazolo[1,5-a]pyridin-7-yl)-1-methyl-1H-pyrazole-5-carboxamide Using the methyl 4-(5-cyclopropyl-4-methylthiazol-2-yl)-1-methyl-1H-pyrazole-5-carboxylate (11 mg) obtained in (Example 5.43) <Step 1> and the (2-(4-fluorophenyl)-5,6,7,8-tetrahydro-[1,2,4]triazolo[1,5-a]pyridin-7-amine hydrochloride (10 mg) obtained in (Example 5.2) <Step 5>, the title compound (9.6 mg) was obtained in the form of a colorless solid by the same method as that of (Example 1.3) <Step 2> or a method equivalent thereto.

Example 5.44

Synthesis of 4-(5-acetyl-2-methylthiazol-4-yl)-N-(2-(3-fluorophenyl)-5,6,7,8-tetrahydro-[1,2,4]triazolo[1,5-a]pyridin-7-yl)-1-methyl-1H-pyrazole-5-carboxamide <Step 1> Synthesis of methyl 4-(5-acetyl-2-methyl-thiazol-4-yl)-1-methyl-1H-pyrazole-5-carboxylate Using the methyl 4-(5-bromo-2-methylthiazol-4-yl)-1-methyl-1H-pyrazole-5-carboxylate (25 mg) obtained in (Example 5.13) <Step 1>, the title compound (15 mg) was obtained in a light yellow amorphous form by the same method as that of (Example 5.30) or a method equivalent thereto.

<Step 2> Synthesis of 4-(5-acetyl-2-methylthiazol-4-yl)-N-(2-(3-fluorophenyl)-5,6,7,8-tetrahydro-[1,2,4]triazolo[1,5-a]pyridin-7-yl)-1-methyl-1H-pyrazole-5-carboxamide Using the methyl 4-(5-acetyl-2-methylthiazol-4-yl)-1-methyl-1H-pyrazole-5-carboxylate (14 mg) obtained in (Example 5.44) <Step 1> and the 2-(3-fluorophenyl)-5,6,7,8-tetrahydro-[1,2,4]triazolo[1,5-a]pyridin-7-amine hydrochloride (13 mg) obtained in (Example 5.33) <Step 1>, the title compound (11 mg) was obtained in a white amorphous form by the same method as that of (Example 1.3) <Step 2> or a method equivalent thereto.

Example 5.45

Synthesis of 4-(4,5-dimethylthiazol-2-yl)-1-methyl-N-(2-(pyrrolidin-1-yl)-5,6,7,8-tetrahydro-[1,2,4]triazolo[1,5-a]pyridin-7-yl)-1H-pyrazole-5-carboxamide <Step 1> Synthesis of 4-(4,5-dimethylthiazol-2-yl)-1-methyl-1H-pyrazole-5-carboxylic acid Using the methyl 4-(4,5-dimethylthiazol-2-yl)-1-methyl-1H-pyrazole-5-carboxylate (180 mg) obtained in (Example 2.2) <Step 1>, the title compound (137 mg) was obtained in the form of a whitish brown solid by the same method as that of (Example 1.1) <Step 3> or a method equivalent thereto.

<Step 2> Synthesis of N-(2-bromo-5,6,7,8-tetrahydro-[1,2,4]triazolo[1,5-a]pyridin-7-yl)-4-(4,5-dimethylthiazol-2-yl)-1-methyl-1H-pyrazole-5-carboxamide Using the 4-(4,5-dimethylthiazol-2-yl)-1-methyl-1H-pyrazole-5-carboxylic acid (14 mg) obtained in (Example 5.45) <Step 1> and the 2-bromo-5,6,7,8-tetrahydro-[1,2,4]triazolo[1,5-a]pyridin-7-amine hydrochloride (15 mg) obtained in (Example 5.16) <Step 6>, the title compound (16 mg) was obtained in a white amorphous form by the same method as that of (Example 1.1) <Step 4> or a method equivalent thereto.

<Step 3> Synthesis of 4-(4,5-dimethylthiazol-2-yl)-1-methyl-N-(2-(pyrrolidin-1-yl)-5,6,7,8-tetrahydro-[1,2,4]triazolo[1,5-a]pyridin-7-yl)-1H-pyrazole-5-carboxamide Using the N-(2-bromo-5,6,7,8-tetrahydro-[1,2,4]triazolo[1,5-a]pyridin-7-yl)-4-(4,5-dimethylthiazol-2-yl)-1-methyl-1H-pyrazole-5-carboxamide (8 mg) obtained in (Example 5.45) <Step 2> and pyrrolidine (0.5 ml), the title compound (2 mg) was obtained in a light yellow amorphous form by the same method as that of (Example 4.1) or a method equivalent thereto.

Example 5.46

Synthesis of 1-methyl-N-(2-(pyrrolidin-1-yl)-5,6,7,8-tetrahydro-[1,2,4]triazolo[1,5-a]pyridin-7-yl)-4-(4-(trifluoromethyl)thiazol-2-yl)-1H-pyrazole-5-carboxamide <Step 1> Synthesis of N-(2-bromo-5,6,7,8-tetrahydro-[1,2,4]triazolo[1,5-a]pyridin-7-yl)-1-methyl-4-(4-(trifluoromethyl)thiazol-2-yl)-1H-pyrazole-5-carboxamide Using the 1-methyl-4-(4-(trifluoromethyl)thiazol-2-yl)-1H-pyrazole-5-carboxylic acid (16 mg) obtained in (Example 4.10) <Step 1> and the 2-bromo-5,6,7,8-tetrahydro-[1,2,4]triazolo[1,5-a]pyridin-7-amine hydrochloride (15 mg) obtained in (Example 5.16) <Step 6>, the title compound (18 mg) was obtained in the form of a whitish brown solid by the same method as that of (Example 1.1) <Step 4> or a method equivalent thereto.

<Step 2> Synthesis of 1-methyl-N-(2-(pyrrolidin-1-yl)-5,6,7,8-tetrahydro-[1,2,4]triazolo[1,5-a]pyridin-7-yl)-4-(4-(trifluoromethyl)thiazol-2-yl)-1H-pyrazole-5-carboxamide Using the N-(2-bromo-5,6,7,8-tetrahydro-[1,2,4]triazolo[1,5-a]pyridin-7-yl)-1-methyl-4-(4-(trifluoromethyl)thiazol-2-yl)-1H-pyrazole-5-carboxamide (16 mg) obtained in (Example 5.46) <Step 1> and pyrrolidine (0.5 ml), the title compound (7.8 mg) was obtained in a light yellow amorphous form by the same method as that of (Example 4.1) or a method equivalent thereto.

Example 5.47

Synthesis of 1-methyl-4-(6-methylpyridin-2-yl)-N-(2-(pyrrolidin-1-yl)-5,6,7,8-tetrahydro-[1,2,4]triazolo[1,5-a]pyridin-7-yl)-1H-pyrazole-5-carboxamide <Step 1> Synthesis of 1-methyl-4-(6-methylpyridin-2-yl)-1H-pyrazole-5-carbonyl chloride Oxalyl chloride (0.85 ml) was added to a mixed solution of methylene chloride (5 ml) and N,N-dimethylformamide (5 µl) containing the 1-methyl-4-(6-methylpyridin-2-yl)-1H-pyrazole-5-carboxylic acid (210 mg) obtained in (Example 3.3) <Step 1>, and the obtained mixture was then stirred for 2 hours. Thereafter, the reaction solution was concentrated under reduced pressure to obtain a crude product (230 mg) of the title compound in the form of an orange solid.

<Step 2> Synthesis of N-(2-bromo-5,6,7,8-tetrahydro-[1,2,4]triazolo[1,5-a]pyridin-7-yl)-1-methyl-4-(6-methylpyridin-2-yl)-1H-pyrazole-5-carboxamide The 2-bromo-5,6,7,8-tetrahydro-[1,2,4]triazolo[1,5-a]pyridin-7-amine hydrochloride (38 mg) obtained in (Example 5.16) <Step 6> was added at 0° C. to a methylene chloride (1 ml) solution of the 1-methyl-4-(6-methylpyridin-2-yl)-1H-pyrazole-5-carbonyl chloride (35 mg) obtained in (Example 5.47) <Step 1> and triethylamine (0.06 ml). The obtained mixture was stirred for 30 minutes. Thereafter, a saturated sodium hydrogen carbonate aqueous solution (2 ml) was added to the reaction solution, and the mixed solution was then purified by LC/MS, so as to obtain the title compound (29 mg) in the form of a white solid.

<Step 3> Synthesis of 1-methyl-4-(6-methylpyridin-2-yl)-N-(2-(pyrrolidin-1-yl)-5,6,7,8-tetrahydro-[1,2,4]triazolo[1,5-a]pyridin-7-yl)-1H-pyrazole-5-carboxamide Using the N-(2-bromo-5,6,7,8-tetrahydro-[1,2,4]triazolo[1,5-a]pyridin-7-yl)-1-methyl-4-(6-methylpyridin-2-yl)-1H-pyrazole-5-carboxamide (13 mg) obtained in (Example 5.47) <Step 2> and pyrrolidine (0.2 ml), the title compound (4.4 mg) was obtained in a white amorphous form by the same method as that of (Example 4.1) or a method equivalent thereto.

Specific embodiments disclosed in the present specification are intended to illustrate several embodiments of the present invention. Accordingly, the present invention described and claimed in the present specification is not limited to the scope of such embodiments. It is intended that any given equivalent embodiments are included in the scope of the present invention. As a matter of fact, from the aforementioned descriptions, a person skilled in the art could understand that the present invention includes various modifications, as well as those described in the present specification. It is intended that such modifications are also included in the scope of the claims attached herewith.

The structures of the final compounds synthesized in the above described (Example 1.1) to (Example 5.47) will be shown in the following drawings (Structural Formula 1 to Structural Formula 10). The NMR data (Table 4 to Table 12) and LC/MS data (Table 13 to Table 16) of the final compounds described in these Examples will also be shown in the following tables.

Moreover, the structures of the intermediate compounds synthesized in individual Examples will be shown in the following drawings (Structural Formula 11 to Structural Formula 19). The NMR data (Table 17 to Table 20) and LC/MS data (Table 21 to Table 24) of the intermediate compounds will also be shown in the following tables.

It is to be noted that, with regard to the intermediate compounds, the compound obtained in (Example 1.1) <Step 1>, for example, is indicated as (Example 1.1-1).

Structural Formulae 1

[Formula 116]

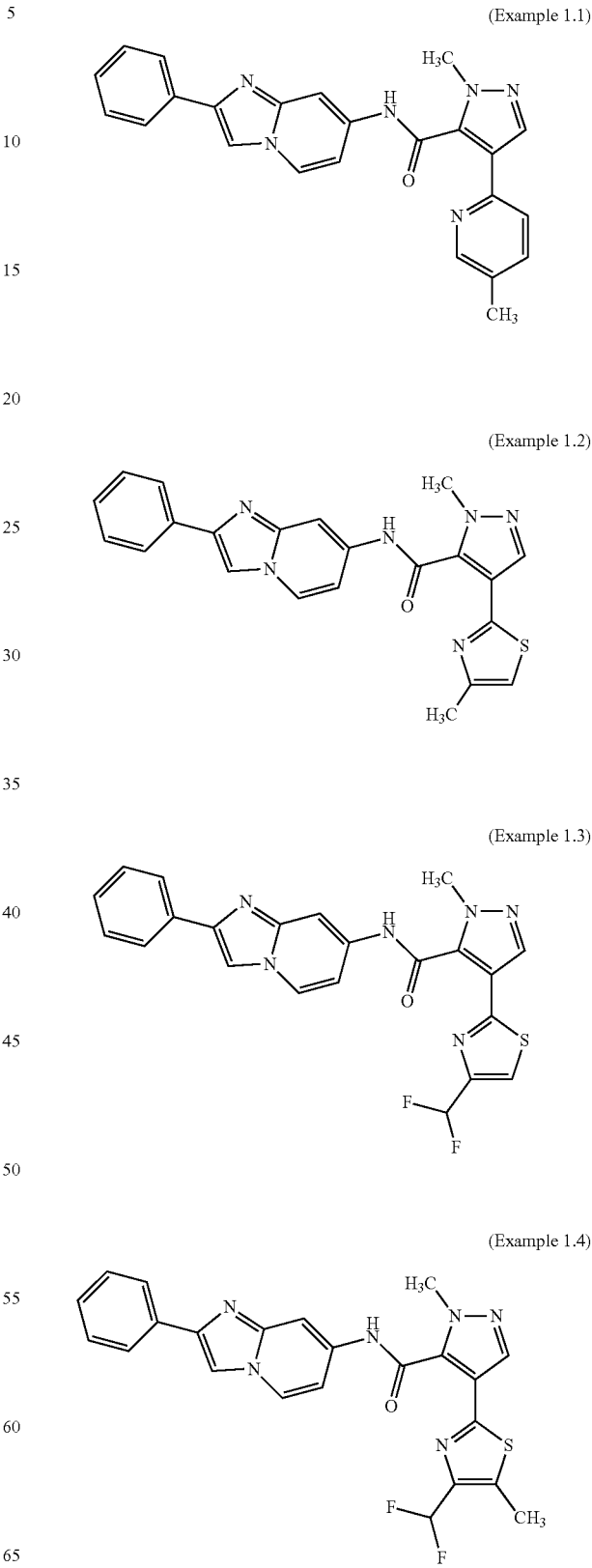

-continued
(Example 1.5)
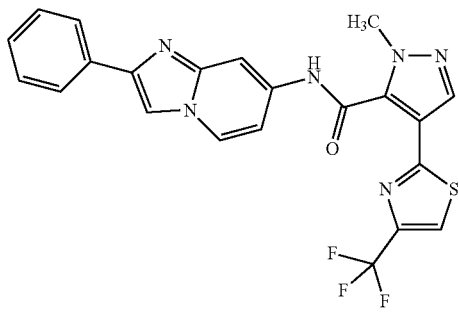
(Example 1.6)
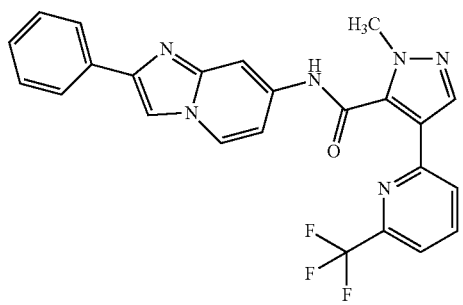
(Example 1.7)
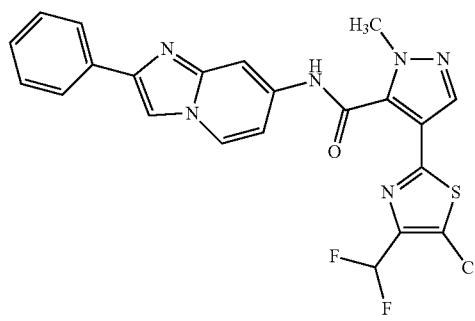
(Example 2.1)
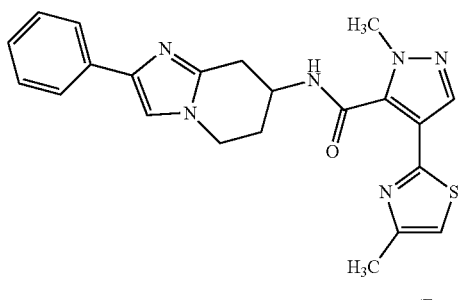
(Example 2.2)
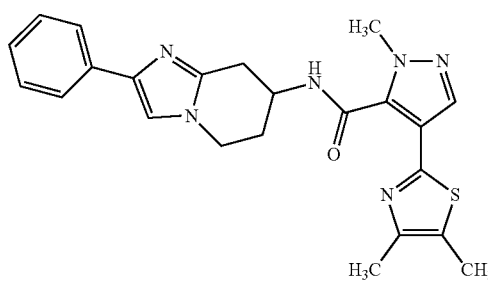
-continued
(Example 2.3)
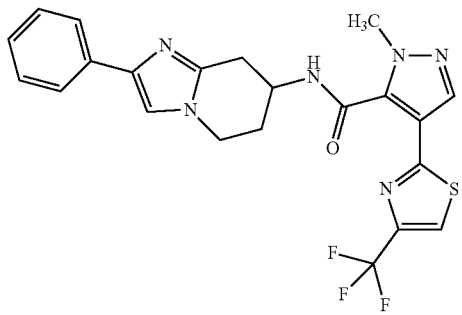
(Example 2.4)
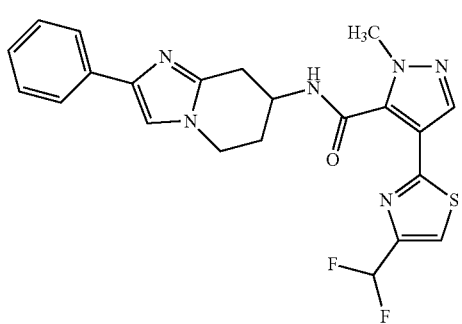
(Example 2.5)
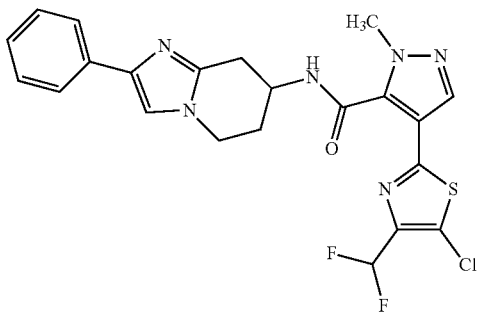
(Example 2.6)
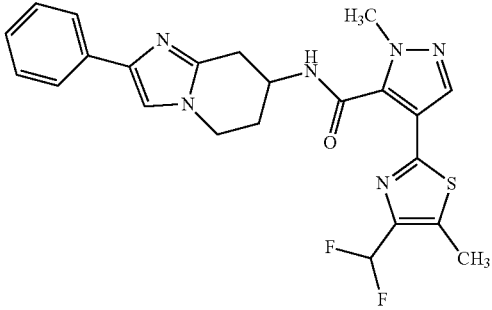

-continued (Example 2.7)

(Example 2.8)

(Example 2.9)

Structural Formulae 2
[Formula 117]

(Example 2.10)

(Example 2.11)

-continued (Example 2.12)

(Example 2.13)

(Example 2.14)

(Example 2.15)

(Example 2.16)

(Example 2.17)
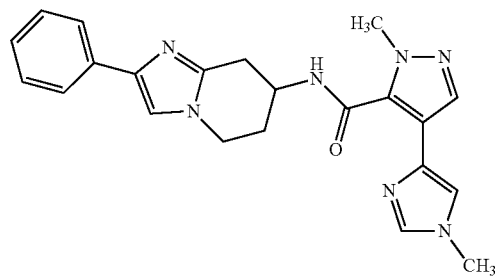
(Example 2.18)
(Example 2.19)
(Example 2.20)
(Example 2.21)
(Example 2.22)
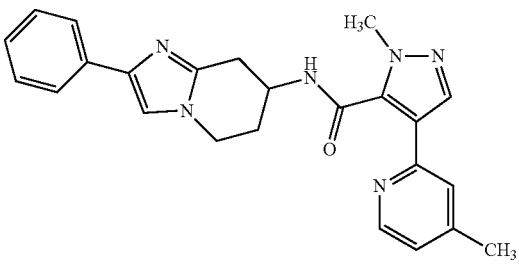
(Example 2.23)
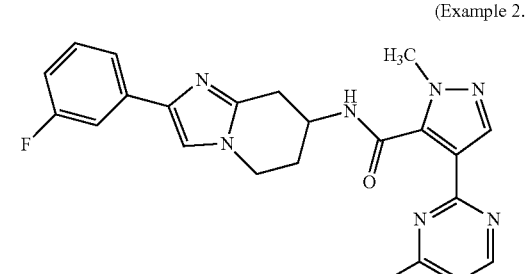
(Example 2.24)
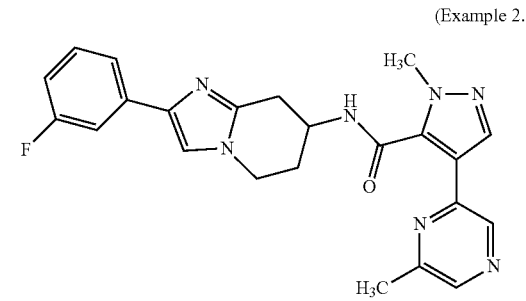
(Example 2.25)
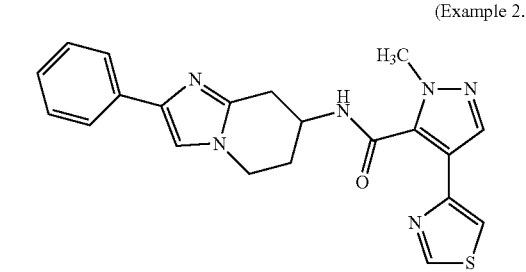
(Example 2.26)
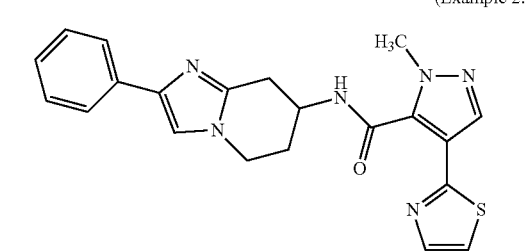

(Example 2.27)
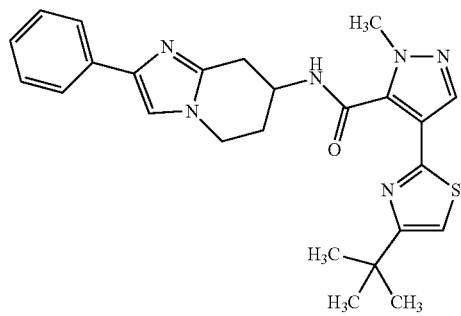
Structural Formulae 3
[Formula 118]
(Example 2.28)
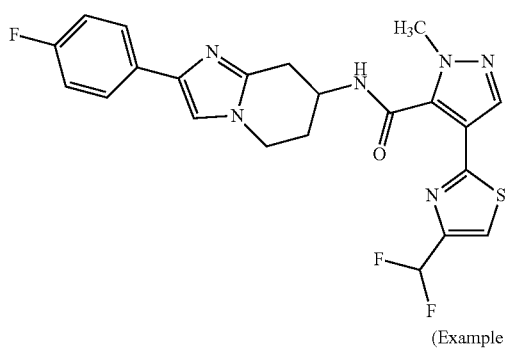
(Example 2.29)
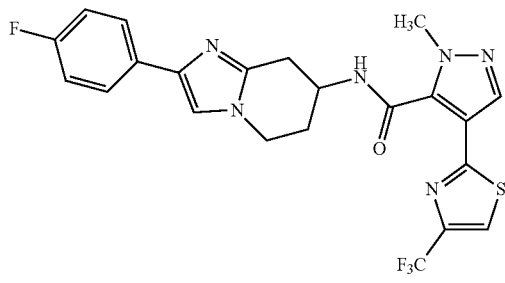
(Example 3.1)
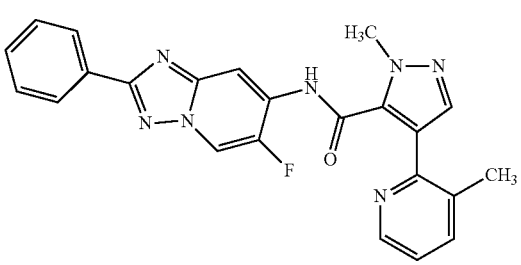
(Example 3.2)
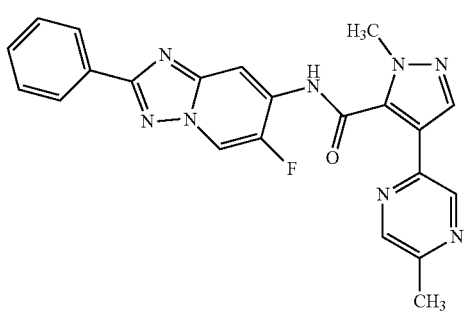
(Example 3.3)
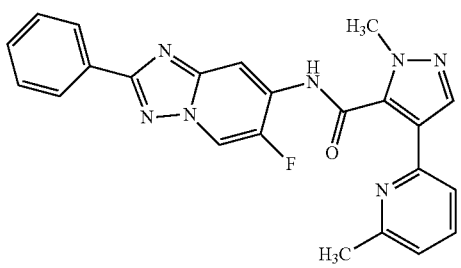
(Example 3.4)
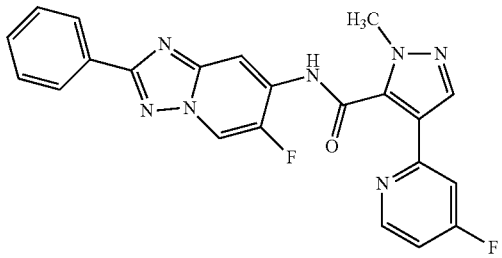
(Example 3.5)
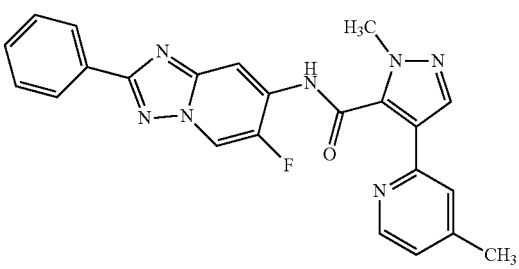
(Example 3.6)
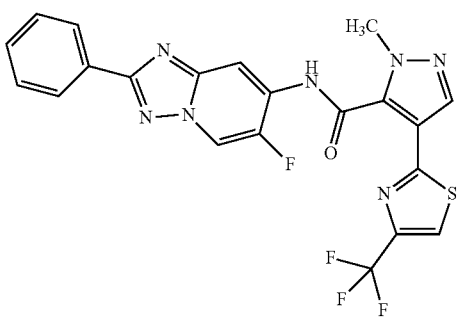
(Example 3.7)
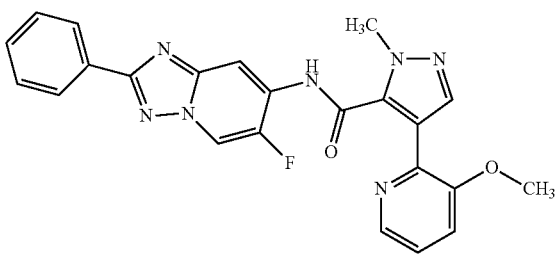

(Example 3.8)
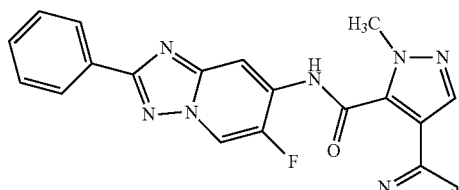
(Example 3.9)
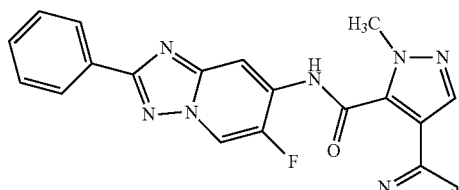
(Example 3.10)
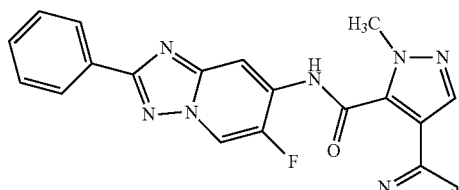
(Example 3.11)
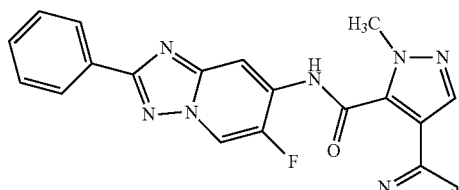
(Example 3.12)
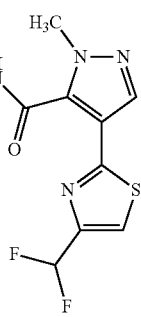
(Example 3.13)
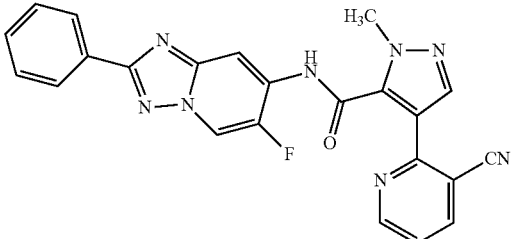
(Example 3.14)
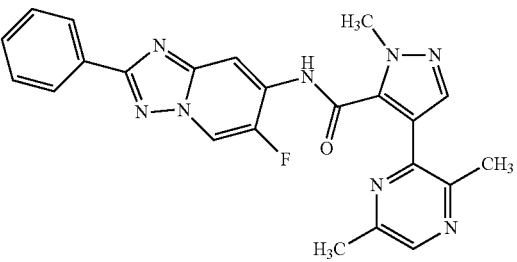
(Example 3.15)
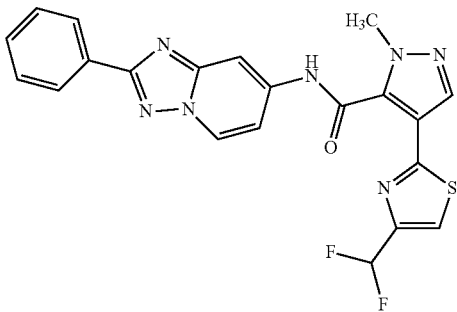
Structural Formulae 4
[Formula 119]
(Example 3.16)
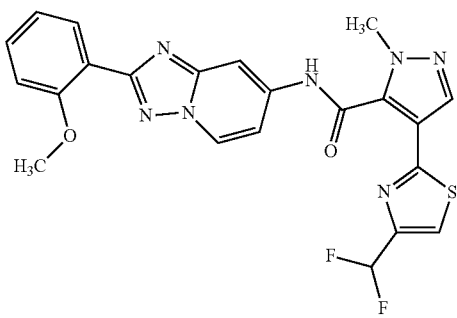
(Example 3.17)
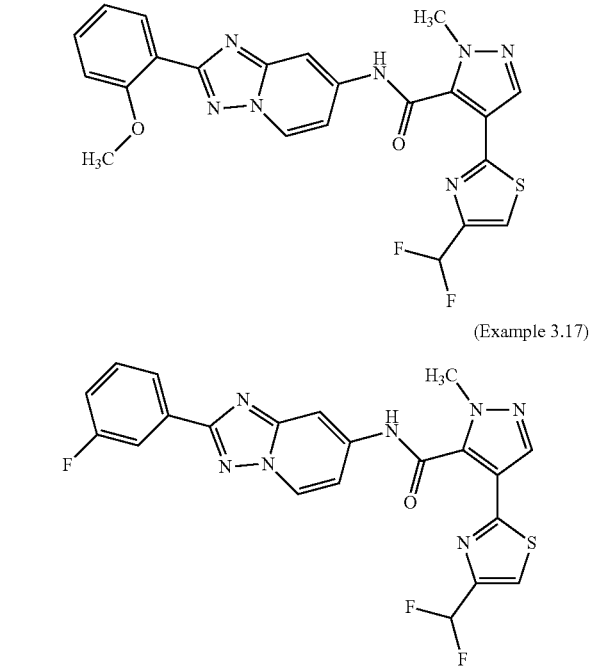

(Example 3.18)
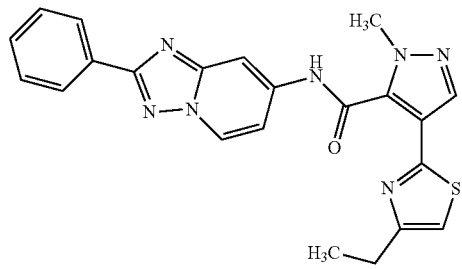
(Example 3.19)
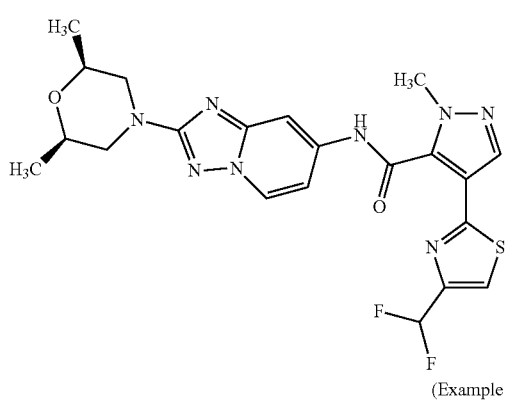
(Example 3.20)
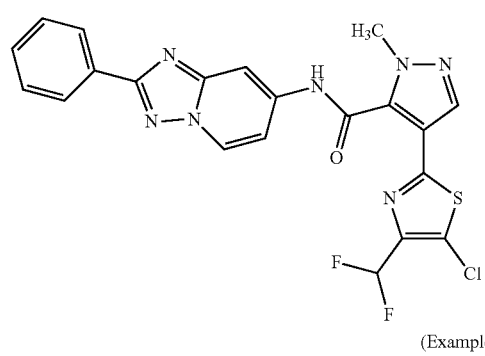
(Example 3.21)
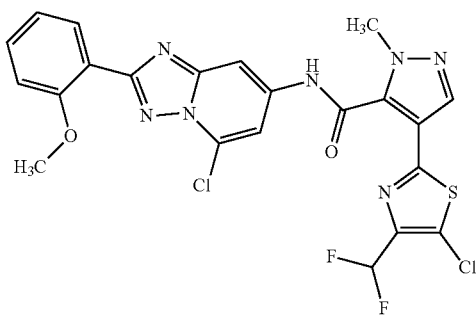
(Example 3.22)
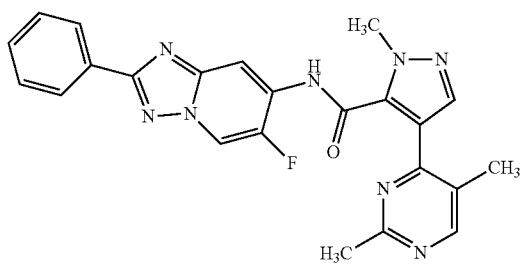
(Example 3.23)
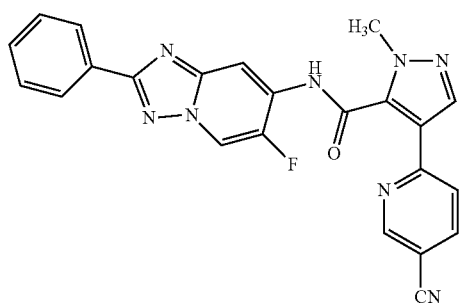
(Example 3.24)
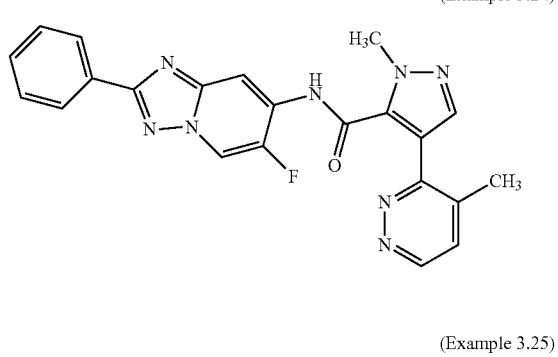
(Example 3.25)
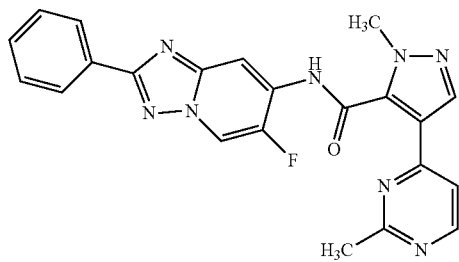
(Example 3.26)
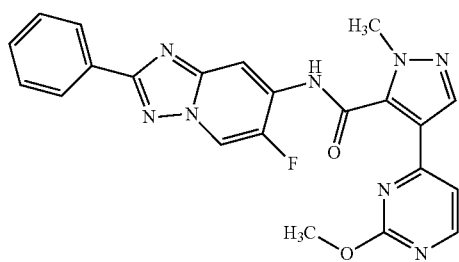
(Example 3.27)

(Example 3.28)
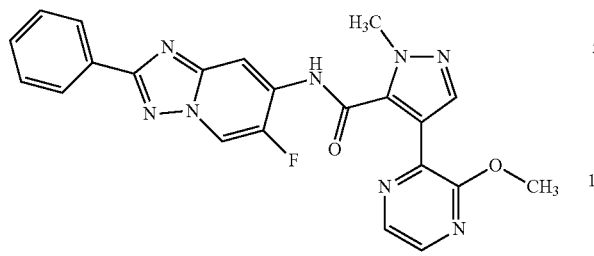
(Example 3.29)
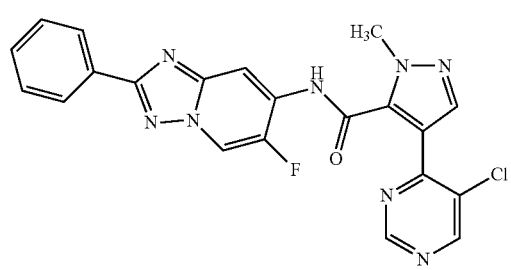
(Example 3.30)
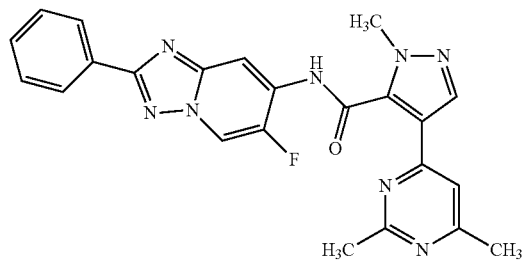
(Example 3.31)
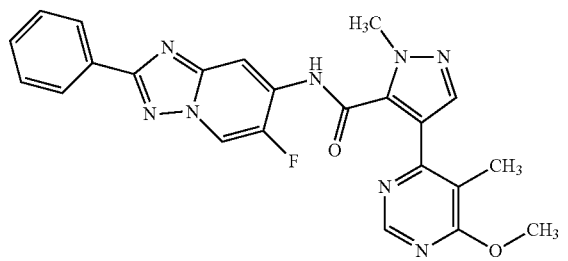
(Example 3.32)
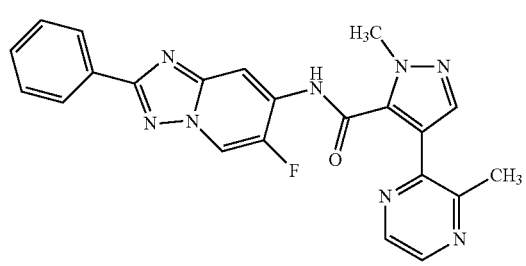
(Example 3.33)
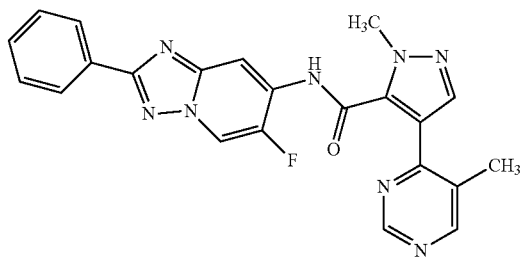
Structural Formulae 5
[Formula 120]
(Example 3.34)
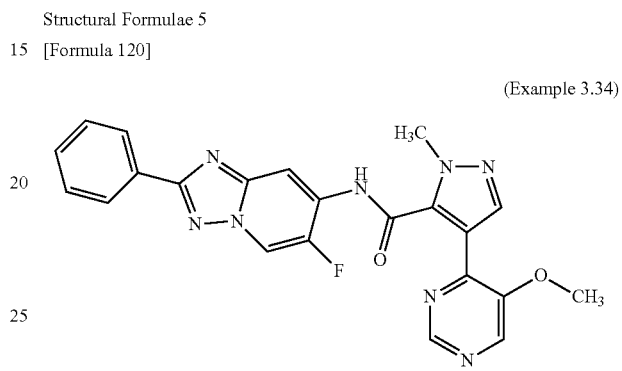
(Example 3.35)
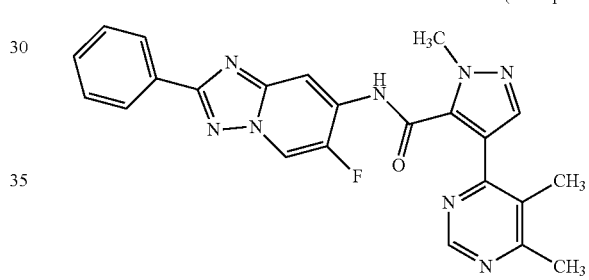
(Example 3.36)
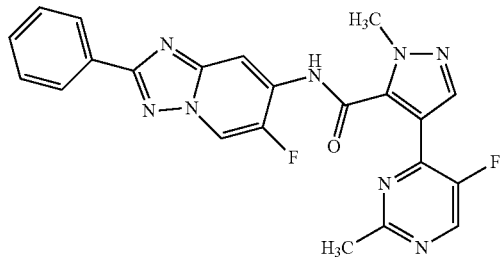
(Example 3.37)
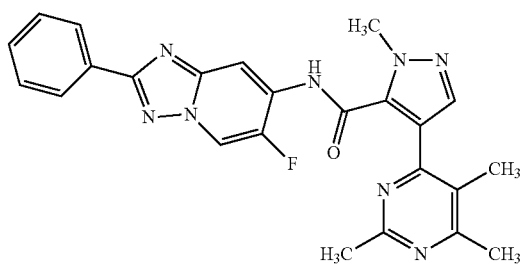

-continued
(Example 3.38)
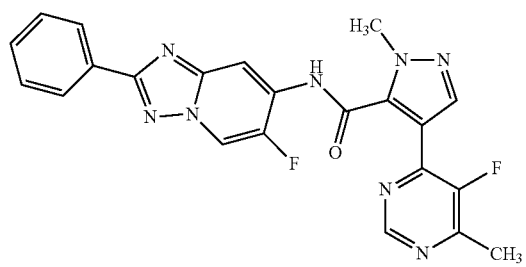
(Example 3.39)
(Example 3.40)
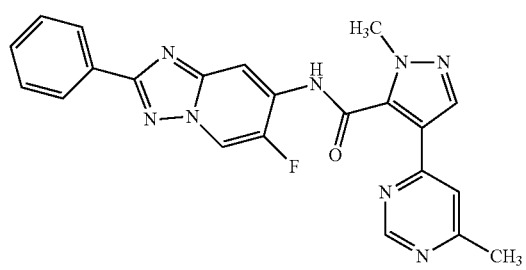
(Example 3.41)
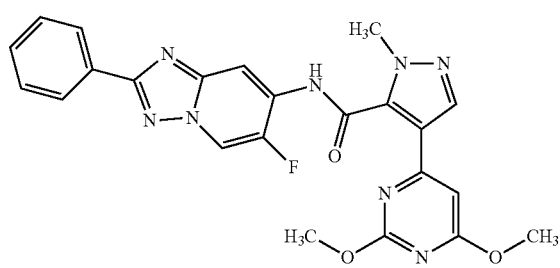
(Example 3.42)
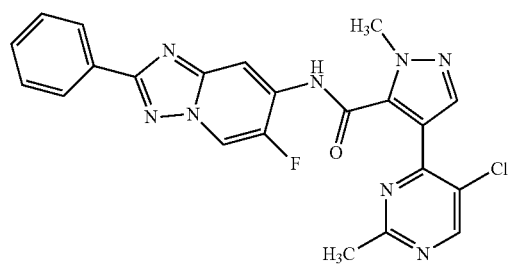
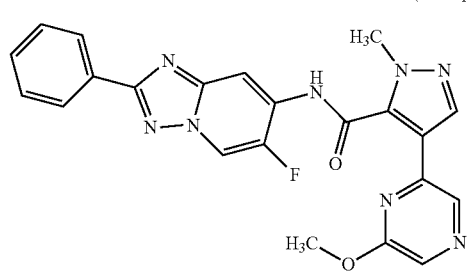
-continued
(Example 3.43)
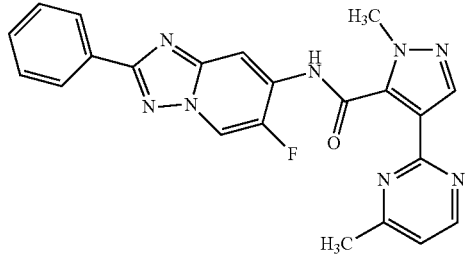
(Example 3.44)
(Example 3.45)
(Example 3.46)
(Example 3.47)

(Example 3.48)
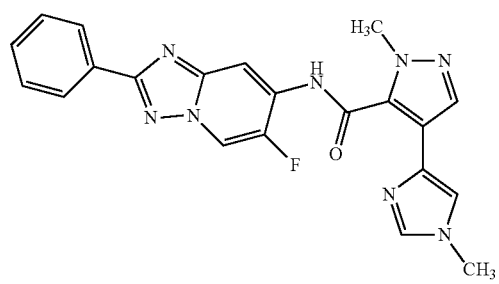
(Example 3.49)
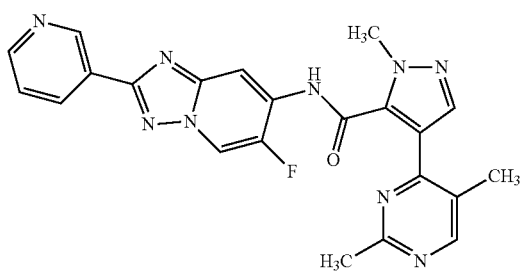
(Example 3.50)
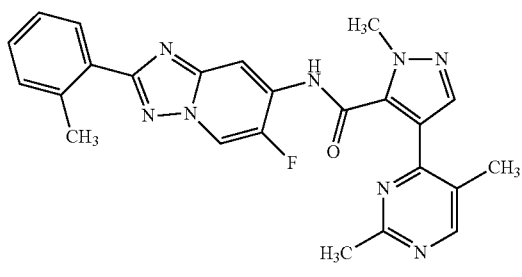
(Example 3.51)
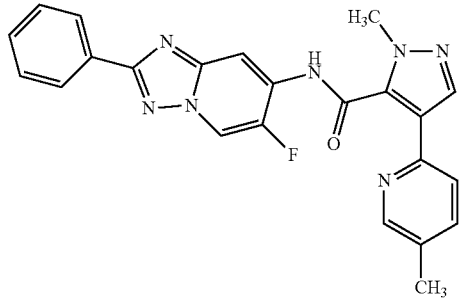
Structural Formulae 6
[Formula 121]
(Example 3.52)
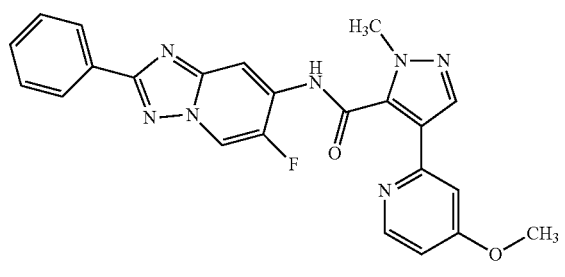
(Example 3.53)
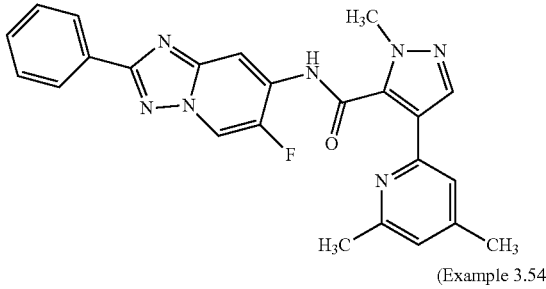
(Example 3.54)
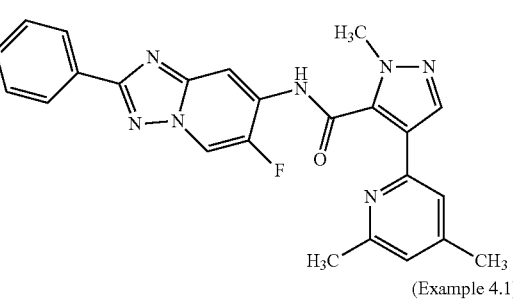
(Example 4.1)
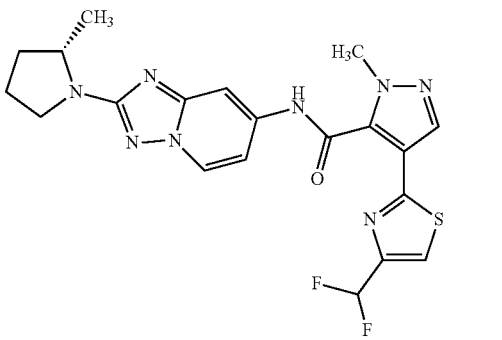
(Example 4.2)
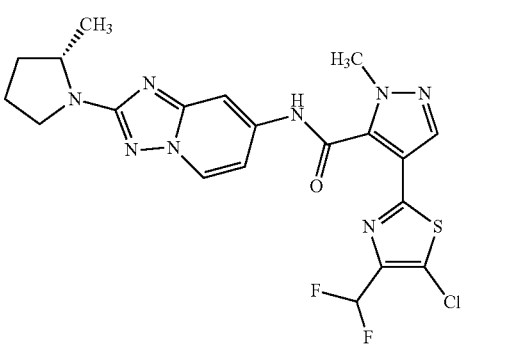
(Example 4.3)
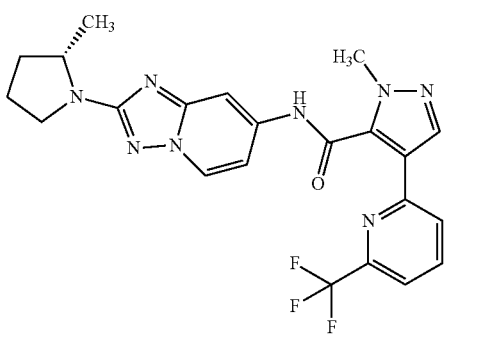

(Example 4.4)
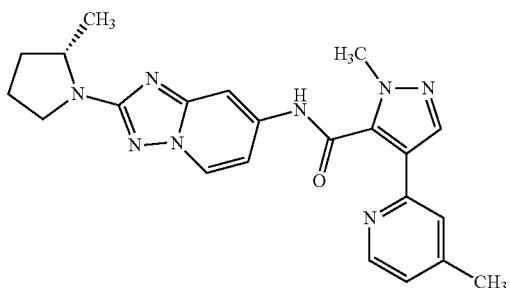
(Example 4.5)
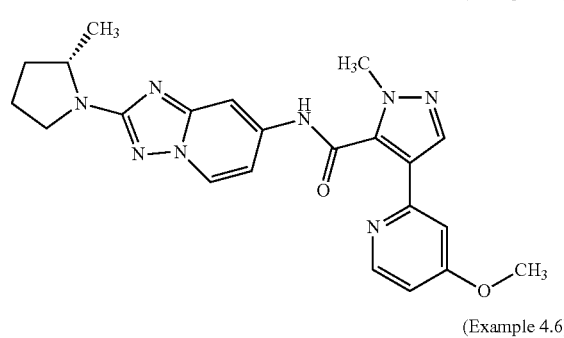
(Example 4.6)
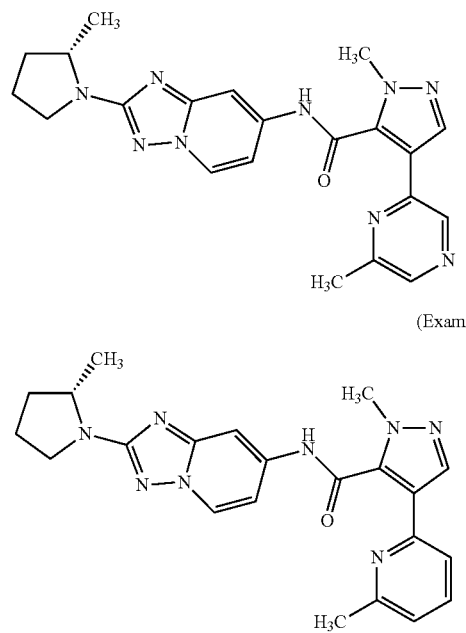
(Example 4.7)
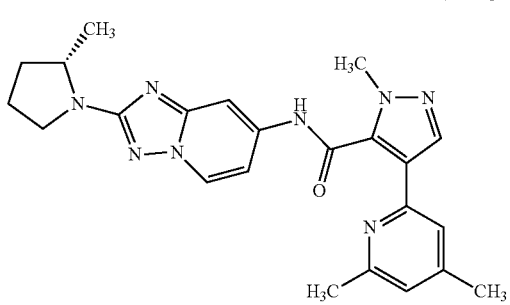
(Example 4.8)
(Example 4.9)
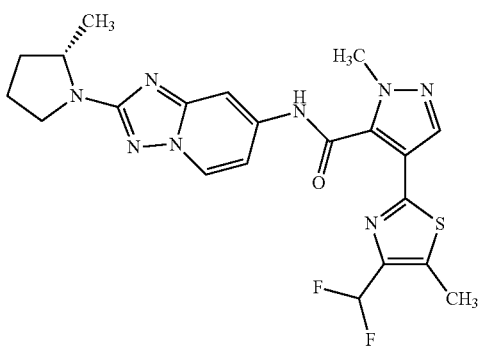
(Example 4.10)
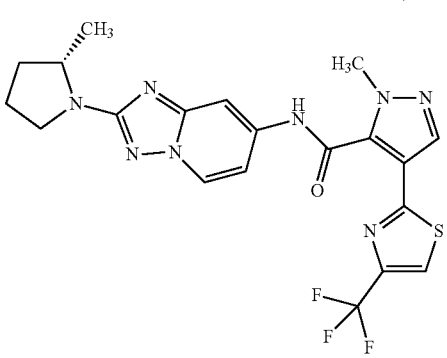
(Example 4.11)
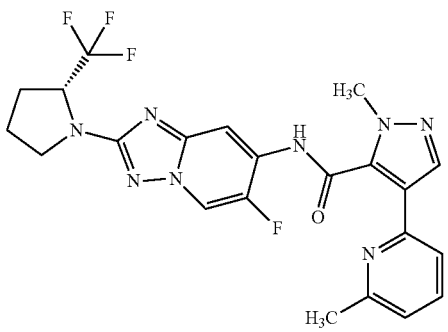
(Example 4.12)
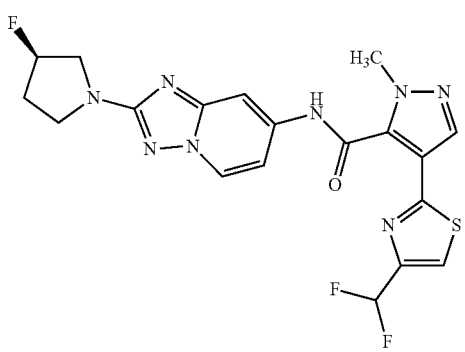

(Example 4.13)

(Example 4.14)

(Example 4.15)

Structural Formulae 7
[Formula 122]

(Example 4.16)

(Example 4.17)

(Example 4.18)

(Example 4.19)

(Example 4.20)

(Example 4.21)

-continued
(Example 4.22)
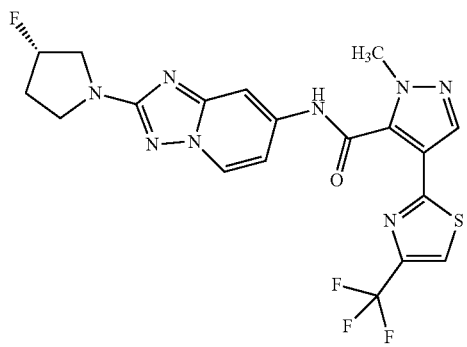
(Example 4.23)
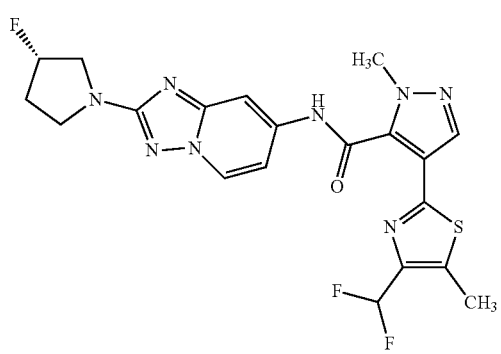
(Example 4, 24)
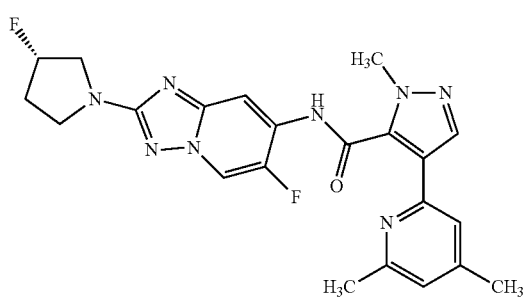
(Example 4.25)
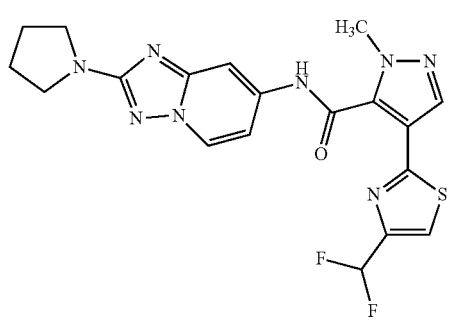
-continued
(Example 4.26)
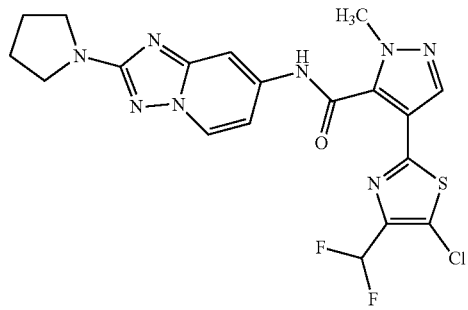
(Example 4.27)
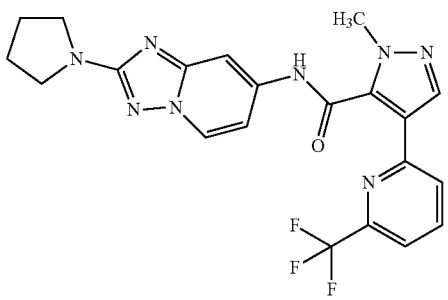
(Example 4.28)
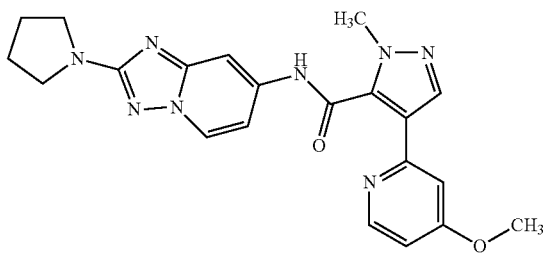
(Example 4.29)
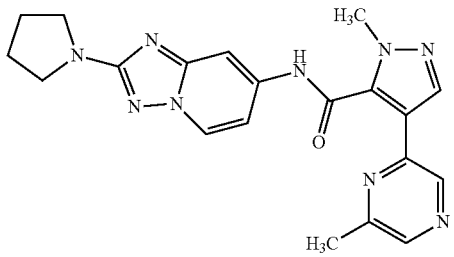
(Example 4.30)
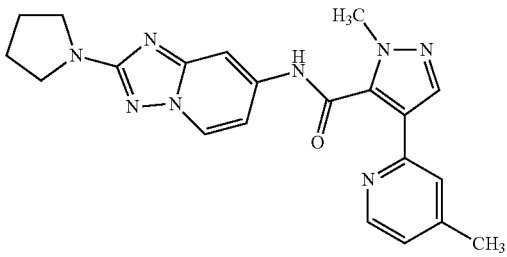

(Example 4.31)
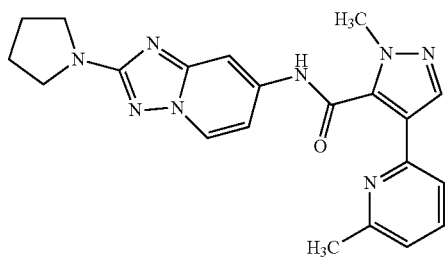
(Example 4.32)
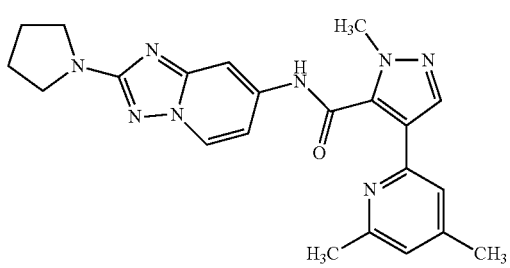
(Example 4.33)
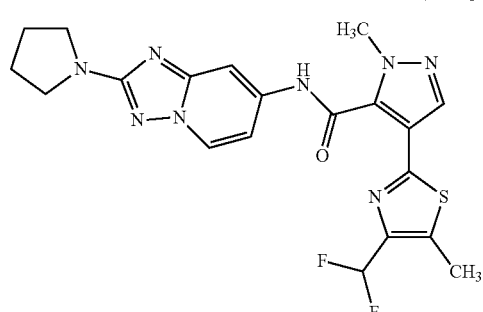
Structural Formulae 8
[Formula 123]
(Example 4.34)
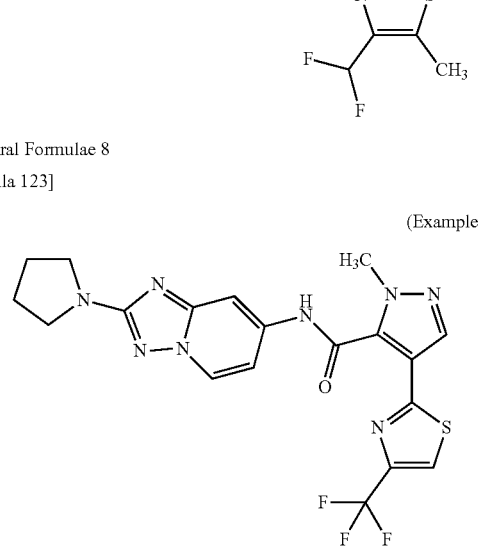
(Example 4.35)
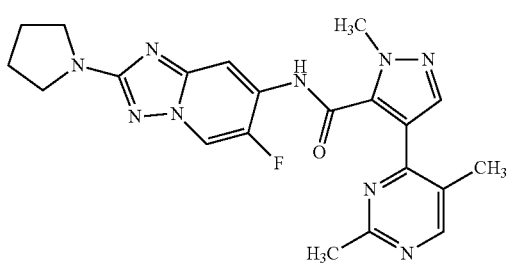
(Example 4.36)
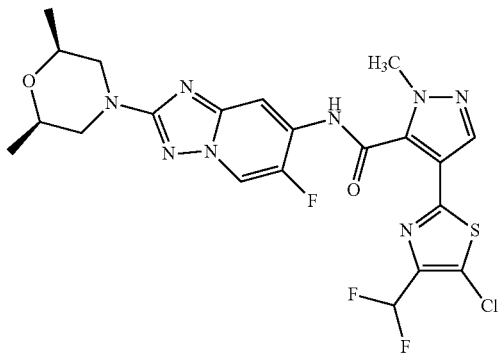
(Example 5.1)
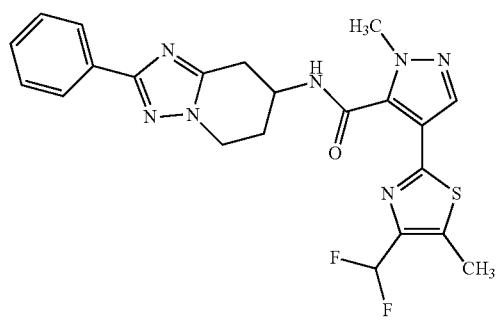
(Example 5.2)
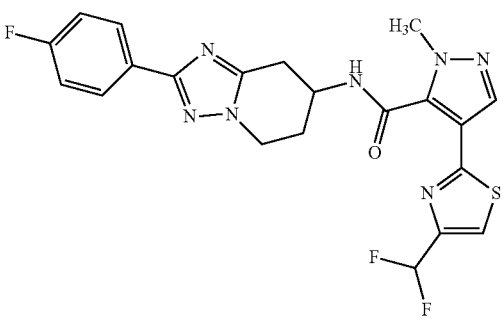
(Example 5.3)
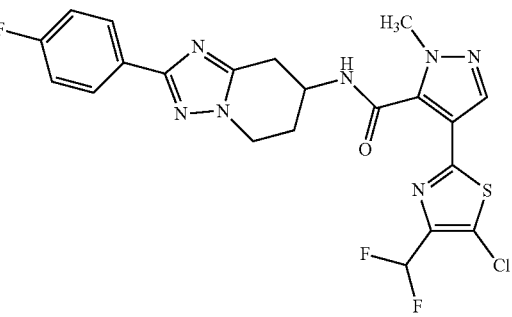

-continued
(Example 5.4)
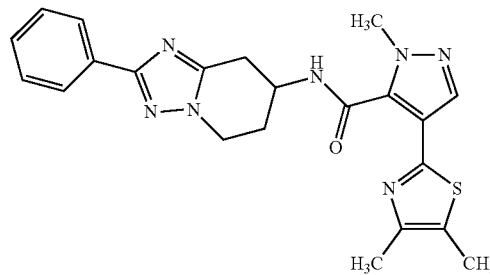
(Example 5.5)
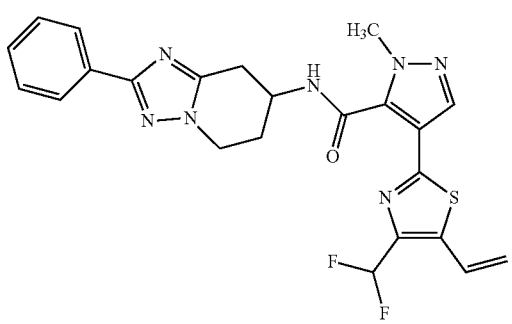
(Example 5.6)
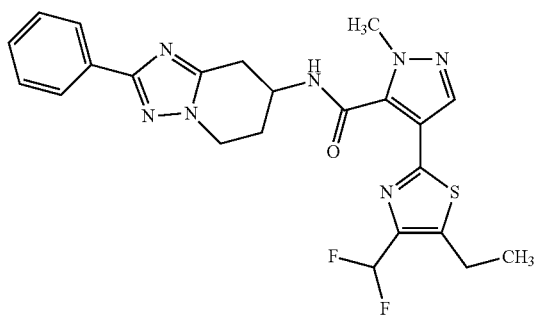
(Example 5.7)
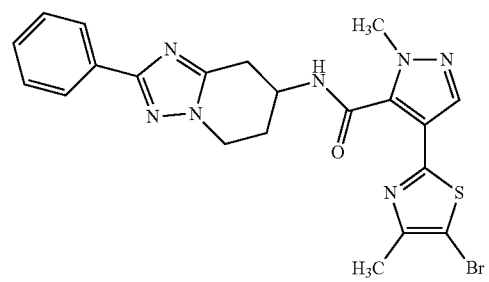
(Example 5.8)
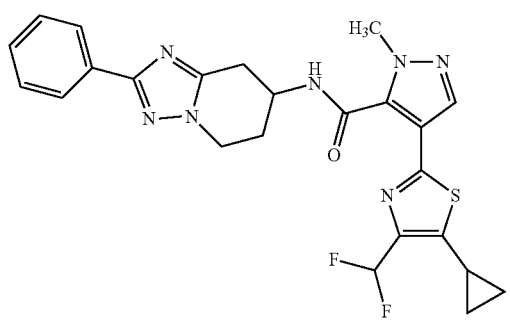
-continued
(Example 5.9)
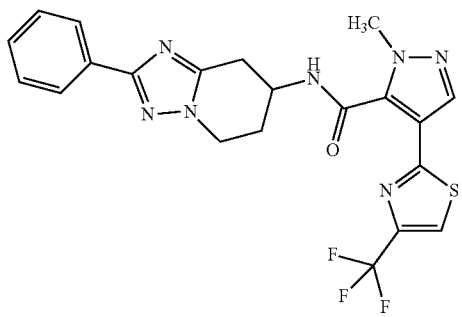
(Example 5.10)
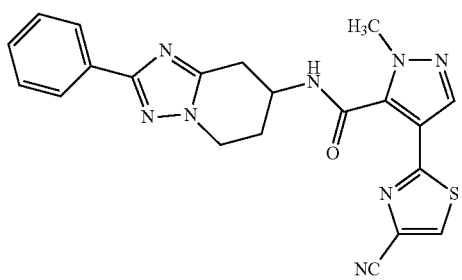
(Example 5.11)
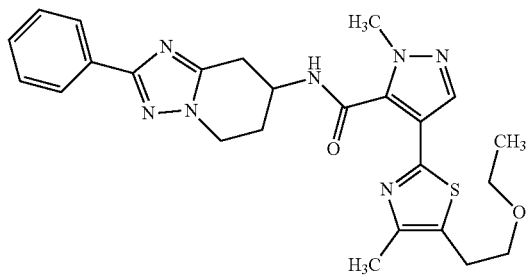
(Example 5.12)
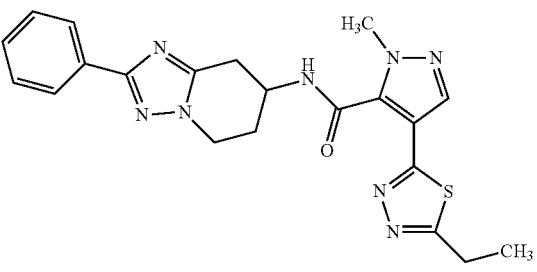
(Example 5.13)

-continued
(Example 5.14)
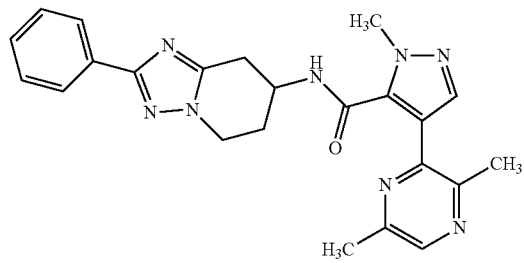
(Example 5.15)
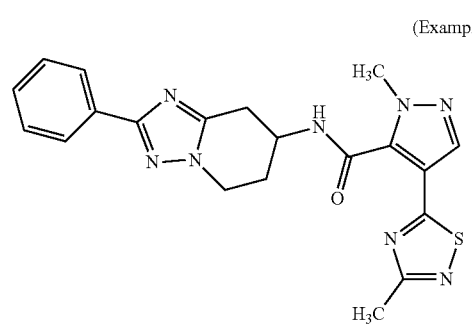
Structural Formulae 9
[Formula 124]
(Example 5.16)
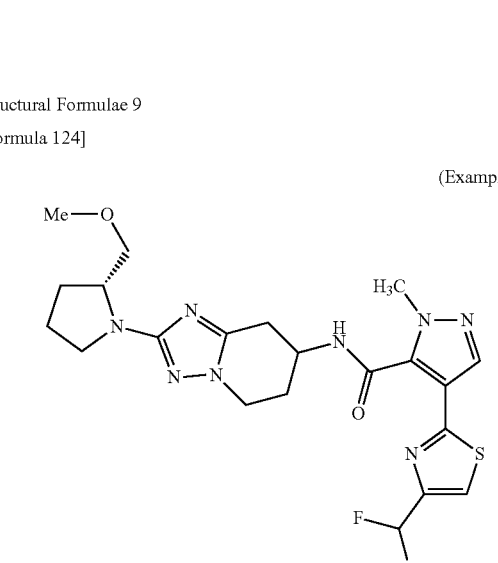
(Example 5.17)
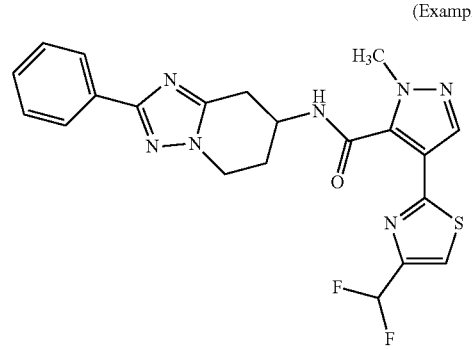
-continued
(Example 5.18)
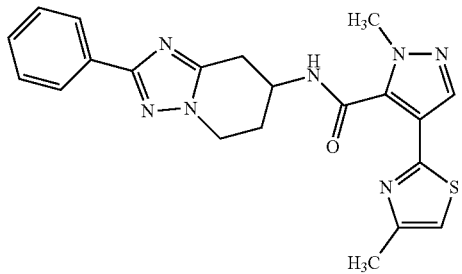
(Example 5.19)
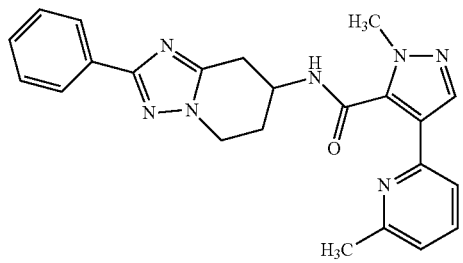
(Example 5.20)
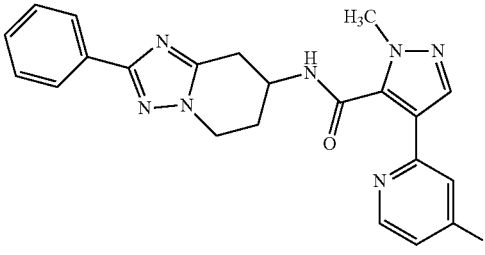
(Example 5.21)
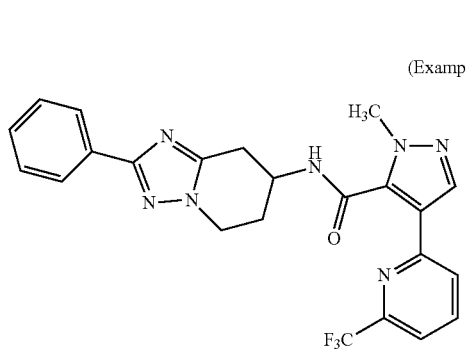
(Example 5.22)
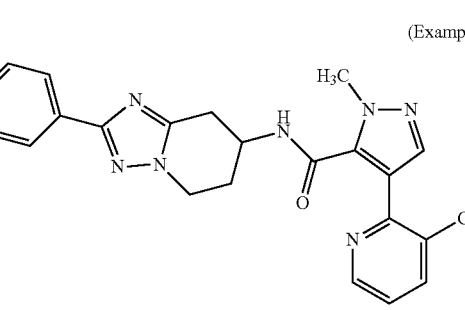

(Example 5.23)
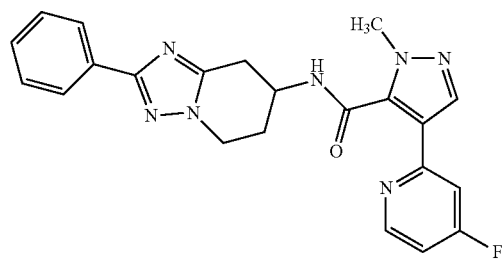
(Example 5.24)
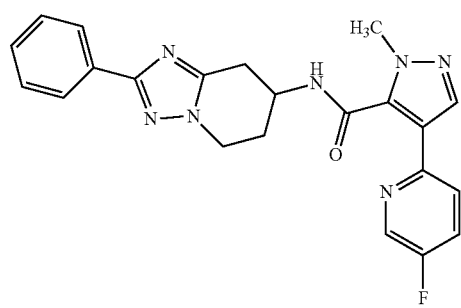
(Example 5.25)
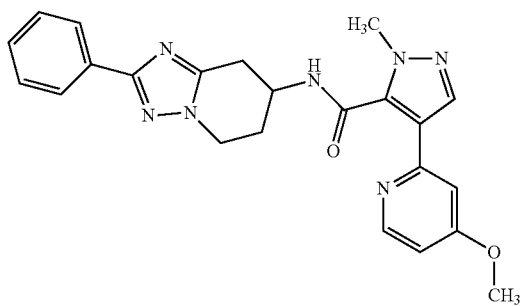
(Example 5.26)
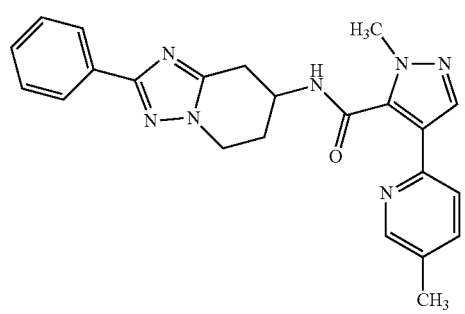
(Example 5.27)
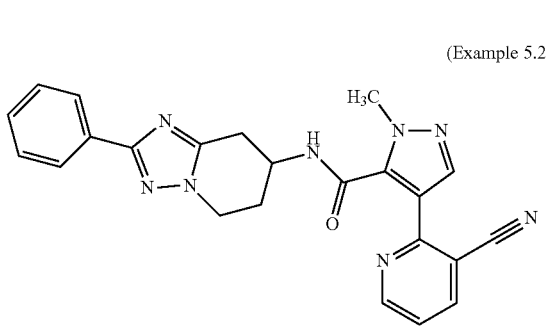
(Example 5.28)
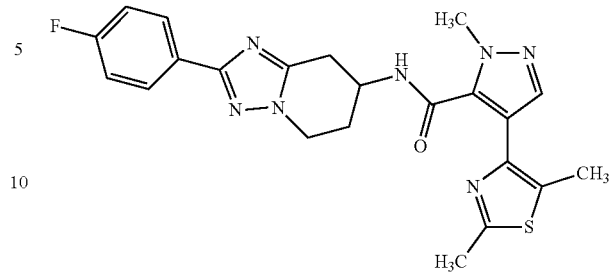
(Example 5.29)
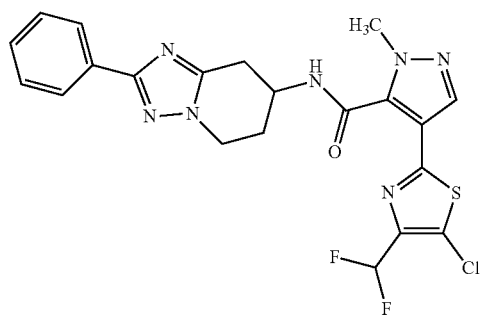
(Example 5.30)
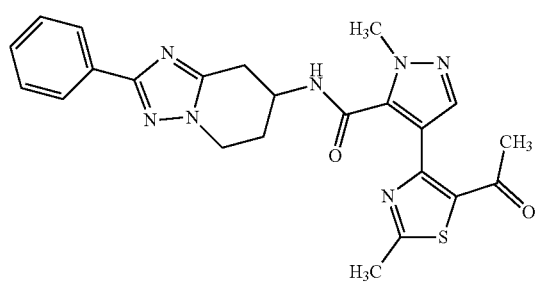
(Example 5.31)
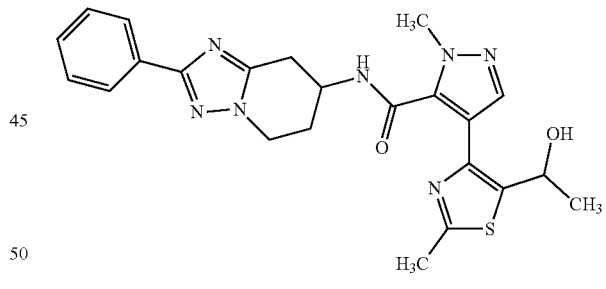
(Example 5.32)
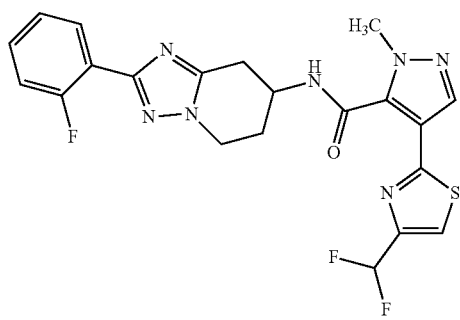

(Example 5.33)
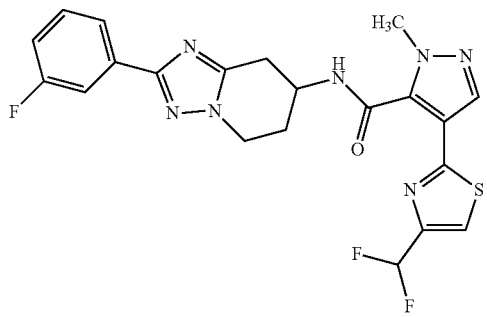
Structural Formulae 10
[Formula 125]
(Example 5.34)
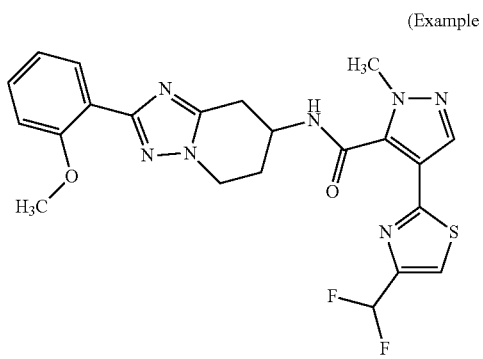
(Example 5.35)
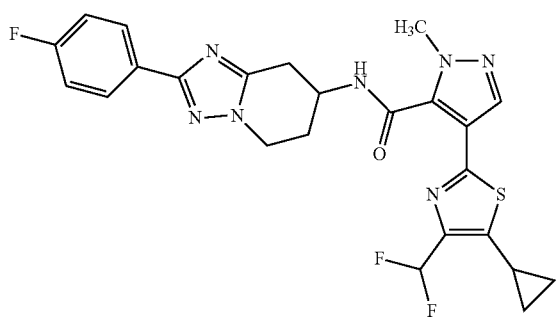
(Example 5.36)
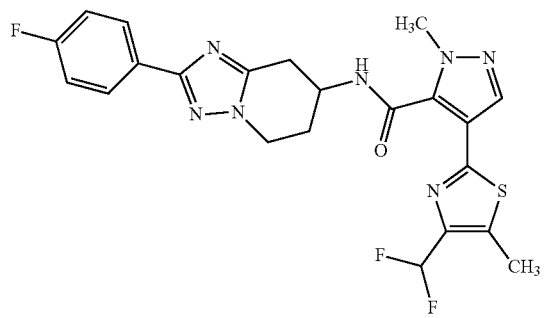
(Example 5.37)
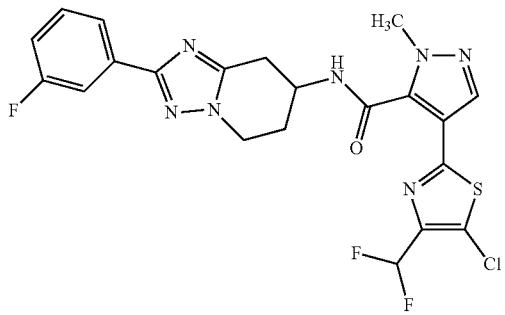
(Example 5.38)
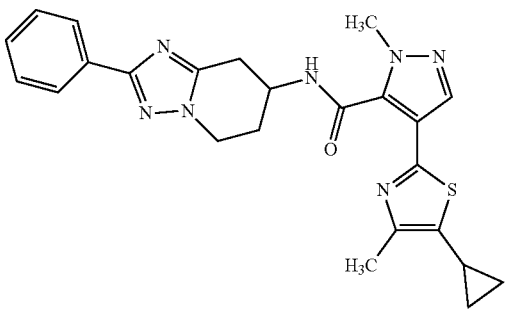
(Example 5.39)
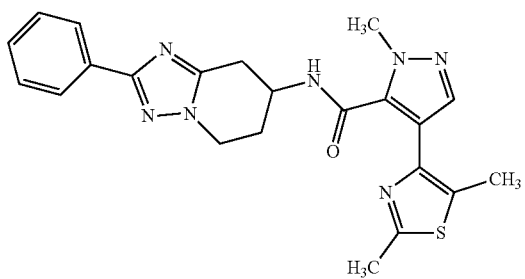
(Example 5.40)
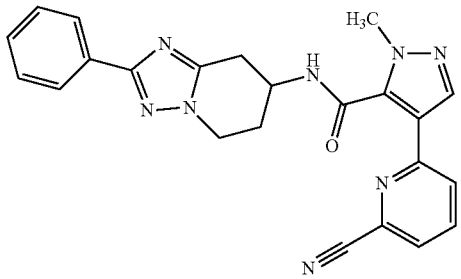
(Example 5.41)
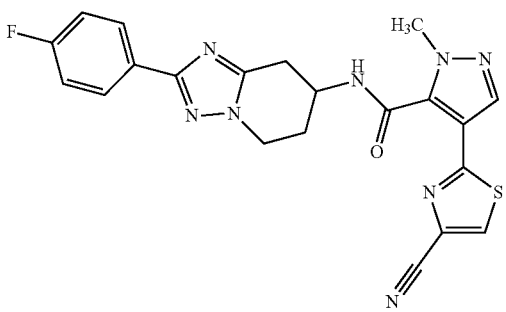

(Example 5.42)
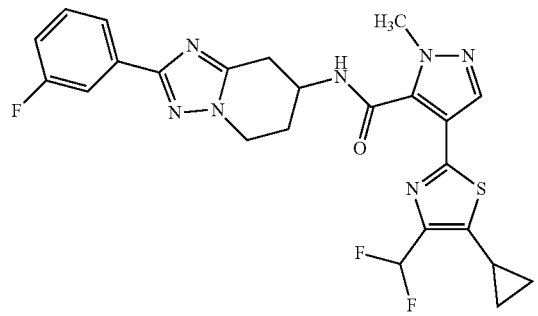

(Example 5.43)
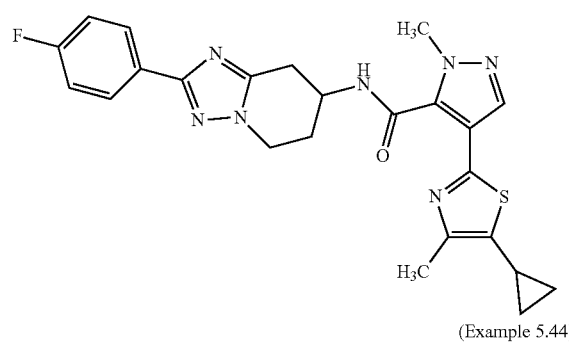

(Example 5.44)
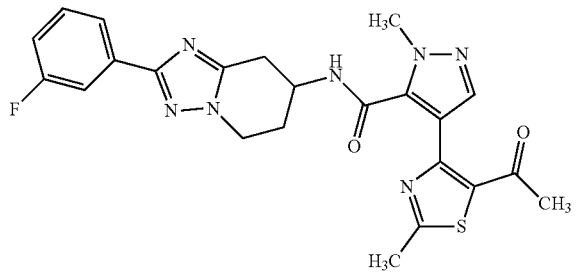

(Example 5.45)
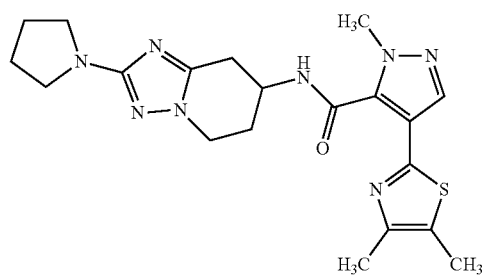

(Example 5.46)
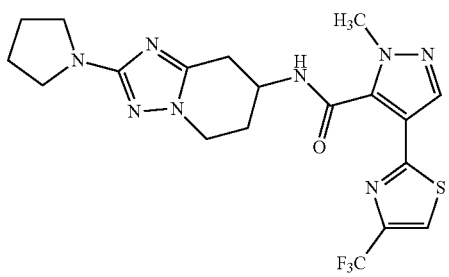

(Example 5.47)
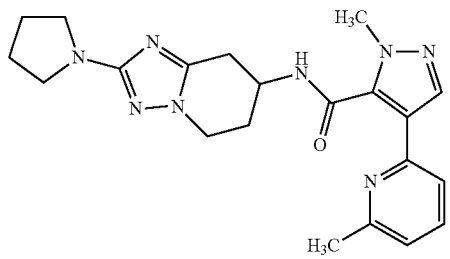

TABLE 4

| Example | NMR data (δ: ppm) |
|---|---|
| 1.1 | $^1$H-NMR (CDCl$_3$) δ: 8.66 (1H, s), 8.11 (1H, d, J = 7 Hz), 7.98-7.93 (2H, m), 7.86 (1H, s), 7.84-7.72 (2H, m), 7.81 (1H, s), 7.68 (1H, dd, J = 8.2 Hz), 7.62 (1H, d, J = 8 Hz), 7.48-7.42 (2H, m), 7.35 (1H, t, J = 7 Hz), 7.28-7.23 (1H, m), 4.36 (3H, s), 2.45 (3H, s). |
| 1.2 | $^1$H-NMR (CDCl$_3$) δ: 13.80 (1H, brs), 8.12 (1H, d, J = 7 Hz), 8.04 (1H, s), 7.97-7.93 (2H, m), 7.88 (1H, s), 7.81 (1H, s), 7.45 (2H, t, J = 8 Hz), 7.36 (1H, d, J = 8 Hz), 7.27-7.23 (1H, m), 6.94 (1H, d, J = 1 Hz), 4.37 (3H, s), 2.66 (3H, s). |
| 1.3* | $^1$H-NMR (CDCl$_3$) δ: 11.84 (1H, s), 8.64 (1H, d, J = 8 Hz), 8.48 (1H, s), 8.23 (1H, s), 8.17 (1H, s), 8.13 (1H, t, J = 2 Hz), 7.98-7.90 (2H, m), 7.60-7.45 (2H, m), 7.45-7.34 (1H, m), 7.23 (1H, d, J = 8 Hz), 7.12 (1H, t, J = 54 Hz) 4.09 (3H, s). |
| 1.6* | $^1$H-NMR (CDCl$_3$) δ: 11.99 (1H, s), 8.17-7.83 (7H, m), 7.68 (2H, d, J = 8 Hz), 7.42 (2H, t, J = 7 Hz), 7.32 (1H, t, J = 7 Hz), 7.15 (1H, dd, J = 7.1 Hz), 4.3 (3H, s). |
| 2.1 | $^1$H-NMR (CDCl$_3$) δ: 11.74 (1H, d, J = 6 Hz), 7.82 (1H, s), 7.76-7.72 (2H, m), 7.39-7.33 (2H, m), 7.25-7.21 (1H, m), 7.12 (1H, s), 6.82 (1H, d, J = 1 Hz), 4.64-4.54 (1H, m), 4.32 (3H, s), 4.20-4.05 (2H, m), 3.47 (1H, dd, J = 16.5 Hz), 3.08 (1H, dd, J = 16.8 Hz), 2.80 (3H, s), 2.50-2.41 (1H, m), 2.37 (3H, d, J = 1 Hz), 2.23-2.12 (1H, m). |

TABLE 5

| Example | NMR data (δ: ppm) |
| --- | --- |
| 2.7* | ¹H-NMR (CDCl₃) δ: 10.93 (1H, d, J = 6 Hz), 7.76 (1H, S), 7.72-7.58 (1H, m), 7.58-7.38 (2H, m), 7.12 (1H, s), 6.95-6.82 (1H, m), 6.68 (1H, t, J = 54 Hz), 4.63-4.20 (1H,m), 4.30 (3H, s), 4.21-3.95 (2H, m), 3.50-3.23 (1H, m), 3.07-2.84 (1H, m), 2.58 (3H,s), 2.42-2.30 (1H, m), 2.30-2.00 (1H, m). |
| 2.9 | ¹H-NMR (CDCl₃) δ: 11.56 (1H, d, J = 7 Hz), 7.75-7.71 (3H, m), 7.68 (1H, t, J = 8 Hz), 7.42 (1H, d, J = 8 Hz), 7.39-7.33 (2H, m), 7.24-7.20 (1H, m), 7.11 (1H, s), 7.08 (1H, d, J = 8 Hz), 4.65-4.54 (1H, m), 4.29 (3H, s), 4.15-4.05 (2H, m), 3.48-3.40 (1H, m), 2.97 (1H, dd, J = 16, 10 Hz), 2.53 (3H, s), 2.48-2.39 (1H, m), 2.18-2.05 (1H, m). |
| 2.11* | ¹H-NMR (CDCl₃) δ: 12.23 (1H, d, J = 3 Hz), 7.82-7.73 (4H, m), 7.51-7.41 (3H, m),7.29 (1H, d, J = 9 Hz), 7.18 (1H, s), 6.69 (1H, d, J = 9.0 Hz), 4.59-4.58 (1H m), 4.29 (3H, s), 4.29-4.20 (2H, m), 3.91 (3H, s), 3.79 (1H, dd, J = 18.6 Hz), 3.52 (1H, dd, J = 18 Hz, 9 Hz), 2.57-2.51 (1H, m), 2.40-2.35 (1H, m). |
| 2.13 | ¹H-NMR (CDCl₃) δ: 11.16 (m, d, J = 6 Hz), 8.79 (1H, s), 8.44 (1H, s), 7.88 (1H, s), 7.70 (2H, d, J = 8 Hz), 7.50-7.43 (3H, m), 7.21 (1H, s), 4.65-4.54 (1H, m), 4.37-4.21 (2H, m), 4.31 (3H, s), 3.88 (1H, dd, J = 18.5 Hz), 3.30 (1H, dd, J = 18.10 Hz), 2.72-2.60 (1H, m), 2.62 (3H, s), 2.40-2.15 (1H, m). |

TABLE 6

| Example | NMR data (δ: ppm) |
| --- | --- |
| 2.15 | ¹H-NMR (CDCl₃) δ: 11.87 (1H, d, J = 7 Hz), 7.81-7.76 (2H, m), 7.72 (1H, s), 7.42-7.36 (2H, m), 7.29-7.23 (1H, m), 7.14 (1H, s), 7.02-6.98 (1H, m), 4.72-4.62 (1H, m), 4.31 (3H, s), 4.15-4.02 (2H, m), 3.33 (1H, dd, J = 17.5 Hz), 3.17 (1H, dd, J = 17.5 Hz), 2.39-2.28 (2H, m), 2.32 (3H, s). |
| 2.19 | ¹H-NMR (CDCl₃) δ: 10.63 (1H, d, J = 6 Hz), 7.90-7.86 (1H, m), 7.81-7.74 (3H, m),7.43-7.35 (2H, m), 7.25-7.18 (1H, m), 4.58-4.43 (1H, m), 4.39-4.26 (3H, m), 4.20-4.08 (1H, m), 4.00-3.88 (1H, m), 3.41-3.31 (1H, m), 3.00-2.74 (1H, m), 2.51-2.41 (1H, m), 2.17-2.00 (1H, m). |
| 3.1 | ¹H-NMR (CDCl₃) δ: 13.28 (1H, s), 9.04 (1H, d, J = 7 Hz), 8.60-8.53 (2H, m), 8.27-8.23 (2H, m), 7.74-7.69 (2H, m), 7.54-7.44 (3H, m), 7.35-7.25 (1H, m), 4.31 (3H, s), 2.51 (3H, s). |
| 3.3 | ¹H-NMR (DMSO-d₆) δ: 13.14 (1H, s), 9.30 (1H, d, J = 5 Hz), 8.37 (1H, d, J = 7 Hz), 8.17 (2H, dd, J = 8.2 Hz), 8.07 (1H, s), 7.81 (1H, t, J = 8 Hz), 7.67 (1H, d, J = 8 Hz), 7.54-7.45 (3H, m), 7.23 (1H, d, J = 8 Hz), 4.16 (3H, s), 2.51-2.45 (3H, m). |
| 3.4 | ¹H-NMR (DMSO-d₆) δ: 9.24-9.15 (1H, m), 8.68-8.60 (1H, m), 8.22-8.10 (3H, m), 8.00-7.92 (1H, m), 7.67-7.58 (1H, m), 7.58-7.41 (3H, m), 7.33-7.23 (1H, m), 4.21 (3H, s). |

TABLE 7

| Example | NMR data (δ: ppm) |
| --- | --- |
| 3.6 | ¹H-NMR (CDCl₃) δ: 12.32 (1H, s), 8.86-8.80 (1H, m), 8.65-8.60 (1H, m), 8.30-8.22 (2H, m), 7.96-7.90 (1H, m), 7.85-7.80 (1H, m), 7.54-7.43 (3H, m), 4.37 (3H, s). |
| 3.9 | ¹H-NMR (CDCl₃) δ: 12.67 (1H, s), 8.82 (1H, s), 8.76 (1H, d, J = 7 Hz), 8.63 (1H, d, J = 5 Hz), 8.48 (1H, s), 8.28-8.23 (2H, m), 7.92 (1H, s), 7.54-7.46 (3H, m), 4.35 (3H, s), 2.66-2.64 (3H, s). |
| 3.12 | ¹H-NMR (CDCl₃) δ: 12.85 (1H, s), 8.99 (1H, d, J = 6 Hz), 8.64 (1H, d, J = 6 Hz), 8.28-8.26 (2H, m), 7.94 (1H, s), 7.72 (1H, s), 7.53-7.50 (3H, m), 6.88 (1H, t, J = 39 Hz), 4.39 (3H, s). |
| 3.13 | ¹H-NMR (CDCl₃) δ: 13.08 (1H, s), 9.08 (1H, d, J = 6 Hz), 8.92-8.91 (1H, m), 8.60 (1H, d, J = 6 Hz), 8.27-8.20 (4H, m), 7.51-7.48 (4H, m), 4.37 (3H, s). |
| 3.14 | ¹H-NMR (CDCl₃) δ: 11.13 (1H, s), 8.82-8.80 (1H, m), 8.57-8.56 (1H, m), 8.42 (1H, s), 8.26-8.24 (2H, m), 7.67 (1H, s), 7.50-7.49 (3H, m), 4.30 (3H, s), 2.66 (3H, s), 2.63 (3H, s). |
| 3.19* | ¹H-NMR (DMSO-d₆) δ: 11.76 (1H, br-s), 8.63 (1H, d, J = 1 Hz), 8.16 (1H, s), 8.14-8.11 (1H, m), 7.89 (1H, d, J = 2 Hz), 7.15 (1H, dd, J = 7.2 Hz), 7.12 (1H, t, J = 54 Hz), 4.08 (3H, s), 4.00-3.92 (2H, m), 3.73-3.60 (2H, m), 2.63-2.53 (2H, m), 1.16 (6H, d, J = 6 Hz). |

TABLE 8

| Example | NMR data (δ: ppm) |
|---|---|
| 3.22 | $^1$H-NMR (CDCl$_3$) δ: 11.72 (1H, s), 8.78 (1H, d, J = 8 Hz), 8.63 (1H, s), 8.59 (1H, d, J = 8 Hz), 8.27-8.24 (2H, m), 7.70 (1H, s), 7.51-7.49 (3H, m), 4.31 (3H, s), 2.78 (3H, s), 2.42 (3H, s). |
| 3.25 | $^1$H-NMR (CDCl$_3$) δ: 13.39 (1H, s), 8.75-8.64 (3H, m), 8.28-8.26 (2H, m), 7.96 (1H, s), 7.52-7.47 (4H, m), 4.36 (3H, s), 2.79 (3H, s). |
| 3.29* | $^1$H-NMR (CDCl$_3$) δ: 12.82 (1H, br), 9.20 (1H, d, J = 2 Hz), 9.07 (1H, d, J = 8 Hz), 8.90 (1H, s), 8.62 (1H, d, J = 5 Hz), 8.38-8.28 (2H, m), 8.23 (1H, s), 7.54-7.46 (3H, m), 4.34 (3H, s). |
| 3.31 | $^1$H-NMR (CDCl$_3$) δ: 13.25 (1H, s), 9.05-9.03 (1H, m), 8.76 (1H, s), 8.57 (1H, m), 8.26-8.25 (2H, m), 7.68 (1H, d, J = 4 Hz), 7.50-7.48 (3H, m), 4.31 (3H, s), 4.08 (3H, s), 2.31 (3H, s). |
| 3.32 | $^1$H-NMR (CDCl$_3$) δ: 12.56 (1H, brs), 9.03, (1H, d, J = 7.3 Hz), 8.57-8.51 (3H, m), 8.24 (2H, dd, J = 7.8 Hz, 1.8 Hz), 7.77 (1H, s), 7.51-7.44 (3H, m), 4.32 (3H, s), 2.76 (3H, s). |
| 3.33 | $^1$H-NMR (CDCl$_3$) δ: 13.17 (1H, s), 9.19 (1H, s), 9.08-9.05 (1H, m), 8.75-8.74 (1H, m), 8.62-8.60 (1H, m), 8.27-8.26 (2H, m), 7.82 (1H, d, J = 8 Hz), 7.51-7.49 (3H, m), 4.34 (3H, s), 2.53 (3H, s). |
| 3.36 | $^1$H-NMR (CDCl$_3$) δ: 12.53 (1H, s), 8.74 (1H, d, J = 7 Hz), 8.63 (1H, d, J = 2 Hz), 8.62 (1H, s), 8.28-8.23 (2H, m), 8.09 (1H, d, J = 5 Hz), 7.53-7.44 (3H, m), 4.33 (3H, s), 2.75 (3H, s). |

TABLE 9

| Example | NMR data (δ: ppm) |
|---|---|
| 4.1* | $^1$H-NMR (DMSO-d$_6$) δ: 11.70 (1H, s), 8.62 (1H, d, J = 7 Hz), 8.15 (1H, s), 8.14-8.10 (1H, m), 7.86 (1H, d, J = 2 Hz), 7.12 (1H, t, J = 54 Hz), 7.10 (1H, dd, J = 7 Hz, J = 2 Hz), 4.07 (3H, s), 4.04-3.94 (1H, m), 3.57-3.38 (2H, m), 2.16-1.81 (3H, m), 1.70-1.61 (1H, m), 1.26 (3H, d, J = 6 Hz). |
| 4.3* | $^1$H-NMR (CDCl$_3$) δ: 11.86 (1H, s), 8.28 (1H, d, J = 7 Hz), 8.04 (1H, t, J = 8 Hz), 7.80-7.88 (3H, m), 7.68 (1H, dd, J = 8.1 Hz), 7.00 (1H, dd, J = 7, 2 Hz), 4.30 (3H, s), 4.10-4.20 (1H, m), 3.64-3.72 (1H, m), 3.50-3.60 (1H, m), 1.90-2.21 (3H, m), 1.68-1.77 (1H, m), 1.34 (3H, d, J = 6 Hz). |
| 4.6 | $^1$H-NMR (DMSO-d$_6$) δ: 11.16 (1H, s), 8.84 (1H, s), 8.60 (1H, d, J = 8 Hz), 8.37 (1H, s), 8.23 (1H, s), 7.83 (1H, d, J = 4 Hz), 7.03 (1H, dd, J = 8.4 Hz), 4.00 (3H, s), 4.00-3.97 (1H, m), 3.54-3.48 (1H, m), 3.42-3.36 (1H, m), 2.28 (3H, s), 2.11-1.99 (2H, m), 1.92-1.87 (1H, m), 1.67-1.63 (1H, m), 1.26 (3H, d, J = 8 Hz). |
| 4.10 | $^1$H-NMR (CDCl$_3$) δ: 12.77 (1H, s), 8.36 (1H, d, J = 2 Hz), 8.30 (1H, d, J = 7 Hz), 7.94 (1H, s), 7.84 (1H, s), 7.46 (1H, dd, J = 7.2 Hz), 4.37 (3H, s), 4.25-4.14 (1H, m), 3.80-3.70 (1H, m), 3.64-3.52 (1H, m), 2.23-1.86 (3H, m), 1.81-1.73 (1H, m), 1.31 (3H, d, J =6 Hz).. |

TABLE 10

| Example | NMR data (δ: ppm) |
|---|---|
| 4.11 | $^1$H-NMR (DMSO-d$_6$) δ: 8.99 (1H, s), 8.05-7.99 (2H, m), 7.82-7.74 (1H, m), 7.66 (1H ,d, J = 8 Hz), 7.20 (1H, d, J = 8 Hz), 4.74-4.64 (1H, m), 4.12 (3H, s), 3.76-3.54 (4H, m), 2.44 (3H, s), 2.22-1.95 (2H, m). |
| 4.13* | $^1$H-NMR (CDCl$_3$) δ: 12.35 1H, s), 8.28 (1H, d, J = 7 Hz), 8.19 (H, d, J = 2 Hz), 7.92 (1H, s), 7.83 (1H, d, J = 1 Hz), 7.04 (1H, dd, J = 7.2 Hz), 5.28-5.50 (1H, m), 4.37 (3H, s), 3.67-4.03 (4H, m), 2.00-2.48 (2H, m). |
| 4.23* | $^1$H-NMR (CDCl$_3$) δ: 12.76 (1H, s), 8.27 (1H, d, J = 6 Hz), 8.13 (1H, s), 7.83 (1H, s), 7.27-7.20 (1H, m), 6.88 (1H, t, J = 54 Hz), 5.48-5.30 (1H, m), 4.36 (3H, s), 4.01-3.68 (4H, m), 2.64 (3H, s), 2.40-2.11 (2H, m). |
| 4.24* | $^1$H-NMR (CDCl$_3$) δ: 13.96 (1H, br s), 8.37 (1H, d, J = 5 Hz), 8.18 (1H, d, J = 7 Hz), 7.82 (1H, s), 7.32 (1H, s), 6.98 (1H, s), 5.50-5.25 (1H, m), 4.31 (3H, s), 4.00-3.65 (4H, m), 2.52 (3H, d, J = 2 Hz), 2.41 (3H, s), 2.48-2.00 (2H, m). |
| 4.25* | $^1$H-NMR (DMSO-d$_6$) δ: 11.70 (1H, br-s), 8.60 (1H, d, J = 7 Hz), 8.14 (1H, s), 8.12-8.09 (1H, m), 7.83 (1H, d, J = 2 Hz), 7.11 (1H, t, J = 54 Hz), 7.10 (1H, dd, J = 7.2Hz), 4.06 (3H, s), 3.46-3.39 (4H, m), 1.98-1.88 (4H, m). |

TABLE 11

| Example | NMR data (δ: ppm) |
|---|---|
| 4.27* | $^1$H-NMR(CDCl$_3$) δ: 12.03 (1H, s), 8.28 (1H, d, J = 9 Hz), 8.03 (1H, dd, J = 10 Hz), 7.95 (1H, br), 7.87-7.84 (2H, m), 7.68 (1H, d, J = 6 Hz), 7.32-7.29 (1H, m), 4.28 (3H, s), 3.71-3.49 (4H, m), 2.13-1.96 (4H, m). |
| 4.29 | $^1$H-NMR (DMSO-d$_6$) δ: 11.17 (1H, s), 8.84 (1H, s), 8.59 (1H, d, J = 8 Hz), 8.37 (1H, s), 8.23 (1H, s), 7.83 (1H, d, J = 4 Hz), 7.04 (1H, dd, J = 8.4 Hz), 4.00 (3H, s), 3.45-3.41 (4H, m), 2.28 (3H, s), 1.96-1.93 (4H, m). |
| 4.34 | $^1$H-NMR (CDCl$_3$) δ: 12.57 (1H, s), 8.30-8.25 (2H, m), 7.93 (1H, s), 7.84-7.82 (1H, m), 7.29-7.24 (1H, m), 4.37 (3H, s), 3.64-3.57 (4H, m), 2.07-2.01 (4H, m). |
| 5.2 | $^1$H-NMR (DMSO-d$_6$) δ: 9.68 (1H, d, J = 8 Hz), 8.13-7.92 (4H, m), 7.32-7.23 (2H, m), 7.12 (1H, t, J = 39 Hz), 4.62-4.52 (1H, m), 4.27-4.24 (2H, m), 3.96 (3H, s), 3.47-3.20 (1H, m), 3.00-2.86 (1H, m), 2.33-2.14 (2H, m). |
| 5.9* | $^1$H-NMR (CDCl$_3$) δ: 10.74 (1H, d, J = 7 Hz), 8.12-8.05 (2H, m), 7.90 (1H, s), 7.79 (1H, d, J = 1), 7.48-7.38 (3H, m), 4.68-4.54 (1H, m), 4.50-4.42 (1H, m), 4.34 (3H, s), 4.36-4.24 (1H, m), 3.58-3.48 (1H, m), 3.01 (1H, dd, J = 16.10 Hz), 2.60-2.49 (1H, m), 2.32-2.16 (1H, m). |

TABLE 12

| Example | NMR data (δ: ppm) |
|---|---|
| 5.10* | $^1$H-NMR (DMSO-d$_6$) δ: 9.43 (1H, d, J = 7 Hz), 8.77 (1H, s), 8.06 (1H, s), 8.00-7.94 (2H, m), 7.48-7.35 (3H, m), 4.67-4.55 (1H, m), 4.3-4.20 (2H, m), 3.92 (3H, s), 3.00-2.88 (1H, m), 2.18-2.42 (2H, m). |
| 5.12 | $^1$H-NMR (CDCl$_3$) δ: 11.34 (1H, s), 8.12-8.07 (2H, m), 7.74 (1H, s), 7.45-7.36 (3H, m), 4.73-4.65 (1H, m), 4.57-4.50 (1H, m), 4.42-4.33 (1H, m), 4.34 (3H, s), 3.42 (1H, dd, J = 17.5 Hz), 3.25 (1H, dd, J = 17.7 Hz), 3.07 (2H, q, J = 7 Hz), 2.56-2.35 (2H, m), 1.40 (3H, t, J = 1 Hz). |
| 5.16* | $^1$H-NMR (CDCl$_3$) δ: 10.83 (1H, d, J = 6 Hz), 7.86 (1H, s), 7.62-7.58 (1H, m), 6.72 (1H, dt, J = 55.2 Hz), 4.64-4.49 (1H, m), 4.32 (3H, s), 4.17-3.97 (2H, m), 3.70-3.48 (4H, m), 3.42-3.21 (2H, s), 3.39 (3H, s) 3.00-2.85 (1H, m), 2.44-2.17 (2H, m), 2.13-1.83 (4H, m). |

Example No. with symbol *: measured at 300 MHz NMR; and Example No. without symbol *: measured at 400 MHz NMR.

TABLE 13

| Example | MS-ESI (m/z) [M + H]$^+$ | Retention time(min) | Example | MS-ESI (m/z) [M+H]$^+$ | Retention time (min) |
|---|---|---|---|---|---|
| 1.1 | 409 | 5.02 | 2.17 | 402 | 2.55 |
| 1.2 | 415 | 5.28 | 2.18$^\#$ | 456 | 3.82 |
| 1.3$^{\#\#}$ | 451 | 0.96 | 2.19$^{\#\#}$ | 491 | 1.04 |
| 1.4$^{\#\#}$ | 465 | 0.99 | 2.20$^{\#\#}$ | 473 | 0.83 |
| 1.5$^{\#\#}$ | 469 | 0.97 | 2.21 | 413 | 4.22 |
| 1.6 | 463 | 4.67 | 2.22$^{\#\#}$ | 413 | 0.73 |
| 1.7 | 485 | 5.42 | 2.23$^\#$ | 432 | 3.77 |
| 2.1$^{\#\#}$ | 419 | 0.84 | 2.24$^\#$ | 432 | 3.55 |
| 2.2$^\#$ | 433 | 4.37 | 2.25$^\#$ | 405 | 3.67 |
| 2.3$^\#$ | 473 | 4.17 | 2.26$^\#$ | 405 | 3.90 |
| 2.4$^{\#\#}$ | 455 | 0.84 | 2.27$^{\#\#}$ | 461 | 0.92 |
| 2.5 | 489 | 4.38 | 2.28$^{\#\#}$ | 473 | 0.83 |
| 2.6 | 469 | 4.25 | 2.29 | 491 | 4.55 |
| 2.7$^{\#\#}$ | 487 | 0.87 | 3.1$^\#$ | 428 | 1.22 |
| 2.8$^{\#\#}$ | 491 | 0.87 | 3.2$^\#$ | 429 | 1.24 |
| 2.9$^{\#\#}$ | 413 | 0.66 | 3.3$^\#$ | 428 | 1.21 |
| 2.10$^{\#\#}$ | 420 | 0.77 | 3.4$^\#$ | 432 | 1.27 |
| 2.11$^\#$ | 429 | 3.97 | 3.5$^{\#\#}$ | 428 | 1.31 |
| 2.12$^\#$ | 419 | 3.83 | 3.6$^\#$ | 488 | 1.25 |
| 2.13$^\#$ | 414 | 3.43 | 3.7$^\#$ | 444 | 1.25 |
| 2.14$^{\#\#}$ | 448 | 0.88 | 3.8 | 432 | 6.37 |
| 2.15$^{\#\#}$ | 419 | 0.87 | 3.9$^{\#\#}$ | 429 | 1.16 |
| 2.16$^\#$ | 414 | 3.65 | 3.10 | 482 | 5.92 |

Example No. without symbol: HPLC (AcOH) system;
Example No. with symbol $^\#$: HPLC (TFA) system; and
Example No. with symbol $^{\#\#}$: UPLC system.
In MS-ESI (m/z), $^*$: [M − H]$^-$; and $^{**}$: [M + Na]$^+$.

TABLE 14

| Example | MS-ESI (m/z) [M + H]$^+$ | Retention time (min) | Example | MS-ESI (m/z) [M+H]$^+$ | Retention time (min) |
|---|---|---|---|---|---|
| 3.11$^{\#\#}$ | 442 | 1.22 | 3.35$^{\#\#}$ | 443 | 1.23 |
| 3.12$^{\#\#}$ | 470 | 1.24 | 3.36$^{\#\#}$ | 447 | 1.14 |
| 3.13$^{\#\#}$ | 439 | 1.17 | 3.37$^{\#\#}$ | 457 | 1.12 |
| 3.14$^{\#\#}$ | 443 | 1.14 | 3.38$^\#$ | 447 | 6.30 |
| 3.15$^{\#\#}$ | 452 | 1.25 | 3.39 | 429 | 6.05 |
| 3.16$^{\#\#}$ | 482 | 1.14 | 3.40$^{\#\#}$ | 475 | 1.26 |
| 3.17$^{\#\#}$ | 470 | 1.25 | 3.41$^{\#\#}$ | 463 | 1.15 |
| 3.18$^{\#\#}$ | 430 | 1.33 | 3.42$^{\#\#}$ | 445 | 1.11 |
| 3.19 | 489 | 6.00 | 3.43 | 429 | 6.28 |
| 3.20$^{\#\#}$ | 486 | 1.21 | 3.44$^{\#\#}$ | 443 | 6.17 |
| 3.21$^{\#\#}$ | 550 | 1.22 | 3.45$^{\#\#}$ | 429 | 1.18 |
| 3.22$^{\#\#}$ | 443 | 1.13 | 3.46$^{\#\#}$ | 429 | 1.20 |
| 3.23$^{\#\#}$ | 439 | 1.21 | 3.47$^{\#\#}$ | 415 | 1.17 |
| 3.24 | 429 | 5.55 | 3.48$^{\#\#}$ | 417 | 1.07 |
| 3.25$^{\#\#}$ | 429 | 1.16 | 3.49 | 444 | 5.02 |
| 3.26$^{\#\#}$ | 445 | 1.16 | 3.50$^{\#\#}$ | 457 | 1.14 |
| 3.27$^{\#\#}$ | 463 | 1.13 | 3.51$^{\#\#}$ | 428 | 1.33 |
| 3.28 | 445 | 6.23 | 3.52$^{\#\#}$ | 444 | 1.28 |
| 3.29$^\#$ | 449 | 5.83 | 3.53$^{\#\#}$ | 442 | 1.20 |
| 3.30$^\#$ | 443 | 5.72 | 3.54 | 460 | 6.48 |
| 3.31$^{\#\#}$ | 459 | 6.38 | 4.1 | 459 | 6.03 |
| 3.32 | 429 | 5.77 | 4.2$^\#$ | 493 | 6.03 |
| 3.33$^{\#\#}$ | 429 | 1.18 | 4.3 | 471 | 5.65 |
| 3.34$^{\#\#}$ | 445 | 1.23 | 4.4 | 417 | 6.15 |

Example No. without symbol: HPLC (AcOH) system;
Example No. with symbol $^\#$: HPLC (TFA) system; and
Example No. with symbol $^{\#\#}$: UPLC system.
In MS-ESI (m/z), $^*$: [M − H]$^-$; and $^{**}$: [M + Na]$^+$.

TABLE 15

| Example | MS-ESI (m/z) [M + H]+ | Retention time (min) | Example | MS-ESI (m/z) [M + H]+ | Retention time (min) |
|---|---|---|---|---|---|
| 4.5 | 433 | 6.12 | 4.29 | 404 | 5.18 |
| 4.6 | 418 | 5.43 | 4.30 | 403 | 5.95 |
| 4.7 | 417 | 5.93 | 4.31 | 403 | 5.72 |
| 4.8 | 431 | 6.17 | 4.32 | 417 | 5.95 |
| 4.9 | 473 | 6.23 | 4.33 | 459 | 6.07 |
| 4.10 | 477 | 6.13 | 4.34 | 463 | 5.95 |
| 4.11## | 490 | 1.18 | 4.35 | 436 | 1.01 |
| 4.12## | 463 | 1.10 | 4.36# | 523 | 5.98 |
| 4.13 | 481 | 5.72 | 5.1# | 470 | 5.57 |
| 4.14 | 477 | 5.83 | 5.2# | 474 | 1.09 |
| 4.15## | 463 | 1.12 | 5.3 | 508 | 5.83 |
| 4.16 | 475 | 5.23 | 5.4# | 434 | 5.85 |
| 4.17 | 421 | 5.73 | 5.5# | 482 | 5.77 |
| 4.18 | 437 | 5.65 | 5.6# | 484 | 5.82 |
| 4.19 | 422 | 4.93 | 5.7# | 498 | 1.22 |
| 4.20 | 435 | 5.70 | 5.8# | 496 | 5.85 |
| 4.21 | 421 | 5.47 | 5.9 | 474 | 5.52 |
| 4.22 | 481 | 5.72 | 5.10 | 431 | 4.98 |
| 4.23 | 477 | 5.85 | 5.11# | 492 | 5.90 |
| 4.24 | 453 | 5.85 | 5.12 | 435 | 5.12 |
| 4.25 | 445 | 5.83 | 5.13# | 498 | 5.40 |
| 4.26## | 479 | 1.16 | 5.14 | 429 | 4.75 |
| 4.27# | 457 | 5.12 | 5.15 | 421 | 5.23 |
| 4.28 | 419 | 5.90 | 5.16 | 493 | 5.12 |

Example No. without symbol: HPLC (AcOH) system;
Example No. with symbol #: HPLC (TFA) system; and
Example No. with symbol ##: UPLC system.
In MS-ESI (m/z), *: [M − H]−; and **: [M + Na]+.

TABLE 16

| Example | MS-ESI (m/z) [M + H]+ | Retention time (min) | Example | MS-ESI (m/z) [M + H]+ | Retention time (min) |
|---|---|---|---|---|---|
| 5.17 | 456 | 5.35 | 5.33 | 474 | 5.57 |
| 5.18 | 420 | 5.50 | 5.34 | 486 | 5.08 |
| 5.19 | 414 | 5.20 | 5.35# | 514 | 6.00 |
| 5.20 | 414 | 5.45 | 5.36# | 488 | 5.73 |
| 5.21## | 468 | 1.07 | 5.37 | 508 | 5.85 |
| 5.22 | 414 | 5.02 | 5.38# | 460 | 6.12 |
| 5.23 | 418 | 5.33 | 5.39 | 434 | 5.25 |
| 5.24 | 418 | 5.27 | 5.40 | 425 | 5.00 |
| 5.25 | 430 | 5.28 | 5.41# | 449 | 5.22 |
| 5.26 | 414 | 5.48 | 5.42# | 514 | 6.03 |
| 5.27 | 425 | 4.77 | 5.43# | 478 | 6.25 |
| 5.28 | 452 | 5.43 | 5.44 | 480 | 5.02 |
| 5.29## | 490 | 1.12 | 5.45 | 427 | 5.48 |
| 5.30 | 462 | 4.80 | 5.46 | 467 | 5.25 |
| 5.31 | 464 | 4.90 | 5.47## | 407 | 0.72 |
| 5.32 | 474 | 5.20 | | | |

Example No. without symbol: HPLC (AcOH) system;
Example No. with symbol #: HPLC (TFA) system; and
Example No. with symbol ##: UPLC system.
In MS-ESI (m/z), *: [M − H]−; and **: [M + Na]+.

Structural Formulae 11
[Formula 126]

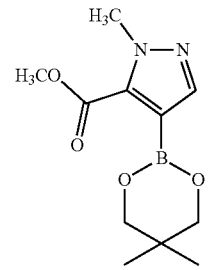

(Example 1.1-1)

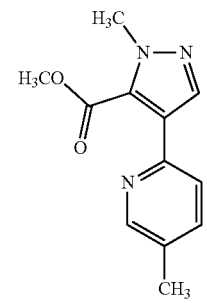

(Example 1.1-2)

(Example 1.1-3)

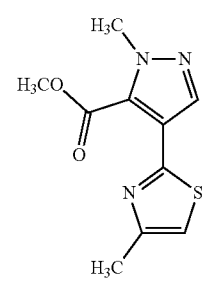

(Example 1.2-1)

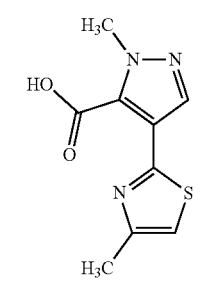

(Example 1.2-2)

-continued (Example 1.3-1)

(Example 1.4-1)

(Example 1.4-2)

(Example 1.5-1)

(Example 1.6-1)

-continued (Example 1.7-1)

(Example 1.7-2)

(Example 2.1-1)

(Example 2.2-1)

(Example 2.2-2)

(Example 2.7-1)

(Example 2.7-2)
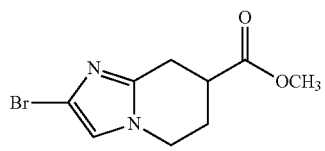
(Example 2.7-3)
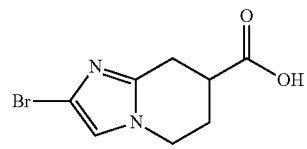
(Example 2.7-4)
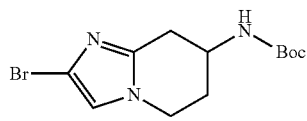
(Example 2.7-5)
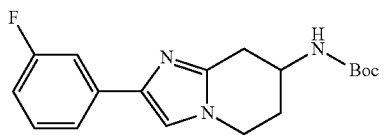
(Example 2.7-6)
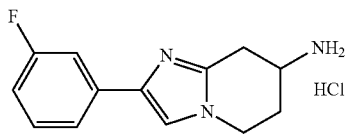
(Example 2.8-1)
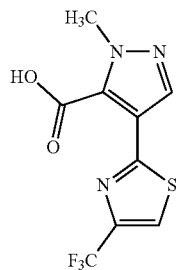
(Example 2.9-1)
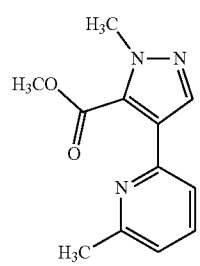
(Example 2.10-1)
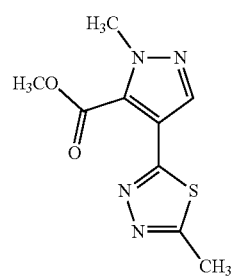
Structural Formulae 12
[Formula 127]
(Example 2.10-2)
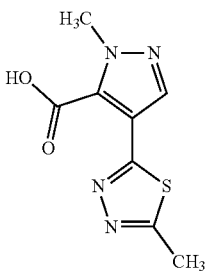
(Example 2.11-1)
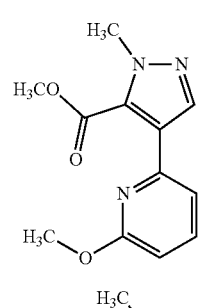
(Example 2.11-2)
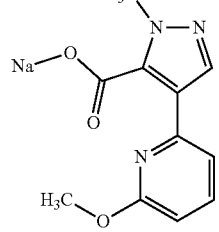
(Example 2.12-1)
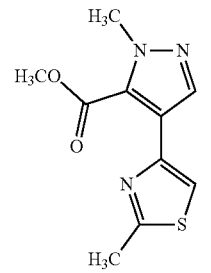
(Example 2.13-1)
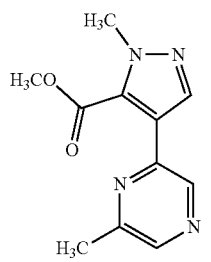
(Example 2.13-2)
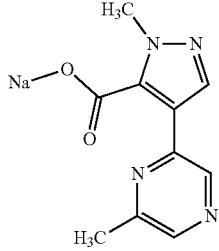

| | |
|---|---|
| (Example 2.14-1) 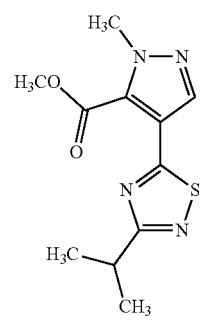 | (Example 2.18-2) 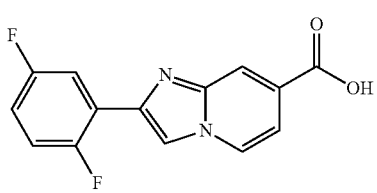 |
| (Example 2.15-1) 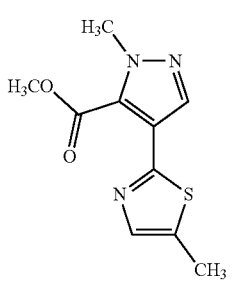 | (Example 2.18-3) 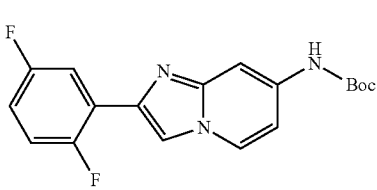 |
| (Example 2.16-1) 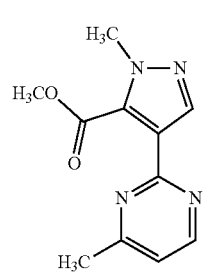 | (Example 2.18-4) 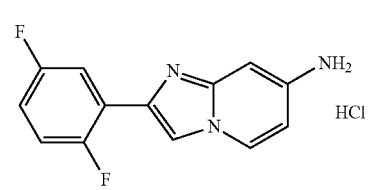 |
| (Example 2.16-2) 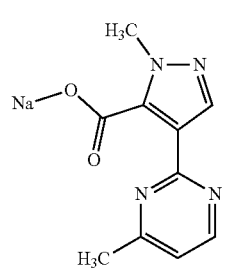 | (Example 2.18-5) 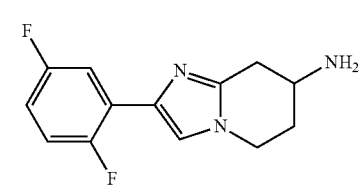 |
| (Example 2.17-1) 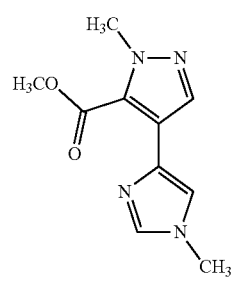 | (Example 2.19-1) 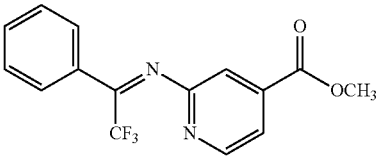 |
| | (Example 2.19-2) 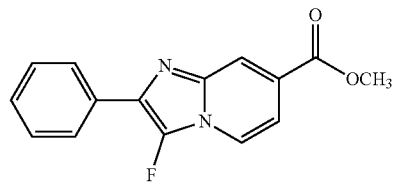 |
| (Example 2.18-1) 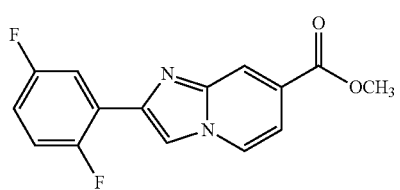 | (Example 2.19-3) 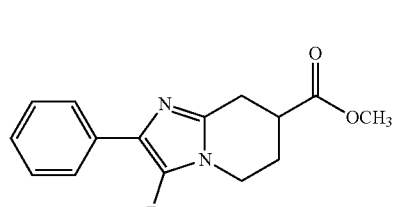 |
| | (Example 2.19-4) 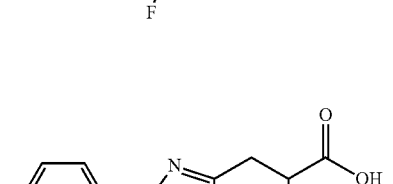 |

333
-continued
(Example 2.19-5)
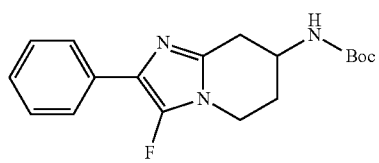
(Example 2.19-6)
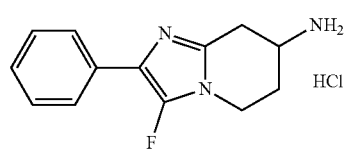
(Example 2.25-1)
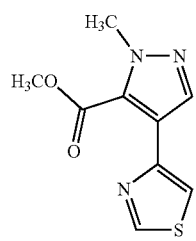
(Example 2.26-1)
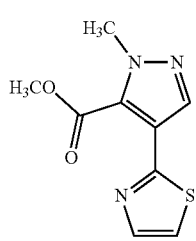
Structural Formulae 13
[Formula 128]
(Example 2.19-7)
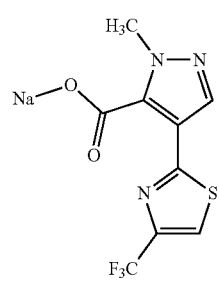
(Example 2.27-1)
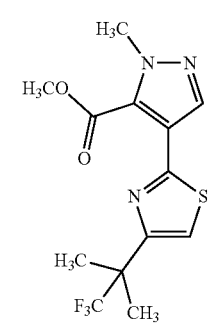
(Example 2.28-1)
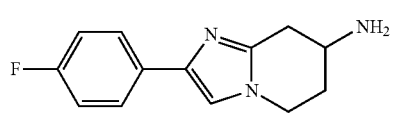
334
-continued
(Example 3.1-1)
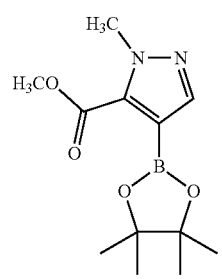
(Example 3.1-2)
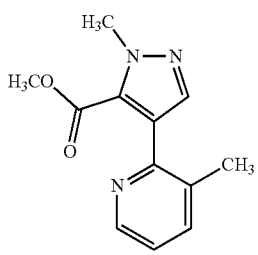
(Example 3.1-3)
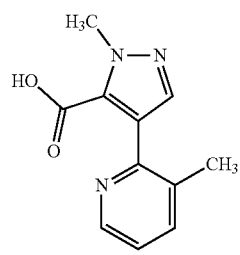
(Example 3.2-1)
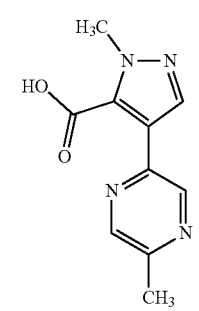
(Example 3.3-1)
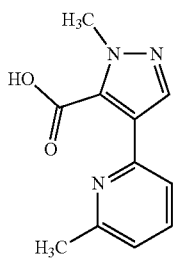
(Example 3.4-1)
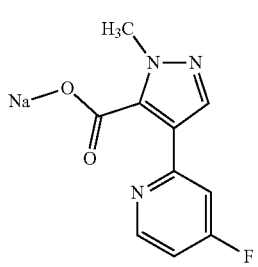

(Example 3.5-1)
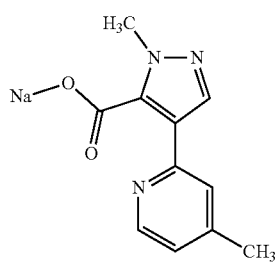
(Example 3.6-1)
(Example 3.7-1)
(Example 3.8-1)
(Example 3.9-1)
(Example 3.9-2)
(Example 3.10-1)
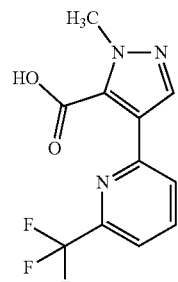
(Example 3.11-1)
(Example 3.12-1)
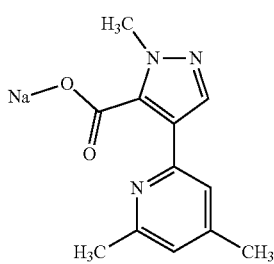
(Example 3.13-1)
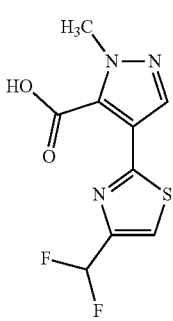
(Example 3.13-2)
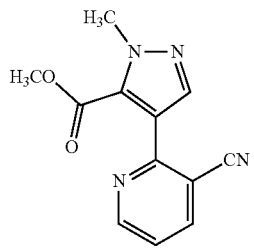
(Example 3.14-1)
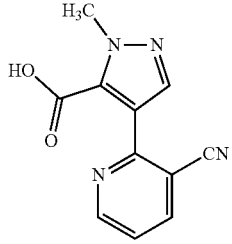

-continued
(Example 3.14-2)
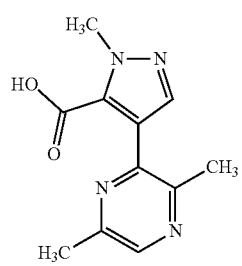
(Example 3.15-1)
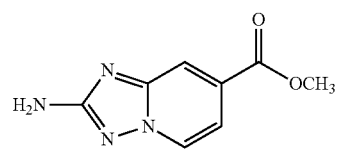
Structural Formulae 14
[Formula 129]
(Example 3.15-2)
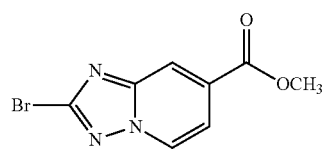
(Example 3.15-3)
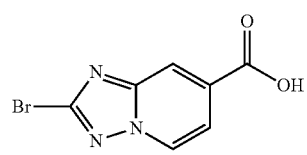
(Example 3.15-4)
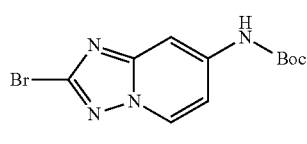
(Example 3.15-5)
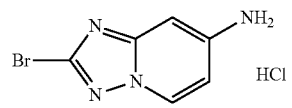
(Example 3.15-6)
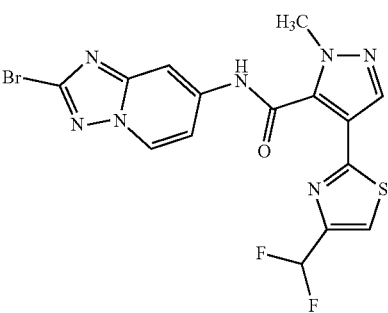
(Example 3.18-1)
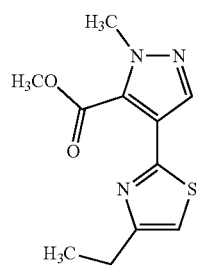
-continued
(Example 3.18-2)
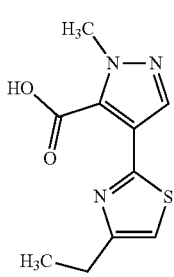
(Example 3.18-3)
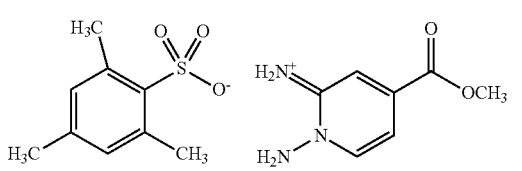
(Example 3.18-4)
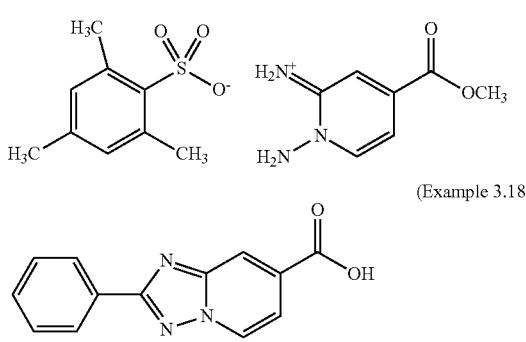
(Example 3.18-5)
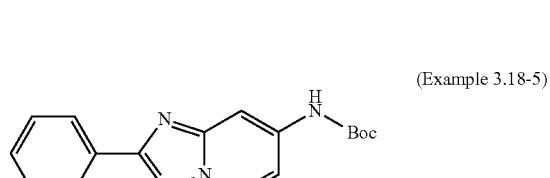
(Example 3.18-6)
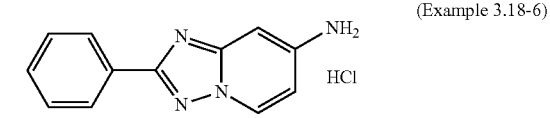
(Example 3.22-1)
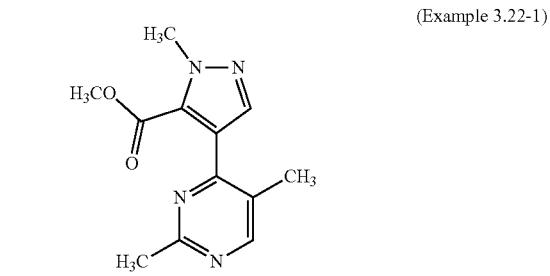
(Example 3.22-2)
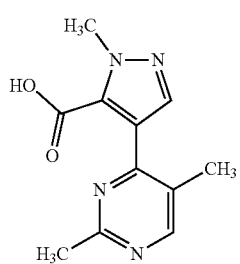

-continued
(Example 3.23-1)
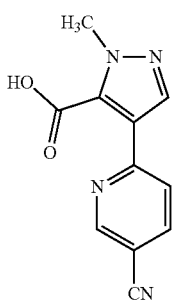
(Example 3.24-1)
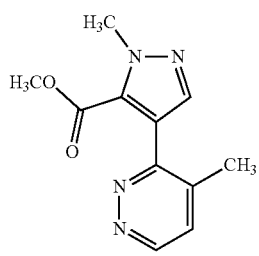
(Example 3.24-2)
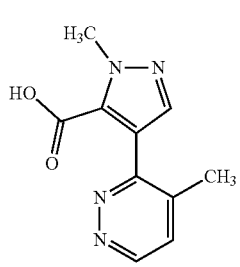
(Example 3.25-1)
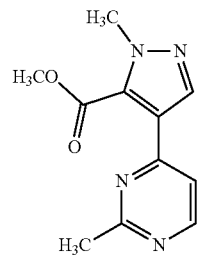
(Example 3.25-2)
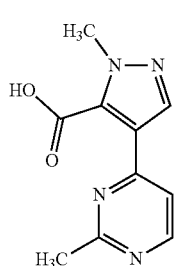
(Example 3.26-1)
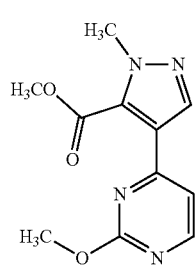
-continued
Structural Formulae 15
[Formula 130]
(Example 3.26-2)
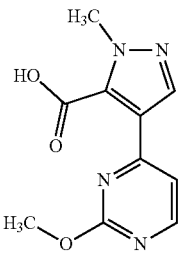
(Example 3.27-1)
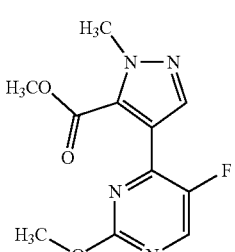
(Example 3.27-2)
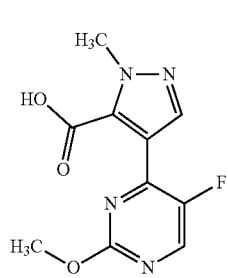
(Example 3.28-1)
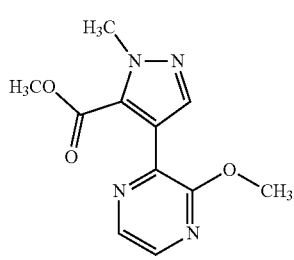
(Example 3.28-2)
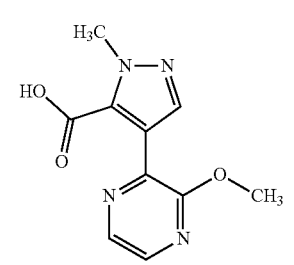
(Example 3.29-1)
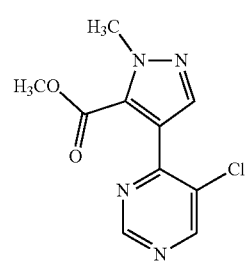

(Example 3.29-2)
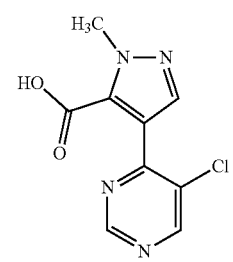
(Example 3.30-1)
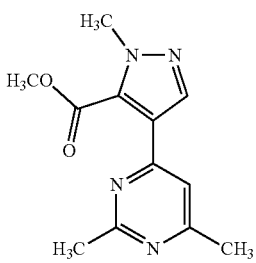
(Example 3.30-2)
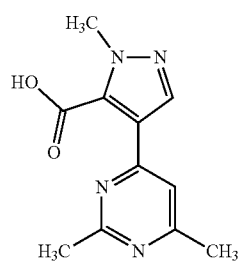
(Example 3.31-1)
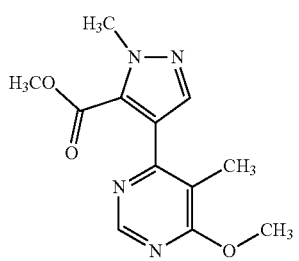
(Example 3.31-2)
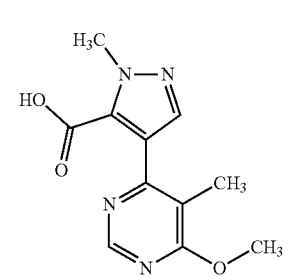
(Example 3.32-1)
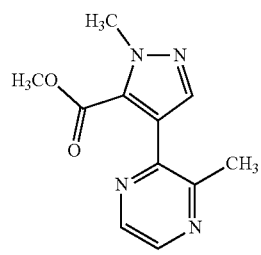
(Example 3.32-2)
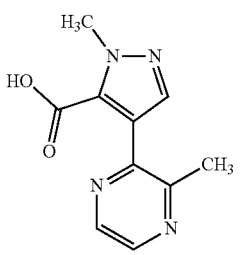
(Example 3.33-1)
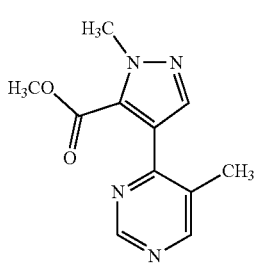
(Example 3.33-2)
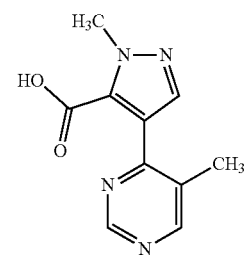
(Example 3.34-1)
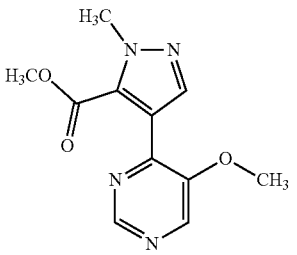
(Example 3.34-2)
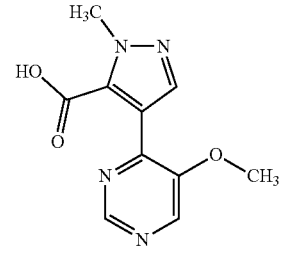
(Example 3.35-1)
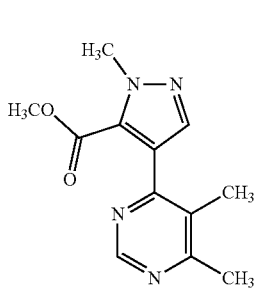

-continued
(Example 3.35-2)
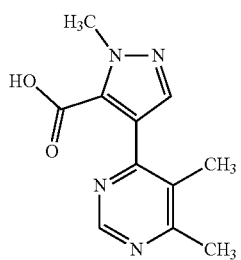
(Example 3.36-1)
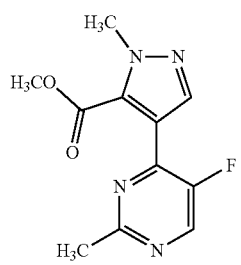
(Example 3.36-2)
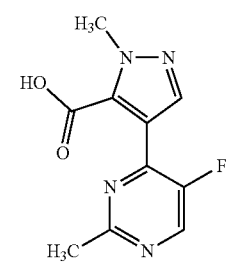
(Example 3.37-1)
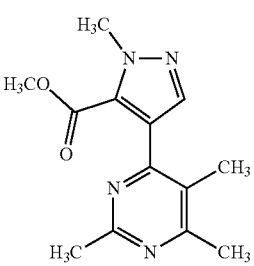
(Example 3.37-2)
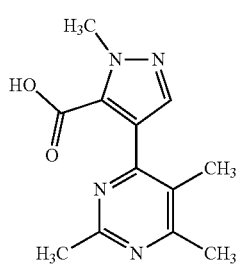
(Example 3.38-1)
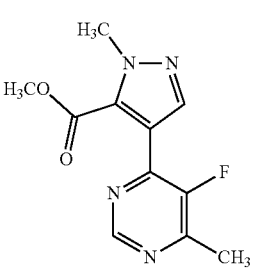
-continued
Structural Formulae 16
[Formula 131]
(Example 3.38-2)
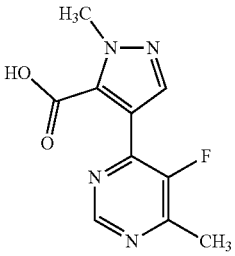
(Example 3.39-1)
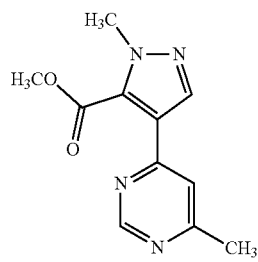
(Example 3.39-2)
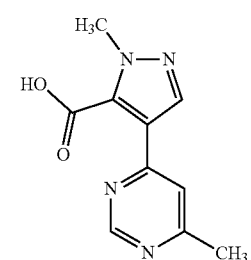
(Example 3.40-1)
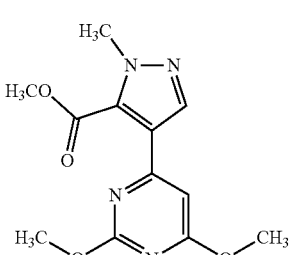
(Example 3.40-2)
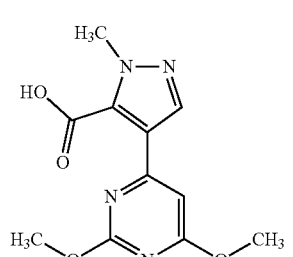
(Example 3.41-1)
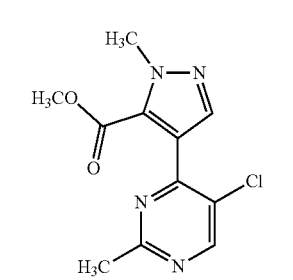

(Example 3.41-2)
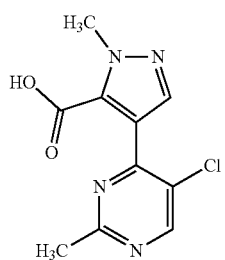
(Example 3.42-1)
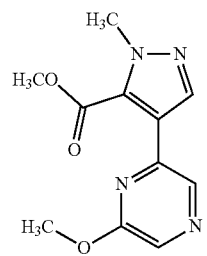
(Example 3.42-2)
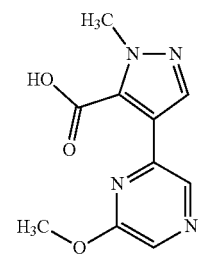
(Example 3.43-1)
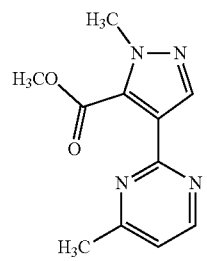
(Example 3.43-2)
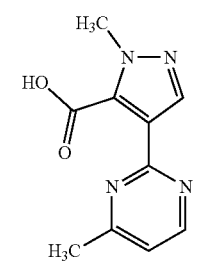
(Example 3.44-1)
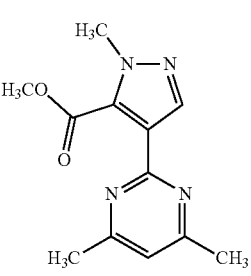
(Example 3.44-2)
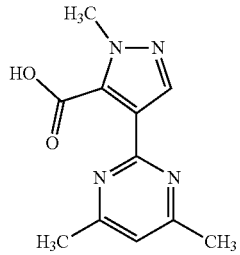
(Example 3.45-1)
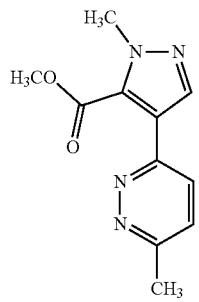
(Example 3.45-2)
(Example 3.46-1)
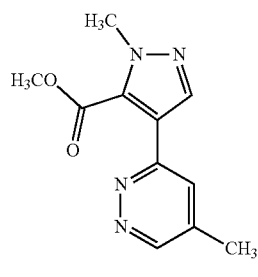
[Example 3.46-2]
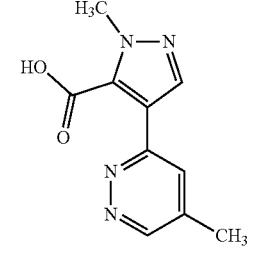
(Example 3.47-1)
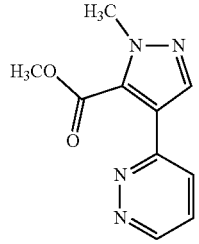

Structural Formulae 17
[Formula 132]

Structural Formulae 18

[Formula 133]

(Example 5.5-1)
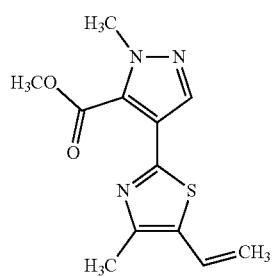
(Example 5.6-1)
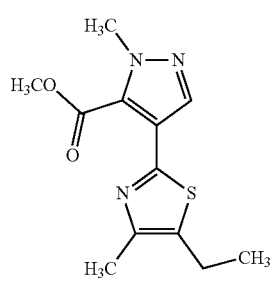
(Example 5.7-1)
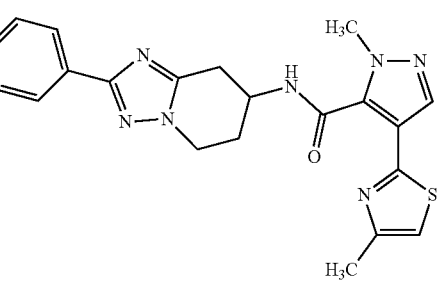
(Example 5.8-1)
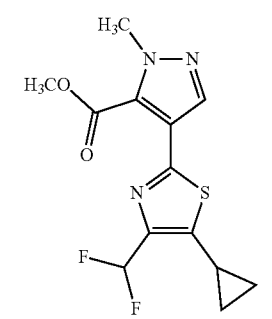
(Example 5.10-1)
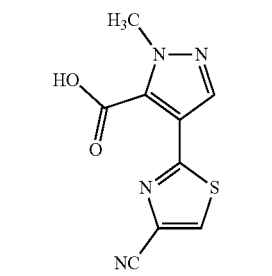
(Example 5.11-1)
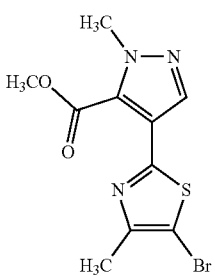
(Example 5.11-2)
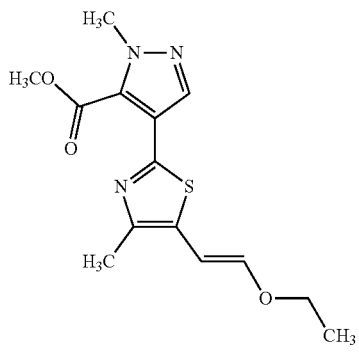
(Example 5.11-3)
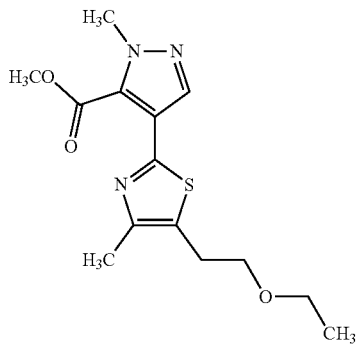
(Example 5.12-1)
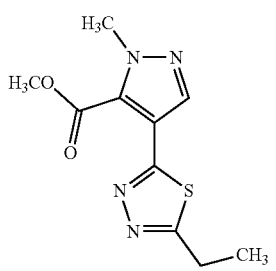
(Example 5.13-1)

Structural Formulae 19
[Formula 134]

(Example 5.43-1)

(Example 5.44-1)

(Example 5.45-1)

(Example 5.45-2)

(Example 5.46-1)

(Example 5.47-1)

(Example 5.47-2)

TABLE 17

| Example | NMR data (δ: ppm) |
|---|---|
| 1.1-1* | $^1$H-NMR (CDCl$_3$) δ: 7.58 (1H, s), 4.11 (3H, s), 3.88 (3H, s), 3.74 (4H, s), 1.05 (6H, s). |
| 2.1-1* | $^1$H-NMR (DMSO-d$_6$) δ: 8.75 (3H, br), 8.11 (1H, s), 7.90-7.83 (2H, m), 7.57-7.37 (3H, m), 4.38-4.09 (2H, m), 3.97-3.73 (1H, m), 3.68-3.52 (1H, m), 3.33-3.17 (1H, m), 2.48-2.13 (2H, m). |
| 2.7-1* | $^1$H-NMR (CDCl$_3$) δ: 4.10-3.98 (1H, m), 3.83-3.74 (1H, m), 3.78 (3H, s), 3.22-2.87 (3H, m), 2.43-2.35 (1H, m), 2.23-2.10 (1H, m). |
| 2.7-2* | $^1$H-NMR (CDCl$_3$) δ: 6.78 (1H, s), 4.14-4.04 (1H, m), 3.97-3.87 (1H, m), 3.76 (3H, s), 3.22-3.14 (1H, m), 3.07-3.03 (1H, m), 2.98-2.90 (1H, m), 2.38-2.32 (1H, m), 2.21-2.12 (1H, m). |
| 2.7-3* | $^1$H-NMR (DMSO-d$_6$) δ: 7.15 (1H, s), 4.04-3.84 (2H, m), 2.98-2.71 (3H, m), 2.30-2.18 (1H, m), 2.04-1.88 (1H, m). |

TABLE 17-continued

| Example | NMR data (δ: ppm) |
|---|---|
| 2.7-4* | $^1$H-NMR (CDCl$_3$) δ: 6.79 (1H, s), 4.58 (1H, brs), 4.18-3.90 (3H, m), 3.20 (1H, dd, J = 17,5 Hz), 2.70 (1H, dd, J = 17,8 Hz), 2.32-2.20 (1H, m), 2.10-1.96 (1H, m), 1.46 (9H, s). |

Example No. with symbol *: measured at 300 MHz NMR; and
Example No. without symbol *: measured at 400 MHz NMR.

TABLE 18

| Example | NMR data (δ: ppm) |
|---|---|
| 3.1-1 | $^1$H-NMR (CDCl$_3$) δ: 7.62 (1H, s), 4.15 (3H, s), 3.89 (3H, s), 1.35 (12H, s). |
| 4.24-1* | $^1$H-NMR (DMSO-d$_6$) δ: 9.00 (1H, d, J = 6 Hz), 6.64 (1H, d, J = 8 Hz). |
| 5.1-3* | $^1$H-NMR (DMSO-d$_6$) δ: 8.70 (3H, m), 8.04-7.95 (1H, m), 7.53-7.39 (3H, m), 4.40-4.15 (2H, m), 3.90-3.75 (1H, m), 3.39 (1H, dd, J = 17,5 Hz), 3.08 (1H, dd, J = 17,9 Hz), 2.50-2.39 (1H, m), 2.48-2.20 (1H, m). |
| 5.16-6* | $^1$H-NMR (DMSO-d$_6$) δ: 8.64 (3H, brs), 4.45-4.01 (2H, m), 3.85-3.65 (1H, m), 3.25 (1H, dd, J = 17,5 Hz), 3.01 (1H, dd, J = 17,9 Hz), 2.43-2.11 (2H, m). |
| 1.1-2 | $^1$H-NMR (CDCl$_3$) δ: 8.45 (1H, d, J = 2 Hz), 7.73 (1H, s), 7.49 (1H, dd, J = 8,2 Hz), 7.38 (1H, d, J = 8 Hz), 4.17 (3H, s), 3.81 (3H, s), 2.37 (3H, s). |
| 1.1-3 | $^1$H-NMR (CDCl$_3$) δ: 8.28 (1H, d, J = 2 Hz), 7.99 (1H, s), 7.79 (1H, dd, J = 8,2 Hz), 7.75 (1H, d, J = 8 Hz), 4.34 (3H, s), 2.44 (3H, s) |
| 1.2-1 | $^1$H-NMR (CDCl$_3$) δ: 8.02 (1H, s), 6.93 (1H, d, J = 1 Hz), 4.19 (3H, s), 3.95 (3H, s), 2.49 (3H, d, J = 1 Hz). |
| 1.2-2 | $^1$H-NMR (CDCl$_3$) δ: 7.88 (1H, s), 6.91 (1H, d, J = 1 Hz), 4.33 (3H, s), 2.49 (3H, d, J = 1 Hz). |

Example No. with symbol *: measured at 300 MHz NMR; and
Example No. without symbol *: measured at 400 MHz NMR.

TABLE 19

| Example | NMR data (δ: ppm) |
|---|---|
| 2.9-1 | $^1$H-NMR (CDCl$_3$) δ: 7.72 (1H, s), 7.57 (1H, dd, J = 7,7 Hz), 7.25 (1H, d, J = 7 Hz), 7.07 (1H, d, J = 7 Hz), 4.15 (3H, s), 3.79 (3H, s), 2.57 (3H, s) |
| 3.1-2* | $^1$H-NMR (CDCl$_3$) δ: 8.45 (1H, d, J = 5 Hz), 7.58-7.51 (2H, m), 7.18 (1H, dd, J = 8,5 Hz), 4.22 (3H, s), 3.65 (3H, s), 2.18 (3H, s). |
| 3.1-3* | $^1$H-NMR (CD$_3$OD) δ: 8.46 (1H, d, J = 5 Hz), 8.11 (1H, d, J = 8 Hz), 7.93 (1H, s), 7.56 (1H, dd, J = 8,5 Hz), 4.23 (3H, s), 2.54 (3H, s). |
| 3.3-1 | $^1$H-NMR (DMSO-d$_6$) δ: 8.49-8.40 (1H, m), 8.14-8.05 (2H, m), 7.48-7.41 (1H, m), 4.18 (3H, s), 2.59 (3H, s). |
| 3.9-1* | $^1$H-NMR (CDCl$_3$) δ: 8.56 (1H, s), 8.37 (1H, s), 7.79 (1H, s), 4.21 (3H, s), 3.83 (3H, s), 2.60 (3H, s). |
| 3.9-2 | $^1$H-NMR (DMSO-d$_6$) δ: 9.03 (1H, s), 8.56 (1H, s), 8.24 (1H, s), 4.15 (3H, s), 2.55 (3H, s). |
| 3.22-1 | $^1$H-NMR (CDCl$_3$) δ: 8.49 (1H, s), 7.57 (1H, s), 4.21 (3H, s), 3.70 (3H, s), 2.71 (3H, s), 2.15 (3H, s). |
| 3.22-2 | $^1$H-NMR (DMSO-d$_6$) δ: 8.49 (1H, s), 7.61 (1H, s), 4.07 (3H, s), 2.55 (3H, s), 2.15 (3H, s). |
| 3.25-1* | $^1$H-NMR (CDCl$_3$) δ: 8.62 (1H, d, J = 5 Hz), 7.85 (1H, s), 7.29 (1H, d, J = 5 Hz), 4.15 (3H, s), 3.87 (3H, s), 2.74 (3H, s). |

Example No. with symbol *: measured at 300 MHz NMR; and
Example No. without symbol *: measured at 400 MHz NMR.

TABLE 20

| Example | NMR data (δ: ppm) |
|---|---|
| 3.25-2* | ¹H-NMR (CDCl₃) δ: 8.79 (1H, d, J = 6 Hz), 8.09 (1H, s), 7.56 (1H, d, J = 6 Hz), 4.36 (3H, s), 2.81 (3H, s). |
| 3.31-1* | ¹H-NMR (CDCl₃) δ: 8.63 (1H, s), 7.54 (1H, s), 4.21 (3H, s), 4.04 (3H, s), 3.72 (3H, s), 2.01 (3H, s). |
| 3.31-2 | ¹H-NMR (CDCl₃) δ: 8.63 (1H, s), 7.92 (1H, s), 4.31 (3H, s), 4.11 (3H, s), 2.43 (3H, s). |
| 3.36-1 | ¹H-NMR (CDCl₃) δ: 8.47 (1H, d, J = 2 Hz), 7.83 (1H, d, J = 1 Hz), 4.16 (3H, s), 3.84 (3H, s), 2.73 (3H, d, J = 1 Hz) |
| 3.36-2 | ¹H-NMR (DMSO-d₆) δ: 8.78 (1H, d, J = 2 Hz), 7.89 (1H, d, J = 1 Hz), 4.10 (3H, s), 2.63 (3H, d, J = 1 Hz) |

Example No. with symbol *: measured at 300 MHz NMR; and
Example No. without symbol *: measured at 400 MHz NMR.

TABLE 21

| Example | MS-ESI (m/z) [M + H]⁺ | Retention time (min) | Example | MS-ESI (m/z) [M + H]⁺ | Retention time (min) |
|---|---|---|---|---|---|
| 1.1-1## | 185♦ | 0.67 | 2.13-1## | 233 | 0.75 |
| 1.2-1## | 238 | 0.91 | 2.13-2## | 219$$ | 0.74 |
| 1.3-1 | 274 | 4.57 | 2.14-1## | 267 | 1.14 |
| 1.4-1## | 352 | 1.11 | 2.15-1## | 238 | 0.93 |
| 1.4-2## | 288 | 1.01 | 2.16-1## | 233 | 0.75 |
| 1.5-1## | 292 | 1.05 | 2.16-2## | 241$$ | 0.77 |
| 1.6-1## | 286 | 1.00 | 2.17-1## | 221 | 0.52 |
| 1.7-1## | 308 | 1.10 | 2.18-1## | 289 | 1.08 |
| 1.7-2## | 316** | 1.02 | 2.18-2## | 275 | 0.97 |
| 2.2-1## | 252 | 0.95 | 2.18-3## | 346 | 0.94 |
| 2.2-2## | 260$ | 0.85 | 2.18-4## | 246 | 0.77 |
| 2.7-1## | 337 | 0.93 | 2.18-5## | 250 | 0.48 |
| 2.7-2## | 259 | 0.52 | 2.19-1## | 309 | 1.09 |
| 2.7-4## | 316 | 0.76 | 2.19-2## | 271 | 1.15 |
| 2.7-6## | 232 | 0.49 | 2.19-3## | 275 | 0.74 |
| 2.8-1# | 278 | 4.98 | 2.19-4## | 239 | 0.74 |
| 2.9-1## | 232 | 0.52 | 2.19-5## | 332 | 0.88 |
| 2.10-1## | 239 | 0.80 | 2.19-6## | 232 | 0.62 |
| 2.10-2## | 247* | 0.69 | 2.19-7## | 300$$ | 0.97 |
| 2.11-1 | 248 | 4.68 | 2.25-1## | 224 | 0.83 |
| 2.11-2## | 256$ | 0.82 | 2.26-1## | 224 | 0.87 |
| 2.12-1## | 238 | 0.90 | 2.27-1## | 280 | 1.15 |

Example No. without symbol: HPLC (AcOH) system;
Example No. with symbol #: HPLC (TFA) system; and
Example No. with symbol ##: UPLC system.
In MS-ESI (m/z), *: [M − H]⁻; and **: [M + Na]⁺;
♦: measured as [M + H]⁺ of the corresponding boronic acid;
$: measured as [M + Na]⁺ of carboxylic acid; and
$$: measured as [M + H]⁺ of carboxylic acid.

TABLE 22

| Example | MS-ESI (m/z) [M + H]⁺ | Retention time (min) | Example | MS-ESI (m/z) [M + H]⁺ | Retention time (min) |
|---|---|---|---|---|---|
| 2.28-1## | 232 | 0.47 | 3.15-6## | 454 | 1.15 |
| 3.1-1## | 267 | 1.00 | 3.18-1## | 252 | 0.99 |
| 3.1-2## | 232 | 0.54 | 3.18-2## | 238 | 0.90 |
| 3.1-3## | 218 | 0.52 | 3.18-4## | 240 | 1.03 |
| 3.2-1# | 219 | 3.62 | 3.18-5## | 311 | 1.116 |
| 3.3-1## | 240** | 0.65 | 3.22-1## | 247 | 0.73 |
| 3.4-1## | 244$ | 0.66 | 3.22-2## | 233 | 0.65 |
| 3.5-1## | 240$ | 0.69 | 3.23-1## | 229 | 0.72 |
| 3.6-1# | 278 | 4.98 | 3.24-1## | 233 | 0.63 |
| 3.7-1## | 256$ | 0.72 | 3.24-2## | 241** | 0.52 |
| 3.8-1## | 244$ | 0.74 | 3.25-1## | 233 | 0.75 |
| 3.9-1 | 233 | 3.85 | 3.25-2## | 219 | 0.67 |
| 3.9-2## | 241** | 0.74 | 3.26-1## | 249 | 0.84 |
| 3.10-1## | 294** | 0.93 | 3.26-2## | 235 | 0.79 |
| 3.11-1## | 254$ | 0.75 | 3.27-1## | 267 | 0.91 |
| 3.12-1## | 260 | 0.85 | 3.27-2## | 275** | 0.81 |
| 3.13-1## | 243 | 0.74 | 3.28-1 | 249 | 4.02 |
| 3.13-2## | 229 | 0.67 | 3.28-2## | 257** | 0.84 |
| 3.14-1## | 247 | 0.78 | 3.29-1## | 253 | 0.84 |
| 3.14-2## | 233 | 0.71 | 3.29-2## | 239 | 0.73 |
| 3.15-1## | 193 | 0.65 | 3.30-1## | — | — |
| 3.15-4 | 313 | 5.30 | 3.30-2## | 233 | 0.72 |
| 3.15-5 | 213 | 3.15 | 3.31-1## | 263 | 0.86 |

Example No. without symbol: HPLC (AcOH) system;
Example No. with symbol #: HPLC (TFA) system; and
Example No. with symbol ##: UPLC system.
In MS-ESI (m/z), *: [M − H]⁻; and **: [M + Na]⁺;
$: measured as [M + Na]⁺ of carboxylic acid; and
$$: measured as [M + H]⁺ of carboxylic acid.

TABLE 23

| Example | MS-ESI (m/z) [M + H]⁺ | Retention time (min) | Example | MS-ESI (m/z) [M + H]⁺ | Retention time (min) |
|---|---|---|---|---|---|
| 3.31-2## | 249 | 0.74 | 3.43-1## | 233 | 0.76 |
| 3.32-1## | 233 | 0.74 | 3.43-2## | 241** | 0.78 |
| 3.32-2## | 219 | 0.67 | 3.44-1## | 247 | 0.79 |
| 3.33-1## | 233 | 0.73 | 3.44-2## | 233 | 0.82 |
| 3.33-2# | 219 | 2.50 | 3.45-1## | 233 | 0.66 |
| 3.34-1## | 249 | 0.75 | 3.45-2## | 219 | 0.64 |
| 3.34-2## | 235 | 0.72 | 3.46-1## | 233 | 0.69 |
| 3.35-1## | 247 | 0.77 | 3.46-2## | 219 | 0.63 |
| 3.35-2## | 233 | 0.66 | 3.47-1## | 219 | 0.64 |
| 3.36-1# | 251 | 4.07 | 3.47-2## | 205 | 0.58 |
| 3.37-1## | 261 | 0.74 | 3.49-1## | 445 | 0.97 |
| 3.37-2# | 247 | 2.75 | 3.54-1## | 369** | 1.17 |
| 3.38-1## | 251 | 0.87 | 3.54-2# | 247 | 4.50 |
| 3.38-2## | 237 | 0.79 | 4.3-1## | 218 | 0.72 |
| 3.39-1 | 233 | 3.72 | 4.4-1 | 232 | 2.90 |
| 3.39-2# | 219 | 3.23 | 4.4-2## | 240 | 0.66 |
| 3.40-1## | 279 | 0.95 | 4.5-1 | 248 | 1.30 |
| 3.40-2## | 265 | 0.89 | 4.5-2## | 234 | 0.66 |
| 3.41-1## | 267 | 0.90 | 4.8-1## | 246 | 0.59 |
| 3.41-2## | 253 | 0.80 | 4.8-2## | 232 | 0.72 |
| 3.42-1## | 249 | 0.93 | 4.9-1## | 296** | 0.93 |
| 3.42-2## | 235 | 0.84 | 4.10-1# | 278 | 4.96 |

Example No. without symbol: HPLC (AcOH) system;
Example No. with symbol #: HPLC (TFA) system; and
Example No. with symbol ##: UPLC system.
In MS-ESI (m/z), *: [M − H]⁻; and **: [M + Na]⁺;
$: measured as [M + Na]⁺ of carboxylic acid; and
$$: measured as [M + H]⁺ of carboxylic acid.

TABLE 24

| Example | MS-ESI (m/z) [M + H]+ | Retention time (min) | Example | MS-ESI (m/z) [M + H]+ | Retention time (min) |
|---|---|---|---|---|---|
| 4.11-1## | 211 | 0.67 | 5.11-1## | 316 | 1.16 |
| 4.11-2## | 274 | 0.86 | 5.11-2## | 308 | 1.13 |
| 4.11-3## | 260 | 0.74 | 5.11-3## | 310 | 1.01 |
| 4.11-4## | 353 | 1.04 | 5.12-1## | 253 | 0.89 |
| 4.11-5## | 412** | 1.12 | 5.13-1## | 316 | 0.98 |
| 4.11-6## | 290 | 0.85 | 5.15-1## | 239 | 0.96 |
| 4.13-1## | 222 | 0.62 | 5.16-1 | 193 | 3.17 |
| 4.16-1## | 222 | 0.61 | 5.16-2 | 197 | 1.02 |
| 4.24-1## | 231 | 0.73 | 5.16-3## | 260 | 0.70 |
| 4.24-24 | 240 | 3.12 | 5.16-4# | 246 | 2.78 |
| 4.27-1## | 204 | 0.63 | 5.16-5 | 317 | 4.42 |
| 4.28-1# | 204 | 3.00 | 5.16-6## | 217 | 0.35 |
| 5.1-1 | 244 | 0.85 | 5.16-7 | 458 | 4.75 |
| 5.1-2 | 315 | 1.02 | 5.33-1## | 233 | 0.69 |
| 5.2-1## | 258 | 1.07 | 5.38-1## | 316 | 1.16 |
| 5.2-2 | 262$$ | 0.89 | 5.38-2# | 264 | 4.78 |
| 5.2-3## | 262 | 0.90 | 5.39-1# | 260** | 3.58 |
| 5.2-4 | 333 | 5.32 | 5.40-1## | 251** | 0.78 |
| 5.2-5 | 233 | 0.70 | 5.41-1# | 233* | 4.00 |
| 5.4-1 | 252 | 0.95 | 5.43-1## | 278 | 1.08 |
| 5.5-1 | 300 | 1.11 | 5.44-1 | 302** | 3.83 |
| 5.6-1 | 302 | 1.08 | 5.45-1# | 238 | 3.95 |
| 5.7-1 | 420 | 5.50 | 5.45-2 | 436 | 5.33 |
| 5.8-1## | 314 | 1.08 | 5.46-1 | 476 | 5.03 |
| 5.10-1# | 233* | 4.00 | 5.47-2# | 416 | 0.67 |

Example No. without symbol: HPLC (AcOH) system;
Example No. with symbol #: HPLC (TFA) system; and
Example No. with symbol ##: UPLC system.
In MS-ESI (m/z), *: [M − H]−; and **: [M + Na]+.

The invention claimed is:
1. A method for treating at least one disease selected from the group consisting of a psychiatric disorder, an anxiety disorder, a motor disorder, a mood disorder, a neurodegenerative disorder, a disorder involving deficits in attention and/or cognition, obesity, and drug addiction, wherein the method comprises administering at least one of a compound according to formula (I-b), a pharmaceutically acceptable salt thereof, or a solvate thereof, in an effective amount for treating the disease, to a subject in need of treatment of the disease:

[Formula (I-b)]

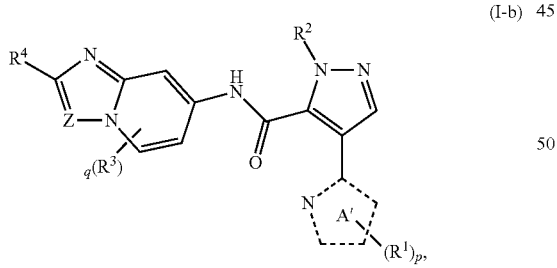

wherein
p represents an integer of 0 to 2;
q represents an integer of 0 to 3;
represents N or CR$^5$;
R$^1$ each independently represents a halogen atom, a hydroxyl group, a nitro group, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxyl group, a halogenated $C_{1-6}$ alkoxyl group, a $C_{1-6}$ alkoxylcarbonyl group, a hydroxy $C_{1-6}$ alkyl group, a $C_{1-6}$ alkoxyl $C_{1-6}$ alkyl group, a $C_{2-7}$ alkanoyl group, a $C_{1-6}$ alkylthio group, a $C_{1-6}$ alkylsulfinyl group, a $C_{1-6}$ alkylsulfonyl group, an —NR$^7$R$^8$ group, or a —CONR$^7$R$^8$ group wherein R$^7$ and R$^8$ in the —NR$^7$R$^8$ group and the —CONR$^7$R$^8$ group each independently represent a substituent selected from among a hydrogen atom, a $C_{1-6}$ alkyl group, a halogenated $C_{1-6}$ alkyl group, a hydroxy $C_{1-6}$ alkyl group, a cyanated $C_{1-6}$ alkyl group, a $C_{2-6}$ alkenyl group, a $C_{2-6}$ alkynyl group, a $C_{3-8}$ cycloalkyl group, a $C_{6-14}$ aryl group, a $C_{7-20}$ aralkyl group, a heterocyclic group, a $C_{2-7}$ alkanoyl group, a hydroxy $C_{2-7}$ alkanoyl group, a halogenated $C_{2-7}$ alkanoyl group, a $C_{3-8}$ cycloalkylcarbonyl group, a $C_{6-14}$ arylcarbonyl group, a $C_{7-20}$ aralkylcarbonyl group, a heterocyclic carbonyl group, a mono-/di-$C_{1-6}$ alkylcarbamoyl group, a mono-/di-halogenated $C_{1-6}$ alkylcarbamoyl group, a mono-/di-$C_{3-8}$ cycloalkylcarbamoyl group, a mono-/di-$C_{6-14}$ arylcarbamoyl group, a mono-/di-$C_{7-20}$ aralkylcarbamoyl group, a mono-/diheterocyclic carbamoyl group, a $C_{1-6}$ alkylsulfonyl group, a halogenated $C_{1-6}$ alkylsulfonyl group, a $C_{3-8}$ cycloalkylsulfonyl group, a $C_{6-14}$ arylsulfonyl group, a $C_{7-20}$ aralkylsulfonyl group, a heterocyclic sulfonyl group, a mono-/di-$C_{1-6}$ alkylsulfamoyl group, a mono-/di-halogenated $C_{1-6}$ alkylsulfamoyl group, a mono-/di-$C_{3-8}$ cycloalkylsulfamoyl group, a mono-/di-$C_{6-14}$ arylsulfamoyl group, a mono-/di-$C_{7-20}$ aralkylsulfamoyl group, and a mono-/di-heterocyclic sulfamoyl group;

R$^2$ represents a hydrogen atom, a $C_{1-6}$ alkyl group, a halogenated $C_{1-6}$ alkyl group, a hydroxy $C_{1-6}$ alkyl group, or a $C_{1-6}$ alkoxyl $C_{1-6}$ alkyl group;

R$^3$ each independently represents a halogen atom, a cyano group, a $C_{1-6}$ alkyl group, a halogenated $C_{1-6}$ alkyl group, a hydroxy $C_{1-6}$ alkyl group, a $C_{1-6}$ alkoxyl group, a halogenated $C_{1-6}$ alkoxyl group, or a $C_{1-6}$ alkoxyl $C_{1-6}$ alkyl group;

R$^4$ represents a halogen atom, a $C_{1-6}$ alkyl group, a halogenated $C_{1-6}$ alkyl group, a $C_{3-8}$ cycloalkyl group, a hydroxy $C_{1-6}$ alkyl group, a $C_{1-6}$ alkoxyl group, a halogenated $C_{1-6}$ alkoxyl group, a $C_{1-6}$ alkoxyl $C_{1-6}$ alkyl group, a $C_{1-6}$ alkylthio group, a $C_{1-6}$ alkylsulfonyl group, a —CONR$^7$R$^8$ group, an —NR$^7$R$^8$ group, a $C_{6-14}$ aryl group, a 3- to 14-membered non-aromatic heterocyclic group, or a 5- to 7-membered monocyclic heteroaryl group, wherein R$^7$ and R$^8$ in the —NR$^7$R$^8$ group and the —CONR$^7$R$^8$ group have the same definitions as those of R$^7$ and R$^8$ in the above R$^1$, and wherein the $C_{3-8}$ cycloalkyl group, the $C_{6-14}$ aryl group, the 3- to 14-membered non-aromatic heterocyclic group, and the 5- to 7-membered monocyclic heteroaryl group, which are represented by R$^4$, are each optionally substituted with one to three groups selected from among a hydroxyl group, a nitro group, a cyano group, a halogen atom, a $C_{1-6}$ alkyl group, a halogenated $C_{1-6}$ alkyl group, a hydroxy $C_{1-6}$ alkyl group, a $C_{1-6}$ alkoxyl group, a halogenated $C_{1-6}$ alkoxyl group, a $C_{1-6}$ alkoxyl $C_{1-6}$ alkyl group, a $C_{1-6}$ alkylthio group, a $C_{1-6}$ alkylsulfonyl group, a —CONR$^7$R$^8$ group, an —NR$^7$R$^8$ group, a $C_{6-14}$ aryl group, a 3- to 14-membered non-aromatic heterocyclic group, and a 5- to 7-membered monocyclic heteroaryl group, wherein R$^7$ and R$^8$ in the —NR$^7$R$^8$ group and the —CONR$^7$R$^8$ group have the same definitions as those of R$^7$ and R$^8$ in the above R$^5$ represents a hydrogen atom, a halogen atom, a $C_{1-6}$ alkyl group, a halogenated $C_{1-6}$ alkyl group, a $C_{1-6}$ alkoxyl group, a halogenated $C_{1-6}$ alkoxyl group, or a $C_{1-6}$ alkoxyl alkyl group; and ring A represented by the following partial structural formula (II'):
[Formula (II')]
(II')
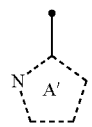
is selected from the group of the heteroaryls consisting of the following:
[Formula ]
(II-1)
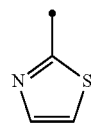
(II-2)
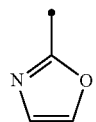
(II-3)
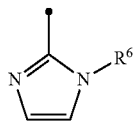
(II-4)
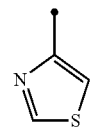
(II-5)
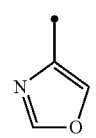
(II-6)
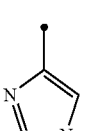
(II-7)
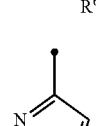
(II-8)
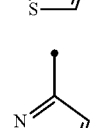
-continued
(II-9)
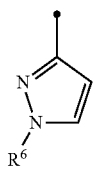
(II-10)
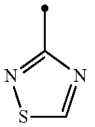
(II-11)
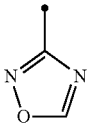
(II-12)
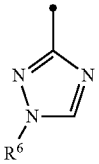
(II-13)
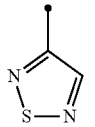
(II-14)
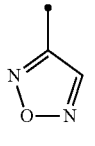
(II-15)
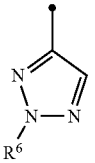
(II-16)
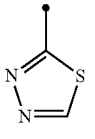
(II-17)
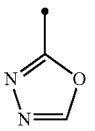
(II-18)
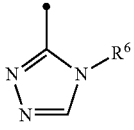

(II-19) 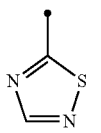

(II-20) 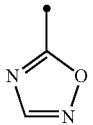

(II-21) 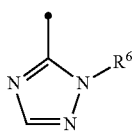

(II-22) 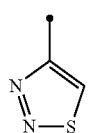

(II-23) 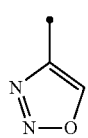

(II-24) 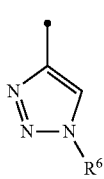

(II-25) 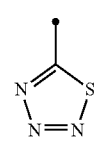

(II-26) 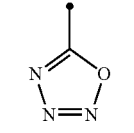

(II-27) 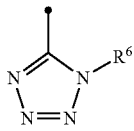

(II-28) 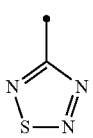

(II-29) 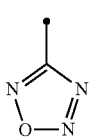

(II-30) 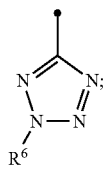

and $R^6$ represents a hydrogen atom, a $C_{1-6}$ alkyl group, a halogenated $C_{1-6}$ alkyl group, or a hydroxy $C_{1-6}$ alkyl group.

2. The method according to claim 1, wherein said at least one of a compound according to formula (I-b), a pharmaceutically acceptable salt thereof, or a solvate thereof, is administered in an effective amount for inhibiting PDE 10, to the subject in need of treatment of the disease.

3. The method according to claim 1, wherein the disease is at least one disease selected from the group consisting of (1) paranoid, disorganized, catatonic, undifferentiated, or residual schizophrenia, (2) schizophreniform disorder, (3) paranoid or depressive schizoaffective disorder, (4) paranoid disorder, (5) substance-induced mental disorder, (6) psychosis induced by alcohol, amphetamine, *cannabis*, cocaine, a hallucinatory drug, an inhalant, opioid, or phencyclidine, (7) paranoic personality disorder, (8) schizotypal personality disorder, (9) Huntington's disease, (10) dyskinesia associated with dopamine agonist therapy, (11) Parkinson's disease, (12) restless legs syndrome, (13) essential tremor, (14) obsessive-compulsive disorder, (15) Tourette's syndrome, (16) tic disorder, (17) panic disorder, (18) agoraphobia, (19) specific phobias, (20) social phobias, (21) posttraumatic stress disorder, (22) acute stress disorder, (23) generalized anxiety disorder, (24) dementia, (25) delirium, (26) amnestic disorder, (27) mental retardation associated psychiatric disorder, (28) learning disorder, (29) attention-deficit hyperactivity disorder, (30) age-related cognitive decline, (31) major depressive episode (mild level, middle level, or severe level type), manic episode, mixed affective episode, or hypomanic episode, (32) atypical depression, (33) melancholic depression, (34) catatonic depression, (35) postpartum mood episode, (36) postapoplectic depression, (37) major depressive disorder, (38) dysthymic disorder/dysthymia, (39) minor depressive disorder, (40) premenstrual dysphoric disorder, (41) postschizophrenic depressive disorder, (42) major depressive disorder occurring with psychiatric disorder, (43) bipolar disorder, (44) cyclothymic disorder, (45) neurodegeneration associated with brain damage, (46) neurodegeneration associated with stroke, or neurodegeneration associated with cerebral infarction, (47) hypoglycemia-induced neurodegeneration, (48) neurodegeneration associated with epileptic seizure, (49) neurodegeneration associated with neurotoxic addiction, (50) multiple system atrophy, and (51) neurodegeneration of striatal medium-sized spiny neurons.

4. The method according to claim 1, wherein said at least one of a compound according to the formula (I-b), a pharmaceutically acceptable salt thereof, or a solvate thereof is administered in combination with one or more drugs selected from the group consisting of (1) atypical antipsychotic agents, (2) typical antipsychotic agents, (3) selective serotonin reuptake inhibitors (SSRI), (4) selective serotonin/noradrenalin reuptake inhibitors (SNRI), (5) selective noradrenalin/dopamine reuptake inhibitors (NDRI), (6) noradrenergic and specific serotonergic antidepressants (NaSSA), (7) triazolopyridine antidepressants (SARI), (8) tetracyclic antidepressants, (9) tricyclic antidepressants, (10) other antidepressants, (11) α7 nicotine receptor agonists, (12) α7 nicotine receptor activity modulators, (13) α7 nicotine receptor partial modulators, (14) other PDE inhibitors, (15) NK2 antagonists, (16) NK3 antagonists, (17) muscarinic M1 acetylcholine receptor activity modulators, (18) muscarinic M2 acetylcholine receptor activity modulators, (19) adenosine receptor modulators, (20) muscarinic M4 acetylcholine receptor activity modulators, (21) muscarinic M5 acetylcholine receptor activity modulators, (22) adenosine receptor modulators, (23) glycine transporter 1 (GlyT1) inhibitors, (24) glutamate enhancers, (25) NMDA receptor inhibitors, (26) metabolic glutamate receptor modulators (mGlu), (27) anti-anxiety agents, (28) sleep inducing drugs, (29) amyloid vaccine, (30) βamyloid degrading enzyme, etc., (31) cerebral function activators, (32) cannabinoid modulators, (33) choline esterase inhibitors, (34) MAO-B inhibitors, (35) Parkinson's disease-treating agents, (36) diabetes-treating agents, (37) antiobestic drugs, (38) hyperlipidemia-treating agents, (39) antihypertensive agents, (40) non-steroidal anti-inflammatory agents, (41) disease modifying antirheumatic drugs (DMARDs), (42) anti-cytokine agents, (43) steroid drugs, (44) sex hormones or derivatives thereof, and (45) parathyroid hormone (PTH).

5. The method according to claim 1, wherein said disease is psychiatric disorder.

6. The method according to claim 3, wherein said disease is at least one psychiatric disorder selected from the group consisting of (1) paranoid, disorganized, catatonic, undifferentiated, or residual schizophrenia, (2) schizophreniform disorder, (3) paranoid or depressive schizoaffective disorder, (4) paranoid disorder, (5) substance-induced mental disorder, (6) psychosis induced by alcohol, amphetamine, *cannabis*, cocaine, a hallucinatory drug, an inhalant, opioid, or phencyclidine, (7) paranoic personality disorder and (8) schizotypal personality disorder.

7. The method of claim 5, wherein a compound according to formula (I-b) is

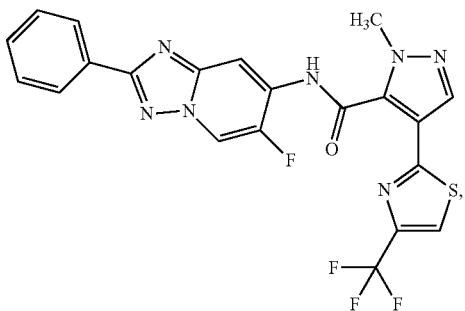 [SMILES: Cn1ncc(-c2nc(C(F)(F)F)cs2)c1C(=O)Nc1cc2nc(-c3ccccc3)nn2cc1F]

a pharmaceutically acceptable salt thereof, or a solvate thereof.

* * * * *